(12) United States Patent
Pache et al.

(10) Patent No.: US 12,359,182 B2
(45) Date of Patent: Jul. 15, 2025

(54) POLYPEPTIDE VARIANTS

(71) Applicant: Novozymes A/S, Bagsvaerd (DK)

(72) Inventors: Roland Alexander Pache, Valby (DK); Anders Gunnar Sandstrom, Sandby (SE); Jan Kjoelhede Vester, Hvidovre (DK); Henrik Friis-Madsen, Ballerup (DK); Dorota Nissen, Vedbaek (DK)

(73) Assignee: Novozymes A/S, Bagsvaerd (DK)

( * ) Notice: Subject to any disclaimer, the term of this patent is extended or adjusted under 35 U.S.C. 154(b) by 375 days.

(21) Appl. No.: 17/759,537

(22) PCT Filed: Feb. 23, 2021

(86) PCT No.: PCT/EP2021/054398
§ 371 (c)(1),
(2) Date: Jul. 27, 2022

(87) PCT Pub. No.: WO2021/170559
PCT Pub. Date: Sep. 2, 2021

(65) Prior Publication Data
US 2023/0220366 A1 Jul. 13, 2023

(30) Foreign Application Priority Data

Feb. 26, 2020 (EP) ..................................... 20159590

(51) Int. Cl.
| | |
|---|---|
| *C12N 9/38* | (2006.01) |
| *A23C 9/12* | (2006.01) |
| *C12N 15/52* | (2006.01) |
| *C12N 15/63* | (2006.01) |

(52) U.S. Cl.
CPC .......... *C12N 9/2471* (2013.01); *A23C 9/1206* (2013.01); *C12N 15/52* (2013.01); *C12N 15/63* (2013.01); *C12Y 302/01023* (2013.01)

(58) Field of Classification Search
CPC ...... C12N 9/2471; C12N 15/52; C12N 15/63; A23C 9/12; A23C 9/06; C12Y 302/01023
See application file for complete search history.

(56) References Cited

U.S. PATENT DOCUMENTS

2016/0333331 A1 11/2016 DeJong

FOREIGN PATENT DOCUMENTS

| CA | 3059275 A1 | 10/2018 |
|---|---|---|
| EP | 1283876 B1 | 1/2007 |
| WO | 2009/071539 A1 | 6/2009 |

OTHER PUBLICATIONS

Hansen et al., EBI Accession No. AX319626 (2001).
Juajun et al., Appl. Microbiol. Biotechnol., vol. 89, pp. 645-654 (2010).

*Primary Examiner* — Ganapathirama Raghu
(74) *Attorney, Agent, or Firm* — Yoshimi D. Barron

(57) ABSTRACT

The present invention relates to novel lactase variants having improved properties relative to the parent lactase, such as decreased galactose inhibition or increased galactose inhibition. The variants of the invention are suitable for production of dairy products, such as low-lactose dairy products or lactose-free dairy products. The present invention also relates to isolated DNA sequences encoding the variants, expression vectors, host cells, and methods for producing and using the lactase variants of the invention.

15 Claims, No Drawings
Specification includes a Sequence Listing.

POLYPEPTIDE VARIANTS

CROSS-REFERENCE TO RELATED APPLICATIONS

This application is a 35 U.S.C. 371 national application of international application no. PCT/EP2021/054398 filed Feb. 23, 2021, which claims priority or the benefit under 35 U.S.C. 119 of European application no. 20159590.7 filed Feb. 26, 2020. The content of each application is fully incorporated herein by reference.

REFERENCE TO SEQUENCE LISTING

This application contains a Sequence Listing in computer readable form, which is incorporated herein by reference. The name of the file containing the Sequence Listing is SQ.txt, which was created on Jan. 17, 2023 and has 179,921 bytes.

FIELD OF THE INVENTION

The present invention relates to novel lactase variants having improved properties relative to the parent lactase, such as decreased galactose inhibition or increased galactose inhibition. The variants of the invention are suitable for production of dairy products, such as low-lactose dairy products or lactose-free dairy products. The present invention also relates to isolated DNA sequences encoding the variants, expression vectors, host cells, and methods for producing and using the lactase variants of the invention.

BACKGROUND OF THE INVENTION

Lactase is used commercially to hydrolyze lactose in milk into its monosaccharides glucose and galactose. Low-lactose or lactose-free dairy products can thus be obtained which are suitable for people with lactose intolerance. Another advantage of low-lactose or lactose-free dairy products is that they have a sweeter taste since glucose and galactose are sweeter than lactose. Dairy products having a sweeter taste can thus be obtained without the addition of any sugar, artificial sweetener or the like. Lactase is also used in the manufacture of ice cream. Lactose crystallises at the low temperatures of ice cream, whereas glucose and galactose stay liquid and contribute to a smoother texture. Lactase is also used in the conversion of whey into syrup. Lactase is also used for production of condensed milk.

WO2009/071539 discloses a C-terminally truncated fragment of an extracellular lactase from *Bifidobacterium bifidum*, which hydrolyzes lactose very efficiently and enables the achievement of low levels of lactose in the dairy product. The enzyme is active at quite high temperature and at both neutral and acidic pH.

The purpose of the present invention is to provide variants of a lactase, such as a lactase derived from *Bifidobacterium*, e.g., *Bifidobacterium bifidum*, which have improved properties relative to the parent lactase, such as decreased galactose inhibition or increased galactose inhibition.

Variants with decreased or increased galactose inhibition may be beneficial since they allow for a fine-tuning of the galactose inhibition propensity of the lactase. A decreased galactose inhibition will allow the enzyme to retain more activity at higher levels of galactose and thus allow for degradation of lactose down to a lower final lactose level. An increased galactose inhibition may reduce or stop the activity of the enzyme when a certain decreased level of lactose has been obtained which may be advantageous in some commercial applications.

SUMMARY OF THE INVENTION

The present inventors have for the first time produced protein engineered variants of a bacterial lactase, more specifically to a *Bifidobacterium bifidum* lactase which is widely used in the industry today.

The present inventors have found lactase variants having decreased or increased galactose inhibition compared to the parent lactase. The decreased or increased galactose inhibition has been determined by a shift in ratio of activity as measured by the galactose inhibition assay as disclosed herein.

Variants with decreased or increased galactose inhibition may be beneficial since they allow for a fine-tuning of the galactose inhibition propensity of the lactase. A decreased galactose inhibition will allow the enzyme to retain more activity at higher levels of galactose and thus allow for degradation of lactose down to a lower final lactose level. An increased galactose inhibition may reduce or stop the activity of the enzyme when a certain decreased level of lactose has been obtained which may be advantageous in some commercial applications.

The present invention is therefore directed to lactase variant having an amino acid sequence which is at least 80% identical to SEQ ID NO: 1 which comprises an alteration, preferably a substitution, at one or more positions corresponding to positions 2, 3, 4, 5, 6, 7, 9, 10, 11, 12, 13, 14, 15, 16, 17, 21, 22, 23, 24, 25, 26, 27, 28, 29, 31, 32, 33, 34, 35, 36, 37, 38, 39, 40, 41, 42, 43, 44, 45, 47, 48, 49, 51, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 206, 207, 208, 209, 210, 211, 212, 213, 214, 215, 216, 217, 218, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 265, 267, 268, 269, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 406, 407, 408, 409, 410, 411, 412, 413, 414, 415, 416, 417, 418, 419, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 459, 461, 462, 463, 464, 465, 466, 467, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 514, 516, 517, 518, 519, 520, 521, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 608, 609, 610, 611, 612, 613, 631, 633, 634, 635, 636, 637, 638, 639, 640, 641, 642, 643, 644, 645, 646, 647, 648, 649, 650, 651, 652, 653, 654, 655, 656, 657, 659, 661, 662, 669, 670, 672, 673, 674, 675, 676, 677, 678, 679, 680, 681, 682, 683, 684, 685, 686, 687, 688, 689, 690, 693, 694, 695, 696, 697, 698, 700, 701, 703, 704, 705, 706, 708, 709, 710, 711, 712, 713, 714, 715, 718, 720, 721, 723, 724, 725, 726, 727, 728, 729, 730, 731, 732, 733, 734, 735, 736, 737, 738, 739, 740, 741, 742, 743, 744, 745, 746, 747, 748, 750, 751, 752, 753, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 840, 841, 842, 843, 844, 845, 846, 847, 848, 849, 850, 851, 852, 853, 854, 855, 857, 858, 859, 860, 861, 862, 863, 864, 865, 866, 870, 871, 872, 873, 874, 875, 877, 879, 880, 881, 882, 883, 884, 885, 886, 887, 888, 889, 893, 894, 895, 896, 897, 898, 899, 900, 901, 902, 903, 904, 905, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 973, 974, 975, 976, 977, 978, 979, 980, 981, 984, 985, 986, 987, 988, 989, 990, 991, 992, 993, 994, 995, 996, 997, 998, 999, 1000, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1055, 1057, 1058, 1059, 1060, 1062, 1063, 1064, 1065, 1066, 1067, 1068, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1161, 1162, 1166, 1167, 1168, 1169, 1170, 1171, 1172, 1173, 1174, 1175, 1177, 1178, 1179, 1180, 1181, 1182, 1184, 1185, 1186, 1188, 1189, 1190, 1191, 1192, 1193, 1194, 1195, 1197, 1198, 1199, 1202, 1203, 1204, 1205, 1208, 1209, 1210, 1211, 1213, 1214, 1215, 1217, 1218, 1219, 1220, 1221, 1222, 1223, 1224, 1225, 1226, 1227, 1228, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1.

The invention is also directed to lactase variant having an amino acid sequence which is at least 80% identical to SEQ ID NO: 1 which comprises one or more of the following substitutions, wherein each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, S14Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60C, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71G, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, G149H, G149I, G149M, G149Q, G149Y, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191Q, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205W, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213D, K213S, K213T, K213V, K213Y, V214A, V214C, V214T, V214W, A215D, A215E, A215F, A215I, A215K, A215L, A215Q, A215R, A215S, A215V, N216D, N216K, N216V, D217F, D217G, D217L, D217M, D217T, D217V, T218D, T218G, T218H, K219A, K219C, K219F, K219H, K219M, A220C, A220G, A220I, A220L, A220M, A220T, A220V, A220W, A221C, A221D, A221E, A221L, A221N, A221R, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, F231A, F231E, F231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S248I, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, S267A, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284I, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321I, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364R, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396C, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405V, I406D, I406N, A407C, A407G, A407K, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L426C, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444C, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457T, S457V, G458A, G458C, G458F, G458L, G458P, G458Q, G458S, G458V, G458W, F459A, F459C, F459E, F459G, F459N, F459R, F459S, F459T, F459W, P460C, P460M, P460Q, P460W, P460Y, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K465C, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, A468D, A468E, A468F, A468K, A468L, A468P, A468S, A468V, A468W, W469A, W469C, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477F, R477L, P478A, P478D, P478L, P478V, M479G, M479I, M479R, M479W, T480C, T480G, T480Q, K485E, K485R, K487A, K487C, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496T, G497D, D498A, D498C, D498M, D498S, N499K, N499R, N499T, N499Y, L500A, L500E, L500N, L500V, T501C, T501G, T501M, A502L, A502Q, N503A, N503E, N503M, N503S, G504H, G504K, G504P, G505A, G505D, G505E, G505H, G505L, G505N, G505R, G505S, G505V, V506C, V506D, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514R, A515C, A515D, A515E, A515F, A515G, A515K, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521V, T522G, T522I, T522N, T523A, T523M, H524R, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, S577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606S, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627G, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644G, D644Y, D645S, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667R, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701M, K701P, K701S, K701W, T703E, T703I, T703K, T703W, T704M, T704R, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711A, Q711D, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716V, D717C, D717G, D717L, D717S, K718A, K718L, K718Q, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M,

I739W, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749M, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811Y, D812E, D812F, D812I, D812Q, V813F, V813W, V813T, V813W, K814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, K818Y, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, K839A, K839C, K839D, K839E, K839G, K839L, K839N, K839P, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858G, I858K, I858M, I858P, I858Q, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888G, R889G, Y892D, Y892P, Y892R, Y893E, Y893G, S894D, S894G, R895M, N896M, Y897V, Y898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906S, I906T, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927G, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937G, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973Q, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982P, G982Q, G982W, R984R, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001G, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, S1052C, A1052K, A1052M, A1052P, A1052R, L1053A, L1053W, R1054C, R1054L, R1054N, L1055R, L1055T, Q1057A, Q1057E, Q1057P, Q1057R, N1058R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069G, D1069K, D1069R, D1069W, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118H, Q1118S, Q1118T, Q1118W, I1119D, I1119E, I1119G, I1119N, I1119S, V1120N, V1120S, V1120T, M1121G, M1121K, M1121N, M1121P, M1121S, M1121V, M1121Y, Y1122A, Y1122C, Y1122I, Y1122K, Y1122R, Y1122V, Y1122W, F1123E, F1123H, F1123R, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, YI172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200W, L1202A, L1202C, T1203E, T1203K, E1204G, E1204S, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216L, T1216P, T1216Q, T1216R, N1217A, N1217D, N1217E, N1217F, N1217P, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236W, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257L, G1257I, G1257Q, G1257R, G1257W, N1258C, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

Preferably, the lactase variant has a decreased or an increased galactose inhibition, preferably measured as a galactose inhibition improvement factor (GI-IF) of at least 1.1 or at most 0.9, compared to the lactase of SEQ ID NO: 1.

The invention is also directed to an isolated polynucleotide encoding the variant, a nucleic acid construct, an expression vector, a recombinant host cell, and a method of producing a lactase variant of the invention.

The invention is also directed to a method for producing a dairy product comprising:
 a) providing a milk-based substrate comprising lactose; and
 b) treating said substrate with a variant of the invention.

The invention is also directed to use of such variant for production of a dairy product.

The invention is also directed to a liquid composition comprising such variant and 20-70% glycerol.

The invention is also directed to a method for obtaining a lactase variant, comprising:

a) introducing into a parent lactase having an amino acid sequence which is at least 80%, 85%, 90%, or 95%, preferably at least 97%, 98%, or 99%, more preferably at least 99.5%, 99.7%, 99.8%, 99.9%, or 100%, identical to SEQ ID NO: 1 an alteration, preferably a substitution, at one or more positions corresponding to positions 1, 2, 3, 4, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 51, 53, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 149, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 264, 265, 266, 267, 268, 269, 270, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 607, 608, 609, 610, 611, 612, 613, 614, 615, 616, 619, 620, 621, 624, 625, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 659, 661, 662, 667, 669, 670, 672, 673, 674, 675, 676, 677, 678, 679, 680, 681, 682, 683, 684, 685, 686, 687, 688, 689, 690, 691, 692, 693, 694, 695, 696, 697, 698, 700, 701, 703, 704, 705, 706, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 857, 858, 859, 860, 861, 862, 863, 864, 865, 866, 867, 870, 871, 872, 873, 874, 875, 877, 879, 880, 881, 882, 883, 884, 885, 886, 887, 888, 889, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 973, 974, 975, 976, 977, 978, 979, 980, 981, 982, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1054, 1055, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1160, 1161, 1162, 1165, 1166, 1167, 1168, 1169, 1170, 1171, 1172, 1173, 1174, 1175, 1177, 1178, 1179, 1180, 1181, 1182, 1183, 1184, 1185, 1186, 1188, 1189, 1190, 1191, 1192, 1193, 1194, 1195, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1, and b) recovering the variant.

DETAILED DESCRIPTION OF THE INVENTION

Definitions

Sequence identity: The relatedness between two amino acid sequences is described by the parameter "sequence identity".

For purposes of the present invention, the sequence identity between two amino acid sequences is determined as the output of "longest identity" using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are a gap open penalty of 10, a gap extension penalty of 0.5, and the EBLOSUM62 (EMBOSS version of BLOSUM62) substitution matrix. In order for the Needle program to report the longest identity, the nobrief option must be specified in the command line. The output of Needle labeled "longest identity" is calculated as follows:

(Identical Residues×100)/(Length of Alignment–
Total Number of Gaps in Alignment)

Conventions for Designation of Variants: For purposes of the present invention, the polypeptide disclosed in SEQ ID NO: 1 is used to determine the corresponding amino acid position in another enzyme. The amino acid sequence of another enzyme is aligned with the polypeptide disclosed in SEQ ID NO: 1, and based on the alignment, the amino acid position number corresponding to any amino acid residue in the polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are gap open penalty of 10, gap extension penalty of 0.5, and the EBLOSUM62 (EMBOSS version of BLOSUM62) substitution matrix.

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations may be separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Different substitutions. Where different substitutions can be introduced at a position, the different substitutions may be separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Lactase: A "lactase" in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108. Enzymes assigned to other subclasses, such as, e.g., EC 3.2.1.23, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity.

Lactase activity may be determined using, e.g., a LAU-B assay. In the context of the present invention, the activity in LAU-B/g of a specific lactase may be determined by direct measurement of o-nitrophenyl (ONP) released from o-nitrophenyl β-D-galactopyranoside (ONPG) in a buffer containing 1.46 mg/ml substrate in 0.05 M MES, 1 mM MgSO4 7H2O, 450 mg/L Brij 35 at pH6.5 and 30° C. After 600 seconds incubation, the reaction is stopped by adding 0.2 M Na2CO3 and the released ONP is measured at 405 nm after 126 seconds incubation. The skilled person will know how to execute this assay and determine such activity. Here, the activity is obtained by comparing to a standard curve run with a lactase of known activity, and the activity of the unknown sample calculated from this. The lactase of known activity may, e.g., be Saphera® obtained from Novozymes A/S, Denmark.

Isolated: The term "isolated" means a polypeptide, nucleic acid, cell, or other specified material or component that is separated from at least one other material or component with which it is naturally associated as found in nature, including but not limited to, for example, other proteins, nucleic acids, cells, etc. An isolated polypeptide includes, but is not limited to, a culture broth containing the secreted polypeptide.

Variant: The term "variant" or "lactase variant" means a polypeptide having lactase activity comprising a substitution, an insertion, and/or a deletion, at one or more (e.g., several) positions compared to a reference sequence. Variants of the present invention preferably comprise a substitution at one or more positions. A substitution means replacement of the amino acid occupying a position with a different amino acid; a deletion means removal of the amino acid occupying a position; and an insertion means adding one or more amino acid(s) adjacent to and immediately following the amino acid occupying a position. The variants of the present invention may have at least 20%, e.g., at least 40%, at least 50%, at least 60%, at least 70%, at least 80%, at least 90%, at least 95%, or at least 100% of the lactase activity of the polypeptide of SEQ ID NO: 1. A lactase variant is thus a variant compared to a reference sequence.

Parent: The term "parent" lactase or lactase "parent" is to be understood as a lactase into which at least one alteration is made in the amino acid sequence to produce a lactase variant having an amino acid sequence which is less than 100% identical to the amino acid sequence of the parent lactase. In a particular aspect the lactase parent is a lactase having an amino acid sequence which is at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or 100% identical to SEQ ID NO: 1.

Milk: The term "milk" means the lacteal secretion obtained by milking any mammal, such as cows, sheep, goats, buffaloes or camels. Preferably milk is cow's milk.

Milk-based substrate: The term "milk-based substrate", in the context of the present invention, may be any raw and/or processed milk material. Useful milk-based substrates include, but are not limited to, solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream. Preferably, the milk-based substrate is milk or an aqueous solution of skim milk powder.

Dairy product: A "dairy product" in the context of the present invention may be any food product wherein one of the major constituents is milk-based. Preferable, the major constituent is milk-based. More preferably, the major constituent is a milk-based substrate which has been treated with an enzyme having lactase activity according to the invention. In the context of the present invention "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 75% or more than 80%, more preferably more than 90% or more than 95%, of the total dry matter of the dairy product.

Lactase Variants

The present invention provides novel lactases. In a preferred embodiment, the lactases are obtained from *Bifidobacterium*, in particular *Bifidobacterium bifidum*. In another preferred embodiment, the lactases may be variants of parent lactases, preferably obtained from *Bifidobacterium*, in particular *Bifidobacterium bifidum*.

The lactase variants of the present invention are variants compared to a reference sequence, preferably SEQ ID NO: 1.

The lactase variants of the invention preferably have an amino acid sequence which is at least 80%, 85%, 90%, or 95%, preferably at least 97%, 98%, or 99%, more preferably at least 99.5%, 99.7%, 99.8% or 99.9%, but less than 100%, identical to SEQ ID NO: 1.

In an embodiment, the lactase variants of the invention have an amino acid sequence which is at least 80%, 85%, 90%, or 95%, preferably at least 97%, 98%, or 99%, more preferably at least 99.5%, 99.7%, 99.8% or 99.9%, but less than 100%, identical to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15.

The lactase variants of the invention comprise an alteration, preferably a substitution, of at least one amino acid compared to the lactase of SEQ ID NO: 1. In some aspects, a lactase variant of the invention comprise at least two substitutions compared to the lactase of SEQ ID NO: 1, such as at least 3 substitutions, at least 4 substitutions, at least 5 substitutions, such as at least 6, 7, 8, 9 or 10 substitutions.

The lactase variants of the invention may have 1-50 substitutions, preferably 1-30, 1-20, 1-10 or 1-5, such as 1, 2, 3, 4, 5, 6, 7, 8, 9, 10, 11, 12, 13, 14, 15, 16, 17, 18, 19 or 20 substitutions, compared to the lactase of SEQ ID NO: 1.

The lactase variants of the invention have lactase activity.

The lactase variants of the invention may be isolated.

In an embodiment, the lactase variants of the invention have a length of 850-2000 amino acids, such as 880-1350 amino acids.

In a preferred embodiment, the lactase variants of the invention have a length of 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

In a more preferred embodiment, the lactase variants of the invention comprise the same number of amino acid residues as the lactase of SEQ ID NO: 1.

In another preferred embodiment, the lactase variants of the invention have a ratio of beta-galactosidase activity to transgalactosylating activity of at least 2, preferably at least 3, such as at least 4, more preferably at least 5, such as at least 10, where said ratio is measured as [Galactose]/([Glucose]−[Galactose]) after incubation of the enzyme in cow's milk at 37° C. for 3 hours.

The lactase variants of the present invention preferably have at least one improved property compared to a reference lactase. The reference lactase may be the parent lactase from which the variant is obtained. In a preferred embodiment, the reference lactase is the lactase of SEQ ID NO: 1.

In a preferred embodiment, the lactase variants of the present invention have a galactose inhibition improvement factor (GI-IF) of at least 1.1 or at most 0.9, compared to the lactase of SEQ ID NO: 1. The GI-IF is preferably calculated as described in Example 2.

I.e., the galactose inhibition improvement factor (GI-IF) of a given variant may be calculated as the RA (ratio of activity) of the variant relative to the RA of the lactase of SEQ ID NO: 1, which is normalized to have a GI-IF=1.0, where the RA is calculated as (Abs405 Galactose sample−Abs405 Galactose Blank)/(Abs405 Reference sample−Abs405 Reference Blank). The variants and the lactase of SEQ ID NO: 1 may be grown in reference solution (MES (100 mM), ONPG (10.66 mM), DMSO (140 mM), pH 6.0) and assay solution (reference solution plus D-(+)-Galactose (80 mM)) for 30 min at 23° C. Stop solution is added (Na2CO3, 10% w/v in H2O), and the absorbance at 405 nm is recorded. "Abs405 Galactose sample" is the absorbance for the lactase grown in assay solution, "Abs405 Galactose Blank" is the absorbance for non-inoculated assay solution, "Abs405 Reference sample" is the absorbance for the lactase grown in reference solution, and "Abs405 Reference Blank" is the absorbance for non-inoculated reference solution.

A GI-IF above 1 means that the variant has a decreased galactose inhibition compared to the reference lactase of SEQ ID NO: 1, whereas a GI-IF below 1 means that the variant has an increased galactose inhibition compared to the reference lactase of SEQ ID NO: 1.

Variants showing decreased galactose inhibition (i.e. GI-IF of at least 1.9, or at least 1.8, or at least 1.7, or at least 1.6, or at least 1.5, or at least 1.4, or at least 1.3, or at least 1.2, or at least 1.1, but more than 1.0) are beneficial in application, since they lead to higher lactase performance. Moreover, variants showing increased galactose inhibition (i.e. GI-IF of at most 0.1, or at most 0.2, or at most 0.3, or at most 0.4, or at most 0.5, or at most 0.6, or at most 0.7, or at most 0.8, or at most 0.9, but less than 1.0) are also beneficial in application, since they allow to fine-tune the galactose inhibition propensity of the lactase.

The lactase variants of the present invention may have at least one other improved property compared to a reference lactase, preferably the lactase of SEQ ID NO: 1.

The lactase variants of the present invention may have at least one other improved property compared to the parent lactase, preferably the lactase of SEQ ID NO: 1.

Such properties may include one or more of the following: Increased specific activity, increased thermostability, decreased thermostability, or increased acidic stability.

An increased specific activity may be advantageous, e.g., because more lactose hydrolysis can be obtained using a smaller amount of enzyme.

An increased thermostability allows for treatment of the milk or dairy product at higher temperature. This may reduce the microbial count and thereby improve the quality of the milk or dairy product.

A decreased thermostability may allow for using a lower temperature for thermal inactivation of the lactase.

An increased acidic stability is especially useful for the production of fermented dairy products, since the enzyme is still active during and after fermentation.

The lactase variants of the present invention comprise an alteration, preferably a substitution, at one or more positions corresponding to positions 1, 2, 3, 4, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 51, 53, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 149, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 264, 265, 266, 267, 268, 269, 270, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 607, 608, 609, 610, 611, 612, 613, 614, 615, 616, 619, 620, 621, 624, 625, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 659, 661, 662, 667, 669, 670, 672, 673, 674, 675, 676, 677, 678, 679, 680, 681, 682, 683, 684, 685, 686, 687, 688, 689, 690, 691, 692, 693, 694, 695, 696, 697, 698, 700, 701, 703, 704, 705, 706, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 857, 858, 859, 860, 861, 862, 863, 864, 865, 866, 867, 870, 871, 872, 873, 874, 875, 877, 879, 880, 881, 882, 883, 884, 885, 886, 887, 888, 889, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 973, 974, 975, 976, 977, 978, 979, 980, 981, 982, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1054, 1055, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1160, 1161, 1162, 1165, 1166, 1167, 1168, 1169, 1170, 1171, 1172, 1173, 1174, 1175, 1177, 1178, 1179, 1180, 1181, 1182, 1183, 1184, 1185, 1186, 1188, 1189, 1190, 1191, 1192, 1193, 1194, 1195, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1.

In a preferred embodiment, the lactase variants of the present invention comprise an alteration, preferably a substitution, at one or more positions corresponding to positions 2, 3, 4, 5, 6, 7, 9, 10, 11, 12, 13, 14, 15, 16, 17, 21, 22, 23, 24, 25, 26, 27, 28, 29, 31, 32, 33, 34, 35, 36, 37, 38, 39, 40, 41, 42, 43, 44, 45, 47, 48, 49, 51, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 206, 207, 208, 209, 210, 211, 212, 213, 214, 215, 216, 217, 218, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 265, 267, 268, 269, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 406, 407, 408, 409, 410, 411, 412, 413, 414, 415, 416, 417, 418, 419, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 459, 461, 462, 463, 464, 465, 466, 467, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 514, 516, 517, 518, 519, 520, 521, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 608, 609, 610, 611, 612, 613, 631, 633, 634, 635, 636, 637, 638, 639, 640, 641, 642, 643, 644, 645, 646, 647, 648, 649, 650, 651, 652, 653, 654, 655, 656, 657, 659, 661, 662, 669, 670, 672, 673, 674, 675, 676, 677, 678, 679, 680, 681, 682, 683, 684, 685, 686, 687, 688, 689, 690, 693, 694, 695, 696, 697, 698, 700, 701, 703, 704, 705, 706, 708, 709, 710, 711, 712, 713, 714, 715, 718, 720, 721, 723, 724, 725, 726, 727, 728, 729, 730, 731, 732, 733, 734, 735, 736, 737, 738, 739, 740, 741, 742, 743, 744, 745, 746, 747, 748, 750, 751, 752, 753, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 840, 841, 842, 843, 844, 845, 846, 847, 848, 849, 850, 851, 852, 853, 854, 855, 857, 858, 859, 860, 861, 862, 863, 864, 865, 866, 870, 871, 872, 873, 874, 875, 877, 879, 880, 881, 882, 883, 884, 885, 886, 887, 888, 889, 893, 894, 895, 896, 897, 898, 899, 900, 901, 902, 903, 904, 905, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 973, 974, 975, 976, 977, 978, 979, 980, 981, 984, 985, 986, 987, 988, 989, 990, 991, 992, 993, 994, 995, 996, 997, 998, 999, 1000, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1055, 1057, 1058, 1059, 1060, 1062, 1063, 1064, 1065, 1066, 1067, 1068, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1161, 1162, 1166, 1167, 1168, 1169, 1170, 1171, 1172, 1173, 1174, 1175, 1177, 1178, 1179, 1180, 1181, 1182, 1184, 1185, 1186, 1188, 1189, 1190, 1191, 1192, 1193, 1194, 1195, 1197, 1198, 1199, 1202, 1203, 1204, 1205, 1208, 1209, 1210, 1211, 1213, 1214, 1215, 1217, 1218, 1219, 1220, 1221, 1222, 1223, 1224, 1225, 1226, 1227, 1228, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1.

In other preferred embodiments, the lactase variants of the present invention comprise an alteration, preferably a substitution, at one or more positions corresponding to the positions listed in any one of embodiments 5, 7, 9, 11, 13, 15, 17 19, 21, 23, 25, 27, 29, 31, 33, 35, 37, 39, 41, 43, 45, 47, 49, 51, 53, 55, 57, 59, 61, 63, 65, 67, 69 or 71 of the "PREFERRED EMBODIMENTS" section right before the "EXAMPLES" section of the present application.

Preferably, the lactase variants of the present invention comprise one or more of the following substitutions, wherein each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, S14Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, 527A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53T, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60C, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, G149E, G149H, G149I, G149M, G149Q, G149Y, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191C, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205W, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209Y, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, K219A, K219C, K219F, K219H, K219M, A220C, A220G, A220I, A220L, A220M, A220T, A220V, A220W, A221C, A221D, A221E, A221L, A221N, A221R, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, T231A, T231E, T231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S248I, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, A266T, S267A, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277K, N277R, N277L, L278A, L278G, L278H, L278I, L278K, L278L, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328M, H328R, H328T, D329S, D329T, G331V, A335C, A335G, A335L, A337D, A337F, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369N, I369V, I369W, D370C, D370L, D370Q, D370R, D370S, D370T, V371D, V371F, V371I, V371L, V371Q, V371S, C372P, N373G, N373L, N373R, E374K, E374L, E374R, K375D, K375I, K375N, K375Q, K375S, G376A, G376S, V377A, V377M, V377T,
L378I, L378P, L378W, L378Y, V379A, V379C, V379M, V379N, V380M, V380P, V380S, E381A, E381C, E381G, E381L, E381Q, E381T, V383A, V383K, V383L, M386G, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405T, A405V, I406C, I406D, I406N, A407C, A407G, A407M, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L426C, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444C, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457T, S457V, G458A, G458C, G458D, G458F, G458L, G458P, G458Q, G458S, G458V, G458W, F459A, F459C, F459E, F459G, F459N, F459R, F459S, F459T, F459W, P460C, P460M, P460Q, P460Y, A461D, A461G, A461N, A461Q, A461S, A461V, A461Y, I462C, T462E, T462F, T462L, T462M, T462S, A463G, S463K, S463Q, S463R, S463T, S463V, A464E, A464H, A464L, A464M, A464P, A464V, A464W, K465C, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, A468D, A468E, A468F, A468K, A468L, A468P, A468S, A468V, A468W, W469A, W469C, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K487C, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496T, G497D, D498A, D498C, D498M, D498S, N499K, N499R, N499T, N499Y, L500A, L500E, L500N, L500V, T501C, T501G, T501M, A502L, A502Q, N503A, N503E, N503M, N503S, G504H, G504K, G504P, G505A, G505D, G505E, G505L, G505N, G505S, G505V, V506D, V506E, V506G, V506I, V506L, V506P, V506R, V506S, V506T, V506W, V507A, V507F, V507G, V507L, V507N, V507P, V507R, V507S, V507T, V508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514R, A515C, A515D, A515E, A515F, A515G, A515K, A515P, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521Q, R521V, T522G, T522I, T522N, T523A, T523M, H524R, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577F, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583C, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604N, N604S, G605R, T606S, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627G, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644D, D644Y, D645C, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667R, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683Y, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700Y, K701A, K701D, K701E, K701G, K701H, K701L, K701M, K701P, K701S, K701W, T703E, T703I, T703K, T703W, T704M, T704R, T704Y, A705C, A705D, A705E, A705K, A705N, A705P, A705R, A705V, A705W, A706C, A706I, A706T, A706W, A706Y, Y708C, Y708F, Y708G, Y708K, Y708L, Y708P, Y708T, T709M, Y710C, Y710D, Y710G, Y710K, Y710M, Y710N, Y710T, Y710V, Q711A, Q711D, Q711G, Q711L, Q711M, Q711T, Q711Y, V712G, V712M, V712P, V712Q, V712R, V712Y, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716T, A716V, D717C, D717G, D717L, D717S, K718A, K718L, K718Q, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, A722V, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739W, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749M, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, G754R, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791T, E791M, E791S, E791T, E791V, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811Y, D812E, D812F, D812I, D812Q, V813F, V813H, V813T, V813W, V813Y, K814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818W, L819W, L819Y, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830N, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, R838W, K839A, K839C, K839D, K839E, K839G, K839L, K839N, K839P, K839R, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858K, I858M, I858N, I858P, I858Q, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874A, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888G, R889G, Y892D, Y892R, Y893E, Y893G, S894D, S894G, R895M, N896M, Y897V, Y898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906N, I906S, I906T, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927G, W927P, D928A, D928E, D928H, D928L, D928Q, A929C, A929P, A929V, V930A, V930E, V930I, V930K, V930M, V930T, S931G, S931N, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937G, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973Q, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982Q, G982W, R984P, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001C, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, R1054C, R1054L, R1054N, L1055R, L1055T, Q1057A, Q1057E, Q1057P, Q1057R, N1058R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069G, D1069K, D1069R, D1069V, A1070P, A1070T, I1071M, I1071R, I1071W, K1072E, K1072K, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091I, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097F, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119N, I1119S, V1120N, V1120S, V1120T, M1121G, M1121K, M1121N, M1121P, M1121S, M1121V, M1121Y, Y1122A, Y1122C, Y1122I, Y1122K, Y1122V, Y1123E, F1123H, F1123R, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, N1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165D, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, Y1172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177Q, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200V, A1200W, L1202A, L1202C, T1203E, T1203K, E1204G, E1204S, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216A, T1216L, T1216P, T1216Q, T1216R, N1217A, N1217D, N1217E, N1217F, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1221L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239V, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257K, G1257L, G1257Q, G1257R, G1257W, N1258C, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288R, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

In preferred embodiments, the lactase variants of the present invention comprise one or more of the substitutions listed in any one of embodiments 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144 or 146 of the "PREFERRED EMBODIMENTS" section right before the "EXAMPLES" section of the present application.

In a particularly preferred embodiment, the lactase variants of the invention have an amino acid sequence which is at least 99.4% identical to SEQ ID NO: 1, have a galactose inhibition improvement factor (GI-IF) of at least 1.4 or at most 0.6 compared to the lactase of SEQ ID NO: 1 and comprise one or more of the following substitutions, wherein each position corresponds to a position in SEQ ID NO: 1: E2V, D3I, D3S, D3V, S7P, M13R, S15C, S15I, S15K, S15Y, T16C, V20P, Y21C, Y21R, Y21T, S23L, S23M, A24F, A24T, D26C, 527A, K28C, Q29L, Q29M, Q29R, R31E, R31V, T32S, D34S, F35E, K40F, K40I, M42E, L43T, D45P, V47K, V47R, A49D, A49H, A49R, A49T, D51I, D51K, D51P, A53S, D55H, D55M, S57C, S57E, S57G, A58T, W59P, V62N, L64E, H66Y, K73D, S75G, S75L, S75R, Q76G, S77E, S77F, S77H, S77K, N78C, E79H, E79S, E79T, E81A, E81Q, L85F, L85S, L85V, L85W, P86Q, G87D, G88F, G88Q, G90T, W91Y, Y92H, Y92M, Y92S, Y92V, R93A, R93D, R93F, R93H, R93L, R93N, R93T, R93V, R93Y, K94S, S95C, S95G, S95I, F96A, F96C, F96I, F96S, F96V, T97F, 198H, R100T, D101A, D101P, L102P, I109M, N110T, F111A, F111L, D112T, V114R, Y115E, V120A, W121R, W121V, G124E, H130A, H130T, Y132E, P136R, F137L, K146A, G149M, E150L, I153A, V157P, E158G, E158H, N159T, L161K, L161S, L161W, P162N, P162T, P162W, R165H, W166S, Y167A, S170Q, 1172P, R174E, V176E, V176K, T177K, L178I, L178Q, T179C, V180G, H185G, H185L, N188V, N189E, G190C, S197C, D217L, D217M, T218G, A220G, A220V, A222R, N223S, Q228R, K233P, K236M, T237D, A239G, A239T, G242Y, A247P, A247R, S248E, K249G, K249Y, 1251Y, A252F, A252W, A252Y, G254I, G254R, A255K, S256Y, S261R, T262D, T264M, P268R, S272W, L278V, Y279W, L286F, V291D, V291P, L292V, D293C, D296F, E298I, E298R, F301C, W303A, T304P, G305N, G305P, G305W, T309D, F312H, K320V, K320W, S325G, M326E, M326G, M326T, M326Y, H328C, H328M, H328T, A337G, A337L, R340A, A341M, I342K, E343N, Q345G, Q345K, Q345S, I348D, Q350G, T359E, T360V, N362S, N362T, P363I, P363L, P363M, A364I, A364M, A364P, A365C, L368E, L368Q, L368S, 1369G, I369K, I369W, D370L, N373G, N373L, G376A, G376S, V377M, V379A, V380P, E381A, E381T, M386G, M386N, M386S, W387L, N388L, N388R, R389A, R389E, R389Q, R389S, R389T, S390C, S390D, S390G, S390P, S390Q, S390T, K391E, N392D, G393R, G393V, N394L, T395C, T395H, T395N, T395S, T395W, E396K, E396L, E396V, E396W, Y398N, G399S, K400A, K400C, K400N, K400P, K400S, K400V, W401F, W401K, F402W, F402Y, G403A, G403K, G403V, Q404F, Q404H, Q404L, Q404M, Q404P, Q404V, A405C, A405E, A405H, A405R, I406D, I406N, G408W, D409N, A411E, L413P, G414A, G414R, D416I, D416Y, K417F, D418P, D418R, E419M, E419R, T420K, T420R, K423D, F424C, F424L, L426M, T427D, T427Q, T427S, T429D, N431M, D433P, D433W, R434N, R434V, N435L, A436L, V439C, V439G, V439K, V439T, W442E, W442G, W442R, S443C, S443Y, L444V, G445A, G445C, G445V, M448C, M448L, M448S, M449D, M449T, M449W, M449Y, E450F, E450S, E450T, E450V, E450W, G451C, G451F, G451L, G451P, G451V, G451W, I452K, G454L, S455P, S455R, V456D, V456E, V456F, V456K, S457T, S457V, G458A, G458P, F459R, F459S, K465Y, L466P, L466V, A468D, A472G, A472Y, S475E, R477L, M479G, M479R, K485E, K487F, K487N, A488N, N491W, S493M, S493Q, T495W, D498C, N499R, N499T, N499Y, L500A, G504H, G505D, G505S, V506C, V506E, V506R, V507L, V507R, G508C, G508E, T509K, T509M, N510A, N510F, N510I, Y511A, S512F, S512T, S512Y, D513L, D513P, D513R, G514F, A515E, N516C, Y517G, D518Y, K519C, K519I, I520G, I520H, I520S, R521N, R521V, T522N, H524R, H524V, P525T, S526G, W527N, W527R, W527S, A528E, G531T, A537P, S540E, R546L, R546P, R546S, T547A, T547S, T548F, T548K, T548P, G549P, G549W, G550S, A551Q, S553N, S554N, D555S, K556W, L558P, T559Y, S564C, S564F, A565E, A565I, A565R, G567Q, G567V, A570K, A570M, A572S, S574W, W576Y, Y577L, V579G, R582L, D583W, V585I, A586K, T588D, T592C, T592L, T592S, F594L, D595Q, P600A, P600E, P600G, P600S, G607Q, S608V, G609N, G609R, A610M, V611K, W614A, N619L, S620G, V625M, V625Y, F630G, T634V, Y635R, Q639R, D644C, H650R, W655R, N656V, A661E, P669T, V670C, Y673S, A676P, K680I, T684V, G687P, S688L, R692H, I694L, I694W, G695C, G695L, G695W, K697R, S698E, T700C, K701A, K701G, K701M, A705W, T709M, Y710T, V712M, E714K, A716R, D717G, D717S, K718A, D719T, D719V, T721N, T721S, T721W, H723G, M726D, L728S, N731S, W734G, W734V, A735Q, A735S, I739K, S740D, A741I, D745F, L750S, P752A, P752C, P752Y, G754P, T756N, T756S, E757A, A760N, A769F, A769I, A769N, A769V, A769Y, K770H, K772A, K772C, K772P, A773C, A773H, A773V, D774A, A775L, A775W, D776I, D776L, D776S, R777D, R777E, R777G, R777H, R777P, R777S, T781A, T781G, T781P, T781Y, A782Q, D783C, D783E, D783R, G784L, G784S, K785S, K785W, D786V, L787P, L787T, Y789V, V792G, D793H, V794T, T795P, N798I, G799K, G799L, G799M, G799Q, H800A, H800L, P803S, A806Q, R808C, T810P, V813T, K814H, G815A, A816C, A816F, K818F, K818L, K818W, G821E, G821I, V822D, V822E, S826L, H830R, D831I, D831P, D831V, S832R, A835D, A835H, A835W, D836E, D836H, D836S, D836Y, R838G, K839D, A840G, K844G, Q850C, Q850G, E854C, I858D, I858Q, I858Y, K863F, K863N, D865A, D865G, L867W, S870R, V872C, 1874G, S883L, T887F, T887G, V888A, Y892P, Y892R, Y893E, T901V, T901Y, G902R, G902S, G902W, N903D, K904M, K904V, P905R, P905Y, I906W, P908I, D910W, E912T, R914A, R914F, R914K, R914Y, Y915A, Y915C, Y915M, Y915V, S916G, D917C, D917F, D917S, G918H, T919Q, D921V, R922A, Q923V, W927G, Q934S, I935P, A936V, K937I, K937P, A938C, S940T, S942K, S942V, V943A, V943H, V943R, A944P, T946P, T946V, V947G, A948C, Q950D, V956Q, E961D, E961F, E961S, I962C, I962N, L965C, L965G, L965M, L965P, L965Y, L966A, Y968G, Y968V, S969C, S969I, S969M, P973C, T976K, T976P, P977T, A978M, V979R, L980H, L980N, P981M, P985L, P985W, A986I, V987K, D990W, S995L, N997K, D1001L, W1002A, W1002D, W1002H, W1002N, W1002P, T1003Y, K1004H, A1006S, D1007P, V1018K, A1022H, V1024G, G1026R, K1030W, I1035D, V1048M, V1048Q, G1050S, N1051E, A1052K, L1053A, Q1057E, Q1057R, D1066W, L1068C, I1071W, K1072G, K1072Q, T1082F, G1083E, G1084V, G1085S, P1088E, S1089Q, W1091A, W1091V, T1092W, N1093P, N1093Q, W1094D, W1094E, S1097W, A1099V, N1102E, N1102H, A1104R, T1107S, E1109D, E1109L, E1109W, A1111G, E1113P, Q1114S, Q1114V, Q1115A, Q1115K, L1116K, L1116W, G1117I, G1117S, G1117T, G1117V, G1117W, I1119N, R1125V, R1125W, S1127Q, N1128A, A1129E, V1130A, V1130G, V1130R, P1133D, P1133R, G1136E, K1137R, K1137S, Q1141P, A1144P, A1144S, D1145E, D1145R, D1145T, T1150K, D1151R, D1151W, V1167R, A1175N, G1178M, A1179W, T1180A, T1180G, T1180I, T1180M, T1180Q, T1180Y, V1184E, V1184L, V1184P, V1186S, N1188W, C1199T, K1208W, T1209E, T1209K, A1210D, A1210G, A1210R, A1210T, A1210W, T1211G, T1211P, T1211R, F1214A, F1214K, F1214V, V1215D, T1216L, T1216Q, N1217A, T1218W, S1219A, S1219F, L1222F, L1222V, S1223V, S1224P, S1224W, L1225E, L1225K, T1226P, N1228F, G1229V, T1230K, T1230W, K1231F, S1233P, A1238E, A1238R, N1243T, T1244Q, A1246M, D1250I, D1250S, D1250W, A1259K, P1265W, N1269A, N1269K, I1274F, I1274R, T1275W, S1277W, E1278Q, D1279R, D1279W, H1280E, V1281I, V1281W, K1284G, F1286E, T1287C, T1287W, I1288A, I1288D, I1288G, I1288K, E1302R, E1302S or D1304V. More preferably, the lactase variants of this embodiment, having an amino acid sequence which is at least 99.4% identical to SEQ ID NO: 1 and having a galactose inhibition improvement factor (GI-IF) of at least 1.4 or at most 0.6 compared to the lactase of SEQ ID NO: 1, comprise one or more of the substitutions listed in any one of embodiments 108, 116, 124, 132 or 140 of the "PREFERRED EMBODIMENTS" section right before the "EXAMPLES" section of the present application.

In another particularly preferred embodiment, the lactase variants of the invention have an amino acid sequence which is at least 99.4% identical to SEQ ID NO: 1, have a galactose inhibition improvement factor (GI-IF) of at least 1.3 compared to the lactase of SEQ ID NO: 1 and comprise one or more of the following substitutions, wherein each position corresponds to a position in SEQ ID NO: 1: V1H, V1L, E2D, E2V, D3I, D3V, S7N, S7P, M13C, M13R, S14V, S15C, S15I, S15K, S15T, S15V, T16C, P17I, V20C, V20M, V20P, Y21C, Y21P, Y21R, Y21T, S22W, A24F, A24L, A24T, A24W, V25Q, D26C, 527A, S27C, S27H, K28C, Q29L, Q29M, Q29R, R31E, R31V, T32S, F35C, W39G, K40C, K40F, K40I, F41A, M42T, L43S, D45P, V47K, V47R, A49D, A49H, A49T, D51I, D51K, D55C, D55H, D55M, D55P, S57C, S57E, S57G, A58Q, A58T, W59I, W59N, W59P, Q60R, Q60S, V62N, V62T, V62W, L64E, H66R, K73D, S75G, S75L, S75R, S75V, Q76G, Q76I, S77D, S77E, S77G, S77H, S77K, S77R, N78C, E79H, E79S, E79T, A83T, L85A, L85F, L85N, L85S, L85V, L85W, P86Q, G87D, G88F, G90T, W91P, W91Y, Y92H, Y92I, Y92M, Y92S, Y92T, Y92V, R93A, R93D, R93F, R93H, R93I, R93L, R93N, R93T, R93V, R93Y, K94A, K94S, K94T, S95C, S95D, S95G, S95I, F96A, F96C, F96I, F96K, F96M, F96P, F96V, T97F, I98C, I98H, R100T, D101A, D101P, L102P, R106W, I107S, A108E, I109M, N110A, N110S, N110T, N110W, F111A, F111L, V114R, Y115E, M116C, A118P, V120A, V120K, W121R, W121V, H130A, H130T, Y132E, F137L, T142S, G149M, E150L, V154K, V154L, V157P, V157S, E158H, N159T, L161K, L161M, L161S, L161W, P162N, P162T, P162W, S164A, R165H, W166S, Y167A, S170Q, I172K, I172P, Y173H, R174E, V176E, V176K, T177K, L178I, L178Q, T179C, T179I, T179N, V180D, V180G, T181A, V184R, H185G, H185L, G187D, N188V, G190F, K194I, S197C, A199P, Q201E, N202Q, N202S, N202W, D217L, D217M, T218G, A220G, A222R, N223S, Q228R, K236M, T237D, G242K, I251Y, A252W, A252Y, S261H, A266D, S267V, P268R, S272T, S272W, V281Q, V291P, L292V, D293C, D293W, Y295F, D296F, D296K, E298I, E298R, F301C, W303A, W303C, W303D, T304D, T304K, T304P, G305N, G305P, T309C, T309D, T309E, 5310H, S310L, 5310N, F312H, L314A, L314V, N3155, K318N, K320V, K320W, L321M, K322I, V324T, S325G, M326T, H328C, H328F, H328G, H328M, H328T, G331V, A335G, A335L, A337G, A337L, R340A, R340L, A341M, I342G, E343N, E343Y, R344G, Q345S, V346A, E347A, I348D, I348M, Q350G, M352T, G353K, I357T, T359E, T359L, T360V, N362S, N362T, P363A, P363I, P363L, P363M, A364I, A364M, A364P, A365C, A365I, A365P, A365V, K366L, K366M, K366S, L368A, L368Q, L368S, I369E, I369G, I369K, I369V, I369W, D370L, V371F, V371Q, C372P, N373G, N373L, G376A, G376S, V377M, V377T, V379A, V379N, V380P, E381A, E381G, E381Q, E381T, V383A, M386G, M386N, M386S, W387H, N388L, R389A, R389E, R389Q, R389S, R389T, S390C, S390D, S390P, S390T, G393E, G393R, G393V, T395C, E396K, E396L, E396V, E396W, Y398M, G399S, K400A, K400C, K400N, K400V, W401F, W401K, F402W, F402Y, G403A, G403K, G403Q, G403V, Q404F, Q404L, Q404M, Q404P, Q404V, A405C, A405E, A405K, A405R, I406D, I406N, A407C, A407G, A407Q, N410Y, A411E, G414M, G414N, K417F, K417R, A422P, T427D, T427F, T427Q, T427S, T429D, N431M, D433G, D433I, D433P, D433Q, D433W, R434N, R434V, N435E, N435L, A436L, V439C, V439K, W442E, W442G, S443C, S443G, S443Q, L444E, L444V, N446D, M448C, M448L, M449D, M449T, M449W, M449Y, E450F, E450S, E450T, E450V, E450W, G451C, G451F, G451L, G451P, G451V, G451W, I452K, I452S, I452V, G454L, S455P, S455R, V456D, V456E, V456F, V456K, S457H, S457T, S457V, G458A, G458P, G458S, F459R, A461M, T462E, T462L, K465V, K465Y, L466P, A468D, K471F, A472G, A472Y, S475E, R477L, M479G, K485E, K485R, K487F, K487S, K487W, S493G, S493L, S493Q, N494R, G497D, N499T, G505D, G505R, G505S, V506C, V506E, V506R, V507R, G508C, G508E, T509A, T509K, T509M, N510A, N510F, N510I, Y511A, S512F, S512Q, S512T, S512V, S512Y, D513P, D513R, A515E, N516C, N516E, N516Q, N516V, Y517G, D518Y, K519C, K519I, I520C, I520G, I520H, I520M, I520S, I520T, R521V, H524R, H524V, S526G, W527A, W527H, W527N, W527R, W527S, A528E, A537M, A537P, S540E, G549D, G549P, G549W, L558E, L558P, T559Y, S564C, S564F, S564W, A565D, A565E, A565I, A565L, A565R, A565T, G567C, G567V, A570G, A575D, R582L, D583W, W591F, T592L, G598N, P600A, P600E, P600G, P600S, G607Q, W614A, N619I, N619L, V625M, V625Y, T627K, T627Q, A628D, F630C, F630Y, P631D, T634V, Q639R, W655R, E657R, A661E, A661K, A661Q, N667L, N667R, P669T, Y673S, T674M, A676P, V679S, K680I, G687P, S688K, S688L, T689W, E690D, R692G, R692H, I694L, I694W, G695C, G695L, G695W, K697R, S698E, S698M, K701A, K701G, K701M, K701S, A705W, Y708F, Y710T, V712M, V712Q, E714C, A716R, D717G, D717S, K718A, K718T, D719E, D719I, D719V, T721H, T721L, T721N, T721S, T721V, T721W, H723G, M726D, Y727L, L728S, N731E, V732R, W734G, A735Q, A735S, T738S, I739K, S740D, A741I, Y744R, D745N, L750S, P752C, P752Y, T756N, E757A, A769F, A769I, A769N, A769V, A769Y, K770H, L771A, K772A, K772C, K772P, A773C, A773M, A773R, D774A, D776V, R777H, R777S, K778N, T781A, T781F, T781G, T781P, T781Y, A782Q, D783A, K785S, K785W, K785Y, D786V, Y789V, 1790R, N798I, G799K, G799L, V802Y, P803S, A806I, A806Q, R808F, T810P, T810Q, V813W, K818F, K818L, K818W, K818Y, L819F, G821I, V822D, V822E, S826G, D829S, D831P, S832R, A835D, A835H, A835K, D836C, D836E, D836S, D836V, D836Y, R838N, K839A, K839D, A840G, A840P, A840V, E854C, I858D, T861W, D865A, D865G, G866H, L867W, S870E, V872C, K873G, K873Y, I874G, S883L, K886V, K886W, T887G, V888A, Y892P, Y893E, Y897V, K900E, T901Q, T901R, T901Y, G902F, G902R, G902S, G902W, N903D, K904M, K904N, K904S, K904V, P905C, P905R, P905Y, I906W, L907F, P908I, P908L, D910W, E912T, R914A, R914F, R914I, R914K, R914V, R914Y, Y915A, Y915C, Y915G, Y915M, Y915Q, Y915V, S916G, D917C, D917F, D917S, G918E, G918H, G918T, T919D, T919Q, D921V, R922A, Q923V, T926R, W927P, A929P, D933R, Q934S, I935A, I935C, I935E, I935P, I935W, A936I, A936Q, K937G, K937I, K937P, K937Q, A938C, G939D, S940C, F941C, S942K, S942V, V943A, T946P, V947G, V947R, V947T, A948W, K951S, S953M, R955C, R955W, V956D, V956Q, E961D, E961F, E961S, I962C, I962K, I962N, L965C, L965G, L965K, L965M, L965P, L965Y, L966A, N967M, Y968G, Y968Q, Y968V, S969C, S969I, S969L, S969M, S969Q, A970I, S971V, P973C, P973W, V974T, T976K, T976P, P977C, P977T, A978F, A978M, L980H, L980N, P981M, P985L, P985W, A986I, A986L, V987A, V987F, V987K, D990W, G991Y, S995L, N997K, D1001L, W1002A, W1002D, W1002E, W1002H, W1002N, W1002P, W1002Q, T1003Y, P1005Y, A1006C, A1006S, D1007P, N1011T, T1012Q, G1014I, V1018K, A1022H, V1024G, V1024H, G1026V, K1030D, K1030W, I1035D, Q1041P, V1042N, V1048C, V1048G, V1048M, V1048Q, N1051E, N1051K, A1052K, L1053A, Q1057E, A1061G, D1062M, Q1064M, S1065A, D1066V, T1067M, L1068P, K1072S, G1074L, T1082F, G1083E, G1083F, G1083L, G1084V, G1085S, P1088E, P1088R, S1089G, S1089Q, W1091Y, N1093A, N1093P, N1093Q, W1094D, W1094E, K1098D, A1099V, H1101V, N1102H, T1103E, E1109A, E1109D, E1109L, E1109W, A1111G, E1113P, E1113V, Q1114E, Q1114R, Q1114S, Q1114T, Q1114V, Q1115A, Q1115K, L1116K, L1116W, G1117I, G1117R, G1117S, G1117T, G1117V, G1117W, I1119N, M1121G, R1125V, R1125W, S1127I, S1127Q, N1128A, A1129E, V1130A, V1130R, P1133D, P1133R, A1135L, A1135W, G1136P, K1137R, K1137S, I1140P, Q1141K, I1142Y, A1144N, A1144P, A1144S, A1144V, A1144W, D1145E, D1145R, D1145T, N1148P, W1149C, W1149V, T1150K, D1151W, L1152W, A1153G, E1162A, V1167R, G1178M, G1178T, A1179L, A1179W, T1180A, T1180G, T1180I, T1180M, T1180Q, T1180Y, V1184E, V1184L, V1184P, V1184Q, V1184Y, V1186S, N1188W, D1190T, T1191L, V1197A, E1204G, K1208W, T1209E, T1209K, A1210D, A1210G, A1210K, A1210L, A1210R, A1210T, A1210W, T1211G, T1211K, T1211P, T1211R, T1211S, F1214A, F1214K, F1214S, F1214V, V1215D, V1215L, T1216L, T1216Q, N1217A, N1217S, N1217T, T1218C, T1218E, T1218S, T1218W, L1222A, L1222E, L1222F, L1222V, S1224P, S1224W, L1225E, L1225K, T1226P, G1229V, T1230K, T1230W, V1232R, S1235W, V1236A, V1236G, V1236P, A1238E, A1238R, G1255H, A1259K, T1262R, V1263T, P1265W, I1274F, I1274R, T1275W, S1277L, S1277T, S1277W, E1278Q, D1279R, D1279W, H1280E, V1281I, V1281W, K1284G, F1286E, F1286P, T1287C, T1287S, T1287W, I1288A, I1288D, I1288G, I1288K, E1295K, F1296A, E1302R, E1302S or D1304V. More preferably, the lactase variants of this embodiment, having an amino acid sequence which is at least 99.4% identical to SEQ ID NO: 1 and having a galactose inhibition improvement factor (GI-IF) of at least 1.3 compared to the lactase of SEQ ID NO: 1, comprise one or more of the substitutions listed in any one of embodiments 104, 112, 120, 128, 136 or 144 of the "PREFERRED EMBODIMENTS" section right before the "EXAMPLES" section of the present application.

In one aspect, a variant of the present invention comprises a substitution at position V1 to A, C, D, E, F, G, H, I, K, L, M, N, P, Q, R, S, T, W or Y, preferably to D, F, H, K, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E2 to A, C, D, F, G, H, I, K, L, M, N, P, Q, R, S, T, V, W or Y, preferably to D, G, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D3 to A, C, E, F, G, H, I, K, L, M, N, P, Q, R, S, T, V, W or Y, preferably to A, H, I, N, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A4 to C, D, E, F, G, H, I, K, L, M, N, P, Q, R, S, T, V, W or Y, preferably to C, G, H, I, L, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T5 to A, C, D, E, F, G, H, I, K, L, M, N, P, Q, R, S, V, W or Y, preferably to A, D, F, K, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R6 to A, C, D, E, F, G, H, I, K, L, M, N, P, Q, S, T, V, W or Y, preferably to A, D, F, G, H, L, M, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S7 to A, C, D, E, F, G, H, I, K, L, M, N, P, Q, R, T, V, W or Y, preferably to A, D, I, L, N, P, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S9 to A, C, D, E, F, G, H, I, K, L, M, N, P, Q, R, T, V, W or Y, preferably to G, H, P, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T10 to A, C, D, E, F, G, H, I, K, L, M, N, P, Q, R, S, V, W or Y, preferably to G, K, L, P, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T11 to A, C, D, E, F, G, H, I, K, L, M, N, P, Q, R, S, V, W or Y, preferably to L or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q12 to A, C, D, E, F, G, H, I, K, L, M, N, P, R, S, T, V, W or Y, preferably to L, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M13 to A, C, D, E, F, G, H, I, K, L, N, P, Q, R, S, T, V, W or Y, preferably to C, D, E, F, H, K, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S14 to A, C, D, E, F, G, H, I, K, L, M, N, P, Q, R, T, V, W or Y, preferably to A, G, H, L, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S15 to A, C, D, E, F, G, H, I, K, L, M, N, P, Q, R, T, V, W or Y, preferably to C, F, I, K, L, P, R, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T16 to A, C, D, E, F, G, H, I, K, L, M, N, P, Q, R, S, V, W or Y, preferably to A, C, I, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P17 to A, C, D, E, F, G, H, I, K, L, M, N, Q, R, S, T, V, W or Y, preferably to A, C, D, E, I, L, N, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V19 to A, C, D, E, F, G, H, I, K, L, M, N, P, Q, R, S, T, W or Y, preferably to A, F, G, I, K, L, N, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V20 to A, C, D, E, F, G, H, I, K, L, M, N, P, Q, R, S, T, W or Y, preferably to C, F, G, I, K, L, M, N, P, Q, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y21 to A, C, D, E, F, G, H, I, K, L, M, N, P, Q, R, S, T, V or W, preferably to A, C, D, F, G, H, M, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S22 to A, C, D, E, F, G, H, I, K, L, M, N, P, Q, R, T, V, W or Y, preferably to A, E, F, G, L, M, N, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S23 to A, C, D, E, F, G, H, I, K, L, M, N, P, Q, R, T, V, W or Y, preferably to A, C, D, L, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A24 to C, D, E, F, G, H, I, K, L, M, N, P, Q, R, S, T, V, W or Y, preferably to F, G, L, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V25 to A, C, D, E, F, G, H, I, K, L, M, N, P, Q, R, S, T, W or Y, preferably to D, E, F, G, H, K, L, M, Q, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D26 to A, C, E, F, G, H, I, K, L, M, N, P, Q, R, S, T, V, W or Y, preferably to C, I, L, M, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S27 to A, C, D, E, F, G, H, I, K, L, M, N, P, Q, R, T, V, W or Y, preferably to A, C, F, G, H, P or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K28 to A, C, D, E, F, G, H, I, L, M, N, P, Q, R, S, T, V, W or Y, preferably to C, G, I, L, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q29 to A, C, D, E, F, G, H, I, K, L, M, N, P, R, S, T, V, W or Y, preferably to D, F, G, L, M, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N30 to A, C, D, E, F, G, H, I, K, L, M, P, Q, R, S, T, V, W or Y, preferably to A, G, H, M, P, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R31 to A, C, D, E, F, G, H, I, K, L, M, N, P, Q, S, T, V, W or Y, preferably to E, G, I, M or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T32 to A, C, D, E, F, G, H, I, K, L, M, N, P, Q, R, S, V, W or Y, preferably to M, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S33 to A, C, D, E, F, G, H, I, K, L, M, N, P, Q, R, T, V, W or Y, preferably to C, E, H, K, N, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D34 to A, C, E, F, G, H, I, K, L, M, N, P, Q, R, S, T, V, W or Y, preferably to C, E, F, G, H, L, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F35 to A, C, D, E, G, H, I, K, L, M, N, P, Q, R, S, T, V, W or Y, preferably to A, C, E, G, K, N, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D36 to A, C, E, F, G, H, I, K, L, M, N, P, Q, R, S, T, V, W or Y, preferably to H or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A37 to C, D, E, F, G, H, I, K, L, M, N, P, Q, R, S, T, V, W or Y, preferably to N or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N38 to A, C, D, E, F, G, H, I, K, L, M, P, Q, R, S, T, V, W or Y, preferably to C, G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W39 to A, C, D, E, F, G, H, I, K, L, M, N, P, Q, R, S, T, V or Y, preferably to G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K40 to A, C, D, E, F, G, H, I, L, M, N, P, Q, R, S, T, V, W or Y, preferably to C, D, F, G, I, M, N, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F41 to A, C, D, E, G, H, I, K, L, M, N, P, Q, R, S, T, V, W or Y, preferably to A, C, G, I, Q, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M42 to A, C, D, E, F, G, H, I, K, L, N, P, Q, R, S, T, V, W or Y, preferably to E, N or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L43 to A, C, D, E, F, G, H, I, K, M, N, P, Q, R, S, T, V, W or Y, preferably to A, C, G, I, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S44 to A, C, D, E, F, G, H, I, K, L, M, N, P, Q, R, T, V, W or Y, preferably to C, M, N or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D45 to A, C, E, F, G, H, I, K, L, M, N, P, Q, R, S, T, V, W or Y, preferably to A, L, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V47 to A, C, D, E, F, G, H, I, K, L, M, N, P, Q, R, S, T, W or Y, preferably to K or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q48 to A, C, D, E, F, G, H, I, K, L, M, N, P, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A49 to C, D, E, F, G, H, I, K, L, M, N, P, Q, R, S, T, V, W or Y, preferably to C, D, H, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D51 to A, C, E, F, G, H, I, K, L, M, N, P, Q, R, S, T, V, W or Y, preferably to G, I, K, M, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A53 to C, D, E, F, G, H, I, K, L, M, N, P, Q, R, S, T, V, W or Y, preferably to C, G, L, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F54 to A, C, D, E, G, H, I, K, L, M, N, P, Q, R, S, T, V, W or Y, preferably to M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D55 to A, C, E, F, G, H, I, K, L, M, N, P, Q, R, S, T, V, W or Y, preferably to C, F, G, H, M, N, P, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S57 to A, C, D, E, F, G, H, I, K, L, M, N, P, Q, R, T, V, W or Y, preferably to A, C, E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A58 to C, D, E, F, G, H, I, K, L, M, N, P, Q, R, S, T, V, W or Y, preferably to D, G, I, M, N, Q, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W59 to A, C, D, E, F, G, H, I, K, L, M, N, P, Q, R, S, T, V or Y, preferably to D, I, K, L, N, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q60 to A, C, D, E, F, G, H, I, K, L, M, N, P, R, S, T, V, W or Y, preferably to A, C, E, F, G, K, L, M, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q61 to A, C, D, E, F, G, H, I, K, L, M, N, P, R, S, T, V, W or Y, preferably to K, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V62 to A, C, D, E, F, G, H, I, K, L, M, N, P, Q, R, S, T, W or Y, preferably to G, N, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D63 to A, C, E, F, G, H, I, K, L, M, N, P, Q, R, S, T, V, W or Y, preferably to G, L, P, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L64 to A, C, D, E, F, G, H, I, K, M, N, P, Q, R, S, T, V, W or Y, preferably to E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H66 to A, C, D, E, F, G, I, K, L, M, N, P, Q, R, S, T, V, W or Y, preferably to C, L, R, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D67 to A, C, E, F, G, H, I, K, L, M, N, P, Q, R, S, T, V, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y68 to A, C, D, E, F, G, H, I, K, L, M, N, P, Q, R, S, T, V or W, preferably to P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I70 to A, C, D, E, F, G, H, K, L, M, N, P, Q, R, S, T, V, W or Y, preferably to A, H, K, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T71 to A, C, D, E, F, G, H, I, K, L, M, N, P, Q, R, S, V, W or Y, preferably to C, E, G, H, K, L, N, P, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K73 to A, C, D, E, F, G, H, I, L, M, N, P, Q, R, S, T, V, W or Y, preferably to A, D, F, G, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y74 to A, C, D, E, F, G, H, I, K, L, M, N, P, Q, R, S, T, V or W, preferably to G, K, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S75 to A, C, D, E, F, G, H, I, K, L, M, N, P, Q, R, T, V, W or Y, preferably to G, L, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q76 to A, C, D, E, F, G, H, I, K, L, M, N, P, R, S, T, V, W or Y, preferably to G, I, K, M, P, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S77 to A, C, D, E, F, G, H, I, K, L, M, N, P, Q, R, T, V, W or Y, preferably to C, D, E, F, G, H, I, K, L, M, R, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N78 to A, C, D, E, F, G, H, I, K, L, M, P, Q, R, S, T, V, W or Y, preferably to C, E, F, K, Q, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E79 to A, C, D, F, G, H, I, K, L, M, N, P, Q, R, S, T, V, W or Y, preferably to H, Q, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A80 to C, D, E, F, G, H, I, K, L, M, N, P, Q, R, S, T, V, W or Y, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E81 to A, C, D, F, G, H, I, K, L, M, N, P, Q, R, S, T, V, W or Y, preferably to A or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A83 to C, D, E, F, G, H, I, K, L, M, N, P, Q, R, S, T, V, W or Y, preferably to E or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L85 to A, C, D, E, F, G, H, I, K, M, N, P, Q, R, S, T, V, W or Y, preferably to A, C, D, F, M, N, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P86 to A, C, D, E, F, G, H, I, K, L, M, N, Q, R, S, T, V, W or Y, preferably to E, G, H, N, Q, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G87 to A, C, D, E, F, H, I, K, L, M, N, P, Q, R, S, T, V, W or Y, preferably to A, D, E, N or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G88 to A, C, D, E, F, H, I, K, L, M, N, P, Q, R, S, T, V, W or Y, preferably to A, F, I, M, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T89 to A, C, D, E, F, G, H, I, K, L, M, N, P, Q, R, S, V, W or Y, preferably to C, G, H, K, L, M, N, P, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G90 to A, C, D, E, F, H, I, K, L, M, N, P, Q, R, S, T, V, W or Y, preferably to A, C, D, L, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W91 to A, C, D, E, F, G, H, I, K, L, M, N, P, Q, R, S, T, V or Y, preferably to E, L, P, Q, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y92 to A, C, D, E, F, G, H, I, K, L, M, N, P, Q, R, S, T, V or W, preferably to F, H, I, M, N, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R93 to A, C, D, E, F, G, H, I, K, L, M, N, P, Q, S, T, V, W or Y, preferably to A, D, F, H, I, L, N, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K94 to A, C, D, E, F, G, H, I, L, M, N, P, Q, R, S, T, V, W or Y, preferably to A, C, G, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S95 to A, C, D, E, F, G, H, I, K, L, M, N, P, Q, R, T, V, W or Y, preferably to A, C, D, E, G, I, L, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F96 to A, C, D, E, G, H, I, K, L, M, N, P, Q, R, S, T, V, W or Y, preferably to A, C, I, K, L, M, P, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T97 to A, C, D, E, F, G, H, I, K, L, M, N, P, Q, R, S, V, W or Y, preferably to F, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I98 to A, C, D, E, F, G, H, K, L, M, N, P, Q, R, S, T, V, W or Y, preferably to C, H, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R100 to A, C, D, E, F, G, H, I, K, L, M, N, P, Q, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D101 to A, C, E, F, G, H, I, K, L, M, N, P, Q, R, S, T, V, W or Y, preferably to A, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L102 to A, C, D, E, F, G, H, I, K, M, N, P, Q, R, S, T, V, W or Y, preferably to A, G, M, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G104 to A, C, D, E, F, H, I, K, L, M, N, P, Q, R, S, T, V, W or Y, preferably to C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K105 to A, C, D, E, F, G, H, I, L, M, N, P, Q, R, S, T, V, W or Y, preferably to D, Q, R, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R106 to A, C, D, E, F, G, H, I, K, L, M, N, P, Q, S, T, V, W or Y, preferably to K, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I107 to A, C, D, E, F, G, H, K, L, M, N, P, Q, R, S, T, V, W or Y, preferably to A, F, G, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A108 to C, D, E, F, G, H, I, K, L, M, N, P, Q, R, S, T, V, W or Y, preferably to E, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I109 to A, C, D, E, F, G, H, K, L, M, N, P, Q, R, S, T, V, W or Y, preferably to M or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N110 to A, C, D, E, F, G, H, I, K, L, M, P, Q, R, S, T, V, W or Y, preferably to A, F, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F111 to A, C, D, E, G, H, I, K, L, M, N, P, Q, R, S, T, V, W or Y, preferably to A, C, L, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D112 to A, C, E, F, G, H, I, K, L, M, N, P, Q, R, S, T, V, W or Y, preferably to A, F, G or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G113 to A, C, D, E, F, H, I, K, L, M, N, P, Q, R, S, T, V, W or Y, preferably to A or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V114 to A, C, D, E, F, G, H, I, K, L, M, N, P, Q, R, S, T, W or Y, preferably to F, G, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y115 to A, C, D, E, F, G, H, I, K, L, M, N, P, Q, R, S, T, V or W, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M116 to A, C, D, E, F, G, H, I, K, L, N, P, Q, R, S, T, V, W or Y, preferably to A, C, D, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N117 to A, C, D, E, F, G, H, I, K, L, M, P, Q, R, S, T, V, W or Y, preferably to K, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A118 to C, D, E, F, G, H, I, K, L, M, N, P, Q, R, S, T, V, W or Y, preferably to K, P or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T119 to A, C, D, E, F, G, H, I, K, L, M, N, P, Q, R, S, V, W or Y, preferably to A, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V120 to A, C, D, E, F, G, H, I, K, L, M, N, P, Q, R, S, T, W or Y, preferably to A or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W121 to A, C, D, E, F, G, H, I, K, L, M, N, P, Q, R, S, T, V or Y, preferably to C, D, R, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F122 to A, C, D, E, G, H, I, K, L, M, N, P, Q, R, S, T, V, W or Y, preferably to A, M, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N123 to A, C, D, E, F, G, H, I, K, L, M, P, Q, R, S, T, V, W or Y, preferably to P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G124 to A, C, D, E, F, H, I, K, L, M, N, P, Q, R, S, T, V, W or Y, preferably to E, M, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V125 to A, C, D, E, F, G, H, I, K, L, M, N, P, Q, R, S, T, W or Y, preferably to D, E or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K126 to A, C, D, E, F, G, H, I, L, M, N, P, Q, R, S, T, V, W or Y, preferably to E or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G128 to A, C, D, E, F, H, I, K, L, M, N, P, Q, R, S, T, V, W or Y, preferably to A or D, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T129 to A, C, D, E, F, G, H, I, K, L, M, N, P, Q, R, S, V, W or Y, preferably to E or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H130 to A, C, D, E, F, G, I, K, L, M, N, P, Q, R, S, T, V, W or Y, preferably to A, C, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P131 to A, C, D, E, F, G, H, I, K, L, M, N, Q, R, S, T, V, W or Y, preferably to K, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y132 to A, C, D, E, F, G, H, I, K, L, M, N, P, Q, R, S, T, V or W, preferably to C, E or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G133 to A, C, D, E, F, H, I, K, L, M, N, P, Q, R, S, T, V, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S135 to A, C, D, E, F, G, H, I, K, L, M, N, P, Q, R, T, V, W or Y, preferably to E, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P136 to A, C, D, E, F, G, H, I, K, L, M, N, Q, R, S, T, V, W or Y, preferably to R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F137 to A, C, D, E, G, H, I, K, L, M, N, P, Q, R, S, T, V, W or Y, preferably to A, C, D, G, L or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S138 to A, C, D, E, F, G, H, I, K, L, M, N, P, Q, R, T, V, W or Y, preferably to A, D, G, H, L, M, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F139 to A, C, D, E, G, H, I, K, L, M, N, P, Q, R, S, T, V, W or Y, preferably to A, E, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D140 to A, C, E, F, G, H, I, K, L, M, N, P, Q, R, S, T, V, W or Y, preferably to G, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L141 to A, C, D, E, F, G, H, I, K, M, N, P, Q, R, S, T, V, W or Y, preferably to G or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T142 to A, C, D, E, F, G, H, I, K, L, M, N, P, Q, R, S, V, W or Y, preferably to E, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K146 to A, C, D, E, F, G, H, I, L, M, N, P, Q, R, S, T, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G148 to A, C, D, E, F, H, I, K, L, M, N, P, Q, R, S, T, V, W or Y, preferably to H, K or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G149 to A, C, D, E, F, H, I, K, L, M, N, P, Q, R, S, T, V, W or Y, preferably to E, H, I, M, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E150 to A, C, D, F, G, H, I, K, L, M, N, P, Q, R, S, T, V, W or Y, preferably to A, C, G, L, N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N151 to A, C, D, E, F, G, H, I, K, L, M, P, Q, R, S, T, V, W or Y, preferably to L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I153 to A, C, D, E, F, G, H, K, L, M, N, P, Q, R, S, T, V, W or Y, preferably to A or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V154 to A, C, D, E, F, G, H, I, K, L, M, N, P, Q, R, S, T, W or Y, preferably to E, I, K, L, M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V155 to A, C, D, E, F, G, H, I, K, L, M, N, P, Q, R, S, T, W or Y, preferably to F, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V157 to A, C, D, E, F, G, H, I, K, L, M, N, P, Q, R, S, T, W or Y, preferably to A, G, L, P, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E158 to A, C, D, F, G, H, I, K, L, M, N, P, Q, R, S, T, V, W or Y, preferably to G, H, K, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N159 to A, C, D, E, F, G, H, I, K, L, M, P, Q, R, S, T, V, W or Y, preferably to D, H, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R160 to A, C, D, E, F, G, H, I, K, L, M, N, P, Q, S, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L161 to A, C, D, E, F, G, H, I, K, M, N, P, Q, R, S, T, V, W or Y, preferably to E, K, M, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P162 to A, C, D, E, F, G, H, I, K, L, M, N, Q, R, S, T, V, W or Y, preferably to F, G, N, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S164 to A, C, D, E, F, G, H, I, K, L, M, N, P, Q, R, T, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R165 to A, C, D, E, F, G, H, I, K, L, M, N, P, Q, S, T, V, W or Y, preferably to H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W166 to A, C, D, E, F, G, H, I, K, L, M, N, P, Q, R, S, T, V or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y167 to A, C, D, E, F, G, H, I, K, L, M, N, P, Q, R, S, T, V or W, preferably to A or C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S168 to A, C, D, E, F, G, H, I, K, L, M, N, P, Q, R, T, V, W or Y, preferably to C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G169 to A, C, D, E, F, H, I, K, L, M, N, P, Q, R, S, T, V, W or Y, preferably to A, C, D or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S170 to A, C, D, E, F, G, H, I, K, L, M, N, P, Q, R, T, V, W or Y, preferably to L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G171 to A, C, D, E, F, H, I, K, L, M, N, P, Q, R, S, T, V, W or Y, preferably to C, F or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I172 to A, C, D, E, F, G, H, K, L, M, N, P, Q, R, S, T, V, W or Y, preferably to G, K, P or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y173 to A, C, D, E, F, G, H, I, K, L, M, N, P, Q, R, S, T, V or W, preferably to A, H, M, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R174 to A, C, D, E, F, G, H, I, K, L, M, N, P, Q, S, T, V, W or Y, preferably to E or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D175 to A, C, E, F, G, H, I, K, L, M, N, P, Q, R, S, T, V, W or Y, preferably to E or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V176 to A, C, D, E, F, G, H, I, K, L, M, N, P, Q, R, S, T, W or Y, preferably to E, K or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T177 to A, C, D, E, F, G, H, I, K, L, M, N, P, Q, R, S, V, W or Y, preferably to A, C, E, K or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L178 to A, C, D, E, F, G, H, I, K, M, N, P, Q, R, S, T, V, W or Y, preferably to I, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T179 to A, C, D, E, F, G, H, I, K, L, M, N, P, Q, R, S, V, W or Y, preferably to A, C, D, H, I, K, L, N, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V180 to A, C, D, E, F, G, H, I, K, L, M, N, P, Q, R, S, T, W or Y, preferably to A, C, D, E, G or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T181 to A, C, D, E, F, G, H, I, K, L, M, N, P, Q, R, S, V, W or Y, preferably to A, D, F, K or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D182 to A, C, E, F, G, H, I, K, L, M, N, P, Q, R, S, T, V, W or Y, preferably to F, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G183 to A, C, D, E, F, H, I, K, L, M, N, P, Q, R, S, T, V, W or Y, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V184 to A, C, D, E, F, G, H, I, K, L, M, N, P, Q, R, S, T, W or Y, preferably to F, H, P, Q, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H185 to A, C, D, E, F, G, I, K, L, M, N, P, Q, R, S, T, V, W or Y, preferably to G, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V186 to A, C, D, E, F, G, H, I, K, L, M, N, P, Q, R, S, T, W or Y, preferably to A, E, G or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G187 to A, C, D, E, F, H, I, K, L, M, N, P, Q, R, S, T, V, W or Y, preferably to A, D or H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N188 to A, C, D, E, F, G, H, I, K, L, M, P, Q, R, S, T, V, W or Y, preferably to E, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N189 to A, C, D, E, F, G, H, I, K, L, M, P, Q, R, S, T, V, W or Y, preferably to A or E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G190 to A, C, D, E, F, H, I, K, L, M, N, P, Q, R, S, T, V, W or Y, preferably to C, F, H, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V191 to A, C, D, E, F, G, H, I, K, L, M, N, P, Q, R, S, T, W or Y, preferably to C, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I193 to A, C, D, E, F, G, H, K, L, M, N, P, Q, R, S, T, V, W or Y, preferably to N, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K194 to A, C, D, E, F, G, H, I, L, M, N, P, Q, R, S, T, V, W or Y, preferably to A, I, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T195 to A, C, D, E, F, G, H, I, K, L, M, N, P, Q, R, S, V, W or Y, preferably to A, E, M, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P196 to A, C, D, E, F, G, H, I, K, L, M, N, Q, R, S, T, V, W or Y, preferably to A, H, I, M, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S197 to A, C, D, E, F, G, H, I, K, L, M, N, P, Q, R, T, V, W or Y, preferably to A, C, E, K, L or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L198 to A, C, D, E, F, G, H, I, K, M, N, P, Q, R, S, T, V, W or Y, preferably to E, F, H, I, K, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A199 to C, D, E, F, G, H, I, K, L, M, N, P, Q, R, S, T, V, W or Y, preferably to E, F, K, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q201 to A, C, D, E, F, G, H, I, K, L, M, N, P, R, S, T, V, W or Y, preferably to C, E, I, K, M or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N202 to A, C, D, E, F, G, H, I, K, L, M, P, Q, R, S, T, V, W or Y, preferably to A, D, F, G, K, L, M, Q, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G203 to A, C, D, E, F, H, I, K, L, M, N, P, Q, R, S, T, V, W or Y, preferably to C, K, M, Q, R, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G204 to A, C, D, E, F, H, I, K, L, M, N, P, Q, R, S, T, V, W or Y, preferably to A, C, D, K, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N205 to A, C, D, E, F, G, H, I, K, L, M, P, Q, R, S, T, V, W or Y, preferably to E, G, H, L, P, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V206 to A, C, D, E, F, G, H, I, K, L, M, N, P, Q, R, S, T, W or Y, preferably to A, C, D, F, G, I, K, Q, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T207 to A, C, D, E, F, G, H, I, K, L, M, N, P, Q, R, S, V, W or Y, preferably to A, C, G, I, K, L, M, N, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M208 to A, C, D, E, F, G, H, I, K, L, N, P, Q, R, S, T, V, W or Y, preferably to A, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N209 to A, C, D, E, F, G, H, I, K, L, M, P, Q, R, S, T, V, W or Y, preferably to C, D, G, K, L, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L210 to A, C, D, E, F, G, H, I, K, M, N, P, Q, R, S, T, V, W or Y, preferably to A, C, F, G, H, I, Q, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T211 to A, C, D, E, F, G, H, I, K, L, M, N, P, Q, R, S, V, W or Y, preferably to A, D, E, F, K, N, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T212 to A, C, D, E, F, G, H, I, K, L, M, N, P, Q, R, S, V, W or Y, preferably to A, C, E, F, G, H, K, L, M, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K213 to A, C, D, E, F, G, H, I, L, M, N, P, Q, R, S, T, V, W or Y, preferably to A, C, D, F, I, L, M, N, Q, R, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V214 to A, C, D, E, F, G, H, I, K, L, M, N, P, Q, R, S, T, W or Y, preferably to A, C, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A215 to C, D, E, F, G, H, I, K, L, M, N, P, Q, R, S, T, V, W or Y, preferably to D, E, F, I, K, L, Q, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N216 to A, C, D, E, F, G, H, I, K, L, M, P, Q, R, S, T, V, W or Y, preferably to D, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D217 to A, C, E, F, G, H, I, K, L, M, N, P, Q, R, S, T, V, W or Y, preferably to F, G, L, M, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T218 to A, C, D, E, F, G, H, I, K, L, M, N, P, Q, R, S, V, W or Y, preferably to D, G or H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K219 to A, C, D, E, F, G, H, I, L, M, N, P, Q, R, S, T, V, W or Y, preferably to A, C, F, H or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A220 to C, D, E, F, G, H, I, K, L, M, N, P, Q, R, S, T, V, W or Y, preferably to C, G, I, L, M, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A221 to C, D, E, F, G, H, I, K, L, M, N, P, Q, R, S, T, V, W or Y, preferably to C, D, E, L, N, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A222 to C, D, E, F, G, H, I, K, L, M, N, P, Q, R, S, T, V, W or Y, preferably to D, I, L, P, R, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N223 to A, C, D, E, F, G, H, I, K, L, M, P, Q, R, S, T, V, W or Y, preferably to A, E, F, G, K, L, M, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I224 to A, C, D, E, F, G, H, K, L, M, N, P, Q, R, S, T, V, W or Y, preferably to G or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T225 to A, C, D, E, F, G, H, I, K, L, M, N, P, Q, R, S, V, W or Y, preferably to A, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L226 to A, C, D, E, F, G, H, I, K, M, N, P, Q, R, S, T, V, W or Y, preferably to C, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K227 to A, C, D, E, F, G, H, I, L, M, N, P, Q, R, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q228 to A, C, D, E, F, G, H, I, K, L, M, N, P, R, S, T, V, W or Y, preferably to N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T229 to A, C, D, E, F, G, H, I, K, L, M, N, P, Q, R, S, V, W or Y, preferably to A, C, D, G, H, M, N, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V230 to A, C, D, E, F, G, H, I, K, L, M, N, P, Q, R, S, T, W or Y, preferably to F, L, M, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F231 to A, C, D, E, G, H, I, K, L, M, N, P, Q, R, S, T, V, W or Y, preferably to A, E, G, I, K, L, Q, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P232 to A, C, D, E, F, G, H, I, K, L, M, N, Q, R, S, T, V, W or Y, preferably to G, H, L, M, R, S, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K233 to A, C, D, E, F, G, H, I, L, M, N, P, Q, R, S, T, V, W or Y, preferably to A, C, E, F, G, L, P, R, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G234 to A, C, D, E, F, H, I, K, L, M, N, P, Q, R, S, T, V, W or Y, preferably to A, C, D, E, K, L, Q, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G235 to A, C, D, E, F, H, I, K, L, M, N, P, Q, R, S, T, V, W or Y, preferably to C, F, H, I, K, M, Q, R, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K236 to A, C, D, E, F, G, H, I, L, M, N, P, Q, R, S, T, V, W or Y, preferably to A, D, E, G, L, M, P, R, S, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T237 to A, C, D, E, F, G, H, I, K, L, M, N, P, Q, R, S, V, W or Y, preferably to D, F, I, K, M, Q, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D238 to A, C, E, F, G, H, I, K, L, M, N, P, Q, R, S, T, V, W or Y, preferably to A, E, F, G, H, I, K, L, M, N, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A239 to C, D, E, F, G, H, I, K, L, M, N, P, Q, R, S, T, V, W or Y, preferably to C, E, G, I, K or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A240 to C, D, E, F, G, H, I, K, L, M, N, P, Q, R, S, T, V, W or Y, preferably to C, E, L, P, Q, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I241 to A, C, D, E, F, G, H, K, L, M, N, P, Q, R, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G242 to A, C, D, E, F, H, I, K, L, M, N, P, Q, R, S, T, V, W or Y, preferably to K, L, M, P, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T243 to A, C, D, E, F, G, H, I, K, L, M, N, P, Q, R, S, V, W or Y, preferably to I, M, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V244 to A, C, D, E, F, G, H, I, K, L, M, N, P, Q, R, S, T, W or Y, preferably to A, E, G, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T245 to A, C, D, E, F, G, H, I, K, L, M, N, P, Q, R, S, V, W or Y, preferably to E, G, L, M, N, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T246 to A, C, D, E, F, G, H, I, K, L, M, N, P, Q, R, S, V, W or Y, preferably to D, E, G, K or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A247 to C, D, E, F, G, H, I, K, L, M, N, P, Q, R, S, T, V, W or Y, preferably to D, E, K, N, P, Q, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S248 to A, C, D, E, F, G, H, I, K, L, M, N, P, Q, R, T, V, W or Y, preferably to A, E, F, H, I, L, Q, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K249 to A, C, D, E, F, G, H, I, L, M, N, P, Q, R, S, T, V, W or Y, preferably to A, D, G, H, I, L, M, N, P, Q, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S250 to A, C, D, E, F, G, H, I, K, L, M, N, P, Q, R, T, V, W or Y, preferably to H, M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I251 to A, C, D, E, F, G, H, K, L, M, N, P, Q, R, S, T, V, W or Y, preferably to F, L, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A252 to C, D, E, F, G, H, I, K, L, M, N, P, Q, R, S, T, V, W or Y, preferably to C, E, F, H, I, P, R, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G254 to A, C, D, E, F, H, I, K, L, M, N, P, Q, R, S, T, V, W or Y, preferably to D, F, I, L, M, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A255 to C, D, E, F, G, H, I, K, L, M, N, P, Q, R, S, T, V, W or Y, preferably to C, F, K, L, M, S, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S256 to A, C, D, E, F, G, H, I, K, L, M, N, P, Q, R, T, V, W or Y, preferably to A, C, F, G, K, L, M, N, Q, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A257 to C, D, E, F, G, H, I, K, L, M, N, P, Q, R, S, T, V, W or Y, preferably to D, G, I, N, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D258 to A, C, E, F, G, H, I, K, L, M, N, P, Q, R, S, T, V, W or Y, preferably to A, L, M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V259 to A, C, D, E, F, G, H, I, K, L, M, N, P, Q, R, S, T, W or Y, preferably to E, L, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T260 to A, C, D, E, F, G, H, I, K, L, M, N, P, Q, R, S, V, W or Y, preferably to A, D, G, I, K or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S261 to A, C, D, E, F, G, H, I, K, L, M, N, P, Q, R, T, V, W or Y, preferably to A, D, H, R, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T262 to A, C, D, E, F, G, H, I, K, L, M, N, P, Q, R, S, V, W or Y, preferably to D, E, F, G, H, L, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I263 to A, C, D, E, F, G, H, K, L, M, N, P, Q, R, S, T, V, W or Y, preferably to A, C, G, L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T264 to A, C, D, E, F, G, H, I, K, L, M, N, P, Q, R, S, V, W or Y, preferably to F, G, K, L, M, P, Q, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A265 to C, D, E, F, G, H, I, K, L, M, N, P, Q, R, S, T, V, W or Y, preferably to G, I, K, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A266 to C, D, E, F, G, H, I, K, L, M, N, P, Q, R, S, T, V, W or Y, preferably to D, E, G, K, L, M, P, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S267 to A, C, D, E, F, G, H, I, K, L, M, N, P, Q, R, T, V, W or Y, preferably to A, D, K, M, N, P, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P268 to A, C, D, E, F, G, H, I, K, L, M, N, Q, R, S, T, V, W or Y, preferably to F, G, M, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K269 to A, C, D, E, F, G, H, I, L, M, N, P, Q, R, S, T, V, W or Y, preferably to G, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L270 to A, C, D, E, F, G, H, I, K, M, N, P, Q, R, S, T, V, W or Y, preferably to D, M, N, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W271 to A, C, D, E, F, G, H, I, K, L, M, N, P, Q, R, S, T, V or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S272 to A, C, D, E, F, G, H, I, K, L, M, N, P, Q, R, T, V, W or Y, preferably to E, G, K, L, N, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I273 to A, C, D, E, F, G, H, K, L, M, N, P, Q, R, S, T, V, W or Y, preferably to K, L, P, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K274 to A, C, D, E, F, G, H, I, L, M, N, P, Q, R, S, T, V, W or Y, preferably to D, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N275 to A, C, D, E, F, G, H, I, K, L, M, P, Q, R, S, T, V, W or Y, preferably to K, M, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N277 to A, C, D, E, F, G, H, I, K, L, M, P, Q, R, S, T, V, W or Y, preferably to F, K or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L278 to A, C, D, E, F, G, H, I, K, M, N, P, Q, R, S, T, V, W or Y, preferably to A, G, H, I, K, M, P, Q, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y279 to A, C, D, E, F, G, H, I, K, L, M, N, P, Q, R, S, T, V or W, preferably to M, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T280 to A, C, D, E, F, G, H, I, K, L, M, N, P, Q, R, S, V, W or Y, preferably to A, D, E, F, H, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V281 to A, C, D, E, F, G, H, I, K, L, M, N, P, Q, R, S, T, W or Y, preferably to A, I, L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R282 to A, C, D, E, F, G, H, I, K, L, M, N, P, Q, S, T, V, W or Y, preferably to E, F, H, I, K, N, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T283 to A, C, D, E, F, G, H, I, K, L, M, N, P, Q, R, S, V, W or Y, preferably to M, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E284 to A, C, D, F, G, H, I, K, L, M, N, P, Q, R, S, T, V, W or Y, preferably to A, D, F, H, L, M, N, Q, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V285 to A, C, D, E, F, G, H, I, K, L, M, N, P, Q, R, S, T, W or Y, preferably to H, I or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L286 to A, C, D, E, F, G, H, I, K, M, N, P, Q, R, S, T, V, W or Y, preferably to A, C, D, F, N, R, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N287 to A, C, D, E, F, G, H, I, K, L, M, P, Q, R, S, T, V, W or Y, preferably to I or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G288 to A, C, D, E, F, H, I, K, L, M, N, P, Q, R, S, T, V, W or Y, preferably to F, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V291 to A, C, D, E, F, G, H, I, K, L, M, N, P, Q, R, S, T, W or Y, preferably to C, D, F, G, H, L, P, S, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L292 to A, C, D, E, F, G, H, I, K, M, N, P, Q, R, S, T, V, W or Y, preferably to A, D, E, H, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D293 to A, C, E, F, G, H, I, K, L, M, N, P, Q, R, S, T, V, W or Y, preferably to C, E, F, I, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T294 to A, C, D, E, F, G, H, I, K, L, M, N, P, Q, R, S, V, W or Y, preferably to C, G, M, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y295 to A, C, D, E, F, G, H, I, K, L, M, N, P, Q, R, S, T, V or W, preferably to F, G, I, L, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D296 to A, C, E, F, G, H, I, K, L, M, N, P, Q, R, S, T, V, W or Y, preferably to F, H, K, L, N, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T297 to A, C, D, E, F, G, H, I, K, L, M, N, P, Q, R, S, V, W or Y, preferably to G, I, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E298 to A, C, D, F, G, H, I, K, L, M, N, P, Q, R, S, T, V, W or Y, preferably to G, I, L, M, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y299 to A, C, D, E, F, G, H, I, K, L, M, N, P, Q, R, S, T, V or W, preferably to F or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F301 to A, C, D, E, G, H, I, K, L, M, N, P, Q, R, S, T, V, W or Y, preferably to C or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R302 to A, C, D, E, F, G, H, I, K, L, M, N, P, Q, S, T, V, W or Y, preferably to E, I, K, M, N or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W303 to A, C, D, E, F, G, H, I, K, L, M, N, P, Q, R, S, T, V or Y, preferably to A, C, D, F, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T304 to A, C, D, E, F, G, H, I, K, L, M, N, P, Q, R, S, V, W or Y, preferably to D, E, I, K, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G305 to A, C, D, E, F, H, I, K, L, M, N, P, Q, R, S, T, V, W or Y, preferably to E, F, L, M, N, P, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F306 to A, C, D, E, G, H, I, K, L, M, N, P, Q, R, S, T, V, W or Y, preferably to D, K, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D307 to A, C, E, F, G, H, I, K, L, M, N, P, Q, R, S, T, V, W or Y, preferably to A, E, F, G, L, M, N, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A308 to C, D, E, F, G, H, I, K, L, M, N, P, Q, R, S, T, V, W or Y, preferably to C, E, G, I, M or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T309 to A, C, D, E, F, G, H, I, K, L, M, N, P, Q, R, S, V, W or Y, preferably to C, D, E, I, K, M, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S310 to A, C, D, E, F, G, H, I, K, L, M, N, P, Q, R, T, V, W or Y, preferably to A, C, G, H, I, L, M, N, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G311 to A, C, D, E, F, H, I, K, L, M, N, P, Q, R, S, T, V, W or Y, preferably to E, F, L, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F312 to A, C, D, E, G, H, I, K, L, M, N, P, Q, R, S, T, V, W or Y, preferably to H, L, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L314 to A, C, D, E, F, G, H, I, K, M, N, P, Q, R, S, T, V, W or Y, preferably to A, C, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N315 to A, C, D, E, F, G, H, I, K, L, M, P, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G316 to A, C, D, E, F, H, I, K, L, M, N, P, Q, R, S, T, V, W or Y, preferably to A, C, N, R, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E317 to A, C, D, F, G, H, I, K, L, M, N, P, Q, R, S, T, V, W or Y, preferably to D, H, I, K, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K318 to A, C, D, E, F, G, H, I, L, M, N, P, Q, R, S, T, V, W or Y, preferably to C, E, F, G, H, L, M, N, P, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K320 to A, C, D, E, F, G, H, I, L, M, N, P, Q, R, S, T, V, W or Y, preferably to C, E, F, I, L, R, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L321 to A, C, D, E, F, G, H, I, K, M, N, P, Q, R, S, T, V, W or Y, preferably to C, G, H, M, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K322 to A, C, D, E, F, G, H, I, L, M, N, P, Q, R, S, T, V, W or Y, preferably to C, F, I, N, P, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V324 to A, C, D, E, F, G, H, I, K, L, M, N, P, Q, R, S, T, W or Y, preferably to E, G or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S325 to A, C, D, E, F, G, H, I, K, L, M, N, P, Q, R, T, V, W or Y, preferably to D, G or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M326 to A, C, D, E, F, G, H, I, K, L, N, P, Q, R, S, T, V, W or Y, preferably to E, G, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H328 to A, C, D, E, F, G, I, K, L, M, N, P, Q, R, S, T, V, W or Y, preferably to C, D, F, G, I, L, M, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D329 to A, C, E, F, G, H, I, K, L, M, N, P, Q, R, S, T, V, W or Y, preferably to S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G331 to A, C, D, E, F, H, I, K, L, M, N, P, Q, R, S, T, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A335 to C, D, E, F, G, H, I, K, L, M, N, P, Q, R, S, T, V, W or Y, preferably to C, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A337 to C, D, E, F, G, H, I, K, L, M, N, P, Q, R, S, T, V, W or Y, preferably to D, E, G, L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N338 to A, C, D, E, F, G, H, I, K, L, M, P, Q, R, S, T, V, W or Y, preferably to P, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R340 to A, C, D, E, F, G, H, I, K, L, M, N, P, Q, S, T, V, W or Y, preferably to A, C or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A341 to C, D, E, F, G, H, I, K, L, M, N, P, Q, R, S, T, V, W or Y, preferably to M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I342 to A, C, D, E, F, G, H, K, L, M, N, P, Q, R, S, T, V, W or Y, preferably to A, G, K or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E343 to A, C, D, F, G, H, I, K, L, M, N, P, Q, R, S, T, V, W or Y, preferably to A, H, N, R, S, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R344 to A, C, D, E, F, G, H, I, K, L, M, N, P, Q, S, T, V, W or Y, preferably to G, L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q345 to A, C, D, E, F, G, H, I, K, L, M, N, P, R, S, T, V, W or Y, preferably to F, G, K, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V346 to A, C, D, E, F, G, H, I, K, L, M, N, P, Q, R, S, T, W or Y, preferably to A, C, F, I, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E347 to A, C, D, F, G, H, I, K, L, M, N, P, Q, R, S, T, V, W or Y, preferably to A, C, D, F, I, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I348 to A, C, D, E, F, G, H, K, L, M, N, P, Q, R, S, T, V, W or Y, preferably to A, D, G, M, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L349 to A, C, D, E, F, G, H, I, K, M, N, P, Q, R, S, T, V, W or Y, preferably to A, E, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q350 to A, C, D, E, F, G, H, I, K, L, M, N, P, R, S, T, V, W or Y, preferably to G, N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K351 to A, C, D, E, F, G, H, I, L, M, N, P, Q, R, S, T, V, W or Y, preferably to N, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M352 to A, C, D, E, F, G, H, I, K, L, N, P, Q, R, S, T, V, W or Y, preferably to G, L, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G353 to A, C, D, E, F, H, I, K, L, M, N, P, Q, R, S, T, V, W or Y, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V354 to A, C, D, E, F, G, H, I, K, L, M, N, P, Q, R, S, T, W or Y, preferably to E, G, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N355 to A, C, D, E, F, G, H, I, K, L, M, P, Q, R, S, T, V, W or Y, preferably to H, M, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I357 to A, C, D, E, F, G, H, K, L, M, N, P, Q, R, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T359 to A, C, D, E, F, G, H, I, K, L, M, N, P, Q, R, S, V, W or Y, preferably to E or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T360 to A, C, D, E, F, G, H, I, K, L, M, N, P, Q, R, S, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N362 to A, C, D, E, F, G, H, I, K, L, M, P, Q, R, S, T, V, W or Y, preferably to G, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P363 to A, C, D, E, F, G, H, I, K, L, M, N, Q, R, S, T, V, W or Y, preferably to A, D, I, L, M, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A364 to C, D, E, F, G, H, I, K, L, M, N, P, Q, R, S, T, V, W or Y, preferably to C, E, F, G, I, M, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A365 to C, D, E, F, G, H, I, K, L, M, N, P, Q, R, S, T, V, W or Y, preferably to C, E, I, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K366 to A, C, D, E, F, G, H, I, L, M, N, P, Q, R, S, T, V, W or Y, preferably to A, D, E, I, L, M, P, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A367 to C, D, E, F, G, H, I, K, L, M, N, P, Q, R, S, T, V, W or Y, preferably to C, I, N or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L368 to A, C, D, E, F, G, H, I, K, M, N, P, Q, R, S, T, V, W or Y, preferably to A, E, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I369 to A, C, D, E, F, G, H, K, L, M, N, P, Q, R, S, T, V, W or Y, preferably to A, D, E, G, K, M, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D370 to A, C, E, F, G, H, I, K, L, M, N, P, Q, R, S, T, V, W or Y, preferably to C, L, Q, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V371 to A, C, D, E, F, G, H, I, K, L, M, N, P, Q, R, S, T, W or Y, preferably to D, F, G, I, L, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position C372 to A, D, E, F, G, H, I, K, L, M, N, P, Q, R, S, T, V, W or Y, preferably to P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N373 to A, C, D, E, F, G, H, I, K, L, M, P, Q, R, S, T, V, W or Y, preferably to G, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E374 to A, C, D, F, G, H, I, K, L, M, N, P, Q, R, S, T, V, W or Y, preferably to K, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K375 to A, C, D, E, F, G, H, I, L, M, N, P, Q, R, S, T, V, W or Y, preferably to D, I, N, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G376 to A, C, D, E, F, H, I, K, L, M, N, P, Q, R, S, T, V, W or Y, preferably to A or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V377 to A, C, D, E, F, G, H, I, K, L, M, N, P, Q, R, S, T, W or Y, preferably to A, M or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L378 to A, C, D, E, F, G, H, I, K, M, N, P, Q, R, S, T, V, W or Y, preferably to I, P, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V379 to A, C, D, E, F, G, H, I, K, L, M, N, P, Q, R, S, T, W or Y, preferably to A, C, M or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V380 to A, C, D, E, F, G, H, I, K, L, M, N, P, Q, R, S, T, W or Y, preferably to M, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E381 to A, C, D, F, G, H, I, K, L, M, N, P, Q, R, S, T, V, W or Y, preferably to A, C, G, L, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V383 to A, C, D, E, F, G, H, I, K, L, M, N, P, Q, R, S, T, W or Y, preferably to A, K or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M386 to A, C, D, E, F, G, H, I, K, L, N, P, Q, R, S, T, V, W or Y, preferably to G, N, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W387 to A, C, D, E, F, G, H, I, K, L, M, N, P, Q, R, S, T, V or Y, preferably to H or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N388 to A, C, D, E, F, G, H, I, K, L, M, P, Q, R, S, T, V, W or Y, preferably to A, E, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R389 to A, C, D, E, F, G, H, I, K, L, M, N, P, Q, S, T, V, W or Y, preferably to A, C, E, K, M, N, Q, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S390 to A, C, D, E, F, G, H, I, K, L, M, N, P, Q, R, T, V, W or Y, preferably to C, D, G, H, N, P, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K391 to A, C, D, E, F, G, H, I, L, M, N, P, Q, R, S, T, V, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N392 to A, C, D, E, F, G, H, I, K, L, M, P, Q, R, S, T, V, W or Y, preferably to D, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G393 to A, C, D, E, F, H, I, K, L, M, N, P, Q, R, S, T, V, W or Y, preferably to A, E, N, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N394 to A, C, D, E, F, G, H, I, K, L, M, P, Q, R, S, T, V, W or Y, preferably to L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T395 to A, C, D, E, F, G, H, I, K, L, M, N, P, Q, R, S, V, W or Y, preferably to A, C, F, H, I, M, N, Q, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E396 to A, C, D, F, G, H, I, K, L, M, N, P, Q, R, S, T, V, W or Y, preferably to K, L, M, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y398 to A, C, D, E, F, G, H, I, K, L, M, N, P, Q, R, S, T, V or W, preferably to M or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G399 to A, C, D, E, F, H, I, K, L, M, N, P, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K400 to A, C, D, E, F, G, H, I, L, M, N, P, Q, R, S, T, V, W or Y, preferably to A, C, D, E, M, N, P, Q, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W401 to A, C, D, E, F, G, H, I, K, L, M, N, P, Q, R, S, T, V or Y, preferably to F, H, K, L, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F402 to A, C, D, E, G, H, I, K, L, M, N, P, Q, R, S, T, V, W or Y, preferably to T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G403 to A, C, D, E, F, H, I, K, L, M, N, P, Q, R, S, T, V, W or Y, preferably to A, D, H, K, P, Q, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q404 to A, C, D, E, F, G, H, I, K, L, M, N, P, R, S, T, V, W or Y, preferably to F, H, L, M, P, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A405 to C, D, E, F, G, H, I, K, L, M, N, P, Q, R, S, T, V, W or Y, preferably to C, E, H, K, P, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I406 to A, C, D, E, F, G, H, K, L, M, N, P, Q, R, S, T, V, W or Y, preferably to C, D or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A407 to C, D, E, F, G, H, I, K, L, M, N, P, Q, R, S, T, V, W or Y, preferably to C, G, M, Q, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G408 to A, C, D, E, F, H, I, K, L, M, N, P, Q, R, S, T, V, W or Y, preferably to D, I, M, N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D409 to A, C, E, F, G, H, I, K, L, M, N, P, Q, R, S, T, V, W or Y, preferably to N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N410 to A, C, D, E, F, G, H, I, K, L, M, P, Q, R, S, T, V, W or Y, preferably to C, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A411 to C, D, E, F, G, H, I, K, L, M, N, P, Q, R, S, T, V, W or Y, preferably to E, N, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V412 to A, C, D, E, F, G, H, I, K, L, M, N, P, Q, R, S, T, W or Y, preferably to M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L413 to A, C, D, E, F, G, H, I, K, M, N, P, Q, R, S, T, V, W or Y, preferably to D, E, F, I, P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G414 to A, C, D, E, F, H, I, K, L, M, N, P, Q, R, S, T, V, W or Y, preferably to A, C, M, N, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G415 to A, C, D, E, F, H, I, K, L, M, N, P, Q, R, S, T, V, W or Y, preferably to A, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D416 to A, C, E, F, G, H, I, K, L, M, N, P, Q, R, S, T, V, W or Y, preferably to I, M, R, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K417 to A, C, D, E, F, G, H, I, L, M, N, P, Q, R, S, T, V, W or Y, preferably to C, F, G, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D418 to A, C, E, F, G, H, I, K, L, M, N, P, Q, R, S, T, V, W or Y, preferably to L, P, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E419 to A, C, D, F, G, H, I, K, L, M, N, P, Q, R, S, T, V, W or Y, preferably to M, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T420 to A, C, D, E, F, G, H, I, K, L, M, N, P, Q, R, S, V, W or Y, preferably to E, F, G, K, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W421 to A, C, D, E, F, G, H, I, K, L, M, N, P, Q, R, S, T, V or Y, preferably to L, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A422 to C, D, E, F, G, H, I, K, L, M, N, P, Q, R, S, T, V, W or Y, preferably to P, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K423 to A, C, D, E, F, G, H, I, L, M, N, P, Q, R, S, T, V, W or Y, preferably to D, L, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F424 to A, C, D, E, G, H, I, K, L, M, N, P, Q, R, S, T, V, W or Y, preferably to C, L, N or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D425 to A, C, E, F, G, H, I, K, L, M, N, P, Q, R, S, T, V, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L426 to A, C, D, E, F, G, H, I, K, M, N, P, Q, R, S, T, V, W or Y, preferably to C, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T427 to A, C, D, E, F, G, H, I, K, L, M, N, P, Q, R, S, V, W or Y, preferably to D, F, G, K, M, P, Q, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S428 to A, C, D, E, F, G, H, I, K, L, M, N, P, Q, R, T, V, W or Y, preferably to F, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T429 to A, C, D, E, F, G, H, I, K, L, M, N, P, Q, R, S, V, W or Y, preferably to D or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I430 to A, C, D, E, F, G, H, K, L, M, N, P, Q, R, S, T, V, W or Y, preferably to C, D, E, L, M, Q, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N431 to A, C, D, E, F, G, H, I, K, L, M, P, Q, R, S, T, V, W or Y, preferably to D, E, G, L, M, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R432 to A, C, D, E, F, G, H, I, K, L, M, N, P, Q, S, T, V, W or Y, preferably to A, E, F, G, N, Q, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D433 to A, C, E, F, G, H, I, K, L, M, N, P, Q, R, S, T, V, W or Y, preferably to C, G, H, I, P, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R434 to A, C, D, E, F, G, H, I, K, L, M, N, P, Q, S, T, V, W or Y, preferably to L, M, N, P, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N435 to A, C, D, E, F, G, H, I, K, L, M, P, Q, R, S, T, V, W or Y, preferably to E, F, H, K, L, M, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A436 to C, D, E, F, G, H, I, K, L, M, N, P, Q, R, S, T, V, W or Y, preferably to C, D, E, G, I, L, M, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P437 to A, C, D, E, F, G, H, I, K, L, M, N, Q, R, S, T, V, W or Y, preferably to A, D, K, L, Q, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S438 to A, C, D, E, F, G, H, I, K, L, M, N, P, Q, R, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V439 to A, C, D, E, F, G, H, I, K, L, M, N, P, Q, R, S, T, W or Y, preferably to C, E, G, I, K, Q, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I440 to A, C, D, E, F, G, H, K, L, M, N, P, Q, R, S, T, V, W or Y, preferably to C, D, F, K, P, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M441 to A, C, D, E, F, G, H, I, K, L, N, P, Q, R, S, T, V, W or Y, preferably to A, E, G, Q, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W442 to A, C, D, E, F, G, H, I, K, L, M, N, P, Q, R, S, T, V or Y, preferably to E, G, M, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S443 to A, C, D, E, F, G, H, I, K, L, M, N, P, Q, R, T, V, W or Y, preferably to C, D, G, M, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L444 to A, C, D, E, F, G, H, I, K, M, N, P, Q, R, S, T, V, W or Y, preferably to C, D, E, F, G, H, K, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G445 to A, C, D, E, F, H, I, K, L, M, N, P, Q, R, S, T, V, W or Y, preferably to A, C or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N446 to A, C, D, E, F, G, H, I, K, L, M, P, Q, R, S, T, V, W or Y, preferably to D or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M448 to A, C, D, E, F, G, H, I, K, L, N, P, Q, R, S, T, V, W or Y, preferably to A, C, D, E, I, L, P, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M449 to A, C, D, E, F, G, H, I, K, L, N, P, Q, R, S, T, V, W or Y, preferably to D, E, F, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E450 to A, C, D, F, G, H, I, K, L, M, N, P, Q, R, S, T, V, W or Y, preferably to F, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G451 to A, C, D, E, F, H, I, K, L, M, N, P, Q, R, S, T, V, W or Y, preferably to C, F, L, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I452 to A, C, D, E, F, G, H, K, L, M, N, P, Q, R, S, T, V, W or Y, preferably to G, K, L, M, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S453 to A, C, D, E, F, G, H, I, K, L, M, N, P, Q, R, T, V, W or Y, preferably to C, F, G, H, L, M, N, P, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G454 to A, C, D, E, F, H, I, K, L, M, N, P, Q, R, S, T, V, W or Y, preferably to L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S455 to A, C, D, E, F, G, H, I, K, L, M, N, P, Q, R, T, V, W or Y, preferably to A, E, K, M, P, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V456 to A, C, D, E, F, G, H, I, K, L, M, N, P, Q, R, S, T, W or Y, preferably to A, D, E, F, K, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S457 to A, C, D, E, F, G, H, I, K, L, M, N, P, Q, R, T, V, W or Y, preferably to E, H, K, L, M, P, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G458 to A, C, D, E, F, H, I, K, L, M, N, P, Q, R, S, T, V, W or Y, preferably to A, C, D, F, L, P, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F459 to A, C, D, E, G, H, I, K, L, M, N, P, Q, R, S, T, V, W or Y, preferably to A, C, E, G, N, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P460 to A, C, D, E, F, G, H, I, K, L, M, N, Q, R, S, T, V, W or Y, preferably to C, M, Q, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A461 to C, D, E, F, G, H, I, K, L, M, N, P, Q, R, S, T, V, W or Y, preferably to D, G, M, N, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T462 to A, C, D, E, F, G, H, I, K, L, M, N, P, Q, R, S, V, W or Y, preferably to C, E, F, L, M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S463 to A, C, D, E, F, G, H, I, K, L, M, N, P, Q, R, T, V, W or Y, preferably to G, K, Q, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A464 to C, D, E, F, G, H, I, K, L, M, N, P, Q, R, S, T, V, W or Y, preferably to E, H, L, M, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K465 to A, C, D, E, F, G, H, I, L, M, N, P, Q, R, S, T, V, W or Y, preferably to C, F, G, L, Q, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L466 to A, C, D, E, F, G, H, I, K, M, N, P, Q, R, S, T, V, W or Y, preferably to A, C, D, E, F, G, M, P, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V467 to A, C, D, E, F, G, H, I, K, L, M, N, P, Q, R, S, T, W or Y, preferably to A, C, D, E, G, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A468 to C, D, E, F, G, H, I, K, L, M, N, P, Q, R, S, T, V, W or Y, preferably to D, E, F, K, L, P, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W469 to A, C, D, E, F, G, H, I, K, L, M, N, P, Q, R, S, T, V or Y, preferably to A, C, D, G, L, M, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T470 to A, C, D, E, F, G, H, I, K, L, M, N, P, Q, R, S, V, W or Y, preferably to E, L, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K471 to A, C, D, E, F, G, H, I, L, M, N, P, Q, R, S, T, V, W or Y, preferably to F, G, Q, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A472 to C, D, E, F, G, H, I, K, L, M, N, P, Q, R, S, T, V, W or Y, preferably to G or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A473 to C, D, E, F, G, H, I, K, L, M, N, P, Q, R, S, T, V, W or Y, preferably to E, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D474 to A, C, E, F, G, H, I, K, L, M, N, P, Q, R, S, T, V, W or Y, preferably to A, C, E, K, M, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S475 to A, C, D, E, F, G, H, I, K, L, M, N, P, Q, R, T, V, W or Y, preferably to E, F, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T476 to A, C, D, E, F, G, H, I, K, L, M, N, P, Q, R, S, V, W or Y, preferably to C, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R477 to A, C, D, E, F, G, H, I, K, L, M, N, P, Q, S, T, V, W or Y, preferably to A, C, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P478 to A, C, D, E, F, G, H, I, K, L, M, N, Q, R, S, T, V, W or Y, preferably to A, D, G, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M479 to A, C, D, E, F, G, H, I, K, L, N, P, Q, R, S, T, V, W or Y, preferably to G, I, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T480 to A, C, D, E, F, G, H, I, K, L, M, N, P, Q, R, S, V, W or Y, preferably to C, G or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K485 to A, C, D, E, F, G, H, I, L, M, N, P, Q, R, S, T, V, W or Y, preferably to E or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K487 to A, C, D, E, F, G, H, I, L, M, N, P, Q, R, S, T, V, W or Y, preferably to A, C, F, G, N, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A488 to C, D, E, F, G, H, I, K, L, M, N, P, Q, R, S, T, V, W or Y, preferably to C, G, H, L, N, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N491 to A, C, D, E, F, G, H, I, K, L, M, P, Q, R, S, T, V, W or Y, preferably to A, E or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E492 to A, C, D, F, G, H, I, K, L, M, N, P, Q, R, S, T, V, W or Y, preferably to A or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S493 to A, C, D, E, F, G, H, I, K, L, M, N, P, Q, R, T, V, W or Y, preferably to E, G, H, L, M, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N494 to A, C, D, E, F, G, H, I, K, L, M, P, Q, R, S, T, V, W or Y, preferably to A, I, M, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T495 to A, C, D, E, F, G, H, I, K, L, M, N, P, Q, R, S, V, W or Y, preferably to K, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M496 to A, C, D, E, F, G, H, I, K, L, N, P, Q, R, S, T, V, W or Y, preferably to A, F or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G497 to A, C, D, E, F, H, I, K, L, M, N, P, Q, R, S, T, V, W or Y, preferably to D, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D498 to A, C, E, F, G, H, I, K, L, M, N, P, Q, R, S, T, V, W or Y, preferably to A, C, M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N499 to A, C, D, E, F, G, H, I, K, L, M, P, Q, R, S, T, V, W or Y, preferably to K, R, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L500 to A, C, D, E, F, G, H, I, K, M, N, P, Q, R, S, T, V, W or Y, preferably to A, E, N or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T501 to A, C, D, E, F, G, H, I, K, L, M, N, P, Q, R, S, V, W or Y, preferably to C, G or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A502 to C, D, E, F, G, H, I, K, L, M, N, P, Q, R, S, T, V, W or Y, preferably to L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N503 to A, C, D, E, F, G, H, I, K, L, M, P, Q, R, S, T, V, W or Y, preferably to A, E, M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G504 to A, C, D, E, F, H, I, K, L, M, N, P, Q, R, S, T, V, W or Y, preferably to H, K or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G505 to A, C, D, E, F, H, I, K, L, M, N, P, Q, R, S, T, V, W or Y, preferably to A, D, E, H, L, N, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V506 to A, C, D, E, F, G, H, I, K, L, M, N, P, Q, R, S, T, W or Y, preferably to C, D, E, G, I, L, P, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V507 to A, C, D, E, F, G, H, I, K, L, M, N, P, Q, R, S, T, W or Y, preferably to A, F, G, L, N, P, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G508 to A, C, D, E, F, H, I, K, L, M, N, P, Q, R, S, T, V, W or Y, preferably to C or E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T509 to A, C, D, E, F, G, H, I, K, L, M, N, P, Q, R, S, V, W or Y, preferably to A, D, E, I, K, M, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N510 to A, C, D, E, F, G, H, I, K, L, M, P, Q, R, S, T, V, W or Y, preferably to A, F, I or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y511 to A, C, D, E, F, G, H, I, K, L, M, N, P, Q, R, S, T, V or W, preferably to A or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S512 to A, C, D, E, F, G, H, I, K, L, M, N, P, Q, R, T, V, W or Y, preferably to C, E, F, G, I, M, Q, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D513 to A, C, E, F, G, H, I, K, L, M, N, P, Q, R, S, T, V, W or Y, preferably to C, G, K, L, M, P, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G514 to A, C, D, E, F, H, I, K, L, M, N, P, Q, R, S, T, V, W or Y, preferably to F, L, N, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A515 to C, D, E, F, G, H, I, K, L, M, N, P, Q, R, S, T, V, W or Y, preferably to C, D, E, F, G, K, P, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N516 to A, C, D, E, F, G, H, I, K, L, M, P, Q, R, S, T, V, W or Y, preferably to C, E, G, I, M, Q, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y517 to A, C, D, E, F, G, H, I, K, L, M, N, P, Q, R, S, T, V or W, preferably to G, I or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D518 to A, C, E, F, G, H, I, K, L, M, N, P, Q, R, S, T, V, W or Y, preferably to Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K519 to A, C, D, E, F, G, H, I, L, M, N, P, Q, R, S, T, V, W or Y, preferably to C, E, F, G, I, L, M, N, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I520 to A, C, D, E, F, G, H, K, L, M, N, P, Q, R, S, T, V, W or Y, preferably to A, C, G, H, M, N, Q, S, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R521 to A, C, D, E, F, G, H, I, K, L, M, N, P, Q, S, T, V, W or Y, preferably to A, C, K, N, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T522 to A, C, D, E, F, G, H, I, K, L, M, N, P, Q, R, S, V, W or Y, preferably to G, I or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T523 to A, C, D, E, F, G, H, I, K, L, M, N, P, Q, R, S, V, W or Y, preferably to A or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H524 to A, C, D, E, F, G, I, K, L, M, N, P, Q, R, S, T, V, W or Y, preferably to R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P525 to A, C, D, E, F, G, H, I, K, L, M, N, Q, R, S, T, V, W or Y, preferably to D, G, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S526 to A, C, D, E, F, G, H, I, K, L, M, N, P, Q, R, T, V, W or Y, preferably to G, I or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W527 to A, C, D, E, F, G, H, I, K, L, M, N, P, Q, R, S, T, V or Y, preferably to A, E, G, H, N, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A528 to C, D, E, F, G, H, I, K, L, M, N, P, Q, R, S, T, V, W or Y, preferably to C, E, G, I or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I529 to A, C, D, E, F, G, H, K, L, M, N, P, Q, R, S, T, V, W or Y, preferably to F, G, L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y530 to A, C, D, E, F, G, H, I, K, L, M, N, P, Q, R, S, T, V or W, preferably to A or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G531 to A, C, D, E, F, H, I, K, L, M, N, P, Q, R, S, T, V, W or Y, preferably to E, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T534 to A, C, D, E, F, G, H, I, K, L, M, N, P, Q, R, S, V, W or Y, preferably to A, I or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A535 to C, D, E, F, G, H, I, K, L, M, N, P, Q, R, S, T, V, W or Y, preferably to E, G, I or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A537 to C, D, E, F, G, H, I, K, L, M, N, P, Q, R, S, T, V, W or Y, preferably to D, M, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I538 to A, C, D, E, F, G, H, K, L, M, N, P, Q, R, S, T, V, W or Y, preferably to H or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N539 to A, C, D, E, F, G, H, I, K, L, M, P, Q, R, S, T, V, W or Y, preferably to G or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S540 to A, C, D, E, F, G, H, I, K, L, M, N, P, Q, R, T, V, W or Y, preferably to E, G or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G542 to A, C, D, E, F, H, I, K, L, M, N, P, Q, R, S, T, V, W or Y, preferably to E, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I543 to A, C, D, E, F, G, H, K, L, M, N, P, Q, R, S, T, V, W or Y, preferably to V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N545 to A, C, D, E, F, G, H, I, K, L, M, P, Q, R, S, T, V, W or Y, preferably to G, I, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R546 to A, C, D, E, F, G, H, I, K, L, M, N, P, Q, S, T, V, W or Y, preferably to A, C, L, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T547 to A, C, D, E, F, G, H, I, K, L, M, N, P, Q, R, S, V, W or Y, preferably to A, D, H, K, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T548 to A, C, D, E, F, G, H, I, K, L, M, N, P, Q, R, S, V, W or Y, preferably to D, E, F, K, L, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G549 to A, C, D, E, F, H, I, K, L, M, N, P, Q, R, S, T, V, W or Y, preferably to D, F, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G550 to A, C, D, E, F, H, I, K, L, M, N, P, Q, R, S, T, V, W or Y, preferably to Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A551 to C, D, E, F, G, H, I, K, L, M, N, P, Q, R, S, T, V, W or Y, preferably to D, I or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S553 to A, C, D, E, F, G, H, I, K, L, M, N, P, Q, R, T, V, W or Y, preferably to C, F, N, P, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S554 to A, C, D, E, F, G, H, I, K, L, M, N, P, Q, R, T, V, W or Y, preferably to F, N, R, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D555 to A, C, E, F, G, H, I, K, L, M, N, P, Q, R, S, T, V, W or Y, preferably to E, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K556 to A, C, D, E, F, G, H, I, L, M, N, P, Q, R, S, T, V, W or Y, preferably to A, C, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q557 to A, C, D, E, F, G, H, I, K, L, M, N, P, R, S, T, V, W or Y, preferably to F, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L558 to A, C, D, E, F, G, H, I, K, M, N, P, Q, R, S, T, V, W or Y, preferably to E, H, I or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T559 to A, C, D, E, F, G, H, I, K, L, M, N, P, Q, R, S, V, W or Y, preferably to A, G, I, Q, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S560 to A, C, D, E, F, G, H, I, K, L, M, N, P, Q, R, T, V, W or Y, preferably to P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y561 to A, C, D, E, F, G, H, I, K, L, M, N, P, Q, R, S, T, V or W, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N563 to A, C, D, E, F, G, H, I, K, L, M, P, Q, R, S, T, V, W or Y, preferably to R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S564 to A, C, D, E, F, G, H, I, K, L, M, N, P, Q, R, T, V, W or Y, preferably to A, C, F or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A565 to C, D, E, F, G, H, I, K, L, M, N, P, Q, R, S, T, V, W or Y, preferably to C, D, E, F, G, I, L, M, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G567 to A, C, D, E, F, H, I, K, L, M, N, P, Q, R, S, T, V, W or Y, preferably to N, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A570 to C, D, E, F, G, H, I, K, L, M, N, P, Q, R, S, T, V, W or Y, preferably to G, K, L, M, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V571 to A, C, D, E, F, G, H, I, K, L, M, N, P, Q, R, S, T, W or Y, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A572 to C, D, E, F, G, H, I, K, L, M, N, P, Q, R, S, T, V, W or Y, preferably to S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S573 to A, C, D, E, F, G, H, I, K, L, M, N, P, Q, R, T, V, W or Y, preferably to G, K or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S574 to A, C, D, E, F, G, H, I, K, L, M, N, P, Q, R, T, V, W or Y, preferably to K, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A575 to C, D, E, F, G, H, I, K, L, M, N, P, Q, R, S, T, V, W or Y, preferably to D, M or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W576 to A, C, D, E, F, G, H, I, K, L, M, N, P, Q, R, S, T, V or Y, preferably to A, F, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y577 to A, C, D, E, F, G, H, I, K, L, M, N, P, Q, R, S, T, V or W, preferably to G, I, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D578 to A, C, E, F, G, H, I, K, L, M, N, P, Q, R, S, T, V, W or Y, preferably to E, M, N or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V579 to A, C, D, E, F, G, H, I, K, L, M, N, P, Q, R, S, T, W or Y, preferably to E, G, L or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V580 to A, C, D, E, F, G, H, I, K, L, M, N, P, Q, R, S, T, W or Y, preferably to A, D, E, K, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q581 to A, C, D, E, F, G, H, I, K, L, M, N, P, R, S, T, V, W or Y, preferably to F, G, P, R, S, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R582 to A, C, D, E, F, G, H, I, K, L, M, N, P, Q, S, T, V, W or Y, preferably to A, D, G, I, L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D583 to A, C, E, F, G, H, I, K, L, M, N, P, Q, R, S, T, V, W or Y, preferably to V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F584 to A, C, D, E, G, H, I, K, L, M, N, P, Q, R, S, T, V, W or Y, preferably to E, I or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V585 to A, C, D, E, F, G, H, I, K, L, M, N, P, Q, R, S, T, W or Y, preferably to I, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A586 to C, D, E, F, G, H, I, K, L, M, N, P, Q, R, S, T, V, W or Y, preferably to C, D, H or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G587 to A, C, D, E, F, H, I, K, L, M, N, P, Q, R, S, T, V, W or Y, preferably to A or C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T588 to A, C, D, E, F, G, H, I, K, L, M, N, P, Q, R, S, V, W or Y, preferably to C, D, G, I, L, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y589 to A, C, D, E, F, G, H, I, K, L, M, N, P, Q, R, S, T, V or W, preferably to A, I, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V590 to A, C, D, E, F, G, H, I, K, L, M, N, P, Q, R, S, T, W or Y, preferably to A, H or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W591 to A, C, D, E, F, G, H, I, K, L, M, N, P, Q, R, S, T, V or Y, preferably to F, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T592 to A, C, D, E, F, G, H, I, K, L, M, N, P, Q, R, S, V, W or Y, preferably to C, L, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G593 to A, C, D, E, F, H, I, K, L, M, N, P, Q, R, S, T, V, W or Y, preferably to C or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F594 to A, C, D, E, G, H, I, K, L, M, N, P, Q, R, S, T, V, W or Y, preferably to C, I, L or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D595 to A, C, E, F, G, H, I, K, L, M, N, P, Q, R, S, T, V, W or Y, preferably to E, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L597 to A, C, D, E, F, G, H, I, K, M, N, P, Q, R, S, T, V, W or Y, preferably to C, D, E or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G598 to A, C, D, E, F, H, I, K, L, M, N, P, Q, R, S, T, V, W or Y, preferably to N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P600 to A, C, D, E, F, G, H, I, K, L, M, N, Q, R, S, T, V, W or Y, preferably to A, E, G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N604 to A, C, D, E, F, G, H, I, K, L, M, P, Q, R, S, T, V, W or Y, preferably to E or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G605 to A, C, D, E, F, H, I, K, L, M, N, P, Q, R, S, T, V, W or Y, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T606 to A, C, D, E, F, G, H, I, K, L, M, N, P, Q, R, S, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G607 to A, C, D, E, F, H, I, K, L, M, N, P, Q, R, S, T, V, W or Y, preferably to A, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S608 to A, C, D, E, F, G, H, I, K, L, M, N, P, Q, R, T, V, W or Y, preferably to E, I, M, N, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G609 to A, C, D, E, F, H, I, K, L, M, N, P, Q, R, S, T, V, W or Y, preferably to A, H, L, N, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A610 to C, D, E, F, G, H, I, K, L, M, N, P, Q, R, S, T, V, W or Y, preferably to D, F, M or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V611 to A, C, D, E, F, G, H, I, K, L, M, N, P, Q, R, S, T, W or Y, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G612 to A, C, D, E, F, H, I, K, L, M, N, P, Q, R, S, T, V, W or Y, preferably to N, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S613 to A, C, D, E, F, G, H, I, K, L, M, N, P, Q, R, T, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W614 to A, C, D, E, F, G, H, I, K, L, M, N, P, Q, R, S, T, V or Y, preferably to A, F or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P615 to A, C, D, E, F, G, H, I, K, L, M, N, Q, R, S, T, V, W or Y, preferably to L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S616 to A, C, D, E, F, G, H, I, K, L, M, N, P, Q, R, T, V, W or Y, preferably to A or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N619 to A, C, D, E, F, G, H, I, K, L, M, P, Q, R, S, T, V, W or Y, preferably to A, I, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S620 to A, C, D, E, F, G, H, I, K, L, M, N, P, Q, R, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y621 to A, C, D, E, F, G, H, I, K, L, M, N, P, Q, R, S, T, V or W, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I624 to A, C, D, E, F, G, H, K, L, M, N, P, Q, R, S, T, V, W or Y, preferably to A or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V625 to A, C, D, E, F, G, H, I, K, L, M, N, P, Q, R, S, T, W or Y, preferably to A, E, F, M or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T627 to A, C, D, E, F, G, H, I, K, L, M, N, P, Q, R, S, V, W or Y, preferably to F, G, K or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A628 to C, D, E, F, G, H, I, K, L, M, N, P, Q, R, S, T, V, W or Y, preferably to C, D or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G629 to A, C, D, E, F, H, I, K, L, M, N, P, Q, R, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F630 to A, C, D, E, G, H, I, K, L, M, N, P, Q, R, S, T, V, W or Y, preferably to A, C, D, G, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P631 to A, C, D, E, F, G, H, I, K, L, M, N, Q, R, S, T, V, W or Y, preferably to A, D, G, H, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K632 to A, C, D, E, F, G, H, I, L, M, N, P, Q, R, S, T, V, W or Y, preferably to C, D, G or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D633 to A, C, E, F, G, H, I, K, L, M, N, P, Q, R, S, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T634 to A, C, D, E, F, G, H, I, K, L, M, N, P, Q, R, S, V, W or Y, preferably to A, E, F, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y635 to A, C, D, E, F, G, H, I, K, L, M, N, P, Q, R, S, T, V or W, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y636 to A, C, D, E, F, G, H, I, K, L, M, N, P, Q, R, S, T, V or W, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F637 to A, C, D, E, G, H, I, K, L, M, N, P, Q, R, S, T, V, W or Y, preferably to C, G, I, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y638 to A, C, D, E, F, G, H, I, K, L, M, N, P, Q, R, S, T, V or W, preferably to A or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q639 to A, C, D, E, F, G, H, I, K, L, M, N, P, R, S, T, V, W or Y, preferably to D, N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S640 to A, C, D, E, F, G, H, I, K, L, M, N, P, Q, R, T, V, W or Y, preferably to C or D, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q641 to A, C, D, E, F, G, H, I, K, L, M, N, P, R, S, T, V, W or Y, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W642 to A, C, D, E, F, G, H, I, K, L, M, N, P, Q, R, S, T, V or Y, preferably to I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N643 to A, C, D, E, F, G, H, I, K, L, M, P, Q, R, S, T, V, W or Y, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D644 to A, C, E, F, G, H, I, K, L, M, N, P, Q, R, S, T, V, W or Y, preferably to C, G or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D645 to A, C, E, F, G, H, I, K, L, M, N, P, Q, R, S, T, V, W or Y, preferably to S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V646 to A, C, D, E, F, G, H, I, K, L, M, N, P, Q, R, S, T, W or Y, preferably to C, L, N, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H647 to A, C, D, E, F, G, I, K, L, M, N, P, Q, R, S, T, V, W or Y, preferably to G or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T648 to A, C, D, E, F, G, H, I, K, L, M, N, P, Q, R, S, V, W or Y, preferably to C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L649 to A, C, D, E, F, G, H, I, K, M, N, P, Q, R, S, T, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H650 to A, C, D, E, F, G, I, K, L, M, N, P, Q, R, S, T, V, W or Y, preferably to E, F or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I651 to A, C, D, E, F, G, H, K, L, M, N, P, Q, R, S, T, W or Y, preferably to F, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L652 to A, C, D, E, F, G, H, I, K, M, N, P, Q, R, S, T, V, W or Y, preferably to C, D, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P653 to A, C, D, E, F, G, H, I, K, L, M, N, Q, R, S, T, V, W or Y, preferably to Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A654 to C, D, E, F, G, H, I, K, L, M, N, P, Q, R, S, T, V, W or Y, preferably to D, K, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W655 to A, C, D, E, F, G, H, I, K, L, M, N, P, Q, R, S, T, V or Y, preferably to F or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N656 to A, C, D, E, F, G, H, I, K, L, M, P, Q, R, S, T, V, W or Y, preferably to A, K or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E657 to A, C, D, F, G, H, I, K, L, M, N, P, Q, R, S, T, V, W or Y, preferably to K, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V659 to A, C, D, E, F, G, H, I, K, L, M, N, P, Q, R, S, T, W or Y, preferably to D or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A661 to C, D, E, F, G, H, I, K, L, M, N, P, Q, R, S, T, V, W or Y, preferably to E, G, H, K, L, M, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K662 to A, C, D, E, F, G, H, I, L, M, N, P, Q, R, S, T, V, W or Y, preferably to H, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N667 to A, C, D, E, F, G, H, I, K, L, M, P, Q, R, S, T, V, W or Y, preferably to L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P669 to A, C, D, E, F, G, H, I, K, L, M, N, Q, R, S, T, V, W or Y, preferably to A, E, F, L, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V670 to A, C, D, E, F, G, H, I, K, L, M, N, P, Q, R, S, T, W or Y, preferably to C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V672 to A, C, D, E, F, G, H, I, K, L, M, N, P, Q, R, S, T, W or Y, preferably to L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y673 to A, C, D, E, F, G, H, I, K, L, M, N, P, Q, R, S, T, V or W, preferably to E, G, I, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T674 to A, C, D, E, F, G, H, I, K, L, M, N, P, Q, R, S, V, W or Y, preferably to C, D, G, H, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D675 to A, C, E, F, G, H, I, K, L, M, N, P, Q, R, S, T, V, W or Y, preferably to A, E, P, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A676 to C, D, E, F, G, H, I, K, L, M, N, P, Q, R, S, T, V, W or Y, preferably to C, E, G, K, L, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A677 to C, D, E, F, G, H, I, K, L, M, N, P, Q, R, S, T, V, W or Y, preferably to E, G, L, R, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K678 to A, C, D, E, F, G, H, I, L, M, N, P, Q, R, S, T, V, W or Y, preferably to A, C, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V679 to A, C, D, E, F, G, H, I, K, L, M, N, P, Q, R, S, T, W or Y, preferably to G, Q, S, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K680 to A, C, D, E, F, G, H, I, L, M, N, P, Q, R, S, T, V, W or Y, preferably to A, E, G, H, I, L, N, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L681 to A, C, D, E, F, G, H, I, K, M, N, P, Q, R, S, T, V, W or Y, preferably to E, F, G, M, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y682 to A, C, D, E, F, G, H, I, K, L, M, N, P, Q, R, S, T, V or W, preferably to D, E, I, M, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F683 to A, C, D, E, G, H, I, K, L, M, N, P, Q, R, S, T, V, W or Y, preferably to H, L, M, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T684 to A, C, D, E, F, G, H, I, K, L, M, N, P, Q, R, S, V, W or Y, preferably to A, D, G, L, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P685 to A, C, D, E, F, G, H, I, K, L, M, N, Q, R, S, T, V, W or Y, preferably to A, E, I, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K686 to A, C, D, E, F, G, H, I, L, M, N, P, Q, R, S, T, V, W or Y, preferably to A, E, I, M, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G687 to A, C, D, E, F, H, I, K, L, M, N, P, Q, R, S, T, V, W or Y, preferably to A, K, N, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S688 to A, C, D, E, F, G, H, I, K, L, M, N, P, Q, R, T, V, W or Y, preferably to C, D, E, G, K, L, P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T689 to A, C, D, E, F, G, H, I, K, L, M, N, P, Q, R, S, V, W or Y, preferably to A, D, E, G, L, P, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E690 to A, C, D, F, G, H, I, K, L, M, N, P, Q, R, S, T, V, W or Y, preferably to D, M, P, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K691 to A, C, D, E, F, G, H, I, L, M, N, P, Q, R, S, T, V, W or Y, preferably to E, H, N, P, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R692 to A, C, D, E, F, G, H, I, K, L, M, N, P, Q, S, T, V, W or Y, preferably to G, H, I, L, P, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L693 to A, C, D, E, F, G, H, I, K, M, N, P, Q, R, S, T, V, W or Y, preferably to A, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I694 to A, C, D, E, F, G, H, K, L, M, N, P, Q, R, S, T, V, W or Y, preferably to L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G695 to A, C, D, E, F, H, I, K, L, M, N, P, Q, R, S, T, V, W or Y, preferably to C, K, L, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E696 to A, C, D, F, G, H, I, K, L, M, N, P, Q, R, S, T, V, W or Y, preferably to A, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K697 to A, C, D, E, F, G, H, I, L, M, N, P, Q, R, S, T, V, W or Y, preferably to A, E, G, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S698 to A, C, D, E, F, G, H, I, K, L, M, N, P, Q, R, T, V, W or Y, preferably to C, D, E, I, L, M, P, Q, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T700 to A, C, D, E, F, G, H, I, K, L, M, N, P, Q, R, S, V, W or Y, preferably to A, C, D, E, G, K or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K701 to A, C, D, E, F, G, H, I, L, M, N, P, Q, R, S, T, V, W or Y, preferably to A, D, E, G, H, L, M, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T703 to A, C, D, E, F, G, H, I, K, L, M, N, P, Q, R, S, V, W or Y, preferably to E, I, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T704 to A, C, D, E, F, G, H, I, K, L, M, N, P, Q, R, S, V, W or Y, preferably to M, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A705 to C, D, E, F, G, H, I, K, L, M, N, P, Q, R, S, T, V, W or Y, preferably to C, D, E, K, N, P, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A706 to C, D, E, F, G, H, I, K, L, M, N, P, Q, R, S, T, V, W or Y, preferably to C, G, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y708 to A, C, D, E, F, G, H, I, K, L, M, N, P, Q, R, S, T, V or W, preferably to C, F, G, K, L, P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T709 to A, C, D, E, F, G, H, I, K, L, M, N, P, Q, R, S, V, W or Y, preferably to M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y710 to A, C, D, E, F, G, H, I, K, L, M, N, P, Q, R, S, T, V or W, preferably to C, D, E, G, M, N, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q711 to A, C, D, E, F, G, H, I, K, L, M, N, P, R, S, T, V, W or Y, preferably to A, D, G, L, M, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V712 to A, C, D, E, F, G, H, I, K, L, M, N, P, Q, R, S, T, W or Y, preferably to G, M, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y713 to A, C, D, E, F, G, H, I, K, L, M, N, P, Q, R, S, T, V or W, preferably to A, E, G, L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E714 to A, C, D, F, G, H, I, K, L, M, N, P, Q, R, S, T, V, W or Y, preferably to D, H, I, K, M, N, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G715 to A, C, D, E, F, H, I, K, L, M, N, P, Q, R, S, T, V, W or Y, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A716 to C, D, E, F, G, H, I, K, L, M, N, P, Q, R, S, T, V, W or Y, preferably to C, G, L, M, P, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D717 to A, C, E, F, G, H, I, K, L, M, N, P, Q, R, S, T, V, W or Y, preferably to C, G, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K718 to A, C, D, E, F, G, H, I, L, M, N, P, Q, R, S, T, V, W or Y, preferably to A, L, Q, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D719 to A, C, E, F, G, H, I, K, L, M, N, P, Q, R, S, T, V, W or Y, preferably to E, L, P, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S720 to A, C, D, E, F, G, H, I, K, L, M, N, P, Q, R, T, V, W or Y, preferably to A, M, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T721 to A, C, D, E, F, G, H, I, K, L, M, N, P, Q, R, S, V, W or Y, preferably to D, H, K, L, N, P, Q, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A722 to C, D, E, F, G, H, I, K, L, M, N, P, Q, R, S, T, V, W or Y, preferably to Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H723 to A, C, D, E, F, G, I, K, L, M, N, P, Q, R, S, T, V, W or Y, preferably to G or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K724 to A, C, D, E, F, G, H, I, L, M, N, P, Q, R, S, T, V, W or Y, preferably to A, G or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N725 to A, C, D, E, F, G, H, I, K, L, M, P, Q, R, S, T, V, W or Y, preferably to A, D or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M726 to A, C, D, E, F, G, H, I, K, L, N, P, Q, R, S, T, V, W or Y, preferably to A, D, E, K, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y727 to A, C, D, E, F, G, H, I, K, L, M, N, P, Q, R, S, T, V or W, preferably to L or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L728 to A, C, D, E, F, G, H, I, K, M, N, P, Q, R, S, T, V, W or Y, preferably to C, K, Q, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T729 to A, C, D, E, F, G, H, I, K, L, M, N, P, Q, R, S, V, W or Y, preferably to A, E or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W730 to A, C, D, E, F, G, H, I, K, L, M, N, P, Q, R, S, T, V or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N731 to A, C, D, E, F, G, H, I, K, L, M, P, Q, R, S, T, V, W or Y, preferably to A, E, Q, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V732 to A, C, D, E, F, G, H, I, K, L, M, N, P, Q, R, S, T, W or Y, preferably to G, P, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P733 to A, C, D, E, F, G, H, I, K, L, M, N, Q, R, S, T, V, W or Y, preferably to A, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W734 to A, C, D, E, F, G, H, I, K, L, M, N, P, Q, R, S, T, V or Y, preferably to D, G, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A735 to C, D, E, F, G, H, I, K, L, M, N, P, Q, R, S, T, V, W or Y, preferably to Q, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E736 to A, C, D, F, G, H, I, K, L, M, N, P, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G737 to A, C, D, E, F, H, I, K, L, M, N, P, Q, R, S, T, V, W or Y, preferably to F, K, N or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T738 to A, C, D, E, F, G, H, I, K, L, M, N, P, Q, R, S, V, W or Y, preferably to G, L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I739 to A, C, D, E, F, G, H, K, L, M, N, P, Q, R, S, T, V, W or Y, preferably to E, K, M, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S740 to A, C, D, E, F, G, H, I, K, L, M, N, P, Q, R, T, V, W or Y, preferably to D, E, F, H or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A741 to C, D, E, F, G, H, I, K, L, M, N, P, Q, R, S, T, V, W or Y, preferably to I, P, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E742 to A, C, D, F, G, H, I, K, L, M, N, P, Q, R, S, T, V, W or Y, preferably to D, M, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A743 to C, D, E, F, G, H, I, K, L, M, N, P, Q, R, S, T, V, W or Y, preferably to C, E, H, I or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y744 to A, C, D, E, F, G, H, I, K, L, M, N, P, Q, R, S, T, V or W, preferably to A, E, I, K, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D745 to A, C, E, F, G, H, I, K, L, M, N, P, Q, R, S, T, V, W or Y, preferably to C, F, N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E746 to A, C, D, F, G, H, I, K, L, M, N, P, Q, R, S, T, V, W or Y, preferably to A, C, K or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N747 to A, C, D, E, F, G, H, I, K, L, M, P, Q, R, S, T, V, W or Y, preferably to E, F, G, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N748 to A, C, D, E, F, G, H, I, K, L, M, P, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R749 to A, C, D, E, F, G, H, I, K, L, M, N, P, Q, S, T, V, W or Y, preferably to H, M, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L750 to A, C, D, E, F, G, H, I, K, M, N, P, Q, R, S, T, V, W or Y, preferably to G, M, P, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I751 to A, C, D, E, F, G, H, K, L, M, N, P, Q, R, S, T, V, W or Y, preferably to C, H, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P752 to A, C, D, E, F, G, H, I, K, L, M, N, Q, R, S, T, V, W or Y, preferably to A, C, H, L, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E753 to A, C, D, F, G, H, I, K, L, M, N, P, Q, R, S, T, V, W or Y, preferably to Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G754 to A, C, D, E, F, H, I, K, L, M, N, P, Q, R, S, T, V, W or Y, preferably to H, I, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S755 to A, C, D, E, F, G, H, I, K, L, M, N, P, Q, R, T, V, W or Y, preferably to C, I or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T756 to A, C, D, E, F, G, H, I, K, L, M, N, P, Q, R, S, V, W or Y, preferably to E, N, P, Q, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E757 to A, C, D, F, G, H, I, K, L, M, N, P, Q, R, S, T, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G758 to A, C, D, E, F, H, I, K, L, M, N, P, Q, R, S, T, V, W or Y, preferably to A or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N759 to A, C, D, E, F, G, H, I, K, L, M, P, Q, R, S, T, V, W or Y, preferably to D, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A760 to C, D, E, F, G, H, I, K, L, M, N, P, Q, R, S, T, V, W or Y, preferably to G, N, P or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S761 to A, C, D, E, F, G, H, I, K, L, M, N, P, Q, R, T, V, W or Y, preferably to A, K or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V762 to A, C, D, E, F, G, H, I, K, L, M, N, P, Q, R, S, T, W or Y, preferably to D, G, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T765 to A, C, D, E, F, G, H, I, K, L, M, N, P, Q, R, S, V, W or Y, preferably to A, P, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G766 to A, C, D, E, F, H, I, K, L, M, N, P, Q, R, S, T, V, W or Y, preferably to M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A768 to C, D, E, F, G, H, I, K, L, M, N, P, Q, R, S, T, V, W or Y, preferably to H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A769 to C, D, E, F, G, H, I, K, L, M, N, P, Q, R, S, T, V, W or Y, preferably to F, G, I, N, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K770 to A, C, D, E, F, G, H, I, L, M, N, P, Q, R, S, T, V, W or Y, preferably to H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L771 to A, C, D, E, F, G, H, I, K, M, N, P, Q, R, S, T, V, W or Y, preferably to A or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K772 to A, C, D, E, F, G, H, I, L, M, N, P, Q, R, S, T, V, W or Y, preferably to A, C, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A773 to C, D, E, F, G, H, I, K, L, M, N, P, Q, R, S, T, V, W or Y, preferably to C, G, H, M, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D774 to A, C, E, F, G, H, I, K, L, M, N, P, Q, R, S, T, V, W or Y, preferably to A or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A775 to C, D, E, F, G, H, I, K, L, M, N, P, Q, R, S, T, V, W or Y, preferably to L, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D776 to A, C, E, F, G, H, I, K, L, M, N, P, Q, R, S, T, V, W or Y, preferably to I, L, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R777 to A, C, D, E, F, G, H, I, K, L, M, N, P, Q, S, T, V, W or Y, preferably to D, E, G, H, P, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K778 to A, C, D, E, F, G, H, I, L, M, N, P, Q, R, S, T, V, W or Y, preferably to A, C, F, G, L, N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T779 to A, C, D, E, F, G, H, I, K, L, M, N, P, Q, R, S, V, W or Y, preferably to C or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I780 to A, C, D, E, F, G, H, K, L, M, N, P, Q, R, S, T, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T781 to A, C, D, E, F, G, H, I, K, L, M, N, P, Q, R, S, V, W or Y, preferably to A, C, E, F, G, M, P, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A782 to C, D, E, F, G, H, I, K, L, M, N, P, Q, R, S, T, V, W or Y, preferably to C, E, K, N, P, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D783 to A, C, E, F, G, H, I, K, L, M, N, P, Q, R, S, T, V, W or Y, preferably to A, C, E or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G784 to A, C, D, E, F, H, I, K, L, M, N, P, Q, R, S, T, V, W or Y, preferably to A, F, L, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K785 to A, C, D, E, F, G, H, I, L, M, N, P, Q, R, S, T, V, W or Y, preferably to C, I, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D786 to A, C, E, F, G, H, I, K, L, M, N, P, Q, R, S, T, V, W or Y, preferably to S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L787 to A, C, D, E, F, G, H, I, K, M, N, P, Q, R, S, T, V, W or Y, preferably to D, K, P, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S788 to A, C, D, E, F, G, H, I, K, L, M, N, P, Q, R, T, V, W or Y, preferably to A, G or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y789 to A, C, D, E, F, G, H, I, K, L, M, N, P, Q, R, S, T, V or W, preferably to C, D, I or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I790 to A, C, D, E, F, G, H, K, L, M, N, P, Q, R, S, T, V, W or Y, preferably to A, C, F, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E791 to A, C, D, F, G, H, I, K, L, M, N, P, Q, R, S, T, V, W or Y, preferably to A, D, F, M, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V792 to A, C, D, E, F, G, H, I, K, L, M, N, P, Q, R, S, T, W or Y, preferably to C, G, L, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D793 to A, C, E, F, G, H, I, K, L, M, N, P, Q, R, S, T, V, W or Y, preferably to C, F, H, K, N or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V794 to A, C, D, E, F, G, H, I, K, L, M, N, P, Q, R, S, T, W or Y, preferably to C, D, L, Q, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T795 to A, C, D, E, F, G, H, I, K, L, M, N, P, Q, R, S, V, W or Y, preferably to P or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D796 to A, C, E, F, G, H, I, K, L, M, N, P, Q, R, S, T, V, W or Y, preferably to M, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A797 to C, D, E, F, G, H, I, K, L, M, N, P, Q, R, S, T, V, W or Y, preferably to H or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N798 to A, C, D, E, F, G, H, I, K, L, M, P, Q, R, S, T, V, W or Y, preferably to G, I, P or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G799 to A, C, D, E, F, H, I, K, L, M, N, P, Q, R, S, T, V, W or Y, preferably to D, K, L, M, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H800 to A, C, D, E, F, G, I, K, L, M, N, P, Q, R, S, T, V, W or Y, preferably to A, F, G, L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I801 to A, C, D, E, F, G, H, K, L, M, N, P, Q, R, S, T, V, W or Y, preferably to C, E or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V802 to A, C, D, E, F, G, H, I, K, L, M, N, P, Q, R, S, T, W or Y, preferably to E, I, P, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P803 to A, C, D, E, F, G, H, I, K, L, M, N, Q, R, S, T, V, W or Y, preferably to A, F, G, K, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D804 to A, C, E, F, G, H, I, K, L, M, N, P, Q, R, S, T, V, W or Y, preferably to E, G, K, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A805 to C, D, E, F, G, H, I, K, L, M, N, P, Q, R, S, T, V, W or Y, preferably to C, F, G, I, N or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A806 to C, D, E, F, G, H, I, K, L, M, N, P, Q, R, S, T, V, W or Y, preferably to F, I or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N807 to A, C, D, E, F, G, H, I, K, L, M, P, Q, R, S, T, V, W or Y, preferably to F, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R808 to A, C, D, E, F, G, H, I, K, L, M, N, P, Q, S, T, V, W or Y, preferably to C, F, G, I, N, P or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V809 to A, C, D, E, F, G, H, I, K, L, M, N, P, Q, R, S, T, W or Y, preferably to A, C, L, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T810 to A, C, D, E, F, G, H, I, K, L, M, N, P, Q, R, S, V, W or Y, preferably to L, P, Q, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F811 to A, C, D, E, G, H, I, K, L, M, N, P, Q, R, S, T, V, W or Y, preferably to L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D812 to A, C, E, F, G, H, I, K, L, M, N, P, Q, R, S, T, V, W or Y, preferably to E, F, I or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V813 to A, C, D, E, F, G, H, I, K, L, M, N, P, Q, R, S, T, W or Y, preferably to F, H, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K814 to A, C, D, E, F, G, H, I, L, M, N, P, Q, R, S, T, V, W or Y, preferably to G, H, I, L or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G815 to A, C, D, E, F, H, I, K, L, M, N, P, Q, R, S, T, V, W or Y, preferably to A, F, M, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A816 to C, D, E, F, G, H, I, K, L, M, N, P, Q, R, S, T, V, W or Y, preferably to C, D, F, I, N, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G817 to A, C, D, E, F, H, I, K, L, M, N, P, Q, R, S, T, V, W or Y, preferably to C, H, I, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K818 to A, C, D, E, F, G, H, I, L, M, N, P, Q, R, S, T, V, W or Y, preferably to D, F, L, Q, R, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L819 to A, C, D, E, F, G, H, I, K, M, N, P, Q, R, S, T, V, W or Y, preferably to F or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V820 to A, C, D, E, F, G, H, I, K, L, M, N, P, Q, R, S, T, W or Y, preferably to C, F, I, K, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G821 to A, C, D, E, F, H, I, K, L, M, N, P, Q, R, S, T, V, W or Y, preferably to A, C, E, F, I, K, M, N, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V822 to A, C, D, E, F, G, H, I, K, L, M, N, P, Q, R, S, T, W or Y, preferably to A, D, E or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D823 to A, C, E, F, G, H, I, K, L, M, N, P, Q, R, S, T, V, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N824 to A, C, D, E, F, G, H, I, K, L, M, P, Q, R, S, T, V, W or Y, preferably to A, C, G or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G825 to A, C, D, E, F, H, I, K, L, M, N, P, Q, R, S, T, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S826 to A, C, D, E, F, G, H, I, K, L, M, N, P, Q, R, T, V, W or Y, preferably to A, F, G, I, L, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S827 to A, C, D, E, F, G, H, I, K, L, M, N, P, Q, R, T, V, W or Y, preferably to C or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P828 to A, C, D, E, F, G, H, I, K, L, M, N, Q, R, S, T, V, W or Y, preferably to C, G, I, L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D829 to A, C, E, F, G, H, I, K, L, M, N, P, Q, R, S, T, V, W or Y, preferably to C, I, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H830 to A, C, D, E, F, G, I, K, L, M, N, P, Q, R, S, T, V, W or Y, preferably to E, G, M, P, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D831 to A, C, E, F, G, H, I, K, L, M, N, P, Q, R, S, T, V, W or Y, preferably to A, F, G, I, M, P, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S832 to A, C, D, E, F, G, H, I, K, L, M, N, P, Q, R, T, V, W or Y, preferably to E, F, G, L, M, P, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y833 to A, C, D, E, F, G, H, I, K, L, M, N, P, Q, R, S, T, V or W, preferably to C, D, E, I, K, N, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q834 to A, C, D, E, F, G, H, I, K, L, M, N, P, R, S, T, V, W or Y, preferably to F, G or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A835 to C, D, E, F, G, H, I, K, L, M, N, P, Q, R, S, T, V, W or Y, preferably to D, E, F, H, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D836 to A, C, E, F, G, H, I, K, L, M, N, P, Q, R, S, T, V, W or Y, preferably to C, E, H, Q, R, S, T, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N837 to A, C, D, E, F, G, H, I, K, L, M, P, Q, R, S, T, V, W or Y, preferably to D, F, G, H, L, P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R838 to A, C, D, E, F, G, H, I, K, L, M, N, P, Q, S, T, V, W or Y, preferably to D, F, G, K, M, N, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K839 to A, C, D, E, F, G, H, I, L, M, N, P, Q, R, S, T, V, W or Y, preferably to A, C, D, E, G, L, N, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A840 to C, D, E, F, G, H, I, K, L, M, N, P, Q, R, S, T, V, W or Y, preferably to G, I, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F841 to A, C, D, E, G, H, I, K, L, M, N, P, Q, R, S, T, V, W or Y, preferably to C, D, I, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S842 to A, C, D, E, F, G, H, I, K, L, M, N, P, Q, R, T, V, W or Y, preferably to A, L or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G843 to A, C, D, E, F, H, I, K, L, M, N, P, Q, R, S, T, V, W or Y, preferably to A or C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K844 to A, C, D, E, F, G, H, I, L, M, N, P, Q, R, S, T, V, W or Y, preferably to A, G, L, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V845 to A, C, D, E, F, G, H, I, K, L, M, N, P, Q, R, S, T, W or Y, preferably to N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L846 to A, C, D, E, F, G, H, I, K, M, N, P, Q, R, S, T, V, W or Y, preferably to G, I, M or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A847 to C, D, E, F, G, H, I, K, L, M, N, P, Q, R, S, T, V, W or Y, preferably to L or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I848 to A, C, D, E, F, G, H, K, L, M, N, P, Q, R, S, T, V, W or Y, preferably to M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V849 to A, C, D, E, F, G, H, I, K, L, M, N, P, Q, R, S, T, W or Y, preferably to A, L, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q850 to A, C, D, E, F, G, H, I, K, L, M, N, P, R, S, T, V, W or Y, preferably to C, G, I, L, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S851 to A, C, D, E, F, G, H, I, K, L, M, N, P, Q, R, T, V, W or Y, preferably to C, D, E, L or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T852 to A, C, D, E, F, G, H, I, K, L, M, N, P, Q, R, S, V, W or Y, preferably to D, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K853 to A, C, D, E, F, G, H, I, L, M, N, P, Q, R, S, T, V, W or Y, preferably to N, P, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E854 to A, C, D, F, G, H, I, K, L, M, N, P, Q, R, S, T, V, W or Y, preferably to C, I, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A855 to C, D, E, F, G, H, I, K, L, M, N, P, Q, R, S, T, V, W or Y, preferably to K, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E857 to A, C, D, F, G, H, I, K, L, M, N, P, Q, R, S, T, V, W or Y, preferably to P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I858 to A, C, D, E, F, G, H, K, L, M, N, P, Q, R, S, T, V, W or Y, preferably to D, E, F, G, K, M, P, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T859 to A, C, D, E, F, G, H, I, K, L, M, N, P, Q, R, S, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V860 to A, C, D, E, F, G, H, I, K, L, M, N, P, Q, R, S, T, W or Y, preferably to T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T861 to A, C, D, E, F, G, H, I, K, L, M, N, P, Q, R, S, V, W or Y, preferably to F, I, Q, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A862 to C, D, E, F, G, H, I, K, L, M, N, P, Q, R, S, T, V, W or Y, preferably to C, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K863 to A, C, D, E, F, G, H, I, L, M, N, P, Q, R, S, T, V, W or Y, preferably to F, I, L, N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A864 to C, D, E, F, G, H, I, K, L, M, N, P, Q, R, S, T, V, W or Y, preferably to E, H, K or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D865 to A, C, E, F, G, H, I, K, L, M, N, P, Q, R, S, T, V, W or Y, preferably to A or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G866 to A, C, D, E, F, H, I, K, L, M, N, P, Q, R, S, T, V, W or Y, preferably to H or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L867 to A, C, D, E, F, G, H, I, K, M, N, P, Q, R, S, T, V, W or Y, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S870 to A, C, D, E, F, G, H, I, K, L, M, N, P, Q, R, T, V, W or Y, preferably to E, M, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T871 to A, C, D, E, F, G, H, I, K, L, M, N, P, Q, R, S, V, W or Y, preferably to P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V872 to A, C, D, E, F, G, H, I, K, L, M, N, P, Q, R, S, T, W or Y, preferably to C or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K873 to A, C, D, E, F, G, H, I, L, M, N, P, Q, R, S, T, V, W or Y, preferably to G or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I874 to A, C, D, E, F, G, H, K, L, M, N, P, Q, R, S, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A875 to C, D, E, F, G, H, I, K, L, M, N, P, Q, R, S, T, V, W or Y, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T877 to A, C, D, E, F, G, H, I, K, L, M, N, P, Q, R, S, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V879 to A, C, D, E, F, G, H, I, K, L, M, N, P, Q, R, S, T, W or Y, preferably to P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P880 to A, C, D, E, F, G, H, I, K, L, M, N, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G881 to A, C, D, E, F, H, I, K, L, M, N, P, Q, R, S, T, V, W or Y, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T882 to A, C, D, E, F, G, H, I, K, L, M, N, P, Q, R, S, V, W or Y, preferably to A, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S883 to A, C, D, E, F, G, H, I, K, L, M, N, P, Q, R, T, V, W or Y, preferably to L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T884 to A, C, D, E, F, G, H, I, K, L, M, N, P, Q, R, S, V, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E885 to A, C, D, F, G, H, I, K, L, M, N, P, Q, R, S, T, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K886 to A, C, D, E, F, G, H, I, L, M, N, P, Q, R, S, T, V, W or Y, preferably to E, L, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T887 to A, C, D, E, F, G, H, I, K, L, M, N, P, Q, R, S, V, W or Y, preferably to A, D, F, G, N, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V888 to A, C, D, E, F, G, H, I, K, L, M, N, P, Q, R, S, T, W or Y, preferably to A, D or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R889 to A, C, D, E, F, G, H, I, K, L, M, N, P, Q, S, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y892 to A, C, D, E, F, G, H, I, K, L, M, N, P, Q, R, S, T, V or W, preferably to D, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y893 to A, C, D, E, F, G, H, I, K, L, M, N, P, Q, R, S, T, V or W, preferably to E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S894 to A, C, D, E, F, G, H, I, K, L, M, N, P, Q, R, T, V, W or Y, preferably to D or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R895 to A, C, D, E, F, G, H, I, K, L, M, N, P, Q, S, T, V, W or Y, preferably to M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N896 to A, C, D, E, F, G, H, I, K, L, M, P, Q, R, S, T, V, W or Y, preferably to M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y897 to A, C, D, E, F, G, H, I, K, L, M, N, P, Q, R, S, T, V or W, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y898 to A, C, D, E, F, G, H, I, K, L, M, N, P, Q, R, S, T, V or W, preferably to T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V899 to A, C, D, E, F, G, H, I, K, L, M, N, P, Q, R, S, T, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K900 to A, C, D, E, F, G, H, I, L, M, N, P, Q, R, S, T, V, W or Y, preferably to E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T901 to A, C, D, E, F, G, H, I, K, L, M, N, P, Q, R, S, V, W or Y, preferably to G, Q, R, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G902 to A, C, D, E, F, H, I, K, L, M, N, P, Q, R, S, T, V, W or Y, preferably to A, D, F, L, P, Q, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N903 to A, C, D, E, F, G, H, I, K, L, M, P, Q, R, S, T, V, W or Y, preferably to D or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K904 to A, C, D, E, F, G, H, I, L, M, N, P, Q, R, S, T, V, W or Y, preferably to D, E, M, N, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P905 to A, C, D, E, F, G, H, I, K, L, M, N, Q, R, S, T, V, W or Y, preferably to A, C, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I906 to A, C, D, E, F, G, H, K, L, M, N, P, Q, R, S, T, V, W or Y, preferably to A, D, N, S, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L907 to A, C, D, E, F, G, H, I, K, M, N, P, Q, R, S, T, V, W or Y, preferably to F, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P908 to A, C, D, E, F, G, H, I, K, M, N, Q, R, S, T, V, W or Y, preferably to C, D, G, I, L, M or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S909 to A, C, D, E, F, G, H, I, K, L, M, N, P, Q, R, T, V, W or Y, preferably to E, F, G, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D910 to A, C, E, F, G, H, I, K, L, M, N, P, Q, R, S, T, V, W or Y, preferably to C, I, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V911 to A, C, D, E, F, G, H, I, K, L, M, N, P, Q, R, S, T, W or Y, preferably to A or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E912 to A, C, D, F, G, H, I, K, L, M, N, P, Q, R, S, T, V, W or Y, preferably to A, K, L, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V913 to A, C, D, E, F, G, H, I, K, L, M, N, P, Q, R, S, T, W or Y, preferably to G, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R914 to A, C, D, E, F, G, H, I, K, L, M, N, P, Q, S, T, V, W or Y, preferably to A, E, F, I, K, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y915 to A, C, D, E, F, G, H, I, K, L, M, N, P, Q, R, S, T, V or W, preferably to A, C, G, I, M, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S916 to A, C, D, E, F, G, H, I, K, L, M, N, P, Q, R, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D917 to A, C, E, F, G, H, I, K, L, M, N, P, Q, R, S, T, V, W or Y, preferably to C, E, F, L, M, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G918 to A, C, D, E, F, H, I, K, L, M, N, P, Q, R, S, T, V, W or Y, preferably to E, H, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T919 to A, C, D, E, F, G, H, I, K, L, M, N, P, Q, R, S, V, W or Y, preferably to D, K, Q, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S920 to A, C, D, E, F, G, H, I, K, L, M, N, P, Q, R, T, V, W or Y, preferably to C, E, M, P, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D921 to A, C, E, F, G, H, I, K, L, M, N, P, Q, R, S, T, V, W or Y, preferably to C, P, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R922 to A, C, D, E, F, G, H, I, K, L, M, N, P, Q, S, T, V, W or Y, preferably to A, G, M, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q923 to A, C, D, E, F, G, H, I, K, L, M, N, P, R, S, T, V, W or Y, preferably to A, C, E, L, M, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N924 to A, C, D, E, F, G, H, I, K, L, M, P, Q, R, S, T, V, W or Y, preferably to A, L, P, Q, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V925 to A, C, D, E, F, G, H, I, K, L, M, N, P, Q, R, S, T, W or Y, preferably to A, C, E, G, K, N, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T926 to A, C, D, E, F, G, H, I, K, L, M, N, P, Q, R, S, V, W or Y, preferably to G, P, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W927 to A, C, D, E, F, G, H, I, K, L, M, N, P, Q, R, S, T, V or Y, preferably to C, G or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D928 to A, C, E, F, G, H, I, K, L, M, N, P, Q, R, S, T, V, W or Y, preferably to A, E, H, L or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A929 to C, D, E, F, G, H, I, K, L, M, N, P, Q, R, S, T, V, W or Y, preferably to C, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V930 to A, C, D, E, F, G, H, I, K, L, M, N, P, Q, R, S, T, W or Y, preferably to A, E, I, K, M or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S931 to A, C, D, E, F, G, H, I, K, L, M, N, P, Q, R, T, V, W or Y, preferably to G, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D932 to A, C, E, F, G, H, I, K, L, M, N, P, Q, R, S, T, V, W or Y, preferably to F, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D933 to A, C, E, F, G, H, I, K, L, M, N, P, Q, R, S, T, V, W or Y, preferably to I, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q934 to A, C, D, E, F, G, H, I, K, L, M, N, P, R, S, T, V, W or Y, preferably to S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I935 to A, C, D, E, F, G, H, K, L, M, N, P, Q, R, S, T, V, W or Y, preferably to A, C, D, E, L, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A936 to C, D, E, F, G, H, I, K, L, M, N, P, Q, R, S, T, V, W or Y, preferably to I, L, Q, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K937 to A, C, D, E, F, G, H, I, L, M, N, P, Q, R, S, T, V, W or Y, preferably to G, I, M, P, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A938 to C, D, E, F, G, H, I, K, L, M, N, P, Q, R, S, T, V, W or Y, preferably to C, H, N, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G939 to A, C, D, E, F, H, I, K, L, M, N, P, Q, R, S, T, V, W or Y, preferably to D or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S940 to A, C, D, E, F, G, H, I, K, L, M, N, P, Q, R, T, V, W or Y, preferably to C, E, M, R, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F941 to A, C, D, E, G, H, I, K, L, M, N, P, Q, R, S, T, V, W or Y, preferably to C, M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S942 to A, C, D, E, F, G, H, I, K, L, M, N, P, Q, R, T, V, W or Y, preferably to A, E, K, L, P, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V943 to A, C, D, E, F, G, H, I, K, L, M, N, P, Q, R, S, T, W or Y, preferably to A, G, H, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A944 to C, D, E, F, G, H, I, K, L, M, N, P, Q, R, S, T, V, W or Y, preferably to D, G, H, P, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G945 to A, C, D, E, F, H, I, K, L, M, N, P, Q, R, S, T, V, W or Y, preferably to E, P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T946 to A, C, D, E, F, G, H, I, K, L, M, N, P, Q, R, S, V, W or Y, preferably to A, E, G, L, P, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V947 to A, C, D, E, F, G, H, I, K, L, M, N, P, Q, R, S, T, W or Y, preferably to G, H, L, M, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A948 to C, D, E, F, G, H, I, K, L, M, N, P, Q, R, S, T, V, W or Y, preferably to C, I, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G949 to A, C, D, E, F, H, I, K, L, M, N, P, Q, R, S, T, V, W or Y, preferably to A, F or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q950 to A, C, D, E, F, G, H, I, K, L, M, N, P, R, S, T, V, W or Y, preferably to D, G, K, M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K951 to A, C, D, E, F, G, H, I, L, M, N, P, Q, R, S, T, V, W or Y, preferably to D, G, P, Q, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I952 to A, C, D, E, F, G, H, K, L, M, N, P, Q, R, S, T, V, W or Y, preferably to H or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S953 to A, C, D, E, F, G, H, I, K, L, M, N, P, Q, R, T, V, W or Y, preferably to F, M, N, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V954 to A, C, D, E, F, G, H, I, K, L, M, N, P, Q, R, S, T, W or Y, preferably to D, L, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R955 to A, C, D, E, F, G, H, I, K, L, M, N, P, Q, S, T, V, W or Y, preferably to A, C, E, K, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V956 to A, C, D, E, F, G, H, I, K, L, M, N, P, Q, R, S, T, W or Y, preferably to A, D, G, H, I, M, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T957 to A, C, D, E, F, G, H, I, K, L, M, N, P, Q, R, S, V, W or Y, preferably to D, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M958 to A, C, D, E, F, G, H, I, K, L, N, P, Q, R, S, T, V, W or Y, preferably to D, I or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I959 to A, C, D, E, F, G, H, K, L, M, N, P, Q, R, S, T, V, W or Y, preferably to A, L, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D960 to A, C, E, F, G, H, I, K, L, M, N, P, Q, R, S, T, V, W or Y, preferably to G, H, L, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E961 to A, C, D, F, G, H, I, K, L, M, N, P, Q, R, S, T, V, W or Y, preferably to D, F, K, P, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I962 to A, C, D, E, F, G, H, K, L, M, N, P, Q, R, S, T, V, W or Y, preferably to A, C, D, G, K, N, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G963 to A, C, D, E, F, H, I, K, L, M, N, P, Q, R, S, T, V, W or Y, preferably to C, E, L or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A964 to C, D, E, F, G, H, I, K, L, M, N, P, Q, R, S, T, V, W or Y, preferably to C, E or H, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L965 to A, C, D, E, F, G, H, I, K, M, N, P, Q, R, S, T, V, W or Y, preferably to C, E, G, K, M, P, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L966 to A, C, D, E, F, G, H, I, K, M, N, P, Q, R, S, T, V, W or Y, preferably to A, G, H, K, N, P, Q, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N967 to A, C, D, E, F, G, H, I, K, L, M, P, Q, R, S, T, V, W or Y, preferably to C, D, I, L, M, P, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y968 to A, C, D, E, F, G, H, I, K, L, M, N, P, Q, R, S, T, V or W, preferably to G, L, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S969 to A, C, D, E, F, G, H, I, K, L, M, N, P, Q, R, T, V, W or Y, preferably to C, D, G, H, I, L, M, P, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A970 to C, D, E, F, G, H, I, K, L, M, N, P, Q, R, S, T, V, W or Y, preferably to I or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S971 to A, C, D, E, F, G, H, I, K, L, M, N, P, Q, R, T, V, W or Y, preferably to E, F, G, H, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P973 to A, C, D, E, F, G, H, I, K, L, M, N, Q, R, S, T, V, W or Y, preferably to C, D, K, N, Q, R, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V974 to A, C, D, E, F, G, H, I, K, L, M, N, P, Q, R, S, T, W or Y, preferably to C, E, G, N, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G975 to A, C, D, E, F, H, I, K, L, M, N, P, Q, R, S, T, V, W or Y, preferably to D, F, K, L, Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T976 to A, C, D, E, F, G, H, I, K, L, M, N, P, Q, R, S, V, W or Y, preferably to D, F, G, K, L, P, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P977 to A, C, D, E, F, G, H, I, K, L, M, N, Q, R, S, T, V, W or Y, preferably to A, C, K, R, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A978 to C, D, E, F, G, H, I, K, L, M, N, P, Q, R, S, T, V, W or Y, preferably to F, G, M, N, P, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V979 to A, C, D, E, F, G, H, I, K, L, M, N, P, Q, R, S, T, W or Y, preferably to G, N, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L980 to A, C, D, E, F, G, H, I, K, M, N, P, Q, R, S, T, V, W or Y, preferably to A, F, H, I, K, N, Q, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P981 to A, C, D, E, F, G, H, I, K, L, M, N, Q, R, S, T, V, W or Y, preferably to L or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G982 to A, C, D, E, F, H, I, K, L, M, N, P, Q, R, S, T, V, W or Y, preferably to A, H, M, P, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R984 to A, C, D, E, F, G, H, I, K, L, M, N, P, Q, S, T, V, W or Y, preferably to P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P985 to A, C, D, E, F, G, H, I, K, L, M, N, Q, R, S, T, V, W or Y, preferably to E, F, H, K, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A986 to C, D, E, F, G, H, I, K, L, M, N, P, Q, R, S, T, V, W or Y, preferably to C, E, F, I, K, L, M, N, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V987 to A, C, D, E, F, G, H, I, K, L, M, N, P, Q, R, S, T, W or Y, preferably to A, C, F, I, K, L, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L988 to A, C, D, E, F, G, H, I, K, M, N, P, Q, R, S, T, V, W or Y, preferably to A, C, E, G, H, M, Q, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P989 to A, C, D, E, F, G, H, I, K, L, M, N, Q, R, S, T, V, W or Y, preferably to A, C, D, G, H, I, M, N, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D990 to A, C, E, F, G, H, I, K, L, M, N, P, Q, R, S, T, V, W or Y, preferably to F, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G991 to A, C, D, E, F, H, I, K, L, M, N, P, Q, R, S, T, V, W or Y, preferably to C, F, H, K, P or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T992 to A, C, D, E, F, G, H, I, K, L, M, N, P, Q, R, S, V, W or Y, preferably to E, H, M, N or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V993 to A, C, D, E, F, G, H, I, K, L, M, N, P, Q, R, S, T, W or Y, preferably to D, G, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T994 to A, C, D, E, F, G, H, I, K, L, M, N, P, Q, R, S, V, W or Y, preferably to I, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S995 to A, C, D, E, F, G, H, I, K, L, M, N, P, Q, R, T, V, W or Y, preferably to E, L, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A996 to C, D, E, F, G, H, I, K, L, M, N, P, Q, R, S, T, V, W or Y, preferably to Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N997 to A, C, D, E, F, G, H, I, K, L, M, P, Q, R, S, T, V, W or Y, preferably to A, C, E, K, L, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F998 to A, C, D, E, G, H, I, K, L, M, N, P, Q, R, S, T, V, W or Y, preferably to M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A999 to C, D, E, F, G, H, I, K, L, M, N, P, Q, R, S, T, V, W or Y, preferably to F, G, L, M, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1000 to A, C, D, E, F, G, H, I, K, L, M, N, P, Q, R, S, T, W or Y, preferably to C, L, M, N, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1001 to A, C, E, F, G, H, I, K, L, M, N, P, Q, R, S, T, V, W or Y, preferably to G, K, L, M, Q, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W1002 to A, C, D, E, F, G, H, I, K, L, M, N, P, Q, R, S, T, V or Y, preferably to A, D, E, H, N, P, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1003 to A, C, D, E, F, G, H, I, K, L, M, N, P, Q, R, S, V, W or Y, preferably to F, G, L, N, P, R, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1004 to A, C, D, E, F, G, H, I, L, M, N, P, Q, R, S, T, V, W or Y, preferably to D, E, F, G, H, M, P, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1005 to A, C, D, E, F, G, H, I, K, L, M, N, Q, R, S, T, V, W or Y, preferably to I, N, Q, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1006 to C, D, E, F, G, H, I, K, L, M, N, P, Q, R, S, T, V, W or Y, preferably to C, I, N, P, S, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1007 to A, C, E, F, G, H, I, K, L, M, N, P, Q, R, S, T, V, W or Y, preferably to C, L, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1008 to A, C, D, E, F, G, H, I, K, L, M, N, P, Q, R, S, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1009 to A, C, D, E, F, G, H, I, K, L, M, N, P, Q, R, S, T, W or Y, preferably to G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1010 to A, C, D, E, F, G, H, I, K, L, M, N, P, Q, R, S, T, V or W, preferably to A, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1011 to A, C, D, E, F, G, H, I, K, L, M, P, Q, R, S, T, V, W or Y, preferably to A, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1012 to A, C, D, E, F, G, H, I, K, L, M, N, P, Q, R, S, V, W or Y, preferably to E, H, I, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1013 to C, D, E, F, G, H, I, K, L, M, N, P, Q, R, S, T, V, W or Y, preferably to D, K, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1014 to A, C, D, E, F, H, I, K, L, M, N, P, Q, R, S, T, V, W or Y, preferably to E, I, L, M, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1015 to A, C, D, E, F, G, H, I, K, L, M, N, P, Q, R, S, V, W or Y, preferably to A, F, G or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1016 to A, C, D, E, F, G, H, I, K, L, M, N, P, Q, R, S, T, W or Y, preferably to C, D or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1017 to A, C, D, E, F, G, H, I, L, M, N, P, Q, R, S, T, V, W or Y, preferably to E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1018 to A, C, D, E, F, G, H, I, K, L, M, N, P, Q, R, S, T, W or Y, preferably to I, K, L, M, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1021 to A, C, D, E, F, G, H, I, K, L, M, N, P, Q, R, S, V, W or Y, preferably to C, E, F, G, K, L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1022 to C, D, E, F, G, H, I, K, L, M, N, P, Q, R, S, T, V, W or Y, preferably to H, L, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1023 to A, C, D, E, F, G, H, I, K, L, M, N, P, Q, R, S, V, W or Y, preferably to D, M, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1024 to A, C, D, E, F, G, H, I, K, L, M, N, P, Q, R, S, T, W or Y, preferably to E, G, H, K, N, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1026 to A, C, D, E, F, H, I, K, L, M, N, P, Q, R, S, T, V, W or Y, preferably to E, H, L, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1027 to A, C, D, E, F, G, H, I, L, M, N, P, Q, R, S, T, V, W or Y, preferably to C, N, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1028 to A, C, D, F, G, H, I, K, L, M, N, P, Q, R, S, T, V, W or Y, preferably to G, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1029 to A, C, D, E, G, H, I, K, L, M, N, P, Q, R, S, T, V, W or Y, preferably to I, K, L, P, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1030 to A, C, D, E, F, G, H, I, L, M, N, P, Q, R, S, T, V, W or Y, preferably to D, F, H, L, M or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1031 to A, C, D, E, F, G, H, I, K, L, M, N, P, Q, R, S, T, W or Y, preferably to H, K or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1033 to C, D, E, F, G, H, I, K, L, M, N, P, Q, R, S, T, V, W or Y, preferably to G, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1034 to A, C, D, E, F, G, H, I, K, L, M, N, P, Q, R, S, V, W or Y, preferably to G, H, N or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1035 to A, C, D, E, F, G, H, K, L, M, N, P, Q, R, S, T, V, W or Y, preferably to D, G or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1036 to A, C, D, E, F, G, H, I, K, L, M, N, P, Q, S, T, V, W or Y, preferably to G, L, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1037 to A, C, D, E, F, G, H, I, K, L, M, N, P, Q, R, S, T, W or Y, preferably to C, F, P or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1038 to A, C, D, E, F, G, H, I, K, L, M, N, P, R, S, T, V, W or Y, preferably to A, D or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1039 to A, C, D, E, F, G, H, I, K, L, M, N, P, Q, S, T, V, W or Y, preferably to S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1040 to A, C, D, E, F, G, H, I, K, L, M, N, P, Q, R, T, V, W or Y, preferably to A, M, N, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1041 to A, C, D, E, F, G, H, I, K, L, M, N, P, R, S, T, V, W or Y, preferably to P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1042 to A, C, D, E, F, G, H, I, K, L, M, N, P, Q, R, S, T, W or Y, preferably to N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1043 to A, C, D, E, F, G, H, I, K, L, M, N, P, Q, R, S, V, W or Y, preferably to F, G, N or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1044 to A, C, D, E, F, G, H, K, L, M, N, P, Q, R, S, T, V, W or Y, preferably to A or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1045 to A, C, D, E, F, H, I, K, L, M, N, P, Q, R, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1046 to A, C, D, E, F, G, H, I, K, L, M, N, P, Q, R, T, V, W or Y, preferably to I or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1047 to A, C, D, E, F, G, H, I, K, L, M, N, P, Q, R, T, V, W or Y, preferably to D, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1048 to A, C, D, E, F, G, H, I, K, L, M, N, P, Q, R, S, T, W or Y, preferably to C, F, G, I, M or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1050 to A, C, D, E, F, H, I, K, L, M, N, P, Q, R, S, T, V, W or Y, preferably to L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1051 to A, C, D, E, F, G, H, I, K, L, M, P, Q, R, S, T, V, W or Y, preferably to A, E or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1052 to C, D, E, F, G, H, I, K, L, M, N, P, Q, R, S, T, V, W or Y, preferably to C, K, M, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1053 to A, C, D, E, F, G, H, I, K, M, N, P, Q, R, S, T, V, W or Y, preferably to A or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1054 to A, C, D, E, F, G, H, I, K, L, M, N, P, Q, S, T, V, W or Y, preferably to C, L or N, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1055 to A, C, D, E, F, G, H, I, K, M, N, P, Q, R, S, T, V, W or Y, preferably to R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1057 to A, C, D, E, F, G, H, I, K, L, M, N, P, R, S, T, V, W or Y, preferably to A, E, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1058 to A, C, D, E, F, G, H, I, K, L, M, P, Q, R, S, T, V, W or Y, preferably to R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1059 to A, C, D, E, F, G, H, K, L, M, N, P, Q, R, S, T, V, W or Y, preferably to W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1060 to A, C, D, E, F, G, H, I, K, L, M, N, Q, R, S, T, V, W or Y, preferably to G, N, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1061 to C, D, E, F, G, H, I, K, L, M, N, P, Q, R, S, T, V, W or Y, preferably to E, G, K or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1062 to A, C, E, F, G, H, I, K, L, M, N, P, Q, R, S, T, V, W or Y, preferably to A, F, G, I, L, M, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1063 to A, C, D, E, F, G, H, I, L, M, N, P, Q, R, S, T, V, W or Y, preferably to D or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1064 to A, C, D, E, F, G, H, I, K, L, M, N, P, R, S, T, V, W or Y, preferably to C, M, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1065 to A, C, D, E, F, G, H, I, K, L, M, N, P, Q, R, T, V, W or Y, preferably to A, C, E, G, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1066 to A, C, E, F, G, H, I, K, L, M, N, P, Q, R, S, T, V, W or Y, preferably to A, G, M, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1067 to A, C, D, E, F, G, H, I, K, L, M, N, P, Q, R, S, V, W or Y, preferably to G or M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1068 to A, C, D, E, F, G, H, I, K, M, N, P, Q, R, S, T, V, W or Y, preferably to C, E, P, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1069 to A, C, E, F, G, H, I, K, L, M, N, P, Q, R, S, T, V, W or Y, preferably to G, K, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1070 to C, D, E, F, G, H, I, K, L, M, N, P, Q, R, S, T, V, W or Y, preferably to P or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1071 to A, C, D, E, F, G, H, K, L, M, N, P, Q, R, S, T, V, W or Y, preferably to M, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1072 to A, C, D, E, F, G, H, I, L, M, N, P, Q, R, S, T, V, W or Y, preferably to E, G, P, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1073 to A, C, E, F, G, H, I, K, L, M, N, P, Q, R, S, T, V, W or Y, preferably to F, L, M, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1074 to A, C, D, E, F, H, I, K, L, M, N, P, Q, R, S, T, V, W or Y, preferably to I, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1075 to A, C, D, E, F, G, H, I, K, L, M, N, P, Q, R, T, V, W or Y, preferably to C, G, I, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1076 to A, C, D, E, F, G, H, I, K, L, M, N, P, Q, R, S, V, W or Y, preferably to C, E, H, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1077 to A, C, D, E, F, G, H, I, K, L, M, N, P, Q, R, S, V, W or Y, preferably to K, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1078 to A, C, D, E, F, G, H, I, K, L, M, N, P, Q, R, S, T, W or Y, preferably to D, E, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1079 to A, C, E, F, G, H, I, K, L, M, N, P, Q, R, S, T, W or Y, preferably to G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1081 to A, C, D, E, F, G, H, I, K, L, M, P, Q, R, S, T, V, W or Y, preferably to D, E or G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1082 to A, C, D, E, F, G, H, I, K, L, M, N, P, Q, R, S, V, W or Y, preferably to A, C, E, F, G, K, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1083 to A, C, D, E, F, H, I, K, L, M, N, P, Q, R, S, T, V, W or Y, preferably to E, F, L, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1084 to A, C, D, E, F, H, I, K, L, M, N, P, Q, R, S, T, V, W or Y, preferably to C, M, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1085 to A, C, D, E, F, H, I, K, L, M, N, P, Q, R, S, T, V, W or Y, preferably to A, P, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1086 to C, D, E, F, G, H, I, K, L, M, N, P, Q, R, S, T, V, W or Y, preferably to H, K, Q, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1087 to A, C, D, E, F, G, H, I, K, L, M, P, Q, R, S, T, V, W or Y, preferably to A, E, I, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1088 to A, C, D, E, F, G, H, I, K, L, M, N, Q, R, S, T, V, W or Y, preferably to D, E, G, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1089 to A, C, D, E, F, G, H, I, K, L, M, N, P, Q, R, T, V, W or Y, preferably to C, E, G, K, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1090 to C, D, E, F, G, H, I, K, L, M, N, P, Q, R, S, T, V, W or Y, preferably to F, G, I or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W1091 to A, C, D, E, F, G, H, I, K, L, M, N, P, Q, R, S, T, V or Y, preferably to A, E, G, H, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1092 to A, C, D, E, F, G, H, I, K, L, M, N, P, Q, R, S, V, W or Y, preferably to A, E, G, K, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1093 to A, C, D, E, F, G, H, I, K, L, M, P, Q, R, S, T, V, W or Y, preferably to A, G, L, P, Q, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W1094 to A, C, D, E, F, G, H, I, K, L, M, N, P, Q, R, S, T, V or Y, preferably to D, E, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1095 to C, D, E, F, G, H, I, K, L, M, N, P, Q, R, S, T, V, W or Y, preferably to P, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1096 to A, C, D, E, F, G, H, I, K, L, M, N, P, Q, R, S, T, V or W, preferably to A, D, H, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1097 to A, C, D, E, F, G, H, I, K, L, M, N, P, Q, R, T, V, W or Y, preferably to D, E, K, L, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1098 to A, C, D, E, F, G, H, I, L, M, N, P, Q, R, S, T, V, W or Y, preferably to D, F, G, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1099 to C, D, E, F, G, H, I, K, L, M, N, P, Q, R, S, T, V, W or Y, preferably to C, D, F, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1100 to A, C, D, E, F, H, I, K, L, M, N, P, Q, R, S, T, V, W or Y, preferably to D, E, H, M, N or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H1101 to A, C, D, E, F, G, I, K, L, M, N, P, Q, R, S, T, V, W or Y, preferably to K, L, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1102 to A, C, D, E, F, G, H, I, K, L, M, P, Q, R, S, T, V, W or Y, preferably to E, F, H, K, L, Q, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1103 to A, C, D, E, F, G, H, I, K, L, M, N, P, Q, R, S, V, W or Y, preferably to A, E, H, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1104 to C, D, E, F, G, H, I, K, L, M, N, P, Q, R, S, T, V, W or Y, preferably to I, K or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1105 to A, C, D, F, G, H, I, K, L, M, N, P, Q, R, S, T, V, W or Y, preferably to L or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1106 to A, C, D, E, F, G, H, K, L, M, N, P, Q, R, S, T, V, W or Y, preferably to T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1107 to A, C, D, E, F, G, H, I, K, L, M, N, P, Q, R, S, V, W or Y, preferably to C, M, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1108 to A, C, D, E, G, H, I, K, L, M, N, P, Q, R, S, T, V, W or Y, preferably to D, K, L, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1109 to A, C, D, F, G, H, I, K, L, M, N, P, Q, R, S, T, V, W or Y, preferably to A, D, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1111 to C, D, E, F, G, H, I, K, L, M, N, P, Q, R, S, T, V, W or Y, preferably to G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1113 to A, C, D, F, G, H, I, K, L, M, N, P, Q, R, S, T, V, W or Y, preferably to D, G, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1114 to A, C, D, E, F, G, H, I, K, L, M, N, P, R, S, T, V, W or Y, preferably to E, I, L, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1115 to A, C, D, E, F, G, H, I, K, L, M, N, P, R, S, T, V, W or Y, preferably to A, K, L, P, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1116 to A, C, D, E, F, G, H, I, K, M, N, P, Q, R, S, T, V, W or Y, preferably to D, G, H, K, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1117 to A, C, D, E, F, H, I, K, L, M, N, P, Q, R, S, T, V, W or Y, preferably to E, I, M, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1118 to A, C, D, E, F, G, H, I, K, L, M, N, P, R, S, T, V, W or Y, preferably to A, M, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1119 to A, C, D, E, F, G, H, K, L, M, N, P, Q, R, S, T, V, W or Y, preferably to D, E, G, N or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1120 to A, C, D, E, F, G, H, I, K, L, M, N, P, Q, R, S, T, W or Y, preferably to N, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position M1121 to A, C, D, E, F, G, H, I, K, L, N, P, Q, R, S, T, V, W or Y, preferably to G, K, N, P, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1122 to A, C, D, E, F, G, H, I, K, L, M, N, P, Q, R, S, T, V or W, preferably to A, C, I, K, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1123 to A, C, D, E, G, H, I, K, L, M, N, P, Q, R, S, T, V, W or Y, preferably to E, H, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1124 to A, C, D, E, G, H, I, K, L, M, N, P, Q, R, S, T, V, W or Y, preferably to E, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1125 to A, C, D, E, F, G, H, I, K, L, M, N, P, Q, S, T, V, W or Y, preferably to D, E, F, K, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1126 to A, C, E, F, G, H, I, K, L, M, N, P, Q, R, S, T, V, W or Y, preferably to H, K, L or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1127 to A, C, D, E, F, G, H, I, K, L, M, N, P, Q, R, T, V, W or Y, preferably to F, I, K, M, Q, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1128 to A, C, D, E, F, G, H, I, K, L, M, P, Q, R, S, T, V, W or Y, preferably to A, C, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1129 to C, D, E, F, G, H, I, K, L, M, N, P, Q, R, S, T, V, W or Y, preferably to E, L, N, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1130 to A, C, D, E, F, G, H, I, K, L, M, N, P, Q, R, S, T, W or Y, preferably to A, G, P, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1131 to A, C, D, E, F, G, H, I, K, L, M, N, P, Q, S, T, V, W or Y, preferably to A, N, Q, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1132 to A, C, D, E, G, H, I, K, L, M, N, P, Q, R, S, T, V, W or Y, preferably to E, K, M, P, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1133 to A, C, D, E, F, G, H, I, K, L, M, N, Q, R, S, T, V, W or Y, preferably to D, G, L, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1134 to A, C, E, F, G, H, I, K, L, M, N, P, Q, R, S, T, V, W or Y, preferably to E, G or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1135 to C, D, E, F, G, H, I, K, L, M, N, P, Q, R, S, T, V, W or Y, preferably to E, K, L, M, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1136 to A, C, D, E, F, H, I, K, L, M, N, P, Q, R, S, T, V, W or Y, preferably to A, E, P, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1137 to A, C, D, E, F, G, H, I, L, M, N, P, Q, R, S, T, V, W or Y, preferably to A, C, G, L, P, Q, R, S, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1138 to A, C, D, E, F, G, H, I, K, L, M, N, P, Q, R, S, V, W or Y, preferably to R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1139 to A, C, D, E, F, G, H, I, L, M, N, P, Q, R, S, T, V, W or Y, preferably to A, L, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1140 to A, C, D, E, F, G, H, K, L, M, N, P, Q, R, S, T, V, W or Y, preferably to A, C, G, L, M, P, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1141 to A, C, D, E, F, G, H, I, K, L, M, N, P, R, S, T, V, W or Y, preferably to A, C, G, K, N, P, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1142 to A, C, D, E, F, G, H, K, L, M, N, P, Q, R, S, T, V, W or Y, preferably to E, R, S, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1143 to A, C, D, E, F, G, H, I, K, L, M, N, P, Q, R, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1144 to C, D, E, F, G, H, I, K, L, M, N, P, Q, R, S, T, V, W or Y, preferably to C, D, E, N, P, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1145 to A, C, E, F, G, H, I, K, L, M, N, P, Q, R, S, T, V, W or Y, preferably to E, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1146 to A, C, D, E, F, H, I, K, L, M, N, P, Q, R, S, T, V, W or Y, preferably to A, C, D, K, L, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1147 to A, C, D, E, F, G, H, I, L, M, N, P, Q, R, S, T, V, W or Y, preferably to A, G, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1148 to A, C, D, E, F, G, H, I, K, L, M, P, Q, R, S, T, V, W or Y, preferably to H, I, K, P, Q, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position W1149 to A, C, D, E, F, G, H, I, K, L, M, N, P, Q, R, S, T, V or Y, preferably to C, G, I, K, N, Q, S, T, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1150 to A, C, D, E, F, G, H, I, K, L, M, N, P, Q, R, S, V, W or Y, preferably to G, K or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1151 to A, C, E, F, G, H, I, K, L, M, N, P, Q, R, S, T, V, W or Y, preferably to C, G, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1152 to A, C, D, E, F, G, H, I, K, M, N, P, Q, R, S, T, V, W or Y, preferably to A, C, E, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1153 to C, D, E, F, G, H, I, K, L, M, N, P, Q, R, S, T, V, W or Y, preferably to E, G, K or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1154 to C, D, E, F, G, H, I, K, L, M, N, P, Q, R, S, T, V, W or Y, preferably to C, D, E, G, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1155 to A, C, D, E, F, G, H, I, K, L, M, N, P, Q, R, S, V, W or Y, preferably to E, L, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1157 to A, C, D, E, F, G, H, I, K, L, M, N, P, Q, R, S, V, W or Y, preferably to V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1158 to A, C, D, E, F, G, H, K, L, M, N, P, Q, R, S, T, V, W or Y, preferably to R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1159 to C, D, E, F, G, H, I, K, L, M, N, P, Q, R, S, T, V, W or Y, preferably to C, E, I, P, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1160 to C, D, E, F, G, H, I, K, L, M, N, P, Q, R, S, T, V, W or Y, preferably to K, L, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1161 to A, C, D, E, F, G, H, I, K, L, M, N, P, R, S, T, V, W or Y, preferably to A, P or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1162 to A, C, D, F, G, H, I, K, L, M, N, P, Q, R, S, T, V, W or Y, preferably to A, C, D, F, I, N, Q, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1165 to A, C, D, F, G, H, I, K, L, M, N, P, Q, R, S, T, V, W or Y, preferably to D, H, L, M, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1166 to A, C, D, E, F, G, H, I, K, L, M, N, P, Q, S, T, V, W or Y, preferably to D, K or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1167 to A, C, D, E, F, G, H, I, K, L, M, N, P, Q, R, S, T, W or Y, preferably to A, C, L, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1168 to A, C, D, E, F, G, H, I, L, M, N, P, Q, R, S, T, V, W or Y, preferably to L, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1169 to A, C, D, E, F, G, H, I, K, L, M, N, Q, R, S, T, V, W or Y, preferably to M, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1170 to A, C, D, E, F, G, H, I, K, L, M, N, P, Q, R, S, T, V or W, preferably to E, K, M, Q, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1171 to A, C, D, E, F, G, H, I, K, L, M, N, P, Q, R, S, V, W or Y, preferably to A, G, M, Q, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1172 to A, C, D, E, F, G, H, I, K, L, M, N, P, Q, R, S, T, V or W, preferably to D, E, H, I, K, L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1173 to A, C, E, F, G, H, I, K, L, M, N, P, Q, R, S, T, V, W or Y, preferably to A, E, F, G, K, L, P, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1174 to A, C, D, E, G, H, I, K, L, M, N, P, Q, R, S, T, V, W or Y, preferably to D, P, Q, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1175 to C, D, E, F, G, H, I, K, L, M, N, P, Q, R, S, T, V, W or Y, preferably to G, I, N, Q, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1177 to A, C, D, E, F, G, H, I, K, L, M, N, P, Q, R, S, T, W or Y, preferably to N, P, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1178 to A, C, D, E, F, H, I, K, L, M, N, P, Q, R, S, T, V, W or Y, preferably to M, Q, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1179 to C, D, E, F, G, H, I, K, L, M, N, P, Q, R, S, T, V, W or Y, preferably to L, P, Q or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1180 to A, C, D, E, F, G, H, I, K, L, M, N, P, Q, R, S, V, W or Y, preferably to A, G, I, L, M, Q, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1181 to A, C, D, E, G, H, I, K, L, M, N, P, Q, R, S, T, V, W or Y, preferably to E, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1182 to A, C, D, E, F, G, H, I, K, L, M, N, P, Q, R, S, T, W or Y, preferably to M, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1183 to A, C, D, E, F, G, H, I, L, M, N, P, Q, R, S, T, V, W or Y, preferably to A, E, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1184 to A, C, D, E, F, G, H, I, K, L, M, N, P, Q, R, S, T, W or Y, preferably to C, E, K, L, P, Q or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1185 to A, C, D, E, F, G, H, I, K, L, M, N, P, Q, R, S, V, W or Y, preferably to Q or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1186 to A, C, D, E, F, G, H, I, K, L, M, N, P, Q, R, S, T, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1188 to A, C, D, E, F, G, H, I, K, L, M, P, Q, R, S, T, V, W or Y, preferably to V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1189 to C, D, E, F, G, H, I, K, L, M, N, P, Q, R, S, T, V, W or Y, preferably to C, K, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1190 to A, C, E, F, G, H, I, K, L, M, N, P, Q, R, S, T, V, W or Y, preferably to R, S, T or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1191 to A, C, D, E, F, G, H, I, K, L, M, N, P, Q, R, S, V, W or Y, preferably to E or L, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1192 to A, C, D, E, F, G, H, I, K, L, M, N, P, Q, R, S, V, W or Y, preferably to H or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1193 to A, C, D, E, F, G, H, I, K, L, M, N, P, Q, R, S, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1194 to A, C, D, E, F, G, H, I, K, L, M, N, Q, R, S, T, V, W or Y, preferably to A, E, G or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1195 to A, C, D, E, F, G, H, I, K, L, M, N, P, Q, R, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1197 to A, C, D, E, F, G, H, I, K, L, M, N, P, Q, R, S, T, W or Y, preferably to A, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1198 to A, C, D, E, F, G, H, I, K, L, M, N, P, Q, R, S, T, W or Y, preferably to E, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position C1199 to A, D, E, F, G, H, I, K, L, M, N, P, Q, R, S, T, V, W or Y, preferably to D or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1200 to C, D, E, F, G, H, I, K, L, M, N, P, Q, R, S, T, V, W or Y, preferably to G, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1202 to A, C, D, E, F, G, H, I, K, M, N, P, Q, R, S, T, V, W or Y, preferably to A or C, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1203 to A, C, D, E, F, G, H, I, K, L, M, N, P, Q, R, S, V, W or Y, preferably to E or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1204 to A, C, D, F, G, H, I, K, L, M, N, P, Q, R, S, T, V, W or Y, preferably to G or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1205 to A, C, D, E, F, G, H, K, L, M, N, P, Q, R, S, T, V, W or Y, preferably to V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1208 to A, C, D, E, F, G, H, I, L, M, N, P, Q, R, S, T, V, W or Y, preferably to R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1209 to A, C, D, E, F, G, H, I, K, L, M, N, P, Q, R, S, V, W or Y, preferably to A, C, E, K, N, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1210 to C, D, E, F, G, H, I, K, L, M, N, P, Q, R, S, T, V, W or Y, preferably to D, E, G, K, L, Q, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1211 to A, C, D, E, F, G, H, I, K, L, M, N, P, Q, R, S, V, W or Y, preferably to C, D, E, G, H, K, P, Q, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1213 to A, C, D, E, F, G, H, I, L, M, N, P, Q, R, S, T, V, W or Y, preferably to A, D, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1214 to A, C, D, E, G, H, I, K, L, M, N, P, Q, R, S, T, V, W or Y, preferably to A, E, K, L, P, R, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1215 to A, C, D, E, F, G, H, I, K, L, M, N, P, Q, R, S, T, W or Y, preferably to D, E, K, L, Q, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1216 to A, C, D, E, F, G, H, I, K, L, M, N, P, Q, R, S, V, W or Y, preferably to A, L, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1217 to A, C, D, E, F, G, H, I, K, L, M, P, Q, R, S, T, V, W or Y, preferably to A, D, E, F, P, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1218 to A, C, D, E, F, G, H, I, K, L, M, N, P, Q, R, S, V, W or Y, preferably to A, C, E, G, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1219 to A, C, D, E, F, G, H, I, K, L, M, N, P, Q, R, T, V, W or Y, preferably to A, E, F, I, K, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1220 to C, D, E, F, G, H, I, K, L, M, N, P, Q, R, S, T, V, W or Y, preferably to C, G, L, P, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1221 to C, D, E, F, G, H, I, K, L, M, N, P, Q, R, S, T, V, W or Y, preferably to D, G, K, L, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1222 to A, C, D, E, F, G, H, I, K, M, N, P, Q, R, S, T, V, W or Y, preferably to A, C, E, F, Q, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1223 to A, C, D, E, F, G, H, I, K, L, M, N, P, Q, R, T, V, W or Y, preferably to C, F, G, K, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1224 to A, C, D, E, F, G, H, I, K, L, M, N, P, Q, R, T, V, W or Y, preferably to A, D, G, L, M, P, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1225 to A, C, D, E, F, G, H, I, K, M, N, P, Q, R, S, T, V, W or Y, preferably to C, D, E, F, G, K, P, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1226 to A, C, D, E, F, G, H, I, K, L, M, N, P, Q, R, S, V, W or Y, preferably to A, G, M, P, R, S, V or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1227 to A, C, D, E, F, G, H, I, K, L, M, N, P, Q, R, S, T, W or Y, preferably to A, C, D, E, G, L, P, Q or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1228 to A, C, D, E, F, G, H, I, K, L, M, P, Q, R, S, T, V, W or Y, preferably to A, D, F, K, L or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1229 to A, C, D, E, F, H, I, K, L, M, N, P, Q, R, S, T, V, W or Y, preferably to A, C, E, Q, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1230 to A, C, D, E, F, G, H, I, K, L, M, N, P, Q, R, S, V, W or Y, preferably to F, H, I, K, L, P, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1231 to A, C, D, E, F, G, H, I, L, M, N, P, Q, R, S, T, V, W or Y, preferably to F, G, L, M, P, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1232 to A, C, D, E, F, G, H, I, K, L, M, N, P, Q, R, S, T, W or Y, preferably to E, K, Q, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1233 to A, C, D, E, F, G, H, I, K, L, M, N, P, Q, R, T, V, W or Y, preferably to P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1234 to A, C, E, F, G, H, I, K, L, M, N, P, Q, R, S, T, V, W or Y, preferably to G, K, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1235 to A, C, D, E, F, G, H, I, K, L, M, N, P, Q, R, T, V, W or Y, preferably to D, E, G, L, P, R, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1236 to A, C, D, E, F, G, H, I, K, L, M, N, P, Q, R, S, T, W or Y, preferably to A, C, G, I, P, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1237 to A, C, D, E, F, G, H, I, K, M, N, P, Q, R, S, T, V, W or Y, preferably to D, E, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1238 to C, D, E, F, G, H, I, K, L, M, N, P, Q, R, S, T, V, W or Y, preferably to D, E, K, L, N, P, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1239 to C, D, E, F, G, H, I, K, L, M, N, P, Q, R, S, T, V, W or Y, preferably to D, P or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1240 to A, C, D, E, F, H, I, K, L, M, N, P, Q, R, S, T, V, W or Y, preferably to D, L, N, Q, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1241 to A, C, D, E, F, G, H, I, K, L, M, N, P, Q, R, T, V, W or Y, preferably to D, G, I, L, M or P, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Y1242 to A, C, D, E, F, G, H, I, K, L, M, N, P, Q, R, S, T, V or W, preferably to C, E, K, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1243 to A, C, D, E, F, G, H, I, K, L, M, P, Q, R, S, T, V, W or Y, preferably to C, L, M, P, Q, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1244 to A, C, D, E, F, G, H, I, K, L, M, N, P, Q, R, S, V, W or Y, preferably to A, D, E, G, L, Q, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1246 to C, D, E, F, G, H, I, K, L, M, N, P, Q, R, S, T, V, W or Y, preferably to F, M, N, P, Q, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1247 to A, C, D, E, F, G, H, K, L, M, N, P, Q, R, S, T, V, W or Y, preferably to A, G, M, Q, R, S, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1248 to A, C, D, E, F, G, H, K, L, M, N, P, Q, R, S, T, V, W or Y, preferably to A, G, K, L, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1249 to C, D, E, F, G, H, I, K, L, M, N, P, Q, R, S, T, V, W or Y, preferably to E, G, H, I, R, T or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1250 to A, C, E, F, G, H, I, K, L, M, N, P, Q, R, S, T, V, W or Y, preferably to I, K, S, T, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1251 to A, C, D, E, F, G, H, I, K, L, M, N, P, Q, R, S, T, W or Y, preferably to I, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1252 to A, C, D, E, F, G, H, I, L, M, N, P, Q, R, S, T, V, W or Y, preferably to D, G, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1253 to C, D, E, F, G, H, I, K, L, M, N, P, Q, R, S, T, V, W or Y, preferably to P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1254 to A, C, D, F, G, H, I, K, L, M, N, P, Q, R, S, T, V, W or Y, preferably to F, G, H, L, R or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1255 to A, C, D, E, F, H, I, K, L, M, N, P, Q, R, S, T, V, W or Y, preferably to H, M, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1256 to A, C, D, F, G, H, I, K, L, M, N, P, Q, R, S, T, V, W or Y, preferably to G, M, N, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1257 to A, C, D, E, F, H, I, K, L, M, N, P, Q, R, S, T, V, W or Y, preferably to F, K, L, Q, R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1258 to A, C, D, E, F, G, H, I, K, L, M, P, Q, R, S, T, V, W or Y, preferably to C, G, H, K or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1259 to C, D, E, F, G, H, I, K, L, M, N, P, Q, R, S, T, V, W or Y, preferably to K, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1261 to A, C, D, E, F, G, H, I, K, L, M, N, P, Q, R, S, T, W or Y, preferably to I, L, P, Q, R or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1262 to A, C, D, E, F, G, H, I, K, L, M, N, P, Q, R, S, V, W or Y, preferably to A, F, M, Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1263 to A, C, D, E, F, G, H, I, K, L, M, N, P, Q, R, S, T, W or Y, preferably to E, G, Q, R, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1264 to A, C, D, E, F, G, H, I, K, M, N, P, Q, R, S, T, V, W or Y, preferably to A, E, H, R, S or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1265 to A, C, D, E, F, G, H, I, K, L, M, N, Q, R, S, T, V, W or Y, preferably to C, K, L, R, S, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1266 to C, D, E, F, G, H, I, K, L, M, N, P, Q, R, S, T, V, W or Y, preferably to F, L, P, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H1267 to A, C, D, E, F, G, I, K, L, M, N, P, Q, R, S, T, V, W or Y, preferably to A, E or F, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1269 to A, C, D, E, F, G, H, I, K, L, M, P, Q, R, S, T, V, W or Y, preferably to A, E, K, R, S, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1270 to A, C, D, E, F, G, H, I, K, L, M, N, P, Q, R, S, T, W or Y, preferably to D, E, G, I, L, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1271 to A, C, D, E, F, G, H, K, L, M, N, P, Q, R, S, T, V, W or Y, preferably to A, H or Q, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1272 to A, C, D, E, F, G, H, I, K, L, M, N, P, Q, S, T, V, W or Y, preferably to E, F, M, P or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1273 to A, C, D, E, F, G, H, I, K, L, M, N, P, Q, R, S, T, W or Y, preferably to R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1274 to A, C, D, E, F, G, H, K, L, M, N, P, Q, R, S, T, V, W or Y, preferably to F, M or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1275 to A, C, D, E, F, G, H, I, K, L, M, N, P, Q, R, S, V, W or Y, preferably to A, L or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1276 to A, C, D, F, G, H, I, K, L, M, N, P, Q, R, S, T, V, W or Y, preferably to R or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position S1277 to A, C, D, E, F, G, H, I, K, L, M, N, P, Q, R, T, V, W or Y, preferably to L, T or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1278 to A, C, D, F, G, H, I, K, L, M, N, P, Q, R, S, T, V, W or Y, preferably to Q or R, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1279 to A, C, E, F, G, H, I, K, L, M, N, P, Q, R, S, T, V, W or Y, preferably to G, I, R, T, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position H1280 to A, C, D, E, F, G, I, K, L, M, N, P, Q, R, S, T, V, W or Y, preferably to C, E, G, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position V1281 to A, C, D, E, F, G, H, I, K, L, M, N, P, Q, R, S, T, W or Y, preferably to F, I, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1282 to A, C, D, E, F, G, H, I, K, L, M, N, P, Q, R, S, V, W or Y, preferably to D, L or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1283 to A, C, D, E, F, G, H, I, K, L, M, N, P, Q, S, T, V, W or Y, preferably to A, D, E, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position K1284 to A, C, D, E, F, G, H, I, L, M, N, P, Q, R, S, T, V, W or Y, preferably to G, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1285 to A, C, D, E, F, G, H, I, K, L, M, N, P, Q, R, S, V, W or Y, preferably to A, E, F, G, M, R or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1286 to A, C, D, E, G, H, I, K, L, M, N, P, Q, R, S, T, V, W or Y, preferably to A, E, P, R, S or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1287 to A, C, D, E, F, G, H, I, K, L, M, N, P, Q, R, S, V, W or Y, preferably to C, K, L, M, Q, R, S or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position I1288 to A, C, D, E, F, G, H, K, L, M, N, P, Q, R, S, T, V, W or Y, preferably to A, D, F, G or K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position N1289 to A, C, D, E, F, G, H, I, K, L, M, P, Q, R, S, T, V, W or Y, preferably to A, Q or T, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position L1290 to A, C, D, E, F, G, H, I, K, M, N, P, Q, R, S, T, V, W or Y, preferably to A, G, R, V or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position G1291 to A, C, D, E, F, H, I, K, L, M, N, P, Q, R, S, T, V, W or Y, preferably to K, P, V, W or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position T1292 to A, C, D, E, F, G, H, I, K, L, M, N, P, Q, R, S, V, W or Y, preferably to G, L or Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1293 to A, C, D, F, G, H, I, K, L, M, N, P, Q, R, S, T, V, W or Y, preferably to G, K, L, S or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position Q1294 to A, C, D, E, F, G, H, I, K, L, M, N, P, R, S, T, V, W or Y, preferably to E, L, P or W, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1295 to A, C, D, F, G, H, I, K, L, M, N, P, Q, R, S, T, V, W or Y, preferably to K, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position F1296 to A, C, D, E, G, H, I, K, L, M, N, P, Q, R, S, T, V, W or Y, preferably to A, G or I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position P1297 to A, C, D, E, F, G, H, I, K, L, M, N, Q, R, S, T, V, W or Y, preferably to F, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position A1298 to C, D, E, F, G, H, I, K, L, M, N, P, Q, R, S, T, V, W or Y, preferably to Y, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1301 to A, C, E, F, G, H, I, K, L, M, N, P, Q, R, S, T, V, W or Y, preferably to I, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position E1302 to A, C, D, F, G, H, I, K, L, M, N, P, Q, R, S, T, V, W or Y, preferably to G, R or S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position R1303 to A, C, D, E, F, G, H, I, K, L, M, N, P, Q, S, T, V, W or Y, preferably to S, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

In another aspect, the variant comprises a substitution at position D1304 to A, C, E, F, G, H, I, K, L, M, N, P, Q, R, S, T, V, W or Y, preferably to A or V, wherein the variant has at least 80%, 85%, 90%, or 95%, preferably at least 96%, 97%, 98% or 99%, more preferably at least 99.5%, 99.7%, 99.8% or 99.9%, but less than 100%, sequence identity to SEQ ID NO: 1.

Preferably, the lactase variants of the present invention have a decreased or an increased galactose inhibition, preferably measured as a galactose inhibition improvement factor (GI-IF) of at least 1.1 or at most 0.9, compared to the lactase of SEQ ID NO: 1.

In a preferred embodiment, the lactase variants of the present invention have a decreased galactose inhibition, preferably measured as a galactose inhibition improvement factor (GI-IF) of at least 1.1, such as at least 1.2, at least 1.3, at least 1.4 or at least 1.5, at least 1.6, at least 1.7, at least 1.8, or at least 1.9.

The present invention also relates to an isolated polynucleotide encoding a variant of the invention. And to a nucleic acid construct or expression vector comprising such polynucleotide. And to a recombinant host cell transformed with such polynucleotide.

The present invention also relates to a method of producing a lactase variant of the invention, comprising:
a. cultivating the recombinant host cell mentioned in the preceding paragraph under conditions suitable for expression of the variant; and
b. recovering the variant.

The invention also relates to a whole broth formulation or cell culture composition comprising a variant of the invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., I98C, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CU P1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. Zooepidemicus cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacte-* riol. 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium* Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a lactase variant of the present invention, comprising (a) cultivating a cell, under conditions conducive for production of the lactase variants; and optionally, (b) recovering the lactase variant. In some aspects, the cell is a *Bifidobacterium* cell. In another aspect, the cell is a *Bifidobacterium bifidum* cell.

The present invention also relates to methods of producing a lactase variant of the present invention, comprising (a) cultivating a recombinant host cell of the present invention under conditions conducive for production of the lactase variant; and optionally, (b) recovering the lactase variant.

The recombinant host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Enzyme Compositions

The present invention also relates to a liquid composition comprising a variant of the invention and 20-70% glycerol.

The present invention also relates to compositions comprising a variant of the present invention. Preferably, the compositions are enriched in such a variant. The term "enriched" indicates that the lactase activity of the composition has been increased, e.g., with an enrichment factor of at least 1.1.

The compositions may comprise a variant of the present invention as the major enzymatic component, e.g., a monocomponent composition. Alternatively, the compositions may comprise multiple enzymatic activities, such as one or more enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Method for Obtaining a Lactase Variant

In one aspect, the present invention relates to a method for obtaining a lactase variant, comprising:

a. introducing into a parent lactase, preferably a parent lactase having an amino acid sequence which is at least 80%, 85%, 90%, or 95%, preferably at least 97%, 98%, or 99%, more preferably at least 99.5%, 99.7%, 99.8%, 99.9%, or 100%, identical to SEQ ID NO: 1, an alteration, preferably a substitution, at one or more positions corresponding to positions 1, 2, 3, 4, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 51, 53, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 149, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 264, 265, 266, 267, 268, 269, 270, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 607, 608, 609, 610, 611, 612, 613, 614, 615, 616, 619, 620, 621, 624, 625, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 659, 661, 662, 667, 669, 670, 672, 673, 674, 675, 676, 677, 678, 679, 680, 681, 682, 683, 684, 685, 686, 687, 688, 689, 690, 691, 692, 693, 694, 695, 696, 697, 698, 700, 701, 703, 704, 705, 706, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 857, 858, 859, 860, 861, 862, 863, 864, 865, 866, 867, 870, 871, 872, 873, 874, 875, 877, 879, 880, 881, 882, 883, 884, 885, 886, 887, 888, 889, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 973, 974, 975, 976, 977, 978, 979, 980, 981, 982, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1054, 1055, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1160, 1161, 1162, 1165, 1166, 1167, 1168, 1169, 1170, 1171, 1172, 1173, 1174, 1175, 1177, 1178, 1179, 1180, 1181, 1182, 1183, 1184, 1185, 1186, 1188, 1189, 1190, 1191, 1192, 1193, 1194, 1195, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1, and b. recovering the variant.

In preferred embodiments, an alteration, preferably a substitution, is introduced at one or more positions corresponding to the positions listed in any one of embodiments 3, 5, 7, 9, 11, 13, 15, 17 19, 21, 23, 25, 27, 29, 31, 33, 35, 37, 39, 41, 43, 45, 47, 49, 51, 53, 55, 57, 59, 61, 63, 65, 67, 69 or 71 of the "PREFERRED EMBODIMENTS" section right before the "EXAMPLES" section of the present application.

In a preferred aspect, the method for obtaining a lactase variant, comprises:

a. introducing into a parent lactase, preferably a parent lactase having an amino acid sequence which is at least 80%, 85%, 90%, or 95%, preferably at least 97%, 98%, or 99%, more preferably at least 99.5%, 99.7%, 99.8%, 99.9%, or 100%, identical to SEQ ID NO: 1, one or more of the following substitutions, wherein each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, S14Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41O, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53T, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60C, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138V, F139A, F139E, F139Q, F139W, D140G, D140L, D140V, L141G, L141T, T142E, T142S, T142V, K146A, G148H, G148K, G148T, G149E, G149H, G149I, G149M, G149Q, G149Y, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191C, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205W, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, K219A, K219C, K219F, K219H, K219M, A220C, A220G, A220I, A220L, A220M, A220T, A220V, A220W, A221C, A221D, A221E, A221L, A221N, A221R, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229N, T229Q, T229R, T229V, V230F, V230L, V230M, V230Q, V230R, V230S, F231A, F231E, F231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S248I, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, A266T, S267A, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274W, N275M, N275W, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311M, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348C, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405T, A405V, I406C, I406D, I406N, A407C, A407G, A407M, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L426O, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444O, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457T, S457V, G458A, G458C, G458D, G458F, G458L, G458P, G458Q, G458S, G458V, G458W, F459A, F459C, F459E, F459G, F459N, F459R, F459S, F459T, F459W, P460C, P460M, P460Q, P460W, P460Y, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K465O, K465F, K465G, K465L, K465Q, K465R, K465V, K465W, K465Y, L466A, L466D, L466E, L466F, L466G, L466M, L466P, L466Q, L466S, L466V, L466Y, V467A, V467O, V467D, V467E, V467G, V467T, V467W, A468D, A468E, A468F, A468K, A468L, A468P, A468S, A468V, A468W, W469A, W469O, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K487O, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496T, G497D, D498A, D498C, D498M, D498N, D498S, N499K, N499R, N499T, N499Y, L500A, L500E, L500N, L500V, T501C, T501G, T501M, A502A, A502Q, N503C, N503E, N503M, N503S, G504H, G504K, G504P, G505A, G505D, G505E, G505H, G505L, G505N, G505R, G505S, G505V, V506C, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514Q, G514R, A515C, A515D, A515E, A515F, A515G, A515K, A515P, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521Q, R521V, T522G, T522I, T522N, T523A, T523M, H524R, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606S, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627G, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637L, F637T, Y638A, Y638W, Q639D, Q639N, Q639R, S640O, S640D, Q641T, W642I, N643R, D644C, D644G, D644Y, D645S, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667R, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701M, K701P, K701S, K701W, T703E, T703I, T703K, T703W, T704M, T704R, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711A, Q711D, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716T, A716V, D717C, D717G, D717L, D717S, K718A, K718L, K718N, D717T, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, A722V, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739W, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749N, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, G754R, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811Y, D812E, D812F, D812I, D812Q, V813F, V813H, V813T, V813W, V813Y, K814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, K818Y, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, R838W, K839A, K839C, K839D, K839E, K839G, K839L, K839N, K839P, K839R, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858V, I858K, I858M, I858P, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, T888A, V888D, V888G, R889G, Y892D, Y892P, Y892R, Y893E, Y893G, S894D, S894G, R895M, N896M, Y897V, Y898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906N, I906S, I906T, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927G, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937G, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I1962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982P, G982Q, G982W, R984P, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001G, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003V, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, R1054C, R1054L, R1054N, L1055R, L1055T, Q1057A, Q1057E, Q1057P, Q1057R, N1058R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069D, D1069K, D1069R, D1069W, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119N, I1119S, V1120N, V1120S, V1120T, M1121G, M1121K, M1121N, M1121P, M1121S, M1121V, M1121Y, Y1122A, Y1122C, Y1122I, Y1122K, Y1122R, Y1122V, Y1122W, F1123E, F1123H, F1123R, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165D, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, Y1172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200V, A1200W, L1202A, L1202C, T1203E, T1203K, E1204G, E1204S, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216A, T1216L, T1216P, T1216Q, T1216R, N1217A, N1217D, N1217E, N1217F, N1217P, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257K, G1257L, G1257Q, G1257R, G1257W, N1258C, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V, and b. recovering the variant.

In preferred embodiments, the method comprises introducing into the parent lactase one or more of the substitutions listed in any one of embodiments 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144 or 146 of the "PREFERRED EMBODIMENTS" section right before the "EXAMPLES" section of the present application.

In a preferred embodiment, the parent lactase used in the method for obtaining a lactase variant is obtained from *Bifidobacterium*, in particular *Bifidobacterium bifidum*.

In a preferred embodiment, the parent lactase is the lactase of SEQ ID NO: 1.

In an embodiment, the parent lactase may have an amino acid sequence which is at least 80%, 85%, 90%, or 95%, preferably at least 97%, 98%, or 99%, more preferably at least 99.5%, 99.7%, 99.8%, 99.9%, or 100%, identical to any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15.

Said parent lactase may have a length of 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

In one embodiment, the parent lactase comprises the same number of amino acid residues as the lactase of SEQ ID NO: 1.

In an embodiment, the parent lactase has a length of 850-2000 amino acids, preferably 880-1350 amino acids.

A variant obtained from the method of the invention preferably has 1-50 substitutions, more preferably 1-30, 1-20, 1-10 or 1-5, such as 1, 2, 3, 4, 5, 6, 7, 8, 9, 10, 11, 12, 13, 14, 15, 16, 17, 18, 19 or 20 substitutions, compared to the parent lactase.

A variant obtained from the method of the invention comprises an alteration, preferably a substitution, of at least one amino acid compared to the parent lactase. In some aspects, a variant obtained from the method of the invention comprises at least two substitutions compared to the parent lactase, such as at least 3 substitutions, at least 4 substitutions, at least 5 substitutions, such as at least 6, 7, 8, 9 or 10 substitutions.

A variant obtained from the method of the invention has lactase activity.

A variant obtained from the method of the invention preferably has a decreased or an increased galactose inhibition, preferably measured as a galactose inhibition improvement factor (GI-IF) of at least 1.1, such as at least 1.2, at least 1.3, at least 1.4, at least 1.5, at least 1.6, at least 1.7, at least 1.8 or at least 1.9, or at most 0.9, such as at most 0.8, at most 0.7, at most 0.6, at most 0.5, at most 0.4, at most 0.3, at most 0.2 or at most 0.1, compared to the parent lactase.

In a preferred embodiment, a variant obtained from the method of the invention has a decreased galactose inhibition, preferably measured as a galactose inhibition improvement factor (GI-IF) of at least 1.1, such as at least 1.2, at least 1.3, at least 1.4, at least 1.5, at least 1.6, at least 1.7, at least 1.8 or at least 1.9.

A variant obtained from the method of the invention preferably has a ratio of beta-galactosidase activity to transgalactosylating activity of at least 2, preferably at least 3, such as at least 4, more preferably at least 5, such as at least 10, where said ratio is measured as [Galactose]/([Glucose]−[Galactose]) after incubation of the enzyme in cow's milk at 37° C. for 3 hours.

The variants of the invention may be prepared by procedures such as those mentioned below.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The variants of the application may be prepared and identified by site saturated library methods, such described in: "Methods and applications in protein engineering", Rodrigo M. P. Siloto, Randall J. Weselake. *Biocatalysis and Agricultural Biotechnology* 1 (2012) 181-189.

Stabilization of an enzyme may entail running a site saturation library (SSL) screening campaign. An SSL library allows all 20 amino acids at the given amino acid position and a library is normally constructed for each amino acid position in the protein. The number of SSL libraries are thus typically counted in the hundreds for a typical enzyme molecule. The entire campaign tends to be very time consuming and resource demanding. The process will typically require construction of libraries, plating, colony picking, sequencing, re-gridding and high-throughput screening (HTS).

The screening itself is based on the principle that an exponential decay is observed for degradation of a protein when exposed to stress conditions, e.g. elevated temperature, protease, surfactant. A stability improved variant can be found in a screening situation regardless of its initial concentration, as the stable variant after sufficient stress will always surpass the concentration of a reference sample by comparison, given a sufficiently sensitive detection method is available. The concentration may be reflected in e.g. an activity measurement.

It is clear to the skilled artisan that the term improved refers to the polypeptide variants being improved compared to a reference polypeptide, which may be the parent polypeptide or the polypeptide of SEQ ID NO 1.

Method for Producing a Dairy Product

In one aspect, the present invention relates to a method for producing a dairy product comprising:
  a) providing a milk-based substrate comprising lactose; and
  b) treating said substrate with a variant of the invention.

Preferably, step b) results in a lactose reduction of at least 70%, more preferably at least 80%, even more preferably at least 90%, most preferably at least 95% or at least 98%.

In one aspect, the present invention relates to a method for producing a fermented dairy product comprising:
  a) providing a milk-based substrate comprising lactose;
  b) treating said substrate with a variant of the invention;
  c) fermenting said substrate with a microorganism.
  Step b) and step c) may be performed essentially at the same time.

Preferably, the treatment with the lactase variant results in a lactose reduction of at least 50%, preferably at least 70% or at least 90%, compared to a similar method without addition of the lactase variant.

The lactose content in the dairy product, such as the fermented dairy product, obtained in a method of the invention is preferably below 2% w/v, more preferably below 1%, even more preferably below 0.5% or below 0.1%, and most preferably below 0.05% or below 0.01% w/v.

In one aspect, the present invention relates to the use of a variant of the invention for production of a dairy product, preferably a low-lactose dairy product having a lactose content of below 2% w/v, preferably below 1%, more preferably below 0.5% or below 0.1%, and most preferably below 0.05% or below 0.01% w/v.

The dosage of the lactase variant and other conditions under which the lactase variant or a composition comprising the lactase variant is used may be determined on the basis of methods known in the art.

Preferred Embodiments

1. A lactase variant comprising an alteration, preferably a substitution, at one or more positions corresponding to positions 1, 2, 3, 4, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 51, 53, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 149, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 264, 265, 266, 267, 268, 269, 270, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 607, 608, 609, 610, 611, 612, 613, 614, 615, 616, 619, 620, 621, 624, 625, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 659, 661, 662, 667, 669, 670, 672, 673, 674, 675, 676, 677, 678, 679, 680, 681, 682, 683, 684, 685, 686, 687, 688, 689, 690, 691, 692, 693, 694, 695, 696, 697, 698, 700, 701, 703, 704, 705, 706, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 857, 858, 859, 860, 861, 862, 863, 864, 865, 866, 867, 870, 871, 872, 873, 874, 875, 877, 879, 880, 881, 882, 883, 884, 885, 886, 887, 888, 889, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 973, 974, 975, 976, 977, 978, 979, 980, 981, 982, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1054, 1055, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1160, 1161, 1162, 1165, 1166, 1167, 1168, 1169, 1170, 1171, 1172, 1173, 1174, 1175, 1177, 1178, 1179, 1180, 1181, 1182, 1183, 1184, 1185, 1186, 1188, 1189, 1190, 1191, 1192, 1193, 1194, 1195, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1.

2. The lactase variant of the preceding embodiment, wherein the variant has a decreased or an increased galactose inhibition, preferably measured as a galactose inhibition improvement factor (GI-IF) of at least 1.1 or at most 0.9, compared to the lactase of SEQ ID NO: 1.

3. The lactase variant of embodiment 1 comprising an alteration, preferably a substitution, at one or more positions corresponding to positions 2, 3, 4, 5, 6, 7, 9, 10, 11, 12, 13, 14, 15, 16, 17, 21, 22, 23, 24, 25, 26, 27, 28, 29, 31, 32, 33, 34, 35, 36, 37, 38, 39, 40, 41, 42, 43, 44, 45, 47, 48, 49, 51, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 206, 207, 208, 209, 210, 211, 212, 213, 214, 215, 216, 217, 218, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 265, 267, 268, 269, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 406, 407, 408, 409, 410, 411, 412, 413, 414, 415, 416, 417, 418, 419, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 459, 461, 462, 463, 464, 465, 466, 467, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 514, 516, 517, 518, 519, 520, 521, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 608, 609, 610, 611, 612, 613, 631, 633, 634, 635, 636, 637, 638, 639, 640, 641, 642, 643, 644, 645, 646, 647, 648, 649, 650, 651, 652, 653, 654, 655, 656, 657, 659, 661, 662, 669, 670, 672, 673, 674, 675, 676, 677, 678, 679, 680, 681, 682, 683, 684, 685, 686, 687, 688, 689, 690, 693, 694, 695, 696, 697, 698, 700, 701, 703, 704, 705, 706, 708, 709, 710, 711, 712, 713, 714, 715, 718, 720, 721, 723, 724, 725, 726, 727, 728, 729, 730, 731, 732, 733, 734, 735, 736, 737, 738, 739, 740, 741, 742, 743, 744, 745, 746, 747, 748, 750, 751, 752, 753, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 840, 841, 842, 843, 844, 845, 846, 847, 848, 849, 850, 851, 852, 853, 854, 855, 857, 858, 859, 860, 861, 862, 863, 864, 865, 866, 870, 871, 872, 873, 874, 875, 877, 879, 880, 881, 882, 883, 884, 885, 886, 887, 888, 889, 893, 894, 895, 896, 897, 898, 899, 900, 901, 902, 903, 904, 905, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 973, 974, 975, 976, 977, 978, 979, 980, 981, 984, 985, 986, 987, 988, 989, 990, 991, 992, 993, 994, 995, 996, 997, 998, 999, 1000, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1055, 1057, 1058, 1059, 1060, 1062, 1063, 1064, 1065, 1066, 1067, 1068, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1161, 1162, 1166, 1167, 1168, 1169, 1170, 1171, 1172, 1173, 1174, 1175, 1177, 1178, 1179, 1180, 1181, 1182, 1184, 1185, 1186, 1188, 1189, 1190, 1191, 1192, 1193, 1194, 1195, 1197, 1198, 1199, 1202, 1203, 1204, 1205, 1208, 1209, 1210, 1211, 1213, 1214, 1215, 1217, 1218, 1219, 1220, 1221, 1222, 1223, 1224, 1225, 1226, 1227, 1228, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1.

4. The lactase variant of the preceding embodiment, wherein the variant has a decreased or an increased galactose inhibition, preferably measured as a galactose inhibition improvement factor (GI-IF) of at least 1.1 or at most 0.9, compared to the lactase of SEQ ID NO: 1.

5. The lactase variant of embodiment 1 comprising an alteration, preferably a substitution, at one or more positions corresponding to positions 1, 2, 3, 4, 5, 6, 7, 9, 10, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 49, 51, 53, 55, 57, 58, 59, 60, 61, 62, 63, 64, 66, 70, 71, 73, 74, 75, 76, 77, 78, 79, 83, 85, 86, 87, 88, 89, 90, 91, 92, 93, 94, 95, 96, 97, 98, 100, 101, 102, 104, 105, 106, 107, 108, 109, 110, 111, 112, 114, 115, 116, 117, 118, 119, 120, 121, 124, 125, 126, 129, 130, 131, 132, 137, 138, 140, 141, 142, 148, 149, 150, 151, 154, 157, 158, 159, 160, 161, 162, 164, 165, 166, 167, 169, 170, 171, 172, 173, 174, 175, 176, 177, 178, 179, 180, 181, 183, 184, 185, 186, 187, 188, 189, 190, 191, 193, 194, 195, 196, 197, 198, 199, 201, 202, 203, 204, 205, 206, 207, 213, 215, 216, 217, 218, 219, 220, 221, 222, 223, 224, 225, 226, 228, 231, 232, 234, 235, 236, 237, 238, 240, 242, 243, 247, 248, 251, 252, 257, 260, 261, 262, 263, 264, 266, 267, 268, 270, 271, 272, 273, 274, 275, 277, 280, 281, 282, 283, 285, 286, 291, 292, 293, 294, 295, 296, 297, 298, 299, 301, 302, 303, 304, 305, 307, 308, 309, 310, 311, 312, 314, 315, 316, 317, 318, 320, 321, 322, 324, 325, 326, 328, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 393, 395, 396, 398, 399, 400, 401, 402, 403, 404, 405, 406, 407, 410, 411, 412, 414, 415, 416, 417, 422, 423, 426, 427, 429, 430, 431, 432, 433, 434, 435, 436, 437, 438, 439, 440, 441, 442, 443, 444, 446, 448, 449, 450, 451, 452, 453, 454, 455, 456, 457, 458, 459, 460, 461, 462, 464, 465, 466, 467, 468, 469, 471, 472, 473, 474, 475, 476, 477, 478, 479, 480, 485, 487, 488, 493, 494, 495, 497, 499, 505, 506, 507, 508, 509, 510, 511, 512, 513, 515, 516, 517, 518, 519, 520, 521, 523, 524, 525, 526, 527, 528, 529, 535, 537, 538, 540, 545, 547, 549, 550, 553, 555, 556, 558, 559, 560, 564, 565, 567, 570, 572, 574, 575, 577, 578, 580, 581, 582, 583, 584, 586, 588, 589, 591, 592, 593, 594, 597, 598, 600, 604, 605, 607, 608, 609, 610, 612, 613, 614, 615, 619, 621, 625, 627, 628, 629, 630, 631, 632, 633, 634, 636, 637, 639, 643, 644, 645, 646, 647, 648, 649, 650, 651, 652, 653, 654, 655, 656, 657, 661, 662, 667, 669, 672, 673, 674, 675, 676, 677, 679, 680, 682, 683, 684, 686, 687, 688, 689, 690, 691, 692, 693, 694, 695, 696, 697, 698, 700, 701, 703, 705, 706, 708, 710, 711, 712, 713, 714, 715, 716, 717, 718, 719, 720, 721, 722, 723, 724, 725, 726, 727, 728, 729, 731, 732, 733, 734, 735, 737, 738, 739, 740, 741, 742, 743, 744, 745, 746, 747, 749, 750, 751, 752, 754, 755, 756, 757, 758, 759, 760, 761, 762, 765, 766, 769, 770, 771, 772, 773, 774, 775, 776, 777, 778, 779, 781, 782, 783, 785, 786, 787, 789, 790, 791, 792, 793, 794, 796, 797, 798, 799, 800, 801, 802, 803, 804, 805, 806, 807, 808, 809, 810, 811, 813, 814, 815, 816, 817, 818, 819, 820, 821, 822, 823, 824, 825, 826, 828, 829, 830, 831, 832, 833, 834, 835, 836, 838, 839, 840, 841, 842, 844, 847, 848, 850, 851, 852, 853, 854, 855, 858, 860, 861, 862, 864, 865, 866, 867, 870, 872, 873, 874, 875, 879, 882, 883, 885, 886, 887, 888, 889, 892, 893, 894, 897, 898, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 933, 934, 935, 936, 937, 938, 939, 940, 941, 942, 943, 946, 947, 948, 949, 950, 951, 952, 953, 954, 955, 956, 957, 959, 960, 961, 962, 963, 965, 966, 967, 968, 969, 970, 971, 973, 974, 975, 976, 977, 978, 979, 980, 981, 984, 985, 986, 987, 988, 989, 990, 991, 992, 993, 995, 996, 997, 998, 1000, 1001, 1002, 1003, 1004, 1005, 1006, 1007, 1008, 1010, 1011, 1012, 1013, 1014, 1015, 1016, 1017, 1018, 1021, 1022, 1024, 1026, 1027, 1028, 1029, 1030, 1031, 1033, 1034, 1035, 1036, 1037, 1038, 1039, 1040, 1041, 1042, 1043, 1044, 1046, 1048, 1051, 1052, 1053, 1054, 1055, 1057, 1058, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1093, 1094, 1095, 1096, 1097, 1098, 1099, 1100, 1101, 1102, 1103, 1105, 1109, 1111, 1113, 1114, 1115, 1116, 1117, 1118, 1119, 1120, 1121, 1123, 1124, 1125, 1127, 1128, 1129, 1130, 1131, 1132, 1133, 1135, 1136, 1137, 1138, 1140, 1141, 1142, 1143, 1144, 1145, 1146, 1148, 1149, 1150, 1151, 1152, 1153, 1154, 1158, 1159, 1161, 1162, 1165, 1166, 1167, 1168, 1169, 1170, 1172, 1173, 1174, 1175, 1178, 1179, 1180, 1181, 1182, 1183, 1184, 1185, 1186, 1188, 1189, 1190, 1191, 1193, 1194, 1197, 1199, 1200, 1203, 1204, 1205, 1208, 1209, 1210, 1211, 1213, 1214, 1215, 1216, 1217, 1218, 1219, 1220, 1221, 1222, 1224, 1225, 1226, 1227, 1229, 1230, 1231, 1232, 1234, 1235, 1236, 1237, 1238, 1239, 1240, 1243, 1247, 1255, 1259, 1261, 1262, 1263, 1264, 1265, 1273, 1274, 1275, 1276, 1277, 1278, 1279, 1280, 1281, 1284, 1285, 1286, 1287, 1288, 1293, 1294, 1295, 1296, 1302, 1303 or 1304 of the polypeptide of SEQ ID NO: 1.

6. The lactase variant of the preceding embodiment, wherein the variant has a decreased galactose inhibition, preferably measured as a galactose inhibition improvement factor (GI-IF) of at least 1.1, compared to the lactase of SEQ ID NO: 1.

7. The lactase variant of embodiment 1 comprising an alteration, preferably a substitution, at one or more positions corresponding to positions 2, 3, 4, 5, 6, 7, 9, 10, 12, 13, 14, 15, 16, 17, 21, 22, 23, 24, 25, 26, 27, 28, 29, 31, 32, 33, 34, 35, 36, 37, 38, 39, 40, 41, 42, 43, 44, 45, 47, 49, 51, 55, 57, 58, 59, 60, 61, 62, 63, 64, 66, 70, 71, 73, 74, 75, 76, 77, 78, 79, 83, 85, 86, 87, 88, 89, 90, 91, 92, 93, 94, 95, 96, 97, 98, 100, 101, 102, 104, 105, 106, 107, 108, 109, 110, 111, 112, 114, 115, 116, 117, 118, 119, 120, 121, 124, 125, 126, 129, 130, 131, 132, 137, 138, 140, 141, 142, 148, 150, 151, 154, 157, 158, 159, 160, 161, 162, 164, 165, 166, 167, 169, 170, 171, 172, 173, 174, 175, 176, 177, 178, 179, 180, 181, 183, 184, 185, 186, 187, 188, 189, 190, 191, 193, 194, 195, 196, 197, 198, 199, 201, 202, 203, 204, 206, 207, 213, 215, 216, 217, 218, 220, 221, 222, 223, 224, 225, 226, 228, 231, 232, 234, 235, 236, 237, 238, 240, 242, 243, 247, 248, 251, 252, 257, 260, 261, 262, 263, 267, 268, 271, 272, 273, 274, 275, 277, 280, 281, 282, 283, 285, 286, 291, 292, 293, 294, 295, 296, 297, 298, 299, 301, 302, 303, 304, 305, 307, 308, 310, 311, 312, 314, 315, 316, 317, 318, 320, 321, 322, 324, 325, 326, 328, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 393, 395, 396, 398, 399, 400, 401, 402, 403, 404, 406, 407, 410, 411, 412, 414, 415, 416, 417, 422, 423, 426, 427, 429, 430, 431, 432, 433, 434, 435, 436, 437, 438, 439, 440, 441, 442, 443, 444, 446, 448, 449, 450, 451, 452, 453, 454, 455, 456, 457, 459, 461, 462, 464, 465, 466, 467, 469, 471, 472, 473, 474, 475, 476, 477, 478, 479, 480, 485, 487, 488, 493, 494, 495, 497, 499, 505, 506, 507, 508, 509, 510, 511, 512, 516, 517, 518, 519, 520, 521, 524, 525, 526, 527, 528, 529, 535, 537, 538, 540, 545, 547, 549, 550, 553, 555, 556, 558, 559, 560, 564, 565, 567, 570, 572, 574, 575, 577, 578, 580, 581, 582, 583, 584, 586, 588, 589, 591, 592, 593, 594, 597, 598, 600, 604, 605, 608, 609, 610, 612, 613, 631, 633, 634, 636, 637, 639, 643, 644, 645, 646, 647, 648, 649, 650, 651, 652, 653, 654, 655, 656, 657, 661, 662, 669, 672, 673, 674, 675, 676, 677, 679, 680, 682, 683, 684, 686, 687, 688, 689, 690, 693, 694, 695, 696, 697, 698, 700, 701, 703, 705, 706, 708, 710, 711, 712, 713, 714, 715, 718, 720, 721, 723, 724, 725, 726, 727, 728, 729, 731, 732, 733, 734, 735, 737, 738, 739, 740, 741, 742, 743, 744, 745, 746, 747, 750, 751, 752, 755, 756, 757, 758, 759, 760, 761, 762, 765, 766, 769, 770, 771, 772, 773, 774, 775, 776, 777, 778, 779, 781, 782, 783, 785, 786, 787, 789, 790, 791, 792, 793, 794, 796, 798, 799, 800, 801, 802, 803, 804, 805, 806, 807, 808, 809, 810, 811, 813, 814, 815, 816, 817, 818, 819, 820, 821, 822, 823, 824, 825, 826, 828, 829, 830, 831, 832, 833, 834, 835, 836, 838, 840, 841, 842, 844, 847, 848, 850, 851, 852, 853, 854, 855, 858, 860, 861, 862, 864, 865, 866, 870, 872, 873, 874, 875, 879, 882, 883, 885, 886, 887, 888, 889, 893, 894, 897, 898, 900, 901, 902, 903, 904, 905, 907, 908, 909, 910, 911, 912, 913, 914, 915, 916, 917, 918, 919, 920, 921, 922, 923, 924, 925, 926, 927, 928, 929, 930, 931, 933, 934, 935, 936, 937, 938, 939, 940, 941, 942, 943, 946, 947, 948, 949, 950, 951, 952, 953, 954, 955, 956, 957, 959, 960, 961, 962, 963, 965, 966, 967, 968, 969, 970, 973, 974, 975, 976, 977, 978, 979, 980, 981, 984, 985, 986, 987, 988, 989, 990, 991, 992, 993, 995, 996, 997, 998, 1000, 1002, 1003, 1004, 1005, 1006, 1007, 1008, 1010, 1011, 1012, 1013, 1014, 1015, 1016, 1017, 1018, 1021, 1022, 1024, 1026, 1027, 1028, 1029, 1030, 1031, 1033, 1034, 1035, 1036, 1037, 1038, 1039, 1040, 1041, 1042, 1043, 1044, 1046, 1048, 1051, 1052, 1053, 1055, 1057, 1058, 1060, 1062, 1063, 1064, 1065, 1066, 1067, 1068, 1070, 1071, 1072, 1073, 1074, 1075, 1076, 1077, 1078, 1079, 1081, 1082, 1083, 1084, 1085, 1086, 1087, 1088, 1089, 1090, 1091, 1093, 1094, 1095, 1096, 1097, 1098, 1099, 1100, 1101, 1102, 1103, 1105, 1109, 1111, 1113, 1114, 1115, 1116, 1117, 1118, 1119, 1120, 1121, 1123, 1124, 1125, 1127, 1128, 1129, 1130, 1131, 1132, 1133, 1135, 1136, 1137, 1138, 1140, 1141, 1142, 1143, 1144, 1145, 1146, 1148, 1149, 1150, 1151, 1152, 1153, 1154, 1158, 1159, 1161, 1162, 1166, 1167, 1168, 1169, 1170, 1172, 1173, 1174, 1175, 1178, 1179, 1180, 1181, 1182, 1184, 1185, 1186, 1188, 1189, 1190, 1191, 1193, 1194, 1197, 1199, 1203, 1204, 1205, 1208, 1209, 1210, 1211, 1213, 1214, 1215, 1217, 1218, 1219, 1220, 1221, 1222, 1224, 1225, 1226, 1227, 1230, 1231, 1232, 1234, 1235, 1236, 1237, 1238, 1239, 1240, 1243, 1247, 1255, 1259, 1261, 1262, 1263, 1264, 1265, 1273, 1274, 1275, 1276, 1277, 1278, 1279, 1280, 1281, 1284, 1285, 1286, 1287, 1288, 1293, 1294, 1295, 1296, 1302, 1303 or 1304 of the polypeptide of SEQ ID NO: 1.

8. The lactase variant of the preceding embodiment, wherein the variant has a decreased galactose inhibition, preferably measured as a galactose inhibition improvement factor (GI-IF) of at least 1.1, compared to the lactase of SEQ ID NO: 1.

9. The lactase variant of embodiment 1 comprising an alteration, preferably a substitution, at one or more positions corresponding to positions 1, 2, 3, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 38, 39, 40, 41, 42, 43, 44, 45, 47, 49, 51, 53, 55, 57, 58, 59, 60, 61, 62, 63, 64, 66, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 106, 107, 108, 109, 110, 111, 112, 113, 114, 115, 116, 117, 118, 119, 120, 121, 122, 123, 124, 125, 128, 129, 130, 132, 136, 137, 138, 139, 140, 141, 142, 146, 148, 149, 150, 153, 154, 155, 157, 158, 159, 161, 162, 164, 165, 166, 167, 169, 170, 171, 172, 173, 174, 176, 177, 178, 179, 180, 181, 182, 183, 184, 185, 186, 187, 188, 189, 190, 193, 194, 195, 196, 197, 198, 199, 201, 202, 203, 204, 205, 206, 207, 208, 209, 210, 211, 212, 213, 214, 215, 217, 218, 219, 220, 221, 222, 223, 226, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 264, 265, 266, 267, 268, 269, 270, 272, 273, 275, 277, 278, 279, 280, 281, 282, 283, 284, 285, 286, 288, 291, 292, 293, 294, 295, 296, 297, 298, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 379, 380, 381, 383, 386, 387, 388, 389, 390, 391, 392, 393, 394, 395, 396, 398, 399, 400, 401, 402, 403, 404, 405, 406, 407, 408, 409, 410, 411, 413, 414, 415, 416, 417, 418, 419, 420, 421, 422, 423, 424, 426, 427, 428, 429, 430, 431, 432, 433, 434, 435, 436, 437, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 474, 475, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 561, 563, 564, 565, 567, 570, 572, 573, 574, 575, 576, 577, 578, 579, 580, 581, 582, 583, 584, 585, 586, 587, 588, 589, 590, 591, 592, 593, 594, 595, 597, 598, 600, 604, 606, 607, 608, 609, 610, 611, 612, 614, 615, 616, 619, 620, 624, 625, 627, 628, 629, 630, 631, 632, 634, 635, 637, 638, 639, 644, 645, 646, 647, 648, 650, 651, 652, 653, 654, 655, 656, 657, 659, 661, 662, 667, 669, 670, 673, 674, 675, 676, 677, 678, 679, 680, 681, 682, 683, 684, 686, 687, 688, 689, 690, 691, 692, 694, 695, 696, 697, 698, 700, 701, 704, 705, 706, 708, 709, 710, 711, 712, 713, 714, 715, 716, 717, 718, 719, 720, 721, 722, 723, 726, 727, 728, 729, 731, 732, 733, 734, 735, 737, 738, 739, 740, 741, 742, 744, 745, 747, 750, 751, 752, 754, 756, 757, 759, 760, 766, 769, 770, 771, 772, 773, 774, 775, 776, 777, 778, 780, 781, 782, 783, 784, 785, 786, 787, 788, 789, 790, 791, 792, 793, 794, 795, 796, 798, 799, 800, 801, 802, 803, 804, 805, 806, 807, 808, 809, 810, 811, 812, 813, 814, 815, 816, 817, 818, 819, 820, 821, 822, 825, 826, 827, 828, 829, 830, 831, 832, 833, 834, 835, 836, 837, 838, 839, 840, 841, 842, 843, 844, 845, 846, 849, 850, 853, 854, 857, 858, 859, 860, 861, 862, 863, 864, 865, 866, 867, 870, 871, 872, 873, 874, 877, 880, 881, 882, 883, 884, 885, 886, 887, 888, 889, 892, 893, 894, 896, 897, 899, 900, 901, 902, 903, 904, 905, 906, 907, 908, 910, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 965, 966, 967, 968, 969, 970, 971, 973, 974, 975, 976, 977, 978, 979, 980, 981, 982, 985, 986, 987, 988, 989, 990, 991, 992, 994, 995, 996, 997, 998, 999, 1000, 1001, 1002, 1003, 1004, 1005, 1006, 1007, 1009, 1010, 1011, 1012, 1013, 1014, 1015, 1016, 1018, 1021, 1022, 1023, 1024, 1026, 1027, 1029, 1030, 1031, 1034, 1035, 1036, 1037, 1041, 1042, 1043, 1044, 1046, 1048, 1050, 1051, 1052, 1053, 1055, 1057, 1058, 1059, 1060, 1061, 1062, 1063, 1064, 1065, 1066, 1067, 1068, 1070, 1071, 1072, 1073, 1074, 1075, 1076, 1078, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1140, 1141, 1142, 1143, 1144, 1145, 1146, 1147, 1148, 1149, 1150, 1151, 1152, 1153, 1154, 1155, 1158, 1159, 1160, 1161, 1162, 1165, 1167, 1168, 1169, 1170, 1171, 1172, 1173, 1174, 1175, 1177, 1178, 1179, 1180, 1182, 1183, 1184, 1186, 1188, 1189, 1190, 1191, 1192, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1254, 1255, 1256, 1257, 1258, 1259, 1261, 1262, 1263, 1264, 1265, 1266, 1267, 1269, 1270, 1271, 1272, 1273, 1274, 1275, 1277, 1278, 1279, 1280, 1281, 1282, 1283, 1284, 1285, 1286, 1287, 1288, 1289, 1290, 1291, 1292, 1293, 1294, 1295, 1296, 1297, 1302, 1303 or 1304 of the polypeptide of SEQ ID NO: 1.

10. The lactase variant of the preceding embodiment, wherein the variant has a decreased or an increased galactose inhibition, preferably measured as a galactose inhibition improvement factor (GI-IF) of at least 1.2 or at most 0.8, compared to the lactase of SEQ ID NO: 1.

11. The lactase variant of embodiment 1 comprising an alteration, preferably a substitution, at one or more positions corresponding to positions 2, 3, 5, 6, 7, 9, 10, 11, 12, 13, 14, 15, 16, 17, 21, 22, 23, 24, 25, 26, 27, 28, 29, 31, 32, 33, 34, 35, 36, 38, 39, 40, 41, 42, 43, 44, 45, 47, 49, 51, 55, 57, 58, 59, 60, 61, 62, 63, 64, 66, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 106, 107, 108, 109, 110, 111, 112, 113, 114, 115, 116, 117, 118, 119, 120, 121, 122, 123, 124, 125, 128, 129, 130, 132, 136, 137, 138, 139, 140, 141, 142, 146, 148, 150, 153, 154, 155, 157, 158, 159, 161, 162, 164, 165, 166, 167, 169, 170, 171, 172, 173, 174, 176, 177, 178, 179, 180, 181, 182, 183, 184, 185, 186, 187, 188, 189, 190, 193, 194, 195, 196, 197, 198, 199, 201, 202, 203, 204, 206, 207, 208, 209, 210, 211, 212, 213, 214, 215, 217, 218, 220, 221, 222, 223, 226, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 265, 267, 268, 269, 272, 273, 275, 277, 278, 279, 280, 281, 282, 283, 284, 285, 286, 288, 291, 292, 293, 294, 295, 296, 297, 298, 301, 302, 303, 304, 305, 306, 307, 308, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 379, 380, 381, 383, 386, 387, 388, 389, 390, 391, 392, 393, 394, 395, 396, 398, 399, 400, 401, 402, 403, 404, 406, 407, 408, 409, 410, 411, 413, 414, 415, 416, 417, 418, 419, 421, 422, 423, 424, 426, 427, 428, 429, 430, 431, 432, 433, 434, 435, 436, 437, 439, 440, 441, 442, 443, 444, 445, 446, 448, 449, 450, 451, 452, 453, 454, 455, 456, 457, 459, 461, 462, 463, 464, 465, 466, 467, 469, 470, 471, 472, 474, 475, 477, 478, 479, 480, 485, 487, 488, 491, 492, 493, 494, 495, 496, 497, 498, 499, 500, 501, 502, 503, 504, 505, 506, 507, 508, 509, 510, 511, 512, 514, 516, 517, 518, 519, 520, 521, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 561, 563, 564, 565, 567, 570, 572, 573, 574, 575, 576, 577, 578, 579, 580, 581, 582, 583, 584, 585, 586, 587, 588, 589, 590, 591, 592, 593, 594, 595, 597, 598, 600, 604, 606, 608, 609, 610, 611, 612, 631, 634, 635, 637, 638, 639, 644, 645, 646, 647, 648, 650, 651, 652, 653, 654, 655, 656, 657, 659, 661, 662, 669, 670, 673, 674, 675, 676, 677, 678, 679, 680, 681, 682, 683, 684, 686, 687, 688, 689, 690, 694, 695, 696, 697, 698, 700, 701, 704, 705, 706, 708, 709, 710, 711, 712, 713, 714, 715, 718, 720, 721, 723, 726, 727, 728, 729, 731, 732, 733, 734, 735, 737, 738, 739, 740, 741, 742, 744, 745, 747, 750, 751, 752, 756, 757, 759, 760, 766, 769, 770, 771, 772, 773, 774, 775, 776, 777, 778, 780, 781, 782, 783, 784, 785, 786, 787, 788, 789, 790, 791, 792, 793, 794, 795, 796, 798, 799, 800, 801, 802, 803, 804, 805, 806, 807, 808, 809, 810, 811, 812, 813, 814, 815, 816, 817, 818, 819, 820, 821, 822, 825, 826, 827, 828, 829, 830, 831, 832, 833, 834, 835, 836, 837, 838, 840, 841, 842, 843, 844, 845, 846, 849, 850, 853, 854, 857, 858, 859, 860, 861, 862, 863, 864, 865, 866, 870, 871, 872, 873, 874, 877, 880, 881, 882, 883, 884, 885, 886, 887, 888, 889, 893, 894, 896, 897, 899, 900, 901, 902, 903, 904, 905, 907, 908, 910, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 965, 966, 967, 968, 969, 970, 973, 974, 975, 976, 977, 978, 979, 980, 981, 985, 986, 987, 988, 989, 990, 991, 992, 994, 995, 996, 997, 998, 999, 1000, 1002, 1003, 1004, 1005, 1006, 1007, 1009, 1010, 1011, 1012, 1013, 1014, 1015, 1016, 1018, 1021, 1022, 1023, 1024, 1026, 1027, 1029, 1030, 1031, 1034, 1035, 1036, 1037, 1041, 1042, 1043, 1044, 1046, 1048, 1050, 1051, 1052, 1053, 1055, 1057, 1058, 1059, 1060, 1062, 1063, 1064, 1065, 1066, 1067, 1068, 1070, 1071, 1072, 1073, 1074, 1075, 1076, 1078, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1140, 1141, 1142, 1143, 1144, 1145, 1146, 1147, 1148, 1149, 1150, 1151, 1152, 1153, 1154, 1155, 1158, 1159, 1161, 1162, 1167, 1168, 1169, 1170, 1171, 1172, 1173, 1174, 1175, 1177, 1178, 1179, 1180, 1182, 1184, 1186, 1188, 1189, 1190, 1191, 1192, 1197, 1198, 1199, 1202, 1203, 1204, 1205, 1208, 1209, 1210, 1211, 1213, 1214, 1215, 1217, 1218, 1219, 1220, 1221, 1222, 1223, 1224, 1225, 1226, 1227, 1228, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1254, 1255, 1256, 1257, 1258, 1259, 1261, 1262, 1263, 1264, 1265, 1266, 1267, 1269, 1270, 1271, 1272, 1273, 1274, 1275, 1277, 1278, 1279, 1280, 1281, 1282, 1283, 1284, 1285, 1286, 1287, 1288, 1289, 1290, 1291, 1292, 1293, 1294, 1295, 1296, 1297, 1302, 1303 or 1304 of the polypeptide of SEQ ID NO: 1.

12. The lactase variant of the preceding embodiment, wherein the variant has a decreased or an increased galactose inhibition, preferably measured as a galactose inhibition improvement factor (GI-IF) of at least 1.2 or at most 0.8, compared to the lactase of SEQ ID NO: 1.

13. The lactase variant of embodiment 1 comprising an alteration, preferably a substitution, at one or more positions corresponding to positions 1, 2, 3, 5, 7, 9, 10, 13, 14, 15, 16, 17, 19, 20, 21, 22, 24, 25, 26, 27, 28, 29, 30, 31, 32, 34, 35, 36, 38, 39, 40, 41, 42, 43, 45, 47, 49, 51, 55, 57, 58, 59, 60, 61, 62, 63, 64, 66, 70, 73, 74, 75, 76, 77, 78, 79, 83, 85, 86, 87, 88, 89, 90, 91, 92, 93, 94, 95, 96, 97, 98, 100, 101, 102, 106, 107, 108, 109, 110, 111, 114, 115, 116, 118, 120, 121, 124, 130, 132, 137, 138, 140, 141, 142, 149, 150, 154, 157, 158, 159, 161, 162, 164, 165, 166, 167, 170, 171, 172, 173, 174, 176, 177, 178, 179, 180, 181, 183, 184, 185, 186, 187, 188, 190, 193, 194, 195, 196, 197, 199, 201, 202, 215, 217, 218, 220, 222, 223, 226, 228, 231, 234, 235, 236, 237, 242, 243, 247, 251, 252, 257, 261, 266, 267, 268, 270, 272, 277, 281, 282, 286, 291, 292, 293, 294, 295, 296, 297, 298, 301, 302, 303, 304, 305, 307, 309, 310, 312, 314, 315, 316, 317, 318, 320, 321, 322, 324, 325, 326, 328, 331, 335, 337, 338, 340, 341, 342, 343, 344, 345, 346, 347, 348, 349, 350, 352, 353, 354, 357, 359, 360, 362, 363, 364, 365, 366, 367, 368, 369, 370, 371, 372, 373, 375, 376, 377, 379, 380, 381, 383, 386, 387, 388, 389, 390, 393, 395, 396, 398, 399, 400, 401, 402, 403, 404, 405, 406, 407, 410, 411, 414, 415, 417, 422, 426, 427, 429, 430, 431, 432, 433, 434, 435, 436, 439, 442, 443, 444, 446, 448, 449, 450, 451, 452, 453, 454, 455, 456, 457, 458, 459, 460, 461, 462, 464, 465, 466, 467, 468, 471, 472, 474, 475, 477, 478, 479, 485, 487, 488, 493, 494, 497, 499, 505, 506, 507, 508, 509, 510, 511, 512, 513, 515, 516, 517, 518, 519, 520, 521, 524, 526, 527, 528, 529, 535, 537, 538, 540, 549, 553, 556, 558, 559, 564, 565, 567, 570, 572, 575, 580, 581, 582, 583, 584, 586, 589, 591, 592, 597, 598, 600, 604, 607, 608, 609, 610, 614, 619, 625, 627, 628, 629, 630, 631, 632, 634, 637, 639, 644, 645, 646, 647, 648, 651, 652, 653, 654, 655, 657, 661, 662, 667, 669, 673, 674, 675, 676, 679, 680, 687, 688, 689, 690, 691, 692, 694, 695, 696, 697, 698, 701, 705, 706, 708, 710, 711, 712, 713, 714, 715, 716, 717, 718, 719, 720, 721, 722, 723, 726, 727, 728, 729, 731, 732, 733, 734, 735, 737, 738, 739, 740, 741, 744, 745, 747, 750, 751, 752, 754, 756, 757, 759, 766, 769, 770, 771, 772, 773, 774, 776, 777, 778, 781, 782, 783, 785, 786, 789, 790, 791, 792, 798, 799, 800, 802, 803, 805, 806, 808, 809, 810, 811, 813, 814, 815, 816, 818, 819, 820, 821, 822, 825, 826, 829, 831, 832, 833, 834, 835, 836, 838, 839, 840, 844, 853, 854, 858, 861, 865, 866, 867, 870, 872, 873, 874, 882, 883, 885, 886, 887, 888, 889, 892, 893, 894, 897, 900, 901, 902, 903, 904, 905, 906, 907, 908, 910, 912, 914, 915, 916, 917, 918, 919, 921, 922, 923, 925, 926, 927, 928, 929, 930, 931, 933, 934, 935, 936, 937, 938, 939, 940, 941, 942, 943, 946, 947, 948, 949, 951, 953, 954, 955, 956, 957, 959, 960, 961, 962, 965, 966, 967, 968, 969, 970, 971, 973, 974, 976, 977, 978, 980, 981, 985, 986, 987, 989, 990, 991, 992, 995, 997, 998, 1001, 1002, 1003, 1005, 1006, 1007, 1010, 1011, 1012, 1013, 1014, 1016, 1018, 1021, 1022, 1024, 1026, 1029, 1030, 1031, 1034, 1035, 1036, 1041, 1042, 1043, 1044, 1046, 1048, 1051, 1052, 1053, 1055, 1057, 1058, 1060, 1061, 1062, 1064, 1065, 1066, 1067, 1068, 1072, 1074, 1075, 1076, 1082, 1083, 1084, 1085, 1086, 1087, 1088, 1089, 1091, 1093, 1094, 1095, 1096, 1097, 1098, 1099, 1100, 1101, 1102, 1103, 1105, 1109, 1111, 1113, 1114, 1115, 1116, 1117, 1118, 1119, 1121, 1123, 1124, 1125, 1127, 1128, 1129, 1130, 1133, 1135, 1136, 1137, 1138, 1140, 1141, 1142, 1143, 1144, 1145, 1146, 1148, 1149, 1150, 1151, 1152, 1153, 1154, 1158, 1159, 1161, 1162, 1165, 1167, 1169, 1170, 1175, 1178, 1179, 1180, 1182, 1183, 1184, 1186, 1188, 1189, 1190, 1191, 1197, 1200, 1203, 1204, 1205, 1208, 1209, 1210, 1211, 1213, 1214, 1215, 1216, 1217, 1218, 1219, 1220, 1221, 1222, 1224, 1225, 1226, 1227, 1229, 1230, 1232, 1235, 1236, 1238, 1239, 1240, 1247, 1255, 1259, 1262, 1263, 1264, 1265, 1273, 1274, 1275, 1277, 1278, 1279, 1280, 1281, 1284, 1286, 1287, 1288, 1293, 1294, 1295, 1296, 1302, 1303 or 1304 of the polypeptide of SEQ ID NO: 1.

14. The lactase variant of the preceding embodiment, wherein the variant has a decreased galactose inhibition, preferably measured as a galactose inhibition improvement factor (GI-IF) of at least 1.2, compared to the lactase of SEQ ID NO: 1.

15. The lactase variant of embodiment 1 comprising an alteration, preferably a substitution, at one or more positions corresponding to positions 2, 3, 5, 7, 9, 10, 13, 14, 15, 16, 17, 21, 22, 24, 25, 26, 27, 28, 29, 31, 32, 34, 35, 36, 38, 39, 40, 41, 42, 43, 45, 47, 49, 51, 55, 57, 58, 59, 60, 61, 62, 63, 64, 66, 70, 73, 74, 75, 76, 77, 78, 79, 83, 85, 86, 87, 88, 89, 90, 91, 92, 93, 94, 95, 96, 97, 98, 100, 101, 102, 106, 107, 108, 109, 110, 111, 114, 115, 116, 118, 120, 121, 124, 130, 132, 137, 138, 140, 141, 142, 150, 154, 157, 158, 159, 161, 162, 164, 165, 166, 167, 170, 171, 172, 173, 174, 176, 177, 178, 179, 180, 181, 183, 184, 185, 186, 187, 188, 190, 193, 194, 195, 196, 197, 199, 201, 202, 215, 217, 218, 220, 222, 223, 226, 228, 231, 234, 235, 236, 237, 242, 243, 247, 251, 252, 257, 261, 267, 268, 272, 277, 281, 282, 286, 291, 292, 293, 294, 295, 296, 297, 298, 301, 302, 303, 304, 305, 307, 310, 312, 314, 315, 316, 317, 318, 320, 321, 322, 324, 325, 326, 328, 331, 335, 337, 338, 340, 341, 342, 343, 344, 345, 346, 347, 348, 349, 350, 352, 353, 354, 357, 359, 360, 362, 363, 364, 365, 366, 367, 368, 369, 370, 371, 372, 373, 375, 376, 377, 379, 380, 381, 383, 386, 387, 388, 389, 390, 393, 395, 396, 398, 399, 400, 401, 402, 403, 404, 406, 407, 410, 411, 414, 415, 417, 422, 426, 427, 429, 430, 431, 432, 433, 434, 435, 436, 439, 442, 443, 444, 446, 448, 449, 450, 451, 452, 453, 454, 455, 456, 457, 459, 461, 462, 464, 465, 466, 467, 471, 472, 474, 475, 477, 478, 479, 485, 487, 488, 493, 494, 497, 499, 505, 506, 507, 508, 509, 510, 511, 512, 516, 517, 518, 519, 520, 521, 524, 526, 527, 528, 529, 535, 537, 538, 540, 549, 553, 556, 558, 559, 564, 565, 567, 570, 572, 575, 580, 581, 582, 583, 584, 586, 589, 591, 592, 597, 598, 600, 604, 608, 609, 610, 631, 634, 637, 639, 644, 645, 646, 647, 648, 651, 652, 653, 654, 655, 657, 661, 662, 669, 673, 674, 675, 676, 679, 680, 687, 688, 689, 690, 694, 695, 696, 697, 698, 701, 705, 706, 708, 710, 711, 712, 713, 714, 715, 718, 720, 721, 723, 726, 727, 728, 729, 731, 732, 733, 734, 735, 737, 738, 739, 740, 741, 744, 745, 747, 750, 751, 752, 756, 757, 759, 766, 769, 770, 771, 772, 773, 774, 776, 777, 778, 781, 782, 783, 785, 786, 789, 790, 791, 792, 798, 799, 800, 802, 803, 805, 806, 808, 809, 810, 811, 813, 814, 815, 816, 818, 819, 820, 821, 822, 825, 826, 829, 831, 832, 833, 834, 835, 836, 838, 840, 844, 853, 854, 858, 861, 865, 866, 870, 872, 873, 874, 882, 883, 885, 886, 887, 888, 889, 893, 894, 897, 900, 901, 902, 903, 904, 905, 907, 908, 910, 912, 914, 915, 916, 917, 918, 919, 921, 922, 923, 925, 926, 927, 928, 929, 930, 931, 933, 934, 935, 936, 937, 938, 939, 940, 941, 942, 943, 946, 947, 948, 949, 951, 953, 954, 955, 956, 957, 959, 960, 961, 962, 965, 966, 967, 968, 969, 970, 973, 974, 976, 977, 978, 980, 981, 985, 986, 987, 989, 990, 991, 992, 995, 997, 998, 1002, 1003, 1005, 1006, 1007, 1010, 1011, 1012, 1013, 1014, 1016, 1018, 1021, 1022, 1024, 1026, 1029, 1030, 1031, 1034, 1035, 1036, 1041, 1042, 1043, 1044, 1046, 1048, 1051, 1052, 1053, 1055, 1057, 1058, 1060, 1062, 1064, 1065, 1066, 1067, 1068, 1072, 1074, 1075, 1076, 1082, 1083, 1084, 1085, 1086, 1087, 1088, 1089, 1091, 1093, 1094, 1095, 1096, 1097, 1098, 1099, 1100, 1101, 1102, 1103, 1105, 1109, 1111, 1113, 1114, 1115, 1116, 1117, 1118, 1119, 1121, 1123, 1124, 1125, 1127, 1128, 1129, 1130, 1133, 1135, 1136, 1137, 1138, 1140, 1141, 1142, 1143, 1144, 1145, 1146, 1148, 1149, 1150, 1151, 1152, 1153, 1154, 1158, 1159, 1161, 1162, 1167, 1169, 1170, 1175, 1178, 1179, 1180, 1182, 1184, 1186, 1188, 1189, 1190, 1191, 1197, 1203, 1204, 1205, 1208, 1209, 1210, 1211, 1213, 1214, 1215, 1217, 1218, 1219, 1220, 1221, 1222, 1224, 1225, 1226, 1227, 1230, 1232, 1235, 1236, 1238, 1239, 1240, 1247, 1255, 1259, 1262, 1263, 1264, 1265, 1273, 1274, 1275, 1277, 1278, 1279, 1280, 1281, 1284, 1286, 1287, 1288, 1293, 1294, 1295, 1296, 1302, 1303 or 1304 of the polypeptide of SEQ ID NO: 1.

16. The lactase variant of the preceding embodiment, wherein the variant has a decreased galactose inhibition, preferably measured as a galactose inhibition improvement factor (GI-IF) of at least 1.2, compared to the lactase of SEQ ID NO: 1.

17. The lactase variant of embodiment 1 comprising an alteration, preferably a substitution, at one or more positions corresponding to positions 1, 2, 3, 6, 7, 13, 14, 15, 16, 17, 19, 20, 21, 22, 23, 24, 25, 26, 27, 28, 29, 31, 32, 33, 34, 35, 39, 40, 41, 42, 43, 45, 47, 49, 51, 53, 55, 57, 58, 59, 60, 62, 64, 66, 68, 73, 75, 76, 77, 78, 79, 81, 83, 85, 86, 87, 88, 90, 91, 92, 93, 94, 95, 96, 97, 98, 100, 101, 102, 106, 107, 108, 109, 110, 111, 112, 114, 115, 116, 118, 120, 121, 122, 123, 124, 130, 132, 136, 137, 142, 146, 149, 150, 153, 154, 157, 158, 159, 161, 162, 164, 165, 166, 167, 169, 170, 172, 173, 174, 176, 177, 178, 179, 180, 181, 184, 185, 187, 188, 189, 190, 194, 195, 197, 198, 199, 201, 202, 203, 204, 205, 206, 207, 209, 211, 212, 213, 214, 215, 217, 218, 220, 221, 222, 223, 228, 229, 230, 231, 232, 233, 234, 235, 236, 237, 238, 239, 240, 242, 243, 245, 247, 248, 249, 251, 252, 254, 255, 256, 258, 261, 262, 264, 266, 267, 268, 272, 278, 279, 280, 281, 282, 284, 285, 286, 291, 292, 293, 295, 296, 298, 301, 303, 304, 305, 308, 309, 310, 311, 312, 314, 315, 318, 320, 321, 322, 324, 325, 326, 328, 331, 335, 337, 340, 341, 342, 343, 344, 345, 346, 347, 348, 350, 352, 353, 357, 359, 360, 362, 363, 364, 365, 366, 368, 369, 370, 371, 372, 373, 376, 377, 379, 380, 381, 383, 386, 387, 388, 389, 390, 391, 392, 393, 394, 395, 396, 398, 399, 400, 401, 402, 403, 404, 405, 406, 407, 408, 409, 410, 411, 413, 414, 415, 416, 417, 418, 419, 420, 421, 422, 423, 424, 426, 427, 429, 430, 431, 433, 434, 435, 436, 437, 439, 440, 441, 442, 443, 444, 445, 446, 448, 449, 450, 451, 452, 454, 455, 456, 457, 458, 459, 461, 462, 463, 464, 465, 466, 468, 470, 471, 472, 474, 475, 477, 479, 480, 485, 487, 488, 491, 492, 493, 494, 495, 497, 498, 499, 500, 501, 504, 505, 506, 507, 508, 509, 510, 511, 512, 513, 514, 515, 516, 517, 518, 519, 520, 521, 522, 524, 525, 526, 527, 528, 530, 531, 534, 535, 537, 540, 542, 543, 545, 546, 547, 548, 549, 550, 551, 553, 554, 555, 556, 558, 559, 561, 563, 564, 565, 567, 570, 572, 573, 574, 575, 576, 577, 578, 579, 580, 581, 582, 583, 584, 585, 586, 587, 588, 589, 590, 591, 592, 594, 595, 598, 600, 606, 607, 608, 609, 610, 611, 614, 619, 620, 625, 627, 628, 630, 631, 634, 635, 639, 644, 650, 655, 656, 657, 661, 667, 669, 670, 673, 674, 675, 676, 677, 678, 679, 680, 681, 684, 687, 688, 689, 690, 692, 694, 695, 697, 698, 700, 701, 704, 705, 708, 709, 710, 711, 712, 714, 716, 717, 718, 719, 721, 723, 726, 727, 728, 731, 732, 734, 735, 738, 739, 740, 741, 744, 745, 747, 750, 752, 754, 756, 757, 760, 769, 770, 771, 772, 773, 774, 775, 776, 777, 778, 781, 782, 783, 784, 785, 786, 787, 788, 789, 790, 792, 793, 794, 795, 796, 798, 799, 800, 802, 803, 804, 806, 807, 808, 810, 812, 813, 814, 815, 816, 818, 819, 820, 821, 822, 826, 828, 829, 830, 831, 832, 833, 835, 836, 837, 838, 839, 840, 841, 844, 845, 849, 850, 854, 857, 858, 859, 860, 861, 862, 863, 865, 866, 867, 870, 872, 873, 874, 877, 881, 883, 884, 886, 887, 888, 892, 893, 896, 897, 900, 901, 902, 903, 904, 905, 906, 907, 908, 910, 912, 914, 915, 916, 917, 918, 919, 920, 921, 922, 923, 926, 927, 929, 933, 934, 935, 936, 937, 938, 939, 940, 941, 942, 943, 944, 946, 947, 948, 950, 951, 953, 955, 956, 958, 961, 962, 965, 966, 967, 968, 969, 970, 971, 973, 974, 976, 977, 978, 979, 980, 981, 985, 986, 987, 990, 991, 995, 997, 999, 1000, 1001, 1002, 1003, 1004, 1005, 1006, 1007, 1011, 1012, 1014, 1018, 1021, 1022, 1024, 1026, 1030, 1035, 1041, 1042, 1048, 1050, 1051, 1052, 1053, 1057, 1058, 1059, 1061, 1062, 1064, 1065, 1066, 1067, 1068, 1070, 1071, 1072, 1073, 1074, 1075, 1082, 1083, 1084, 1085, 1088, 1089, 1091, 1092, 1093, 1094, 1097, 1098, 1099, 1100, 1101, 1102, 1103, 1104, 1106, 1107, 1108, 1109, 1111, 1113, 1114, 1115, 1116, 1117, 1119, 1121, 1125, 1126, 1127, 1128, 1129, 1130, 1133, 1134, 1135, 1136, 1137, 1140, 1141, 1142, 1144, 1145, 1148, 1149, 1150, 1151, 1152, 1153, 1154, 1162, 1165, 1167, 1168, 1170, 1171, 1175, 1177, 1178, 1179, 1180, 1184, 1186, 1188, 1190, 1191, 1192, 1197, 1199, 1200, 1202, 1204, 1208, 1209, 1210, 1211, 1214, 1215, 1216, 1217, 1218, 1219, 1220, 1222, 1223, 1224, 1225, 1226, 1228, 1229, 1230, 1231, 1232, 1233, 1235, 1236, 1237, 1238, 1240, 1242, 1243, 1244, 1246, 1248, 1249, 1250, 1252, 1255, 1258, 1259, 1262, 1263, 1265, 1269, 1274, 1275, 1277, 1278, 1279, 1280, 1281, 1284, 1286, 1287, 1288, 1291, 1292, 1295, 1296, 1302 or 1304 of the polypeptide of SEQ ID NO: 1.

18. The lactase variant of the preceding embodiment, wherein the variant has a decreased or an increased galactose inhibition, preferably measured as a galactose inhibition improvement factor (GI-IF) of at least 1.3 or at most 0.7, compared to the lactase of SEQ ID NO: 1.

19. The lactase variant of embodiment 1 comprising an alteration, preferably a substitution, at one or more positions corresponding to positions 2, 3, 6, 7, 13, 14, 15, 16, 17, 21, 22, 23, 24, 25, 26, 27, 28, 29, 31, 32, 33, 34, 35, 39, 40, 41, 42, 43, 45, 47, 49, 51, 55, 57, 58, 59, 60, 62, 64, 66, 68, 73, 75, 76, 77, 78, 79, 81, 83, 85, 86, 87, 88, 90, 91, 92, 93, 94, 95, 96, 97, 98, 100, 101, 102, 106, 107, 108, 109, 110, 111, 112, 114, 115, 116, 118, 120, 121, 122, 123, 124, 130, 132, 136, 137, 142, 146, 150, 153, 154, 157, 158, 159, 161, 162, 164, 165, 166, 167, 169, 170, 172, 173, 174, 176, 177, 178, 179, 180, 181, 184, 185, 187, 188, 189, 190, 194, 195, 197, 198, 199, 201, 202, 203, 204, 206, 207, 209, 211, 212, 213, 214, 215, 217, 218, 220, 221, 222, 223, 228, 229, 230, 231, 232, 233, 234, 235, 236, 237, 238, 239, 240, 242, 243, 245, 247, 248, 249, 251, 252, 254, 255, 256, 258, 261, 262, 267, 268, 272, 278, 279, 280, 281, 282, 284, 285, 286, 291, 292, 293, 295, 296, 298, 301, 303, 304, 305, 308, 310, 311, 312, 314, 315, 318, 320, 321, 322, 324, 325, 326, 328, 331, 335, 337, 340, 341, 342, 343, 344, 345, 346, 347, 348, 350, 352, 353, 357, 359, 360, 362, 363, 364, 365, 366, 368, 369, 370, 371, 372, 373, 376, 377, 379, 380, 381, 383, 386, 387, 388, 389, 390, 391, 392, 393, 394, 395, 396, 398, 399, 400, 401, 402, 403, 404, 406, 407, 408, 409, 410, 411, 413, 414, 415, 416, 417, 418, 419, 421, 422, 423, 424, 426, 427, 429, 430, 431, 433, 434, 435, 436, 437, 439, 440, 441, 442, 443, 444, 445, 446, 448, 449, 450, 451, 452, 454, 455, 456, 457, 459, 461, 462, 463, 464, 465, 466, 470, 471, 472, 474, 475, 477, 479, 480, 485, 487, 488, 491, 492, 493, 494, 495, 497, 498, 499, 500, 501, 504, 505, 506, 507, 508, 509, 510, 511, 512, 514, 516, 517, 518, 519, 520, 521, 524, 525, 526, 527, 528, 530, 531, 534, 535, 537, 540, 542, 543, 545, 546, 547, 548, 549, 550, 551, 553, 554, 555, 556, 558, 559, 561, 563, 564, 565, 567, 570, 572, 573, 574, 575, 576, 577, 578, 579, 580, 581, 582, 583, 584, 585, 586, 587, 588, 589, 590, 591, 592, 594, 595, 598, 600, 606, 608, 609, 610, 611, 631, 634, 635, 639, 644, 650, 655, 656, 657, 661, 669, 670, 673, 674, 675, 676, 677, 678, 679, 680, 681, 684, 687, 688, 689, 690, 694, 695, 697, 698, 700, 701, 704, 705, 708, 709, 710, 711, 712, 714, 718, 721, 723, 726, 727, 728, 731, 732, 734, 735, 738, 739, 740, 741, 744, 745, 747, 750, 752, 756, 757, 760, 769, 770, 771, 772, 773, 774, 775, 776, 777, 778, 781, 782, 783, 784, 785, 786, 787, 788, 789, 790, 792, 793, 794, 795, 796, 798, 799, 800, 802, 803, 804, 806, 807, 808, 810, 812, 813, 814, 815, 816, 818, 819, 820, 821, 822, 826, 828, 829, 830, 831, 832, 833, 835, 836, 837, 838, 840, 841, 844, 845, 849, 850, 854, 857, 858, 859, 860, 861, 862, 863, 865, 866, 870, 872, 873, 874, 877, 881, 883, 884, 886, 887, 888, 893, 896, 897, 900, 901, 902, 903, 904, 905, 907, 908, 910, 912, 914, 915, 916, 917, 918, 919, 920, 921, 922, 923, 926, 927, 929, 933, 934, 935, 936, 937, 938, 939, 940, 941, 942, 943, 944, 946, 947, 948, 950, 951, 953, 955, 956, 958, 961, 962, 965, 966, 967, 968, 969, 970, 973, 974, 976, 977, 978, 979, 980, 981, 985, 986, 987, 990, 991, 995, 997, 999, 1000, 1002, 1003, 1004, 1005, 1006, 1007, 1011, 1012, 1014, 1018, 1021, 1022, 1024, 1026, 1030, 1035, 1041, 1042, 1048, 1050, 1051, 1052, 1053, 1057, 1058, 1059, 1062, 1064, 1065, 1066, 1067, 1068, 1070, 1071, 1072, 1073, 1074, 1075, 1082, 1083, 1084, 1085, 1088, 1089, 1091, 1092, 1093, 1094, 1097, 1098, 1099, 1100, 1101, 1102, 1103, 1104, 1106, 1107, 1108, 1109, 1111, 1113, 1114, 1115, 1116, 1117, 1119, 1121, 1125, 1126, 1127, 1128, 1129, 1130, 1133, 1134, 1135, 1136, 1137, 1140, 1141, 1142, 1144, 1145, 1148, 1149, 1150, 1151, 1152, 1153, 1154, 1162, 1167, 1168, 1170, 1171, 1175, 1177, 1178, 1179, 1180, 1184, 1186, 1188, 1190, 1191, 1192, 1197, 1199, 1202, 1204, 1208, 1209, 1210, 1211, 1214, 1215, 1217, 1218, 1219, 1220, 1222, 1223, 1224, 1225, 1226, 1228, 1230, 1231, 1232, 1233, 1235, 1236, 1237, 1238, 1240, 1242, 1243, 1244, 1246, 1248, 1249, 1250, 1252, 1255, 1258, 1259, 1262, 1263, 1265, 1269, 1274, 1275, 1277, 1278, 1279, 1280, 1281, 1284, 1286, 1287, 1288, 1291, 1292, 1295, 1296, 1302 or 1304 of the polypeptide of SEQ ID NO: 1.

20. The lactase variant of the preceding embodiment, wherein the variant has a decreased or an increased galactose inhibition, preferably measured as a galactose inhibition improvement factor (GI-IF) of at least 1.3 or at most 0.7, compared to the lactase of SEQ ID NO: 1.

21. The lactase variant of embodiment 1 comprising an alteration, preferably a substitution, at one or more positions corresponding to positions 1, 2, 3, 7, 13, 14, 15, 16, 17, 20, 21, 22, 24, 25, 26, 27, 28, 29, 31, 32, 35, 39, 40, 41, 42, 43, 45, 47, 49, 51, 55, 57, 58, 59, 60, 62, 64, 66, 73, 75, 76, 77, 78, 79, 83, 85, 86, 87, 88, 90, 91, 92, 93, 94, 95, 96, 97, 98, 100, 101, 102, 106, 107, 108, 109, 110, 111, 114, 115, 116, 118, 120, 121, 130, 132, 137, 142, 149, 150, 154, 157, 158, 159, 161, 162, 164, 165, 166, 167, 170, 172, 173, 174, 176, 177, 178, 179, 180, 181, 184, 185, 187, 188, 190, 194, 197, 199, 201, 202, 217, 218, 220, 222, 223, 228, 236, 237, 242, 251, 252, 261, 266, 267, 268, 272, 281, 291, 292, 293, 295, 296, 298, 301, 303, 304, 305, 309, 310, 312, 314, 315, 318, 320, 321, 322, 324, 325, 326, 328, 331, 335, 337, 340, 341, 342, 343, 344, 345, 346, 347, 348, 350, 352, 353, 357, 359, 360, 362, 363, 364, 365, 366, 368, 369, 370, 371, 372, 373, 376, 377, 379, 380, 381, 383, 386, 387, 388, 389, 390, 393, 395, 396, 398, 399, 400, 401, 402, 403, 404, 405, 406, 407, 410, 411, 414, 417, 422, 427, 429, 431, 433, 434, 435, 436, 439, 442, 443, 444, 446, 448, 449, 450, 451, 452, 454, 455, 456, 457, 458, 459, 461, 462, 465, 466, 468, 471, 472, 475, 477, 479, 485, 487, 493, 494, 497, 499, 505, 506, 507, 508, 509, 510, 511, 512, 513, 515, 516, 517, 518, 519, 520, 521, 524, 526, 527, 528, 537, 540, 549, 558, 559, 564, 565, 567, 570, 575, 582, 583, 591, 592, 598, 600, 607, 614, 619, 625, 627, 628, 630, 631, 634, 639, 655, 657, 661, 667, 669, 673, 674, 676, 679, 680, 687, 688, 689, 690, 692, 694, 695, 697, 698, 701, 705, 708, 710, 712, 714, 716, 717, 718, 719, 721, 723, 726, 727, 728, 731, 732, 734, 735, 738, 739, 740, 741, 744, 745, 750, 752, 756, 757, 769, 770, 771, 772, 773, 774, 776, 777, 778, 781, 782, 783, 785, 786, 789, 790, 798, 799, 802, 803, 806, 808, 810, 813, 818, 819, 821, 822, 826, 829, 831, 832, 835, 836, 838, 839, 840, 854, 858, 861, 865, 866, 867, 870, 872, 873, 874, 883, 886, 887, 888, 892, 893, 897, 900, 901, 902, 903, 904, 905, 906, 907, 908, 910, 912, 914, 915, 916, 917, 918, 919, 921, 922, 923, 926, 927, 929, 933, 934, 935, 936, 937, 938, 939, 940, 941, 942, 943, 946, 947, 948, 951, 953, 955, 956, 961, 962, 965, 966, 967, 968, 969, 970, 971, 973, 974, 976, 977, 978, 980, 981, 985, 986, 987, 990, 991, 995, 997, 1001, 1002, 1003, 1005, 1006, 1007, 1011, 1012, 1014, 1018, 1022, 1024, 1026, 1030, 1035, 1041, 1042, 1048, 1051, 1052, 1053, 1057, 1061, 1062, 1064, 1065, 1066, 1067, 1068, 1072, 1074, 1082, 1083, 1084, 1085, 1088, 1089, 1091, 1093, 1094, 1098, 1099, 1101, 1102, 1103, 1109, 1111, 1113, 1114, 1115, 1116, 1117, 1119, 1121, 1125, 1127, 1128, 1129, 1130, 1133, 1135, 1136, 1137, 1140, 1141, 1142, 1144, 1145, 1148, 1149, 1150, 1151, 1152, 1153, 1162, 1167, 1178, 1179, 1180, 1184, 1186, 1188, 1190, 1191, 1197, 1204, 1208, 1209, 1210, 1211, 1214, 1215, 1216, 1217, 1218, 1222, 1224, 1225, 1226, 1229, 1230, 1232, 1235, 1236, 1238, 1255, 1259, 1262, 1263, 1265, 1274, 1275, 1277, 1278, 1279, 1280, 1281, 1284, 1286, 1287, 1288, 1295, 1296, 1302 or 1304 of the polypeptide of SEQ ID NO: 1.

22. The lactase variant of the preceding embodiment, wherein the variant has a decreased galactose inhibition, preferably measured as a galactose inhibition improvement factor (GI-IF) of at least 1.3, compared to the lactase of SEQ ID NO: 1.

23. The lactase variant of embodiment 1 comprising an alteration, preferably a substitution, at one or more positions corresponding to positions 2, 3, 7, 13, 14, 15, 16, 17, 21, 22, 24, 25, 26, 27, 28, 29, 31, 32, 35, 39, 40, 41, 42, 43, 45, 47, 49, 51, 55, 57, 58, 59, 60, 62, 64, 66, 73, 75, 76, 77, 78, 79, 83, 85, 86, 87, 88, 90, 91, 92, 93, 94, 95, 96, 97, 98, 100, 101, 102, 106, 107, 108, 109, 110, 111, 114, 115, 116, 118, 120, 121, 130, 132, 137, 142, 150, 154, 157, 158, 159, 161, 162, 164, 165, 166, 167, 170, 172, 173, 174, 176, 177, 178, 179, 180, 181, 184, 185, 187, 188, 190, 194, 197, 199, 201, 202, 217, 218, 220, 222, 223, 228, 236, 237, 242, 251, 252, 261, 267, 268, 272, 281, 291, 292, 293, 295, 296, 298, 301, 303, 304, 305, 310, 312, 314, 315, 318, 320, 321, 322, 324, 325, 326, 328, 331, 335, 337, 340, 341, 342, 343, 344, 345, 346, 347, 348, 350, 352, 353, 357, 359, 360, 362, 363, 364, 365, 366, 368, 369, 370, 371, 372, 373, 376, 377, 379, 380, 381, 383, 386, 387, 388, 389, 390, 393, 395, 396, 398, 399, 400, 401, 402, 403, 404, 406, 407, 410, 411, 414, 417, 422, 427, 429, 431, 433, 434, 435, 436, 439, 442, 443, 444, 446, 448, 449, 450, 451, 452, 454, 455, 456, 457, 459, 461, 462, 465, 466, 471, 472, 475, 477, 479, 485, 487, 493, 494, 497, 499, 505, 506, 507, 508, 509, 510, 511, 512, 516, 517, 518, 519, 520, 521, 524, 526, 527, 528, 537, 540, 549, 558, 559, 564, 565, 567, 570, 575, 582, 583, 591, 592, 598, 600, 631, 634, 639, 655, 657, 661, 669, 673, 674, 676, 679, 680, 687, 688, 689, 690, 694, 695, 697, 698, 701, 705, 708, 710, 712, 714, 718, 721, 723, 726, 727, 728, 731, 732, 734, 735, 738, 739, 740, 741, 744, 745, 750, 752, 756, 757, 769, 770, 771, 772, 773, 774, 776, 777, 778, 781, 782, 783, 785, 786, 789, 790, 798, 799, 802, 803, 806, 808, 810, 813, 818, 819, 821, 822, 826, 829, 831, 832, 835, 836, 838, 840, 854, 858, 861, 865, 866, 870, 872, 873, 874, 883, 886, 887, 888, 893, 897, 900, 901, 902, 903, 904, 905, 907, 908, 910, 912, 914, 915, 916, 917, 918, 919, 921, 922, 923, 926, 927, 929, 933, 934, 935, 936, 937, 938, 939, 940, 941, 942, 943, 946, 947, 948, 951, 953, 955, 956, 961, 962, 965, 966, 967, 968, 969, 970, 973, 974, 976, 977, 978, 980, 981, 985, 986, 987, 990, 991, 995, 997, 1002, 1003, 1005, 1006, 1007, 1011, 1012, 1014, 1018, 1022, 1024, 1026, 1030, 1035, 1041, 1042, 1048, 1051, 1052, 1053, 1057, 1062, 1064, 1065, 1066, 1067, 1068, 1072, 1074, 1082, 1083, 1084, 1085, 1088, 1089, 1091, 1093, 1094, 1098, 1099, 1101, 1102, 1103, 1109, 1111, 1113, 1114, 1115, 1116, 1117, 1119, 1121, 1125, 1127, 1128, 1129, 1130, 1133, 1135, 1136, 1137, 1140, 1141, 1142, 1144, 1145, 1148, 1149, 1150, 1151, 1152, 1153, 1162, 1167, 1178, 1179, 1180, 1184, 1186, 1188, 1190, 1191, 1197, 1204, 1208, 1209, 1210, 1211, 1214, 1215, 1217, 1218, 1222, 1224, 1225, 1226, 1230, 1232, 1235, 1236, 1238, 1255, 1259, 1262, 1263, 1265, 1274, 1275, 1277, 1278, 1279, 1280, 1281, 1284, 1286, 1287, 1288, 1295, 1296, 1302 or 1304 of the polypeptide of SEQ ID NO: 1.

24. The lactase variant of the preceding embodiment, wherein the variant has a decreased galactose inhibition, preferably measured as a galactose inhibition improvement factor (GI-IF) of at least 1.3, compared to the lactase of SEQ ID NO: 1.

25. The lactase variant of embodiment 1 comprising an alteration, preferably a substitution, at one or more positions corresponding to positions 2, 3, 7, 13, 15, 16, 20, 21, 23, 24, 26, 27, 28, 29, 31, 32, 34, 35, 40, 42, 43, 45, 47, 49, 51, 53, 55, 57, 58, 59, 62, 64, 66, 73, 75, 76, 77, 78, 79, 81, 85, 86, 87, 88, 90, 91, 92, 93, 94, 95, 96, 97, 98, 100, 101, 102, 109, 110, 111, 112, 114, 115, 120, 121, 124, 130, 132, 136, 137, 146, 149, 150, 153, 157, 158, 159, 161, 162, 165, 166, 167, 170, 172, 174, 176, 177, 178, 179, 180, 185, 188, 189, 190, 197, 217, 218, 220, 222, 223, 228, 233, 236, 237, 239, 242, 247, 248, 249, 251, 252, 254, 255, 256, 261, 262, 264, 268, 272, 278, 279, 286, 291, 292, 293, 296, 298, 301, 303, 304, 305, 309, 312, 320, 325, 326, 328, 337, 340, 341, 342, 343, 345, 348, 350, 359, 360, 362, 363, 364, 365, 368, 369, 370, 373, 376, 377, 379, 380, 381, 386, 387, 388, 389, 390, 391, 392, 393, 394, 395, 396, 398, 399, 400, 401, 402, 403, 404, 405, 406, 408, 409, 411, 413, 414, 416, 417, 418, 419, 420, 423, 424, 426, 427, 429, 431, 433, 434, 435, 436, 439, 442, 443, 444, 445, 448, 449, 450, 451, 452, 454, 455, 456, 457, 458, 459, 465, 466, 468, 472, 475, 477, 479, 485, 487, 488, 491, 493, 495, 498, 499, 500, 504, 505, 506, 507, 508, 509, 510, 511, 512, 513, 514, 515, 516, 517, 518, 519, 520, 521, 522, 524, 525, 526, 527, 528, 531, 537, 540, 546, 547, 548, 549, 550, 551, 553, 554, 555, 556, 558, 559, 564, 565, 567, 570, 572, 574, 576, 577, 579, 582, 583, 585, 586, 588, 592, 594, 595, 600, 607, 608, 609, 610, 611, 614, 619, 620, 625, 630, 634, 635, 639, 644, 650, 655, 656, 661, 669, 670, 673, 676, 680, 684, 687, 688, 692, 694, 695, 697, 698, 700, 701, 705, 709, 710, 712, 714, 716, 717, 718, 719, 721, 723, 726, 728, 731, 734, 735, 739, 740, 741, 745, 750, 752, 754, 756, 757, 760, 769, 770, 772, 773, 774, 775, 776, 777, 781, 782, 783, 784, 785, 786, 787, 789, 792, 793, 794, 795, 798, 799, 800, 803, 806, 808, 810, 813, 814, 815, 816, 818, 821, 822, 826, 830, 831, 832, 835, 836, 838, 839, 840, 844, 850, 854, 858, 863, 865, 867, 870, 872, 874, 883, 887, 888, 892, 893, 901, 902, 903, 904, 905, 906, 908, 910, 912, 914, 915, 916, 917, 918, 919, 921, 922, 923, 927, 934, 935, 936, 937, 938, 940, 942, 943, 944, 946, 947, 948, 950, 956, 961, 962, 965, 966, 968, 969, 973, 976, 977, 978, 979, 980, 981, 985, 986, 987, 990, 995, 997, 1001, 1002, 1003, 1004, 1006, 1007, 1018, 1022, 1024, 1026, 1030, 1035, 1048, 1050, 1051, 1052, 1053, 1057, 1066, 1068, 1071, 1072, 1082, 1083, 1084, 1085, 1088, 1089, 1091, 1092, 1093, 1094, 1097, 1099, 1102, 1104, 1107, 1109, 1111, 1113, 1114, 1115, 1116, 1117, 1119, 1125, 1127, 1128, 1129, 1130, 1133, 1136, 1137, 1141, 1144, 1145, 1150, 1151, 1167, 1175, 1178, 1179, 1180, 1184, 1186, 1188, 1199, 1208, 1209, 1210, 1211, 1214, 1215, 1216, 1217, 1218, 1219, 1222, 1223, 1224, 1225, 1226, 1228, 1229, 1230, 1231, 1233, 1238, 1243, 1244, 1246, 1250, 1259, 1265, 1269, 1274, 1275, 1277, 1278, 1279, 1280, 1281, 1284, 1286, 1287, 1288, 1302 or 1304 of the polypeptide of SEQ ID NO: 1.

26. The lactase variant of the preceding embodiment, wherein the variant has a decreased or an increased galactose inhibition, preferably measured as a galactose inhibition improvement factor (GI-IF) of at least 1.4 or at most 0.6, compared to the lactase of SEQ ID NO: 1.

27. The lactase variant of embodiment 1 comprising an alteration, preferably a substitution, at one or more positions corresponding to positions 2, 3, 7, 13, 15, 16, 21, 23, 24, 26, 27, 28, 29, 31, 32, 34, 35, 40, 42, 43, 45, 47, 49, 51, 55, 57, 58, 59, 62, 64, 66, 73, 75, 76, 77, 78, 79, 81, 85, 86, 87, 88, 90, 91, 92, 93, 94, 95, 96, 97, 98, 100, 101, 102, 109, 110, 111, 112, 114, 115, 120, 121, 124, 130, 132, 136, 137, 146, 150, 153, 157, 158, 159, 161, 162, 165, 166, 167, 170, 172, 174, 176, 177, 178, 179, 180, 185, 188, 189, 190, 197, 217, 218, 220, 222, 223, 228, 233, 236, 237, 239, 242, 247, 248, 249, 251, 252, 254, 255, 256, 261, 262, 268, 272, 278, 279, 286, 291, 292, 293, 296, 298, 301, 303, 304, 305, 312, 320, 325, 326, 328, 337, 340, 341, 342, 343, 345, 348, 350, 359, 360, 362, 363, 364, 365, 368, 369, 370, 373, 376, 377, 379, 380, 381, 386, 387, 388, 389, 390, 391, 392, 393, 394, 395, 396, 398, 399, 400, 401, 402, 403, 404, 406, 408, 409, 411, 413, 414, 416, 417, 418, 419, 423, 424, 426, 427, 429, 431, 433, 434, 435, 436, 439, 442, 443, 444, 445, 448, 449, 450, 451, 452, 454, 455, 456, 457, 459, 465, 466, 472, 475, 477, 479, 485, 487, 488, 491, 493, 495, 498, 499, 500, 504, 505, 506, 507, 508, 509, 510, 511, 512, 514, 516, 517, 518, 519, 520, 521, 524, 525, 526, 527, 528, 531, 537, 540, 546, 547, 548, 549, 550, 551, 553, 554, 555, 556, 558, 559, 564, 565, 567, 570, 572, 574, 576, 577, 579, 582, 583, 585, 586, 588, 592, 594, 595, 600, 608, 609, 610, 611, 634, 635, 639, 644, 650, 655, 656, 661, 669, 670, 673, 676, 680, 684, 687, 688, 694, 695, 697, 698, 700, 701, 705, 709, 710, 712, 714, 718, 721, 723, 726, 728, 731, 734, 735, 739, 740, 741, 745, 750, 752, 756, 757, 760, 769, 770, 772, 773, 774, 775, 776, 777, 781, 782, 783, 784, 785, 786, 787, 789, 792, 793, 794, 795, 798, 799, 800, 803, 806, 808, 810, 813, 814, 815, 816, 818, 821, 822, 826, 830, 831, 832, 835, 836, 838, 840, 844, 850, 854, 858, 863, 865, 870, 872, 874, 883, 887, 888, 893, 901, 902, 903, 904, 905, 908, 910, 912, 914, 915, 916, 917, 918, 919, 921, 922, 923, 927, 934, 935, 936, 937, 938, 940, 942, 943, 944, 946, 947, 948, 950, 956, 961, 962, 965, 966, 968, 969, 973, 976, 977, 978, 979, 980, 981, 985, 986, 987, 990, 995, 997, 1002, 1003, 1004, 1006, 1007, 1018, 1022, 1024, 1026, 1030, 1035, 1048, 1050, 1051, 1052, 1053, 1057, 1066, 1068, 1071, 1072, 1082, 1083, 1084, 1085, 1088, 1089, 1091, 1092, 1093, 1094, 1097, 1099, 1102, 1104, 1107, 1109, 1111, 1113, 1114, 1115, 1116, 1117, 1119, 1125, 1127, 1128, 1129, 1130, 1133, 1136, 1137, 1141, 1144, 1145, 1150, 1151, 1167, 1175, 1178, 1179, 1180, 1184, 1186, 1188, 1199, 1208, 1209, 1210, 1211, 1214, 1215, 1217, 1218, 1219, 1222, 1223, 1224, 1225, 1226, 1228, 1230, 1231, 1233, 1238, 1243, 1244, 1246, 1250, 1259, 1265, 1269, 1274, 1275, 1277, 1278, 1279, 1280, 1281, 1284, 1286, 1287, 1288, 1302 or 1304 of the polypeptide of SEQ ID NO: 1.

28. The lactase variant of the preceding embodiment, wherein the variant has a decreased or an increased galactose inhibition, preferably measured as a galactose inhibition improvement factor (GI-IF) of at least 1.4 or at most 0.6, compared to the lactase of SEQ ID NO: 1.

29. The lactase variant of embodiment 1 comprising an alteration, preferably a substitution, at one or more positions corresponding to positions 2, 3, 7, 13, 15, 16, 20, 21, 24, 26, 27, 28, 29, 31, 32, 40, 45, 47, 49, 51, 55, 57, 58, 59, 62, 64, 73, 75, 76, 77, 78, 79, 85, 86, 87, 88, 90, 91, 92, 93, 94, 95, 96, 97, 98, 100, 101, 102, 109, 110, 111, 114, 115, 120, 121, 130, 132, 137, 149, 150, 157, 158, 159, 161, 162, 165, 166, 167, 170, 172, 174, 176, 177, 178, 179, 180, 185, 188, 197, 217, 218, 220, 222, 223, 228, 236, 237, 251, 252, 268, 272, 291, 292, 293, 296, 298, 301, 303, 304, 305, 309, 312, 320, 325, 326, 328, 337, 340, 341, 343, 345, 348, 350, 359, 360, 362, 363, 364, 365, 368, 369, 370, 373, 376, 377, 379, 380, 381, 386, 388, 389, 390, 393, 395, 396, 399, 400, 401, 402, 403, 404, 405, 406, 411, 417, 427, 429, 431, 433, 434, 435, 436, 439, 442, 443, 444, 448, 449, 450, 451, 452, 454, 455, 456, 457, 458, 459, 465, 466, 468, 472, 475, 477, 479, 485, 487, 493, 499, 505, 506, 507, 508, 509, 510, 511, 512, 513, 515, 516, 517, 518, 519, 520, 521, 524, 526, 527, 528, 537, 540, 549, 558, 559, 564, 565, 567, 582, 583, 585, 592, 600, 607, 614, 619, 625, 634, 639, 655, 661, 669, 673, 676, 680, 687, 688, 692, 694, 695, 697, 698, 701, 705, 710, 712, 714, 716, 717, 718, 719, 721, 723, 726, 728, 734, 735, 739, 740, 741, 750, 752, 756, 757, 769, 770, 772, 773, 774, 777, 781, 782, 785, 786, 789, 798, 799, 803, 806, 810, 818, 821, 822, 831, 832, 835, 836, 839, 840, 854, 858, 865, 867, 872, 874, 883, 887, 888, 892, 893, 901, 902, 903, 904, 905, 906, 908, 910, 912, 914, 915, 916, 917, 918, 919, 921, 922, 923, 934, 935, 936, 937, 938, 942, 943, 946, 947, 956, 961, 962, 965, 966, 968, 969, 973, 976, 977, 978, 980, 981, 985, 986, 987, 990, 995, 997, 1001, 1002, 1003, 1006, 1007, 1018, 1022, 1024, 1030, 1035, 1048, 1051, 1052, 1053, 1057, 1082, 1083, 1084, 1085, 1088, 1089, 1093, 1094, 1099, 1102, 1109, 1111, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1186, 1188, 1208, 1209, 1210, 1211, 1214, 1215, 1216, 1217, 1218, 1222, 1224, 1225, 1226, 1229, 1230, 1238, 1259, 1265, 1274, 1275, 1277, 1278, 1279, 1280, 1281, 1284, 1286, 1287, 1288, 1302 or 1304 of the polypeptide of SEQ ID NO: 1.

30. The lactase variant of the preceding embodiment, wherein the variant has a decreased galactose inhibition, preferably measured as a galactose inhibition improvement factor (GI-IF) of at least 1.4, compared to the lactase of SEQ ID NO: 1.

31. The lactase variant of embodiment 1 comprising an alteration, preferably a substitution, at one or more positions corresponding to positions 2, 3, 7, 13, 15, 16, 21, 24, 26, 27, 28, 29, 31, 32, 40, 45, 47, 49, 51, 55, 57, 58, 59, 62, 64, 73, 75, 76, 77, 78, 79, 85, 86, 87, 88, 90, 91, 92, 93, 94, 95, 96, 97, 98, 100, 101, 102, 109, 110, 111, 114, 115, 120, 121, 130, 132, 137, 150, 157, 158, 159, 161, 162, 165, 166, 167, 170, 172, 174, 176, 177, 178, 179, 180, 185, 188, 197, 217, 218, 220, 222, 223, 228, 236, 237, 251, 252, 268, 272, 291, 292, 293, 296, 298, 301, 303, 304, 305, 312, 320, 325, 326, 328, 337, 340, 341, 343, 345, 348, 350, 359, 360, 362, 363, 364, 365, 368, 369, 370, 373, 376, 377, 379, 380, 381, 386, 388, 389, 390, 393, 395, 396, 399, 400, 401, 402, 403, 404, 406, 411, 417, 427, 429, 431, 433, 434, 435, 436, 439, 442, 443, 444, 448, 449, 450, 451, 452, 454, 455, 456, 457, 459, 465, 466, 472, 475, 477, 479, 485, 487, 493, 499, 505, 506, 507, 508, 509, 510, 511, 512, 516, 517, 518, 519, 520, 521, 524, 526, 527, 528, 537, 540, 549, 558, 559, 564, 565, 567, 582, 583, 592, 600, 634, 639, 655, 661, 669, 673, 676, 680, 687, 688, 694, 695, 697, 698, 701, 705, 710, 712, 714, 718, 721, 723, 726, 728, 734, 735, 739, 740, 741, 750, 752, 756, 757, 769, 770, 772, 773, 774, 777, 781, 782, 785, 786, 789, 798, 799, 803, 806, 810, 818, 821, 822, 831, 832, 835, 836, 840, 854, 858, 865, 872, 874, 883, 887, 888, 893, 901, 902, 903, 904, 905, 908, 910, 912, 914, 915, 916, 917, 918, 919, 921, 922, 923, 934, 935, 936, 937, 938, 942, 943, 946, 947, 956, 961, 962, 965, 966, 968, 969, 973, 976, 977, 978, 980, 981, 985, 986, 987, 990, 995, 997, 1002, 1003, 1006, 1007, 1018, 1022, 1024, 1030, 1035, 1048, 1051, 1052, 1053, 1057, 1082, 1083, 1084, 1085, 1088, 1089, 1093, 1094, 1099, 1102, 1109, 1111, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1186, 1188, 1208, 1209, 1210, 1211, 1214, 1215, 1217, 1218, 1222, 1224, 1225, 1226, 1230, 1238, 1259, 1265, 1274, 1275, 1277, 1278, 1279, 1280, 1281, 1284, 1286, 1287, 1288, 1302 or 1304 of the polypeptide of SEQ ID NO: 1.

32. The lactase variant of the preceding embodiment, wherein the variant has a decreased galactose inhibition, preferably measured as a galactose inhibition improvement factor (GI-IF) of at least 1.4, compared to the lactase of SEQ ID NO: 1.

33. The lactase variant of embodiment 1 comprising an alteration, preferably a substitution, at one or more positions corresponding to positions 7, 15, 16, 20, 24, 27, 28, 29, 31, 32, 45, 47, 49, 51, 55, 57, 58, 59, 66, 75, 76, 77, 81, 85, 86, 87, 88, 90, 92, 93, 94, 95, 96, 98, 101, 102, 109, 112, 120, 121, 124, 137, 149, 153, 158, 159, 161, 162, 165, 166, 167, 170, 172, 174, 178, 185, 188, 189, 217, 218, 220, 222, 223, 236, 237, 239, 247, 251, 252, 254, 264, 268, 272, 279, 291, 298, 301, 303, 304, 305, 326, 337, 341, 345, 348, 359, 362, 363, 364, 368, 369, 370, 373, 376, 381, 386, 387, 389, 390, 391, 392, 393, 394, 395, 396, 398, 399, 400, 401, 402, 403, 404, 405, 406, 413, 414, 416, 417, 418, 420, 423, 424, 427, 429, 431, 433, 434, 435, 436, 439, 442, 444, 445, 448, 449, 450, 451, 452, 455, 456, 457, 458, 459, 465, 466, 468, 472, 479, 487, 488, 491, 493, 499, 500, 504, 505, 506, 507, 508, 509, 510, 511, 512, 513, 515, 516, 517, 518, 521, 522, 524, 526, 527, 537, 540, 546, 548, 549, 550, 551, 554, 555, 556, 558, 564, 565, 567, 570, 574, 582, 583, 586, 592, 594, 595, 600, 608, 609, 614, 625, 630, 639, 644, 650, 655, 656, 661, 669, 670, 673, 688, 694, 695, 697, 698, 700, 701, 709, 710, 714, 717, 718, 719, 721, 728, 731, 734, 735, 739, 741, 745, 750, 752, 754, 756, 757, 769, 770, 772, 775, 776, 777, 781, 783, 784, 785, 786, 787, 792, 793, 794, 795, 799, 803, 810, 814, 815, 816, 818, 821, 822, 826, 830, 835, 836, 839, 844, 850, 854, 865, 867, 872, 883, 893, 901, 902, 904, 912, 914, 915, 916, 917, 918, 919, 921, 922, 923, 934, 935, 936, 937, 943, 944, 946, 956, 961, 965, 968, 969, 973, 981, 985, 986, 1002, 1006, 1007, 1030, 1035, 1048, 1050, 1051, 1053, 1066, 1068, 1084, 1085, 1089, 1093, 1094, 1097, 1102, 1109, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1208, 1210, 1211, 1214, 1216, 1219, 1222, 1223, 1224, 1225, 1226, 1229, 1230, 1238, 1259, 1265, 1269, 1274, 1275, 1277, 1278, 1279, 1281, 1284, 1286, 1287, 1288, 1302 or 1304 of the polypeptide of SEQ ID NO: 1.

34. The lactase variant of the preceding embodiment, wherein the variant has a decreased or an increased galactose inhibition, preferably measured as a galactose inhibition improvement factor (GI-IF) of at least 1.5 or at most 0.5, compared to the lactase of SEQ ID NO: 1.

35. The lactase variant of embodiment 1 comprising an alteration, preferably a substitution, at one or more positions corresponding to positions 7, 15, 16, 24, 27, 28, 29, 31, 32, 45, 47, 49, 51, 55, 57, 58, 59, 66, 75, 76, 77, 81, 85, 86, 87, 88, 90, 92, 93, 94, 95, 96, 98, 101, 102, 109, 112, 120, 121, 124, 137, 153, 158, 159, 161, 162, 165, 166, 167, 170, 172, 174, 178, 185, 188, 189, 217, 218, 220, 222, 223, 236, 237, 239, 247, 251, 252, 254, 268, 272, 279, 291, 298, 301, 303, 304, 305, 326, 337, 341, 345, 348, 359, 362, 363, 364, 368, 369, 370, 373, 376, 381, 386, 387, 389, 390, 391, 392, 393, 394, 395, 396, 398, 399, 400, 401, 402, 403, 404, 406, 413, 414, 416, 417, 418, 423, 424, 427, 429, 431, 433, 434, 435, 436, 439, 442, 444, 445, 448, 449, 450, 451, 452, 455, 456, 457, 459, 465, 466, 472, 479, 487, 488, 491, 493, 499, 500, 504, 505, 506, 507, 508, 509, 510, 511, 512, 516, 517, 518, 521, 524, 526, 527, 537, 540, 546, 548, 549, 550, 551, 554, 555, 556, 558, 564, 565, 567, 570, 574, 582, 583, 586, 592, 594, 595, 600, 608, 609, 639, 644, 650, 655, 656, 661, 669, 670, 673, 688, 694, 695, 697, 698, 700, 701, 709, 710, 714, 718, 721, 728, 731, 734, 735, 739, 741, 745, 750, 752, 756, 757, 769, 770, 772, 775, 776, 777, 781, 783, 784, 785, 786, 787, 792, 793, 794, 795, 799, 803, 810, 814, 815, 816, 818, 821, 822, 826, 830, 835, 836, 844, 850, 854, 865, 872, 883, 893, 901, 902, 904, 912, 914, 915, 916, 917, 918, 919, 921, 922, 923, 934, 935, 936, 937, 943, 944, 946, 956, 961, 965, 968, 969, 973, 981, 985, 986, 1002, 1006, 1007, 1030, 1035, 1048, 1050, 1051, 1053, 1066, 1068, 1084, 1085, 1089, 1093, 1094, 1097, 1102, 1109, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1208, 1210, 1211, 1214, 1219, 1222, 1223, 1224, 1225, 1226, 1230, 1238, 1259, 1265, 1269, 1274, 1275, 1277, 1278, 1279, 1281, 1284, 1286, 1287, 1288, 1302 or 1304 of the polypeptide of SEQ ID NO: 1.

36. The lactase variant of the preceding embodiment, wherein the variant has a decreased or an increased galactose inhibition, preferably measured as a galactose inhibition improvement factor (GI-IF) of at least 1.5 or at most 0.5, compared to the lactase of SEQ ID NO: 1.

37. The lactase variant of embodiment 1 comprising an alteration, preferably a substitution, at one or more positions corresponding to positions 7, 15, 16, 20, 24, 27, 28, 29, 31, 32, 45, 47, 49, 51, 55, 57, 58, 59, 75, 76, 77, 85, 86, 87, 88, 90, 92, 93, 94, 95, 96, 98, 101, 102, 109, 120, 121, 137, 149, 158, 159, 161, 162, 165, 166, 167, 170, 172, 174, 178, 185, 188, 217, 218, 220, 222, 223, 236, 237, 251, 252, 268, 272, 291, 298, 301, 303, 304, 326, 337, 341, 345, 348, 359, 362, 363, 364, 368, 369, 370, 373, 376, 381, 386, 389, 390, 393, 395, 396, 399, 400, 401, 402, 403, 404, 405, 406, 417, 427, 429, 431, 433, 434, 435, 436, 439, 442, 444, 448, 449, 450, 451, 452, 455, 456, 457, 458, 459, 465, 466, 468, 472, 479, 487, 499, 505, 506, 507, 508, 509, 510, 511, 512, 513, 515, 516, 517, 518, 521, 524, 526, 527, 537, 540, 549, 558, 564, 565, 567, 582, 583, 600, 614, 625, 639, 655, 661, 669, 673, 688, 694, 695, 697, 698, 701, 710, 714, 717, 718, 719, 721, 728, 735, 739, 741, 750, 752, 756, 757, 769, 770, 772, 777, 781, 785, 786, 799, 803, 810, 818, 821, 822, 835, 836, 839, 854, 865, 867, 872, 883, 893, 901, 902, 904, 912, 914, 915, 916, 917, 918, 919, 921, 922, 923, 934, 935, 936, 937, 943, 956, 961, 965, 968, 969, 973, 981, 985, 986, 1002, 1006, 1007, 1030, 1035, 1048, 1051, 1053, 1084, 1085, 1089, 1093, 1094, 1102, 1109, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1208, 1210, 1211, 1214, 1216, 1222, 1224, 1225, 1226, 1229, 1230, 1238, 1259, 1265, 1274, 1275, 1277, 1278, 1279, 1281, 1284, 1286, 1287, 1288, 1302 or 1304 of the polypeptide of SEQ ID NO: 1.

38. The lactase variant of the preceding embodiment, wherein the variant has a decreased galactose inhibition, preferably measured as a galactose inhibition improvement factor (GI-IF) of at least 1.5, compared to the lactase of SEQ ID NO: 1.

39. The lactase variant of embodiment 1 comprising an alteration, preferably a substitution, at one or more positions corresponding to positions 7, 15, 16, 24, 27, 28, 29, 31, 32, 45, 47, 49, 51, 55, 57, 58, 59, 75, 76, 77, 85, 86, 87, 88, 90, 92, 93, 94, 95, 96, 98, 101, 102, 109, 120, 121, 137, 158, 159, 161, 162, 165, 166, 167, 170, 172, 174, 178, 185, 188, 217, 218, 220, 222, 223, 236, 237, 251, 252, 268, 272, 291, 298, 301, 303, 304, 326, 337, 341, 345, 348, 359, 362, 363, 364, 368, 369, 370, 373, 376, 381, 386, 389, 390, 393, 395, 396, 399, 400, 401, 402, 403, 404, 406, 417, 427, 429, 431, 433, 434, 435, 436, 439, 442, 444, 448, 449, 450, 451, 452, 455, 456, 457, 459, 465, 466, 472, 479, 487, 499, 505, 506, 507, 508, 509, 510, 511, 512, 516, 517, 518, 521, 524, 526, 527, 537, 540, 549, 558, 564, 565, 567, 582, 583, 600, 639, 655, 661, 669, 673, 688, 694, 695, 697, 698, 701, 710, 714, 718, 721, 728, 735, 739, 741, 750, 752, 756, 757, 769, 770, 772, 777, 781, 785, 786, 799, 803, 810, 818, 821, 822, 835, 836, 854, 865, 872, 883, 893, 901, 902, 904, 912, 914, 915, 916, 917, 918, 919, 921, 922, 923, 934, 935, 936, 937, 943, 956, 961, 965, 968, 969, 973, 981, 985, 986, 1002, 1006, 1007, 1030, 1035, 1048, 1051, 1053, 1084, 1085, 1089, 1093, 1094, 1102, 1109, 1113, 1114, 1115, 1116, 1117, 1119, 1125, 1127, 1128, 1129, 1130, 1133, 1137, 1144, 1145, 1150, 1151, 1167, 1178, 1179, 1180, 1184, 1208, 1210, 1211, 1214, 1222, 1224, 1225, 1226, 1230, 1238, 1259, 1265, 1274, 1275, 1277, 1278, 1279, 1281, 1284, 1286, 1287, 1288, 1302 or 1304 of the polypeptide of SEQ ID NO: 1.

40. The lactase variant of the preceding embodiment, wherein the variant has a decreased galactose inhibition, preferably measured as a galactose inhibition improvement factor (GI-IF) of at least 1.5, compared to the lactase of SEQ ID NO: 1.

41. The lactase variant of embodiment 1 comprising an alteration, preferably a substitution, at one or more positions corresponding to positions 7, 15, 20, 24, 27, 31, 45, 47, 49, 51, 57, 59, 77, 85, 86, 87, 88, 90, 92, 93, 94, 96, 101, 112, 121, 161, 162, 165, 166, 167, 170, 174, 185, 217, 218, 220, 222, 223, 236, 237, 239, 252, 268, 298, 301, 303, 304, 337, 362, 364, 368, 369, 373, 376, 381, 386, 389, 390, 391, 392, 393, 394, 395, 396, 398, 400, 401, 402, 403, 404, 405, 406, 418, 420, 427, 429, 433, 434, 444, 445, 448, 449, 450, 451, 452, 455, 456, 459, 466, 468, 472, 479, 488, 491, 499, 504, 505, 506, 507, 508, 509, 510, 511, 512, 513, 515, 517, 521, 522, 524, 526, 527, 546, 549, 550, 554, 555, 556, 558, 564, 567, 570, 582, 583, 592, 594, 600, 608, 609, 614, 625, 630, 639, 644, 650, 655, 661, 669, 670, 673, 688, 694, 695, 698, 700, 701, 710, 714, 721, 731, 734, 745, 750, 752, 756, 757, 769, 770, 772, 775, 776, 777, 781, 783, 784, 785, 787, 792, 794, 803, 810, 814, 822, 826, 830, 835, 836, 839, 844, 865, 867, 872, 902, 912, 914, 915, 916, 917, 919, 922, 923, 937, 943, 944, 946, 961, 969, 973, 985, 986, 1002, 1006, 1007, 1048, 1051, 1066, 1068, 1084, 1085, 1093, 1094, 1097, 1102, 1109, 1113, 1114, 1116, 1117, 1125, 1127, 1129, 1133, 1137, 1145, 1151, 1167, 1178, 1179, 1180, 1184, 1210, 1211, 1214, 1216, 1222, 1223, 1225, 1226, 1230, 1238, 1265, 1274, 1275, 1277, 1278, 1279, 1281, 1284, 1286, 1287, 1288 or 1302 of the polypeptide of SEQ ID NO: 1.

42. The lactase variant of the preceding embodiment, wherein the variant has a decreased or an increased galactose inhibition, preferably measured as a galactose inhibition improvement factor (GI-IF) of at least 1.6 or at most 0.4, compared to the lactase of SEQ ID NO: 1.

43. The lactase variant of embodiment 1 comprising an alteration, preferably a substitution, at one or more positions corresponding to positions 7, 15, 24, 27, 31, 45, 47, 49, 51, 57, 59, 77, 85, 86, 87, 88, 90, 92, 93, 94, 96, 101, 112, 121, 161, 162, 165, 166, 167, 170, 174, 185, 217, 218, 220, 222, 223, 236, 237, 239, 252, 268, 298, 301, 303, 304, 337, 362, 364, 368, 369, 373, 376, 381, 386, 389, 390, 391, 392, 393, 394, 395, 396, 398, 400, 401, 402, 403, 404, 406, 418, 427, 429, 433, 434, 444, 445, 448, 449, 450, 451, 452, 455, 456, 459, 466, 472, 479, 488, 491, 499, 504, 505, 506, 507, 508, 509, 510, 511, 512, 517, 521, 524, 526, 527, 546, 549, 550, 554, 555, 556, 558, 564, 567, 570, 582, 583, 592, 594, 600, 608, 609, 639, 644, 650, 655, 661, 669, 670, 673, 688, 694, 695, 698, 700, 701, 710, 714, 721, 731, 734, 745, 750, 752, 756, 757, 769, 770, 772, 775, 776, 777, 781, 783, 784, 785, 787, 792, 794, 803, 810, 814, 822, 826, 830, 835, 836, 844, 865, 872, 902, 912, 914, 915, 916, 917, 919, 922, 923, 937, 943, 944, 946, 961, 969, 973, 985, 986, 1002, 1006, 1007, 1048, 1051, 1066, 1068, 1084, 1085, 1093, 1094, 1097, 1102, 1109, 1113, 1114, 1116, 1117, 1125, 1127, 1129, 1133, 1137, 1145, 1151, 1167, 1178, 1179, 1180, 1184, 1210, 1211, 1214, 1222, 1223, 1225, 1226, 1230, 1238, 1265, 1274, 1275, 1277, 1278, 1279, 1281, 1284, 1286, 1287, 1288 or 1302 of the polypeptide of SEQ ID NO: 1.

44. The lactase variant of the preceding embodiment, wherein the variant has a decreased or an increased galactose inhibition, preferably measured as a galactose inhibition improvement factor (GI-IF) of at least 1.6 or at most 0.4, compared to the lactase of SEQ ID NO: 1.

45. The lactase variant of embodiment 1 comprising an alteration, preferably a substitution, at one or more positions corresponding to positions 7, 15, 20, 24, 27, 31, 45, 47, 49, 51, 57, 59, 77, 85, 86, 87, 88, 90, 92, 93, 94, 96, 101, 121, 161, 162, 165, 166, 167, 170, 174, 185, 217, 218, 220, 222, 223, 236, 237, 252, 268, 298, 301, 303, 304, 337, 362, 364, 368, 369, 373, 376, 381, 386, 389, 390, 393, 396, 400, 401, 402, 403, 404, 405, 406, 427, 429, 433, 434, 444, 448, 449, 450, 451, 452, 455, 456, 459, 466, 468, 472, 479, 505, 506, 507, 508, 509, 510, 511, 512, 513, 515, 517, 521, 524, 526, 527, 549, 558, 564, 567, 582, 583, 600, 614, 625, 639, 655, 661, 669, 673, 688, 694, 695, 698, 701, 710, 714, 721, 750, 752, 756, 757, 769, 770, 772, 777, 781, 785, 803, 810, 822, 835, 836, 839, 865, 867, 872, 902, 912, 914, 915, 916, 917, 919, 922, 923, 937, 943, 961, 969, 973, 985, 986, 1002, 1006, 1007, 1048, 1051, 1084, 1085, 1093, 1094, 1102, 1109, 1113, 1114, 1116, 1117, 1125, 1127, 1129, 1133, 1137, 1145, 1167, 1178, 1179, 1180, 1184, 1210, 1211, 1214, 1216, 1222, 1225, 1226, 1230, 1238, 1265, 1274, 1275, 1277, 1278, 1279, 1281, 1284, 1286, 1287, 1288 or 1302 of the polypeptide of SEQ ID NO: 1.

46. The lactase variant of the preceding embodiment, wherein the variant has a decreased galactose inhibition, preferably measured as a galactose inhibition improvement factor (GI-IF) of at least 1.6, compared to the lactase of SEQ ID NO: 1.

47. The lactase variant of embodiment 1 comprising an alteration, preferably a substitution, at one or more positions corresponding to positions 7, 15, 24, 27, 31, 45, 47, 49, 51, 57, 59, 77, 85, 86, 87, 88, 90, 92, 93, 94, 96, 101, 121, 161, 162, 165, 166, 167, 170, 174, 185, 217, 218, 220, 222, 223, 236, 237, 252, 268, 298, 301, 303, 304, 337, 362, 364, 368, 369, 373, 376, 381, 386, 389, 390, 393, 396, 400, 401, 402, 403, 404, 406, 427, 429, 433, 434, 444, 448, 449, 450, 451, 452, 455, 456, 459, 466, 472, 479, 505, 506, 507, 508, 509, 510, 511, 512, 517, 521, 524, 526, 527, 549, 558, 564, 567, 582, 583, 600, 639, 655, 661, 669, 673, 688, 694, 695, 698, 701, 710, 714, 721, 750, 752, 756, 757, 769, 770, 772, 777, 781, 785, 803, 810, 822, 835, 836, 865, 872, 902, 912, 914, 915, 916, 917, 919, 922, 923, 937, 943, 961, 969, 973, 985, 986, 1002, 1006, 1007, 1048, 1051, 1084, 1085, 1093, 1094, 1102, 1109, 1113, 1114, 1116, 1117, 1125, 1127, 1129, 1133, 1137, 1145, 1167, 1178, 1179, 1180, 1184, 1210, 1211, 1214, 1222, 1225, 1226, 1230, 1238, 1265, 1274, 1275, 1277, 1278, 1279, 1281, 1284, 1286, 1287, 1288 or 1302 of the polypeptide of SEQ ID NO: 1.

48. The lactase variant of the preceding embodiment, wherein the variant has a decreased galactose inhibition, preferably measured as a galactose inhibition improvement factor (GI-IF) of at least 1.6, compared to the lactase of SEQ ID NO: 1.

49. The lactase variant of embodiment 1 comprising an alteration, preferably a substitution, at one or more positions corresponding to positions 7, 15, 20, 24, 27, 31, 49, 57, 59, 77, 85, 86, 87, 88, 92, 93, 96, 101, 112, 161, 162, 165, 166, 167, 170, 174, 185, 217, 220, 222, 237, 239, 252, 268, 301, 304, 337, 362, 364, 368, 369, 376, 381, 386, 389, 390, 392, 393, 394, 395, 396, 401, 402, 403, 404, 405, 418, 427, 429, 434, 444, 448, 449, 450, 451, 452, 459, 466, 468, 472, 479, 491, 499, 504, 505, 506, 508, 509, 510, 511, 513, 515, 517, 521, 522, 524, 526, 527, 546, 549, 550, 555, 558, 564, 567, 582, 600, 608, 609, 614, 625, 639, 650, 661, 670, 673, 688, 695, 698, 701, 710, 714, 721, 734, 745, 750, 756, 757, 769, 770, 772, 775, 776, 781, 783, 784, 785, 810, 814, 822, 835, 836, 844, 865, 867, 872, 902, 912, 914, 915, 916, 917, 919, 922, 923, 943, 944, 961, 969, 973, 985, 986, 1002, 1006, 1051, 1084, 1085, 1093, 1109, 1114, 1116, 1117, 1125, 1133, 1178, 1179, 1184, 1210, 1211, 1214, 1216, 1222, 1225, 1226, 1230, 1238, 1265, 1274, 1275, 1277, 1278, 1279, 1281, 1284, 1287, 1288 or 1302 of the polypeptide of SEQ ID NO: 1.

50. The lactase variant of the preceding embodiment, wherein the variant has a decreased or an increased galactose inhibition, preferably measured as a galactose inhibition improvement factor (GI-IF) of at least 1.7 or at most 0.3, compared to the lactase of SEQ ID NO: 1.

51. The lactase variant of embodiment 1 comprising an alteration, preferably a substitution, at one or more positions corresponding to positions 7, 15, 24, 27, 31, 49, 57, 59, 77, 85, 86, 87, 88, 92, 93, 96, 101, 112, 161, 162, 165, 166, 167, 170, 174, 185, 217, 220, 222, 237, 239, 252, 268, 301, 304, 337, 362, 364, 368, 369, 376, 381, 386, 389, 390, 392, 393, 394, 395, 396, 401, 402, 403, 404, 418, 427, 429, 434, 444, 448, 449, 450, 451, 452, 459, 466, 472, 479, 491, 499, 504, 505, 506, 508, 509, 510, 511, 517, 521, 524, 526, 527, 546, 549, 550, 555, 558, 564, 567, 582, 600, 608, 609, 639, 650, 661, 670, 673, 688, 695, 698, 701, 710, 714, 721, 734, 745, 750, 756, 757, 769, 770, 772, 775, 776, 781, 783, 784, 785, 810, 814, 822, 835, 836, 844, 865, 872, 902, 912, 914, 915, 916, 917, 919, 922, 923, 943, 944, 961, 969, 973, 985, 986, 1002, 1006, 1051, 1084, 1085, 1093, 1109, 1114, 1116, 1117, 1125, 1133, 1178, 1179, 1184, 1210, 1211, 1214, 1222, 1225, 1226, 1230, 1238, 1265, 1274, 1275, 1277, 1278, 1279, 1281, 1284, 1287, 1288 or 1302 of the polypeptide of SEQ ID NO: 1.

52. The lactase variant of the preceding embodiment, wherein the variant has a decreased or an increased galactose inhibition, preferably measured as a galactose inhibition improvement factor (GI-IF) of at least 1.7 or at most 0.3, compared to the lactase of SEQ ID NO: 1.

53. The lactase variant of embodiment 1 comprising an alteration, preferably a substitution, at one or more positions corresponding to positions 7, 15, 20, 24, 27, 31, 49, 57, 59, 77, 85, 86, 87, 88, 92, 93, 96, 101, 161, 162, 165, 166, 167, 170, 174, 185, 217, 220, 222, 237, 252, 268, 301, 304, 337, 362, 364, 368, 369, 376, 381, 386, 389, 390, 393, 396, 401, 402, 403, 404, 405, 427, 429, 434, 444, 448, 449, 450, 451, 452, 459, 466, 468, 472, 479, 505, 506, 508, 509, 510, 511, 513, 515, 517, 521, 524, 526, 527, 549, 558, 564, 567, 582, 600, 614, 625, 639, 661, 673, 688, 695, 698, 701, 710, 714, 721, 750, 756, 757, 769, 770, 772, 781, 785, 810, 822, 835, 836, 865, 867, 872, 902, 912, 914, 915, 916, 917, 919, 922, 923, 961, 969, 973, 985, 986, 1002, 1006, 1051, 1084, 1085, 1093, 1109, 1114, 1116, 1117, 1125, 1133, 1178, 1179, 1184, 1210, 1211, 1214, 1216, 1222, 1225, 1226, 1230, 1238, 1265, 1274, 1275, 1277, 1278, 1279, 1281, 1284, 1287, 1288 or 1302 of the polypeptide of SEQ ID NO: 1.

54. The lactase variant of the preceding embodiment, wherein the variant has a decreased galactose inhibition, preferably measured as a galactose inhibition improvement factor (GI-IF) of at least 1.7, compared to the lactase of SEQ ID NO: 1.

55. The lactase variant of embodiment 1 comprising an alteration, preferably a substitution, at one or more positions corresponding to positions 7, 15, 24, 27, 31, 49, 57, 59, 77, 85, 86, 87, 88, 92, 93, 96, 101, 161, 162, 165, 166, 167, 170, 174, 185, 217, 220, 222, 237, 252, 268, 301, 304, 337, 362, 364, 368, 369, 376, 381, 386, 389, 390, 393, 396, 401, 402, 403, 404, 427, 429, 434, 444, 448, 449, 450, 451, 452, 459, 466, 472, 479, 505, 506, 508, 509, 510, 511, 517, 521, 524, 526, 527, 549, 558, 564, 567, 582, 600, 639, 661, 673, 688, 695, 698, 701, 710, 714, 721, 750, 756, 757, 769, 770, 772, 781, 785, 810, 822, 835, 836, 865, 872, 902, 912, 914, 915, 916, 917, 919, 922, 923, 961, 969, 973, 985, 986, 1002, 1006, 1051, 1084, 1085, 1093, 1109, 1114, 1116, 1117, 1125, 1133, 1178, 1179, 1184, 1210, 1211, 1214, 1222, 1225, 1226, 1230, 1238, 1265, 1274, 1275, 1277, 1278, 1279, 1281, 1284, 1287, 1288 or 1302 of the polypeptide of SEQ ID NO: 1.

56. The lactase variant of the preceding embodiment, wherein the variant has a decreased galactose inhibition, preferably measured as a galactose inhibition improvement factor (GI-IF) of at least 1.7, compared to the lactase of SEQ ID NO: 1.

57. The lactase variant of embodiment 1 comprising an alteration, preferably a substitution, at one or more positions corresponding to positions 7, 15, 20, 24, 57, 59, 85, 86, 93, 162, 165, 166, 167, 174, 217, 222, 237, 268, 304, 337, 362, 364, 368, 369, 376, 386, 389, 390, 392, 393, 394, 395, 396, 401, 402, 403, 404, 405, 427, 429, 434, 448, 449, 450, 451, 459, 468, 472, 479, 491, 499, 505, 506, 508, 509, 510, 511, 513, 515, 517, 521, 526, 527, 546, 564, 567, 582, 600, 608, 614, 625, 650, 670, 673, 688, 695, 701, 710, 714, 721, 745, 750, 756, 757, 769, 770, 772, 776, 781, 783, 784, 785, 810, 814, 835, 844, 912, 914, 917, 919, 922, 923, 961, 985, 986, 1006, 1051, 1093, 1116, 1117, 1125, 1178, 1179, 1184, 1210, 1211, 1225, 1238, 1265, 1274, 1275, 1277, 1284, 1287, 1288 or 1302 of the polypeptide of SEQ ID NO: 1.

58. The lactase variant of the preceding embodiment, wherein the variant has a decreased or an increased galactose inhibition, preferably measured as a galactose inhibition improvement factor (GI-IF) of at least 1.8 or at most 0.2, compared to the lactase of SEQ ID NO: 1.

59. The lactase variant of embodiment 1 comprising an alteration, preferably a substitution, at one or more positions corresponding to positions 7, 15, 24, 57, 59, 85, 86, 93, 162, 165, 166, 167, 174, 217, 222, 237, 268, 304, 337, 362, 364, 368, 369, 376, 386, 389, 390, 392, 393, 394, 395, 396, 401, 402, 403, 404, 427, 429, 434, 448, 449, 450, 451, 459, 472, 479, 491, 499, 505, 506, 508, 509, 510, 511, 517, 521, 526, 527, 546, 564, 567, 582, 600, 608, 650, 670, 673, 688, 695, 701, 710, 714, 721, 745, 750, 756, 757, 769, 770, 772, 776, 781, 783, 784, 785, 810, 814, 835, 844, 912, 914, 917, 919, 922, 923, 961, 985, 986, 1006, 1051, 1093, 1116, 1117, 1125, 1178, 1179, 1184, 1210, 1211, 1225, 1238, 1265, 1274, 1275, 1277, 1284, 1287, 1288 or 1302 of the polypeptide of SEQ ID NO: 1.

60. The lactase variant of the preceding embodiment, wherein the variant has a decreased or an increased galactose inhibition, preferably measured as a galactose inhibition improvement factor (GI-IF) of at least 1.8 or at most 0.2, compared to the lactase of SEQ ID NO: 1.

61. The lactase variant of embodiment 1 comprising an alteration, preferably a substitution, at one or more positions corresponding to positions 7, 15, 20, 24, 57, 59, 85, 86, 93, 162, 165, 166, 167, 174, 217, 222, 237, 268, 304, 337, 362, 364, 368, 369, 376, 386, 389, 390, 393, 396, 401, 402, 403, 404, 405, 427, 429, 434, 448, 449, 450, 451, 459, 468, 472, 479, 505, 506, 508, 509, 510, 511, 513, 515, 517, 521, 526, 527, 564, 567, 582, 600, 614, 625, 673, 688, 695, 701, 710, 714, 721, 750, 756, 757, 769, 770, 772, 781, 785, 810, 835, 912, 914, 917, 919, 922, 923, 961, 985, 986, 1006, 1051, 1093, 1116, 1117, 1125, 1178, 1179, 1184, 1210, 1211, 1225, 1238, 1265, 1274, 1275, 1277, 1284, 1287, 1288 or 1302 of the polypeptide of SEQ ID NO: 1.

62. The lactase variant of the preceding embodiment, wherein the variant has a decreased galactose inhibition, preferably measured as a galactose inhibition improvement factor (GI-IF) of at least 1.8, compared to the lactase of SEQ ID NO: 1.

63. The lactase variant of embodiment 1 comprising an alteration, preferably a substitution, at one or more positions corresponding to positions 7, 15, 24, 57, 59, 85, 86, 93, 162, 165, 166, 167, 174, 217, 222, 237, 268, 304, 337, 362, 364, 368, 369, 376, 386, 389, 390, 393, 396, 401, 402, 403, 404, 427, 429, 434, 448, 449, 450, 451, 459, 472, 479, 505, 506, 508, 509, 510, 511, 517, 521, 526, 527, 564, 567, 582, 600, 673, 688, 695, 701, 710, 714, 721, 750, 756, 757, 769, 770, 772, 781, 785, 810, 835, 912, 914, 917, 919, 922, 923, 961, 985, 986, 1006, 1051, 1093, 1116, 1117, 1125, 1178, 1179, 1184, 1210, 1211, 1225, 1238, 1265, 1274, 1275, 1277, 1284, 1287, 1288 or 1302 of the polypeptide of SEQ ID NO: 1.

64. The lactase variant of the preceding embodiment, wherein the variant has a decreased galactose inhibition, preferably measured as a galactose inhibition improvement factor (GI-IF) of at least 1.8, compared to the lactase of SEQ ID NO: 1.

65. The lactase variant of embodiment 1 comprising an alteration, preferably a substitution, at one or more positions corresponding to positions 7, 15, 24, 57, 85, 86, 93, 162, 167, 174, 217, 222, 237, 268, 304, 362, 364, 369, 386, 389, 392, 393, 395, 396, 401, 403, 404, 405, 427, 448, 449, 450, 451, 459, 468, 472, 479, 491, 505, 506, 508, 510, 511, 513, 515, 517, 521, 526, 527, 567, 600, 625, 670, 673, 688, 695, 701, 710, 714, 721, 750, 757, 769, 772, 784, 785, 810, 912, 919, 922, 923, 961, 985, 1006, 1051, 1093, 1116, 1117, 1179, 1210, 1211, 1238, 1265, 1274, 1275, 1277, 1284, 1287, 1288 or 1302 of the polypeptide of SEQ ID NO: 1.

66. The lactase variant of the preceding embodiment, wherein the variant has a decreased or an increased galactose inhibition, preferably measured as a galactose inhibition improvement factor (GI-IF) of at least 1.9 or at most 0.1, compared to the lactase of SEQ ID NO: 1.

67. The lactase variant of embodiment 1 comprising an alteration, preferably a substitution, at one or more positions corresponding to positions 7, 15, 24, 57, 85, 86, 93, 162, 167, 174, 217, 222, 237, 268, 304, 362, 364, 369, 386, 389, 392, 393, 395, 396, 401, 403, 404, 427, 448, 449, 450, 451, 459, 472, 479, 491, 505, 506, 508, 510, 511, 517, 521, 526, 527, 567, 600, 670, 673, 688, 695, 701, 710, 714, 721, 750, 757, 769, 772, 784, 785, 810, 912, 919, 922, 923, 961, 985, 1006, 1051, 1093, 1116, 1117, 1179, 1210, 1211, 1238, 1265, 1274, 1275, 1277, 1284, 1287, 1288 or 1302 of the polypeptide of SEQ ID NO: 1.

68. The lactase variant of the preceding embodiment, wherein the variant has a decreased or an increased galactose inhibition, preferably measured as a galactose inhibition improvement factor (GI-IF) of at least 1.9 or at most 0.1, compared to the lactase of SEQ ID NO: 1.

69. The lactase variant of embodiment 1 comprising an alteration, preferably a substitution, at one or more positions corresponding to positions 7, 15, 24, 57, 85, 86, 93, 162, 167, 174, 217, 222, 237, 268, 304, 362, 364, 369, 386, 389, 393, 396, 401, 403, 404, 405, 427, 448, 449, 450, 451, 459, 468, 472, 479, 505, 506, 508, 510, 511, 513, 515, 517, 521, 526, 527, 567, 600, 625, 673, 688, 695, 701, 710, 714, 721, 750, 757, 769, 772, 785, 810, 912, 919, 922, 923, 961, 985, 1006, 1051, 1093, 1116, 1117, 1179, 1210, 1211, 1238, 1265, 1274, 1275, 1277, 1284, 1287, 1288 or 1302 of the polypeptide of SEQ ID NO: 1.

70. The lactase variant of the preceding embodiment, wherein the variant has a decreased galactose inhibition, preferably measured as a galactose inhibition improvement factor (GI-IF) of at least 1.9, compared to the lactase of SEQ ID NO: 1.

71. The lactase variant of embodiment 1 comprising an alteration, preferably a substitution, at one or more positions corresponding to positions 7, 15, 24, 57, 85, 86, 93, 162, 167, 174, 217, 222, 237, 268, 304, 362, 364, 369, 386, 389, 393, 396, 401, 403, 404, 427, 448, 449, 450, 451, 459, 472, 479, 505, 506, 508, 510, 511, 517, 521, 526, 527, 567, 600, 673, 688, 695, 701, 710, 714, 721, 750, 757, 769, 772, 785, 810, 912, 919, 922, 923, 961, 985, 1006, 1051, 1093, 1116, 1117, 1179, 1210, 1211, 1238, 1265, 1274, 1275, 1277, 1284, 1287, 1288 or 1302 of the polypeptide of SEQ ID NO: 1.

72. The lactase variant of the preceding embodiment, wherein the variant has a decreased galactose inhibition, preferably measured as a galactose inhibition improvement factor (GI-IF) of at least 1.9, compared to the lactase of SEQ ID NO: 1.

73. The lactase variant of any of the preceding embodiments wherein the alteration is a substitution.

74. The lactase variant of embodiment 1 which comprises one or more of the following substitutions, wherein each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, S14Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53T, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60C, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, G149E, G149H, G149I, G149M, G149Q, G149Y, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185A, H185L, H185R, V186A, V186E, V186G, V186N, G187A, G187D, G187H, N188E, N188R, N188S, N188V, N188Y, N189A, N189E, N189G, G190C, G190F, G190H, G190Q, G190V, V191C, V191T, V191W, V191Y, I193N, I193T, I193V, K194A, K194I, K194L, K194R, T195A, T195E, T195M, T195S, T195W, P196A, P196H, P196I, P196M, P196S, P196W, S197A, S197C, S197E, S197K, 5197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205W, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, K219A, K219C, K219F, K219H, K219M, A220C, A220G, A220I, A220L, A220M, A220T, A220V, A220W, A221C, A221D, A221E, A221L, A221N, A221R, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, F231A, F231E, F231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S248I, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256Q, S256R, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, A266T, S267A, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351Y, M352G, M352I, M352T, M352W, G353L, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405T, A405V, I406C, I406D, I406N, A407C, A407G, A407M, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L426C, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431H, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444C, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457V, S457T, G458A, G458C, G458D, G458F, G458L, G458P, G458Q, G458S, G458V, G458W, F459A, F459C, F459E, F459G, F459N, F459R, F459S, F459T, F459W, P460C, P460M, P460Q, P460W, P460Y, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K465C, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, A468D, A468E, A468F, A468K, A468L, A468P, A468S, A468V, A468W, W469A, W469C, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K487C, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496I, G497D, D498A, D498C, D498M, D498S, N499K, N499R, N499T, N499Y, L500A, L500E, L500N, L500V, T501C, T501G, T501M, A502L, A502Q, N503A, N503E, N503M, N503S, G504H, G504K, G504P, G505A, G505D, G505E, G505H, G505L, G505N, G505R, G505S, G505V, V506C, V506D, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514R, A515C, A515D, A515E, A515F, A515G, A515K, A515P, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521Q, R521V, T522G, T522I, T522N, T523A, T523M, H524R, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550G, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606S, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627G, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644G, D644Y, D645S, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667R, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701M, K701P, K701S, K701W, T703E, T703I, T703K, T703W, T704M, T704R, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711A, Q711D, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716T, A716V, D717C, D717G, D717L, D717S, K718A, K718L, K718Q, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, A722V, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749M, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, G754R, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, W776I, D776L, D776R, D776S, D776W, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789G, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811Y, D812E, D812F, D812I, D812Q, V813F, V813H, V813T, V813W, V813Y, K814G, K814H, K814I, K814L, K814P, G815A, G815F, G815K, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, K818Y, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, R838W, K839A, K839C, K839D, K839E, K839G, K839I, K839N, K839P, K839R, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858G, I858K, I858M, I858P, I858Q, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888R, R889G, Y892D, Y892P, Y892R, Y893E, Y893G, S894D, S894G, R895M, N896M, Y897C, Y898T, Y899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906N, I906S, I906T, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927G, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937F, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973Q, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982P, G982Q, G982W, R984P, R984S, P985E, P985F, P985H, P985K, P985L, P985W, A986C, A986E, A986F, A986I, A986K, A986L, A986M, A986N, A986S, A986W, A987V, A987C, A987F, A987I, A987K, V987L, V987Q, V987T, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001G, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, R1054C, R1054L, R1054N, L1055R, L1055T, Q1057A, Q1057E, Q1057P, Q1057R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069G, D1069K, D1069R, D1069W, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111I, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119N, I1119S, V1120N, V1120S, V1120T, M1121H, M1121K, M1121N, M1121P, M1121S, M1121V, M1121Y, Y1122A, Y1122C, Y1122I, Y1122K, Y1122R, Y1122V, Y1122W, F1123E, F1123H, F1123R, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165D, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, Y1172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200V, A1200W, L1202A, L1202C, T1203E, T1203K, E1204G, E1204K, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216A, T1216L, T1216P, T1216Q, T1216R, N1217A, N1217D, N1217E, N1217F, N1217P, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257K, G1257L, G1257Q, G1257R, G1257W, N1258C, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

75. The lactase variant of the preceding embodiment, wherein the variant has a decreased or an increased galactose inhibition, preferably measured as a galactose inhibition improvement factor (GI-IF) of at least 1.1 or at most 0.9, compared to the lactase of SEQ ID NO: 1.

76. The lactase variant of embodiment 1 which comprises one or more of the following substitutions, wherein each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, 514Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60O, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76B, Q761, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106N, I107A, I107F, I107O, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, G149H, G149I, G149M, G149Q, G149Y, E150A, E150C, E150G, E150L, E150N, E150R, N151L, I153A, 1153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191C, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205W, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, K219A, K219C, K219F, K219H, K219M, A220C, A220G, A220I, A220L, A220M, A220T, A220V, A220W, A221C, A221D, A221E, A221L, A221N, A221R, A221V, A221Y, A221D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, F231A, F231E, F231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S2481, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, S267C, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318N, K318N, K318P, K318Q, K318V, K320C, K320E, K320F, K320I, K320L, K320N, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363V, A364C, A364E, A364F, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405V, I406C, I406N, A407C, A407G, A407M, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L426C, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433I, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444C, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455S, S455M, S455P, S455R, S455V, S455W, V456A, V456D, V456E, V456F, V456K, V456L, V456W, S457E, S457H, S457K, S457L, S457M, S457P, S457Q, S457T, S457V, G458A, G458C, G458F, G458L, G458P, G458Q, G458S, G458V, G458W, F459A, F459C, F459E, F459G, F459N, F459R, F459S, F459T, F459W, P460C, P460M, P460Q, P460W, P460Y, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K465C, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, A468D, A468E, A468F, A468K, A468L, A468P, A468S, A468V, A468W, W469A, W469C, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K487C, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495V, T495W, M496A, M496F, M496T, G497D, D498A, D498C, D498M, D498S, N499K, N499R, N499T, N499Y, L500A, L500E, L500N, L500V, T501O, T501G, T501M, A502L, A502Q, N503A, N503E, N503M, N503S, G504H, G504K, G504P, G505A, G505D, G505E, G505H, G505L, G505N, G505R, G505S, G505V, V506C, V506D, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514R, A515C, A515D, A515E, A515F, A515G, A515K, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520L, I520C, I520G, I520H, I520M, I520N, I520Q, I520S, I520T, I520W, I520Y, R521A, R521C, R521K, R521N, R521Q, R521V, T522G, T522I, T522N, T523A, T523M, H524E, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560W, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606S, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627G, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644G, D644Y, D645S, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667R, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676E, A676G, A676K, A676L, A676P, A676S, A676W, A677F, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701N, K701P, K701S, K701W, T703E, T703I, T703K, T703W, T704M, T704R, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711A, Q711D, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716V, D717C, D717G, D717L, D717S, K718A, K718L, K718Q, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739W, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749M, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811P, D812L, D812F, D812I, D812Q, V813H, V813T, V813W, V813Y, K814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, K818Y, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, R838W, K839A, K839C, K839D, K839E, K839G, K839L, K839N, K839P, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858G, I858K, I858M, I858P, I858Q, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888G, R889G, Y892D, Y892P, Y892R, Y893E, Y893G, S894D, S894G, R895M, N896M, Y897V, Y898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906S, I906T, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934T, I935A, I935C, I935D, I935E, I935L, I935V, I935W, A936I, A936L, A936Q, A936R, A936Y, K937G, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973Q, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982P, G982Q, G982W, R984R, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992N, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001G, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016F, K1017C, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, R1054C, R1054L, R1054N, L1055R, L1055T, Q1057A, Q1057E, Q1057P, Q1057R, N1058R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069G, D1069K, D1069R, D1069W, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091H, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119N, I1119S, V1120N, V1120S, V1120T, M1121G, M1121K, M1121N, M1121P, M1121S, M1121V, M1121Y, Y1122A, Y1122C, Y1122I, Y1122K, Y1122R, Y1122V, Y1122W, F1123E, F1123H, F1123R, F1123T, F1124E, F1124R, F1124V, F1124W, R1125D, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, Y1172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200W, L1202A, L1202C, T1203E, T1203K, E1204G, E1204S, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213P, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216L, T1216P, T1216Q, T1216R, N1217A, N1217D, N1217E, N1217F, N1217H, N1217P, N1217R, N1217S, N1217Q, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255V, G1255Y, E1256G, E1256M, E1256N, E1256R, E1256V, E1256W, G1257F, G1257K, G1257L, G1257Q, G1257R, G1257W, N1258O, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

77. The lactase variant of the preceding embodiment, wherein the variant has a decreased or an increased galactose inhibition, preferably measured as a galactose inhibition improvement factor (GI-IF) of at least 1.1 or at most 0.9, compared to the lactase of SEQ ID NO: 1.

78. The lactase variant of embodiment 1 which comprises one or more of the following substitutions, wherein each position corresponds to a position in SEQ ID NO: 1: V1D, V1F, V1H, V1K, V1L, V1R, E2D, E2G, E2Q, E2V, D3A, D3I, D3N, D3V, A4H, TSA, TSS, R6G, R6H, R6L, R6W, S7L, S7N, S7P, S7T, S9G, S9H, S9W, T10K, T10L, T10S, Q12V, M13C, M13D, M13E, M13H, M13K, M13R, M13W, S14G, S14H, S14T, S14V, 514Y, S15C, S15F, S15I, S15K, S15L, S15P, S15R, S15T, S15V, S15W, T16C, T16I, P17A, P17I, P17S, V19A, V19F, V19I, V19K, V19L, V19N, V19S, V20C, V20F, V20G, V20I, V20L, V20M, V20P, V20Q, V20R, V20T, Y21A, Y21C, Y21D, Y21G, Y21H, Y21M, Y21P, Y21R, Y21T, S22A, S22N, S22R, S22T, S22W, S23A, A24F, A24L, A24R, A24T, A24W, V25D, V25E, V25F, V25G, V25M, V25Q, V25S, V25T, V25W, D26C, D26I, D26L, D26M, D26V, S27A, S27C, S27G, S27H, S27P, S27Y, K28C, K28G, K28I, K28L, K28R, K28S, K28V, K28W, Q29F, Q29G, Q29L, Q29M, Q29R, Q29S, N30M, N30V, N30W, N30Y, R31E, R31M, R31V, T32Q, T32S, S33K, D34F, D34G, D34H, F35A, F35C, F35G, F35V, D36Q, A37N, N38S, W39G, W39S, K40C, K40F, K40G, K40I, K40M, K40P, K40W, F41A, F41C, M42T, L43A, L43G, L43I, L43S, S44M, D45L, D45P, D45V, V47K, V47R, A49C, A49D, A49H, A49T, D51G, D51I, D51K, D51M, A53G, D55C, D55F, D55G, D55H, D55M, D55N, D55P, D55S, D55V, S57A, S57C, S57E, S57G, A58I, A58N, A58Q, A58R, A58T, W59D, W59I, W59K, W59L, W59N, W59P, W59V, Q60E, Q60F, Q60G, Q60L, Q60M, Q60R, Q60S, Q60V, Q60Y, Q61P, V62G, V62N, V62T, V62W, D63G, D63L, D63S, L64E, L64G, H66R, H66T, I70H, I70K, I70P, I70R, T71H, T71L, T71P, T71R, T71S, K73A, K73D, K73G, K73Q, K73V, Y74G, Y74K, S75G, S75L, S75Q, S75R, S75V, Q76G, Q76I, Q76P, S77C, S77D, S77E, S77G, S77H, S77I, S77K, S77L, S77M, S77R, S77T, S77V, S77W, N78C, N78F, N78S, E79H, E79S, E79T, A83E, A83T, L85A, L85C, L85D, L85F, L85N, L85S, L85V, L85W, P86E, P86G, P86Q, P86R, P86V, P86W, P86Y, G87D, G87N, G88A, G88F, G88M, T89C, T89L, T89M, T89N, T89W, T89Y, G90A, G90D, G90L, G90S, G90T, W91E, W91L, W91P, W91Q, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106V, R106W, I107A, I107F, I107S, A108E, A108V, I109M, I109T, N110A, N110F, N110S, N110T, N110V, N110W, F111A, F111C, F111L, F111Q, F111V, D112A, V114F, V114R, Y115E, M116A, M116C, M116D, M116W, N117K, A118P, T119G, V120A, V120K, W121C, W121D, W121R, W121T, W121V, G124M, V125D, K126E, K126V, T129V, H130A, H130C, H130S, H130T, P131K, Y132E, F137C, F137D, F137L, F137P, S138A, S138D, S138H, S138M, D140V, L141G, T142S, G148K, G149E, G1491, G149M, G149Y, E150A, E150C, E150G, E150L, E150N, E150R, N151L, V154E, V154I, V154K, V154L, V154M, V157A, V157G, V157P, V157Q, V157S, E158H, E158K, E158Q, E158V, N159D, N159H, N159T, R160G, L161E, L161K, L161M, L161S, L161W, P162F, P162G, P162N, P162T, P162W, S164A, R165H, W166S, Y167A, Y167C, G169A, G169S, S170Q, G171C, G171F, I172G, I172K, I172P, I172Q, Y173A, Y173H, Y173M, Y173P, Y173S, R174E, R174K, D175Y, V176E, V176K, V176T, T177C, T177E, T177K, L178I, L178Q, L178W, T179A, T179C, T179D, T179H, T1791, T179K, T179L, T179N, T179P, T179S, V180A, V180C, V180D, V180E, V180G, V180M, T181A, T181F, G183W, V184F, V184H, V184P, V184Q, V184R, V184S, V184W, H185G, H185L, H185R, V186A, V186E, V186G, V186N, G187A, G187D, G187H, N188R, N188S, N188V, N188W, N189A, G190F, G190V, V191T, V191Y, I193N, I193Q, I193T, I193V, K194I, T195M, T195W, P196A, P196I, P196M, P196S, P196W, S197C, S197E, S197L, L198I, A199E, A199P, A199T, Q201E, Q201K, N202A, N202M, N202Q, N202S, N202W, G203Q, G204R, N205W, V206C, T207L, K213A, A215D, N216D, D217F, D217G, D217L, D217M, T218D, T218G, T218H, K219A, A220G, A221O, A221D, A222R, N223S, I224G, T225L, L226Q, Q228N, Q228R, F231L, P232T, G234V, G235K, K236M, K236P, T237D, D238K, A240Q, G242K, G242L, G242M, G242P, T243I, A247K, S248F, I251F, I251W, I251Y, A252H, A252P, A252W, A252Y, A257D, A257G, A257N, A257V, T260V, S261A, S261H, S261Y, T262E, T262F, T262P, I263A, T264L, A266D, S267V, P268F, P268R, L270N, W271T, S272T, S272W, I273W, K274Q, N275W, N277F, T280D, V281Q, R282W, T283M, V285H, L286W, V291H, V291L, V291P, V291S, L292A, L292D, L292E, L292Q, L292S, L292V, D293C, D293I, D293W, T294C, T294M, T294Q, T294S, Y295F, Y295G, Y295L, Y295S, D296F, D296H, D296K, T297I, T297S, E298I, E298L, E298M, E298R, E298T, Y299F, Y299S, F301C, R302I, R302K, R302M, R302T, W303A, W303C, W303D, W303F, W303T, T304D, T304E, T304I, T304K, T304P, T304S, T304W, G305E, G305L, G305M, G305N, G305P, G305T, D307A, D307E, D307F, D307S, D307V, D307W, A308G, A308I, T309C, T309D, T309E, T309I, T309K, T309V, S310A, S310C, S310G, S310H, S310I, S310L, S310M, S310N, S310R, S310V, G311F, G311L, F312H, F312L, F312V, L314A, L314V, L314Y, N315G, G316N, G316R, G316W, G316Y, E317V, E317W, E317Y, K318C, K318E, K318F, K318H, K318M, K318N, K318P, K318Q, K320E, K320I, K320V, K320W, L321H, L321M, L321Y, K322C, K322I, V324E, V324G, V324T, S325G, M326T, M326V, H328C, H328D, H328F, H328G, H328I, H328L, H328M, H328R, H328T, G331V, A335C, A335G, A335L, A337D, A337E, A337G, A337L, N338P, N338R, R340A, R340L, A341M, I342A, I342G, I342P, E343A, E343N, E343R, E343T, E343Y, R344G, R344Y, Q345F, Q345N, Q345S, V346A, V346I, V346S, E347A, E347D, E347I, I348A, I348D, I348G, I348M, I348Q, I348R, L349A, L349E, L349S, L349V, Q350G, Q350N, Q350W, K351R, K351W, M352L, M352T, G353K, V354E, V354G, V354S, V354W, N355H, I357T, T359E, T359L, T360V, N362S, N362T, P363A, P363D, P363I, P363L, P363M, P363S, P363V, A364C, A364E, A364F, A364G, A364I, A364M, A364P, A364V, A364W, A365C, A365I, A365P, A365V, A365W, K366D, K366I, K366L, K366M, K366P, K366S, K366V, A367I, A367N, A367Q, L368A, L368Q, L368S, L368V, L368Y, I369A, I369D, I369E, I369G, I369K, I369M, I369V, I369W, D370L, D370Q, D370R, D370T, V371F, V371G, V371I, V371L, V371Q, C372P, N373G, N373L, N373R, E374L, K375D, K375I, K375N, K375Q, K375S, G376A, G376S, V377L, V377M, V377T, L378I, L378P, L378Y, V379A, V379C, V379M, V379N, V380P, V380S, E381A, E381C, E381G, E381Q, E381T, V383A, M386G, M386N, M386S, M386V, W387H, N388E, N388L, R389A, R389C, R389E, R389K, R389M, R389Q, R389S, R389T, R389V, S390C, S390D, S390H, S390P, S390T, G393E, G393R, G393V, T395A, T395C, T395F, E396K, E396L, E396V, E396W, Y398M, G399S, K400A, K400C, K400M, K400N, K400T, K400V, W401F, W401K, F402W, F402Y, G403A, G403D, G403H, G403K, G403Q, G403T, G403V, G403Y, Q404F, Q404L, Q404M, Q404P, Q404S, Q404V, A405C, A405E, A405K, A405R, A405T, A405V, I406C, I406D, I406N, A407C, A407G, A407Q, N410R, N410Y, A411E, A411R, A411S, V412S, G414M, G414N, G414T, G415A, G415Q, D416M, K417F, K417R, A422P, K423L, K423R, L426C, T427D, T427F, T427Q, T427S, T427W, T429D, T429P, I430L, I430M, N431L, N431M, R432F, R432G, R432Q, R432Y, D433C, D433G, D433I, D433P, D433Q, D433W, R434N, R434T, R434V, N435E, N435F, N435H, N435L, N435V, A436C, A436G, A436L, A436M, P437K, P437L, P437W, S438G, V439C, V439K, I440S, I440T, I440V, M441R, M441T, W442E, W442G, S443C, S443G, S443M, S443Q, L444E, L444F, L444V, N446D, M448C, M448E, M448L, M449D, M449E, M449F, M449T, M449V, M449W, M449Y, E450F, E450S, E450T, E450V, E450W, G451O, G451F, G451L, G451P, G451V, G451W, I452K, I452L, I452Q, I452S, I452V, S453C, S453G, S453H, S453L, S453M, S453N, S453P, S453Q, S453R, S453V, G454L, G454W, S455E, S455M, S455P, S455R, S455V, V456D, V456E, V456F, V456K, S457H, S457Q, S457T, S457V, G458A, G458D, G458P, G458S, F459C, F459R, P460M, P460Y, A461G, A461M, A461S, T462E, T462L, A464W, K465C, K465G, K465L, K465Q, K465V, K465Y, L466G, L466P, V467T, A468D, W469L, W469R, K471F, K471Q, K471Y, A472G, A472Y, A473M, A473P, D474C, D474E, D474M, D474W, S475E, S475T, T476L, T476S, R477A, R477G, R477L, P478A, P478D, P478V, M479G, T480Q, K485E, K485R, K487A, K487C, K487F, K487S, K487W, A488C, A488L, A488V, S493E, S493G, S493H, S493L, S493Q, N494A, N494I, N494M, N494R, N494V, T495K, G497D, N499T, G505D, G505I, G505L, G505Q, G505S, G505V, V506C, V506E, V506R, V507F, V507P, V507R, G508C, G508E, T509A, T509D, T509E, T509I, T509K, T509M, T509Q, T509S, T509V, T509Y, N510A, N510F, N510I, Y511A, S512C, S512E, S512F, S512I, S512M, S512Q, S512T, S512V, S512Y, D513G, D513P, D513R, A515E, A515F, A515G, A515P, A515S, N516C, N516E, N516G, N516I, N516M, N516Q, N516S, N516T, N516V, Y517G, Y517I, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521Q, R521V, T523A, T523M, H524R, H524V, P525R, S526G, W527A, W527E, W527G, W527H, W527N, W527R, W527S, A528E, A528G, A528L, I529G, A535E, A535G, A535I, A537M, A537P, A537S, I538H, I538M, S540E, N545G, T547K, G549D, G549P, G549W, G550Q, G550R, S553P, S553R, D555E, D555P, K556C, K556R, L558E, L558H, L558P, T559G, T559Q, T559V, T559Y, S560P, S560V, S564A, S564C, S564F, S564W, A565C, A565D, A565E, A565F, A565I, A565M, A565N, A565S, A565T, A565V, A565W, G567N, G567Q, G567V, A570G, A570L, A572W, S574V, S575D, Y577R, D578T, V580D, Q581T, Q581Y, R582A, R582G, R582I, R582L, D583V, D583W, F584I, F584W, A586D, T588P, Y589I, Y589Q, W591F, T592L, G593C, F594C, L597D, L597T, G598N, P600A, P600E, P600G, P600S, N604E, N604S, G605R, G607Q, G607S, S608E, S608I, S608N, S608Q, S608T, G609A, G609S, A610T, G612V, S613A, W614A, P615V, N619I, N619L, N619S, Y621W, V625A, V625E, V625F, V625M, V625Y, T627K, T627Q, A628C, A628D, A628N, G629T, F630C, F630Y, P631D, P631Y, K632C, K632D, K632G, D633G, T634F, T634S, T634V, Y636K, F637C, F637G, F637I, F637S, F637T, F637V, Q639R, N643R, D644Y, D645Y, D645V, V646C, V646L, V646N, V646R, V646S, H647G, H647V, T648C, L649V, H650F, I651T, I651V, L652C, L652D, L652V, L652W, P653Q, A654D, A654R, W655F, W655R, N656K, E657K, E657R, E657V, A661E, A661G, A661H, A661K, A661L, A661M, A661Q, A661W, K662H, K662S, K662V, K662W, K662Y, N667L, N667R, P669A, P669E, P669L, P669R, P669T, P669W, V672L, Y673S, T674D, T674M, T674Q, D675A, D675V, D675Y, A676L, A676P, A677T, V679Q, V679S, K680I, K680N, Y682V, F683W, T684R, K686E, G687P, S688K, S688L, T689G, T689W, E690D, K691E, K691H, K691P, K691R, R692G, R692H, R692I, R692L, R692P, R692S, R692T, R692V, R692W, L693M, L693P, I694L, I694W, G695C, G695K, G695L, G695R, G695W, E696R, K697A, K697C, K697R, K697V, K697W, S698D, S698E, S698M, S698Q, S698R, T700A, T700D, T700Y, K701A, K701D, K701G, K701H, K701L, K701M, K701P, K701S, T703K, A705D, A705K, A705P, A705R, A705W, A706C, A706T, A706W, Y708F, Y708L, Y710E, Y710T, Y710V, Q711A, Q711D, Q711T, V712M, V712P, V712Q, Y713E, Y713G, E714H, E714I, E714K, E714N, G715K, A716M, A716P, A716R, A716T, D717G, D717L, D717S, K718A, K718Q, K718T, K718W, K718Y, D719E, D719S, D719T, D719V, S720A, S720M, S720R, S720Y, T721D, T721H, T721K, T721L, T721N, T721P, T721Q, T721S, T721V, T721W, T721Y, A722Q, A722T, A722V, H723G, H723P, K724A, K724G, N725A, N725I, M726D, M726Q, Y727L, L728C, L728K, L728S, L728W, T729A, T729E, T729M, N731E, N731Q, V732R, P733W, W734G, W734R, A735Q, A735R, A735S, A735T, G737F, G737K, G737N, G737Y, T738L, T738S, I739E, I739K, S740D, S740F, A741I, A741P, A741S, A741V, E742V, A743E, A743I, Y744L, Y744R, D745C, D745N, D745R, E746C, E746E, E746T, N747E, N747F, N747P, R749M, L750M, L750P, L750Q, L750S, I751C, I751H, P752C, P752Y, G754H, G754I, G754R, S755T, T756N, T756Q, E757A, G758V, N759S, N759V, A760G, S761A, V762W, T765P, G766M, A769F, A769G, A769I, A769N, A769V, A769Y, K770H, L771A, K772A, K772C, K772P, K772W, A773C, A773M, A773R, D774A, A775V, D776R, D776V, R777H, R777S, R777T, K778F, K778G, K778N, K778R, T779I, T781A, T781E, T781F, T781G, T781P, T781Y, A782C, A782N, A782Q, A782Y, D783A, K785C, K785I, K785S, K785V, K785W, K785Y, D786V, L787D, L787K, Y789V, I790R, I790V, E791D, E791F, E791S, E791V, E791W, V792S, V792Y, D793C, D793Y, V794D, V796S, V796Y, A797H, N798I, N798Q, G799D, G799K, G799L, G799Y, H800F, H800G, H800V, I801W, V802E, V802I, V802S, V802Y, P803G, P803S, P803Y, D804E, A805C, A805F, A805I, A805N, A805P, A806F, A806I, A806Q, N807F, R808F, R808G, R808I, R808P, V809L, V809M, V809T, T810L, T810P, T810Q, T810R, T810Y, F811L, V813H, V813W, V813Y, K814G, K814P, G815F, G815M, G815N, A816D, A816N, A816W, G817H, K818F, K818L, K818Q, K818R, K818S, K818W, K818Y, L819F, V820C, V820R, V820W, G821I, V822A, V822D, V822E, V822T, D823E, N824A, G825A, S826A, S826G, S826I, S826W, P828G, D829C, D829I, D829S, H830Q, D831A, D831M, D831P, S832P, S832R, S832W, Y833C, Y833D, Y833E, Y833N, Q834M, A835D, A835H, A835K, D836C, D836E, D836Q, D836R, D836S, D836T, D836V, D836Y, R838N, R838S, K839A, K839D, K839L, K839N, A840G, A840I, A840P, A840V, F841I, F841K, S842A, K844A, K844Y, A847T, I848M, Q850L, S851C, S851D, S851E, S851T, T852L, K853P, E854C, E854I, A855K, A855V, A855Y, I858D, I858G, I858K, I858P, V860Y, T861F, T861I, T861Q, T861V, T861W, A862C, A864K, D865A, D865G, G866H, G866R, L867W, S870E, S870M, S870T, V872C, V872G, K873G, K873Y, I874G, A875R, V879S, T882A, T882M, T882R, S883L, E885V, K886L, K886V, K886W, T887A, T887D, T887G, T887N, V888A, R889G, Y892P, Y893E, Y893G, S894D, S894G, Y897V, Y898T, K900E, K900G, T901Q, T901R, T901Y, G902A, G902D, G902F, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906N, I906T, I906W, L907F, L907S, P908C, P908D, P908G, P908I, P908L, P908T, S909E, S909F, S909G, S909W, S909Y, D910I, D910W, V911A, E912A, E912K, E912L, E912T, E912V, V913G, V913R, R914A, R914E, R914F, R914I, R914K, R914V, R914W, R914Y, Y915A, Y915C, Y915G, Y915I, Y915M, Y915Q, Y915V, S916G, Y917C, D917E, D917F, D917L, D917M, D917Q, D917S, G918E, G918H, G918T, G918V, T919D, T919K, T919Q, T919W, S920P, S920V, D921C, D921V, R922A, R922M, R922V, R922W, Q923A, Q923E, Q923L, Q923M, Q923V, N924Q, N924S, V925C, V925E, V925G, V925K, V925N, V925W, T926P, T926R, W927P, D928A, D928H, D928Q, A929P, V930E, V930I, V930T, S931P, S931R, D933R, Q934S, Q934V, I935A, I935C, I935D, I935E, I935L, I935P, I935V, I935W, A936I, A936L, A936Q, A936R, A936Y, K937G, K937I, K937M, K937P, K937Q, A938C, A938H, A938N, A938T, A938V, A938W, G939D, G939K, S940C, S940E, S940R, S940V, F941C, F941M, S942A, S942E, S942K, S942P, S942V, V943A, V943G, V943Q, T946A, T946L, T946P, T946W, V947G, V947L, V947P, V947R, V947T, A948I, A948W, G949A, G949V, Q950K, Q950W, K951D, K951G, K951P, K951S, K951W, K951Y, I952Q, S953F, S953M, S953N, S953R, V954D, V954Q, R955A, R955C, R955K, R955Q, R955W, V956A, V956D, V956G, V956H, V956I, V956M, V956Q, V956W, T957D, T957S, T957W, I959A, I959L, I959S, I959V, I959Y, D960P, D960S, E961D, E961F, E961K, E961S, E961T, I962A, I962C, I962D, I962G, I962K, I962N, G963C, G963E, G963P, L965C, L965E, L965G, L965K, L965M, L965P, L965Q, L965S, L965V, L965Y, L966A, L966K, L966N, L966Q, L966S, L966V, N967D, N967I, N967L, N967M, N967P, N967T, N967V, Y968G, Y968L, Y968Q, Y968V, S969C, S969D, S969G, S969H, S969I, S969L, S969M, S969P, S969Q, S969Y, A970I, A970L, S971G, S971V, S971W, P973C, P973D, P973K, P973N, P973Q, P973R, P973V, P973W, P973Y, V974C, V974E, V974G, V974N, V974T, V974Y, G975F, G975K, T976D, T976F, T976G, T976K, T976L, T976P, T976S, P977C, P977K, P977R, P977T, P977Y, A978F, A978G, A978M, A978N, A978R, A978S, A978Y, V979G, V979N, V979Y, L980A, L980F, L980H, L980I, L980K, L980N, L980Q, L980T, L980Y, P981L, P981M, R984P, P985F, P985H, P985K, P985L, P985W, A986C, A986I, A986L, A986M, A986W, V987A, V987C, V987F, V987K, L988V, P989M, P989W, D990F, D990P, D990W, G991C, G991F, G991H, G991K, G991P, G991Y, T992M, T992N, V993G, S995E, S995L, S995W, A996E, N997K, N997V, F998M, F998W, V1000W, D1001L, D1001S, W1002A, W1002D, W1002E, W1002H, W1002N, W1002P, W1002Q, W1002S, T1003F, T1003G, T1003N, T1003R, T1003S, T1003W, T1003Y, K1004D, K1004E, K1004S, P1005I, P1005N, P1005V, P1005Y, A1006C, A1006N, A1006P, A1006S, A1006V, A1006W, A1006Y, D1007C, D1007L, D1007P, D1007V, T1008G, Y1010A, Y1010P, Y1010R, Y1010T, N1011A, N1011S, N1011T, N1011W, T1012H, T1012I, T1012Q, A1013D, A1013Q, A1013V, G1014I, G1014M, G1014V, G1014W, T1015A, V1016D, V1016P, K1017E, K1017G, V1018K, V1018L, V1018R, V1018S, T1021C, T1021E, T1021G, A1022H, V1024G, V1024H, V1024K, V1024R, V1024S, V1024W, G1026E, G1026S, G1026V, G1026Y, K1027Q, K1027R, E1028G, E1028T, F1029I, F1029K, F1029P, F1029V, K1030D, K1030H, K1030M, K1030W, V1031H, V1031K, A1033V, T1034G, T1034H, T1034N, I1035D, I1035G, I1035Q, R1036G, R1036L, R1036T, R1036Y, V1037C, Q1038D, R1039V, S1040M, Q1041P, V1042N, T1043F, T1043G, T1043R, I1044A, I1044L, S1046M, V1048C, V1048F, V1048G, V1048I, V1048M, V1048Q, N1051A, N1051E, N1051K, A1052C, A1052K, A1052R, L1053A, L1053W, R1054C, R1054L, L1055R, L1055T, Q1057A, Q1057E, Q1057P, N1058R, N1058S, P1060G, P1060N, P1060Q, A1061G, A1061K, A1061W, D1062A, D1062G, D1062I, D1062M, K1063M, Q1064M, Q1064R, Q1064T, Q1064V, S1065A, S1065C, Q1066A, Q1066G, Q1066V, T1067G, T1067M, L1068P, L1068Q, L1068Y, D1069R, A1070T, I1071M, K1072P, K1072S, D1073F, D1073W, G1074L, G1074R, S1075G, S1075L, T1076E, T1076S, T1077R, V1078D, V1078W, D1079G, D1079L, N1081E, T1082E, T1082F, T1082G, T1082K, G1083E, G1083F, G1083L, G1084M, G1084V, G1084W, G1084Y, G1085P, G1085R, G1085S, A1086H, A1086K, A1086R, N1087A, N1087E, N1087I, N1087R, P1088D, P1088E, P1088G, P1088R, P1088W, S1089G, S1089K, S1089Q, S1089V, A1090F, W1091Y, N1093A, N1093G, N1093L, N1093P, N1093Q, W1094D, W1094E, W1094P, W1094R, W1094T, A1095P, A1095T, A1095W, Y1096D, Y1096L, S1097E, S1097K, S1097T, K1098D, K1098F, K1098G, K1098Q, K1098S, A1099D, A1099S, A1099V, A1099W, G1100E, G1100H, G1100N, H1101K, H1101Q, H1101R, H1101V, N1102H, N1102Q, N1102T, T1103A, T1103E, T1103S, T1103W, E1105L, E1105S, E1109A, E1109D, E1109L, E1109W, A1111G, A1111S, E1113G, E1113P, E1113V, Q1114E, Q1114L, Q1114R, Q1114S, Q1114T, Q1114V, Q1115A, Q1115K, Q1115L, Q1115P, L1116E, L1116G, L1116H, L1116K, L1116W, G1117E, G1117I, G1117M, G1117R, G1117S, G1117T, G1117V, G1117W, Q1118M, Q1118W, I1119D, I1119E, I1119N, I1119S, V1120N, V1120S, M1121G, M1121K, M1121N, M1121P, M1121S, F1123E, F1123R, F1124V, F1124W, R1125D, R1125F, R1125K, R1125V, R1125W, S1127I, S1127Q, N1128A, A1129E, A1129R, V1130A, V1130R, R1131W, F1132M, F1132P, F1132Q, P1133D, P1133G, P1133L, P1133R, A1135E, A1135K, A1135L, A1135W, G1136P, K1137G, K1137P, K1137R, K1137S, K1137T, K1137V, T1138R, T1138Y, I1140C, I1140P, I1140R, Q1141A, Q1141G, Q1141K, Q1141N, Q1141T, I1142E, I1142R, I1142Y, S1143G, A1144D, A1144N, A1144P, A1144S, A1144T, A1144V, A1144W, D1145E, D1145R, D1145T, G1146A, G1146K, G1146R, G1146V, N1148H, N1148I, N1148P, N1148Q, N1148R, N1148S, N1148T, W1149C, W1149G, W1149K, W1149S, W1149V, T1150K, T1150P, D1151C, D1151W, L1152A, L1152C, L1152E, L1152Q, L1152W, A1153A, A1153G, A1153L, A1154D, A1154E, A1154L, I1158S, I1158W, A1159E, A1159I, Q1161P, Q1161S, E1162A, E1162C, E1162Q, E1162W, E1165M, E1165S, R1166Q, V1167A, V1167R, K1168L, K1168R, P1169M, P1169S, Y1170K, Y1170M, Y1170V, Y1172H, Y1172S, D1173G, D1173T, F1174D, A1175S, G1178M, G1178Q, G1178S, G1178T, A1179L, A1179Q, A1179W, T1180A, T1180G, T1180I, T1180L, T1180M, T1180Q, T1180S, T1180Y, F1181E, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190T, D1190Y, T1191L, T1193G, P1194E, P1194W, V1197A, C1199D, A1200G, T1203K, E1204G, E1204S, I1205V, K1208R, K1208V, K1208W, T1209A, T1209C, T1209E, T1209K, T1209N, T1209Q, T1209R, T1209W, A1210D, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, F1214A, F1214E, F1214K, F1214L, F1214P, F1214S, F1214V, V1215D, V1215E, V1215L, V1215Q, V1215W, T1216A, T1216L, T1216P, T1216Q, T1216R, N1217A, N1217E, N1217P, N1217R, N1217S, N1217T, T1218A, T1218C, T1218E, T1218G, T1218Q, T1218S, T1218V, T1218W, S1219I, S1219K, S1219R, S1219V, A1220C, A1220G, A1220P, A1221K, A1221R, A1221V, A1221W, L1222A, L1222E, L1222F, L1222Q, L1222R, L1222V, L1222W, S1224P, S1224W, L1225E, L1225K, L1225V, T1226P, V1227C, V1227D, V1227P, V1227Q, G1229C, G1229E, G1229V, T1230H, T1230K, T1230W, K1231G, V1232E, V1232Q, V1232R, D1234V, S1235D, S1235E, S1235G, S1235P, S1235R, S1235W, S1235Y, V1236A, V1236C, V1236G, V1236P, V1236Q, L1237V, A1238D, A1238E, A1238L, A1238R, A1239R, G1240D, G1240Q, N1243C, I1247R, G1255H, A1259K, V1261R, T1262F, T1262M, T1262R, V1263T, L1264H, L1264R, P1265W, V1273R, I1274F, I1274R, T1275A, T1275W, E1276R, S1277L, S1277T, S1277W, E1278Q, E1278R, D1279I, D1279R, D1279W, H1280C, H1280E, H1280G, V1281I, V1281W, K1284G, T1285A, T1285M, F1286A, F1286E, F1286P, F1286R, T1287C, T1287L, T1287S, T1287W, I1288A, I1288D, I1288G, I1288K, E1293K, E1293L, Q1294E, E1295K, F1296A, E1302G, E1302R, E1302S, R1303S or D1304V.

79. The lactase variant of the preceding embodiment, wherein the variant has a decreased galactose inhibition, preferably measured as a galactose inhibition improvement factor (GI-IF) of at least 1.1, compared to the lactase of SEQ ID NO: 1.

80. The lactase variant of embodiment 1 which comprises one or more of the following substitutions, wherein each position corresponds to a position in SEQ ID NO: 1: V1D, V1F, V1H, V1K, V1L, V1R, E2D, E2G, E2Q, E2V, D3A, D3I, D3N, D3V, A4H, TSA, TSS, R6G, R6H, R6L, R6W, S7L, S7N, S7P, S7T, S9G, S9H, S9W, T10K, T10L, T10S, Q12V, M13C, M13D, M13E, M13H, M13K, M13R, M13W, S14G, S14H, S14T, S14V, S14Y, S15C, S15F, S15I, S15K, S15L, S15P, S15R, S15T, S15V, S15W, T16C, T16I, P17A, P17I, P17S, V19A, V19F, V19I, V19K, V19L, V19N, V19S, V20C, V20F, V20G, V20I, V20L, V20M, V20P, V20Q, V20R, V20T, Y21A, Y21C, Y21D, Y21G, Y21H, Y21M, Y21P, Y21R, Y21T, S22A, S22N, S22R, S22T, S22W, S23A, A24F, A24L, A24R, A24T, A24W, V25D, V25E, V25F, V25G, V25M, V25Q, V25S, V25T, V25W, D26C, D26I, D26L, D26M, D26V, S27A, S27C, S27G, S27H, S27P, S27Y, K28C, K28G, K28I, K28L, K28R, K28S, K28V, K28W, Q29F, Q29G, Q29L, Q29M, Q29R, Q29S, N30M, N30V, N30W, N30Y, R31E, R31M, R31V, T32Q, T32S, S33K, D34F, D34G, D34H, F35A, F35C, F35G, F35V, D36Q, A37N, N38S, W39G, W39S, K40C, K40F, K40G, K40I, K40M, K40P, K40W, F41A, F41C, M42T, L43A, L43G, L43I, L43S, S44M, D45L, D45P, D45V, V47K, V47R, A49C, A49D, A49H, A49T, D51G, D51I, D51K, D51M, A53G, D55C, D55F, D55G, D55H, D55M, D55N, D55P, D55S, D55V, S57A, S57C, S57E, S57G, A58I, A58N, A58Q, A58R, A58T, W59D, W59I, W59K, W59L, W59N, W59P, W59V, Q60E, Q60F, Q60G, Q60L, Q60M, Q60R, Q60S, Q60V, Q60Y, Q61P, V62G, V62N, V62T, V62W, D63G, D63L, D63S, L64E, L64G, H66R, H66T, I70H, I70K, I70P, I70R, T71H, T71L, T71P, T71R, T71S, K73A, K73D, K73G, K73Q, K73V, Y74G, Y74K, S75G, S75L, S75Q, S75R, S75V, Q76G, Q76I, Q76P, S77C, S77D, S77E, S77G, S77H, S77I, S77K, S77L, S77M, S77R, S77T, S77V, S77W, N78C, N78F, N78S, E79H, E79S, E79T, A83E, A83T, L85A, L85C, L85D, L85F, L85N, L85S, L85V, L85W, P86E, P86G, P86Q, P86R, P86V, P86W, P86Y, G87D, G87N, G88A, G88F, G88M, T89C, T89L, T89M, T89N, T89W, T89Y, G90A, G90D, G90L, G90S, G90T, W91E, W91L, W91P, W91Q, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106V, R106W, I107A, I107F, I107S, A108E, A108V, I109M, I109T, N110A, N110F, N110S, N110T, N110V, N110W, F111A, F111C, F111L, F111Q, F111V, D112A, V114F, V114R, Y115E, M116A, M116C, M116D, M116W, N117K, A118P, T119G, V120A, V120K, W121C, W121D, W121R, W121T, W121V, G124M, V125D, K126E, K126V, T129V, H130A, H130C, H130S, H130T, P131K, Y132E, F137C, F137D, F137L, F137P, S138A, S138D, S138H, S138M, D140V, L141G, T142S, G148K, G149I, G149M, G149Y, E150A, E150C, E150G, E150L, E150N, E150R, N151L, V154E, V154I, V154K, V154L, V154M, V157A, V157G, V157P, V157Q, V157S, E158H, E158K, E158Q, E158V, N159D, N159H, N159T, R160G, L161E, L161K, L161M, L161S, L161W, P162F, P162G, P162N, P162T, P162W, S164A, R165H, W166S, Y167A, Y167C, G169A, G169S, S170Q, G171C, G171F, I172G, I172K, I172P, I172Q, Y173A, Y173H, Y173M, Y173P, Y173S, R174E, R174K, D175Y, V176C, V176K, V176T, T177C, T177E, T177K, L178I, L178Q, L178W, T179A, T179C, T179D, T179H, T179I, T179K, T179L, T179N, T179P, T179S, V180A, V180C, V180D, V180E, V180G, V180M, T181A, T181F, G183W, V184F, V184H, V184P, V184Q, V184R, V184S, V184W, H185G, H185L, H185R, V186A, V186E, V186G, V186N, G187A, G187D, G187H, N188R, N188S, N188V, N188W, N189A, G190F, G190V, V191T, V191Y, I193N, I193Q, I193T, I193V, K194I, T195M, T195W, P196A, P196I, P196M, P196S, P196W, S197C, S197E, S197L, L198I, A199E, A199P, A199T, Q201E, Q201K, N202A, N202M, N202Q, N202S, N202W, G203Q, G204R, N205W, V206C, T207L, K213A, A215D, N216D, D217F, D217G, D217L, D217M, T218D, T218G, T218H, K219A, A220G, A221O, A221D, A222R, N223S, I224G, T225L, L226Q, Q228N, Q228R, F231L, P232T, G234V, G235K, K236M, K236P, T237D, D238K, A240Q, G242K, G242L, G242M, G242P, T243I, A247K, S248F, I251F, I251W, I251Y, A252H, A252P, A252W, A252Y, A257D, A257G, A257N, A257V, T260V, S261A, S261H, S261Y, T262E, T262F, T262P, I263A, T264L, A266D, S267V, P268F, P268R, L270N, W271T, S272T, S272W, I273W, K274Q, N275M, N277F, T280D, V281Q, R282W, T283M, V285H, L286W, V291H, V291L, V291P, V291S, L292A, L292D, L292E, L292Q, L292S, L292V, D293C, D293I, D293W, T294C, T294M, T294Q, T294S, Y295F, Y295G, Y295L, Y295S, D296F, D296H, D296K, T297I, T297S, E298I, E298L, E298M, E298R, E298T, Y299F, Y299S, F301C, R302I, R302K, R302M, R302T, W303A, W303C, W303D, W303F, W303T, T304D, T304E, T304I, T304K, T304P, T304S, T304W, G305E, G305L, G305M, G305N, G305P, G305T, D307A, D307E, D307F, D307S, D307V, D307W, A308G, A308I, T309C, T309D, T309E, T309I, T309K, T309V, S310A, S310C, S310G, S310H, S310I, S310L, S310M, S310N, S310R, S310V, G311F, G311L, F312H, F312L, F312V, L314A, L314V, L314Y, N315S, G316N, G316R, G316W, G316Y, E317V, E317W, E317Y, K318C, K318E, K318F, K318H, K318M, K318N, K318P, K318Q, K320E, K320I, K320V, K320W, L321H, L321M, L321Y, K322C, K322I, V324E, V324G, V324T, S325G, M326T, M326V, H328C, H328D, H328F, H328G, H328I, H328L, H328M, H328R, H328T, G331V, A335C, A335G, A335L, A337D, A337E, A337G, A337L, N338P, N338R, R340A, R340L, A341M, I342A, I342G, I342P, E343A, E343N, E343R, E343T, E343Y, R344G, R344Y, Q345F, Q345N, Q345S, V346A, V346I, V346S, E347A, E347D, E347I, I348A, I348L, I348G, I348Q, I348R, L349A, L349E, L349S, L349V, Q350G, Q350N, Q350W, K351R, K351W, M352L, M352T, G353K, V354E, V354G, V354W, N355H, I357T, T359E, T359L, T360V, N362S, N362T, P363A, P363D, P363I, P363L, P363M, P363S, P363V, A364C, A364E, A364F, A364G, A364I, A364M, A364P, A364V, A364W, A365C, A365I, A365P, A365V, A365W, K366D, K366I, K366L, K366M, K366P, K366S, K366V, A367I, A367N, A367Q, L368A, L368Q, L368S, L368V, L368Y, I369A, I369D, I369E, I369G, I369K, I369M, I369V, I369W, D370L, D370Q, D370R, D370T, V371F, V371G, V371I, V371L, V371Q, C372P, N373G, N373L, N373R, E374L, K375D, K375I, K375N, K375Q, K375S, G376A, G376S, V377A, V377M, V377T, L378I, L378P, L378Y, V379A, V379C, V379M, V379N, V380P, V380S, E381A, E381C, E381G, E381Q, E381T, V383A, M386G, M386N, M386S, M386V, W387H, N388E, N388L, R389A, R389C, R389E, R389K, R389M, R389Q, R389S, R389T, R389V, S390C, S390D, S390H, S390P, S390T, G393E, G393R, G393V, T395A, T395C, T395F, E396E, E396L, E396V, E396W, Y398M, G399S, K400A, K400C, K400M, K400N, K400T, K400V, W401F, W401K, F402W, F402Y, G403A, G403D, G403H, G403K, G403Q, G403T, G403V, G403Y, Q404F, Q404L, Q404M, Q404P, Q404S, Q404V, A405C, A405E, A405K, A405R, A405V, I406C, I406D, I406N, A407C, A407G, A407Q, N410R, N410Y, A411E, A411R, A411S, V412S, G414M, G414N, G414T, G415A, G415Q, D416M, K417F, K417R, A422P, K423L, K423R, L426C, T427D, T427F, T427Q, T427S, T427W, T429D, T429P, I430L, I430M, N431L, N431M, R432F, R432G, R432Q, R432Y, D433C, D433G, D433I, D433P, D433Q, D433W, R434N, R434T, R434V, N435E, N435F, N435H, N435L, N435V, A436C, A436G, A436L, A436M, P437K, P437L, P437W, S438G, V439C, V439K, I440S, I440T, I440V, M441R, M441T, W442E, W442G, S443C, S443G, S443M, S443Q, L444E, L444F, L444V, N446D, M448C, M448E, M448L, M449D, M449E, M449F, M449T, M449V, M449W, M449Y, E450F, E450S, E450T, E450V, E450W, G451C, G451F, G451L, G451P, G451V, G451W, I452K, I452L, I452Q, I452S, I452V, S453C, S453G, S453H, S453L, S453M, S453N, S453P, S453Q, S453R, S453V, G454L, G454W, S455E, S455M, S455P, S455R, S455V, V456D, V456E, V456F, V456K, S457H, S457Q, S457T, S457V, G458A, G458P, G458S, F459C, F459R, P460M, P460Y, A461G, A461M, A461S, T462E, T462L, A464W, K465C, K465G, K465L, K465Q, K465V, K465Y, L466G, L466P, V467T, A468D, W469L, W469R, K471F, K471Q, K471Y, A472G, A472Y, A473M, A473P, D474C, D474E, D474M, D474W, S475E, S475T, T476L, T476S, R477A, R477G, R477L, P478A, P478D, P478V, M479G, T480Q, K485E, K485R, K487A, K487C, K487F, K487S, K487W, A488C, A488L, A488V, S493E, S493G, S493H, S493L, S493Q, N494A, N494I, N494M, N494R, N494V, T495K, G497D, N499T, G505D, G505H, G505L, G505R, G505S, G505V, V506C, V506E, V506R, V507F, V507P, V507R, G508C, G508E, T509A, T509D, T509E, T509I, T509K, T509M, T509Q, T509S, T509V, T509Y, N510A, N510F, N510I, Y511A, S512C, S512E, S512F, S512I, S512M, S512Q, S512T, S512V, S512Y, D513G, D513P, D513R, A515E, A515F, A515G, A515S, N516C, N516E, N516G, N516I, N516M, N516Q, N516S, N516T, N516V, Y517G, Y517I, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521Q, R521V, T523A, T523M, H524R, H524V, P525R, S526G, W527A, W527E, W527G, W527H, W527N, W527R, W527S, A528E, A528G, A528L, I529G, A535E, A535G, A535I, A537M, A537P, A537S, I538H, I538M, S540E, N545G, T547K, G549D, G549P, G549W, G550Q, G550R, S553P, S553R, D555E, D555P, K556C, K556R, L558E, L558H, L558P, T559G, T559Q, T559V, T559Y, S560P, S560V, S564A, S564C, S564F, S564W, A565C, A565D, A565E, A565F, A565G, A565I, A565L, A565M, A565R, A565S, A565T, A565V, A565W, G567N, G567Q, G567V, A570G, A570L, A572V, S574V, A575D, Y577R, D578T, V580D, Q581T, Q581Y, R582A, R582G, R582I, R582L, D583V, D583W, F584I, F584W, A586D, T588P, Y589I, Y589Q, W591F, T592L, G593C, F594C, L597D, L597T, G598N, P600A, P600E, P600G, P600S, N604E, N604S, G605R, G607Q, G607S, S608E, S608I, S608N, S608Q, S608T, G609A, G609S, A610T, G612V, S613A, W614A, P615V, N619I, N619L, N619S, Y621W, V625A, V625E, V625F, V625M, V625Y, T627K, T627Q, A628C, A628D, A628N, G629T, F630C, F630Y, P631D, P631Y, K632C, K632D, K632G, D633G, T634F, T634S, T634V, Y636K, F637C, F637G, F637I, F637S, F637T, F637V, Q639R, N643R, D644Y, D645S, D645V, V646C, V646L, V646N, V646R, V646S, H647K, H647V, T648C, L649V, H650F, I651T, I651V, L652C, L652D, L652V, L652W, P653Q, A654D, A654R, W655V, W655R, N656K, E657K, E657R, E657V, A661E, A661G, A661H, A661K, A661L, A661M, A661Q, A661W, K662H, K662S, K662V, K662W, K662Y, N667L, N667R, P669A, P669E, P669L, P669R, P669T, P669W, V672L, Y673S, T674D, T674M, T674Q, D675A, D675V, D675Y, A676L, A676P, A677T, V679Q, V679S, K680I, K680N, Y682V, F683W, T684R, K686E, G687P, S688K, S688L, T689G, T689W, E690D, K691E, K691H, K691P, K691R, R692G, R692H, R692I, R692L, R692P, R692S, R692T, R692V, R692W, L693M, L693P, I694L, I694W, G695C, G695K, G695L, G695R, G695W, E696R, K697A, K697G, K697R, K697V, K697W, S698D, S698E, S698M, S698Q, S698R, T700A, T700D, T700Y, K701A, K701D, K701G, K701H, K701L, K701M, K701P, K701S, T703K, A705D, A705K, A705P, A705R, A705W, A706C, A706T, A706W, Y708F, Y708L, Y710E, Y710T, Y710V, Q711A, Q711D, Q711T, V712M, V712P, V712Q, Y713E, Y713S, E714I, E714I, E714K, E714L, G715K, A716M, A716P, A716R, D717C, D717L, D717S, K718A, K718Q, K718T, K718W, K718Y, D719E, D719S, D719T, D719V, S720A, S720M, S720R, S720Y, T721D, T721H, T721K, T721L, T721N, T721P, T721Q, T721S, T721V, T721W, T721Y, A722Q, A722T, H723C, H723P, K724A, K724G, N725A, N725I, M726D, M726Q, Y727L, L728C, L728K, L728S, L728W, T729A, T729E, T729M, N731E, N731Q, V732R, P733W, W734G, W734R, A735Q, A735R, A735S, A735T, G737F, G737K, G737N, G737Y, T738L, T738S, I739E, I739K, S740D, S740F, A741I, A741P, A741S, A741V, E742V, A743E, A743I, Y744L, Y744R, D745C, D745N, D745R, E746C, E746K, E746T, N747E, N747F, N747P, R749M, L750M, L750P, L750Q, L750S, I751C, I751H, P752C, P752Y, G754H, G754I, S755T, T756N, T756Q, E757A, G758V, N759S, N759V, A760G, S761A, V762W, T765P, G766M, A769F, A769G, A769I, A769N, A769V, A769Y, K770H, L771A, K772A, K772C, K772P, K772W, A773C, A773M, A773R, D774A, A775V, D776R, D776V, R777H, R777S, R777T, K778F, K778G, K778N, K778R, T779I, T781A, T781E, T781F, T781G, T781P, T781Y, A782C, A782N, A782Q, A782Y, D783A, K785C, K785I, K785S, K785V, K785W, K785Y, D786V, L787D, L787K, Y789V, I790R, I790V, E791D, E791F, E791S, E791V, E791W, V792S, V792Y, D793C, D793Y, V794D, D796S, D796T, A797H, N798I, N798Q, G799D, G799K, G799L, G799Y, H800F, H800G, H800V, I801W, V802E, V802I, V802S, V802Y, P803G, P803S, P803Y, D804E, A805C, A805F, A805I, A805N, A805P, A806F, A806I, A806Q, N807F, R808F, R808G, R808I, R808P, V809L, V809M, V809P, T810L, T810P, T810Q, T810R, T810Y, F811L, V813H, V813W, V813Y, K814G, K814P, G815F, G815M, G815P, A816D, A816N, A816W, G817H, K818D, K818F, K818L, K818Q, K818R, K818S, K818W, K818Y, L819F, V820C, V820R, V820W, G821I, V822A, V822D, V822E, V822T, D823E, N824A, G825A, S826A, S826G, S826I, S826W, P828G, D829C, D829I, D829S, H830Q, D831A, D831M, D831P, S832P, S832R, S832W, Y833C, Y833D, Y833E, Y833N, Q834M, A835D, A835H, A835K, D836C, D836E, D836Q, D836R, D836S, D836T, D836V, D836Y, R838N, R838S, K839A, K839D, K839L, K839N, A840G, A840I, A840P, A840V, F841I, F841K, S842A, K844A, K844Y, A847T, I848M, Q850L, S851C, S851D, S851E, S851T, T852L, K853P, E854C, E854I, A855K, A855V, A855Y, I858D, I858G, I858K, I858P, V860Y, T861F, T861I, T861Q, T861V, T861W, A862C, A864N, D865A, D865G, G866H, G866R, L867W, S870E, S870M, S870T, V872C, V872G, K873G, K873Y, I874G, A875R, V879S, T882A, T882M, T882R, S883L, E885V, K886L, K886V, K886W, T887A, T887D, T887G, T887N, V888A, R889G, Y892P, Y893E, Y893G, S894D, S894G, Y897V, Y898T, K900E, K900G, T901Q, T901R, T901Y, G902A, G902D, G902F, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906T, I906W, L907F, L907S, P908C, P908D, P908G, P908I, P908L, P908T, S909E, S909F, S909G, S909W, S909Y, D910I, D910W, V911A, E912A, E912K, E912L, E912T, E912V, V913G, V913R, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, T919D, T919K, T919Q, T919W, S920P, S920V, D921C, D921V, R922A, R922M, R922V, R922W, Q923A, Q923E, Q923L, Q923M, Q923V, N924Q, N924S, V925C, V925E, V925G, V925K, V925N, V925W, T926P, T926R, W927P, D928A, D928H, D928Q, A929P, V930E, V930I, V930T, S931P, S931R, D933R, Q934S, Q934V, I935A, I935C, I935D, I935E, I935L, I935P, I935V, I935W, A936I, A936L, A936Q, A936R, A936Y, K937G, K937I, K937M, K937P, K937Q, A938C, A938H, A938N, A938T, A938V, A938W, G939D, G939K, S940C, S940E, S940R, S940V, F941C, F941M, S942A, S942E, S942K, S942P, S942V, V943A, V943G, V943Q, T946A, T946L, T946P, T946W, V947C, V947L, V947P, V947R, V947T, A948I, A948W, G949A, G949V, Q950K, Q950W, K951D, K951G, K951P, K951S, K951W, K951Y, I952Q, S953F, S953M, S953N, S953R, V954D, V954Q, R955A, R955C, R955K, R955Q, R955W, V956A, V956D, V956G, V956H, V956I, V956M, V956Q, V956W, T957D, T957S, T957W, I959A, I959L, I959S, I959V, I959Y, D960P, D960S, E961D, E961F, E961K, E961S, E961T, I962A, I962C, I962D, I962G, I962K, I962N, G963C, G963E, G963P, L965C, L965E, L965G, L965K, L965M, L965P, L965Q, L965S, L965V, L965Y, L966A, L966K, L966N, L966Q, L966S, L966V, N967D, N967I, N967L, N967M, N967P, N967T, N967V, Y968G, Y968L, Y968Q, Y968V, S969C, S969D, S969G, S969H, S969I, S969L, S969M, S969P, S969Q, S969Y, A970I, A970L, S971G, S971V, S971W, P973C, P973D, P973K, P973N, P973Q, P973R, P973V, P973W, P973Y, V974C, V974E, V974G, V974N, V974T, V974Y, G975F, G975K, T976D, T976F, T976G, T976K, T976L, T976P, T976S, P977C, P977K, P977R, P977T, P977Y, A978F, A978G, A978M, A978N, A978R, A978S, A978Y, V979G, V979N, V979Y, L980A, L980F, L980H, L980I, L980K, L980N, L980Q, L980T, L980Y, P981L, P981M, R984P, P985F, P985H, P985K, P985L, P985W, A986C, A986I, A986L, A986M, A986W, V987A, V987C, V987F, V987K, L988V, P989M, P989W, D990F, D990P, D990W, G991C, G991F, G991H, G991K, G991P, G991Y, T992M, T992N, V993G, S995E, S995L, S995R, A996R, N997K, N997V, F998M, F998W, V1000W, D1001L, D1001S, W1002A, W1002D, W1002E, W1002H, W1002N, W1002P, W1002Q, W1002S, T1003F, T1003G, T1003N, T1003R, T1003S, T1003W, T1003Y, K1004D, K1004E, K1004S, P1005I, P1005N, P1005V, P1005Y, A1006C, A1006N, A1006P, A1006S, A1006V, A1006W, A1006Y, D1007C, D1007L, D1007P, D1007V, T1008G, Y1010A, Y1010P, Y1010R, Y1010T, N1011A, N1011S, N1011T, N1011W, T1012H, T1012I, T1012Q, A1013D, A1013Q, A1013V, G1014I, G1014M, G1014V, G1014W, T1015A, V1016D, V1016P, K1017E, K1017G, V1018K, V1018L, V1018R, V1018S, T1021C, T1021E, T1021G, A1022H, V1024G, V1024H, V1024K, V1024R, V1024S, V1024W, G1026E, G1026S, G1026V, G1026Y, K1027Q, K1027R, E1028G, E1028T, F1029I, F1029K, F1029P, F1029V, K1030D, K1030H, K1030M, K1030W, V1031H, V1031K, A1033V, T1034G, T1034H, T1034N, I1035D, I1035G, I1035Q, R1036G, R1036L, R1036T, R1036Y, V1037C, Q1038D, R1039V, S1040M, Q1041P, V1042N, T1043F, T1043G, T1043R, I1044A, I1044L, S1046M, V1048C, V1048F, V1048G, V1048I, V1048M, V1048Q, N1051A, N1051E, N1051K, A1052C, A1052K, A1052R, L1053A, L1053W, R1054C, R1054L, L1055R, L1055T, Q1057A, Q1057E, Q1057P, N1058R, N1058S, P1060G, P1060N, P1060Q, A1061G, A1061K, A1061W, D1062A, D1062G, D1062I, D1062M, K1063M, Q1064M, Q1064R, Q1064T, Q1064V, S1065A, S1065C, D1066A, D1066G, D1066V, T1067G, T1067M, L1068P, L1068Q, L1068Y, D1069R, A1070T, I1071M, K1072P, K1072S, D1073F, D1073W, G1074L, G1074R, S1075G, S1075L, T1076E, T1076S, T1077R, V1078D, V1078W, D1079G, D1079L, N1081E, T1082E, T1082F, T1082G, T1082K, G1083E, G1083F, G1083L, G1084M, G1084V, G1084W, G1084Y, G1085P, G1085R, G1085S, A1086H, A1086K, A1086R, N1087A, N1087E, N1087I, N1087R, P1088D, P1088E, P1088G, P1088R, P1088W, S1089G, S1089K, S1089Q, S1089V, A1090F, W1091Y, N1093A, N1093G, N1093L, N1093P, N1093Q, W1094D, W1094E, W1094P, W1094R, W1094T, A1095P, A1095T, A1095W, Y1096D, Y1096L, S1097E, S1097K, S1097T, K1098D, K1098F, K1098G, K1098Q, K1098S, A1099D, A1099S, A1099V, A1099W, G1100E, G1100H, G1100N, H1101K, H1101Q, H1101R, H1101V, N1102H, N1102Q, N1102T, T1103A, T1103E, T1103S, T1103W, E1105L, E1105S, E1109A, E1109D, E1109L, E1109W, A1111G, A1111S, E1113G, E1113P, E1113V, Q1114E, Q1114L, Q1114R, Q1114S, Q1114T, Q1114V, Q1115A, Q1115K, Q1115L, Q1115P, L1116D, L1116G, L1116H, L1116K, L1116W, G1117E, G1117I, G1117M, G1117R, G1117S, G1117T, G1117V, G1117W, Q1118M, Q1118W, I1119D, I1119E, I1119N, I1119S, V1120N, V1120S, M1121G, M1121K, M1121N, M1121P, M1121S, F1123E, F1123R, F1124V, F1124W, R1125D, R1125F, R1125K, R1125V, R1125W, S1127I, S1127Q, N1128A, A1129E, A1129R, V1130A, V1130R, R1131W, F1132M, F1132P, F1132Q, P1133D, P1133G, P1133L, P1133R, A1135E, A1135K, A1135L, A1135W, G1136P, K1137G, K1137P, K1137R, K1137S, K1137T, K1137V, T1138R, T1138Y, I1140C, I1140P, I1140R, Q1141A, Q1141G, Q1141K, Q1141N, Q1141T, I1142E, I1142R, I1142Y, S1143G, A1144D, A1144N, A1144P, A1144S, A1144T, A1144V, A1144W, D1145E, D1145R, D1145T, G1146A, G1146K, G1146R, G1146V, N1148H, N1148I, N1148P, N1148Q, N1148R, N1148S, N1148T, W1149C, W1149G, W1149K, W1149S, W1149V, T1150K, T1150P, D1151C, D1151W, L1152A, L1152C, L1152E, L1152Q, L1152W, A1153E, A1153G, A1153L, A1154D, A1154E, A1154R, I1158S, I1158W, A1159E, A1159I, Q1161P, Q1161S, E1162A, E1162C, E1162Q, E1162W, E1165M, E1165S, R1166Q, V1167A, V1167R, K1168L, K1168R, P1169M, P1169S, Y1170K, Y1170M, Y1170V, Y1172H, Y1172S, D1173G, D1173T, F1174D, A1175S, G1178M, G1178Q, G1178S, G1178T, A1179L, A1179Q, A1179W, T1180A, T1180G, T1180I, T1180L, T1180M, T1180Q, T1180S, T1180Y, F1181E, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190T, D1190Y, T1191L, T1193G, P1194E, P1194W, V1197A, C1199D, A1200G, T1203K, E1204G, E1204S, I1205V, K1208R, K1208V, K1208W, T1209A, T1209C, T1209E, T1209K, T1209N, T1209Q, T1209R, T1209W, A1210D, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, F1214A, F1214E, F1214K, F1214L, F1214P, F1214S, F1214V, V1215D, V1215E, V1215L, V1215Q, V1215W, T1216L, T1216P, T1216Q, T1216R, N1217A, N1217E, N1217P, N1217R, N1217S, N1217T, T1218A, T1218C, T1218E, T1218G, T1218Q, T1218S, T1218V, T1218W, S1219I, S1219K, S1219R, S1219V, A1220C, A1220G, A1220P, A1221K, A1221R, A1221V, A1221W, L1222A, L1222E, L1222F, L1222Q, L1222R, L1222V, L1222W, S1224P, S1224W, L1225E, L1225K, L1225V, T1226P, V1227C, V1227D, V1227P, V1227Q, G1229C, G1229E, G1229V, T1230H, T1230K, T1230W, K1231G, V1232E, V1232Q, V1232R, D1234V, S1235D, S1235E, S1235G, S1235P, S1235R, S1235W, S1235Y, V1236A, V1236C, V1236G, V1236P, V1236Q, L1237V, A1238D, A1238E, A1238L, A1238R, A1239R, G1240D, G1240Q, N1243C, I1247R, G1255H, A1259K, V1261R, T1262F, T1262M, T1262R, V1263T, L1264H, L1264R, P1265W, V1273R, I1274F, I1274R, T1275A, T1275W, E1276R, S1277L, S1277T, S1277W, E1278Q, E1278R, D1279I, D1279R, D1279W, H1280C, H1280E, H1280G, V1281I, V1281W, K1284G, T1285A, T1285M, T1286A, F1286E, F1286P, F1286R, T1287C, T1287L, T1287S, T1287W, I1288A, I1288D, I1288G, I1288K, E1293K, E1293L, Q1294E, E1295K, F1296A, E1302G, E1302R, E1302S, R1303S or D1304V.

81. The lactase variant of the preceding embodiment, wherein the variant has a decreased galactose inhibition, preferably measured as a galactose inhibition improvement factor (GI-IF) of at least 1.1, compared to the lactase of SEQ ID NO: 1.

82. The lactase variant of embodiment 1 which comprises one or more of the following substitutions, wherein each position corresponds to a position in SEQ ID NO: 1: V1D, V1F, V1H, V1L, E2D, E2Q, E2V, D3I, D3S, D3V, D3W, T5D, T5S, R6A, R6F, R6M, R6P, S7D, S7I, S7N, S7P, S9H, S9P, T10L, T10P, T10S, T11L, T11P, Q12R, M13C, M13D, M13F, M13K, M13R, S14V, S15C, S15I, S15K, S15P, S15R, S15T, S15V, S15Y, T16C, P17D, P17I, P17L, P17T, V19G, V19K, V20C, V20G, V20K, V20L, V20M, V20P, V20Q, V20R, V20W, Y21C, Y21P, Y21R, Y21T, S22E, S22G, S22N, S22T, S22W, S23C, S23L, S23M, S23R, A24F, A24L, A24R, A24T, A24W, V25D, V25K, V25M, V25Q, V25S, D26C, D26I, D26L, S27A, S27C, S27F, S27G, S27H, S27Y, K28C, K28L, K28V, Q29G, Q29L, Q29M, Q29R, Q29V, Q29W, N30A, N30M, N30V, R31E, R31G, R31I, R31M, R31V, T32S, S33C, S33N, S33Q, S33R, D34C, D34E, D34G, D34H, D34L, D34S, D34W, D34Y, F35C, F35E, F35K, F35N, D36Q, N38S, W39G, W39S, K40C, K40D, K40F, K40G, K40I, K40N, K40W, F41A, F41C, F41G, F41I, F41Q, M42E, M42N, M42T, L43A, L43C, L43I, L43S, L43T, L43V, S44C, D45A, D45P, V47K, V47R, A49D, A49H, A49R, A49S, A49T, A49V, D51G, D51I, D51K, D51P, D51V, A53C, A53R, A53S, A53V, A53W, D55C, D55F, D55G, D55H, D55M, D55P, D55S, S57A, S57C, S57E, S57G, A58D, A58G, A58Q, A58T, W59I, W59K, W59P, W59V, Q60K, Q60M, Q60R, Q60S, Q60Y, Q61P, V62N, V62S, V62T, V62W, D63G, L64E, L64G, H66L, H66R, H66Y, Y68P, I70A, I70K, T71C, T71K, T71Q, K73D, Y74K, S75G, S75L, S75Q, S75R, S75V, Q76G, Q76I, Q76K, Q76V, S77C, S77D, S77E, S77F, S77G, S77H, S77K, S77L, S77M, S77R, S77T, S77V, N78C, N78E, N78K, N78Q, N78R, N78S, E79H, E79Q, E79S, E79T, A80K, E81A, E81Q, A83T, L85A, L85F, L85N, L85S, L85V, L85W, P86G, P86N, P86Q, P86R, P86V, P86W, P86Y, G87D, G87N, G87Q, G88F, G88Q, G88S, T89H, T89K, T89M, T89Y, G90A, G90L, G90S, G90T, G90V, W91E, W91L, W91P, W91Q, W91R, W91Y, Y92F, Y92H, Y92I, Y92M, Y92N, Y92S, Y92T, Y92V, R93A, R93D, R93F, R93H, R93I, R93L, R93N, R93T, R93V, R93Y, K94A, K94C, K94G, K94S, K94T, K94V, S95A, S95C, S95D, S95G, S95I, S95Q, S95R, F96A, F96C, F96I, F96K, F96M, F96P, F96S, F96V, F96W, T97F, T97V, I98H, I98H, I98W, R100T, D101A, D101P, D101V, L102P, R106V, R106W, I107F, I107G, I107S, A108E, A108S, I109M, N110A, N110S, N110T, N110V, N110W, F111A, F111L, F111Q, D112F, D112T, G113S, V114F, V114R, Y115E, M116C, N117W, A118K, A118P, A118Y, T119A, V120A, V120K, W121D, W121R, W121V, W121Y, F122A, F122S, F122Y, N123P, G124E, G124M, G124Q, G124R, V125E, V125I, G128D, T129E, H130A, H130C, H130S, H130T, Y132C, Y132E, P136R, P136Y, F137C, F137L, S138A, S138L, S138R, F139Q, D140V, L141G, T142S, T142V, K146A, G148T, G149E, G149M, G149Q, G149Y, E150C, E150G, E150L, E150R, I153A, V154I, V154K, V154L, V155F, V157L, V157P, V157S, E158G, E158H, E158V, N159H, N159S, N159T, L161K, L161M, L161S, L161W, P162N, P162T, P162W, S164A, R165H, W166S, Y167A, Y167C, G169D, S170L, S170Q, G171C, G171T, I172K, I172P, Y173H, Y173M, Y173W, R174E, R174K, V176E, V176K, V176T, T177K, L178I, L178Q, L178W, T179A, T179C, T179D, T179I, T179K, T179N, T179P, T179S, V180A, V180D, V180G, T181A, T181F, D182F, G183W, V184F, V184P, V184R, V184S, V184W, H185G, H185L, V186E, V186N, G187D, G187H, N188E, N188R, N188V, N189E, G190C, G190F, I193N, I193Q, K194I, T195S, T195W, P196A, P196I, S197C, S197E, S197L, L198R, L198V, A199E, A199K, A199P, Q201E, N202D, N202L, N202Q, N202R, N202S, N202T, N202W, G203C, G203K, G203S, G203V, G203W, G203Y, G204A, G204K, G204Y, N205E, N205G, N205H, N205L, V206I, V206K, V206S, T207A, T207C, T207G, T207I, T207K, T207Q, M208S, N209D, N209K, N209V, L210G, L210I, L210Q, L210V, T211A, T211F, T211Q, T211R, T212E, T212G, T212H, T212L, T212S, K213C, K213D, K213F, K213L, K213T, K213Y, V214A, V214C, V214W, A215D, A215E, A215I, A215K, A215L, A215Q, A215R, A215V, D217F, D217L, D217M, D217T, T218G, K219F, K219H, K219M, A220C, A220G, A220L, A220V, A221E, A221L, A221R, A222D, A222I, A222L, A222P, A222R, A222W, N223E, N223F, N223K, N223L, N223S, N223T, L226M, L226Q, Q228N, Q228R, T229A, T229C, T229D, T229G, T229M, T229N, T229Q, T229R, T229V, V230L, V230M, V230R, V230S, F231E, F231G, F231I, F231L, F231V, F231W, F231Y, P232G, P232M, P232S, K233C, K233E, K233F, K233L, K233P, K233R, G234A, G234C, G234D, G234E, G234L, G234Q, G234R, G234V, G234Y, G235H, G235I, G235K, G235M, G235Q, G235T, G235W, G235Y, K236A, K236D, K236L, K236M, K236P, K236R, K236S, K236W, K236Y, T237D, T237K, T237R, D238A, D238E, D238F, D238G, D238M, D238P, D238R, A239E, A239G, A239I, A239T, A240C, A240L, A240P, A240T, A240Y, I241T, G242K, G242L, G242M, G242P, G242Y, T243I, T243M, T243R, V244E, V244R, T245E, T245G, T245Q, T245R, T246G, T246K, A247E, A247K, A247P, A247R, A247S, A247V, A247W, S248A, S248E, S248L, S248Q, S248T, K249A, K249D, K249G, K249H, K249L, K249N, K249P, K249Q, K249V, K249Y, S250H, I251L, I251W, I251Y, A252F, A252W, A252Y, G254D, G254F, G254I, G254L, G254M, G254Q, G254W, A255K, A255S, A255Y, S256A, S256C, S256K, S256M, S256N, S256R, S256Y, A257D, A257I, A257N, A257V, D258A, D258L, D258W, V259E, V259T, T260D, T260G, S261D, S261H, S261R, S261W, T262D, T262W, T264F, T264M, T264Q, T264Y, A265I, A265S, A266D, A266G, A266K, A266Q, A266T, S267A, S267M, S267N, S267P, S267R, S267V, P268F, P268G, P268R, P268W, P268Y, K269V, K269Y, L270D, L270N, S272G, S272T, S272W, I273L, I273R, N275W, N277F, N277R, L278H, L278I, L278K, L278M, L278Q, L278R, L278V, Y279W, T280A, T280E, T280F, T280Q, V281I, V281Q, R282E, R282F, R282H, R282I, R282K, R282N, R282S, R282V, R282W, T283R, T283V, E284A, E284D, E284H, E284L, E284R, E284Y, V285T, L286F, L286N, L286T, L286W, G288S, V291D, V291F, V291P, V291T, V291Y, L292D, L292H, L292V, D293C, D293I, D293S, D293W, T294Q, T294S, Y295F, Y295W, D296F, D296H, D296K, D296R, D296V, T297I, E298I, E298L, E298R, F301C, R302I, R302N, W303A, W303C, W303D, W303F, W303S, T304D, T304E, T304I, T304K, T304P, G305L, G305N, G305P, G305T, G305W, F306L, F306L, D307A, D307E, D307G, D307S, D307W, A308E, A308M, A308Y, T309C, T309D, T309E, T309I, T309S, T309V, S310A, S310H, S310L, S310M, S310N, S310V, G311V, F312H, F312R, L314A, L314C, L314T, L314V,
N315S, G316R, G316S, E317K, E317W, K318C, K318N, K320C, K320E, K320F, K320I, K320L, K320R, K320T, K320V, K320W, L321M, K322F, K322I, K322P, K322S, V324T, S325D, S325G, S325T, M326E, M326G, M326T, M326Y, H328C, H328F, H328G, H328L, H328M, H328R, H328T, D329S, G331V, A335C, A335G, A335L, A337E, A337G, A337L, N338F, R340A, R340C, R340L, A341M, A341S, I342G, I342K, I342P, E343N, E343T, E343Y, R344G, Q345F, Q345G, Q345K, Q345N, Q345S, V346A, V346C, V346I, V346S, E347A, E347C, E347F, E347I, E347R, I348D, I348M, I348Q, I348R, L349A, L349Q, L349S, Q350G, Q350N, K351V, M352G, M352T, M352W, G353K, V354E, V354S, V354W, N355M, N355W, I357T, T359E, T359L, T360V, N362S, N362T, P363A, P363D, P363I, P363L, P363M, P363S, P363V, A364C, A364E, A364F, A364G, A364I, A364M, A364P, A364V, A365C, A365E, A365I, A365P, A365V, A365W, K366A, K366D, K366L, K366M, K366P, K366S, K366V, A367Q, L368A, L368E, L368Q, L368S, L368Y, I369A, I369D, I369E, I369G, I369K, I369M, I369R, I369V, I369W, D370L, D370Q, D370S, V371D, V371F, V371L, V371Q, V371S, C372P, N373G, N373L, E374R, K375D, K375S, G376A, G376S, V377A, V377M, V377T, V379A, V379N, V380P, E381A, E381G, E381Q, E381T, V383A, V383K, V383L, M386F, M386N, M386S, M386V, W387H, W387T, N388A, N388E, N388L, N388R, R389A, R389C, R389E, R389N, R389Q, R389S, R389T, S390C, S390D, S390G, S390P, S390Q, S390T, S390V, K391E, N392D, G393A, G393E, G393N, G393R, G393S, G393V, N394L, T395C, T395F, T395H, T395M, T395N, T395S, T395W, E396K, E396L, E396M, E396V, E396W, Y398M, Y398N, G399S, K400A, K400C, K400N, K400P, K400Q, K400S, K400T, K400V, W401F, W401H, W401K, W401L, F402F, F402Y, G403A, G403D, G403K, G403P, G403Q, G403S, G403V, G403Y, Q404F, Q404H, Q404L, Q404M, Q404P, Q404R, Q404S, Q404V, A405C, A405E, A405H, A405K, A405P, A405R, A405T, I406C, I406D, I406N, A407C, A407G, A407Q, A407T, G408I, G408M, G408N, G408W, D409N, N410R, N410Y, A411E, A411R, A411S, A411V, L413I, L413P, L413T, G414A, G414C, G414M, G414N, G414R, G415Q, G415R, D416I, D416R, D416Y, K417C, K417F, K417G, K417R, K417T, D418F, D418R, E419M, E419R, E419W, T420E, T420F, T420G, T420K, T420R, T420V, W421L, W421Q, A422P, A422T, K423D, F424C, F424L, F424N, L426C, L426M, L426Q, T427D, T427F, T427G, T427K, T427M, T427P, T427Q, T427S, T427W, S428F, S428K, T429D, I430C, I430L, I430M, I430Q, I430S, I430T, N431D, N431E, N431M, N431Y, R432A, R432E, R432N, R432Q, R432Y, D433G, D433I, D433P, D433Q, D433W, R434N, R434S, R434V, N435E, N435F, N435K, N435L, N435R, N435V, N435W, A436G, A436L, P437A, P437Q, P437R, P437V, V439C, V439E, V439G, V439I, V439K, V439T, V439Y, I440F, I440K, I440R, I440W, M441A, M441E, M441Q, W442E, W442G, W442P, W442R, S443C, S443M, S443Q, S443Y, L444D, L444E, L444F, L444G, L444K, L444Q, L444V, L444W, G445A, G445C, G445V, N446D, N446T, M448A, M448C, M448D, M448I, M448L, M448P, M448Q, M448S, M448V, M449D, M449E, M449T, M449W, M449Y, E450F, E450S, E450T, E450V, E450W, G451C, G451F, G451L, G451P, G451V, G451W, I452G, I452K, I452L, I452M, I452Q, I452S, I452V, S453F, S453H, S453L, S453N, S453Q, G454L, G454W, S455E, S455K, S455M, S455P, S455R, S455W, V456D, V456E, V456F, V456K, V456L, S457H, S457K, S457P, S457Q, S457T, S457V, G458A, G458P, G458S, G458V, G458W, F459C, F459N, F459R, F459S, P460Y, A461D, A461G, A461M, A461N, A461Y, T462C, T462E, T462F, T462L, S463K, S463Q, S463T, S463V, A464M, A464P, A464V, A464W, K465F, K465L, K465V, K465Y, L466A, L466E, L466F, L466G, L466M, L466P, L466Q, L466S, L466Y, V467D, V467E, V467G, V467T, V467W, A468D, A468E, A468F, A468K, A468L, A468V, A468W, W469A, W469G, W469M, T470M, K471F, K471Q, K471W, A472G, A472Y, D474R, D474W, S475E, S475F, R477L, P478G, P478L, P478V, M479G, M479I, M479R, M479W, T480C, T480G, K485E, K485R, K487A, K487F, K487G, K487N, K487S, K487W, A488C, A488G, A488H, A488N, A488S, N491A, N491W, E492A, E492W, S493E, S493G, S493H, S493L, S493M, S493Q, N494M, N494R, N494V, T495R, T495V, T495W, M496F, G497D, D498A, D498C, D498M, D498S, N499R, N499T, N499Y, L500A, L500N, T501G, T501M, A502L, N503A, N503E, N503M, G504H, G504K, G504P, G505A, G505D, G505E, G505H, G505L, G505N, G505R, G505S, V506C, V506D, V506E, V506G, V506L, V506P, V506R, V506S, V507A, V507G, V507L, V507N, V507R, V507S, G508C, G508E, T509A, T509I, T509K, T509M, T509V, T509Y, N510A, N510F, N510I, N510Q, Y511A, S512C, S512F, S512G, S512I, S512M, S512Q, S512T, S512V, S512Y, D513K, D513L, D513P, D513R, G514F, G514L, A515C, A515D, A515G, A515K, A515P, A515R, N516C, N516E, N516I, N516Q, N516T, N516V, Y517G, Y517N, D518Q, D518Y, K519C, K519E, K519G, K519I, K519Q, I520A, I520C, I520G, I520H, I520M, I520N, I520Q, I520S, I520T, I520W, R521N, R521V, T522G, T522N, H524R, H524V, P525G, P525T, S526G, W527A, W527E, W527G, W527H, W527N, W527R, W527S, A528C, A528E, A528I, I529G, Y530A, Y530M, G531E, G531S, G531T, T534A, T534I, A535I, A535M, A537D, A537M, A537R, A537S, I538M, N539W, S540E, S540G, G542Q, I543V, N545Q, N545S, R546C, R546L, R546P, R546S, T547A, T547D, T547N, T547S, T548E, T548F, T548K, T548L, T548P, G549D, G549F, G549P, G549W, G550S, A551I, A551Q, S553F, S553N, S553P, S554N, S554V, D555S, K556A, K556R, K556W, Q557R, L558E, L558H, L558P, T559Q, T559Y, Y561R, N563S, S564A, S564C, S564F, S564W, A565C, A565D, A565E, A565F, A565G, A565I, A565L, A565R, A565S, A565T, G567Q, G567V, A570G, A570K, A570M, A570W, A572S, A572W, S573G, S573K, S574K, S574Q, S574W, A575D, A575V, W576F, W576V, W576Y, S577Q, S577L, D578M, D578N, V579E, V579G, V579L, V579T, V580A, V580D, V580K, V580L, V580S, Q581F, Q581G, Q581Q, Q581S, Q581Y, R582A, R582G, R582L, R582Y, D583W, F584E, F584W, V585I, V585M, A586D, A586H, A586K, G587A, G587C, T588C, T588D, T588I, T588L, T588M, Y589I, Y589Q, Y589V, Y589W, V590A, V590H, W591F, T592C, T592L, T592S, G593I, F594L, D595E, D595Q, D595S, L597D, L597E, G598N, P600A, P600E, P600G, P600S, N604E, T606S, G607Q, G607S, S608T, S608V, G609A, G609L, G609N, G609R, A610F, A610M, A610T, V611K, G612N, G612T, W614A, W614P, P615L, S616W, N619A, N619I, N619L, S620G, I624A, V625E, V625M, V625Y, T627K, T627Q, A628D, A628N, G629T, F630C, F630D, F630G, F630Y, P631A, P631D, P631V, P631Y, K632D, K632G, K632T, T634A, T634E, T634V, Y635R, F637G, F637I, F637S, F637T, F637V, Y638A, Y638W, Q639R, D644C, D644Y, D645S, V646R, H647G, T648C, H650E, H650R, I651T, L652C, L652W, P653Q, A654K, A654M, A654R, W655G, N656R, E657R, V659N, A661E, A661I, A661K, A661M, A661Q, A661W, K662S, K662V, K662Y, N667L, N667Q, P669L, P669T, P669W, V670C, Y673E, Y673G, Y673R, Y673S, T674C, T674M, D675A, D675P, D675Q, A676C, A676E, A676P, A677E, A677G, K678A, K678T, V679G, V679Q, V679S, V679Y, K680H, K680I, K680N, K680V, L681E, L681F, L681S, L681T, Y682E, F683M, F683Q, T684G, T684V, K686M, G687A, G687P, G687Q, G687R, S688E, S688K, S688L, S688T, T689D, T689G, T689P, T689W, E690D, E690V, K691P, K691R, R692G, R692H, R692I, R692S, R692T, I694L, I694W, G695C, G695L, G695R, G695W, E696A, E696K, G697A, G697E, K697G, K697R, S698E, S698I, S698L, S698M, S698T, T700C, K701A, K701D, K701G, K701L, K701M, K701S, T704M, T704Y, A705C, A705E, A705N, A705R, A705W, A706C, A706T, A706Y, Y708C, Y708F, Y708T, T709M, Y710D, Y710G, Y710N, Y710T, Y710V, Y710W, Q711A, Q711L, Q711M, Q711Y, V712M, V712P, V712Q, Y713G, E714H, E714K, E714V, G715K, A716C, A716L, A716R, A716T, A716V, D717C, D717G, D717S, K718A, K718L, K718Q, K718T, K718Y, D719E, D719T, D719V, S720A, T721H, T721L, T721N, T721S, T721V, T721W, A722T, A722V, H723G, H723P, M726D, M726Y, Y727L, L728S, T729M, N731E, N731Q, N731S, V732R, V732W, P733R, P733W, W734G, W734V, A735Q, A735R, A735S, G737F, T738S, I739K, S740D, S740F, A741I, A741P, A741S, E742Q, Y744R, D745C, D745F, D745N, N747F, N747R, L750S, I751C, P752A, P752C, P752Y, G754F, G754P, G754R, T756S, E757A, N759S, N759V, A760N, G766M, A769F, A769G, A769I, A769N, A769V, A769Y, K770H, L771A, L771I, K772A, K772C, K772P, K772V, K772W, A773C, A773H, A773M, A773R, A773S, A773V, D774A, D774R, A775L, A775W, D776I, D776L, D776S, D776V, R777D, R777E, R777G, R777H, R777P, R777S, K778A, K778F, K778G, K778L, K778N, I780V, T781A, T781C, T781F, T781G, T781M, T781P, T781R, T781Y, A782E, A782K, A782P, A782Q, A782Y, D783A, D783C, D783E, D783R, D784A, G784L, G784S, G784T, K785C, K785S, K785W, K785Y, D786V, L787P, L787T, S788A, S788G, S788I, Y789V, I790A, I790C, I790F, I790R, E791S, E791T, V792G, V792S, D793H, D793K, V794C, V794T, V794W, T795P, D796Q, N798I, G799K, G799L, G799M, G799Q, H800A, H800L, H800V, I801C, V802I, V802S, V802Y, P803F, P803K, P803S, P803Y, D804G, D804K, D804S, A805F, A806I, A806Q, N807Q, N807W, R808C, R808F, R808G, R808I, R808N, R808Q, V809C, V809L, V809M, T810P, T810Q, T810Y, F811L, F811Y, D812Q, V813T, V813W, K814G, K814H, K814L, K814P, G815A, G815M, G815P, G815V, A816C, A816D, A816F, A816V, A816W, G817I, G817N, K818D, K818F, K818L, K818Q, K818W, K818Y, L819F, V820C, V820K, V820R, G821A, G821E, G821F, G821I, G821N, G821V, V822A, V822D, V822E, G825A, S826F, S826G, S826L, S826R, S827Q, P828C, P828Y, D829S, H830E, H830G, H830M, H830P, H830R, H830V, D831F, D831I, D831P, D831R, D831V, S832G, S832L, S832M, S832R, Y833E, Y833I, Y833K, Y833P, Y833V, Q834F, Q834M, A835D, A835E, A835H, A835K, A835W, D836C, D836E, D836H, D836Q, D836S, D836T, D836V, D836W, D836Y, N837D, N837G, N837H, N837L, R838G, R838M, R838N, R838W, K839A, K839D, K839E, A840G, A840I, A840P, A840V, F841C, F841W, S842M, G843C, K844A, K844G, V845V, V845W, L846I, L846M, V849A, V849L, V849S, Q850C, Q850G, Q850Y, K853N, K853P, K853Q, E854C, E854I, E857P, I858D, I858E, I858K, I858M, I858P, I858Q, I858Y, T859V, V860T, T861F, T861I, T861W, A862V, K863F, K863I, K863N, K863W, A864L, D865A, D865G, G866H, G866R, L867W, S870E, S870M, S870R, S870T, T871P, V872C, V872G, K873G, K873Y, I874C, T877A, P880S, G881W, T882A, T882R, S883L, T884A, E885V, K886E, K886L, K886V, K886W, T887A, T887D, T887F, T887G, T887N, T887V, V888A, V888D, R889G, Y892D, Y892P, Y892R, Y893E, S894D, N896M, Y897V, V899G, K900E, T901G, T901Q, T901R, T901V, T901Y, G902A, G902F, G902L, G902P, G902Q, G902R, G902S, G902W, N903D, N903I, K904D, K904E, K904M, K904N, K904R, K904S, K904V, P905C, P905R, P905W, P905Y, I906N, I906S, I906W, I906Y, L907F, L907S, P908D, P908G, P908I, P908L, D910W, E912T, V913Q, R914A, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, T919D, T919Q, T919W, T919Y, S920E, S920W, D921Q, D921V, R922A, R922G, R922M, R922W, Q923A, Q923V, N924L, V925A, V925C, V925K, V925S, T926G, T926R, T926S, W927C, W927G, W927P, D928A, D928Q, A929C, A929P, V930A, V930I, S931G, S931R, D932F, D932S, D932T, D932V, D933I, D933R, Q934S, Q934V, I935A, I935C, I935E, I935P, I935W, A936I, A936Q, A936Y, K937G, K937I, K937M, K937P, K937Q, K937R, A938C, A938T, G939D, S940C, S940E, S940R, S940T, S940V, S940W, F941C, F941W, S942K, S942L, S942V, V943A, V943H, V943R, A944D, A944H, A944P, A944R, G945T, T946A, T946G, T946P, T946V, T946W, V947G, V947L, V947M, V947P, V947R, V947T, A948C, A948I, A948R, A948W, G949A, Q950D, Q950G, K951D, K951Q, K951S, K951W, K951Y, I952H, S953F, S953M, S953R, S953W, V954D, V954Q, V954T, R955C, R955W, V956D, V956Q, T957S, M958D, M958I, I959V, I959Y, D960H, D960L, D960S, E961D, E961F, E961S, E961T, I962A, I962C, I962K, I962N, L965C, L965G, L965K, L965M, L965P, L965V, L965Y, L966A, L966G, L966H, L966N, L966P, L966T, N967D, N967M, N967P, N967S, N967T, Y968G, Y968L, Y968Q, Y968V, S969C, S969D, S969H, S969I, S969L, S969M, S969Q, S969Y, A970I, S971H, S971V, S971W, P973C, P973D, P973N, P973R, P973W, V974E, V974T, V974Y, G975Q, T976F, T976G, T976K, T976P, P977C, P977T, P977Y, A978F, A978M, A978N, A978R, V979R, L980A, L980H, L980I, L980N, L980Q, L980T, P981M, G982P, G982Q, P985E, P985L, P985W, A986I, A986L, A986N, A986W, V987A, V987F, V987K, L988E, L988G, L988S, P989A, P989M, D990W, G991F, G991H, G991Y, T992M, T994S, S995L, S995V, A996Q, A996V, N997A, N997E, N997K, N997L, N997Y, F998M, F998W, A999G, A999M, A999R, A999S, V1000C, V1000L, V1000M, V1000N, D1001G, D1001K, D1001L, D1001T, D1001V, W1002A, W1002D, W1002E, W1002H, W1002N, W1002P, W1002Q, T1003L, T1003P, T1003Y, K1004F, K1004H, K1004P, K1004R, K1004V, P1005I, P1005Y, A1006C, A1006I, A1006S, D1007L, D1007P, D1007V, V1009G, Y1010T, N1011A, N1011T, T1012Q, A1013Q, A1013V, G1014I, G1014L, T1015G, V1016C, V1016D, V1018K, T1021F, T1021G, T1021V, A1022H, A1022L, T1023D, V1024G, V1024H, V1024K, V1024N, V1024R, V1024S, V1024W, G1026L, G1026R, G1026S, G1026V, K1027C, K1027N, F1029K, F1029P, F1029V, K1030D, K1030W, V1031H, V1031K, T1034H, I1035D, R1036G, R1036L, R1036T, V1037F, Q1041P, V1042N, T1043F, I1044A, S1046M, V1048C, V1048F, V1048G, V1048M, V1048Q, G1050S, N1051E, N1051K, A1052K, L1053A, L1053W, L1055R, Q1057E, Q1057R, N1058R, N1058S, N1058V, I1059W, P1060G, P1060N, P1060T, A1061G, D1062A, D1062L, D1062M, K1063D, Q1064M, Q1064R, S1065A, S1065C, S1065E, D1066A, D1066G, D1066M, D1066V, D1066W, T1067M, L1068C, L1068P, L1068Q, A1070P, I1071R, I1071M, K1072E, K1072G, K1072Q, K1072S, D1073L, D1073P, G1074I, G1074L, G1074R, S1075C, S1075L, T1076H, T1076Q, T1076S, V1078L, T1082E, T1082F, G1083E, G1083F, G1083L, G1083S, G1084V, G1084Y, G1085S, A1086H, A1086Q, N1087R, N1087W, P1088E, P1088R, S1089C, S1089G, S1089K, S1089Q, S1089R, A1090W, W1091A, W1091E, W1091G, W1091H, W1091T, W1091V, W1091Y, T1092G, T1092Q, T1092S, T1092V, N1093A, N1093P, N1093Q, N1093T, N1093V, W1094D, W1094E, W1094P, A1095W, Y1096A, Y1096D, S1097L, S1097T, S1097W, K1098D, K1098F, A1099C, A1099D, A1099S, A1099V, G1100H, G1100M, G1100T, H1101V, N1102E, N1102H, N1102K, T1103E, A1104R, E1105L, I1106T, T1107R, T1107S, F1108D, F1108L, F1108T, E1109A, E1109D, E1109L, E1109W, A1111G, E1113D, E1113P, E1113V, Q1114E, Q1114R, Q1114S, Q1114T, Q1114V, Q1115A, Q1115K, Q1115L, Q1115P, L1116G, L1116K, L1116W, G1117E, G1117I, G1117M, G1117R, G1117S, G1117T, G1117V, G1117W, Q1118W, I1119E, I1119G, I1119N, I1119S, V1120T, M1121G, M1121K, M1121V, Y1122K, Y1122R, Y1122V, F1123R, F1123T, F1124V, F1124W, R1125D, R1125E, R1125K, R1125V, R1125W, D1126H, D1126L, S1127F, S1127I, S1127K, S1127Q, S1127W, N1128A, N1128R, N1128S, N1128W, A1129E, A1129L, A1129Q, A1129V, V1130A, V1130G, V1130R, V1130S, R1131A, R1131S, F1132E, P1133D, P1133G, P1133R, D1134G, D1134L, A1135L, A1135S, A1135W, A1135Y, G1136A, G1136E, G1136P, K1137C, K1137L, K1137P, K1137Q, K1137R, K1137S, T1138R, I1140C, I1140G, I1140L, I1140P, Q1141K, Q1141P, Q1141W, I1142Y, S1143G, A1144C, A1144N, A1144P, A1144S, A1144T, A1144V, A1144W, D1145E, D1145R, D1145T, G1146D, G1146L, G1146V, K1147T, K1147V, N1148P, W1149C, W1149G, W1149I, W1149N, W1149Q, W1149S, W1149V, T1150K, D1151R, D1151W, L1152A, L1152E, L1152Q, L1152W, A1153G, A1154C, A1154R, T1155L, I1158R, I1158W, A1159I, A1159R, A1159V, A1160Q, Q1161A, Q1161P, Q1161S, E1162A, E1162C, E1162I, E1162Q, E1162Y, E1165D, E1165L, E1165S, V1167R, K1168Q, K1168W, P1169S, Y1170E, Y1170K, T1171A, T1171G, Y1172E, YI172K, D1173A, D1173F, D1173K, D1173L, F1174P, F1174T, F1174V, F1174W, A1175N, A1175Q, A1175S, A1175V, A1175Y, V1177N, V1177T, G1178M, G1178Q, G1178T, A1179L, A1179W, T1180A, T1180G, T1180I, T1180M, T1180Q, T1180Y, V1182M, K1183E, V1184C, V1184E, V1184K, V1184L, V1184P, V1184Q, V1184Y, V1186S, N1188M, A1189C, A1189K, A1189T, A1189V, D1190R, D1190T, T1191H, T1191L, T1192H, V1197A, V1198E, C1199T, A1200G, A1200V, A1200W, L1202A, T1203K, E1204G, I1205V, K1208R, K1208V, K1208W, T1209A, T1209C, T1209E, T1209K, T1209N, T1209Q, A1210D, A1210E, A1210G, A1210K, A1210L, A1210R, A1210T, A1210W, T1211D, T1211G, T1211K, T1211P, T1211R, T1211S, K1213T, F1214A, F1214E, F1214K, F1214L, F1214P, F1214S, F1214V, V1215D, V1215L, V1215Q, T1216A, T1216L, T1216P, T1216Q, N1217A, N1217F, N1217P, N1217R, N1217S, N1217T, T1218A, T1218C, T1218E, T1218G, T1218S, T1218W, S1219A, S1219F, S1219I, S1219R, A1220L, A1220P, A1220R, A1221D, A1221R, A1221V, A1221W, L1222A, L1222E, L1222F, L1222V, L1222W, S1223F, S1223K, S1223L, S1223V, S1224A, S1224D, S1224G, S1224P, S1224W, L1225C, L1225E, L1225F, L1225K, L1225W, T1226A, T1226G, T1226P, T1226S, T1226V, V1227A, V1227D, V1227L, V1227P, V1227S, N1228D, N1228F, N1228T, G1229V, T1230H, T1230I, T1230K, T1230S, T1230W, K1231F, K1231L, K1231M, K1231P, V1232K, V1232R, S1233P, S1233W, D1234K, D1234R, S1235E, S1235G, S1235R, S1235W, V1236A, V1236G, V1236I, V1236P, V1236Q, L1237D, L1237E, A1238E, A1238L, A1238N, A1238P, A1238R, A1239D, A1239P, A1239R, G1240D, G1240N, G1240W, S1241D, Y1242E, Y1242R, N1243M, N1243P, N1243T, N1243V, N1243W, T1244A, T1244E, T1244Q, T1244W, A1246M, A1246N, A1246P, A1246Q, A1246R, I1247G, I1247Q, I1247R, I1247S, I1247W, I1248G, I1248L, I1248R, I1248S, A1249G, A1249H, A1249I, A1249R, A1249T, A1249V, D1250I, D1250K, D1250S, D1250T, D1250W, D1250Y, V1251T, V1251W, K1252D, K1252V, K1252W, E1254V, G1255H, G1255M, E1256M, E1256N, E1256V, E1256W, G1257F, G1257L, G1257Q, N1258H, N1258S, A1259K, V1261I, V1261L, T1262A, T1262Q, T1262R, V1263E, V1263R, V1263T, V1263W, L1264H, P1265L, P1265R, P1265W, A1266P, A1266V, H1267E, N1269A, N1269K, N1269R, N1269S, V1270D, I1271H, R1272M, R1272V, V1273R, I1274F, I1274R, T1275L, T1275W, S1277L, S1277T, S1277W, E1278Q, D1279G, D1279I, D1279R, D1279T, D1279W, H1280E, H1280G, V1281I, V1281W, T1282D, R1283A, R1283D, R1283E, R1283W, K1284G, T1285F, F1286A, F1286E, F1286P, F1286S, T1287C, T1287R, T1287S, T1287W, I1288A, I1288D, I1288G, I1288K, N1289A, N1289T, L1290A, L1290R, G1291P, G1291V, G1291Y, T1292Y, E1293K, E1293L, E1293S, E1293V, Q1294E, Q1294P, Q1294W, E1295K, F1296A, P1297F, E1302R, E1302S, R1303S, D1304A or D1304V.

83. The lactase variant of the preceding embodiment, wherein the variant has a decreased or an increased galactose inhibition, preferably measured as a galactose inhibition improvement factor (GI-IF) of at least 1.2 or at most 0.8, compared to the lactase of SEQ ID NO: 1.

84. The lactase variant of embodiment 1 which comprises one or more of the following substitutions, wherein each position corresponds to a position in SEQ ID NO: 1: V1D, V1F, V1H, V1L, E2D, E2Q, E2V, D3I, D3S, D3V, D3W, T5D, T5S, R6A, R6F, R6M, R6P, S7D, S7I, S7N, S7P, S9H, S9P, T10L, T10P, T10S, T11L, T11P, Q12R, M13C, M13D, M13F, M13K, M13R, S14V, S15C, S15I, S15K, S15P, S15R, S15T, S15V, S15Y, T16C, P17D, P17I, P17L, P17T, V19G, V19K, V20C, V20G, V20K, V20L, V20M, V20P, V20Q, V20R, V20W, Y21C, Y21P, Y21R, Y21T, S22E, S22G, S22N, S22T, S22W, S23C, S23L, S23M, S23R, A24F, A24L, A24R, A24T, A24W, V25D, V25K, V25M, V25Q, V25S, D26C, D26I, D26L, S27A, S27C, S27F, S27G, S27H, S27Y, K28C, K28L, K28V, Q29G, Q29L, Q29M, Q29R, Q29V, Q29W, N30A, N30M, N30V, R31E, R31G, R31I, R31M, R31V, T32S, S33C, S33N, S33Q, S33R, D34C, D34E, D34G, D34H, D34L, D34S, D34W, D34Y, F35C, F35E, F35K, F35N, D36Q, N38S, W39G, W39S, K40C, K40D, K40F, K40G, K40I, K40N, K40W, F41A, F41C, F41G, F41I, F41Q, M42E, M42N, M42T, L43A, L43C, L43I, L43S, L43T, L43V, S44C, D45A, D45P, V47K, V47R, A49D, A49H, A49R, A49S, A49T, A49V, D51G, D51I, D51K, D51P, D51V, A53C, A53R, A53S, A53V, A53W, D55C, D55F, D55G, D55H, D55M, D55P, D55S, 557A, S57C, S57E, S57G, A58D, A58G, A58Q, A58T, W59I, W59K, W59P, W59V, Q60K, Q60M, Q60R, Q60S, Q60Y, Q61P, V62N, V62S, V62T, V62W, D63G, L64E, L64G, H66L, H66R, H66Y, Y68P, I70A, I70K, T71C, T71K, T71Q, K73D, Y74K, S75G, S75L, S75Q, S75R, S75V, Q76G, Q76I, Q76K, Q76V, S77C, S77D, S77E, S77F, S77G, S77H, S77K, S77L, S77M, S77R, S77T, S77V, N78C, N78E, N78K, N78Q, N78R, N78S, E79H, E79Q, E79S, E79T, A80K, E81A, E81Q, A83T, L85A, L85F, L85N, L85S, L85V, L85W, P86G, P86N, P86Q, P86R, P86V, P86W, P86Y, G87D, G87N, G87Q, G88F, G88Q, G88S, T89H, T89K, T89M, T89Y, G90A, G90L, G90S, G90T, G90V, W91E, W91L, W91P, W91Q, W91R, W91Y, Y92F, Y92H, Y92I, Y92M, Y92N, Y92S, Y92T, Y92V, R93A, R93D, R93F, R93H, R93I, R93L, R93N, R93T, R93V, R93Y, K94A, K94C, K94G, K94S, K94T, K94V, S95A, S95C, S95D, S95G, S95I, S95Q, S95R, F96A, F96C, F96I, F96K, F96M, F96P, F96S, F96V, F96W, T97F, T97V, I98C, I98H, I98W, R100T, D101A, D101P, D101V, L102P, R106V, R106W, I107F, I107G, I107S, A108E, A108S, I109M, N110A, N110S, N110T, N110V, N110W, F111A, F111L, F111Q, D112F, D112T, G113S, V114F, V114R, Y115E, M116C, N117W, A118K, A118P, A118Y, T119A, V120A, V120K, W121D, W121R, W121V, W121Y, F122A, F122S, F122Y, N123P, G124E, G124M, G124Q, G124R, V125E, V125I, G128D, T129E, H130A, H130C, H130S, H130T, Y132C, Y132E, P136R, P136Y, F137F, F137L, S138A, S138L, S138R, F139Q, D140V, L141G, T142S, T142V, K146A, G148T, G149M, G149Q, G149Y, E150C, E150G, E150L, E150R, I153A, V154I, V154K, V154L, V155F, V157L, V157P, V157S, E158G, E158H, E158V, N159H, N159S, N159T, L161K, L161M, L161S, L161W, P162N, P162T, P162W, S164A, R165H, W166S, Y167A, Y167C, G169D, S170L, S170Q, G171C, G171I, I172K, I172P, Y173H, Y173M, Y173W, R174E, R174K, V176E, V176K, V176T, T177K, L178I, L178Q, L178W, T179A, T179C, T179D, T179I, T179K, T179N, T179P, T179S, V180A, V180D, V180G, T181A, T181F, D182F, G183W, V184F, V184P, V184R, V184S, V184W, H185G, H185L, V186E, V186N, G187D, G187H, N188E, N188R, N188V, N189E, G190C, G190F, I193N, I193Q, K194I, T195S, T195W, P196A, P196I, S197C, S197F, S197L, L198R, L198V, A199E, A199K, A199P, Q201E, N202D, N202L, N202Q, N202R, N202S, N202T, N202W, G203C, G203K, G203S, G203V, G203W, G203Y, G204A, G204K, G204Y, N205E, N205G, N205H, N205L, V206I, V206K, V206S, T207A, T207C, T207G, T207I, T207K, T207Q, M208S, N209D, N209K, N209V, L210G, L210I, L210Q, L210V, T211A, T211F, T211Q, T211R, T212E, T212G, T212H, T212L, T212S, K213C, K213D, K213F, K213L, K213T, K213Y, V214A, V214C, V214W, A215D, A215E, A215I, A215K, A215L, A215Q, A215R, A215V, D217F, D217L, D217M, D217T, T218G, K219F, K219H, K219M, A220C, A220G, A220L, A220V, A221E, A221L, A221R, A222D, A222I, A222L, A222P, A222R, A222W, N223E, N223F, N223K, N223L, N223S, N223T, L226M, L226Q, Q228N, Q228R, T229A, T229C, T229D, T229G, T229M, T229N, T229Q, T229R, T229V, V230L, V230M, V230R, V230S, F231E, F231G, F231I, F231L, F231V, F231W, F231Y, P232G, P232M, P232S, K233C, K233E, K233F, K233L, K233P, K233R, G234A, G234C, G234D, G234E, G234L, G234Q, G234R, G234V, G234Y, G235H, G235I, G235K, G235M, G235Q, G235T, G235W, G235Y, K236A, K236D, K236L, K236M, K236P, K236R, K236S, K236W, K236Y, T237D, T237K, T237R, D238A, D238E, D238F, D238G, D238M, D238P, D238R, A239E, A239G, A239I, A239T, A240C, A240L, A240P, A240T, A240Y, I241T, G242K, G242L, G242M, G242P, G242Y, T243I, T243M, T243R, V244E, V244R, T245E, T245G, T245Q, T245R, T246G, T246K, A247E, A247K, A247P, A247R, A247S, A247V, A247W, S248A, S248E, S248L, S248Q, S248T, K249A, K249D, K249G, K249H, K249L, K249N, K249P, K249Q, K249V, K249Y, S250H, I251L, I251W, I251Y, A252F, A252W, A252Y, G254D, G254F, G254I, G254L, G254M, G254Q, G254R, G254W, A255K, A255S, A255Y, S256A, S256C, S256K, S256M, S256N, S256R, S256W, S256Y, A257D, A257I, A257N, A257V, D258A, D258L, D258W, V259E, V259T, T260D, T260G, S261D, S261H, S261I, S261W, T262D, T262W, T264F, T264M, T264Q, T264Y, A265I, A265S, A266D, A266G, A266K, A266Q, S267A, S267M, S267N, S267P, S267R, S267V, P268F, P268G, P268R, P268W, P268Y, K269V, K269Y, L270D, L270N, S272G, S272T, S272W, I273L, I273R, N275W, N277F, N277R, L278H, L278I, L278K, L278M, L278Q, L278R, L278V, Y279W, T280A, T280E, T280F, T280Q, V281I, V281Q, R282E, R282F, R282H, R282I, R282K, R282N, R282S, R282V, R282W, T283R, T283V, E284A, E284D, E284H, E284L, E284R, E284Y, V285T, L286F, L286N, L286T, L286W, G288S, V291D, V291F, V291P, V291T, V291Y, L292D, L292H, L292V, D293C, D293I, D293S, D293W, T294Q, T294S, Y295F, Y295W, D296F, D296H, D296K, D296R, D296V, T297I, E298I, E298L, E298R, F301C, R302I, R302N, W303A, W303C, W303D, W303F, W303S, T304D, T304E, T304I, T304K, T304P, G305L, G305N, G305P, G305T, G305W, F306K, F306L, D307A, D307E, D307G, D307S, D307W, A308E, A308M, A308Y, T309C, T309D, T309E, T309I, T309S, T309V, S310A, S310H, S310L, S310M, S310N, S310V, G311V, F312H, F312R, L314A, L314C, L314T, L314V, N315S, G316R, G316S, E317K, E317W, K318C, K318N, K320C, K320E, K320F, K320I, K320L, K320R, K320T, K320V, K320W, L321M, K322F, K322I, K322P, K322S, V324T, S325D, S325G, S325T, M326E, M326G, M326T, M326Y, H328C, H328F, H328G, H328L, H328M, H328R, H328T, D329S, G331V, A335C, A335G, A335L, A337E, A337G, A337L, N338P, R340A, R340C, R340L, A341M, A341S, I342G, I342K, I342P, E343N, E343T, E343Y, R344G, Q345F, Q345G, Q345K, Q345N, Q345S, V346A, V346C, V346I, V346S, E347A, E347C, E347F, E347I, E347R, I348D, I348M, I348Q, I348R, L349A, L349Q, L349S, Q350G, Q350N, K351V, M352G, M352T, M352W, G353K, V354E, V354S, V354W, N355M, N355W, I357T, T359E, T359L, T360V, N362S, N362T, P363A, P363D, P363I, P363L, P363M, P363S, P363V, A364C, A364E, A364F, A364G, A364I, A364M, A364P, A364V, A365C, A365E, A365I, A365P, A365V, A365W, K366A, K366D, K366L, K366M, K366P, K366S, K366V, A367Q, L368A, L368E, L368Q, L368S, L368Y, I369A, I369D, I369E, I369G, I369K, I369M, I369R, I369V, I369W, D370L, D370Q, D370S, V371D, V371F, V371L, V371Q, V371S, C372P, N373G, N373L, E374R, K375D, K375S, G376A, G376S, V377A, V377M, V377T, V379A, V379N, V380P, E381A, E381G, E381Q, E381T, V383A, V383K, V383L, M386G, M386N, M386S, M386W, W387H, W387L, N388A, N388E, N388L, N388R, R389A, R389C, R389E, R389N, R389Q, R389S, R389T, S390C, S390D, S390G, S390P, S390Q, S390T, S390V, K391E, N392D, G393A, G393E, G393N, G393R, G393S, G393V, N394L, T395C, T395F, T395H, T395M, T395N, T395S, T395W, E396K, E396L, E396M, E396V, E396W, Y398M, Y398N, G399S, K400A, K400C, K400N, K400P, K400Q, K400S, K400T, K400V, W401F, W401H, W401K, W401L, F402W, F402Y, G403A, G403D, G403K, G403P, G403Q, G403S, G403V, G403Y, Q404F, Q404H, Q404L, Q404M, Q404P, Q404R, Q404S, Q404V, A405C, A405E, A405H, A405K, A405P, A405R, I406C, I406D, I406N, A407C, A407G, A407Q, A407T, G408I, G408M, G408N, G408W, D409N, N410R, N410Y, A411E, A411R, A411S, A411V, L413I, L413P, L413T, G414A, G414C, G414M, G414N, G414R, G415Q, G415R, D416I, D416R, D416Y, K417C, K417F, K417G, K417R, K417T, D418P, D418R, E419M, E419R, E419W, T420E, T420F, T420G, T420K, T420R, T420V, W421L, W421Q, A422P, A422T, K423D, F424C, F424L, F424N, L426C, L426M, L426Q, T427F, T427G, T427I, T427M, T427N, T427Q, T427S, T427W, S428F, S428K, T429D, I430C, I430L, I430M, I430Q, I430S, I430T, N431D, N431E, N431M, N431Y, R432A, R432E, R432N, R432Q, R432Y, D433G, D433I, D433P, D433Q, D433W, R434N, R434S, R434V, N435E, N435F, N435K, N435L, N435N, N435V, N435W, A436G, A436L, P437A, P437Q, P437R, P437V, V439C, V439E, V439G, V439I, V439K, V439T, V439Y, I440F, I440K, I440R, I440W, M441A, M441E, M441Q, W442E, W442G, W442P, W442R, S443C, S443G, S443M, S443Q, S443Y, L444D, L444E, L444F, L444G, L444K, L444Q, L444V, L444W, G445A, G445C, G445V, N446D, N446T, M448A, M448C, M448D, M448I, M448L, M448P, M448Q, M448S, M448V, M449D, M449E, M449T, M449W, M449Y, E450F, E450S, E450T, E450V, E450W, G451C, G451F, G451L, G451P, G451V, G451W, I452G, I452K, I452L, I452M, I452Q, I452S, I452V, S453F, S453H, S453L, S453N, S453Q, G454L, G454W, S455E, S455K, S455M, S455P, S455R, S455W, V456D, V456E, V456F, V456K, V456L, S457H, S457K, S457P, S457Q, S457T, S457V, G458A, G458P, G458S, G458V, G458W, F459C, F459N, F459R, F459S, P460Y, A461D, A461G, A461M, A461N, A461Y, T462C, T462E, T462F, T462L, S463K, S463Q, S463T, S463V, A464M, A464P, A464V, A464W, K465F, K465L, K465V, K465Y, L466A, L466E, L466F, L466G, L466M, L466P, L466Q, L466S, L466V, L466Y, V467D, V467E, V467G, V467T, V467W, V468D, A468E, A468F, A468K, A468L, A468V, A468W, W469A, W469G, W469M, T470M, K471F, K471Q, K471W, A472G, A472Y, D474R, D474W, S475E, S475F, R477L, P478G, P478L, P478V, M479G, M479I, M479R, M479W, T480C, T480G, K485E, K485R, K487A, K487F, K487G, K487N, K487S, K487W, A488C, A488G, A488H, A488N, A488S, N491A, N491W, E492A, E492W, S493E, S493G, S493H, S493L, S493M, S493Q, N494M, N494R, N494V, T495R, T495V, T495W, M496F, G497D, D498A, D498C, D498M, D498S, N499R, N499T, N499Y, L500A, L500N, T501G, T501M, A502L, N503A, N503E, N503M, G504H, G504K, G504P, G505A, G505D, G505E, G505H, G505L, G505N, G505R, G505S, V506C, V506D, V506E, V506G, V506L, V506P, V506R, V506S, V507A, V507G, V507L, V507N, V507R, V507S, G508C, G508E, T509A, T509I, T509K, T509M, T509V, T509Y, N510A, N510F, N510I, N510Q, Y511A, S512C, S512F, S512G, S512I, S512M, S512Q, S512T, S512V, S512Y, D513K, D513L, D513P, D513R, G514F, G514L, A515C, A515D, A515E, A515G, A515K, A515R, N516E, N516K, N516G, N516I, N516Q, N516T, N516V, Y517G, Y517N, D518Q, D518V, K519C, K519E, K519G, K519I, K519Q, I520A, I520C, I520G, I520H, I520M, I520N, I520Q, I520S, I520T, I520W, R521N, R521V, T522G, T522N, H524R, H524V, P525G, P525T, S526G, W527A, W527E, W527G, W527H, W527N, W527R, W527S, A528C, A528E, A528I, I529G, Y530A, Y530M, G531E, G531S, G531T, T534A, T534I, A535I, A535M, A537D, A537M, A537P, A537S, I538M, N539W, S540E, S540G, G542Q, I543V, N545Q, N545S, R546C, R546L, R546P, R546S, T547A, T547D, T547N, T547S, T548E, T548F, T548K, T548L, T548P, G549D, G549F, G549P, G549W, G550S, A551I, A551Q, S553F, S553N, S553P, S554N, S554V, D555S, K556A, K556R, K556W, Q557R, L558E, L558H, L558P, T559Q, T559Y, Y561R, N563S, S564A, S564C, S564F, S564W, A565C, A565D, A565E, A565F, A565G, A565I, A565L, A565R, A565S, A565T, G567Q, G567V, A570G, A570K, A570M, A570W, A572S, A572W, S573G, S573K, S574K, S574Q, S574W, A575D, A575V, W576F, W576V, W576Y, Y577G, Y577L, D578M, D578N, V579E, V579G, V579T, V580A, V580D, V580K, V580L, V580S, Q581G, Q581P, Q581S, Q581Y, R582A, R582G, R582L, R582Y, D583W, F584E, F584W, V585I, V585M, A586D, A586H, A586K, A586V, G587A, G587C, T588C, T588D, T588I, T588L, T588M, Y589I, Y589Q, Y589V, Y589W, V590A, V590H, W591F, T592C, T592L, T592S, G593I, F594L, D595E, D595Q, D595S, L597D, L597E, G598N, P600A, P600E, P600G, P600S, N604E, T606S, G607Q, G607S, S608T, S608V, G609A, G609L, G609N, G609R, A610F, A610M, A610T, V611K, G612N, G612T, W614G, W614P, P615L, S616W, N619A, N619I, N619L, S620G, I624A, V625E, V625M, V625Y, T627K, T627Q, A628D, A628N, G629T, F630C, F630D, F630G, F630Y, P631A, P631D, P631V, P631Y, K632D, K632G, K632T, T634A, T634E, T634V, Y635R, F637G, F637I, F637S, F637T, F637V, Y638A, Y638W, Q639R, D644C, D644Y, D645S, V646R, H647G, T648C, H650E, H650R, I651T, L652C, L652W, P653Q, A654K, A654M, A654R, W655R, N656V, E657R, V659N, A661E, A661H, A661K, A661M, A661Q, A661W, K662S, K662V, K662Y, N667L, N667R, P669L, P669T, P669W, V670C, Y673E, Y673G, Y673R, Y673S, T674C, T674M, D675A, D675P, D675Q, A676C, A676E, A676P, A677E, A677G, K678A, K678T, V679G, V679Q, V679S, V679Y, K680H, K680I, K680N, K680V, L681E, L681F, L681S, L681T, Y682E, F683M, F683Q, T684G, T684V, K686M, G687A, G687P, G687Q, G687R, S688E, S688K, S688L, S688T, T689D, T689G, T689P, T689W, E690D, E690V, K691P, K691R, R692G, R692H, R692I, R692S, R692T, I694G, I694W, G695C, G695L, G695R, G695W, E696A, E696R, K697A, K697E, K697G, K697R, S698E, S698I, S698L, S698M, S698T, T700C, K701A, K701D, K701G, K701L, K701M, K701S, T704M, T704Y, A705C, A705E, A705N, A705R, A705W, A706C, A706T, A706Y, Y708C, Y708F, Y708T, T709M, Y710D, Y710G, Y710N, Y710T, Y710V, Y710W, Q711A, Q711L, Q711M, Q711Y, V712M, V712P, V712Q, Y713G, E714H, E714K, E714V, G715K, A716C, A716L, A716R, A716V, D717C, D717G, D717S, K718A, K718L, K718Q, K718T, K718Y, D719E, D719T, D719V, S720A, T721H, T721L, T721N, T721S, T721V, T721W, A722T, H723G, H723P, M726D, M726V, Y727L, L728S, T729M, N731E, N731Q, N731S, V732R, V732W, P733R, P733W, W734G, W734V, A735G, A735N, A735S, G737F, T738S, I739K, S740D, S740F, A741I, A741P, A741S, E742Q, Y744R, D745C, D745F, D745N, N747F, N747R, L750S, I751C, P752A, P752C, P752Y, G754H, G754P, T756N, T756S, E757A, N759S, N759V, A760N, G766M, A769F, A769G, A769I, A769N, A769V, A769Y, K770H, L771A, L771I, K772A, K772C, K772P, K772V, K772W, A773C, A773H, A773M, A773R, A773S, A773V, D774A, D774K, A775L, A775W, D776I, D776L, D776S, D776V, R777D, R777E, R777G, R777H, R777P, R777S, K778A, K778F, K778G, K778L, K778N, I780V, T781A, T781C, T781F, T781G, T781M, T781P, T781R, T781Y, A782E, A782K, A782P, A782Q, A782Y, D783A, D783C, D783E, D783R, G784A, G784L, G784S, G784T, K785C, K785S, K785W, K785Y, D786V, L787P, L787T, S788A, S788G, S788I, Y789V, I790A, I790C, I790F, I790R, E791S, E791T, V792G, V792S, D793H, D793K, V794C, V794T, V794W, T795P, D796Q, N798I, G799K, G799L, G799M, G799Q, H800A, H800L, H800V, I801C, V802I, V802S, V802Y, P803F, P803K, P803S, P803Y, D804G, D804K, D804S, A805F, A806I, A806Q, N807Q, N807W, R808C, R808F, R808G, R808I, R808N, R808Q, V809C, V809L, V809M, T810P, T810Q, T810Y, F811L, F811Y, D812Q, V813T, V813W, K814G, K814H, K814L, K814P, G815A, G815M, G815P, G815V, A816C, A816D, A816F, A816V, A816W, G817I, G817N, D818E, K818F, K818L, K818Q, K818W, K818Y, L819F, V820C, V820K, V820R, G821E, G821F, G821I, G821N, G821V, V822A, V822D, V822E, G825A, S826F, S826G, S826L, S826R, S827Q, P828C, P828Y, D829S, H830E, H830G, H830M, H830P, H830R, H830V, D831F, D831I, D831P, D831R, D831V, S832G, S832L, S832M, S832R, Y833E, Y833I, Y833K, Y833P, Y833V, Q834F, Q834M, A835D, A835E, A835H, A835K, A835W, D836C, D836E, D836H, D836Q, D836S, D836T, D836V, D836W, D836Y, N837D, N837G, N837H, N837L, R838G, R838M, R838N, R838W, K839A, K839D, K839E, A840G, A840I, A840P, A840V, F841C, F841W, S842M, G843C, K844A, K844G, V845N, V845W, L846I, L846M, V849A, V849L, V849S, Q850C, Q850G, Q850Y, K853N, K853P, K853Q, E854C, E854I, E857P, I858D, I858E, I858K, I858M, I858P, I858Q, I858Y, T859V, V860T, T861F, T861I, T861W, A862V, K863F, K863I, K863N, K863W, A864L, D865A, D865G, G866H, G866R, L867W, S870E, S870M, S870R, S870T, T871P, V872C, V872G, K873G, K873Y, I874G, T877A, P880S, G881W, T882A, T882R, S883L, T884A, E885V, K886E, K886L, K886V, K886W, T887A, T887D, T887F, T887G, T887N, T887V, V888A, V888D, R889G, Y892D, Y892E, Y892R, Y893E, S894D, N896M, Y897V, V899G, K900E, T901G, T901Q, T901R, T901V, T901Y, G902A, G902F, G902L, G902P, G902Q, G902R, G902S, G902W, N903D, N903I, K904D, K904E, K904M, K904N, K904R, K904S, K904V, P905C, P905R, P905W, P905Y, I906S, I906W, I906Y, L907F, L907S, P908D, P908G, P908I, P908L, D910W, E912T, V913Q, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, T919D, T919Q, T919W, T919Y, S920E, S920W, D921Q, D921V, R922A, R922G, R922M, R922W, Q923A, Q923V, N924L, V925A, V925C, V925K, V925S, T926G, T926R, T926S, W927C, W927G, W927P, D928A, D928Q, A929C, A929P, V930A, V930I, S931G, S931R, D932F, D932S, D932T, D932V, D933I, D933R, Q934S, Q934V, I935A, I935C, I935E, I935P, I935W, A936I, A936Q, A936Y, K937G, K937I, K937M, K937P, K937Q, K937R, A938C, A938T, G939D, S940C, S940E, S940R, S940T, S940V, S940W, F941C, F941W, S942K, S942L, S942V, V943A, V943H, V943R, A944D, A944H, A944P, A944R, G945T, T946A, T946G, T946P, T946V, T946W, V947G, V947L, V947M, V947P, V947R, V947T, A948C, A948I, A948R, A948W, G949A, Q950D, Q950G, K951D, K951Q, K951S, K951W, K951Y, I952H, S953F, S953M, S953R, S953W, V954D, V954Q, V954T, R955C, R955W, V956D, V956Q, T957S, M958D, M958I, I959V, I959Y, D960H, D960L, D960S, E961D, E961F, E961S, E961T, I962A, I962C, I962K, I962N, L965C, L965G, L965K, L965M, L965P, L965V, L965Y, L966A, L966G, L966H, L966N, L966P, L966T, N967D, N967M, N967P, N967S, N967T, Y968G, Y968L, Y968Q, Y968V, S969C, S969D, S969H, S969I, S969L, S969M, S969Q, S969Y, A970I, S971H, S971V, S971W, P973C, P973D, P973N, P973R, P973W, V974E, V974T, V974Y, G975Q, T976F, T976G, T976K, T976P, P977C, P977T, P977Y, A978F, A978M, A978N, A978R, V979R, L980A, L980H, L980I, L980N, L980Q, L980T, P981M, G982P, G982Q, P985E, P985L, P985W, A986I, A986L, A986N, A986W, V987A, V987F, V987K, L988E, L988G, L988S, P989A, P989M, D990W, G991F, G991H, G991Y, T992M, T994S, S995L, S995V, A996Q, A996V, N997A, N997E, N997K, N997L, N997Y, F998M, F998W, A999G, A999M, A999R, A999S, V1000C, V1000L, V1000M, V1000N, D1001G, D1001K, D1001L, D1001T, D1001V, W1002A, W1002D, W1002E, W1002H, W1002N, W1002P, W1002Q, T1003L, T1003P, T1003V, K1004F, K1004H, K1004P, K1004R, K1004V, P1005I, P1005Y, A1006I, A1006I, A1006S, D1007L, D1007P, D1007V, V1009G, Y1010T, N1011A, N1011T, T1012Q, A1013Q, A1013V, G1014I, G1014L, T1015G, V1016C, V1016D, V1018K, T1021F, T1021G, T1021V, A1022H, A1022L, T1023D, V1024G, V1024H, V1024K, V1024N, V1024R, V1024S, V1024W, G1026L, G1026R, G1026S, G1026V, K1027C, K1027N, F1029K, F1029P, F1029V, K1030D, K1030W, V1031H, V1031K, T1034H, I1035D, R1036G, R1036L, R1036T, V1037F, Q1041P, V1042N, T1043F, I1044A, S1046M, V1048C, V1048F, V1048N, V1048G, V1048M, V1048Q, G1050S, N1051E, N1051K, A1052K, L1053A, L1053W, L1055R, Q1057E, Q1057R, N1058R, N1058S, N1058V, I1059W, P1060G, P1060N, P1060T, A1061G, D1062A, D1062L, D1062M, K1063D, Q1064M, Q1064R, S1065A, S1065C, S1065E, D1066A, D1066G, D1066M, D1066V, D1066W, T1067M, L1068C, L1068P, L1068Q, A1070P, I1071R, I1071W, K1072E, K1072G, K1072Q, K1072S, D1073L, D1073P, G1074I, G1074L, G1074R, S1075C, S1075L, T1076H, T1076Q, T1076S, V1078L, T1082E, T1082F, G1083E, G1083F, G1083L, G1083S, G1084V, G1084Y, G1085S, A1086H, A1086Q, N1087R, N1087W, P1088E, P1088R, S1089C, S1089G, S1089K, S1089Q, S1089R, A1090G, W1091A, W1091E, W1091G, W1091H, W1091T, W1091V, W1091Y, T1092G, T1092Q, T1092S, T1092V, N1093A, N1093P, N1093Q, N1093T, N1093V, W1094D, W1094E, W1094P, A1095W, Y1096A, Y1096D, S1097L, S1097T, S1097W, K1098D, K1098F, A1099C, A1099D, A1099S, A1099V, G1100H, G1100M, G1100T, H1101V, N1102E, N1102H, N1102K, T1103E, A1104R, E1105L, I1106T, T1107R, T1107S, F1108D, F1108L, F1108T, E1109A, E1109D, E1109L, E1109W, A1111G, E1113D, E1113P, E1113V, Q1114E, Q1114R, Q1114S, Q1114T, Q1114V, Q1115A, Q1115K, Q1115L, Q1115P, L1116G, L1116K, L1116W, G1117E, G1117I, G1117M, G1117R, G1117S, G1117T, G1117V, G1117W, Q1118W, I1119E, I1119G, I1119N, I1119S, V1120T, M1121G, M1121K, M1121V, Y1122K, Y1122R, Y1122V, F1123R, F1123T, F1124V, F1124W, R1125D, R1125E, R1125K, R1125V, R1125W, D1126H, D1126L, S1127F, S1127I, S1127K, S1127Q, S1127W, N1128A, N1128R, N1128S, N1128W, A1129E, A1129L, A1129Q, A1129V, V1130A, V1130G, V1130R, V1130S, R1131A, R1131S, F1132E, P1133D, P1133G, P1133R, D1134G, D1134L, A1135L, A1135S, A1135W, A1135Y, G1136A, G1136E, G1136P, K1137C, K1137L, K1137P, K1137Q, K1137R, K1137S, T1138R, I1140C, I1140G, I1140L, I1140P, Q1141K, Q1141P, Q1141W, I1142Y, S1143G, A1144C, A1144N, A1144P, A1144S, A1144T, A1144V, A1144W, D1145E, D1145R, D1145T, G1146D, G1146L, G1146V, K1147T, K1147V, N1148P, W1149C, W1149G, W1149I, W1149N, W1149Q, W1149S, W1149V, T1150K, D1151R, D1151W, L1152A, L1152E, L1152Q, L1152W, A1153G, A1154C, A1154R, T1155L, I1158R, I1158W, A1159I, A1159R, A1159V, A1160Q, Q1161A, Q1161P, Q1161S, E1162A, E1162C, E1162I, E1162Q, E1162Y, E1165L, E1165S, V1167R, K1168Q, K1168W, P1169S, Y1170E, Y1170K, T1171A, T1171G, Y1172E, YI172K, D1173A, D1173F, D1173K, D1173L, F1174P, F1174T, F1174V, F1174W, A1175N, A1175Q, A1175S, A1175V, A1175Y, V1177N, V1177T, G1178M, G1178Q, G1178T, A1179L, A1179W, T1180A, T1180G, T1180I, T1180M, T1180Q, T1180Y, V1182M, K1183E, V1184C, V1184E, V1184K, V1184L, V1184P, V1184Q, V1184Y, V1186S, N1188W, A1189C, A1189K, A1189T, A1189V, D1190R, D1190T, T1191E, T1191L, T1192H, V1197A, V1198E, C1199T, A1200G, A1200W, L1202A, T1203R, E1204D, I1205V, K1208R, K1208V, K1208W, T1209A, T1209C, T1209E, T1209K, T1209N, T1209Q, A1210D, A1210E, A1210G, A1210K, A1210L, A1210R, A1210T, A1210W, T1211D, T1211G, T1211K, T1211P, T1211R, T1211S, K1213T, F1214A, F1214E, F1214K, F1214L, F1214P, F1214S, F1214V, V1215D, V1215L, V1215Q, T1216L, T1216P, T1216Q, N1217A, N1217F, N1217P, N1217R, N1217S, N1217T, T1218A, T1218C, T1218E, T1218G, T1218S, T1218W, S1219A, S1219F, S1219I, S1219R, A1220L, A1220P, A1220R, A1221D, A1221R, A1221V, A1221W, L1222A, L1222E, L1222F, L1222V, L1222W, S1223F, S1223K, S1223L, S1223V, S1224A, S1224D, S1224G, S1224P, S1224W, L1225C, L1225E, L1225F, L1225K, L1225W, T1226A, T1226G, T1226P, T1226S, T1226V, V1227A, V1227D, V1227L, V1227P, V1227S, N1228D, N1228F, N1228T, G1229V, T1230H, T1230I, T1230K, T1230S, T1230W, K1231F, K1231L, K1231M, K1231P, V1232K, V1232R, S1233P, S1233W, D1234K, D1234R, S1235E, S1235G, S1235R, S1235W, V1236A, V1236G, V1236I, V1236P, V1236Q, L1237D, L1237E, A1238E, A1238L, A1238N, A1238P, A1238R, A1239D, A1239P, A1239R, G1240D, G1240N, G1240W, S1241D, Y1242E, Y1242R, N1243M, N1243P, N1243T, N1243V, N1243W, T1244A, T1244E, T1244Q, T1244W, A1246M, A1246N, A1246P, A1246Q, A1246R, I1247G, I1247Q, I1247R, I1247S, I1247W, I1248G, I1248L, I1248R, I1248S, A1249G, A1249H, A1249I, A1249R, A1249T, A1249V, D1250I, D1250K, D1250S, D1250T, D1250W, D1250Y, V1251T, V1251W, K1252D, K1252V, K1252W, E1254V, G1255H, G1255M, E1256M, E1256N, E1256V, E1256W, G1257F, G1257L, G1257Q, N1258H, N1258S, A1259K, V1261I, V1261L, T1262A, T1262Q, T1262R, V1263E, V1263R, V1263T, V1263W, L1264H, P1265L, P1265R, P1265W, A1266P, A1266V, H1267E, N1269A, N1269K, N1269R, N1269S, V1270D, I1271H, R1272M, R1272V, V1273R, I1274F, I1274R, T1275L, T1275W, S1277L, S1277T, S1277W, E1278Q, D1279G, D1279I, D1279R, D1279T, D1279W, H1280E, H1280G, V1281I, V1281W, T1282D, R1283A, R1283D, R1283E, R1283W, K1284G, T1285F, F1286A, F1286E, F1286P, F1286S, T1287C, T1287R, T1287S, T1287W, I1288A, I1288D, I1288G, I1288K, N1289A, N1289T, L1290A, L1290R, G1291P, G1291V, G1291Y, T1292Y, E1293K, E1293L, E1293S, E1293V, Q1294E, Q1294P, Q1294W, E1295K, F1296A, P1297F, E1302R, E1302S, R1303S, D1304A or D1304V.

85. The lactase variant of the preceding embodiment, wherein the variant has a decreased or an increased galactose inhibition, preferably measured as a galactose inhibition improvement factor (GI-IF) of at least 1.2 or at most 0.8, compared to the lactase of SEQ ID NO: 1.

86. The lactase variant of embodiment 1 which comprises one or more of the following substitutions, wherein each position corresponds to a position in SEQ ID NO: 1: V1D, V1F, V1H, V1L, E2D, E2Q, E2V, D3I, D3V, TSS, S7N, S7P, S9H, T10L, T10S, M13C, M13D, M13K, M13R, S14V, S15C, S15I, S15K, S15P, S15R, S15T, S15V, T16C, P17I, V19K, V20C, V20G, V20L, V20M, V20P, V20Q, V20R, Y21C, Y21P, Y21R, Y21T, S22N, S22T, S22W, A24F, A24L, A24R, A24T, A24W, V25D, V25M, V25Q, V25S, D26C, D26I, D26L, S27A, S27C, S27G, S27H, S27Y, K28C, K28L, K28V, Q29G, Q29L, Q29M, Q29R, N30M, N30V, R31E, R31M, R31V, T32S, D34G, D34H, F35C, D36Q, N38S, W39G, W39S, K40C, K40F, K40G, K40I, K40W, F41A, F41C, M42T, L43A, L43I, L43S, D45P, V47K, V47R, A49D, A49H, A49T, D51G, D51I, D51K, D55C, D55F, D55G, D55H, D55M, D55P, D55S, 557A, S57C, S57E, S57G, A58Q, A58T, W59I, W59K, W59P, W59V, Q60M, Q60R, Q60S, Q60Y, Q61P, V62N, V62T, V62W, D63G, L64E, L64G, H66R, I70K, K73D, Y74K, S75G, S75L, S75Q, S75R, S75V, Q76G, Q76I, S77C, S77D, S77E, S77G, S77H, S77K, S77L, S77M, S77R, S77T, S77V, N78C, N78S, E79H, E79S, E79T, A83T, L85A, L85F, L85N, L85S, L85V, L85W, P86G, P86Q, P86R, P86V, P86W, P86Y, G87D, G87N, G88F, T89M, T89Y, G90A, G90L, G90S, G90T, W91E, W91L, W91P, W91Q, W91Y, Y92F, Y92H, Y92I, Y92M, Y92N, Y92S, Y92T, Y92V, R93A, R93D, R93F, R93H, R93I, R93L, R93N, R93T, R93V, R93Y, K94A, K94C, K94G, K94S, K94T, K94V, S95A, S95C, S95D, S95G, S95I, S95Q, S95R, F96A, F96C, F96I, F96K, F96M, F96P, F96V, F96W, T97F, T97V, I98C, I98H, I98W, R100T, D101A, D101P, D101V, L102P, R106V, R106W, I107F, I107S, A108E, I109M, N110A, N110S, N110T, N110V, N110W, F111A, F111L, F111Q, V114F, V114R, Y115E, M116C, A118P, V120A, V120K, W121D, W121R, W121V, G124M, H130A, H130C, H130S, H130T, Y132E, F137C, F137L, S138A, D140V, L141G, T142S, G149E, G149M, G149Y, E150C, E150G, E150L, E150R, V154I, V154K, V154L, V157P, V157S, E158H, E158V, N159H, N159T, L161K, L161M, L161S, L161W, P162N, P162T, P162W, S164A, R165H, W166S, Y167A, Y167C, S170Q, G171C, I172K, I172P, Y173H, Y173M, R174E, R174K, V176E, V176K, V176T, T177K, L178I, L178Q, L178W, T179A, T179C, T179D, T179I, T179K, T179N, T179P, T179S, V180A, V180D, V180G, T181A, T181F, G183W, V184F, V184P, V184S, V184W, H185G, H185R, V186E, V186N, G187D, G187H, N188R, N188V, G190F, I193N, I193Q, K194I, T195W, P196A, P196I, S197C, S197E, S197L, A199E, A199P, Q201E, N202Q, N202S, N202W, A215D, D217F, D217L, D217M, T218G, A220G, A222R, N223S, L226Q, Q228N, Q228R, F231L, G234V, G235K, K236M, K236P, T237D, G242K, G242L, G242M, G242P, T243I, A247K, I251W, I251Y, A252W, A252Y, A257D, A257N, A257V, S261H, A266D, S267V, P268F, P268R, L270N, S272T, S272W, N277F, V281Q, R282W, L286W, V291P, L292D, L292V, D293C, D293I, D293W, T294Q, T294S, Y295F, D296F, D296H, D296K, T297I, E298I, E298L, E298R, F301C, R302I, W303A, W303C, W303D, W303F, T304D, T304E, T304I, T304K, T304P, G305L, G305N, G305P, G305T, D307A, D307E, D307S, D307W, T309C, T309D, T309E, T309I, T309V, S310A, S310H, S310L, S310M, S310N, S310V, F312H, L314A, L314V, N315S, G316R, E317W, K318C, K318N, K320E, K320I, K320V, K320W, L321M, K322I, V324T, S325Q, M326T, H328C, H328F, H328G, H328L, H328M, H328R, H328T, G331V, A335C, A335G, A335L, A337E, A337G, A337L, N338P, R340A, R340L, A341M, I342G, I342P, E343N, E343T, E343Y, R344G, Q345F, Q345N, Q345V, V346A, V346I, V346S, E347A, E347I, I348D, I348M, I348Q, I348R, L349A, L349S, Q350G, Q350N, M352T, G353V, V354E, V354S, V354W, I357T, T359E, T359L, T360V, N362S, N362T, P363A, P363D, P363I, P363L, P363M, P363S, P363V, A364C, A364E, A364F, A364G, A364I, A364M, A364P, A364V, A365C, A365I, A365P, A365V, A365W, K366D, K366L, K366M, K366P, K366S, K366V, K367Q, L368A, L368Q, L368S, L368Y, I369A, I369D, I369E, I369G, I369K, I369M, I369V, I369W, D370L, D370Q, V371F, V371L, V371Q, C372P, N373G, N373L, K375D, K375S, G376A, G376S, V377A, V377M, V377T, V379A, V379N, V380P, E381A, E381G, E381Q, E381T, V383A, M386G, M386N, M386S, M386V, W387H, N388E, N388L, R389A, R389C, R389E, R389Q, R389S, R389T, S390C, S390D, S390P, S390T, G393E, G393R, G393V, T395C, T395F, E396K, E396L, E396V, E396W, Y398M, G399S, K400A, K400C, K400N, K400T, K400V, W401F, W401K, F402W, F402Y, G403A, G403D, G403K, G403Q, G403V, G403Y, Q404F, Q404L, Q404M, Q404P, Q404S, Q404V, A405C, A405E, A405K, A405R, A405T, I406C, I406D, I406N, A407C, A407G, A407Q, N410R, N410Y, A411E, A411R, A411S, G414M, G414N, G415Q, K417F, K417R, A422P, L426C, T427D, T427F, T427Q, T427S, T427W, T429D, I430L, I430M, N431M, R432Q, R432Y, D433G, D433I, D433P, D433Q, D433W, R434N, R434V, N435E, N435F, N435L, N435V, A436G, A436L, V439C, V439K, W442E, W442G, S443C, S443G, S443M, S443Q, L444E, L444F, L444V, N446D, M448C, M448L, M449D, M449E, M449T, M449W, M449Y, E450F, E450S, E450T, E450V, E450W, G451C, G451F, G451L, G451P, G451V, G451W, I452K, I452L, I452Q, I452S, I452V, S453H, S453L, S453N, S453Q, G454L, G454W, S455E, S455M, S455P, S455R, V456D, V456E, V456F, V456K, S457H, S457Q, S457T, S457V, G458A, G458P, G458S, F459C, F459R, P460Y, A461G, A461M, T462E, T462L, A464W, A465L, K465V, K465Y, L466G, L466P, V467T, A468D, K471F, K471Q, A472G, A472Y, D474W, S475E, R477L, P478V, M479G, K485E, K485R, K487A, K487F, K487S, K487W, A488C, S493E, S493G, S493H, S493L, S493Q, N494M, N494R, N494V, G497D, N499T, G505D, G505H, G505L, G505R, G505S, V506C, V506E, V506R, V507R, G508C, G508E, T509A, T509I, T509K, T509M, T509V, T509Y, N510A, N510F, N510I, Y511A, S512C, S512F, S512I, S512M, S512Q, S512T, S512V, S512Y, D513P, D513R, A515E, A515G, A515P, N516C, N516E, N516G, N516I, N516Q, N516T, N516V, Y517G, D518Y, K519C, K519E, K519G, K519I, K519Q, I520A, I520C, I520G, I520H, I520M, I520N, I520Q, I520S, I520T, I520W, R521V, H524R, H524V, S526G, W527A, W527E, W527G, W527H, W527N, W527R, W527S, A528E, I529G, A535I, A537M, A537R, A537S, I538M, S540E, G549D, G549P, G549W, S553R, K556L, L558E, L558H, L558P, T559Q, T559Y, S564A, S564C, S564F, S564W, A565C, A565D, A565E, A565F, A565G, A565I, A565L, A565R, A565S, A565T, G567Q, G567V, A570G, A572W, A575D, V580D, Q581Y, R582A, R582G, R582L, D583W, F584W, A586D, Y589I, Y589Q, W591F, T592L, L597D, G598N, P600A, P600E, P600G, P600S, N604E, G607Q, G607S, S608T, G609A, A610T, W614A, N619I, N619L, V625E, V625M, V625Y, T627K, T627Q, A628D, A628N, G629T, F630C, F630Y, P631D, P631Y, K632D, K632G, T634V, F637G, F637I, F637S, F637T, F637V, Q639R, D644Y, D645S, V646R, H647G, T648C, I651T, L652C, L652W, P653Q, A654R, W655R, E657R, A661E, A661H, A661K, A661M, A661Q, A661W, K662S, K662V, K662Y, N667L, N667R, P669L, P669T, P669W, Y673S, T674M, D675A, A676P, D679Q, V679S, K680I, K680N, G687P, S688K, S688L, T689G, T689W, E690D, K691P, K691R, R692G, R692H, R692I, R692S, R692T, I694L, I694W, G695C, G695L, G695R, G695W, E696R, K697A, K697G, K697R, S698E, S698M, K701A, K701D, K701G, K701L, K701M, K701S, A705R, A705W, A706C, A706T, Y708F, Y710T, Y710V, Q711A, A712M, V712P, V712Q, Y713G, E714H, E714K, G715K, A716R, A716T, D717G, D717S, K718A, K718Q, K718T, K718Y, D719E, D719T, D719V, S720A, T721H, T721L, T721N, T721S, T721V, T721W, A722T, A722V, H723G, H723P, M726D, Y727L, L728S, T729M, N731E, N731Q, V732R, P733W, W734G, A735Q, A735R, A735S, G737F, T738S, I739K, S740D, S740F, A741I, A741P, A741S, Y744R, D745C, D745N, N747L, L750S, I751Q, P752C, P752Y, G754H, G754R, T756N, E757A, N759S, N759V, G766M, A769F, A769G, A769I, A769N, A769V, A769Y, K770H, L771A, K772A, K772C, K772P, A772W, A773C, A773M, A773R, D774A, D776V, R777H, R777S, K778F, K778G, K778N, T781A, T781F, T781G, T781P, T781Y, A782Q, A782Y, D783A, K785C, K785S, K785W, K785Y, D786V, Y789V, I790R, E791S, V792S, N798I, G799K, G799L, H800V, V802I, V802S, V802Y, P803S, P803Y, A805F, A806I, A806Q, R808F, R808G, R808I, V809L, V809M, T810P, T810Q, T810Y, F811L, V813W, K814G, K814P, G815M, G815P, A816D, A816W, K818D, K818F, K818L, K818Q, K818W, K818Y, L819F, V820C, V820R, G821I, V822A, V822D, V822E, G825A, S826G, D829S, D831P, S832R, Y833E, Q834M, A835D, A835H, A835K, D836C, D836E, D836Q, D836S, D836T, D836V, D836Y, R838N, K839A, K839D, A840G, A840I, A840P, A840V, K844A, K853P, E854C, E854I, I858D, I858K, I858P, T861F, T861I, T861W, D865A, D865G, G866H, G866R, L867W, S870E, S870M, S870T, V872C, V872G, K873G, K873Y, I874G, T882A, T882R, S883L, E885V, K886L, K886V, K886W, T887A, T887D, T887G, T887N, V888A, R889G, Y892P, Y893E, S894D, Y897V, K900E, T901Q, T901R, T901Y, G902A, G902F, G902P, G902Q, G902R, G902S, G902W, N903D, N903I, K904D, K904E, K904M, K904N, K904R, K904S, K904V, P905C, P905R, P905W, P905Y, I906N, I906W, L907F, L907S, P908D, P908G, P908I, P908L, D910W, E912T, R914A, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, T919D, T919Q, T919W, D921V, R922A, R922M, R922W, Q923A, Q923V, V925C, V925K, T926R, W927P, D928A, D928Q, A929P, V930I, S931R, D933R, Q934S, Q934V, I935A, I935C, I935E, I935P, I935W, A936I, A936Q, A936Y, K937G, K937I, K937M, K937P, K937Q, A938C, A938T, G939D, S940C, S940E, S940R, S940V, F941C, S942K, S942V, V943A, T946A, T946P, T946W, V947G, V947L, V947P, V947R, V947T, A948I, A948W, G949A, K951D, K951S, K951W, K951Y, S953F, S953M, S953R, V954D, V954Q, R955C, R955W, V956D, V956Q, T957C, I959V, I959Y, D960S, E961D, E961F, E961S, E961T, I962A, I962C, I962K, I962N, L965C, L965G, L965K, L965M, L965P, L965V, L965Y, L966A, L966N, N967D, N967M, N967P, N967T, Y968G, Y968L, Y968Q, Y968V, S969C, S969D, S969H, S969I, S969L, S969M, S969Q, S969Y, A970I, S971V, S971W, P973C, P973D, P973N, P973R, P973W, V974E, V974T, V974Y, T976F, T976G, T976K, T976P, P977C, P977T, P977Y, A978F, A978M, A978N, A978R, L980A, L980H, L980I, L980N, L980Q, L980T, P981M, P985L, P985W, A986I, A986L, A986W, V987A, V987F, V987K, P989M, D990W, G991F, G991H, G991Y, T992M, S995L, N997K, F998M, F998W, D1001L, W1002A, W1002D, W1002E, W1002H, W1002N, W1002P, W1002Q, T1003Y, P1005I, P1005Y, A1006C, A1006S, D1007L, D1007P, D1007V, Y1010T, N1011A, N1011T, T1012Q, A1013Q, A1013V, G1014I, V1016D, V1018K, T1021G, A1022H, A1024G, V1024H, V1024K, V1024R, V1024S, V1024W, G1026S, G1026V, F1029K, F1029P, F1029V, K1030D, K1030W, V1031H, V1031K, T1034H, I1035D, R1036G, R1036L, R1036T, Q1041P, V1042N, T1043F, I1044A, S1046M, V1048C, V1048F, V1048G, V1048M, V1048Q, N1051E, N1051K, A1052K, L1053A, L1053W, L1055R, Q1057E, N1058R, N1058S, P1060G, P1060N, A1061G, D1062A, D1062M, Q1064M, Q1064R, S1065A, S1065C, D1066A, D1066G, D1066V, T1067M, L1068P, L1068Q, K1072S, G1074L, G1074R, S1075L, T1076S, T1082E, T1082F, G1083E, G1083F, G1083L, G1084V, G1084Y, G1085S, A1086H, N1087R, P1088E, P1088R, S1089G, S1089K, S1089Q, W1091Y, N1093A, N1093P, N1093Q, W1094D, W1094E, W1094P, A1095W, Y1096D, S1097T, K1098D, K1098F, A1099D, A1099S, A1099V, G1100H, H1101V, N1102H, T1103E, E1105L, E1109A, E1109D, E1109L, E1109W, A1111G, E1113P, E1113V, Q1114E, Q1114R, Q1114S, Q1114T, Q1114V, Q1115A, Q1115K, Q1115L, Q1115P, L1116G, L1116K, L1116W, G1117E, G1117I, G1117M, G1117R, G1117S, G1117T, G1117V, G1117W, Q1118W, I1119E, I1119N, I1119S, M1121G, M1121K, F1123R, F1124V, F1124W, R1125D, R1125K, R1125V, R1125W, S1127I, S1127Q, N1128A, A1129E, V1130A, V1130R, P1133D, P1133G, P1133R, A1135L, A1135W, G1136P, K1137P, K1137R, K1137S, T1138R, I1140C, I1140P, Q1141K, I1142Y, S1143G, A1144N, A1144P, A1144S, A1144T, A1144V, A1144W, D1145E, D1145R, D1145T, G1146V, N1148P, W1149C, W1149G, W1149S, W1149V, T1150K, D1151W, L1152A, L1152E, L1152Q, L1152W, A1153G, A1154R, I1158W, A1159I, Q1161P, Q1161S, E1162A, E1162C, E1162Q, E1165S, V1167R, P1169S, Y1170K, A1175S, G1178M, G1178Q, G1178T, A1179L, A1179W, T1180A, T1180G, T1180I, T1180M, T1180Q, T1180Y, V1182M, K1183E, V1184C, V1184E, V1184K, V1184L, V1184P, V1184Q, V1184Y, V1186S, N1188W, A1189C, A1189K, A1189T, A1189V, D1190R, D1190T, T1191L, V1197A, A1200G, T1203K, E1204G, I1205V, K1208R, K1208V, K1208W, T1209A, T1209C, T1209E, T1209K, T1209N, T1209Q, A1210D, A1210G, A1210K, A1210L, A1210R, A1210T, A1210W, T1211D, T1211G, T1211K, T1211P, T1211R, T1211S, K1213T, F1214A, F1214E, F1214K, F1214L, F1214P, F1214S, F1214V, V1215D, V1215L, V1215Q, T1216A, T1216L, T1216P, T1216Q, N1217A, N1217P, N1217R, N1217S, N1217T, T1218A, T1218C, T1218E, T1218G, T1218S, T1218W, S1219I, S1219R, A1220P, A1221R, A1221V, A1221W, L1222A, L1222E, L1222F, L1222V, L1222W, S1224P, S1224W, L1225E, L1225K, T1226P, V1227D, V1227P, G1229V, T1230H, T1230K, T1230W, V1232R, S1235E, S1235G, S1235R, S1235W, V1236A, V1236G, V1236P, V1236Q, A1238E, A1238L, A1238R, A1239R, G1240D, I1247R, G1255H, A1259K, T1262R, V1263T, L1264H, P1265W, V1273R, I1274F, I1274R, T1275W, S1277L, S1277T, S1277W, E1278Q, D1279I, D1279R, D1279W, H1280E, H1280G, V1281I, V1281W, K1284G, F1286A, F1286E, F1286P, T1287C, T1287S, T1287W, I1288A, I1288D, I1288G, I1288K, E1293K, E1293L, Q1294E, E1295K, F1296A, E1302R, E1302S, R1303S or D1304V.

87. The lactase variant of the preceding embodiment, wherein the variant has a decreased galactose inhibition, preferably measured as a galactose inhibition improvement factor (GI-IF) of at least 1.2, compared to the lactase of SEQ ID NO: 1.

88. The lactase variant of embodiment 1 which comprises one or more of the following substitutions, wherein each position corresponds to a position in SEQ ID NO: 1: V1D, V1F, V1H, V1L, E2D, E2Q, E2V, D3I, D3V, TSS, S7N, S7P, S9H, T10L, T10S, M13C, M13D, M13K, M13R, S14V, S15C, S15I, S15K, S15P, S15R, S15T, S15V, T16C, P17I, V19K, V20C, V20G, V20L, V20M, V20P, V20Q, V20R, Y21C, Y21P, Y21R, Y21T, S22N, S22T, S22W, A24F, A24L, A24R, A24T, A24W, V25D, V25M, V25Q, V25S, D26C, D26I, D26L, S27A, S27C, S27G, S27H, S27Y, K28C, K28L, K28V, Q29G, Q29L, Q29M, Q29R, N30M, N30V, R31E, R31M, R31V, T32S, D34G, D34H, F35C, D36Q, N38S, W39G, W39S, K40C, K40F, K40G, K40I, K40W, F41A, F41C, M42T, L43A, L43I, L43S, D45P, V47K, V47R, A49D, A49H, A49T, D51G, D51I, D51K, D55C, D55F, D55G, D55H, D55M, D55P, D55S, 557A, S57C, S57E, S57G, A58Q, A58T, W59I, W59K, W59P, W59V, Q60M, Q60R, Q60S, Q60Y, Q61P, V62N, V62T, V62W, D63G, L64E, L64G, H66R, I70K, K73D, Y74K, S75G, S75L, S75Q, S75R, S75V, Q76G, Q76I, S77C, S77D, S77E, S77G, S77H, S77K, S77L, S77M, S77R, S77T, S77V, N78C, N78S, E79H, E79S, E79T, A83T, L85A, L85F, L85N, L85S, L85V, L85W, P86G, P86Q, P86R, P86V, P86W, P86Y, G87D, G87N, G88F, T89M, T89Y, G90A, G90L, G90S, G90T, W91E, W91L, W91P, W91Q, W91Y, Y92F, Y92H, Y92I, Y92M, Y92N, Y92S, Y92T, Y92V, R93A, R93D, R93F, R93H, R93I, R93L, R93N, R93T, R93V, R93Y, K94A, K94C, K94G, K94S, K94T, K94V, S95A, S95C, S95D, S95G, S95I, S95Q, S95R, F96A, F96C, F96I, F96K, F96M, F96P, F96V, F96W, T97F, T97V, I98C, I98H, I98W, R100T, D101A, D101P, D101V, L102P, R106V, R106W, I107F, I107S, A108E, I109M, N110A, N110S, N110T, N110V, N110W, F111A, F111L, F111Q, V114F, V114R, Y115E, M116C, A118P, V120A, V120K, W121D, W121R, W121V, G124M, H130A, H130C, H130S, H130T, Y132E, F137C, F137L, S138A, D140V, L141G, T142S, G149M, G149Y, E150C, E150G, E150L, E150R, V154I, V154K, V154L, V157P, V157S, E158H, E158V, N159H, N159T, L161K, L161M, L161S, L161W, P162N, P162T, P162W, S164A, R165H, W166S, Y167A, Y167C, S170Q, G171C, I172K, I172P, Y173H, Y173M, R174E, R174K, V176E, V176K, V176T, T177K, L178I, L178Q, L178W, T179A, T179C, T179D, T179I, T179K, T179N, T179P, T179S, V180A, V180D, V180G, T181A, T181F, G183W, V184F, V184P, V184R, V184S, V184W, H185E, H185L, V186E, V186N, G187D, G187H, N188R, N188V, G190F, I193N, I193Q, K194I, T195W, P196A, P196I, S197C, S197E, S197L, A199E, A199P, Q201E, N202Q, N202S, N202W, A215D, D217F, D217L, D217M, T218G, A220G, A222R, N223S, L226Q, Q228N, Q228R, F231L, G234V, G235K, K236M, K236P, T237D, G242K, G242L, G242M, G242P, T243I, A247K, I251W, I251Y, A252W, A252Y, A257D, A257N, A257V, S261H, A266D, S267V, P268F, P268R, L270N, S272T, S272W, N277F, V281Q, R282W, L286W, V291P, L292D, L292V, D293C, D293I, D293W, T294Q, T294S, Y295F, D296F, D296H, D296K, T297I, E298I, E298L, E298R, F301C, R302I, W303A, W303C, W303D, W303F, T304D, T304E, T304I, T304K, T304P, G305L, G305N, G305P, G305T, D307A, D307E, D307S, D307W, T309C, T309D, T309E, T309I, T309V, S310A, S310H, S310L, S310M, S310N, S310V, F312H, L314A, L314V, N315S, G316R, E317W, K318C, K318R, K320E, K320I, K320V, K320W, L321M, K322I, V324T, S325G, M326T, H328C, H328F, H328G, H328L, H328M, H328R, H328T, G331V, A335C, A335G, A335L, A337E, A337G, A337L, N338P, R340A, R340L, A341M, I342G, I342P, E343N, E343T, E343Y, R344G, Q345F, Q345N, Q345S, V346A, V346I, V346S, E347A, E347I, I348D, I348M, I348Q, I348R, L349A, L349S, Q350G, Q350N, M352T, G353K, V354E, V354S, V354W, I357T, T359E, T359L, T360V, N362S, N362T, P363A, P363D, P363I, P363L, P363M, P363S, P363V, A364C, A364E, A364F, A364G, A364I, A364M, A364P, A364V, A365C, A365I, A365P, A365V, A365W, K366D, K366L, K366M, K366P, K366S, K366V, A367Q, L368A, L368Q, L368S, L368Y, I369A, I369D, I369E, I369G, I369K, I369M, I369V, I369W, D370L, D370Q, V371F, V371L, V371Q, C372P, N373G, N373L, K375D, K375S, G376A, G376S, V377A, V377M, V377T, V379A, V379N, V380P, E381A, E381G, E381Q, E381T, V383A, M386G, M386N, M386S, M386V, W387H, N388E, N388L, R389A, R389C, R389E, R389Q, R389S, R389T, S390O, S390D, S390P, S390T, G393E, G393R, G393V, T395C, T395F, E396C, E396L, E396V, E396W, Y398M, G399S, K400A, K400C, K400N, K400T, K400V, W401F, W401K, F402F, F402Y, G403A, G403D, G403K, G403Q, G403V, G403Y, Q404F, Q404L, Q404M, Q404P, Q404S, Q404V, A405C, A405E, A405K, A405R, I406C, I406D, I406N, A407C, A407G, A407Q, N410R, N410Y, A411E, A411R, A411S, G414M, G414N, G415Q, K417F, K417R, A422P, L426C, T427D, T427F, T427Q, T427S, T427W, T429D, I430L, I430M, N431M, R432Q, R432Y, D433G, D433I, D433P, D433Q, D433W, R434N, R434V, N435E, N435F, N435L, N435V, A436G, A436L, V439C, V439K, W442E, W442G, S443C, S443G, S443M, S443Q, L444E, L444F, L444V, N446D, M448C, M448L, M449D, M449E, M449T, M449W, M449Y, E450F, E450S, E450T, E450V, E450W, G451C, G451F, G451L, G451P, G451V, G451W, I452K, I452L, I452Q, I452S, I452V, S453H, S453L, S453N, S453Q, G454L, G454W, S455E, S455M, S455P, S455R, V456D, V456E, V456F, V456K, S457H, S457Q, S457T, S457V, G458A, G458P, G458S, F459C, F459R, P460Y, A461G, A461M, T462E, T462L, A464W, K465L, K465V, K465Y, L466G, L466P, V467T, A468D, K471F, K471Q, A472G, A472Y, D474W, S475E, R477L, P478V, M479G, K485E, K485R, K487A, K487F, K487S, K487W, A488C, S493E, S493G, S493H, S493L, S493Q, N494M, N494R, N494V, G497D, N499T, G505D, G505H, G505L, G505R, G505S, V506C, V506E, V506R, V507R, G508C, G508E, T509A, T509I, T509K, T509M, T509V, T509Y, N510A, N510F, N510I, Y511A, S512C, S512F, S512I, S512M, S512Q, S512T, S512V, S512Y, D513P, D513R, A515E, A515S, N516C, N516E, N516G, N516I, N516Q, N516T, N516V, Y517G, D518Y, K519C, K519E, K519G, K519I, K519Q, I520A, I520C, I520G, I520H, I520M, I520N, I520Q, I520S, I520T, I520W, R521V, H524R, H524V, S526G, W527A, W527E, W527G, W527H, W527N, W527R, W527S, A528E, I529A, A535I, A537M, A537P, A537S, I538M, S540E, G549D, G549P, G549W, S553P, K556R, L558E, L558H, L558P, T559Q, T559Y, S564A, S564C, S564F, S564W, A565C, A565D, A565E, A565F, A565G, A565I, A565L, A565R, A565S, A565T, G567Q, G567V, A570G, A572W, A575D, V580D, Q581Y, R582A, R582G, R582L, D583W, F584W, A586D, Y589I, Y589Q, W591F, T592L, L597D, G598N, P600A, P600E, P600G, P600S, N604E, G607Q, G607S, S608T, G609A, A610T, W614A, N619I, N619L, V625E, V625M, V625Y, T627K, T627Q, A628D, A628N, G629T, F630C, F630Y, P631D, P631Y, K632D, K632G, T634W, F637G, F637I, F637S, F637T, F637V, Q639R, D644Y, D645S, V646R, H647G, T648C, I651T, L652C, L652W, P653Q, A654R, W655R, E657R, A661E, A661H, A661K, A661M, A661Q, A661W, K662S, K662V, K662Y, N667L, N667R, P669L, P669T, P669W, Y673S, T674M, D675A, A676P, V679Q, V679S, K680I, K680N, G687P, S688K, S688L, T689G, T689W, E690D, K691P, K691R, R692G, R692H, R692I, R692S, R692T, I694L, I694W, G695C, G695L, G695R, G695W, E696R, K697A, K697G, K697R, S698E, S698M, K701A, K701D, K701G, K701L, K701M, K701S, A705R, A705W, A706C, A706T, Y708F, Y710T, Y710V, Q711A, V712M, V712P, V712Q, Y713G, E714H, E714K, G715K, A716R, D717C, D717S, K718A, K718Q, K718T, K718Y, D719E, D719I, D719V, S720A, T721H, T721L, T721N, T721S, T721V, T721W, A722T, H723G, H723P, M726D, Y727L, L728S, T729M, N731E, N731Q, V732R, P733W, W734G, A735Q, A735R, A735S, G737F, T738S, I739K, S740D, S740F, A741I, A741P, A741S, Y744R, D745C, D745N, N747F, L750S, I751C, P752C, P752Y, G754H, T756N, E757A, N759S, N759V, G766M, A769F, A769G, A769I, A769N, A769V, A769Y, K770H, L771A, K772A, K772C, K772P, K772R, A773C, A773M, A773R, D774A, D776V, R777H, R777S, K778F, K778E, K778N, T781A, T781F, T781H, T781P, T781Y, A782Q, A782Y, D783A, K785C, K785S, K785W, K785Y, D786V, Y789V, I790R, E791S, V792S, N798I, G799K, G799L, H800V, V802I, V802S, V802Y, P803S, P803Y, A805F, A806I, A806Q, R808F, R808G, R808I, V809L, V809M, T810P, T810Q, T810Y, F811L, V813W, K814G, K814P, G815M, G815P, A816D, A816W, K818D, K818F, K818L, K818Q, K818W, K818Y, L819F, V820C, V820R, G821I, V822A, V822D, V822E, G825A, S826G, D829S, D831P, S832R, Y833E, Q834M, A835I, A835H, A835K, D836C, D836E, D836Q, D836S, D836T, D836V, D836Y, R838N, K839A, K839D, A840G, A840I, A840P, A840V, K844A, K853P, E854C, E854I, I858D, I858K, I858P, T861F, T861I, T861W, D865A, D865G, G866H, G866R, L867W, S870E, S870M, S870T, V872C, V872G, K873G, K873Y, I874G, T882A, T882R, S883L, E885V, K886L, K886V, K886W, T887A, T887D, T887G, T887N, V888A, R889G, Y892P, Y893E, S894D, Y897V, K900E, T901Q, T901R, T901Y, G902A, G902F, G902P, G902Q, G902R, G902S, G902W, N903D, N903I, K904D, K904E, K904M, K904N, K904R, K904S, K904V, P905C, P905R, P905W, P905Y, I906W, L907F, L907S, P908D, P908G, P908I, P908L, D910W, E912T, R914A, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, T919D, T919Q, T919W, D921V, R922A, R922M, R922W, Q923A, Q923V, V925C, V925K, T926R, W927P, D928A, D928Q, A929P, V930I, S931R, D933Q, Q934S, Q934V, I935A, I935C, I935E, I935P, I935W, A936I, A936Q, A936Y, K937G, K937I, K937M, K937P, K937Q, A938C, A938T, G939D, S940C, S940E, S940R, S940V, F941C, S942K, S942V, V943A, T946A, T946P, T946W, V947G, V947L, V947P, V947R, V947T, A948I, A948W, G949A, K951D, K951S, K951W, K951Y, S953F, S953M, S953R, V954D, V954Q, R955C, R955W, V956D, V956Q, T957S, I959V, I959Y, D960S, E961D, E961F, E961S, E961T, I962A, I962C, I962K, I962N, L965C, L965G, L965K, L965M, L965P, L965V, L965Y, L966A, L966N, N967D, N967M, N967P, N967T, Y968G, Y968L, Y968Q, Y968V, S969C, S969D, S969H, S969I, S969L, S969M, S969Q, S969Y, A970I, S971V, S971W, P973C, P973D, P973N, P973R, P973W, V974E, V974T, V974Y, T976F, T976G, T976K, T976P, P977C, P977T, P977Y, A978F, A978M, A978N, A978R, L980A, L980H, L980I, L980N, L980Q, L980T, P981M, P985L, P985W, A986I, A986L, A986W, V987A, V987F, V987K, P989M, D990W, G991F, G991H, G991Y, T992M, S995L, N997K, F998M, F998W, D1001L, W1002A, W1002D, W1002E, W1002H, W1002N, W1002P, W1002Q, T1003Y, P1005I, P1005Y, A1006C, A1006S, D1007L, D1007P, D1007V, Y1010T, N1011A, N1011T, T1012Q, A1013Q, A1013V, G1014I, V1016D, V1018K, T1021G, A1022H, V1024G, V1024H, V1024K, V1024R, V1024S, V1024W, G1026S, G1026V, F1029K, F1029P, F1029V, K1030D, K1030W, V1031H, V1031K, T1034H, I1035D, R1036G, R1036L, R1036T, Q1041P, V1042N, T1043F, I1044A, S1046M, V1048C, V1048F, V1048G, V1048M, V1048Q, N1051E, N1051K, A1052K, L1053A, L1053W, L1055R, Q1057E, N1058R, N1058S, P1060G, P1060N, A1061G, D1062A, D1062M, Q1064M, Q1064R, S1065A, S1065C, D1066A, D1066G, D1066V, T1067M, L1068P, L1068Q, K1072S, G1074L, G1074R, S1075L, T1076S, T1082E, T1082F, G1083E, G1083F, G1083L, G1084V, G1084Y, G1085S, A1086H, N1087R, P1088E, P1088R, S1089G, S1089K, S1089Q, W1091Y, N1093A, N1093P, N1093Q, W1094D, W1094E, W1094P, A1095W, Y1096D, S1097T, K1098D, K1098F, A1099D, A1099S, A1099V, G1100H, H1101V, N1102H, T1103E, E1105L, E1109A, E1109D, E1109L, E1109W, A1111G, E1113P, E1113V, Q1114E, Q1114R, Q1114S, Q1114T, Q1114V, Q1115A, Q1115K, Q1115L, Q1115P, L1116G, L1116K, L1116W, G1117E, G1117I, G1117M, G1117R, G1117S, G1117T, G1117V, G1117W, Q1118W, I1119E, I1119N, I1119S, M1121G, M1121K, F1123R, F1124V, F1124W, R1125D, R1125K, R1125V, R1125W, S1127I, S1127Q, N1128A, A1129E, V1130A, V1130R, P1133D, P1133G, P1133R, A1135L, A1135W, G1136P, K1137P, K1137R, K1137S, T1138R, I1140C, I1140P, Q1141K, I1142Y, S1143G, A1144N, A1144P, A1144S, A1144T, A1144V, A1144W, D1145E, D1145R, D1145T, G1146V, N1148P, W1149C, W1149G, W1149S, W1149V, T1150K, D1151W, L1152A, L1152E, L1152Q, L1152W, A1153G, A1154R, I1158W, A1159I, Q1161P, Q1161S, E1162A, E1162C, E1162Q, E1165S, V1167R, P1169S, Y1170K, A1175S, G1178M, G1178Q, G1178T, A1179L, A1179W, T1180A, T1180G, T1180I, T1180M, T1180Q, T1180Y, V1182M, K1183E, V1184C, V1184E, V1184K, V1184L, V1184P, V1184Q, V1184Y, V1186S, N1188W, A1189C, A1189K, A1189T, A1189V, D1190R, D1190T, T1191L, V1197A, A1200G, T1203K, E1204G, I1205V, K1208R, K1208V, K1208W, T1209A, T1209C, T1209E, T1209K, T1209N, T1209Q, A1210D, A1210G, A1210K, A1210L, A1210R, A1210T, A1210W, T1211D, T1211G, T1211K, T1211P, T1211R, T1211S, K1213T, F1214A, F1214E, F1214G, F1214I, F1214L, F1214P, F1214S, F1214V, V1215D, V1215L, V1215Q, T1216L, T1216P, T1216Q, N1217A, N1217P, N1217R, N1217S, N1217T, T1218A, T1218C, T1218E, T1218G, T1218S, T1218W, S1219I, S1219R, A1220P, A1221R, A1221V, A1221W, L1222A, L1222E, L1222F, L1222V, L1222W, S1224P, S1224W, L1225E, L1225K, T1226P, V1227D, V1227P, G1229V, T1230H, T1230K, T1230W, V1232R, S1235E, S1235G, S1235R, S1235W, V1236A, V1236G, V1236P, V1236Q, A1238E, A1238L, A1238R, A1239R, G1240D, I1247R, G1255H, A1259K, T1262R, V1263T, L1264H, P1265W, V1273R, I1274F, I1274R, T1275W, S1277L, S1277T, S1277W, E1278Q, D1279I, D1279R, D1279W, H1280E, H1280G, V1281I, V1281W, K1284G, F1286A, F1286E, F1286P, T1287C, T1287S, T1287W, I1288A, I1288D, I1288G, I1288K, E1293K, E1293L, Q1294E, E1295K, F1296A, E1302R, E1302S, R1303S or D1304V.

89. The lactase variant of the preceding embodiment, wherein the variant has a decreased galactose inhibition, preferably measured as a galactose inhibition improvement factor (GI-IF) of at least 1.2, compared to the lactase of SEQ ID NO: 1.

90. The lactase variant of embodiment 1 which comprises one or more of the following substitutions, wherein each position corresponds to a position in SEQ ID NO: 1: V1H, V1L, E2D, E2V, D3I, D3S, D3V, D3W, R6M, R6P, S7D, S7N, S7P, M13C, M13F, M13R, S14V, S15C, S15I, S15K, S15T, S15V, S15Y, T16C, P17D, P17I, P17L, V19G, V20C, V20M, V20P, Y21C, Y21P, Y21R, Y21T, S22W, S23L, S23M, A24F, A24L, A24T, A24W, V25K, V25Q, D26C, S27A, S27C, S27H, K28C, Q29L, Q29M, Q29R, Q29V, R31E, R31V, T32S, S33C, S33Q, S33R, D34S, D34Y, F35C, F35E, F35N, W39G, K40C, K40F, K40I, F41A, F41G, M42E, M42T, L43C, L43S, L43T, L43V, D45P, V47K, V47R, A49D, A49H, A49R, A49T, D51I, D51K, D51P, D51V, A53S, D55C, D55H, D55M, D55P, S57C, S57E, S57G, A58G, A58Q, A58T, W59I, W59K, W59P, Q60K, Q60R, Q60S, V62N, V62S, V62T, V62W, L64E, H66R, H66Y, Y68P, K73D, S75G, S75L, S75R, S75V, Q76G, Q76I, S77D, S77E, S77F, S77G, S77H, S77K, S77N, N78C, N78E, E79H, E79Q, E79S, E79T, E81A, E81Q, A83T, L85A, L85F, L85N, L85S, L85V, L85W, P86Q, G87D, G88F, G88Q, G90T, W91P, W91Y, Y92H, Y92I, Y92M, Y92S, Y92T, Y92V, R93A, R93D, R93F, R93H, R93I, R93L, R93N, R93T, R93V, R93Y, K94A, K94S, K94T, S95C, S95D, S95G, S95I, F96A, F96C, F96I, F96K, F96M, F96P, F96S, F96V, T97F, I98C, I98H, R100T, D101A, D101P, L102P, R106W, I107G, I107S, A108E, I109M, N110A, N110S, N110T, N110W, F111A, F111L, D112T, V114R, Y115E, M116C, A118K, A118P, A118Y, V120A, V120K, W121R, W121V, W121Y, F122S, F122Y, N123P, G124E, H130A, H130T, Y132C, Y132E, P136R, F137L, T142S, K146A, G149M, E150L, I153A, V154K, V154L, V157L, V157P, V157S, E158G, E158H, N159T, L161K, L161M, L161S, L161W, P162N, P162T, P162W, S164A, R165H, W166S, Y167A, G169D, S170Q, I172K, I172P, Y173H, R174E, V176E, V176K, T177K, L178I, L178Q, T179C, T179I, T179N, V180D, V180G, T181A, V184R, H185G, H185L, G187D, N188E, N188V, N189E, G190C, G190F, K194I, T195S, S197C, L198R, A199P, Q201E, N202Q, N202R, N202S, N202W, G203K, G203V, G204Y, N205E, N205G, N205H, V206K, T207Q, N209D, N209K, T211R, T212E, K213C, K213D, V214A, A215Q, D217L, D217M, T218G, A220G, A220V, A221E, A222R, N223S, Q228R, T229G, T229V, V230M, F231G, F231V, F231Y, P232S, K233C, K233L, K233P, G234L, G234Y, G235H, G235M, G235Y, K236D, K236L, K236M, K236W, K236Y, T237D, D238E, D238F, D238P, A239G, A239T, A240C, G242K, G242Y, T243M, T245G, T245Q, A247P, A247R, A247W, S248E, S248T, K249G, K249N, K249Y, I251Y, A252F, A252W, A252Y, G254I, G254M, G254R, G254W, A255K, A255S, A255Y, S256A, S256K, S256N, S256Y, D258L, D258W, S261H, S261R, S261W, T262D, T264M, A266D, A266K, A266Q, S267V, P268R, S272T, S272W, L278H, L278M, L278Q, L278R, L278V, Y279W, T280E, V281Q, R282H, R282I, E284L, V285T, L286F, V291D, V291P, L292H, L292V, D293C, D293S, D293W, Y295F, Y295W, D296F, D296K, D296R, E298I, E298R, F301C, W303A, W303C, W303D, T304H, T304K, T304P, G305N, G305P, G305W, A308M, A308Y, T309C, T309D, T309E, S310H, S310L, S310N, G311V, F312H, L314A, L314C, L314V, N315S, K318N, K320C, K320V, K320W, L321M, K322F, K322I, V324T, S325D, S325G, S325T, M326E, M326G, M326T, M326Y, H328C, H328F, H328G, H328M, H328T, G331V, A335G, A335L, A337G, A337L, R340A, R340L, A341M, I342G, I342K, E343N, E343Y, R344G, Q345G, Q345K, Q345S, V346A, E347A, I348D, I348M, Q350G, M352T, M352W, G353K, I357T, T359E, T359L, T360V, N362S, N362T, P363A, P363I, P363L, P363M, A364I, A364M, A364P, A365C, A365I, A365P, A365V, K366L, K366M, K366S, L368A, L368E, L368Q, L368S, I369E, I369G, I369K, I369V, I369W, D370L, V371D, V371F, V371Q, C372P, N373G, N373L, G376A, G376S, V377M, V377T, V379A, V379N, V380P, E381A, E381G, E381Q, E381T, V383A, M386G, M386N, M386S, W387H, W387L, N388L, N388R, R389A, R389E, R389Q, R389S, R389T, S390C, S390D, S390G, S390P, S390Q, S390T, S390V, K391E, N392D, G393A, G393E, G393R, G393S, G393V, N394L, T395C, T395H, T395N, T395S, T395W, E396K, E396L, E396M, E396V, E396W, Y398M, Y398N, G399S, K400A, K400C, K400N, K400P, K400Q, K400S, K400V, W401F, W401K, W401L, F402W, F402Y, G403A, G403K, G403Q, G403V, Q404F, Q404H, Q404L, Q404M, Q404P, Q404V, A405C, A405E, A405H, A405K, A405R, A405T, I406D, I406N, A407C, A407G, A407Q, A407T, G408W, D409N, N410Y, A411E, A411V, L413P, G414A, G414M, G414N, G414R, G415R, G416R, D416Y, K417F, K417R, D418P, D418R, E419M, E419R, E419W, T420K, T420R, W421Q, A422P, A422T, K423D, F424C, F424L, F424N, L426M, T427D, T427F, T427K, T427M, T427Q, T427S, T429D, I430S, N431M, D433G, D433I, D433P, D433Q, D433W, R434N, R434V, N435E, N435L, N435R, A436L, P437Q, P437R, V439C, V439E, V439G, V439K, V439T, I440R, M441A, W442E, W442G, W442R, S443C, S443G, S443Q, S443Y, L444E, L444G, L444V, G445A, G445C, G445V, N446D, N446T, M448C, M448L, M448Q, M448S, M448V, M449D, M449T, M449W, M449Y, E450F, E450S, E450T, E450V, E450W, G451C, G451F, G451L, G451P, G451V, G451W, I452G, I452K, I452M, I452S, I452V, G454L, S455P, S455R, S455W, V456D, V456E, V456F, V456K, S457H, S457T, S457V, G458A, G458P, G458S, G458W, F459N, F459R, F459S, A461M, T462E, T462L, S463V, A464P, A464V, K465F, K465V, K465Y, L466A, L466E, L466P, L466S, L466V, A468D, A468W, T470M, K471F, A472G, A472Y, D474R, S475E, R477L, M479G, M479I, M479R, T480C, T480G, K485E, K485R, K487F, K487N, K487S, K487W, A488H, A488N, A488S, N491W, E492A, S493G, S493L, S493M, S493Q, N494R, T495R, T495W, G497D, D498C, D498S, N499R, N499T, N499Y, L500A, T501M, G504H, G504P, G505D, G505N, G505R, G505S, V506C, V506D, V506E, V506G, V506R, V507L, V507R, G508C, G508E, T509A, T509K, T509M, N510A, N510F, N510I, Y511A, S512F, S512Q, S512T, S512V, S512Y, D513K, D513L, D513P, D513R, G514F, A515C, A515E, A515K, A515P, A515R, N516C, N516E, N516Q, N516V, Y517G, D518Y, K519C, K519I, I520C, I520G, I520H, I520M, I520S, I520T, R521N, R521V, T522G, T522N, H524R, H524V, P525T, S526G, W527A, W527H, W527N, W527R, W527S, A528E, Y530M, G531E, G531G, G531T, T534A, A535M, A537D, A537M, A537P, S540E, S540G, G542Q, I543V, N545S, R546L, R546P, R546S, T547A, T547D, T547S, T548E, T548F, T548K, T548P, G549D, G549P, G549W, G550S, A551I, A551P, S553N, S554N, S554V, D555S, K556W, L558E, L558P, T559Y, Y561R, N563S, S564C, S564F, S564W, A565D, A565E, A565I, A565L, A565R, A565T, G567Q, G567V, A570G, A570K, A570M, A570W, A572S, S573K, S574K, S574Q, S574W, A575D, A575V, W576Y, Y577G, Y577L, D578N, V579G, V579T, V580K, V580S, Q581G, R582L, D583W, F584E, V585I, A586K, G587C, T588D, T588I, Y589V, Y589W, V590H, W591F, T592C, T592L, T592S, F594L, D595E, D595Q, D595S, G598N, P600A, P600E, P600G, P600S, T606S, G607Q, S608V, G609N, G609R, A610M, V611K, W614A, W614P, N619I, N619L, S620G, V625M, V625Y, T627K, T627V, A628D, F630C, F630D, F630G, F630Y, P631A, P631D, T634V, Y635R, Q639R, D644C, H650E, H650R, W655R, N656V, E657R, A661E, A661K, A661Q, N667L, N667R, P669T, V670C, Y673R, Y673S, T674M, D675P, A676P, A677G, K678T, V679G, V679S, K680I, L681F, T684G, T684V, G687P, S688K, S688L, T689W, E690D, R692G, R692H, I694L, I694W, G695C, G695L, G695W, K697R, S698E, S698L, S698M, T700C, K701A, K701G, K701M, K701S, K704Y, A705E, A705W, Y708F, T709M, Y710D, Y710T, Y710W, Q711Y, V712M, V712Q, E714K, A716R, D717G, D717S, K718A, K718T, D719E, D719T, D719V, T721H, T721L, T721N, T721S, T721V, T721W, H723G, M726D, Y727L, L728S, N731E, N731S, V732R, W734G, W734V, A735Q, A735S, T738S, I739K, S740D, A741I, Y744R, D745F, D745N, N747R, L750S, P752A, P752C, P752Y, G754P, T756N, T756S, E757A, A760N, A769F, A769I, A769N, A769V, A769Y, K770H, L771A, K772A, K772C, K772P, K772V, A773C, A773H, A773M, A773V, A773V, D774A, D774R, A775L, A775W, D776I, D776L, D776S, D776V, R777D, R777E, R777G, R777H, R777P, R777S, K778L, K778N, T781A, T781F, T781G, T781M, T781P, T781Y, A782P, A782Q, D783A, D783C, D783E, D783R, G784L, G784S, G784T, K785S, K785W, K785Y, D786V, L787P, L787T, S788G, S788I, Y789V, I790C, I790R, V792G, D793H, V794C, V794T, V794W, T795P, D796Q, N798I, G799K, G799L, G799M, G799Q, H800A, H800L, V802Y, P803S, D804G, A806I, A806Q, N807W, R808C, R808F, R808N, T810P, T810Q, D812Q, V813T, V813W, K814H, K814L, G815A, G815V, A816C, A816F, K818F, K818L, K818W, K818Y, L819F, V820K, G821E, G821F, G821I, G821N, V822D, V822E, S826G, S826L, P828C, D829S, H830E, H830R, H830V, D831F, D831I, D831P, D831R, D831V, S832R, Y833K, Y833V, A835D, A835E, A835H, A835K, A835W, D836C, D836E, D836H, D836S, D836V, D836Y, N837D, R838G, R838M, R838N, K839A, K839D, A840G, A840P, A840V, F841C, F841W, K844G, V845W, V849L, V849S, Q850C, Q850G, Q850Y, E854C, E857P, I858D, I858Q, I858Y, T859V, V860T, T861W, A862V, K863F, K863N, K863W, D865A, D865G, G866H, L867W, S870E, S870R, V872C, K873G, K873Y, I874G, T877A, G881W, S883L, T884A, K886E, K886V, K886W, T887F, T887G, V888A, Y892P, Y892R, Y893E, N896M, Y897V, K900E, T901G, T901Q, T901R, T901V, T901Y, G902F, G902L, G902R, G902S, G902W, N903D, K904M, K904N, K904S, K904V, P905C, P905R, P905Y, I906W, L907F, P908I, P908L, D910W, E912T, R914A, R914F, R914I, R914K, R914V, R914Y, Y915A, Y915C, Y915G, Y915M, Y915Q, Y915V, S916G, D917C, D917F, D917S, G918E, G918H, G918T, T919D, T919Q, S920E, D921V, R922A, Q923V, T926G, T926R, W927G, W927P, A929P, D933R, Q934S, I935A, I935C, I935E, I935P, I935W, A936I, A936Q, K937G, K937I, K937P, K937Q, A938C, G939D, S940C, S940T, F941C, S942K, S942V, V943A, V943H, V943R, A944D, A944H, A944P, A944R, T946P, T946V, V947G, V947M, V947R, V947T, A948C, A948R, A948W, Q950D, K951S, S953M, S953W, R955C, R955W, V956D, V956Q, M958D, E961D, E961F, E961S, I962C, I962K, I962N, L965C, L965G, L965K, L965M, L965P, L965Y, L966A, L966H, N967M, Y968G, Y968Q, Y968V, S969C, S969I, S969L, S969M, S969Q, A970I, S971V, P973C, P973W, V974T, T976K, T976P, P977C, P977T, A978F, A978M, V979R, L980H, L980N, P981M, P985L, P985W, A986I, A986L, V987A, V987F, V987K, D990W, G991Y, S995L, N997K, A999G, V1000N, D1001L, W1002A, W1002D, W1002E, W1002H, W1002N, W1002P, W1002Q, T1003L, T1003Y, K1004H, P1005Y, A1006C, A1006S, D1007P, N1011T, T1012Q, G1014I, V1018K, T1021F, A1022H, V1024C, V1024H, G1026R, G1026V, K1030D, K1030W, I1035D, Q1041P, V1042N, V1048C, V1048G, V1048M, V1048Q, G1050S, N1051E, N1051K, A1052K, L1053A, Q1057E, Q1057R, N1058V, I1059W, A1061G, D1062L, D1062M, Q1064M, S1065A, D1066M, D1066V, D1066W, T1067M, L1068C, L1068P, A1070P, I1071W, K1072G, K1072Q, K1072S, D1073P, G1074I, G1074L, S1075C, T1082F, G1083E, G1083F, G1083L, G1083S, G1084V, G1085S, P1088E, P1088R, S1089C, S1089G, S1089Q, W1091A, W1091E, W1091G, W1091T, W1091V, W1091Y, T1092G, T1092Q, N1093A, N1093P, N1093Q, W1094D, W1094E, S1097W, K1098D, A1099V, G1100M, H1101V, N1102E, N1102H, T1103E, A1104R, I1106T, T1107S, F1108D, F1108L, E1109A, E1109D, E1109L, E1109W, A1111G, E1113P, E1113V, Q1114E, Q1114R, Q1114S, Q1114T, Q1114V, Q1115A, Q1115K, L1116K, L1116W, G1117I, G1117R, G1117S, G1117T, G1117V, G1117W, I1119N, M1121G, M1121V, R1125V, R1125W, D1126H, S1127I, S1127Q, N1128A, A1129E, A1129Q, A1129V, V1130A, V1130G, V1130R, P1133D, P1133R, D1134L, A1135L, A1135S, A1135W, G1136A, G1136E, G1136P, K1137C, K1137L, K1137Q, K1137R, K1137S, I1140G, I1140L, I1140P, Q1141K, Q1141P, I1142Y, A1144C, A1144N, A1144P, A1144S, A1144V, A1144W, D1145E, D1145R, D1145T, N1148P, W1149C, W1149I, W1149V, T1150K, D1151R, D1151W, L1152W, A1153G, A1154C, E1162A, E1165L, V1167R, K1168W, Y1170E, T1171A, T1171G, A1175N, A1175Q, V1177N, V1177T, G1178M, G1178T, A1179L, A1179W, T1180A, T1180G, T1180I, T1180M, T1180Q, T1180Y, V1184E, V1184L, V1184P, V1184Q, V1184Y, V1186S, N1188W, D1190T, T1191L, T1192H, V1197A, C1199T, A1200W, L1202A, E1204G, K1208W, T1209E, T1209K, A1210D, A1210E, A1210G, A1210K, A1210L, A1210R, A1210T, A1210W, T1211G, T1211K, T1211P, T1211R, T1211S, F1214A, F1214K, F1214S, F1214V, V1215D, V1215L, T1216L, T1216Q, N1217A, N1217S, N1217T, T1218C, T1218E, T1218S, T1218W, S1219A, S1219F, A1220L, L1222A, L1222E, L1222F, L1222V, S1223V, S1224A, S1224G, S1224P, S1224W, L1225E, L1225K, L1225W, T1226P, T1226S, T1226V, N1228D, N1228F, G1229V, T1230I, T1230K, T1230W, K1231F, K1231P, V1232K, V1232R, S1233P, S1233W, S1235W, V1236A, V1236G, V1236P, L1237D, A1238E, A1238R, G1240W, Y1242E, Y1242R, N1243M, N1243T, T1244Q, A1246M, I1248G, A1249H, A1249I, A1249V, D1250I, D1250K, D1250S, D1250T, D1250W, D1250Y, K1252D, G1255H, N1258H, A1259K, T1262R, V1263T, V1263W, P1265R, P1265W, N1269A, N1269K, I1274F, I1274R, T1275W, S1277L, S1277T, S1277W, E1278Q, D1279R, D1279W, H1280E, V1281I, V1281W, K1284G, F1286E, F1286P, T1287C, T1287S, T1287W, I1288A, I1288D, I1288G, I1288K, G1291P, G1291Y, T1292Y, E1295K, F1296A, E1302R, E1302S or D1304V.

91. The lactase variant of the preceding embodiment, wherein the variant has a decreased or an increased galactose inhibition, preferably measured as a galactose inhibition improvement factor (GI-IF) of at least 1.3 or at most 0.7, compared to the lactase of SEQ ID NO: 1.

92. The lactase variant of embodiment 1 which comprises one or more of the following substitutions, wherein each position corresponds to a position in SEQ ID NO: 1: V1H, V1L, E2D, E2V, D3I, D3S, D3V, D3W, R6M, R6P, S7D, S7N, S7P, M13C, M13F, M13R, S14V, S15C, S15I, S15K, S15T, S15V, S15Y, T16C, P17D, P17I, P17L, V19G, V20C, V20M, V20P, Y21C, Y21P, Y21R, Y21T, S22W, S23L, S23M, A24F, A24L, A24T, A24W, V25K, V25Q, D26C, S27A, S27C, S27H, K28C, Q29L, Q29M, Q29R, Q29V, R31E, R31V, T32S, S33C, S33Q, S33R, D34S, D34Y, F35C, F35E, F35N, W39G, K40C, K40F, K40I, F41A, F41G, M42E, M42T, L43C, L43S, L43T, L43V, D45P, V47K, V47R, A49D, A49H, A49R, A49T, D51I, D51K, D51P, D51V, A53S, D55C, D55H, D55M, D55P, S57C, S57E, S57G, A58G, A58Q, A58T, W59I, W59K, W59P, Q60K, Q60R, Q60S, V62N, V62S, V62T, V62W, L64E, H66R, H66Y, Y68P, K73D, S75G, S75L, S75R, S75V, Q76G, Q76I, S77D, S77E, S77F, S77G, S77H, S77K, S77R, N78C, N78E, E79H, E79Q, E79S, E79T, E81A, E81Q, A83T, L85A, L85F, L85N, L85S, L85V, L85W, P86Q, G87D, G88F, G88Q, G90T, W91P, W91Y, Y92H, Y92I, Y92M, Y92S, Y92T, Y92V, R93A, R93D, R93F, R93H, R93I, R93L, R93N, R93T, R93V, R93Y, K94A, K94S, K94T, S95C, S95D, S95G, S95I, F96A, F96C, F96I, F96K, F96M, F96P, F96S, F96V, T97F, I98C, I98H, R100T, D101A, D101P, L102P, R106W, I107G, I107S, A108E, I109M, N110A, N110S, N110T, N110W, F111A, F111L, D112T, V114R, Y115E, M116C, A118K, A118P, A118Y, V120A, V120K, W121R, W121V, W121Y, F122S, F122Y, N123P, G124E, H130A, H130T, Y132C, Y132E, P136R, F137L, T142S, K146A, G149M, E150L, I153A, V154K, V154L, V157L, V157P, V157S, E158G, E158H, N159T, L161K, L161M, L161S, L161W, P162N, P162T, P162W, S164A, R165H, W166S, Y167A, G169D, S170Q, I172K, I172P, Y173H, R174E, V176E, V176K, T177K, L178I, L178Q, T179C, T179I, T179N, V180D, V180G, T181A, V184R, H185E, H185L, G187D, N188E, N188V, N189E, G190C, G190F, K194I, T195S, S197C, L198R, A199P, Q201E, N202Q, N202R, N202S, N202W, G203K, G203V, G204Y, N205E, N205G, N205H, V206K, T207Q, N209D, N209K, T211R, T212E, K213C, K213D, V214A, A215Q, D217L, D217M, T218G, A220G, A220V, A221E, A222R, N223S, Q228R, T229G, T229V, V230M, F231G, F231V, F231Y, P232S, K233C, K233L, K233P, G234L, G234Y, G235H, G235M, G235Y, K236D, K236L, K236M, K236W, K236Y, T237D, D238E, D238F, D238P, A239G, A239T, A240C, G242K, G242Y, T243M, T245G, T245Q, A247P, A247R, A247W, S248E, S248T, K249G, K249N, K249Y, I251Y, A252F, A252W, A252Y, G254I, G254M, G254R, G254W, A255K, A255S, A255Y, S256A, S256K, S256N, S256Y, D258L, D258W, S261H, S261R, S261W, T262D, T264M, A266D, A266K, A266Q, S267V, P268R, S272T, S272W, L278H, L278L, L278Q, L278R, L278W, Y279W, T280E, V281Q, R282I, R282I, E284L, V285T, L286F, V291D, V291P, L292H, L292V, D293C, D293S, D293W, Y295F, Y295W, D296F, D296K, D296R, E298I, E298R, F301C, W303A, W303C, W303D, T304D, T304K, T304P, G305N, G305P, G305W, A308M, A308Y, T309C, T309D, T309E, S310H, S310L, S310N, G311V, F312H, L314A, L314C, L314V, N315S, K318N, K320C, K320V, K320W, L321M, K322F, K322I, V324T, S325D, S325G, S325T, M326E, M326G, M326T, M326Y, H328C, H328F, H328G, H328M, H328T, G331V, A335G, A335L, A337G, A337L, R340A, R340L, A341M, I342G, I342K, E343N, E343Y, R344G, Q345G, Q345K, Q345S, V346A, E347A, I348D, I348M, Q350G, M352T, M352W, G353K, I357T, T359E, T359L, T360V, N362S, N362T, P363A, P363I, P363L, P363M, A364I, A364M, A364P, A365C, A365I, A365P, A365V, K366L, K366M, K366S, L368A, L368E, L368Q, L368S, I369E, I369G, I369K, I369V, I369W, D370L, V371D, V371F, V371Q, C372P, N373G, N373L, G376A, G376S, V377M, V377T, V379A, V379N, V380P, E381A, E381G, E381Q, E381T, V383A, M386G, M386N, M386S, W387H, W387L, N388L, N388R, R389A, R389E, R389Q, R389S, R389T, S390C, S390D, S390G, S390P, S390Q, S390T, S390V, K391E, N392D, G393A, G393E, G393R, G393S, G393V, N394L, T395C, T395H, T395N, T395S, T395W, E396K, E396L, E396M, E396V, E396W, Y398M, Y398N, G399S, K400A, K400C, K400N, K400P, K400Q, K400S, K400V, W401F, W401K, W401L, F402W, F402Y, G403A, G403K, G403Q, G403V, Q404F, Q404H, Q404L, Q404M, Q404P, Q404V, A405C, A405E, A405H, A405K, A405R, I406D, I406N, A407C, A407G, A407Q, A407T, G408W, D409N, N410Y, A411E, A411V, L413P, G414A, G414M, G414N, G414R, G415R, D416I, D416R, D416Y, K417F, K417R, D418P, D418R, E419M, E419R, E419W, T420K, T420R, W421Q, A422P, A422T, K423D, F424C, F424L, F424N, L426M, T427D, T427F, T427K, T427M, T427Q, T427S, T429D, I430S, N431M, D433G, D433I, D433P, D433Q, D433W, R434N, R434V, N435E, N435L, N435R, A436L, P437Q, P437R, V439C, V439E, V439G, V439K, V439T, I440R, M441A, W442E, W442G, W442R, S443C, S443G, S443Q, S443Y, L444E, L444G, L444V, G445A, G445C, G445V, N446D, N446T, M448C, M448L, M448Q, M448S, M448V, M449D, M449T, M449W, M449Y, E450F, E450S, E450T, E450V, E450W, G451C, G451F, G451L, G451P, G451V, G451W, I452G, I452K, I452M, I452S, I452V, G454L, S455P, S455R, S455W, V456D, V456E, V456F, V456K, S457H, S457T, S457V, G458A, G458P, G458S, G458W, F459N, F459R, F459S, A461M, T462E, T462L, S463V, A464P, A464V, K465F, K465V, K465Y, L466A, L466E, L466P, L466S, L466V, A468D, A468W, T470M, K471F, A472G, A472Y, D474R, S475E, R477L, M479G, M479I, M479R, T480C, T480G, K485E, K485R, K487F, K487N, K487S, K487W, A488H, A488N, A488S, N491W, E492A, S493G, S493L, S493M, S493Q, N494T, T495R, T495W, G497D, D498C, D498S, N499C, N499T, N499Y, L500A, T501M, G504H, G504P, G505D, G505N, G505R, G505S, V506C, V506D, V506E, V506G, V506R, V507L, V507R, G508C, G508E, T509A, T509K, T509M, N510A, N510F, N510I, Y511A, S512F, S512Q, S512T, S512V, S512Y, D513K, D513L, D513P, D513R, G514F, A515C, A515E, A515K, A515R, N516C, N516E, N516Q, N516W, Y517G, D518Y, K519C, K519I, I520C, I520G, I520H, I520M, I520S, I520T, R521N, R521V, T522G, T522N, H524R, H524V, P525T, S526G, W527A, W527H, W527N, W527R, W527S, A528E, Y530M, G531E, G531S, G531T, T534A, A535M, A537D, A537M, A537S, S540E, S540G, S542Q, I543V, N545S, R546L, R546P, R546S, T547A, T547D, T547S, T548E, T548F, T548K, T548P, G549D, G549P, G549W, G550S, A551I, A551Q, S553N, S554N, S554V, D555S, K556W, L558E, L558P, T559Y, Y561R, N563S, S564C, S564F, S564W, A565D, A565E, A565I, A565L, A565R, A565T, G567Q, G567V, A570G, A570K, A570M, A570W, A572S, S573K, S574K, S574P, S574W, A575D, A575V, W576Y, Y577G, Y577L, D578N, V579G, V579T, V580K, V580S, Q581G, R582L, D583W, F584E, V585I, A586K, G587C, T588D, T588I, Y589V, Y589W, V590H, W591F, T592C, T592L, T592S, F594L, D595E, D595Q, D595S, G598N, P600A, P600E, P600G, P600S, T606S, G607Q, S608V, G609N, G609R, A610M, V611K, W614A, W614P, N619I, N619L, S620G, V625M, V625Y, T627K, T627Q, A628D, F630C, F630D, F630G, F630Y, P631A, P631D, T634V, Y635R, Q639R, D644C, H650E, H650R, W655R, N656V, E657R, A661E, A661K, A661Q, N667L, N667R, P669T, V670C, Y673R, Y673S, T674M, D675P, A676P, A677G, K678T, V679G, V679S, K680I, L681F, T684G, T684V, G687P, S688K, S688L, T689W, E690D, R692G, R692H, I694L, I694W, G695C, G695L, G695W, K697R, S698E, S698L, S698M, T700C, K701A, K701G, K701M, K701S, T704Y, A705E, A705W, Y708F, T709M, Y710D, Y710T, Y710W, Q711Y, V712M, V712Q, E714K, A716R, D717G, D717S, K718A, K718T, D719E, D719T, D719V, T721H, T721L, T721N, T721S, T721V, T721W, H723G, M726D, Y727L, L728S, N731E, N731S, V732R, W734G, W734V, A735Q, A735S, T738S, I739K, S740D, A741I, Y744R, D745F, D745N, N747R, L750S, P752A, P752C, P752Y, G754P, T756N, T756S, E757A, A760N, A769F, A769I, A769N, A769V, A769Y, K770H, L771A, K772A, K772C, K772P, K772V, A773C, A773H, A773M, A773R, A773V, D774A, D774R, A775L, A775W, D776I, D776L, D776S, D776V, R777D, R777E, R777G, R777H, R777P, R777S, K778L, K778N, T781A, T781F, T781G, T781M, T781P, T781Y, A782P, A782Q, D783A, D783C, D783E, D783R, G784L, G784S, G784T, K785S, K785W, K785Y, D786V, L787P, L787T, S788G, S788I, Y789V, I790C, I790R, V792G, D793H, V794C, V794T, V794W, T795P, D796Q, N798I, G799K, G799L, G799M, G799Q, H800A, H800L, V802Y, P803S, D804Q, A806I, A806Q, N807W, R808C, R808F, R808N, T810P, T810Q, D812Q, V813T, V813W, K814H, K814L, G815A, G815V, A816C, A816F, K818F, K818L, K818W, K818Y, L819F, V820K, G821E, G821F, G821I, G821N, V822D, V822E, S826G, S826L, P828C, D829S, H830E, H830R, H830V, D831F, D831I, D831P, D831R, D831V, S832R, Y833K, Y833V, A835D, A835F, A835H, A835K, A835W, D836C, D836E, D836H, D836S, D836V, D836Y, N837D, R838G, R838M, R838N, K839A, K839D, A840G, A840P, A840V, F841C, F841W, K844G, V845W, V849L, V849S, Q850C, Q850G, Q850Y, E854C, E857P, I858D, I858Q, I858Y, T859V, V860T, T861W, A862V, K863F, K863N, K863W, D865A, D865G, G866H, L867W, S870E, S870R, V872C, K873G, K873Y, I874G, T877A, G881W, S883L, T884A, K886E, K886V, K886W, T887F, T887G, V888A, Y892P, Y892R, Y893E, N896M, Y897V, K900E, T901G, T901Q, T901R, T901V, T901Y, G902F, G902L, G902R, G902S, G902W, N903D, K904M, K904N, K904S, K904V, P905C, P905R, P905Y, I906W, L907F, P908I, P908L, D910W, E912T, R914A, R914F, R914I, R914K, R914V, R914Y, Y915A, Y915C, Y915G, Y915M, Y915Q, Y915V, S916G, D917C, D917F, D917S, G918E, G918H, G918T, T919D, T919Q, S920E, D921V, R922A, Q923V, T926G, T926R, W927G, W927P, A929P, D933R, Q934S, I935A, I935C, I935E, I935P, I935W, A936I, A936Q, K937G, K937I, K937P, K937Q, A938C, G939D, S940C, S940T, F941C, S942K, S942V, V943A, V943H, V943R, A944D, A944H, A944P, A944R, T946P, T946V, V947G, V947M, V947R, V947T, A948C, A948R, A948W, Q950K, K951S, S953M, S953W, R955C, R955W, V956D, V956Q, M958D, E961D, E961F, E961S, I962C, I962K, I962N, L965C, L965G, L965K, L965M, L965Y, L966A, L966H, N967M, Y968G, Y968Q, Y968V, S969C, S969I, S969L, S969M, S969Q, A970I, S971V, P973C, P973W, V974T, T976K, T976P, P977C, P977T, A978F, A978M, V979R, L980H, L980N, P981M, P985L, P985W, A986I, A986L, V987A, V987F, V987K, D990W, G991Y, S995L, N997K, A999G, V1000N, D1001L, W1002A, W1002D, W1002E, W1002H, W1002N, W1002P, W1002Q, T1003L, T1003Y, K1004H, P1005Y, A1006C, A1006S, D1007P, N1011T, T1012Q, G1014I, V1018K, T1021F, A1022H, V1024G, V1024H, G1026R, G1026V, K1030D, K1030W, I1035D, Q1041P, V1042N, V1048C, V1048G, V1048M, V1048Q, G1050S, N1051E, N1051K, A1052K, L1053A, Q1057E, Q1057R, N1058V, I1059W, A1061G, D1062L, D1062M, Q1064M, S1065A, D1066M, D1066V, D1066W, T1067M, L1068C, L1068P, A1070P, I1071W, K1072G, K1072Q, K1072S, D1073P, G1074I, G1074L, S1075C, T1082F, G1083E, G1083F, G1083L, G1083S, G1084V, G1085S, P1088E, P1088R, S1089C, S1089G, S1089Q, W1091A, W1091E, W1091G, W1091T, W1091V, W1091Y, T1092G, T1092Q, N1093A, N1093P, N1093Q, W1094D, W1094E, S1097W, K1098D, A1099V, G1100M, H1101V, N1102E, N1102H, T1103E, A1104R, I1106T, T1107S, F1108D, F1108L, E1109A, E1109D, E1109L, E1109W, A1111G, E1113P, E1113V, Q1114E, Q1114R, Q1114S, Q1114T, Q1114V, Q1115A, Q1115K, L1116K, L1116W, G1117I, G1117R, G1117S, G1117T, G1117V, G1117W, I1119N, M1121G, M1121V, R1125V, R1125W, D1126H, S1127I, S1127Q, N1128A, A1129E, A1129Q, A1129V, V1130A, V1130G, V1130R, P1133D, P1133R, D1134L, A1135L, A1135S, A1135W, G1136A, G1136E, G1136P, K1137C, K1137L, K1137Q, K1137R, K1137S, I1140G, I1140L, I1140P, Q1141K, Q1141P, I1142Y, A1144C, A1144N, A1144P, A1144S, A1144V, A1144W, D1145E, D1145R, D1145T, N1148P, W1149C, W1149I, W1149V, T1150K, D1151R, D1151W, L1152W, A1153G, A1154C, E1162A, E1165L, A1167R, K1168W, Y1170E, T1171A, T1171G, A1175N, A1175Q, V1177N, V1177T, G1178M, G1178T, A1179L, A1179W, T1180A, T1180G, T1180I, T1180M, T1180Q, T1180Y, V1184E, V1184L, V1184P, V1184Q, V1184Y, V1186S, N1188W, D1190T, T1191L, T1192H, V1197A, C1199T, A1200W, L1202A, E1204G, K1208W, T1209E, T1209K, A1210D, A1210E, A1210G, A1210K, A1210L, A1210R, A1210T, A1210W, T1211G, T1211K, T1211P, T1211R, T1211S, F1214A, F1214K, F1214S, F1214V, V1215D, V1215L, T1216L, T1216Q, N1217A, N1217S, N1217T, T1218C, T1218E, T1218S, T1218W, S1219A, S1219F, A1220L, L1222A, L1222E, L1222F, L1222V, S1223V, S1224A, S1224G, S1224P, S1224W, L1225E, L1225K, L1225W, T1226P, T1226S, T1226V, N1228D, N1228F, G1229V, T1230I, T1230K, T1230W, K1231F, K1231P, V1232K, V1232R, S1233P, S1233W, S1235W, V1236A, V1236G, V1236P, L1237D, A1238E, A1238R, G1240W, Y1242E, Y1242R, N1243M, N1243T, T1244Q, A1246M, I1248G, A1249H, A1249I, A1249V, D1250I, D1250K, D1250S, D1250T, D1250W, D1250Y, K1252D, G1255H, N1258H, A1259K, T1262R, V1263T, V1263W, P1265R, P1265W, N1269A, N1269K, I1274F, I1274R, T1275W, S1277L, S1277T, S1277W, E1278Q, D1279R, D1279W, H1280E, V1281I, V1281W, K1284F, F1286E, F1286P, T1287C, T1287S, T1287W, I1288A, I1288D, I1288G, I1288K, G1291P, G1291Y, T1292Y, E1295K, F1296A, E1302R, E1302S or D1304V.

93. The lactase variant of the preceding embodiment, wherein the variant has a decreased or an increased galactose inhibition, preferably measured as a galactose inhibition improvement factor (GI-IF) of at least 1.3 or at most 0.7, compared to the lactase of SEQ ID NO: 1.

94. The lactase variant of embodiment 1 which comprises one or more of the following substitutions, wherein each position corresponds to a position in SEQ ID NO: 1: V1H, V1L, E2D, E2V, D3I, D3V, S7N, S7P, M13C, M13R, S14V, S15C, S15I, S15K, S15T, S15V, T16C, P17I, V20C, V20M, V20P, Y21C, Y21P, Y21R, Y21T, S22W, A24F, A24L, A24T, A24W, V25Q, D26C, S27A, S27C, S27H, K28C, Q29L, Q29M, Q29R, R31E, R31T, T32S, F35C, W39G, K40C, K40F, K40I, F41A, M42T, L435, D45P, V47K, V47R, A49D, A49H, A49T, D51I, D51K, D55C, D55H, D55M, D55P, S57C, S57E, S57G, A58Q, A58T, W59I, W59K, W59P, Q60R, Q60S, V62N, V62T, V62W, L64E, H66R, K73D, S75G, S75L, S75R, S75V, Q76G, Q76I, S77D, S77E, S77G, S77H, S77K, S77R, N78C, E79H, E79S, E79T, A83T, L85A, L85F, L85N, L85S, L85V, L85W, P86Q, G87D, G88F, G90T, W91P, W91Y, Y92H, Y92I, Y92M, Y92S, Y92T, Y92V, R93A, R93D, R93F, R93H, R93I, R93L, R93N, R93T, R93V, R93Y, K94A, K94S, K94T, S95C, S95D, S95G, S95I, F96A, F96C, F96I, F96K, F96M, F96P, F96V, T97F, I98C, I98H, R100T, D101A, D101P, L102P, R106W, I107S, A108E, I109M, N110A, N110S, N110T, N110W, F111A, F111L, V114R, Y115E, M116C, A118P, V120A, V120K, W121R, W121V, H130A, H130T, Y132E, F137L, T142S, G149M, E150L, V154K, V154L, V157P, V157S, E158H, N159T, L161K, L161M, L161S, L161W, P162N, P162T, P162W, S164A, R165H, W166S, Y167A, S170Q, I172K, I172P, Y173H, R174E, V176E, V176K, T177K, L178I, L178Q, T179C, T179I, T179N, V180D, V180G, T181A, V184R, H185G, H185L, G187D, N188V, G190F, K194I, S197C, A199P, Q201E, N202Q, N202S, N202W, D217L, D217M, T218G, A220G, A222R, N223S, Q228R, K236M, T237G, G242K, I251Y, A252W, A252Y, S261H, A266D, S267V, P268R, S272T, S272W, V281Q, V291P, L292V, D293C, D293W, Y295F, D296F, D296K, E298I, E298R, F301C, W303A, W303C, W303D, T304D, T304K, T304P, G305N, G305P, T309C, T309D, T309E, 5310H, 5310L, 5310N, F312H, L314A, L314V, N315S, K318N, K320V, K320W, L321M, K322I, V324T, S325G, M326T, H328C, H328F, H328G, H328M, H328T, G331V, A335G, A335L, A337G, A337L, R340A, R340L, A341M, I342G, E343N, E343Y, R344G, Q345S, V346A, E347A, I348D, I348M, Q350G, M352T, G353K, I357T, T359E, T359L, T360V, N362S, N362T, P363A, P363I, P363L, P363M, A364I, A364M, A364P, A365C, A365I, A365P, A365V, K366L, K366M, K366S, L368A, L368Q, L368S, I369E, I369G, I369K, I369V, I369W, D370L, V371F, V371Q, C372P, N373G, N373L, G376A, G376S, V377M, V377T, V379A, V379N, V380P, E381A, E381G, E381Q, E381T, V383A, M386G, M386N, M386S, W387H, N388L, R389A, R389E, R389Q, R389S, R389T, S390C, S390D, S390P, S390T, G393E, G393R, G393V, T395C, E396K, E396L, E396V, E396W, Y398M, G399S, K400A, K400C, K400N, K400V, W401F, W401K, F402W, F402Y, G403A, G403K, G403Q, G403V, Q404F, Q404L, Q404M, Q404P, Q404V, A405C, A405E, A405K, A405R, A405T, I406D, I406N, A407C, A407G, A407Q, N410Y, A411E, G414M, G414N, K417F, K417R, A422P, T427D, T427F, T427Q, T427S, T429D, N431M, D433G, D433I, D433P, D433Q, D433W, R434N, R434V, N435E, N435L, A436L, V439C, V439K, W442E, W442G, S443C, S443G, S443Q, L444E, L444V, N446D, M448C, M448L, M449D, M449T, M449W, M449Y, E450F, E450S, E450T, E450V, E450W, G451C, G451F, G451L, G451P, G451V, G451W, I452K, I452S, I452V, G454L, S455P, S455R, V456D, V456E, V456F, V456K, S457H, S457T, S457V, G458A, G458P, G458S, F459R, A461M, T462E, T462L, K465V, K465Y, L466P, A468D, K471F, A472G, A472Y, S475E, R477L, M479G, K485E, K485R, K487F, K487S, K487W, S493G, S493L, S493Q, N494R, G497D, N499T, G505D, G505R, G505S, V506C, V506E, V506R, V507R, G508C, G508E, T509A, T509K, T509M, N510A, N510F, N510I, Y511A, S512F, S512Q, S512T, S512V, S512Y, D513P, D513R, A515E, A515P, N516C, N516E, N516Q, N516V, Y517G, D518Y, K519C, K519I, I520C, I520G, I520H, I520M, I520S, I520T, R521V, H524R, H524V, S526G, W527A, W527H, W527N, W527R, W527S, A528E, A537M, A537P, S540E, G549D, G549P, G549W, L558E, L558P, T559Y, S564C, S564F, S564W, A565D, A565E, A565I, A565L, A565R, A565T, G567Q, G567V, A570G, A575D, R582L, D583W, W591F, T592L, G598N, P600A, P600E, P600G, P600S, G607Q, W614A, N619I, N619L, V625M, V625Y, T627K, T627Q, A628D, F630C, F630Y, P631D, T634W, Q639R, W655R, E657R, A661E, A661K, A661Q, N667L, N667R, P669T, Y673S, T674M, A676P, V679S, K680I, G687P, S688K, S688L, T689W, E690D, R692G, R692H, I694L, I694W, G695C, G695L, G695W, K697R, S698E, S698M, K701A, K701G, K701M, K701S, A705W, Y708F, Y710T, V712M, V712Q, E714K, A716R, D717G, D717S, K718A, K718T, D719E, D719T, D719V, T721H, T721L, T721N, T721S, T721V, T721W, H723G, M726D, Y727L, L728S, N731E, V732R, W734G, A735Q, A735S, T738S, I739K, S740D, A741I, Y744R, D745N, L750S, P752C, P752Y, T756N, E757A, A769F, A769I, A769N, A769V, A769Y, K770H, L771A, K772A, K772C, K772P, A773C, A773M, A773R, D774A, D776V, R777H, R777S, K778N, T781A, T781F, T781G, T781P, T781Y, A782Q, D783A, K785S, K785W, K785Y, D786V, Y789V, I790R, N798I, G799K, G799L, V802Y, P803S, A806I, A806Q, R808F, T810P, T810Q, V813W, K818F, K818L, K818W, K818Y, L819F, G821I, V822D, V822E, S826G, D829S, D831P, S832R, A835D, A835H, A835K, D836C, D836E, D836S, D836V, D836Y, R838N, K839A, K839D, A840G, A840P, A840V, E854C, I858D, T861W, D865A, D865G, G866H, L867V, S870E, V872C, K873G, K873Y, I874G, S883L, K886V, K886W, T887G, V888A, Y892P, Y893E, Y897V, K900E, T901Q, T901R, T901Y, G902F, G902R, G902S, G902W, N903D, K904M, K904N, K904S, K904V, P905C, P905R, P905Y, I906W, L907F, P908I, P908L, D910W, E912T, R914A, R914F, R914I, R914K, R914V, R914Y, Y915A, Y915C, Y915G, Y915M, Y915Q, Y915V, S916G, D917C, D917F, D917S, G918E, G918H, G918T, T919D, T919Q, D921V, R922A, Q923V, T926R, W927P, A929P, D933R, Q934S, I935A, I935C, I935E, I935P, I935W, A936I, A936Q, K937G, K937I, K937P, K937Q, A938C, G939D, S940C, F941C, S942K, S942V, V943A, T946P, V947G, V947R, V947T, A948W, K951S, S953M, R955C, R955W, V956D, V956Q, E961D, E961F, E961S, I962C, I962K, I962N, L965C, L965G, L965K, L965M, L965P, L965Y, L966A, N967M, Y968G, Y968Q, Y968V, S969C, S969I, S969L, S969M, S969Q, A970I, S971V, P973C, P973W, V974T, T976K, T976P, P977C, P977T, A978F, A978M, L980H, L980N, P981M, P985L, P985W, A986I, A986L, V987A, V987F, V987K, D990W, G991Y, S995L, N997K, D1001L, W1002A, W1002D, W1002E, W1002H, W1002N, W1002P, W1002Q, T1003Y, P1005Y, A1006C, A1006S, D1007P, N1011T, T1012Q, G1014I, V1018K, A1022H, V1024G, V1024H, G1026V, K1030D, K1030W, I1035D, Q1041P, V1042N, V1048C, V1048G, V1048M, V1048Q, N1051E, N1051K, A1052K, L1053A, Q1057E, A1061G, D1062M, Q1064M, S1065A, D1066V, T1067M, L1068P, K1072S, G1074L, T1082F, G1083E, G1083F, G1083L, G1084V, G1085S, P1088E, P1088R, S1089G, S1089Q, W1091Y, N1093A, N1093P, N1093Q, W1094D, W1094E, K1098D, A1099V, H1101V, N1102H, T1103E, E1109A, E1109D, E1109L, E1109W, A1111G, E1113P, E1113V, Q1114E, Q1114R, Q1114S, Q1114T, Q1114V, Q1115A, Q1115K, L1116K, L1116W, G1117I, G1117R, G1117S, G1117T, G1117V, G1117W, I1119N, M1121G, R1125V, R1125W, S1127I, S1127Q, N1128A, A1129E, V1130A, V1130R, P1133D, P1133R, A1135L, A1135W, G1136P, K1137R, K1137S, I1140P, Q1141K, I1142Y, A1144N, A1144P, A1144S, A1144V, A1144W, D1145E, D1145R, D1145T, N1148P, W1149C, W1149V, T1150K, D1151W, L1152W, A1153G, E1162A, V1167R, G1178M, G1178T, A1179L, A1179W, T1180A, T1180G, T1180I, T1180M, T1180Q, T1180Y, V1184E, V1184L, V1184P, V1184Q, V1184Y, V1186S, N1188W, D1190T, T1191L, V1197A, E1204G, K1208W, T1209E, T1209K, A1210D, A1210G, A1210K, A1210L, A1210R, A1210T, A1210W, T1211G, T1211K, T1211P, T1211R, T1211S, F1214A, F1214K, F1214S, F1214V, V1215D, V1215L, T1216L, T1216Q, N1217A, N1217S, N1217T, T1218C, T1218E, T1218S, T1218W, L1222A, L1222E, L1222F, L1222V, S1224P, S1224W, L1225E, L1225K, T1226P, G1229V, T1230K, T1230W, V1232R, S1235W, V1236A, V1236G, V1236P, A1238E, A1238R, G1255H, A1259K, T1262R, V1263T, P1265W, I1274F, I1274R, T1275W, S1277L, S1277T, S1277W, E1278Q, D1279R, D1279W, H1280E, V1281I, V1281W, K1284G, F1286E, F1286P, T1287C, T1287S, T1287W, I1288A, I1288D, I1288G, I1288K, E1295K, F1296A, E1302R, E1302S or D1304V.

95. The lactase variant of the preceding embodiment, wherein the variant has a decreased galactose inhibition, preferably measured as a galactose inhibition improvement factor (GI-IF) of at least 1.3, compared to the lactase of SEQ ID NO: 1.

96. The lactase variant of embodiment 1 which comprises one or more of the following substitutions, wherein each position corresponds to a position in SEQ ID NO: 1: V1H, V1L, E2D, E2V, D3I, D3V, S7N, S7P, M13C, M13R, S14V, S15C, S15I, S15K, S15T, S15V, T16C, P17I, V20C, V20M, V20P, Y21C, Y21P, Y21R, Y21T, S22W, A24F, A24L, A24T, A24W, V25Q, D26C, S27A, S27C, S27H, K28C, Q29L, Q29M, Q29R, R31E, R31V, T32S, F35C, W39G, K40C, K40F, K40I, F41A, M42T, L435, D45P, V47K, V47R, A49D, A49H, A49T, D51I, D51K, D55C, D55H, D55M, D55P, S57C, S57E, S57G, A58Q, A58T, W59I, W59K, W59P, Q60R, Q60S, V62N, V62T, V62W, L64E, H66R, K73D, S75G, S75L, S75R, S75V, Q76G, Q76I, S77D, S77E, S77G, S77H, S77K, S77R, N78C, E79H, E79S, E79T, A83T, L85A, L85F, L85N, L85S, L85V, L85W, P86Q, G87D, G88F, G90T, W91P, W91Y, Y92H, Y92I, Y92M, Y92S, Y92T, Y92V, R93A, R93D, R93F, R93H, R93I, R93L, R93N, R93T, R93V, R93Y, K94A, K94S, K94T, S95C, S95D, S95G, S95I, F96A, F96C, F96I, F96K, F96M, F96P, F96V, T97F, I98C, I98H, R100T, D101A, D101P, L102P, R106W, I107S, A108E, I109M, N110A, N110S, N110T, N110W, F111A, F111L, V114R, Y115E, M116C, A118P, V120A, V120K, W121R, W121V, H130A, H130T, Y132E, F137L, T142S, G149M, E150L, V154K, V154L, V157P, V157S, E158H, N159T, L161K, L161M, L161S, L161W, P162N, P162T, P162W, S164A, R165H, W166S, Y167A, S170Q, I172K, I172P, Y173H, R174E, V176E, V176K, T177K, L178I, L178Q, T179C, T179I, T179N, V180D, V180G, T181A, V184R, H185G, H185L, G187D, N188V, G190F, K194I, S197C, A199P, Q201E, N202Q, N202S, N202W, D217L, D217M, T218G, A220G, A222R, N223S, Q228R, K236M, T237D, G242K, I251Y, A252W, A252Y, S261H, A266D, S267V, P268R, S272T, S272W, V281Q, V291P, L292V, D293C, D293W, Y295F, D296F, D296K, E298I, E298R, F301C, W303A, W303C, W303D, T304D, T304K, T304P, G305N, G305P, T309C, T309D, T309E, 5310H, 5310L, 5310N, F312H, L314A, L314V, N315S, K318N, K320V, K320W, L321M, K322I, V324T, S325G, M326T, H328C, H328F, H328G, H328M, H328T, G331V, A335G, A335L, A337G, A337L, R340A, R340L, A341M, I342G, E343N, E343Y, R344G, Q345S, V346A, E347A, I348D, I348M, Q350G, M352T, G353K, I357T, T359E, T359L, T360V, N362S, N362T, P363A, P363I, P363L, P363M, A364I, A364M, A364P, A365C, A365I, A365P, A365V, K366L, K366M, K366S, L368A, L368Q, L368S, I369E, I369G, I369K, I369V, I369W, D370L, V371F, V371Q, C372P, N373G, N373L, G376A, G376S, V377M, V377T, V379A, V379N, V380P, E381A, E381G, E381Q, E381T, V383A, M386G, M386N, M386S, W387H, N388L, R389A, R389E, R389S, R389T, S390C, S390D, S390T, G393E, G393R, G393V, T395C, E396K, E396L, E396V, E396W, Y398M, G399S, K400A, K400C, K400N, K400V, W401F, W401K, F402W, F402Y, G403A, G403K, G403Q, G403V, Q404F, Q404L, Q404M, Q404P, Q404V, A405C, A405E, A405K, A405R, I406D, I406N, A407C, A407G, A407Q, N410Y, A411E, G414M, G414N, K417F, K417R, A422P, T427D, T427F, T427Q, T427S, T429D, N431M, D433G, D433I, D433P, D433Q, D433W, R434N, R434V, N435E, N435L, A436L, V439C, V439K, W442E, W442G, S443C, S443G, S443Q, L444E, L444V, N446D, M448C, M448L, M449D, M449T, M449W, M449Y, E450F, E450S, E450T, E450V, E450W, G451C, G451F, G451L, G451P, G451V, G451W, I452K, I452S, I452V, G454L, S455P, S455R, V456D, V456E, V456F, V456K, S457H, S457T, S457V, G458A, G458P, G458S, F459R, A461M, T462E, T462L, K465V, K465Y, L466P, A468D, K471F, A472G, A472Y, S475E, R477L, M479G, K485E, K485R, K487F, K487S, K487W, S493G, S493L, S493Q, N494R, G497D, N499T, G505D, G505R, G505S, V506C, V506L, V506R, V507C, V507R, V508C, V508G, T509A, T509K, T509M, N510A, N510F, N510I, Y511A, S512F, S512Q, S512T, S512V, S512Y, D513P, D513R, A515E, N516C, N516E, N516Q, N516V, Y517G, D518Y, K519C, K519I, I520C, I520G, I520H, 1520M, I520S, I520T, R521V, H524R, H524V, S526Q, W527A, W527H, W527N, W527R, W527S, A528E, A537M, A537P, S540E, G549D, G549P, G549W, L558E, L558P, T559Y, S564C, S564F, S564W, A565A, A565E, A565I, A565L, A565R, A565T, G567Q, G567V, A570G, A575D, R582L, D583W, W591F, T592L, G598N, P600A, P600E, P600G, P600S, G607Q, W614A, N619I, N619L, V625M, V625Y, T627K, T627Q, A628D, F630C, F630Y, P631D, T634V, Q639R, W655R, E657R, A661E, A661K, A661Q, N667L, N667R, P669T, Y673S, T674M, A676P, V679S, K680I, G687P, S688K, S688L, T689W, E690D, R692G, R692H, I694L, I694W, G695C, G695L, G695W, K697W, S698E, S698M, K701A, K701G, K701M, K701S, A705W, Y708F, Y710T, V712M, V712Q, E714K, A716P, D717G, D717S, K718A, K718T, D719E, D719I, D719V, T721H, T721L, T721N, T721S, T721V, T721W, H723G, M726D, Y727L, L728S, N731E, V732R, W734G, A735Q, A735S, T738S, I739K, S740D, A741I, Y744R, D745N, L750S, P752C, P752Y, T756N, E757A, A769F, A769I, A769N, A769V, A769Y, K770H, L771A, K772A, K772C, K772P, A773C, A773M, A773R, D774A, D776V, R777H, R777S, K778N, T781A, T781F, T781G, T781P, T781Y, A782Q, D783A, K785S, K785W, K785Y, D786V, Y789V, I790R, N798I, G799K, G799L, V802Y, P803S, A806I, A806Q, R808F, T810P, T810Q, V813W, K818F, K818L, K818W, K818Y, L819F, G821I, V822D, V822E, S826G, D829S, D831P, S832R, A835D, A835H, A835K, D836C, D836E, D836S, D836V, D836Y, R838N, K839A, K839D, A840G, A840P, A840V, E854C, I858D, T861W, D865A, D865G, G866H, L867W, S870E, V872C, K873G, K873Y, I874R, S883L, K886V, K886W, T887G, V888A, Y892P, Y893E, Y897V, K900E, T901Q, T901R, T901Y, G902F, G902R, G902S, G902W, N903D, K904M, K904N, K904S, K904V, P905C, P905R, P905Y, I906W, L907F, P908I, P908L, D910W, E912T, R914A, R914F, R914I, R914K, R914V, R914Y, Y915A, Y915C, Y915G, Y915M, Y915Q, Y915V, S916G, D917C, D917F, D917S, G918E, G918H, G918T, T919D, T919Q, D921V, R922A, Q923V, T926R, W927P, A929P, D933R, Q934S, I935A, I935C, I935E, 1935P, I935W, A936I, A936Q, K937G, K937I, K937P, K937Q, A938C, G939D, S940C, F941C, S942K, S942V, V943A, T946P, V947G, V947R, V947I, A948W, K951S, S953M, R955C, R955W, V956D, V956G, E961D, E961F, E961S, I962C, I962K, I962N, L965C, L965G, L965K, L965M, L965P, L965Y, L966A, N967M, Y968G, Y968Q, Y968V, S969C, S969I, S969L, S969M, S969Q, A970I, S971V, P973C, P973W, V974T, T976K, T976P, P977C, P977T, A978F, A978M, L980H, L980N, P981M, P985L, P985W, A986I, A986L, V987A, V987F, V987K, D990W, G991Y, S995L, N997K, D1001L, W1002A, W1002D, W1002E, W1002H, W1002N, W1002P, W1002Q, T1003Y, P1005Y, A1006C, A1006S, D1007P, N1011T, T1012Q, G1014I, V1018K, A1022H, V1024G, V1024H, G1026V, K1030D, K1030W, I1035D, Q1041P, V1042N, V1048C, V1048G, V1048M, V1048Q, N1051E, N1051K, A1052K, L1053A, Q1057E, A1061G, D1062M, Q1064M, S1065A, D1066V, T1067M, L1068P, K1072S, G1074L, T1082F, G1083E, G1083F, G1083L, G1084V, G1085S, P1088E, P1088R, S1089G, S1089Q, W1091Y, N1093A, N1093P, N1093Q, W1094D, W1094E, K1098D, A1099V, H1101V, N1102H, T1103E, E1109A, E1109D, E1109L, E1109W, A1111G, E1113P, E1113V, Q1114E, Q1114R, Q1114S, Q1114T, Q1114V, Q1115A, Q1115E, L1116K, L1116W, G1117I, G1117R, G1117S, G1117T, G1117V, G1117W, I1119N, M1121C, R1125V, R1125W, S1127I, S1127Q, N1128A, A1129E, V1130A, V1130R, P1133D, P1133R, A1135L, A1135W, G1136P, K1137R, K1137S, I1140P, Q1141K, I1142Y, A1144N, A1144P, A1144S, A1144V, A1144W, D1145E, D1145R, D1145T, N1148P, W1149C, W1149V, T1150K, D1151W, L1152W, A1153G, E1162A, V1167R, G1178M, G1178T, A1179L, A1179W, T1180A, T1180G, T1180I, T1180M, T1180Q, T1180Y, V1184E, V1184L, V1184P, V1184Q, V1184Y, V1186S, N1188W, D1190T, T1191L, V1197A, E1204G, K1208W, T1209E, T1209K, A1210D, A1210G, A1210K, A1210L, A1210R, A1210T, A1210W, T1211G, T1211K, T1211P, T1211R, T1211S, F1214A, F1214K, F1214S, F1214V, V1215D, V1215L, T1216L, T1216Q, N1217A, N1217S, N1217T, T1218C, T1218E, T1218S, T1218W, L1222A, L1222E, L1222F, L1222V, S1224P, S1224W, L1225E, L1225K, T1226P, G1229V, T1230K, T1230W, V1232R, S1235W, V1236A, V1236G, V1236P, A1238E, A1238R, G1255H, A1259K, T1262R, V1263T, P1265W, I1274F, I1274R, T1275W, S1277L, S1277T, S1277W, E1278Q, D1279R, D1279W, H1280E, V1281I, V1281W, K1284G, F1286E, F1286P, T1287C, T1287S, T1287W, I1288A, I1288D, I1288G, I1288K, E1295K, F1296A, E1302R, E1302S or D1304V.

97. The lactase variant of the preceding embodiment, wherein the variant has a decreased galactose inhibition, preferably measured as a galactose inhibition improvement factor (GI-IF) of at least 1.3, compared to the lactase of SEQ ID NO: 1.

98. The lactase variant of embodiment 1 which comprises one or more of the following substitutions, wherein each position corresponds to a position in SEQ ID NO: 1: E2V, D3I, D3S, D3V, S7P, M13R, S15C, S15I, S15K, S15Y, T16C, V20P, Y21C, Y21R, Y21T, S23L, S23M, A24F, A24T, D26C, S27A, K28C, Q29L, Q29M, Q29R, R31E, R31V, T32S, D34S, F35E, K40F, K40I, M42E, L43T, D45P, V47K, V47R, A49D, A49H, A49R, A49T, D51I, D51K, D51P, A53S, D55H, D55M, S57C, S57E, S57G, A58T, W59P, V62N, L64E, H66Y, K73S, S75G, S75L, S75R, Q76G, S77E, S77F, S77H, S77K, N78C, E79H, E79S, E79T, E81A, E81Q, L85F, L85S, L85V, L85W, P86Q, G87D, G88F, G88Q, G90T, W91Y, Y92H, Y92M, Y92S, Y92V, R93A, R93D, R93F, R93H, R93L, R93N, R93T, R93V, R93Y, K94S, S95C, S95G, S95I, F96A, F96C, F96I, F96S, F96V, T97F, I98H, R100T, D101A, D101P, L102P, I109M, N110T, F111A, F111L, D112T, V114R, Y115E, V120A, W121R, W121V, G124E, H130A, H130T, Y132E, P136R, F137L, K146A, G149M, E150L, I153A, V157P, E158G, E158H, N159T, L161K, L161S, L161W, P162N, P162T, P162W, R165H, W166S, Y167A, S170Q, I172P, R174E, V176E, V176K, T177K, L178I, L178Q, T179C, V180G, H185G, H185L, N188V, N189E, G190C, S197C, D217L, D217M, T218G, A220G, A220V, A222R, N223S, Q228R, K233P, K236M, T237D, A239G, A239T, G242Y, A247P, A247R, S248E, K249G, K249Y, I251Y, A252F, A252W, A252Y, G254I, G254R, A255K, S256Y, S261R, T262D, T264M, P268R, S272W, L278V, Y279W, L286F, V291D, V291P, L292V, D293C, D296F, E298I, E298R, F301C, W303A, T304P, G305N, G305P, G305W, T309D, F312H, K320V, K320W, S325G, M326E, M326G, M326T, M326Y, H328C, H328M, H328T, A337G, A337L, R340A, A341M, I342K, E343N, Q345G, Q345K, Q345S, I348D, Q350G, T359E, T360V, N362S, N362T, P363I, P363L, P363M, A364I, A364M, A364P, A365C, L368E, L368Q, L368S, I369G, I369K, I369W, D370L, N373G, N373L, G376A, G376S, V377M, V379A, V380P, E381A, E381T, M386G, M386N, M386S, W387L, N388L, N388R, R389A, R389E, R389Q, R389S, R389T, S390C, S390D, S390G, S390P, S390Q, S390T, K391E, N392D, G393R, G393V, N394L, T395C, T395H, T395N, T395S, T395W, E396K, E396L, E396V, E396W, Y398N, G399S, K400A, K400C, K400N, K400P, K400S, K400V, W401F, W401K, F402W, F402Y, G403A, G403K, G403V, Q404F, Q404H, Q404L, Q404M, Q404P, Q404V, A405C, A405E, A405H, A405R, A405T, I406D, I406N, G408W, D409N, A411E, L413P, G414A, G414R, D416I, D416Y, K417F, D418P, D418R, E419M, E419R, T420K, T420R, K423D, F424C, F424L, L426M, T427D, T427Q, T427S, T429D, N431M, D433P, D433W, R434N, R434V, N435L, A436L, V439C, V439G, V439K, V439T, W442E, W442G, W442R, S443C, S443Y, L444V, G445A, G445C, G445V, M448C, M448L, M448S, M449D, M449T, M449W, M449Y, E450F, E450S, E450T, E450V, E450W, G451C, G451F, G451L, G451P, G451V, G451W, I452K, G454L, S455P, S455R, V456D, V456E, V456F, V456K, S457T, S457V, G458A, G458P, F459R, F459S, K465Y, L466P, L466V, A468D, A472G, A472Y, S475E, R477L, M479G, M479K, K485E, K487F, K487N, A488N, N491W, S493M, S493Q, T495W, D498C, N499R, N499T, N499Y, L500A, G504H, G505D, G505S, V506C, V506E, V506R, V507L, V507R, G508C, G508E, T509K, T509M, N510A, N510F, N510I, Y511A, S512F, S512T, S512Y, D513L, D513P, D513R, G514F, A515E, N516C, Y517G, D518Y, K519C, K519I, I520G, I520H, I520S, R521N, R521V, T522N, H524R, H524V, P525T, S526Q, W527N, W527R, W527S, A528E, G531F, A537P, S540E, R546L, R546P, R546S, T547A, T547S, T548F, T548K, T548P, G549P, G549W, G550S, A551Q, S553N, S554N, D555S, K556W, L558P, T559Y, S564C, S564F, A565E, A565I, A565R, G567Q, G567V, A570K, A570M, A572S, S574W, W576Y, Y577L, V579G, R582L, D583W, V585I, A586K, T588D, T592C, T592L, T592S, F594L, D595Q, P600A, P600E, P600G, P600S, G607Q, S608V, G609N, G609R, A610M, V611W, W614A, N619L, S620G, V625M, V625Y, F630G, T634V, Y635R, Q639R, D644C, H650R, W655R, N656V, A661E, P669T, V670C, Y673S, A676P, K680I, T684V, G687P, S688L, R692H, I694L, I694W, G695C, G695L, G695W, K697R, S698E, T700C, K701A, K701G, K701M, A705W, T709M, Y710T, V712M, E714K, A716R, D717G, D717S, K718A, D719T, D719V, T721N, T721S, T721W, H723G, M726D, L728S, N731S, W734G, W734V, A735Q, A735S, I739K, S740D, A741I, D745F, L750S, P752A, P752C, P752Y, G754P, T756N, T756S, E757A, A760N, A769F, A769I, A769N, A769V, A769Y, K770R, K772A, K772C, K772P, A773C, A773H, A773V, D774A, A775L, A775W, D776I, D776L, D776S, R777D, R777E, R777G, R777H, R777P, R777S, T781A, T781G, T781P, T781Y, A782Q, D783C, D783E, D783R, G784L, G784K, K785S, K785W, D786V, L787P, L787T, Y789V, V792G, D793H, V794T, T795P, N798I, G799K, G799L, G799M, G799Q, H800A, H800L, P803A, A806Q, R808C, T810P, V813T, K814G, G815A, A816C, A816F, K818F, K818L, K818W, G821E, G821I, V822D, V822E, S826L, H830R, D831I, D831P, D831V, S832R, A835D, A835H, A835W, D836E, D836H, D836S, D836Y, R838G, K839D, A840G, K844G, Q850C, Q850G, E854C, I858D, I858Q, I858Y, K863F, K863N, D865A, D865G, L867W, S870R, V872C, I874G, S883L, T887F, T887G, V888A, Y892P, Y892R, Y893E, T901V, T901Y, G902R, G902S, G902W, N903D, K904M, K904V, P905R, P905Y, I906W, P908I, D910W, E912T, R914A, R914F, R914K, R914Y, Y915A, Y915C, Y915M, Y915V, S916G, D917C, D917F, D917S, G918H, T919Q, D921V, R922A, Q923V, W927G, Q934S, I935P, A936Q, K937I, K937P, A938C, S940T, S942K, S942V, V943A, V943H, V943R, A944P, T946P, T946V, V947C, A948C, Q950P, V956C, E961D, E961F, E961S, I962C, I962N, L965C, L965G, L965M, L965P, L965Y, L966A, Y968G, Y968V, S969C, S969I, S969M, P973C, T976K, T976P, P977T, A978M, V979R, L980H, L980N, P981M, P985L, P985W, A986I, V987K, D990W, S995L, N997K, D1001L, W1002A, W1002D, W1002H, W1002N, W1002P, T1003Y, K1004H, A1006S, D1007P, V1018K, A1022H, V1024G, G1026R, K1030W, I1035D, V1048M, V1048Q, G1050S, N1051E, A1052K, L1053A, Q1057E, Q1057R, D1066W, L1068C, I1071W, K1072G, K1072Q, T1082F, G1083E, G1084V, G1085S, P1088E, S1089Q, W1091A, W1091V, T1092Q, N1093P, N1093Q, W1094D, W1094E, S1097W, A1099V, N1102E, N1102H, A1104R, T1107S, E1109D, E1109L, E1109W, A1111G, E1113P, Q1114S, Q1114V, Q1115A, Q1115K, L1116K, L1116W, G1117I, G1117S, G1117T, G1117V, G1117W, I1119N, R1125V, R1125W, S1127Q, N1128A, A1129E, V1130A, V1130G, V1130R, P1133D, P1133R, G1136E, K1137R, K1137S, Q1141P, A1144P, A1144S, D1145E, D1145R, D1145T, T1150K, D1151R, D1151W, V1167R, A1175N, G1178M, A1179W, T1180A, T1180G, T1180I, T1180M, T1180Q, T1180Y, V1184E, V1184L, V1184P, V1186S, N1188W, C1199T, K1208W, T1209E, T1209K, A1210D, A1210G, A1210R, A1210T, A1210W, T1211G, T1211P, T1211R, F1214A, F1214K, F1214V, V1215D, T1216L, T1216Q, N1217A, T1218W, S1219A, S1219F, L1222F, L1222V, S1223V, S1224P, S1224W, L1225E, L1225K, T1226P, N1228F, G1229V, T1230K, T1230W, K1231F, S1233P, A1238E, A1238R, N1243T, T1244Q, A1246M, D1250I, D1250S, D1250W, A1259K, P1265W, N1269A, N1269K, I1274F, I1274R, T1275W, S1277W, E1278Q, D1279R, D1279W, H1280E, V1281I, V1281W, K1284G, F1286E, T1287C, T1287W, I1288A, I1288D, I1288G, I1288K, E1302R, E1302S or D1304V.

99. The lactase variant of the preceding embodiment, wherein the variant has a decreased or an increased galactose inhibition, preferably measured as a galactose inhibition improvement factor (GI-IF) of at least 1.4 or at most 0.6, compared to the lactase of SEQ ID NO: 1.

100. The lactase variant of embodiment 1 which comprises one or more of the following substitutions, wherein each position corresponds to a position in SEQ ID NO: 1: E2V, D3I, D3S, D3V, S7P, M13R, S15C, S15I, S15K, S15Y, T16C, V20P, Y21C, Y21R, Y21T, S23L, S23M, A24F, A24T, D26C, S27A, K28C, Q29L, Q29M, Q29R, R31E, R31V, T32S, D34S, F35E, K40F, K40I, M42E, L43T, D45P, V47K, V47R, A49D, A49H, A49R, A49T, D51I, D51K, D51P, A53S, D55H, D55M, S57C, S57E, S57G, A58T, W59P, V62N, L64E, H66Y, K73D, S75G, S75L, S75R, Q76G, S77E, S77F, S77H, S77K, N78C, E79H, E79S, E79T, E81A, E81Q, L85F, L85S, L85V, L85W, P86Q, G87D, G88F, G88Q, G90T, W91Y, Y92H, Y92M, Y92S, Y92V, R93A, R93D, R93F, R93H, R93L, R93N, R93T, R93V, R93Y, K94S, S95C, S95G, S95I, F96A, F96C, F96I, F96S, F96V, T97F, I98H, R100T, D101A, D101P, L102P, I109M, N110T, F111A, F111L, D112T, V114R, Y115E, V120A, W121R, W121V, G124E, H130A, H130T, Y132E, P136R, F137L, K146A, G149M, E150L, I153A, V157P, E158G, E158H, N159T, L161K, L161S, L161W, P162N, P162T, P162W, R165H, W166S, Y167A, S170Q, I172P, R174E, V176E, V176K, T177K, L178I, L178Q, T179C, V180G, H185G, H185L, N188V, N189E, G190C, S197C, D217L, D217M, T218G, A220G, A220V, A222R, N223S, Q228R, K233P, K236M, T237D, A239G, A239T, G242Y, A247P, A247R, S248E, K249G, K249Y, I251Y, A252F, A252W, A252Y, G254I, G254R, A255K, S256Y, S261R, T262D, T264M, P268R, S272W, L278V, Y279W, L286F, V291D, V291P, L292V, D293C, D296F, E298I, E298R, F301C, W303A, T304P, G305N, G305P, G305W, T309D, F312H, K320V, K320W, S325G, M326E, M326G, M326T, M326Y, H328C, H328M, H328T, A337G, A337L, R340A, A341M, I342K, E343N, Q345G, Q345K, Q345S, I348D, Q350G, T359E, T360V, N362S, N362T, P363I, P363L, P363M, A364I, A364M, A364P, A365C, L368E, L368Q, L368S, I369G, I369K, I369W, D370L, N373G, N373L, G376A, G376S, V377M, V379A, V380P, E381A, E381T, M386G, M386N, M386S, W387L, N388L, N388R, R389A, R389E, R389Q, R389S, R389T, S390C, S390D, S390G, S390P, S390Q, S390T, K391E, N392D, G393R, G393V, N394L, T395C, T395H, T395N, T395S, T395W, E396K, E396L, E396V, E396W, Y398N, G399S, K400A, K400C, K400N, K400P, K400S, K400V, W401F, W401K, F402W, F402Y, G403A, G403K, G403V, Q404F, Q404H, Q404L, Q404M, Q404P, Q404V, A405C, A405E, A405H, A405R, I406D, I406N, G408W, D409N, A411E, L413P, G414A, G414R, D416I, D416Y, K417F, D418P, D418R, E419M, E419R, T420K, T420R, K423D, F424C, F424L, L426M, T427D, T427Q, T427S, T429D, N431M, D433P, D433W, R434N, R434V, N435L, A436L, V439C, V439G, V439K, V439T, W442E, W442G, W442R, S443C, S443Y, L444V, G445A, G445C, G445V, M448C, M448L, M448S, M449D, M449T, M449W, M449Y, E450F, E450S, E450T, E450V, E450W, G451C, G451F, G451L, G451P, G451V, G451W, I452K, G454L, S455P, S455R, V456D, V456E, V456F, V456K, S457T, S457V, G458A, G458P, F459R, F459S, K465Y, L466P, L466V, A468D, A472G, A472Y, S475E, R477L, M479G, M479R, K485E, K487F, K487N, A488N, N491W, S493M, S493Q, T495W, D498C, N499R, N499T, N499Y, L500A, G504H, G505D, G505S, V506C, V506E, V506R, V507L, V507R, G508C, G508E, T509K, T509M, N510A, N510F, N510I, Y511A, S512F, S512T, S512Y, D513L, D513P, D513R, G514F, A515E, N516C, Y517G, D518Y, K519C, K519I, I520G, I520H, I520S, R521N, R521V, T522N, H524R, H524V, P525T, S526G, W527N, W527R, W527S, A528E, G531T, A537P, S540E, R546L, R546P, R546S, T547A, T547S, T548F, T548K, T548P, G549P, G549W, G550S, A551Q, S553N, S554N, D555S, K556W, L558P, T559Y, S564C, S564F, A565E, A565I, A565R, G567Q, G567V, A570K, A570M, A572S, S574W, W576Y, Y577L, V579G, R582L, D583W, V585I, A586K, T588D, T592C, T592L, T592S, F594L, D595Q, P600A, P600E, P600G, P600S, G607Q, S608V, G609N, G609R, A610M, V611K, W614A, N619L, S620G, V625M, V625Y, F630G, T634V, Y635R, Q639R, D644C, H650R, W655R, N656V, A661E, P669T, V670C, Y673S, A676P, K680I, T684V, G687P, S688L, R692H, I694L, I694W, G695C, G695L, G695W, K697R, S698E, T700C, K701A, K701G, K701M, A705W, T709M, Y710T, V712M, E714K, A716R, D717G, D717S, K718A, D719T, D719V, T721N, T721S, T721W, H723G, M726D, L728S, N731S, W734G, W734V, A735Q, A735S, I739K, S740D, A741I, D745F, L750S, P752A, P752C, P752Y, G754T, T756N, T756S, E757A, A760N, A769F, A769I, A769N, A769V, A769Y, K770H, K772A, K772C, K772P, A773C, A773H, A773V, D774A, A775L, A775W, D776I, D776L, D776S, R777D, R777E, R777G, R777H, R777P, R777S, T781A, T781G, T781P, T781Y, A782Q, D783C, D783E, D783R, G784L, G784S, K785S, K785W, D786V, L787P, L787T, Y789V, V792G, D793H, V794T, T795P, N798I, G799K, G799L, G799M, G799Q, H800A, H800L, P803S, A806Q, R808C, T810P, V813T, K814H, G815A, A816C, A816F, K818F, K818L, K818W, G821E, G821I, V822D, V822E, S826L, H830R, D831I, D831P, D831V, S832R, A835D, A835H, A835W, D836E, D836H, D836S, D836Y, R838G, K839D, A840Q, K844R, Q850C, Q850G, E854C, I858D, I858Q, I858Y, K863F, K863N, D865A, D865G, L867W, S870R, V872C, I874G, S883L, T887F, T887G, V888A, Y892P, Y892R, Y893E, T901V, T901Y, G902R, G902S, G902W, N903D, K904M, K904V, P905R, P905Y, I906W, P908I, D910W, E912T, R914A, R914F, R914K, R914Y, Y915A, Y915C, Y915M, Y915V, S916G, D917C, D917F, D917S, G918H, T919Q, D921V, R922A, Q923V, W927G, Q934S, I935P, A936Q, K937I, K937P, A938C, S940T, S942K, S942V, V943A, V943H, V943R, A944P, T946P, T946V, V947G, A948C, Q950D, V956Q, E961D, E961F, E961S, I962C, I962N, L965C, L965G, L965M, L965P, L965Y, L966A, Y968G, Y968V, S969C, S969I, S969M, P973C, T976K, T976P, P977T, A978M, V979R, L980H, L980N, P981M, P985L, P985W, A986I, V987K, D990W, S995L, N997K, D1001L, W1002A, W1002D, W1002H, W1002N, W1002P, T1003Y, K1004H, A1006S, D1007P, V1018K, A1022H, V1024G, G1026R, K1030W, I1035D, V1048M, V1048Q, G1050S, N1051E, A1052K, L1053A, Q1057E, Q1057R, D1066W, L1068C, I1071W, K1072G, K1072Q, T1082F, G1083E, G1084V, G1085S, P1088E, S1089Q, W1091A, W1091V, T1092Q, N1093P, N1093Q, W1094D, W1094E, S1097W, A1099V, N1102E, N1102H, A1104R, T1107S, E1109D, E1109L, E1109W, A1111G, E1113P, Q1114S, Q1114V, Q1115A, Q1115K, L1116K, L1116W, G1117I, G1117S, G1117T, G1117V, G1117W, I1119N, R1125V, R1125W, S1127Q, N1128A, A1129E, V1130A, V1130G, V1130R, P1133D, P1133R, G1136E, K1137R, K1137S, Q1141P, A1144P, A1144S, D1145E, D1145R, D1145T, T1150K, D1151R, D1151W, V1167R, A1175N, G1178M, A1179W, T1180A, T1180G, T1180I, T1180M, T1180Q, T1180Y, V1184E, V1184L, V1184P, V1186S, N1188W, C1199T, K1208W, T1209E, T1209K, A1210D, A1210G, A1210R, A1210T, A1210W, T1211G, T1211P, T1211R, F1214A, F1214K, F1214V, V1215D, T1216L, T1216Q, N1217A, T1218W, S1219A, S1219F, L1222F, L1222V, S1223V, S1224P, S1224W, L1225E, L1225K, T1226P, N1228F, G1229V, T1230K, T1230W, K1231F, S1233P, A1238E, A1238R, N1243T, T1244Q, A1246M, D1250I, D1250S, D1250W, A1259K, P1265W, N1269A, N1269K, I1274F, I1274R, T1275W, S1277W, E1278Q, D1279R, D1279W, H1280E, V1281I, V1281W, K1284G, F1286E, T1287C, T1287W, I1288A, I1288D, I1288G, I1288K, E1302R, E1302S or D1304V.

101. The lactase variant of the preceding embodiment, wherein the variant has a decreased or an increased galactose inhibition, preferably measured as a galactose inhibition improvement factor (GI-IF) of at least 1.4 or at most 0.6, compared to the lactase of SEQ ID NO: 1.

102. The lactase variant of embodiment 1 which comprises one or more of the following substitutions, wherein each position corresponds to a position in SEQ ID NO: 1: E2V, D3I, D3V, S7P, M13R, S15C, S15I, S15K, T16C, V20P, Y21C, Y21R, Y21T, A24F, A24T, D26C, S27A, K28C, Q29L, Q29M, Q29R, R31E, R31V, T32S, K40F, K40I, D45P, V47K, V47R, A49D, A49H, A49T, D51I, D51K, D55H, D55M, S57C, S57E, S57G, A58T, W59P, V62N, L64E, K73D, S75G, S75L, S75R, Q76C, S77E, S77H, S77K, N78C, E79H, E79S, E79T, L85F, L85S, L85V, L85W, P86Q, G87D, G88F, G90T, W91Y, Y92H, Y92M, Y92S, Y92V, R93A, R93D, R93F, R93H, R93L, R93N, R93T, R93V, R93Y, K94S, S95C, S95G, S95I, F96A, F96C, F96I, F96V, T97F, I98H, R100T, D101A, D101P, L102P, I109M, N110T, F111A, F111L, V114R, Y115E, V120A, W121R, V121V, H130A, H130T, Y132E, F137L, G149M, E150L, V157P, E158H, N159T, L161K, L161S, L161W, P162N, P162T, P162W, R165H, W166S, Y167A, S170Q, I172R, R174E, V176E, V176K, T177K, L178I, L178Q, T179C, V180G, H185G, H185L, N188V, S197C, D217L, D217M, T218G, A220G, A222R, N223S, Q228R, K236M, T237D, I251Y, A252W, A252Y, P268R, S272W, V291P, L292V, D293C, D296F, E298I, E298R, F301C, W303A, T304P, G305N, G305P, T309D, F312H, K320V, K320W, S325G, M326T, H328C, H328M, H328T, A337G, A337L, R340A, A341M, E343N, Q345S, I348D, Q350G, T359E, T360V, N362S, N362T, P363I, P363L, P363M, A364I, A364M, A364P, A365C, L368Q, L368S, I369G, I369K, I369W, D370L, N373G, N373L, G376A, G376S, V377M, V379A, V380P, E381A, E381T, M386G, M386N, M386S, N388L, R389A, R389E, R389Q, R389S, R389T, S390C, S390D, S390P, S390T, G393R, G393V, T395C, E396K, E396L, E396V, E396W, G399S, K400A, K400C, K400N, K400V, W401F, W401K, F402W, F402Y, G403A, G403K, G403V, Q404F, Q404L, Q404M, Q404P, Q404V, A405C, A405E, A405R, A405T, I406D, I406N, A411E, K417F, T427D, T427Q, T427S, T429D, N431M, D433P, D433W, R434N, R434V, N435L, A436L, V439C, V439K, W442E, W442G, S443C, L444V, M448C, M448L, M449D, M449T, M449W, M449Y, E450F, E450S, E450T, E450V, E450W, G451C, G451F, G451L, G451P, G451V, G451W, I452K, G454L, S455P, S455R, V456D, V456E, V456F, V456K, S457T, S457V, G458A, G458P, F459R, K465Y, L466P, A468D, A472G, A472Y, S475E, R477L, M479G, K485E, K487F, S493Q, N499T, G505D, G505S, V506C, V506E, V506R, V507R, G508C, G508E, T509K, T509M, N510A, N510F, N510I, Y511A, S512F, S512T, S512Y, D513P, D513R, A515E, N516C, Y517G, D518Y, K519C, K519I, I520G, I520H, I520S, R521V, H524R, H524V, S526G, W527N, W527R, W527S, A528E, A537P, S540E, G549P, G549W, L558P, T559Y, S564C, S564F, A565E, A565I, A565R, G567Q, G567V, R582L, D583W, T592L, P600A, P600E, P600G, P600S, G607Q, W614A, N619L, V625M, V625Y, T634V, Q639R, W655R, A661E, P669T, Y673S, A676P, K680I, G687F, S688L, R692H, I694L, I694W, G695C, G695L, G695W, K697R, S698E, K701A, K701G, K701M, A705W, Y710T, V712M, E714K, A716R, D717G, D717S, K718A, D719T, D719V, T721N, T721S, T721W, H723G, M726D, L728S, W734G, A735Q, A735S, I739K, S740D, A741I, L750S, P752C, P752Y, T756N, E757A, A769F, A769I, A769N, A769V, A769Y, K770H, K772A, K772C, K772P, A773C, D774A, R777H, R777S, T781A, T781G, T781P, T781Y, A782Q, K785S, K785W, D786V, Y789V, N798I, G799K, G799L, P803S, A806Q, T810P, K818F, K818L, K818W, G821I, V822D, V822E, D831P, S832R, A835D, A835H, D836E, D836S, D836Y, K839D, A840G, E854C, I858D, D865A, D865G, L867W, V872C, I874G, S883L, T887G, V888A, Y892P, Y893E, T901Y, G902R, G902S, G902W, N903D, K904M, K904V, P905R, P905Y, I906W, P908I, D910W, E912T, R914A, R914F, R914K, R914Y, Y915A, Y915C, Y915M, Y915V, S916G, D917C, D917F, D917S, G918H, T919Q, D921V, R922A, Q923V, Q934S, I935P, A936Q, K937I, K937P, A938C, S942K, S942V, V943A, T946P, V947G, V956Q, E961D, E961F, E961S, I962C, I962N, L965C, L965G, L965M, L965P, L965Y, L966A, Y968G, Y968V, S969C, S969I, S969M, P973C, T976K, T976P, P977T, A978M, L980H, L980N, P981M, P985L, P985W, A986I, V987K, D990W, S995L, N997K, D1001L, W1002A, W1002D, W1002H, W1002N, W1002P, T1003Y, A1006S, D1007P, V1018K, A1022H, V1024G, K1030W, I1035D, V1048M, V1048Q, N1051E, A1052K, L1053A, Q1057E, T1082F, G1083E, G1084V, G1085S, P1088E, S1089Q, N1093P, N1093Q, W1094D, W1094E, A1099V, N1102E, N1102H, E1109D, E1109L, E1109W, A1111G, E1113P, Q1114S, Q1114V, Q1115A, Q1115K, L1116K, L1116W, G1117I, G1117S, G1117T, G1117V, G1117W, I1119N, R1125V, R1125W, S1127Q, N1128A, A1129E, V1130A, V1130R, P1133D, P1133R, K1137R, K1137S, A1144P, A1144S, D1145E, D1145R, D1145T, T1150K, D1151W, V1167R, G1178M, A1179W, T1180A, T1180G, T1180I, T1180M, T1180Q, T1180Y, V1184E, V1184L, V1184P, V1186S, N1188W, K1208W, T1209E, T1209K, A1210D, A1210G, A1210R, A1210T, A1210W, T1211G, T1211P, T1211R, F1214A, F1214K, F1214V, V1215D, T1216L, T1216Q, N1217A, T1218W, L1222F, L1222V, S1224P, S1224W, L1225E, L1225K, T1226P, G1229V, T1230K, T1230W, A1238E, A1238R, A1259K, P1265W, I1274F, I1274R, T1275W, S1277W, E1278Q, D1279R, D1279W, H1280E, V1281I, V1281W, K1284G, F1286E, T1287C, T1287W, I1288A, I1288D, I1288G, I1288K, E1302R, E1302S or D1304V.

103. The lactase variant of the preceding embodiment, wherein the variant has a decreased galactose inhibition, preferably measured as a galactose inhibition improvement factor (GI-IF) of at least 1.4, compared to the lactase of SEQ ID NO: 1.

104. The lactase variant of embodiment 1 which comprises one or more of the following substitutions, wherein each position corresponds to a position in SEQ ID NO: 1: E2V, D3I, D3V, S7P, M13R, S15C, S15I, S15K, T16C, V20P, Y21C, Y21R, Y21T, A24F, A24T, D26C, S27A, K28C, Q29L, Q29M, Q29R, R31E, R31V, T32S, K40F, K40I, D45P, V47K, V47R, A49D, A49H, A49T, D51I, D51K, D55H, D55M, S57C, S57E, S57G, A58T, W59P, V62N, L64E, K73D, S75G, S75L, S75R, Q76G, S77E, S77H, S77K, N78C, E79H, E79S, E79T, L85F, L85S, L85V, L85W, P86Q, G87D, G88F, G90T, W91Y, Y92H, Y92M, Y92S, Y92V, R93A, R93D, R93F, R93H, R93L, R93N, R93T, R93V, R93Y, K94S, S95C, S95G, S95I, F96A, F96C, F96I, F96V, T97F, I98H, R100T, D101A, D101P, L102P, I109M, N110T, F111A, F111L, V114R, Y115E, V120A, W121R, W121V, H130A, H130T, Y132E, F137L, G149M, E150L, V157P, E158H, N159T, L161K, L161S, L161W, P162N, P162T, P162W, R165H, W166S, Y167A, S170Q, I172P, R174E, V176E, V176K, T177K, L178I, L178Q, T179C, V180G, H185G, H185L, N188V, S197C, D217L, D217M, T218G, A220G, A222R, N223S, Q228R, K236M, T237D, I251Y, A252W, A252Y, P268R, S272W, V291P, L292V, D293C, D296F, E298I, E298R, F301C, W303A, T304P, G305N, G305P, T309D, F312H, K320V, K320W, S325G, M326T, H328C, H328M, H328T, A337G, A337L, R340A, A341M, E343H, Q345S, I348D, Q350G, T359E, T360V, N362S, N362T, P363I, P363L, P363M, A364I, A364M, A364P, A365C, L368Q, L368S, I369G, I369K, I369W, D370L, N373G, N373L, G376A, G376S, V377M, V379A, V380P, E381A, E381T, M386G, M386N, M386S, N388L, R389A, R389E, R389Q, R389S, R389T, S390C, S390D, S390P, S390T, G393R, G393V, T395C, E396K, E396L, E396V, E396W, G399S, K400A, K400C, K400N, K400V, W401F, W401K, F402W, F402Y, G403A, G403K, G403V, Q404F, Q404L, Q404M, Q404P, Q404V, A405C, A405E, A405R, I406D, I406N, A411E, K417F, T427D, T427Q, T427S, T429D, N431M, D433P, D433W, R434N, R434V, N435L, A436L, V439C, V439K, W442E, W442G, S443C, L444V, M448C, M448L, M449D, M449T, M449W, M449Y, E450F, E450S, E450T, E450V, E450W, G451C, G451F, G451L, G451P, G451V, G451W, I452K, G454L, S455P, S455R, V456D, V456E, V456F, V456K, S457T, S457V, G458A, G458P, F459R, K465Y, L466P, A468D, A472G, A472Y, S475E, R477L, M479G, K485E, K487F, S493Q, N499T, G505D, G505S, V506C, V506E, V506R, V507R, G508C, G508E, T509K, T509M, N510A, N510F, N510I, Y511A, S512F, S512T, S512Y, D513P, D513R, A515E, N516C, Y517G, D518Y, K519C, K519I, I520G, I520H, I520S, R521V, H524R, H524V, S526G, W527N, W527R, W527S, A528E, A537P, S540E, G549P, G549W, L558P, T559Y, S564C, S564F, A565E, A565I, A565R, G567Q, G567V, R582L, D583W, T592L, P600A, P600E, P600G, P600S, G607Q, W614A, N619L, V625M, V625Y, T634V, Q639R, W655R, A661E, P669T, Y673S, A676P, K680I, G687P, S688L, R692H, I694L, I694W, G695C, G695L, G695W, K697R, S698E, K701A, K701G, K701M, A705W, Y710T, V712M, E714K, A716R, D717G, D717S, K718A, D719T, D719V, T721N, T721S, T721W, H723G, M726D, L728S, W734G, A735Q, A735S, I739K, S740D, A741I, L750S, P752C, P752Y, T756N, E757A, A769F, A769I, A769N, A769V, A769Y, K770H, K772A, K772C, K772P, A773C, D774A, R777H, R777S, T781A, T781G, T781P, T781Y, A782Q, K785S, K785W, D786V, Y789V, N798I, G799K, G799L, P803S, A806Q, T810P, K818F, K818L, K818W, G821I, V822D, V822E, D831P, S832R, A835D, A835H, D836E, D836S, D836Y, K839D, A840G, E854C, I858D, D865A, D865G, L867W, V872C, I874G, S883L, T887G, V888A, Y892P, Y893E, T901Y, G902R, G902S, G902W, N903D, K904M, K904P, P905R, P905Y, I906W, P908I, D910W, E912T, R914A, R914F, R914K, R914Y, Y915A, Y915C, Y915M, Y915V, S916G, D917C, D917F, D917S, G918H, T919Q, D921V, R922A, Q923V, Q934S, 1935P, A936Q, K937I, K937P, A938C, S942K, S942V, V943A, T946P, V947G, V956Q, E961D, E961F, E961S, I962C, I962N, L965C, L965G, L965M, L965P, L965Y, L966A, Y968G, Y968V, S969C, S969I, S969M, P973C, T976C, T976P, P977T, A978M, L980H, L980N, P981M, P985L, P985W, A986I, V987K, D990W, S995L, N997K, D1001L, W1002A, W1002D, W1002H, W1002N, W1002P, T1003Y, A1006S, D1007P, V1018K, A1022H, V1024G, K1030W, I1035D, V1048M, V1048Q, N1051E, A1052K, L1053A, Q1057E, T1082F, G1083E, G1084V, G1085S, P1088E, S1089Q, N1093P, N1093Q, W1094D, W1094E, A1099V, N1102H, E1109D, E1109L, E1109W, A1111G, E1113P, Q1114S, Q1114V, Q1115A, Q1115K, L1116K, L1116W, G1117I, G1117S, G1117T, G1117V, G1117W, I1119N, R1125V, R1125W, S1127Q, N1128A, A1129E, V1130A, V1130R, P1133D, P1133R, K1137R, K1137S, A1144P, A1144S, D1145E, D1145R, D1145T, T1150K, D1151W, V1167R, G1178M, A1179W, T1180A, T1180G, T1180I, T1180M, T1180Q, T1180Y, V1184E, V1184L, V1184P, V1186S, N1188W, K1208W, T1209E, A1210D, A1210G, A1210R, A1210T, A1210W, T1211G, T1211P, T1211R, F1214A, F1214K, F1214V, V1215D, T1216L, T1216Q, N1217A, T1218W, L1222F, L1222V, S1224P, S1224W, L1225E, L1225K, T1226P, G1229V, T1230K, T1230W, A1238E, A1238R, A1259K, P1265W, I1274F, I1274R, T1275W, S1277W, E1278Q, D1279R, D1279W, H1280E, V1281I, V1281W, K1284G, F1286E, T1287C, T1287W, I1288A, I1288D, I1288G, I1288K, E1302R, E1302S or D1304V.

105. The lactase variant of the preceding embodiment, wherein the variant has a decreased galactose inhibition, preferably measured as a galactose inhibition improvement factor (GI-IF) of at least 1.4, compared to the lactase of SEQ ID NO: 1.

106. The lactase variant of embodiment 1 which comprises one or more of the following substitutions, wherein each position corresponds to a position in SEQ ID NO: 1: S7P, S15I, S15K, S15Y, T16C, V20P, A24T, S27A, K28C, Q29L, R31E, T32S, D45P, V47R, A49D, A49H, A49R, D51I, D55H, S57C, S57E, S57G, A58T, W59P, H66Y, S75G, Q76G, S77F, S77H, S77K, E81Q, L85F, L85W, P86Q, G87D, G88F, G90T, Y92M, Y92S, Y92V, R93A, R93F, R93H, R93L, R93N, R93T, R93V, R93Y, K94S, S95G, S95I, F96A, F96C, F96S, F96V, I98H, D101P, L102P, I109M, D112T, V120A, W121R, W121V, G124E, F137L, G149M, I153A, E158H, N159T, L161S, L161W, P162N, P162T, R165H, W166S, Y167A, S170Q, I172P, R174E, L178I, L178Q, H185L, N188V, N189E, D217L, D217M, T218G, A220G, A222R, N223S, K236M, T237D, A239G, A239T, A247R, I251Y, A252Y, G254I, T264M, P268R, S272W, Y279W, V291P, E298I, F301C, W303A, T304P, G305W, M326T, A337L, A341M, Q345S, I348D, T359E, N362T, P363I, A364I, A364M, L368S, I369K, I369W, D370L, N373G, G376S, E381A, E381T, M386G, M386N, M386S, W387L, R389E, R389Q, R389S, R389T, S390C, S390D, S390P, S390Q, S390T, K391E, N392D, G393R, G393V, N394L, T395C, T395H, T395N, T395S, T395W, E396K, E396L, E396V, E396W, Y398N, G399S, K400A, K400C, K400N, K400P, K400S, K400V, W401F, W401K, F402W, F402Y, G403A, G403K, G403V, Q404F, Q404H, Q404L, Q404M, Q404P, Q404V, A405C, A405E, A405R, A405T, I406D, I406N, L413P, G414A, D416I, K417F, D418R, T420K, T420R, K423D, F424L, T427Q, T427S, T429D, N431M, D433W, R434N, R434V, N435L, A436L, V439C, V439G, V439K, W442G, L444V, G445C, G445V, M448L, M449D, M449T, M449W, M449Y, E450F, E450S, E450T, E450V, E450W, G451C, G451F, G451L, G451P, G451V, G451W, I452K, S455P, S455R, V456D, V456F, S457V, G458A, F459R, K465Y, L466P, A468D, A472G, A472Y, M479G, M479R, K487F, A488N, N491W, S493M, N499T, N499Y, L500A, G504H, G505D, G505S, V506C, V506E, V506R, V507L, V507R, G508C, G508E, T509K, T509M, N510A, N510F, N510I, Y511A, S512F, S512T, D513L, D513P, D513R, A515E, N516C, Y517G, D518Y, R521N, R521V, T522N, H524R, H524V, S526G, W527N, W527R, A537P, S540E, R546L, R546S, T548P, G549W, G550S, A551Q, S554N, D555S, K556W, L558P, S564C, S564F, A565I, A565R, G567Q, G567V, A570K, S574W, R582L, D583W, A586K, T592C, T592S, F594L, D595Q, P600A, P600E, P600S, S608V, G609N, G609R, W614A, V625M, V625Y, F630G, Q639R, D644C, H650R, W655R, N656V, A661E, P669T, V670C, Y673S, S688L, I694L, I694W, G695C, G695L, K697R, S698E, T700C, K701A, K701G, K701M, T709M, Y710T, E714K, D717G, K718A, D719T, D719V, T721S, L728S, N731S, W734V, A735S, I739K, A741I, D745F, L750S, P752C, P752Y, G754P, T756N, E757A, A769F, A769I, A769N, A769V, K770H, K772A, K772P, A775L, A775W, D776I, D776L, D776S, R777D, R777G, R777H, R777P, T781A, T781G, T781P, T781Y, D783C, D783E, D783R, G784L, K785S, K785W, D786V, L787P, V792G, D793H, V794T, T795P, G799K, G799L, G799M, S803M, T810P, K814H, G815A, A816C, A816F, K818F, K818W, G821I, V822D, S826L, H830R, A835D, A835H, D836E, D836H, D836S, D836Y, K839D, K844G, Q850G, E854C, D865G, L867W, V872C, S883L, Y893E, T901V, T901Y, G902S, K904V, E912T, R914A, R914F, R914K, R914Y, Y915C, Y915M, Y915V, S916G, D917F, D917S, G918H, T919Q, D921V, R922A, Q923V, Q934S, I935P, A936Q, K937I, K937P, V943A, V943H, V943R, A944P, T946V, V956Q, E961D, E961F, E961S, L965C, L965G, L965M, L965P, L965Y, Y968G, S969I, S969M, P973C, P981M, P985L, A986I, W1002A, W1002D, W1002N, W1002P, A1006S, D1007P, K1030W, I1035D, V1048Q, G1050S, N1051E, L1053A, D1066W, L1068C, G1084V, G1085S, S1089Q, N1093P, W1094D, W1094E, S1097W, N1102H, E1109D, E1109L, E1113P, Q1114S, Q1114V, Q1115A, L1116K, L1116W, G1117S, G1117T, G1117V, G1117W, I1119N, R1125V, R1125W, S1127Q, N1128A, A1129E, V1130R, P1133R, K1137S, A1144S, D1145E, D1145R, D1145T, D1150K, D1151R, D1151W, V1167R, G1178M, A1179W, T1180G, T1180I, T1180M, T1180Q, V1184E, V1184L, V1184P, K1208W, A1210D, A1210G, A1210R, A1210T, T1211G, T1211P, F1214A, F1214K, F1214V, T1216L, T1216Q, S1219A, L1222V, S1223V, S1224P, L1225E, L1225K, T1226P, G1229V, T1230W, A1238E, A1259K, P1265W, N1269A, I1274F, I1274R, T1275W, S1277W, E1278Q, D1279R, D1279W, V1281I, V1281W, K1284G, F1286E, T1287C, T1287W, I1288A, I1288D, I1288G, I1288K, E1302R, E1302S or D1304V.

107. The lactase variant of the preceding embodiment, wherein the variant has a decreased or an increased galactose inhibition, preferably measured as a galactose inhibition improvement factor (GI-IF) of at least 1.5 or at most 0.5, compared to the lactase of SEQ ID NO: 1.

108. The lactase variant of embodiment 1 which comprises one or more of the following substitutions, wherein each position corresponds to a position in SEQ ID NO: 1: S7P, S15I, S15K, S15Y, T16C, V20P, A24T, S27A, K28C, Q29L, R31E, T32S, D45P, V47R, A49D, A49H, A49R, D51I, D55H, S57C, S57E, S57G, A58T, W59P, H66Y, S75G, Q76G, S77F, S77H, S77K, E81Q, L85F, L85W, P86Q, G87D, G88F, G90T, Y92M, Y92S, Y92V, R93A, R93F, R93H, R93L, R93N, R93T, R93V, R93Y, K94S, S95G, S95I, F96A, F96C, F96S, F96V, 198H, D101P, L102P, I109M, D112T, V120A, W121R, W121V, G124E, F137L, G149M, I153A, E158H, N159T, L161S, L161W, P162N, P162T, R165H, W166S, Y167A, S170Q, I172P, R174E, L178I, L178Q, H185L, N188V, N189E, D217L, D217M, T218G, A220G, A222R, N223S, K236M, T237D, A239G, A239T, A247R, I251Y, A252Y, G254I, T264M, P268R, S272W, Y279W, V291P, E298I, F301C, W303A, T304P, G305W, M326T, A337L, A341M, Q345S, I348D, T359E, N362T, P363I, A364I, A364M, L368S, I369K, I369W, D370L, N373G, G376S, E381A, E381T, M386G, M386N, M386S, W387L, R389E, R389Q, R389S, R389T, S390C, S390D, S390P, S390Q, S390T, K391E, N392D, G393R, G393V, N394L, T395C, T395H, T395N, T395S, T395W, E396K, E396L, E396V, E396W, Y398N, G399S, K400A, K400C, K400N, K400P, K400S, K400V, W401F, W401K, F402W, F402Y, G403A, G403K, G403V, Q404F, Q404H, Q404L, Q404M, Q404P, Q404V, A405C, A405E, A405R, I406D, I406N, L413P, G414A, D416I, K417F, D418R, T420K, T420R, K423D, F424L, T427Q, T427S, T429D, N431M, D433W, R434N, R434V, N435L, A436L, V439C, V439G, V439K, W442G, L444V, G445C, G445V, M448L, M449D, M449T, M449W, M449Y, E450F, E450S, E450T, E450V, E450W, G451C, G451F, G451L, G451P, G451V, G451W, I452K, S455P, S455R, V456D, V456F, S457V, G458A, F459R, K465Y, L466P, A468D, A472G, A472Y, M479G, M479R, K487F, A488N, N491W, S493M, N499T, N499Y, L500A, G504H, G505D, G505S, V506C, V506E, V506R, V507L, V507R, G508C, G508E, T509K, T509M, N510A, N510F, N510I, Y511A, S512F, S512T, D513L, D513P, D513R, A515E, N516C, Y517G, D518Y, R521N, R521V, T522N, H524R, H524V, S526G, W527N, W527R, A537P, S540E, R546L, R546S, T548P, G549W, G550S, A551Q, S554N, D555S, K556W, L558P, S564C, S564F, A565I, A565R, G567Q, G567V, A570K, S574W, R582L, D583W, A586K, T592C, T592S, F594L, D595Q, P600A, P600E, P600S, S608V, G609N, G609R, W614A, V625M, V625Y, F630G, Q639R, D644C, H650R, W655R, N656V, A661E, P669T, V670C, Y673S, S688L, I694L, I694W, G695C, G695L, K697R, S698E, T700C, K701A, K701G, K701M, T709M, Y710T, E714K, D717G, K718A, D719T, D719V, T721S, L728S, N731S, W734V, A735S, I739K, A741I, D745F, L750S, P752C, P752Y, G754P, T756N, E757A, A769F, A769I, A769N, A769V, K770H, K772A, K772P, A775L, A775W, D776I, D776L, D776S, R777D, R777G, R777H, R777P, T781A, T781G, T781P, T781Y, D783C, D783E, D783R, G784L, K785S, K785W, D786V, L787P, V792G, D793H, V794T, T795P, G799K, G799L, G799M, P803S, T810P, K814H, G815A, A816C, A816F, K818F, K818W, G821I, V822D, S826L, H830R, A835D, A835H, D836E, D836H, D836S, D836Y, K839D, K844G, Q850G, E854C, D865G, L867W, V872C, S883L, Y893E, T901V, T901Y, G902S, K904V, E912T, R914A, R914F, R914K, R914Y, Y915C, Y915M, Y915V, S916G, D917F, D917S, G918H, T919Q, D921V, R922A, Q923V, Q934S, I935P, A936Q, K937I, K937P, V943A, V943H, V943R, A944P, T946V, V956Q, E961D, E961F, E961S, L965C, L965G, L965M, L965P, L965Y, Y968G, S969I, S969M, P973C, P981M, P985L, A986I, W1002A, W1002D, W1002N, W1002P, A1006S, D1007P, K1030W, I1035D, V1048Q, G1050S, N1051E, L1053A, D1066W, L1068C, G1084V, G1085S, S1089Q, N1093P, W1094D, W1094E, S1097W, N1102H, E1109D, E1109L, E1113P, Q1114S, Q1114V, Q1115A, L1116K, L1116W, G1117S, G1117T, G1117V, G1117W, I1119N, R1125V, R1125W, S1127Q, N1128A, A1129E, V1130R, P1133R, K1137S, A1144S, D1145E, D1145R, D1145T, T1150K, D1151R, D1151W, V1167R, G1178M, A1179W, T1180G, T1180I, T1180M, T1180Q, V1184E, V1184L, V1184P, K1208W, A1210D, A1210G, A1210R, A1210T, T1211G, T1211P, F1214A, F1214K, F1214V, T1216L, T1216Q, S1219A, L1222V, S1223V, S1224P, L1225E, L1225K, T1226P, G1229V, T1230W, A1238E, A1259K, P1265W, N1269A, I1274F, I1274R, T1275W, S1277W, E1278Q, D1279R, D1279W, V1281I, V1281W, K1284G, F1286E, T1287C, T1287W, I1288A, I1288D, I1288G, I1288K, E1302R, E1302S or D1304V.

109. The lactase variant of the preceding embodiment, wherein the variant has a decreased or an increased galactose inhibition, preferably measured as a galactose inhibition improvement factor (GI-IF) of at least 1.5 or at most 0.5, compared to the lactase of SEQ ID NO: 1.

110. The lactase variant of embodiment 1 which comprises one or more of the following substitutions, wherein each position corresponds to a position in SEQ ID NO: 1: S7P, S15I, S15K, T16C, V20P, A24T, S27A, K28C, Q29L, R31E, T32S, D45P, V47R, A49D, A49H, D51I, D55H, S57C, S57E, S57G, A58T, W59P, S75G, Q76G, S77H, S77K, L85F, L85W, P86Q, G87D, G88F, G90T, Y92M, Y92S, Y92V, R93A, R93F, R93H, R93L, R93N, R93T, R93V, R93Y, K94S, S95G, S95I, F96A, F96C, F96V, I98H, D101P, L102P, I109M, V120A, W121R, W121V, F137L, G149M, E158H, N159T, L161S, L161W, P162N, P162T, R165H, W166S, Y167A, S170Q, I172P, R174E, L178I, L178Q, H185L, N188V, D217L, D217M, T218G, A220G, A222R, N223S, K236M, T237D, I251Y, A252Y, P268R, S272W, V291P, E298I, F301C, W303A, T304P, M326T, A337L, A341M, Q345S, I348D, T359E, N362T, P363I, A364I, A364M, L368S, I369K, I369W, D370L, N373G, G376S, E381A, E381T, M386G, M386N, M386S, R389E, R389Q, R389S, R389T, S390C, S390D, S390P, S390T, G393R, G393V, T395C, E396K, E396L, E396V, E396W, G399S, K400A, K400C, K400N, K400V, W401F, W401K, F402W, F402Y, G403A, G403K, G403V, Q404F, Q404L, Q404M, Q404P, Q404V, A405C, A405E, A405R, A405T, I406D, I406N, K417F, T427Q, T427S, T429D, N431M, D433N, R434N, R434V, N435L, A436L, V439C, V439K, W442G, L444V, M448L, M449D, M449T, M449W, M449Y, E450F, E450S, E450T, E450V, E450W, G451C, G451F, G451L, G451P, G451V, G451W, I452K, S455P, S455R, V456D, V456F, S457V, G458A, F459R, K465Y, L466P, A468D, A472G, A472Y, M479G, K487F, N499T, G505D, G505S, V506C, V506E, V506R, V507R, G508C, G508E, T509K, T509M, N510A, N510F, N510I, Y511A, S512F, S512T, D513P, D513R, A515E, N516C, Y517G, D518Y, R521V, H524R, H524V, S526G, W527N, W527R, A537P, S540E, G549W, L558P, S564C, S564F, A565I, A565R, G567Q, G567V, R582L, D583W, P600A, P600E, P600S, W614A, V625M, V625Y, Q639R, W655R, A661E, P669T, Y673S, S688L, I694L, I694W, G695C, G695L, K697R, S698E, K701A, K701G, K701M, Y710T, E714K, D717G, K718A, D719T, D719V, T721S, L728S, A735S, I739K, A741I, L750S, P752C, P752Y, T756N, E757A, A769F, A769I, A769N, A769V, K770H, K772A, K772P, R777H, T781A, T781G, T781P, T781Y, K785S, K785W, D786V, G799K, G799L, P803S, T810P, K818F, K818W, G821I, V822D, A835D, A835H, D836E, D836S, D836Y, K839D, E854C, D865G, L867W, V872C, S883L, Y893E, T901Y, G902S, K904V, E912T, R914A, R914F, R914K, R914Y, Y915C, Y915M, Y915V, S916G, D917F, D917S, G918H, T919Q, D921V, R922A, Q923V, Q934S, I935P, A936Q, K937I, K937P, V943A, V956Q, E961D, E961F, E961S, L965C, L965G, L965M, L965P, L965Y, Y968G, S969I, S969M, P973C, P981M, P985L, A986I, W1002A, W1002D, W1002N, W1002P, A1006S, D1007P, K1030W, I1035D, V1048Q, N1051E, L1053A, G1084V, G1085S, S1089Q, N1093P, W1094D, W1094E, N1102H, E1109D, E1109L, E1113P, Q1114S, Q1114V, Q1115A, L1116K, L1116W, G1117S, G1117T, G1117V, G1117W, I1119N, R1125V, R1125W, S1127Q, N1128A, A1129E, V1130R, P1133R, K1137S, A1144S, D1145E, D1145R, D1145T, T1150K, D1151W, V1167R, G1178M, A1179W, T1180G, T1180I, T1180M, T1180Q, V1184E, V1184L, V1184P, K1208W, A1210D, A1210G, A1210R, A1210T, T1211G, T1211P, F1214A, F1214K, F1214V, T1216L, T1216Q, L1222V, S1224P, L1225E, L1225K, T1226P, G1229V, T1230W, A1238E, A1259K, P1265W, I1274F, I1274R, T1275W, S1277W, E1278Q, D1279R, D1279W, V1281I, V1281W, K1284G, F1286E, T1287C, T1287W, I1288A, I1288D, I1288G, I1288K, E1302R, E1302S or D1304V.

111. The lactase variant of the preceding embodiment, wherein the variant has a decreased galactose inhibition, preferably measured as a galactose inhibition improvement factor (GI-IF) of at least 1.5, compared to the lactase of SEQ ID NO: 1.

112. The lactase variant of embodiment 1 which comprises one or more of the following substitutions, wherein each position corresponds to a position in SEQ ID NO: 1: S7P, S15I, S15K, T16C, V20P, A24T, S27A, K28C, Q29L, R31E, T32S, D45P, V47R, A49D, A49H, D51I, D55H, S57C, S57E, S57G, A58T, W59P, S75G, Q76G, S77H, S77K, L85F, L85W, P86Q, G87D, G88F, G90T, Y92M, Y92S, Y92V, R93A, R93F, R93H, R93L, R93N, R93T, R93V, R93Y, K94S, S95G, S95I, F96A, F96C, F96V, I98H, D101P, L102P, I109M, V120A, W121R, W121V, F137L, G149M, E158H, N159T, L161S, L161W, P162N, P162T, R165H, W166S, Y167A, S170Q, I172P, R174E, L178I, L178Q, H185L, N188V, D217L, D217M, T218G, A220G, A222R, N223S, K236M, T237D, I251Y, A252Y, P268R, S272W, V291P, E298I, F301C, W303A, T304P, M326T, A337L, A341M, Q345S, I348D, T359E, N362T, P363I, A364I, A364M, L368S, I369K, I369W, D370L, N373G, G376S, E381A, E381T, M386G, M386N, M386S, R389E, R389Q, R389S, R389T, S390C, S390D, S390P, S390T, G393R, G393V, T395C, E396K, E396L, E396V, E396W, G399S, K400A, K400C, K400N, K400V, W401F, W401K, F402W, F402Y, G403A, G403K, G403V, Q404F, Q404L, Q404M, Q404P, Q404V, A405C, A405E, A405R, I406D, I406N, K417F, T427Q, T427S, T429D, N431M, D433W, R434N, R434V, N435L, A436L, V439C, V439K, W442G, L444V, M448L, M449D, M449T, M449W, M449Y, E450F, E450S, E450T, E450V, E450W, G451C, G451F, G451L, G451P, G451V, G451W, I452K, S455P, S455R, V456D, V456F, S457V, G458A, F459R, K465Y, L466P, A468D, A472G, A472Y, M479G, K487T, N499T, G505D, G505S, V506C, V506E, V506R, V507R, G508C, G508E, T509K, T509M, N510A, N510F, N510I, Y511A, S512F, S512T, D513P, D513R, A515E, N516C, Y517G, D518Y, R521V, H524R, H524V, S526G, W527N, W527R, A537P, S540E, G549W, L558P, S564C, S564F, A565I, A565R, G567Q, G567V, R582L, D583W, P600A, P600E, P600S, W614A, V625M, V625Y, Q639R, W655R, A661E, P669T, Y673S, S688L, I694L, I694W, G695C, G695L, K697R, S698E, K701A, K701G, K701M, Y710T, E714K, D717G, K718A, D719T, D719V, T721S, L728S, A735S, I739K, A741I, L750S, P752C, P752Y, T756N, E757A, A769F, A769I, A769N, A769V, K770H, K772A, K772P, R777H, T781A, T781G, T781P, T781Y, K785S, K785W, D786V, G799K, G799L, P803S, T810P, K818F, K818W, G821I, V822D, A835D, A835H, D836E, D836S, D836Y, K839D, E854C, D865G, L867W, V872C, S883L, Y893E, T901Y, G902S, K904V, E912T, R914A, R914F, R914K, R914Y, Y915C, Y915M, Y915V, S916G, D917F, D917S, G918H, T919Q, D921V, R922A, Q923V, Q934S, I935P, A936Q, K937I, K937P, V943A, V956Q, E961D, E961F, E961S, L965C, L965G, L965M, L965P, L965Y, Y968G, S969I, S969M, P973C, P981M, P985L, A986I, W1002A, W1002D, W1002N, W1002P, A1006S, D1007P, K1030W, I1035D, V1048Q, N1051E, L1053A, G1084V, G1085S, S1089Q, N1093P, W1094D, W1094E, N1102H, E1109D, E1109L, E1113P, Q1114S, Q1114V, Q1115A, L1116K, L1116W, G1117S, G1117T, G1117V, G1117W, I1119N, R1125V, R1125W, S1127Q, N1128A, A1129E, V1130R, P1133R, K1137S, A1144S, D1145E, D1145R, D1145T, T1150K, D1151W, V1167R, G1178M, A1179W, T1180G, T1180I, T1180M, T1180Q, V1184E, V1184L, V1184P, K1208W, A1210D, A1210G, A1210R, A1210T, T1211G, T1211P, F1214A, F1214K, F1214V, T1216L, T1216Q, L1222V, S1224P, L1225E, L1225K, T1226P, G1229V, T1230W, A1238E, A1259K, P1265W, I1274F, I1274R, T1275W, S1277W, E1278Q, D1279R, D1279W, V1281I, V1281W, K1284G, F1286E, T1287C, T1287W, T1288A, I1288D, I1288G, I1288K, E1302R, E1302S or D1304V.

113. The lactase variant of the preceding embodiment, wherein the variant has a decreased galactose inhibition, preferably measured as a galactose inhibition improvement factor (GI-IF) of at least 1.5, compared to the lactase of SEQ ID NO: 1.

114. The lactase variant of embodiment 1 which comprises one or more of the following substitutions, wherein each position corresponds to a position in SEQ ID NO: 1: S7P, S15I, V20P, A24T, S27A, R31E, D45P, V47R, A49H, A49R, D51I, S57C, S57E, S57G, W59P, S77H, L85F, P86Q, G87D, G88F, G90T, Y92M, Y92S, Y92V, R93A, R93F, R93L, R93T, R93V, R93Y, K94S, F96A, F96C, F96S, F96V, D101P, D112T, W121R, L161S, P162N, P162T, R165H, W166S, Y167A, S170Q, R174E, H185L, D217L, D217M, T218G, A220G, A222R, N223S, K236M, T237D, A239G, A252Y, P268R, E298I, F301C, W303A, T304P, A337L, N362T, A364I, L368S, I369K, N373G, G376S, E381T, M386G, M386S, R389E, R389Q, R389S, S390C, S390D, S390Q, S390T, K391E, N392D, G393R, G393V, N394L, T395H, T395N, T395W, E396K, E396L, E396V, E396W, Y398N, K400N, K400S, W401K, F402W, F402Y, G403A, G403K, G403V, Q404F, Q404L, Q404M, Q404P, Q404V, A405C, A405T, I406D, I406N, D418R, T420R, T427Q, T427S, T429D, D433W, R434N, R434V, L444V, G445V, M448L, M449D, M449W, M449Y, E450F, E450S, E450T, E450V, E450W, G451C, G451F, G451L, G451P, G451W, I452K, S455P, S455R, V456F, F459R, L466P, A468D, A472G, A472Y, M479G, A488N, N491W, N499Y, G504H, G505D, G505S, V506C, V506E, V506R, V507L, V507R, G508C, G508E, T509K, N510A, N510F, N510I, Y511A, S512T, D513P, D513R, A515E, Y517G, R521N, R521V, T522N, H524R, S526G, W527N, R546S, G549W, G550S, S554N, D555S, K556W, L558P, S564F, G567Q, G567V, A570K, R582L, D583W, T592S, F594L, P600E, P600S, S608V, G609R, W614A, V625M, V625Y, F630G, Q639R, D644C, H650R, W655R, A661E, P669T, V670C, Y673S, S688L, I694L, G695C, G695L, S698E, T700C, K701A, K701G, K701M, Y710T, E714K, T721S, N731S, W734V, D745F, L750S, P752C, T756N, E757A, A769F, A769I, A769N, A769V, K770H, K772A, A775L, A775W, D776I, D776L, R777D, R777G, R777H, R777P, T781A, T781G, D783C, D783E, D783R, G784L, K785S, K785W, L787P, V792G, V794T, P803S, T810P, K814H, V822D, S826L, H830R, A835D, A835H, D836E, D836S, D836Y, K839D, K844G, D865G, L867W, V872C, G902S, E912T, R914A, R914F, R914K, Y915M, S916G, D917F, D917S, T919Q, R922A, Q923V, K937I, V943A, V943H, V943R, A944P, T946V, E961F, S969I, S969M, P973C, P985L, A986I, W1002A, W1002D, W1002N, W1002P, A1006S, D1007P, V1048Q, N1051E, D1066W, L1068C, G1084V, G1085S, N1093P, W1094D, S1097W, N1102H, E1109D, E1109L, E1113P, Q1114S, Q1114V, L1116K, G1117V, G1117W, R1125V, R1125W, S1127Q, A1129E, P1133R, K1137S, D1145E, D1145T, D1151R, V1167R, G1178M, A1179W, T1180Q, V1184E, V1184L, V1184P, A1210G, A1210T, T1211G, T1211P, F1214K, F1214V, T1216Q, L1222V, S1223V, L1225E, L1225K, T1226P, T1230W, A1238E, P1265W, I1274F, I1274R, T1275W, S1277W, E1278Q, D1279R, D1279W, V1281I, K1284G, F1286E, T1287C, T1287W, I1288A, I1288D, I1288K, E1302R or E1302S.

115. The lactase variant of the preceding embodiment, wherein the variant has a decreased or an increased galactose inhibition, preferably measured as a galactose inhibition improvement factor (GI-IF) of at least 1.6 or at most 0.4, compared to the lactase of SEQ ID NO: 1.

116. The lactase variant of embodiment 1 which comprises one or more of the following substitutions, wherein each position corresponds to a position in SEQ ID NO: 1: S7P, S15I, V20P, A24T, S27A, R31E, D45P, V47R, A49H, A49R, D51I, S57C, S57E, S57G, W59P, S77H, L85F, P86Q, G87D, G88F, G90T, Y92M, Y92S, Y92V, R93A, R93F, R93L, R93T, R93V, R93Y, K94S, F96A, F96C, F96S, F96V, D101P, D112T, W121R, L161S, P162N, P162T, R165H, W166S, Y167A, S170Q, R174E, H185L, D217L, D217M, T218G, A220G, A222R, N223S, K236M, T237D, A239G, A252Y, P268R, E298I, F301C, W303A, T304P, A337L, N362T, A364I, L368S, I369K, N373G, G376S, E381T, M386G, M386S, R389E, R389Q, R389S, S390C, S390D, S390Q, S390T, K391E, N392D, G393R, G393V, N394L, T395H, T395N, T395W, E396K, E396L, E396V, E396W, Y398N, K400N, K400S, W401K, F402W, F402Y, G403A, G403K, G403V, Q404F, Q404L, Q404M, Q404P, Q404V, A405C, I406D, I406N, D418R, T420R, T427Q, T427S, T429D, D433W, R434N, R434V, L444V, G445V, M448L, M449D, M449W, M449Y, E450F, E450S, E450T, E450V, E450W, G451C, G451F, G451L, G451P, G451W, I452K, S455P, S455R, V456F, F459R, L466P, A468D, A472G, A472Y, M479G, A488N, N491W, N499Y, G504H, G505D, G505S, V506C, V506E, V506R, V507L, V507R, G508C, G508E, T509K, N510A, N510F, N510I, Y511A, S512T, D513P, D513R, A515E, Y517G, R521N, R521V, T522N, H524R, S526G, W527N, R546S, G549W, G550S, S554N, D555S, K556W, L558P, S564F, S567Q, G567V, A570K, R582L, D583W, T592S, F594L, P600E, P600S, S608V, G609R, W614A, V625M, V625Y, F630G, Q639R, D644C, H650R, W655R, A661E, P669T, V670C, Y673S, S688L, I694L, G695C, G695L, S698E, T700C, K701A, K701G, K701M, Y710T, E714K, T721S, N731S, W734V, D745F, L750S, P752C, T756N, E757A, A769F, A769I, A769N, A769V, K770H, K772P, A775L, A775W, D776I, D776L, R777D, R777G, R777H, R777P, T781A, T781G, D783C, D783E, D783R, G784L, K7855, K785W, L787P, V792G, V794T, P803S, T810P, K814H, V822D, S826L, H830R, A835D, A835H, D836S, D836Y, K839D, K844G, D865G, L867W, V872C, G9025, E912T, R914A, R914F, R914K, Y915M, S916G, D917F, D9175, T919Q, R922A, Q923V, K937I, V943A, V943H, V943R, A944P, T946V, E961F, S969I, S969M, P973C, P985L, A986I, W1002A, W1002D, W1002N, W1002P, A1006S, D1007P, V1048Q, N1051E, D1066W, L1068C, G1084V, G1085S, N1093P, W1094D, S1097W, N1102H, E1109D, E1109L, E1113P, Q1114S, Q1114V, L1116K, G1117V, G1117W, R1125V, R1125W, S1127Q, A1129E, P1133R, K1137S, D1145E, D1145T, D1151R, V1167R, G1178M, A1179W, T1180Q, V1184E, V1184L, V1184P, A1210G, A1210T, T1211G, T1211P, F1214K, F1214V, T1216Q, L1222V, S1223V, L1225E, L1225K, T1226P, T1230W, A1238E, P1265W, I1274F, I1274R, T1275W, S1277W, E1278Q, D1279R, D1279W, V1281I, K1284G, F1286E, T1287C, T1287W, I1288A, I1288D, I1288K, E1302R or E1302S.

117. The lactase variant of the preceding embodiment, wherein the variant has a decreased or an increased galactose inhibition, preferably measured as a galactose inhibition improvement factor (GI-IF) of at least 1.6 or at most 0.4, compared to the lactase of SEQ ID NO: 1.

118. The lactase variant of embodiment 1 which comprises one or more of the following substitutions, wherein each position corresponds to a position in SEQ ID NO: 1: S7P, S15I, V20P, A24T, S27A, R31E, D45P, V47R, A49H, D51I, S57C, S57E, S57G, W59P, S77H, L85F, P86Q, G87D, G88F, G90T, Y92M, Y92S, Y92V, R93A, R93F, R93L, R93T, R93V, R93Y, K94S, F96A, F96C, F96V, D101P, W121R, L161S, P162N, P162T, R165H, W166S, Y167A, S170Q, R174E, H185L, D217L, D217M, T218G, A220G, A222R, N223S, K236M, T237D, A252Y, P268R, E298I, F301C, W303A, T304P, A337L, N362T, A364I, L368S, I369K, N373G, G376S, E381T, M386G, M386S, R389E, R389Q, R389S, S390C, S390D, S390T, G393R, G393V, E396K, E396L, E396V, E396W, K400N, W401K, F402W, F402Y, G403A, G403K, G403V, Q404F, Q404L, Q404M, Q404P, Q404V, A405C, A405T, I406D, I406N, T427Q, T427S, T429D, D433W, R434N, R434V, L444V, M448L, M449D, M449W, M449Y, E450F, E450S, E450T, E450V, E450W, G451C, G451F, G451L, G451P, G451W, I452K, S455P, S455R, V456F, F459R, L466P, A468D, A472G, A472Y, M479G, G505D, G505S, V506C, V506E, V506R, V507R, G508C, G508E, T509K, N510A, N510F, N510I, Y511A, S512T, D513P, D513R, A515E, Y517G, R521V, H524R, S526G, W527N, G549W, L558P, S564F, G567Q, G567V, R582L, D583W, P600E, P600S, W614A, V625M, V625Y, Q639R, W655R, A661E, P669T, Y673S, S688L, I694L, G695C, G695L, S698E, K701A, K701G, K701M, Y710T, E714K, T721S, L750S, P752C, T756N, E757A, A769F, A769I, A769N, A769V, K770H, K772P, R777H, T781A, T781G, K7855, K785W, P803S, T810P, V822D, A835D, A835H, D836S, D836Y, K839D, D865G, L867W, V872C, G9025, E912T, R914A, R914F, R914K, Y915M, S916G, D917F, D9175, T919Q, R922A, Q923V, K937I, V943A, E961F, S9691, S969M, P973C, P985L, A986I, W1002A, W1002D, W1002N, W1002P, A1006S, D1007P, V1048Q, N1051E, G1084V, G1085S, N1093P, W1094D, N1102H, E1109D, E1109L, E1113P, Q1114S, Q1114V, L1116K, G1117V, G1117W, R1125V, R1125W, S1127Q, A1129E, P1133R, K1137S, D1145E, D1145T, V1167R, G1178M, A1179W, T1180Q, V1184E, V1184L, V1184P, A1210G, A1210T, T1211G, T1211P, F1214K, F1214V, T1216Q, L1222V, L1225E, L1225K, T1226P, T1230W, A1238E, P1265W, I1274F, I1274R, T1275W, S1277W, E1278Q, D1279R, D1279W, V1281I, K1284G, F1286E, T1287C, T1287W, I1288A, I1288D, I1288K, E1302R or E1302S.

119. The lactase variant of the preceding embodiment, wherein the variant has a decreased galactose inhibition, preferably measured as a galactose inhibition improvement factor (GI-IF) of at least 1.6, compared to the lactase of SEQ ID NO: 1.

120. The lactase variant of embodiment 1 which comprises one or more of the following substitutions, wherein each position corresponds to a position in SEQ ID NO: 1: S7P, S15I, V20P, A24T, S27A, R31E, D45P, V47R, A49H, D51I, S57C, S57E, S57G, W59P, S77H, L85F, P86Q, G87D, G88F, G90T, Y92M, Y92S, Y92V, R93A, R93F, R93L, R93T, R93V, R93Y, K94S, F96A, F96C, F96V, D101P, W121R, L161S, P162N, P162T, R165H, W166S, Y167A, S170Q, R174E, H185L, D217L, D217M, T218G, A220G, A222R, N223S, K236M, T237D, A252Y, P268R, E298I, F301C, W303A, T304P, A337L, N362T, A364I, L368S, I369K, N373G, G376S, E381T, M386G, M386S, R389E, R389Q, R389S, S390C, S390D, S390T, G393R, G393V, E396K, E396L, E396V, E396W, K400N, W401K, F402W, F402Y, G403A, G403K, G403V, Q404F, Q404L, Q404M, Q404P, Q404V, A405C, I406D, I406N, T427Q, T427S, T429D, D433W, R434N, R434V, L444V, M448L, M449D, M449W, M449Y, E450F, E450S, E450T, E450V, E450W, G451C, G451F, G451L, G451P, G451W, I452K, S455P, S455R, V456F, F459R, L466P, A468D, A472G, A472Y, M479G, G505D, G505S, V506C, V506E, V506R, V507R, G508C, G508E, T509K, N510A, N510F, N510I, Y511A, S512T, D513P, D513R, A515E, Y517G, R521V, H524R, S526G, W527N, G549W, L558P, S564F, G567Q, G567V, R582L, D583W, P600E, P600S, W614A, V625M, V625Y, Q639R, W655R, A661E, P669T, Y673S, S688L, I694L, G695C, G695L, S698E, K701A, K701G, K701M, Y710T, E714K, T721S, L750S, P752C, T756N, E757A, A769F, A769I, A769N, A769V, K770H, K772P, R777H, T781A, T781G, K7855, K785W, P803S, T810P, V822D, A835D, A835H, D836S, D836Y, K839D, D865G, L867W, V872C, G9025, E912T, R914A, R914F, R914K, Y915M, S916G, D917F, D9175, T919Q, R922A, Q923V, K937I, V943A, E961F, S969I, S969M, P973C, P985L, A986I, W1002A, W1002D, W1002N, W1002P, A1006S, D1007P, V1048Q, N1051E, G1084V, G1085S, N1093P, W1094D, N1102H, E1109D, E1109L, E1113P, Q1114S, Q1114V, L1116K, G1117V, G1117W, R1125V, R1125W, S1127Q, A1129E, P1133R, K1137S, D1145E, D1145T, V1167R, G1178M, A1179W, T1180Q, V1184E, V1184L, V1184P, A1210G, A1210T, T1211G, T1211P, F1214K, F1214V, T1216Q, L1222V, L1225E, L1225K, T1226P, T1230W, A1238E, P1265W, I1274F, I1274R, T1275W, S1277W, E1278Q, D1279R, D1279W, V1281I, K1284G, F1286E, T1287C, T1287W, I1288A, I1288D, I1288K, E1302R or E1302S.

121. The lactase variant of the preceding embodiment, wherein the variant has a decreased galactose inhibition, preferably measured as a galactose inhibition improvement factor (GI-IF) of at least 1.6, compared to the lactase of SEQ ID NO: 1.

122. The lactase variant of embodiment 1 which comprises one or more of the following substitutions, wherein each position corresponds to a position in SEQ ID NO: 1: S7P, S15I, V20P, A24T, S27A, R31E, A49H, S57E, S57G, W59P, S77H, L85F, P86Q, G87D, G88F, Y92S, Y92V, R93A, R93F, R93L, R93T, R93V, R93Y, F96A, F96S, D101P, D112T, L161S, P162N, R165H, W166S, Y167A, S170Q, R174E, H185L, D217L, D217M, A220G, A222R, T237D, A239G, A252Y, P268R, F301C, T304P, A337L, N362T, A364I, L368S, I369K, G376S, E381T, M386S, R389Q, R389S, S390C, S390Q, N392D, G393R, G393V, N394L, T395N, T395W, E396K, E396L, E396V, E396W, W401K, F402W, F402Y, G403A, G403K, Q404L, Q404M, Q404P, Q404V, A405C, A405T, D418R, T427Q, T429D, R434N, R434V, L444V, M448L, M449D, M449W, M449Y, E450F, E450S, E450T, E450V, E450W, G451C, G451F, G451L, G451P, G451W, I452K, F459R, L466P, A468D, A472G, A472Y, M479G, N491W, N499Y, G504H, G505D, G505S, V506C, V506E, V506R, G508C, G508E, T509K, N510A, N510I, Y511A, D513P, A515E, Y517G, R521V, T522N, H524R, S526G, W527N, R546S, G549W, G550S, D555S, L558P, S564F, G567Q, G567V, R582L, P600E, P600S, S608V, G609R, W614A, V625M, V625Y, Q639R, H650R, A661E, V670C, Y673S, S688L, G695C, G695L, S698E, K701A, K701M, Y710T, E714K, T721S, W734V, D745F, L750S, T756N, E757A, A769F, A769N, A769V, K770H, K772P, A775W, D776I, D776L, T781A, D783C, D783E, D783R, G784L, K785W, T810P, K814H, V822D, A835D, A835H, D836S, D836Y, K844G, D865G, L867W, V872C, G902S, E912T, R914A, R914F, R914K, Y915M, S916G, D917F, D917S, T919Q, R922A, Q923V, V943R, A944P, E961F, S969M, P973C, P985L, A986I, W1002D, W1002N, A1006S, N1051E, G1084V, G1085S, N1093P, E1109D, E1109L, Q1114V, L1116K, G1117V, G1117W, R1125V, P1133R, G1178M, A1179W, V1184E, V1184L, A1210G, A1210T, T1211G, T1211P, F1214K, T1216Q, L1222V, L1225K, T1226P, T1230W, A1238E, P1265W, I1274F, T1275W, S1277W, E1278Q, D1279W, V1281I, K1284G, T1287C, T1287W, I1288A, I1288D, E1302R or E1302S.

123. The lactase variant of the preceding embodiment, wherein the variant has a decreased or an increased galactose inhibition, preferably measured as a galactose inhibition improvement factor (GI-IF) of at least 1.7 or at most 0.3, compared to the lactase of SEQ ID NO: 1.

124. The lactase variant of embodiment 1 which comprises one or more of the following substitutions, wherein each position corresponds to a position in SEQ ID NO: 1: S7P, S15I, V20P, A24T, S27A, R31E, A49H, S57E, S57G, W59P, S77H, L85F, P86Q, G87D, G88F, Y92S, Y92V, R93A, R93F, R93L, R93T, R93V, R93Y, F96A, F96S, D101P, D112T, L161S, P162N, R165H, W166S, Y167A, S170Q, R174E, H185L, D217L, D217M, A220G, A222R, T237D, A239G, A252Y, P268R, F301C, T304P, A337L, N362T, A364I, L368S, I369K, G376S, E381T, M386S, R389Q, R389S, S390C, S390Q, N392D, G393R, G393V, N394L, T395N, T395W, E396K, E396L, E396V, E396W, W401K, F402W, F402Y, G403A, G403K, Q404L, Q404M, Q404P, Q404V, A405C, A405T, D418R, T427Q, T429D, R434N, R434V, L444V, M448L, M449D, M449W, M449Y, E450F, E450S, E450T, E450V, E450W, G451C, G451F, G451L, G451P, G451W, I452K, F459R, L466P, A468D, A472G, A472Y, M479G, N491W, N499Y, G504H, G505D, G505S, V506C, V506E, V506R, G508C, G508E, T509K, N510A, N510I, Y511A, D513P, A515E, Y517G, R521V, T522N, H524R, S526G, W527N, R546S, G549W, G550S, D555S, L558P, S564F, G567Q, G567V, R582L, P600E, P600S, S608V, G609R, W614A, V625M, V625Y, Q639R, H650R, A661E, V670C, Y673S, S688L, G695C, G695L, S698E, K701A, K701M, Y710T, E714K, T721S, W734V, D745F, L750S, T756N, E757A, A769F, A769N, A769V, K770H, K772P, A775W, D776I, D776L, T781A, D783C, D783E, D783R, G784L, K785W, T810P, K814H, V822D, A835D, A835H, D836S, D836Y, K844G, D865G, L867W, V872C, G902S, E912T, R914A, R914F, R914K, Y915M, S916G, D917F, D917S, T919Q, R922A, Q923V, V943R, A944P, E961F, S969M, P973C, P985L, A986I, W1002D, W1002N, A1006S, N1051E, G1084V, G1085S, N1093P, E1109D, E1109L, Q1114V, L1116K, G1117V, G1117W, R1125V, P1133R, G1178M, A1179W, V1184E, V1184L, A1210G, A1210T, T1211G, T1211P, F1214K, T1216Q, L1222V, L1225K, T1226P, T1230W, A1238E, P1265W, I1274F, T1275W, S1277W, E1278Q, D1279W, V1281I, K1284G, T1287C, T1287W, I1288A, I1288D, E1302R or E1302S.

125. The lactase variant of the preceding embodiment, wherein the variant has a decreased or an increased galactose inhibition, preferably measured as a galactose inhibition improvement factor (GI-IF) of at least 1.7 or at most 0.3, compared to the lactase of SEQ ID NO: 1.

126. The lactase variant of embodiment 1 which comprises one or more of the following substitutions, wherein each position corresponds to a position in SEQ ID NO: 1: S7P, S15I, V20P, A24T, S27A, R31E, A49H, S57E, S57G, W59P, S77H, L85F, P86Q, G87D, G88F, Y92S, Y92V, R93A, R93F, R93L, R93T, R93V, R93Y, F96A, D101P, L161S, P162N, R165H, W166S, Y167A, S170Q, R174E, H185L, D217L, D217M, A220G, A222R, T237D, A252Y, P268R, F301C, T304P, A337L, N362T, A364I, L368S, I369K, G376S, E381T, M386S, R389Q, R389S, S390C, G393R, G393V, E396K, E396L, E396V, E396W, W401K, F402W, F402Y, G403A, G403K, Q404L, Q404M, Q404P, Q404V, A405C, A405T, T427Q, T429D, R434N, R434V, L444V, M448L, M449D, M449W, M449Y, E450F, E450S, E450T, E450V, E450W, G451C, G451F, G451L, G451P, G451W, I452K, F459R, L466P, A468D, A472G, A472Y, M479G, G505D, G505S, V506C, V506E, V506R, G508C, G508E, T509K, N510A, N510I, Y511A, D513P, A515E, Y517G, R521V, H524R, S526G, W527N, G549W, L558P, S564F, G567Q, G567V, R582L, P600E, P600S, W614A, V625M, V625Y, Q639R, A661E, Y673S, S688L, G695C, G695L, S698E, K701A, K701M, Y710T, E714K, T721S, L750S, T756N, E757A, A769F, A769N, A769V, K770H, K772P, T781A, K785W, T810P, V822D, A835D, A835H, D836S, D836Y, D865G, L867W, V872C, G902S, E912T, R914A, R914F, R914K, Y915M, S916G, D917F, D917S, T919Q, R922A, Q923V, E961F, S969M, P973C, P985L, A986I, W1002D, W1002N, A1006S, N1051E, G1084V, G1085S, N1093P, E1109D, E1109L, Q1114V, L1116K, G1117V, G1117W, R1125V, P1133R, G1178M, A1179W, V1184E, V1184L, A1210G, A1210T, T1211G, T1211P, F1214K, T1216Q, L1222V, L1225K, T1226P, T1230W, A1238E, P1265W, I1274F, T1275W, S1277W, E1278Q, D1279W, V1281I, K1284G, T1287C, T1287W, I1288A, I1288D, E1302R or E1302S.

127. The lactase variant of the preceding embodiment, wherein the variant has a decreased galactose inhibition, preferably measured as a galactose inhibition improvement factor (GI-IF) of at least 1.7, compared to the lactase of SEQ ID NO: 1.

128. The lactase variant of embodiment 1 which comprises one or more of the following substitutions, wherein each position corresponds to a position in SEQ ID NO: 1: S7P, S15I, V20P, A24T, S27A, R31E, A49H, S57E, S57G, W59P, S77H, L85F, P86Q, G87D, G88F, Y92S, Y92V, R93A, R93F, R93L, R93T, R93V, R93Y, F96A, D101P, L161S, P162N, R165H, W166S, Y167A, S170Q, R174E, H185L, D217L, D217M, A220G, A222R, T237D, A252Y, P268R, F301C, T304P, A337L, N362T, A364I, L368S, I369K, G376S, E381T, M386S, R389Q, R389S, S390C, G393R, G393V, E396K, E396L, E396V, E396W, W401K, F402W, F402Y, G403A, G403K, Q404L, Q404M, Q404P, Q404V, A405C, T427Q, T429D, R434N, R434V, L444V, M448L, M449D, M449W, M449Y, E450F, E450S, E450T, E450V, E450W, G451C, G451F, G451L, G451P, G451W, I452K, F459R, L466P, A468D, A472G, A472Y, M479G, G505D, G505S, V506C, V506E, V506R, G508C, G508E, T509K, N510A, N510I, Y511A, D513P, A515E, Y517G, R521V, H524R, S526G, W527N, G549W, L558P, S564F, G567Q, G567V, R582L, P600E, P600S, W614A, V625M, V625Y, Q639R, A661E, Y673S, S688L, G695C, G695L, S698E, K701A, K701M, Y710T, E714K, T721S, L750S, T756N, E757A, A769F, A769N, A769V, K770H, K772P, T781A, K785W, T810P, V822D, A835D, A835H, D836S, D836Y, D865G, L867W, V872C, G902S, E912T, R914A, R914F, R914K, Y915M, S916G, D917F, D917S, T919Q, R922A, Q923V, E961F, S969M, P973C, P985L, A986I, W1002D, W1002N, A1006S, N1051E, G1084V, G1085S, N1093P, E1109D, E1109L, Q1114V, L1116K, G1117V, G1117W, R1125V, P1133R, G1178M, A1179W, V1184E, V1184L, A1210G, A1210T, T1211G, T1211P, F1214K, T1216Q, L1222V, L1225K, T1226P, T1230W, A1238E, P1265W, I1274F, T1275W, S1277W, E1278Q, D1279W, V1281I, K1284G, T1287C, T1287W, I1288A, I1288D, E1302R or E1302S.

129. The lactase variant of the preceding embodiment, wherein the variant has a decreased galactose inhibition, preferably measured as a galactose inhibition improvement factor (GI-IF) of at least 1.7, compared to the lactase of SEQ ID NO: 1.

130. The lactase variant of embodiment 1 which comprises one or more of the following substitutions, wherein each position corresponds to a position in SEQ ID NO: 1: S7P, S15I, V20P, A24T, S57E, W59P, L85F, P86Q, R93A, R93F, R93L, R93T, R93Y, P162N, R165H, W166S, Y167A, R174E, D217L, A222R, T237D, P268R, T304P, A337L, N362T, A364I, L368S, I369K, G376S, M386S, R389Q, R389S, S390C, S390Q, N392D, G393V, N394L, T395N, T395W, E396L, E396V, W401K, F402Y, G403A, Q404M, Q404P, Q404V, A405C, A405T, T427Q, T429D, R434N, M448L, M449D, M449W, M449Y, E450F, E450S, E450T, E450V, E450W, G451C, G451F, G451L, G451P, G451W, F459R, A468D, A472G, A472Y, M479G, N491W, N499Y, G505D, G505S, V506E, G508C, G508E, T509K, N510A, N510I, Y511A, D513P, A515E, Y517G, R521V, S526G, W527N, R546S, S564F, G567Q, R582L, P600E, P600S, S608V, W614A, V625M, V625Y, H650R, V670C, Y673S, S688L, G695C, G695L, K701A, K701M, Y710T, E714K, T721S, D745F, L750S, T756N, E757A, A769F, A769N, A769V, K770H, K772P, D776I, T781A, D783E, G784L, K785W, T810P, K814H, A835D, A835H, K844G, E912T, R914A, R914F, D917S, T919Q, R922A, Q923V, E961F, P985L, A986I, A1006S, N1051E, N1093P, L1116K, G1117V, G1117W, R1125V, G1178M, A1179W, V1184E, A1210T, T1211G, T1211P, L1225K, A1238E, P1265W, I1274F, T1275W, S1277W, K1284G, T1287C, I1288A, I1288D, E1302R or E1302S.

131. The lactase variant of the preceding embodiment, wherein the variant has a decreased or an increased galactose inhibition, preferably measured as a galactose inhibition improvement factor (GI-IF) of at least 1.8 or at most 0.2, compared to the lactase of SEQ ID NO: 1.

132. The lactase variant of embodiment 1 which comprises one or more of the following substitutions, wherein each position corresponds to a position in SEQ ID NO: 1: S7P, S15I, V20P, A24T, S57E, W59P, L85F, P86Q, R93A, R93F, R93L, R93T, R93Y, P162N, R165H, W166S, Y167A, R174E, D217L, A222R, T237D, P268R, T304P, A337L, N362T, A364I, L368S, I369K, G376S, M386S, R389Q, R389S, S390C, S390Q, N392D, G393V, N394L, T395N, T395W, E396L, E396V, W401K, F402Y, G403A, Q404M, Q404P, Q404V, A405C, T427Q, T429D, R434N, M448L, M449D, M449W, M449Y, E450F, E450S, E450T, E450V, E450W, G451C, G451F, G451L, G451P, G451W, F459R, A468D, A472G, A472Y, M479G, N491W, N499Y, G505D, G505S, V506E, G508C, G508E, T509K, N510A, N510I, Y511A, D513P, A515E, Y517G, R521V, S526G, W527N, R546S, S564F, G567Q, R582L, P600E, P600S, S608V, W614A, V625M, V625Y, H650R, V670C, Y673S, S688L, G695C, G695L, K701A, K701M, Y710T, E714K, T721S, D745F, L750S, T756N, E757A, A769F, A769N, A769V, K770H, K772P, D776I, T781A, D783E, G784L, K785W, T810P, K814H, A835D, A835H, K844G, E912T, R914A, R914F, D917S, T919Q, R922A, Q923V, E961F, P985L, A986I, A1006S, N1051E, N1093P, L1116K, G1117V, G1117W, R1125V, G1178M, A1179W, V1184E, A1210T, T1211G, T1211P, L1225K, A1238E, P1265W, I1274F, T1275W, S1277W, K1284G, T1287C, I1288A, I1288D, E1302R or E1302S.

133. The lactase variant of the preceding embodiment, wherein the variant has a decreased or an increased galactose inhibition, preferably measured as a galactose inhibition improvement factor (GI-IF) of at least 1.8 or at most 0.2, compared to the lactase of SEQ ID NO: 1.

134. The lactase variant of embodiment 1 which comprises one or more of the following substitutions, wherein each position corresponds to a position in SEQ ID NO: 1: S7P, S15I, V20P, A24T, S57E, W59P, L85F, P86Q, R93A, R93F, R93L, R93T, R93Y, P162N, R165H, W166S, Y167A, R174E, D217L, A222R, T237D, P268R, T304P, A337L, N362T, A364I, L368S, I369K, G376S, M386S, R389Q, R389S, S390C, G393V, E396L, E396V, W401K, F402Y, G403A, Q404M, Q404P, Q404V, A405C, A405T, T427Q, T429D, R434N, M448L, M449D, M449W, M449Y, E450F, E450S, E450T, E450V, E450W, G451C, G451F, G451L, G451P, G451W, F459R, A468D, A472G, A472Y, M479G, G505D, G505S, V506E, G508C, G508E, T509K, N510A, N510I, Y511A, D513P, A515E, Y517G, R521V, S526G, W527N, S564F, G567Q, R582L, P600E, P600S, W614A, V625M, V625Y, Y673S, S688L, G695C, G695L, K701A, K701M, Y710T, E714K, T721S, L750S, T756N, E757A, A769F, A769N, A769V, K770H, K772P, T781A, K785W, T810P, A835D, A835H, E912T, R914A, R914F, D917S, T919Q, R922A, Q923V, E961F, P985L, A986I, A1006S, N1051E, N1093P, L1116K, G1117V, G1117W, R1125V, G1178M, A1179W, V1184E, A1210T, T1211G, T1211P, L1225K, A1238E, P1265W, I1274F, T1275W, S1277W, K1284G, T1287C, I1288A, I1288D, E1302R or E1302S.

135. The lactase variant of the preceding embodiment, wherein the variant has a decreased galactose inhibition, preferably measured as a galactose inhibition improvement factor (GI-IF) of at least 1.8, compared to the lactase of SEQ ID NO: 1.

136. The lactase variant of embodiment 1 which comprises one or more of the following substitutions, wherein each position corresponds to a position in SEQ ID NO: 1: S7P, S15I, V20P, A24T, S57E, W59P, L85F, P86Q, R93A, R93F, R93L, R93T, R93Y, P162N, R165H, W166S, Y167A, R174E, D217L, A222R, T237P, P268R, T304P, A337L, N362T, A364I, L368S, I369K, G376S, M386S, R389Q, R389S, S390C, G393V, E396L, E396V, W401K, F402Y, G403A, Q404M, Q404P, Q404V, A405C, T427Q, T429D, R434N, M448L, M449D, M449W, M449Y, E450F, E450S, E450T, E450V, E450W, G451C, G451F, G451L, G451P, G451W, F459R, A468D, A472G, A472Y, M479G, G505D, G505S, V506E, G508C, G508E, T509K, N510A, N510I, Y511A, D513P, A515E, Y517G, R521V, S526G, W527N, S564F, G567Q, R582L, P600E, P600S, W614A, V625M, V625Y, Y673S, S688L, G695C, G695L, K701A, K701M, Y710T, E714K, T721S, L750S, T756N, E757A, A769F, A769N, A769V, K770H, K772P, T781A, K785W, T810P, A835D, A835H, E912T, R914A, R914F, D917S, T919Q, R922A, Q923V, E961F, P985L, A986I, A1006S, N1051E, N1093P, L1116K, G1117V, G1117W, R1125V, G1178M, A1179W, V1184E, A1210T, T1211G, T1211P, L1225K, A1238E, P1265W, I1274F, T1275W, S1277W, K1284G, T1287C, I1288A, I1288D, E1302R or E1302S.

137. The lactase variant of the preceding embodiment, wherein the variant has a decreased galactose inhibition, preferably measured as a galactose inhibition improvement factor (GI-IF) of at least 1.8, compared to the lactase of SEQ ID NO: 1.

138. The lactase variant of embodiment 1 which comprises one or more of the following substitutions, wherein each position corresponds to a position in SEQ ID NO: 1: S7P, S15I, A24T, S57E, L85F, P86Q, R93A, R93F, R93L, R93Y, P162N, Y167A, R174E, D217L, A222R, T237D, P268R, T304P, N362T, A364I, I369K, M386S, R389Q, R389S, N392D, G393V, T395W, E396L, E396V, W401K, G403A, Q404M, Q404P, Q404V, A405T, T427Q, M448L, M449Y, E450F, E450S, E450T, E450V, E450W, G451C, G451F, G451L, G451P, F459R, A468D, A472G, A472Y, M479G, N491W, G505D, G505S, V506E, G508C, G508E, N510A, N510I, Y511A, D513P, A515E, Y517G, R521V, S526G, W527N, G567Q, P600E, P600S, V625M, V625Y, V670C, Y673S, S688L, G695L, K701A, Y710T, E714K, T721S, L750S, E757A, A769V, K772P, G784L, K785W, T810P, E912T, T919Q, R922A, Q923V, E961F, P985L, A1006S, N1051E, N1093P, L1116K, G1117W, A1179W, A1210T, T1211P, A1238E, P1265W, I1274F, T1275W, S1277W, K1284G, T1287C, I1288D, E1302R or E1302S.

139. The lactase variant of the preceding embodiment, wherein the variant has a decreased or an increased galactose inhibition, preferably measured as a galactose inhibition improvement factor (GI-IF) of at least 1.9 or at most 0.1, compared to the lactase of SEQ ID NO: 1.

140. The lactase variant of embodiment 1 which comprises one or more of the following substitutions, wherein each position corresponds to a position in SEQ ID NO: 1: S7P, S15I, A24T, S57E, L85F, P86Q, R93A, R93F, R93L, R93Y, P162N, Y167A, R174E, D217L, A222R, T237D, P268R, T304P, N362T, A364I, I369K, M386S, R389Q, R389S, N392D, G393V, T395W, E396L, E396V, W401K, G403A, Q404M, Q404P, Q404V, T427Q, M448L, M449Y, E450F, E450S, E450T, E450V, E450W, G451C, G451F, G451L, G451P, F459R, A468D, A472G, A472Y, M479G, N491W, G505D, G505S, V506E, G508C, G508E, N510A, N510I, Y511A, D513P, A515E, Y517G, R521V, S526G, W527N, G567Q, P600E, P600S, V625M, V625Y, V670C, Y673S, S688L, G695L, K701A, Y710T, E714K, T721S, L750S, E757A, A769V, K772P, G784L, K785W, T810P, E912T, T919Q, R922A, Q923V, E961F, P985L, A1006S, N1051E, N1093P, L1116K, G1117W, A1179W, A1210T, T1211P, A1238E, P1265W, I1274F, T1275W, S1277W, K1284G, T1287C, I1288D, E1302R or E1302S.

141. The lactase variant of the preceding embodiment, wherein the variant has a decreased or an increased galactose inhibition, preferably measured as a galactose inhibition improvement factor (GI-IF) of at least 1.9 or at most 0.1, compared to the lactase of SEQ ID NO: 1.

142. The lactase variant of embodiment 1 which comprises one or more of the following substitutions, wherein each position corresponds to a position in SEQ ID NO: 1: S7P, S15I, A24T, S57E, L85F, P86Q, R93A, R93F, R93L, R93Y, P162N, Y167A, R174E, D217L, A222R, T237D, P268R, T304P, N362T, A364I, I369K, M386S, R389Q, R389S, G393V, E396L, E396V, W401K, G403A, Q404M, Q404P, Q404V, A405T, T427Q, M448L, M449Y, E450F, E450S, E450T, E450V, E450W, G451C, G451F, G451L, G451P, F459R, A468D, A472G, A472Y, M479G, G505D, G505S, V506E, G508C, G508E, N510A, N510I, Y511A, D513P, A515E, Y517G, R521V, S526G, W527N, G567Q, P600E, P600S, V625M, V625Y, Y673S, S688L, G695L, K701A, Y710T, E714K, T721S, L750S, E757A, A769V, K772P, K785W, T810P, E912T, T919Q, R922A, Q923V, E961F, P985L, A1006S, N1051E, N1093P, L1116K, G1117W, A1179W, A1210T, T1211P, A1238E, P1265W, I1274F, T1275W, S1277W, K1284G, T1287C, I1288D, E1302R or E1302S.

143. The lactase variant of the preceding embodiment, wherein the variant has a decreased galactose inhibition, preferably measured as a galactose inhibition improvement factor (GI-IF) of at least 1.9, compared to the lactase of SEQ ID NO: 1.

144. The lactase variant of embodiment 1 which comprises one or more of the following substitutions, wherein each position corresponds to a position in SEQ ID NO: 1: S7P, S15I, A24T, S57E, L85F, P86Q, R93A, R93F, R93L, R93Y, P162N, Y167A, R174E, D217L, A222R, T237D, P268R, T304P, N362T, A364I, I369K, M386S, R389Q, R389S, G393V, E396L, E396V, W401K, G403A, Q404M, Q404P, Q404V, T427Q, M448L, M449Y, E450F, E450S, E450T, E450V, E450W, G451C, G451F, G451L, G451P, F459R, A468D, A472G, A472Y, M479G, G505D, G505S, V506E, G508C, G508E, N510A, N510I, Y511A, D513P, A515E, Y517G, R521V, S526G, W527N, G567Q, P600E, P600S, V625M, V625Y, Y673S, S688L, G695L, K701A, Y710T, E714K, T721S, L750S, E757A, A769V, K772P, K785W, T810P, E912T, T919Q, R922A, Q923V, E961F, P985L, A1006S, N1051E, N1093P, L1116K, G1117W, A1179W, A1210T, T1211P, A1238E, P1265W, I1274F, T1275W, S1277W, K1284G, T1287C, I1288D, E1302R or E1302S.

145. The lactase variant of the preceding embodiment, wherein the variant has a decreased galactose inhibition, preferably measured as a galactose inhibition improvement factor (GI-IF) of at least 1.9, compared to the lactase of SEQ ID NO: 1.

146. The lactase variant of embodiment 1, which comprises one or more of the following substitutions, wherein each position corresponds to a position in SEQ ID NO: 1: E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, 514Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, F54M, F54S, D55C, D55F, D55G, D55H, D55M, D55N, D55P, D55S, D55V, 557A, S57C, S57E, S57G, A58D, A58G, A58I, A58M, A58N, A58Q, A58R, A58T, W59D, W59I, W59K, W59L, W59N, W59P, W59V, Q60A, Q60O, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74G, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86M, P86Q, P86R, P86V, P86W, P86Y, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, K94Y, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167S, S168C, G169A, G169C, G169D, G169S, S170L, S170Q, G171C, G171F, G171T, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191C, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209N, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, A220C, A220G, A220I, A220L, A220M, A220T, A220V, A220W, A221O, A221D, A221E, A221L, A221N, A221R, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, F231A, F231E, F231G, F231I, F231K, F231L, F231Q, F231S, F231V, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235S, G235T, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S248I, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, A265G, A265I, A265K, A265R, A265S, A265V, S267A, S267D, S267K, S267M, S267N, S267P, S267Q, S267R, S267V, P268F, P268G, P268M, P268R, P268V, P268W, P268Y, K269G, K269R, K269V, K269Y, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, S310A, S310C, S310G, S310H, S310I, S310L, S310M, S310N, S310S, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387N, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396N, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, I406C, I406D, I406N, A407C, A407G, A407M, A407Q, A407S, A407T, A407W, G408D, G408I, G408M, G408N, G408W, D409N, D409W, N410C, N410R, N410Y, A411E, A411N, A411R, A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, W421L, W421Q, W421S, A422P, A422T, A422V, K423D, K423L, K423M, K423R, F424C, F424L, F424N, F424T, D425E, L426C, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L444C, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457T, S457V, F459A, F459C, F459E, F459G, F459N, F459R, F459S, F459T, F459W, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K465C, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, W469A, W469C, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K487C, K487F, K487G, K487N, K487S, K487W, A488C, A488G, A488H, A488L, A488N, A488S, A488V, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496T, G497D, D498A, D498C, D498M, D498S, N499K, N499R, N499T, N499Y, L500A, L500E, L500N, L500V, T501C, T501G, T501M, A502L, A502Q, N503A, N503E, N503M, N503S, G504H, G504K, G504P, G505A, G505D, G505E, G505H, G505L, G505N, G505R, G505S, G505V, V506C, V506D, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, G514F, G514L, G514N, G514P, G514R, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521Q, R521V, H524R, H524V, P525D, P525G, P525R, P525T, P525V, S526G, S526I, S526W, W527A, W527E, W527G, W527H, W527N, W527R, W527S, W527V, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, P631A, P631D, P631G, P631H, P631S, P631V, P631Y, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644G, D644Y, D645S, D645V, V646C, V646L, V646N, V646R, V646S, H647G, H647V, T648C, L649V, H650E, H650F, H650R, I651F, I651T, I651V, L652C, L652D, L652V, L652W, P653Q, A654D, A654K, A654M, A654R, W655F, W655R, N656A, N656K, N656V, E657K, E657R, E657V, V659D, V659N, A661E, A661G, A661H, A661K, A661L, A661M, A661Q, A661W, K662H, K662S, K662V, K662W, K662Y, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684M, T684S, T684V, P685A, P685E, P685I, P685L, P685W, K686A, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701M, K701P, K701S, K701W, T703E, T703I, T703K, T703W, T704M, T704R, T704T, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711A, Q711D, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, K718A, K718L, K718Q, K718T, K718W, K718Y, S720A, S720M, S720R, S720Y, T721D, T721H, T721K, T721L, T721N, T721P, T721Q, T721S, T721V, T721W, T721Y, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, W730V, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739W, I739Y, S740D, S740E, S740F, S740H, S740L, A741I, A741P, A741S, A741V, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, L750G, L750M, L750P, L750Q, L750S, I751C, I751H, I751Q, I751S, P752A, P752C, P752H, P752L, P752S, P752V, P752Y, E753Q, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, T810L, T810P, T810Q, T810R, T810Y, F811L, F811Y, D812E, D812F, D812I, D812Q, V813F, V813H, V813I, V813W, V813Y, V814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, K818Y, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, D823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837F, N837F, N837G, N837H, N837L, N837P, N837T, R838D, R838E, R838K, R838M, R838N, R838S, R838W, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858G, I858K, I858M, I858P, I858Q, I858Y, T859V, V860T, V860Y, T861F, T861I, T861Q, T861V, T861W, A862C, A862P, A862V, K863F, K863I, K863L, K863N, K863W, A864E, A864H, A864K, A864L, D865A, D865G, G866H, G866R, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888G, R889G, Y893E, Y893G, S894D, S894G, R895M, N896M, W897V, W898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925S, V925W, T926G, T926P, T926R, T926V, T926W, W927G, W927L, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937G, K937I, K937M, K937P, K937Q, K937R, K937V, A938C, A938H, A938N, A938T, A938V, A938W, G939G, G939K, S940C, S940E, S940M, S940R, S940T, S940V, S940W, F941C, F941M, F941W, S942A, S942E, S942K, S942L, S942P, S942T, S942V, V943A, V943G, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965L, L965K, L965M, L965P, L965Q, L965S, L965Y, L966G, L966H, L966K, L966N, L966P, L966Q, L966S, L966T, L966V, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, P973C, P973D, P973K, P973N, P973Q, P973R, P973V, P973W, P973Y, V974C, V974E, V974G, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, R984P, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, L1055R, L1055T, Q1057A, Q1057E, Q1057P, Q1057R, N1058R, N1058S, N1058V, N1058W, I1059W, P1060G, P1060N, P1060Q, P1060S, P1060T, D1062A, D1062F, D1062G, D1062I, D1062L, D1062M, D1062P, D1062S, K1063D, K1063M, Q1064C, Q1064M, Q1064R, Q1064T, Q1064V, S1065A, S1065C, S1065E, S1065G, S1065T, S1065Y, D1066A, D1066G, D1066M, D1066V, D1066W, T1067G, T1067M, L1068C, L1068E, L1068P, L1068Q, L1068Y, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119I, I1119S, V1120N, V1120S, V1120T, M1121G, M1121K, M1121N, M1121P, M1121S, M1121V, M1121Y, Y1122A, Y1122C, Y1122I, Y1122K, Y1122R, Y1122V, Y1122W, F1123E, F1123H, F1123R, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145E, D1145R, D1145T, G1146A, G1146C, G1146D, G1146K, G1146L, G1146R, G1146V, K1147A, K1147C, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, Q1161A, Q1161P, Q1161S, E1162A, E1162C, E1162D, E1162F, E1162I, E1162N, E1162Q, E1162T, E1162W, E1162Y, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, YI172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179P, A1179Q, A1179W, T1180A, T1180G, T1180I, T1180L, T1180M, T1180Q, T1180S, T1180Y, F1181E, F1181L, F1181V, V1182M, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, L1202A, L1202C, T1203E, T1203K, E1204G, E1204S, I1205K, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, N1217A, N1217D, N1217E, N1217F, N1217P, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234G, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257K, G1257L, G1257Q, G1257R, G1257W, N1258O, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

147. The lactase variant of the preceding embodiment, wherein the variant has a decreased or an increased galactose inhibition, preferably measured as a galactose inhibition improvement factor (GI-IF) of at least 1.1 or at most 0.9, compared to the lactase of SEQ ID NO: 1.

148. The lactase variant of any of the preceding embodiments which has an amino acid sequence which is at least 80%, 85%, 90%, or 95%, preferably at least 97%, 98%, or 99%, more preferably at least 99.5%, 99.7%, 99.8% or 99.9%, but less than 100%, identical to SEQ ID NO: 1.

149. The lactase variant of any of the preceding embodiments wherein the variant has lactase activity.

150. The lactase variant of any of the preceding embodiments, wherein the variant is a variant of a lactase obtained from *Bifidobacterium*, preferably *Bifidobacterium bifidum*.

151. The lactase variant of any of the preceding embodiments wherein the variant has a galactose inhibition improvement factor (GI-IF) of at least 1.1 or at most 0.9, compared to the lactase of SEQ ID NO: 1, and wherein the GI-IF is calculated as described in Example 2.

152. The lactase variant of any of the preceding embodiments wherein the variant has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

153. The lactase variant of any of the preceding embodiments which has an amino acid sequence which is at least 90% identical to SEQ ID NO: 1 and which has a length of 1200-2000 amino acids.

154. The lactase variant of any of the preceding embodiments which has an amino acid sequence which is at least 90% identical to SEQ ID NO: 1 and which has a length of 1200-1500 amino acids.

155. The lactase variant of any of the preceding embodiments which has an amino acid sequence which is at least 90% identical to SEQ ID NO: 1 and which has a length of 1250-1350 amino acids.

156. The lactase variant of any of the preceding embodiments which has an amino acid sequence which is at least 90% identical to SEQ ID NO: 1 and which has a length of 1300-1310 amino acids.

157. The lactase variant of any of the preceding embodiments which has an amino acid sequence which is at least 95% identical to SEQ ID NO: 1 and which has a length of 1200-2000 amino acids.

158. The lactase variant of any of the preceding embodiments which has an amino acid sequence which is at least 95% identical to SEQ ID NO: 1 and which has a length of 1200-1500 amino acids.

159. The lactase variant of any of the preceding embodiments which has an amino acid sequence which is at least 95% identical to SEQ ID NO: 1 and which has a length of 1250-1350 amino acids.

160. The lactase variant of any of the preceding embodiments which has an amino acid sequence which is at least 95% identical to SEQ ID NO: 1 and which has a length of 1300-1310 amino acids.

161. The lactase variant of any of the preceding embodiments which has an amino acid sequence which is at least 99% identical to SEQ ID NO: 1 and which has a length of 1200-2000 amino acids.

162. The lactase variant of any of the preceding embodiments which has an amino acid sequence which is at least 99% identical to SEQ ID NO: 1 and which has a length of 1200-1500 amino acids.

163. The lactase variant of any of the preceding embodiments which has an amino acid sequence which is at least 99% identical to SEQ ID NO: 1 and which has a length of 1250-1350 amino acids.

164. The lactase variant of any of the preceding embodiments which has an amino acid sequence which is at least 99% identical to SEQ ID NO: 1 and which has a length of 1300-1310 amino acids.

165. The lactase variant of the preceding embodiment which comprises the same number of amino acid residues as the lactase of SEQ ID NO: 1.

166. The lactase variant of any of the preceding embodiments wherein the variant has 1-50 substitutions, preferably 1-30, 1-20, 1-10 or 1-5, such as 1, 2, 3, 4, 5, 6, 7, 8, 9, 10, 11, 12, 13, 14, 15, 16, 17, 18, 19 or 20 substitutions, compared to the lactase of SEQ ID NO: 1.

167. The lactase variant of any of the preceding embodiments which is an isolated lactase variant.

168. The lactase variant of any of the preceding embodiments which has a ratio of beta-galactosidase activity to transgalactosylating activity of at least 2, preferably at least 3, such as at least 4, more preferably at least 5, such as at least 10, where said ratio is measured as [Galactose]/([Glucose]−[Galactose]) after incubation of the enzyme in cow's milk at 37° C. for 3 hours.

169. An isolated polynucleotide encoding the variant of any of the preceding embodiments.

170. A nucleic acid construct or expression vector comprising the polynucleotide of the preceding embodiment.

171. A recombinant host cell transformed with the polynucleotide of embodiment 169.

172. A method of producing a lactase variant, comprising:
 a. cultivating the host cell of the preceding embodiment under conditions suitable for expression of the variant; and
 b. recovering the variant 173. A whole broth formulation or cell culture composition comprising the variant of any of embodiments 1-168.

174. A method for producing a dairy product comprising
 a) providing a milk-based substrate comprising lactose; and
 b) treating said substrate with the variant of any of embodiments 1-168.

175. The method of the preceding embodiment wherein step b) results in a lactose reduction of at least 70%, preferably at least 80%, more preferably at least 90%, even more preferably at least 95% or at least 98%.

176. The method of any of the two preceding embodiments, further comprising a step
 c) fermenting said substrate with a microorganism,
 wherein the dairy product is a fermented dairy product 177. The method of the preceding embodiment wherein step b) and step c) are performed essentially at the same time.

178. The method of any of the two preceding embodiments wherein the treatment with the lactase variant results in a lactose reduction of at least 50%, preferably at least 70% or at least 90%, compared to a similar method without addition of the lactase variant.

179. The method of any of the five preceding embodiments wherein the lactose content in the dairy product is below 2% w/v, preferably below 1%, more preferably below 0.5% or below 0.1%, and most preferably below 0.05% or below 0.01% w/v.

180. Use of the variant of any of embodiments 1-168 for production of a dairy product.

181. The use according to the preceding embodiment wherein the dairy product is a low-lactose dairy product having a lactose content of below 2% w/v, preferably below 1%, more preferably below 0.5% or below 0.1%, and most preferably below 0.05% or below 0.01% w/v.

182. A liquid composition comprising the variant of any of embodiments 1-168 and 20-70% glycerol.

183. A method for obtaining a lactase variant, comprising:
  a. introducing into a parent lactase having an amino acid sequence which is at least 80% identical to SEQ ID NO: 1 an alteration, preferably a substitution, at one or more positions corresponding to positions 1, 2, 3, 4, 5, 6, 7, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 47, 48, 49, 51, 53, 54, 55, 57, 58, 59, 60, 61, 62, 63, 64, 66, 67, 68, 70, 71, 73, 74, 75, 76, 77, 78, 79, 80, 81, 83, 85, 86, 87, 88, 89, 90, 91, 92, 93, 94, 95, 96, 97, 98, 100, 101, 102, 104, 105, 106, 107, 108, 109, 110, 111, 112, 113, 114, 115, 116, 117, 118, 119, 120, 121, 122, 123, 124, 125, 126, 128, 129, 130, 131, 132, 133, 135, 136, 137, 138, 139, 140, 141, 142, 146, 148, 149, 150, 151, 153, 154, 155, 157, 158, 159, 160, 161, 162, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 254, 255, 256, 257, 258, 259, 260, 261, 262, 263, 264, 265, 266, 267, 268, 269, 270, 271, 272, 273, 274, 275, 277, 278, 279, 280, 281, 282, 283, 284, 285, 286, 287, 288, 291, 292, 293, 294, 295, 296, 297, 298, 299, 301, 302, 303, 304, 305, 306, 307, 308, 309, 310, 311, 312, 314, 315, 316, 317, 318, 320, 321, 322, 324, 325, 326, 328, 329, 331, 335, 337, 338, 340, 341, 342, 343, 344, 345, 346, 347, 348, 349, 350, 351, 352, 353, 354, 355, 357, 359, 360, 362, 363, 364, 365, 366, 367, 368, 369, 370, 371, 372, 373, 374, 375, 376, 377, 378, 379, 380, 381, 383, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 485, 487, 488, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 534, 535, 537, 538, 539, 540, 542, 543, 545, 546, 547, 548, 549, 550, 551, 553, 554, 555, 556, 557, 558, 559, 560, 561, 563, 564, 565, 567, 570, 571, 572, 573, 574, 575, 576, 577, 578, 579, 580, 581, 582, 583, 584, 585, 586, 587, 588, 589, 590, 591, 592, 593, 594, 595, 597, 598, 600, 604, 605, 606, 607, 608, 609, 610, 611, 612, 613, 614, 615, 616, 619, 620, 621, 624, 625, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 659, 661, 662, 667, 669, 670, 672, 673, 674, 675, 676, 677, 678, 679, 680, 681, 682, 683, 684, 685, 686, 687, 688, 689, 690, 691, 692, 693, 694, 695, 696, 697, 698, 700, 701, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 765, 766, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 857, 858, 859, 860, 861, 862, 863, 864, 865, 866, 867, 870, 871, 872, 873, 874, 875, 877, 879, 880, 881, 882, 883, 884, 885, 886, 887, 888, 889, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 973, 974, 975, 976, 977, 978, 979, 980, 981, 982, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1022, 1023, 1024, 1026, 1027, 1028, 1029, 1030, 1031, 1033, 1034, 1035, 1036, 1037, 1038, 1039, 1040, 1041, 1042, 1043, 1044, 1045, 1046, 1047, 1048, 1050, 1051, 1052, 1053, 1054, 1055, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1111, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1157, 1158, 1159, 1160, 1161, 1162, 1165, 1166, 1167, 1168, 1169, 1170, 1171, 1172, 1173, 1174, 1175, 1177, 1178, 1179, 1180, 1181, 1182, 1183, 1184, 1185, 1186, 1188, 1189, 1190, 1191, 1192, 1193, 1194, 1195, 1197, 1198, 1199, 1200, 1202, 1203, 1204, 1205, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1246, 1247, 1248, 1249, 1250, 1251, 1252, 1253, 1254, 1255, 1256, 1257, 1258, 1259, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1301, 1302, 1303 or 1304 of the polypeptide of SEQ ID NO: 1, and
  b. recovering the variant.

184. The method of the preceding embodiment, wherein the positions are the positions listed in any one of embodiments 3, 5, 7, 9, 11, 13, 15, 17 19, 21, 23, 25, 27, 29, 31, 33, 35, 37, 39, 41, 43, 45, 47, 49, 51, 53, 55, 57, 59, 61, 63, 65, 67, 69 or 71.

185. The method of embodiment 183, wherein one or more of the following substitutions are introduced into the parent lactase, where each position corresponds to a position in SEQ ID NO: 1: V1D, V1F, V1H, V1K, V1L, V1R, E2D, E2G, E2Q, E2V, D3A, D3H, D3I, D3N, D3S, D3V, D3W, A4C, A4G, A4H, A4I, A4L, A4M, A4P, T5A, T5D, T5F, T5K, T5R, T5S, T5V, R6A, R6D, R6F, R6G, R6H, R6L, R6M, R6P, R6S, R6W, S7A, S7D, S7I, S7L, S7N, S7P, S7T, S7W, S9G, S9H, S9P, S9R, S9W, T10G, T10K, T10L, T10P, T10R, T10S, T10W, T11L, T11P, Q12L, Q12R, Q12V, Q12Y, M13C, M13D, M13E, M13F, M13H, M13K, M13R, M13W, S14A, S14G, S14H, S14L, S14T, S14V, S14Y, S15C, S15F, S15I, S15K, S15L, S15P, S15R, S15T, S15V, S15W, S15Y, T16A, T16C, T16I, T16N, T16S, P17A, P17C, P17D, P17E, P17I, P17L, P17N, P17R, P17S, P17T, V19A, V19F, V19G, V19I, V19K, V19L, V19N, V19S, V19W, V20C, V20F, V20G, V20I, V20K, V20L, V20M, V20N, V20P, V20Q, V20R, V20T, V20W, Y21A, Y21C, Y21D, Y21F, Y21G, Y21H, Y21M, Y21P, Y21R, Y21T, S22A, S22E, S22F, S22G, S22L, S22M, S22N, S22R, S22T, S22W, S23A, S23C, S23D, S23L, S23M, S23R, A24F, A24G, A24L, A24R, A24T, A24W, V25D, V25E, V25F, V25G, V25H, V25K, V25L, V25M, V25Q, V25R, V25S, V25T, V25W, D26C, D26I, D26L, D26M, D26T, D26V, S27A, S27C, S27F, S27G, S27H, S27P, S27Y, K28C, K28G, K28I, K28L, K28R, K28S, K28V, K28W, Q29D, Q29F, Q29G, Q29L, Q29M, Q29R, Q29S, Q29V, Q29W, N30A, N30G, N30H, N30M, N30P, N30V, N30W, N30Y, R31E, R31G, R31I, R31M, R31V, T32M, T32Q, T32R, T32S, S33C, S33E, S33H, S33K, S33N, S33Q, S33R, S33V, D34C, D34E, D34F, D34G, D34H, D34L, D34S, D34W, D34Y, F35A, F35C, F35E, F35G, F35K, F35N, F35T, F35V, D36H, D36Q, A37N, A37Q, N38C, N38G, N38S, W39G, W39S, K40C, K40D, K40F, K40G, K40I, K40M, K40N, K40P, K40W, F41A, F41C, F41G, F41I, F41Q, F41S, F41Y, M42E, M42N, M42T, L43A, L43C, L43G, L43I, L43S, L43T, L43V, S44C, S44M, S44N, S44Y, D45A, D45L, D45P, D45V, V47K, V47R, Q48S, A49C, A49D, A49H, A49R, A49S, A49T, A49V, D51G, D51I, D51K, D51M, D51P, D51V, A53C, A53G, A53L, A53R, A53S, A53T, A53V, A53W, F54M, F54S, D55C, D55F, D55G, D55H, D55M, D55N, D55P, D55S, D55V, S57A, S57C, S57E, S57G, A58D, A58G, A58I, A58M, A58N, A58Q, A58R, A58T, W59D, W59I, W59K, W59L, W59N, W59P, W59V, Q60A, Q60O, Q60E, Q60F, Q60G, Q60K, Q60L, Q60M, Q60R, Q60S, Q60V, Q60Y, Q61K, Q61P, Q61S, V62G, V62N, V62S, V62T, V62W, D63G, D63L, D63P, D63S, D63V, L64E, L64G, H66C, H66L, H66R, H66T, H66W, H66Y, D67E, Y68P, Y68V, I70A, I70H, I70K, I70P, I70R, T71C, T71E, T71G, T71H, T71K, T71L, T71N, T71P, T71Q, T71R, T71S, K73A, K73D, K73F, K73G, K73Q, K73V, Y74K, Y74T, Y74W, S75G, S75L, S75Q, S75R, S75V, Q76G, Q76I, Q76K, Q76M, Q76P, Q76S, Q76V, Q76Y, S77C, S77D, S77E, S77F, S77G, S77H, S77I, S77K, S77L, S77M, S77R, S77T, S77V, S77W, S77Y, N78C, N78E, N78F, N78K, N78Q, N78R, N78S, N78T, E79H, E79Q, E79S, E79T, E79W, A80K, E81A, E81Q, A83E, A83T, L85A, L85C, L85D, L85F, L85M, L85N, L85S, L85V, L85W, P86E, P86G, P86H, P86N, P86Q, P86R, P86V, P86W, G87A, G87D, G87E, G87N, G87Q, G88A, G88F, G88I, G88M, G88Q, G88S, T89C, T89G, T89H, T89K, T89L, T89M, T89N, T89P, T89W, T89Y, G90A, G90C, G90D, G90L, G90S, G90T, G90V, W91E, W91L, W91P, W91Q, W91R, W91S, W91Y, Y92F, Y92H, Y92I, Y92M, Y92N, Y92S, Y92T, Y92V, Y92W, R93A, R93D, R93F, R93H, R93I, R93L, R93N, R93T, R93V, R93Y, K94A, K94C, K94G, K94R, K94S, K94T, K94V, S95A, S95C, S95D, S95E, S95G, S95I, S95L, S95Q, S95R, F96A, F96C, F96I, F96K, F96L, F96M, F96P, F96S, F96V, F96W, T97F, T97S, T97V, I98C, I98H, I98S, I98W, R100T, D101A, D101P, D101V, L102A, L102G, L102M, L102P, L102S, G104C, K105D, K105Q, K105R, K105W, K105Y, R106K, R106P, R106V, R106W, I107A, I107F, I107G, I107Q, I107S, A108E, A108S, A108V, I109M, I109T, N110A, N110F, N110S, N110T, N110V, N110W, F111A, F111C, F111L, F111Q, F111V, D112A, D112F, D112G, D112T, G113A, G113S, V114F, V114G, V114M, V114R, Y115E, M116A, M116C, M116D, M116W, M116Y, N117K, N117R, N117T, N117W, A118K, A118P, A118Y, T119A, T119G, T119L, V120A, V120K, W121C, W121D, W121R, W121T, W121V, W121Y, F122A, F122M, F122S, F122Y, N123P, G124E, G124M, G124Q, G124R, V125D, V125E, V125I, K126E, K126V, G128A, G128D, T129E, T129V, H130A, H130C, H130Q, H130S, H130T, P131K, P131L, P131S, Y132C, Y132E, Y132S, G133E, S135E, S135P, S135V, P136R, P136Y, F137A, F137C, F137D, F137G, F137L, F137P, S138A, S138D, S138G, S138H, S138L, S138M, S138R, S138V, F139A, F139E, F139Q, F139W, D140G, D140L, D140V, L141G, L141T, T142E, T142S, T142V, K146A, G148H, G148K, G148T, G149E, G149H, G149I, G149M, G149Q, G149Y, E150A, E150C, E150G, E150L, E150N, E150R, N151L, I153A, I153Y, V154E, V154I, V154K, V154L, V154M, V154S, V155F, V157A, V157G, V157L, V157P, V157Q, V157S, E158G, E158H, E158K, E158Q, E158V, N159D, N159H, N159S, N159T, R160G, L161E, L161K, L161M, L161S, L161W, P162F, P162G, P162N, P162T, P162W, S164A, R165H, W166S, Y167A, Y167C, S168C, G169A, G169C, G169D, G169S, S170L, S170Q, G171C, G171F, G171I, I172G, I172K, I172P, I172Q, Y173A, Y173H, Y173M, Y173P, Y173S, Y173W, R174E, R174K, D175E, D175Y, V176E, V176K, V176T, T177A, T177C, T177E, T177K, T177L, L178I, L178Q, L178W, T179A, T179C, T179D, T179H, T179I, T179K, T179L, T179N, T179P, T179S, V180A, V180C, V180D, V180E, V180G, V180M, T181A, T181D, T181F, T181K, T181R, D182F, D182L, D182S, G183W, V184F, V184H, V184P, V184Q, V184R, V184S, V184W, H185G, H185L, H185R, V186A, V186E, V186G, V186N, G187A, G187D, G187H, N188E, N188R, N188S, N188V, N188W, N189A, N189E, G190C, G190F, G190H, G190Q, G190V, V191C, V191T, V191W, V191Y, I193N, I193Q, I193T, I193V, K194A, K194I, K194L, K194R, T195A, T195E, T195M, T195S, T195W, P196A, P196H, P196I, P196M, P196S, P196W, S197A, S197C, S197E, S197K, S197L, S197P, L198E, L198F, L198H, L198I, L198K, L198R, L198V, L198W, A199E, A199F, A199K, A199P, A199R, A199T, Q201C, Q201E, Q201I, Q201K, Q201M, Q201V, N202A, N202D, N202F, N202G, N202K, N202L, N202M, N202Q, N202R, N202S, N202T, N202W, G203C, G203K, G203M, G203Q, G203R, G203S, G203V, G203W, G203Y, G204A, G204C, G204D, G204K, G204R, G204S, G204Y, N205E, N205G, N205H, N205L, N205P, N205Y, V206A, V206C, V206D, V206F, V206G, V206I, V206K, V206Q, V206R, V206S, V206T, T207A, T207C, T207G, T207I, T207K, T207L, T207M, T207N, T207Q, T207R, T207W, M208A, M208S, M208T, N209C, N209D, N209G, N209K, N209L, N209Q, N209R, N209V, L210A, L210C, L210F, L210G, L210H, L210I, L210Q, L210R, L210S, L210T, L210V, T211A, T211D, T211E, T211F, T211K, T211N, T211Q, T211R, T211S, T212A, T212C, T212E, T212F, T212G, T212H, T212K, T212L, T212M, T212S, T212W, K213A, K213C, K213D, K213F, K213I, K213L, K213M, K213N, K213Q, K213R, K213S, K213T, K213V, K213Y, V214A, V214C, V214T, V214W, A215D, A215E, A215F, A215I, A215K, A215L, A215Q, A215R, A215S, A215V, N216D, N216T, N216V, D217F, D217G, D217L, D217M, D217T, D217V, T218D, T218G, T218H, K219A, K219O, K219F, K219H, K219M, A220C, A220G, A220I, A220L, A220M, A220T, A220V, A220W, A220Y, A221D, A221E, A221L, A221N, A221V, A221Y, A222D, A222I, A222L, A222P, A222R, A222W, A222Y, N223A, N223E, N223F, N223G, N223K, N223L, N223M, N223R, N223S, N223T, N223V, N223W, I224G, I224Q, T225A, T225G, T225L, L226C, L226M, L226Q, K227T, Q228N, Q228R, T229A, T229C, T229D, T229G, T229H, T229M, T229N, T229Q, T229R, T229V, V230F, V230L, V230M, V230Q, V230R, V230S, F231A, F231E, F231G, F231I, F231K, F231L, F231Q, F231S, F231V, F231W, F231Y, P232G, P232H, P232L, P232M, P232R, P232S, P232T, P232V, P232W, P232Y, K233A, K233C, K233E, K233F, K233G, K233L, K233P, K233R, K233S, K233V, K233W, K233Y, G234A, G234C, G234D, G234E, G234K, G234L, G234Q, G234R, G234V, G234W, G234Y, G235C, G235F, G235H, G235I, G235K, G235M, G235Q, G235R, G235T, G235W, G235Y, K236A, K236D, K236E, K236G, K236L, K236M, K236P, K236R, K236S, K236T, K236W, K236Y, T237D, T237F, T237I, T237K, T237M, T237Q, T237R, T237S, T237V, T237Y, D238A, D238E, D238F, D238G, D238H, D238I, D238K, D238L, D238M, D238N, D238P, D238Q, D238R, A239C, A239E, A239G, A239I, A239K, A239T, A240C, A240E, A240L, A240P, A240Q, A240T, A240V, A240W, A240Y, I241T, G242K, G242L, G242M, G242P, G242T, G242Y, T243I, T243M, T243R, T243V, V244A, V244E, V244G, V244L, V244R, T245E, T245G, T245L, T245M, T245N, T245Q, T245R, T245S, T246D, T246E, T246G, T246K, T246V, A247D, A247E, A247K, A247N, A247P, A247Q, A247R, A247S, A247V, A247W, S248A, S248E, S248F, S248H, S2481, S248L, S248Q, S248T, S248Y, K249A, K249D, K249G, K249H, K249I, K249L, K249M, K249N, K249P, K249Q, K249S, K249T, K249V, K249Y, S250H, S250M, S250W, I251F, I251L, I251V, I251W, I251Y, A252C, A252E, A252F, A252H, A252I, A252P, A252R, A252S, A252W, A252Y, G254D, G254F, G254I, G254L, G254M, G254Q, G254R, G254W, A255C, A255F, A255K, A255L, A255M, A255S, A255T, A255W, A255Y, S256A, S256C, S256F, S256G, S256K, S256L, S256M, S256N, S256Q, S256R, S256V, S256W, S256Y, A257D, A257G, A257I, A257N, A257T, A257V, D258A, D258L, D258M, D258W, V259E, V259L, V259S, V259T, T260A, T260D, T260G, T260I, T260K, T260V, S261A, S261D, S261H, S261R, S261W, S261Y, T262D, T262E, T262F, T262G, T262H, T262L, T262P, T262W, I263A, I263C, I263G, I263L, I263S, I263V, T264F, T264G, T264K, T264L, T264M, T264P, T264Q, T264R, T264S, T264Y, A265G, A265I, A265K, A265R, A265S, A265V, A266D, A266E, A266G, A266K, A266L, A266M, A266P, A266Q, A266S, A266T, S267A, S267D, S267K, S267M, S267N, S267P, S267Q, S267R, S267V, P268F, P268G, P268M, P268R, P268V, P268W, P268Y, K269G, K269R, K269V, K269Y, L270D, L270M, L270N, L270R, L270V, W271T, S272E, S272G, S272K, S272L, S272N, S272T, S272W, I273K, I273L, I273P, I273R, I273S, I273W, K274D, K274P, K274Q, K274R, N275K, N275M, N275V, N275W, N277F, N277K, N277R, L278A, L278G, L278H, L278I, L278K, L278M, L278P, L278Q, L278R, L278S, L278V, Y279M, Y279T, Y279W, T280A, T280D, T280E, T280F, T280H, T280M, T280Q, V281A, V281I, V281L, V281Q, R282E, R282F, R282H, R282I, R282K, R282N, R282S, R282T, R282V, R282W, T283M, T283R, T283V, E284A, E284D, E284F, E284H, E284L, E284M, E284N, E284Q, E284R, E284Y, V285H, V285I, V285T, L286A, L286C, L286D, L286F, L286N, L286R, L286T, L286W, L286Y, N287I, N287L, G288F, G288L, G288S, V291C, V291D, V291F, V291G, V291H, V291L, V291P, V291S, V291T, V291Y, L292A, L292D, L292E, L292H, L292Q, L292S, L292V, D293C, D293E, D293F, D293I, D293S, D293V, D293W, T294C, T294G, T294M, T294Q, T294S, Y295F, Y295G, Y295I, Y295L, Y295R, Y295S, Y295W, D296F, D296H, D296K, D296L, D296N, D296R, D296V, T297G, T297I, T297Q, T297R, T297S, E298G, E298I, E298L, E298M, E298R, E298T, Y299F, Y299S, F301C, F301L, R302E, R302I, R302K, R302M, R302N, R302T, W303A, W303C, W303D, W303F, W303S, W303T, T304D, T304E, T304I, T304K, T304P, T304S, T304W, G305E, G305F, G305L, G305M, G305N, G305P, G305T, G305W, F306D, F306K, F306L, F306S, D307A, D307E, D307F, D307G, D307L, D307M, D307N, D307Q, D307S, D307V, D307W, A308C, A308E, A308G, A308I, A308M, A308Y, T309C, T309D, T309E, T309I, T309K, T309M, T309S, T309V, S310A, S310C, S310G, S310H, S310I, S310L, S310M, S310N, S310R, S310V, G311E, G311F, G311L, G311Q, G311R, G311V, F312H, F312L, F312R, F312V, L314A, L314C, L314T, L314V, L314Y, N315S, G316A, G316C, G316N, G316R, G316S, G316W, G316Y, E317D, E317H, E317I, E317K, E317V, E317W, E317Y, K318C, K318E, K318F, K318G, K318H, K318L, K318M, K318N, K318P, K318Q, K318V, K320C, K320E, K320F, K320I, K320L, K320R, K320T, K320V, K320W, L321C, L321G, L321H, L321M, L321V, L321Y, K322C, K322F, K322I, K322N, K322P, K322Q, K322R, K322S, V324E, V324G, V324T, S325D, S325G, S325T, M326E, M326G, M326S, M326T, M326V, M326Y, H328C, H328D, H328F, H328G, H328I, H328L, H328M, H328R, H328T, D329S, D329T, G331V, A335C, A335G, A335L, A337D, A337E, A337G, A337L, A337Q, N338P, N338R, N338V, R340A, R340C, R340L, A341M, A341S, I342A, I342G, I342K, I342P, E343A, E343H, E343N, E343R, E343S, E343T, E343Y, R344G, R344L, R344Y, Q345F, Q345G, Q345K, Q345N, Q345S, V346A, V346C, V346F, V346I, V346L, V346S, E347A, E347C, E347D, E347F, E347I, E347R, E347S, I348A, I348D, I348G, I348M, I348Q, I348R, L349A, L349E, L349Q, L349S, L349V, Q350G, Q350N, Q350W, K351N, K351R, K351V, K351W, M352G, M352L, M352T, M352W, G353K, V354E, V354G, V354S, V354W, N355H, N355M, N355R, N355W, I357T, T359E, T359L, T360V, N362G, N362S, N362T, P363A, P363D, P363I, P363L, P363M, P363S, P363V, A364C, A364E, A364F, A364G, A364I, A364M, A364P, A364V, A364W, A365C, A365E, A365I, A365P, A365V, A365W, K366A, K366D, K366E, K366I, K366L, K366M, K366P, K366S, K366V, A367C, A367I, A367N, A367Q, L368A, L368E, L368Q, L368S, L368V, L368Y, I369A, I369D, I369E, I369G, I369K, I369M, I369R, I369V, I369W, D370C, D370L, D370Q, D370R, D370S, D370T, V371D, V371F, V371G, V371I, V371L, V371Q, V371S, C372P, N373G, N373L, N373R, E374K, E374L, E374R, K375D, K375I, K375N, K375Q, K375S, G376A, G376S, V377A, V377M, V377T, L378I, L378P, L378W, L378Y, V379A, V379C, V379M, V379N, V380M, V380P, V380S, E381A, E381C, E381G, E381L, E381Q, E381T, V383A, V383K, V383L, M386G, M386N, M386Q, M386S, M386V, W387H, W387L, N388A, N388E, N388L, N388R, R389A, R389C, R389E, R389K, R389M, R389N, R389Q, R389S, R389T, R389V, S390C, S390D, S390G, S390H, S390N, S390P, S390Q, S390T, S390V, K391E, N392D, G393A, G393E, G393N, G393R, G393S, G393V, N394L, T395A, T395C, T395F, T395H, T395I, T395M, T395N, T395Q, T395S, T395W, E396K, E396L, E396M, E396V, E396W, Y398M, Y398N, G399S, K400A, K400C, K400D, K400E, K400M, K400N, K400P, K400Q, K400S, K400T, K400V, W401F, W401H, W401K, W401L, W401M, W401R, F402T, F402W, F402Y, G403A, G403D, G403H, G403K, G403P, G403Q, G403S, G403T, G403V, G403Y, Q404F, Q404H, Q404L, Q404M, Q404P, Q404R, Q404S, Q404V, A405C, A405E, A405H, A405K, A405P, A405R, A405T, A405V, I406C, I406D, I406N, A407C, A407G, A407M, A407Q, A407S, A407T, A407W, G408D, G408I, G408M, G408N, G408W, D409N, D409W, N410C, N410R, N410Y, A411E, A411N, A411R,

A411S, A411V, V412M, V412S, L413D, L413E, L413F, L413I, L413P, L413T, G414A, G414C, G414M, G414N, G414R, G414T, G414W, G415A, G415Q, G415R, D416I, D416M, D416R, D416T, D416Y, K417C, K417F, K417G, K417R, K417T, D418L, D418P, D418R, D418Y, E419M, E419R, E419W, T420E, T420F, T420G, T420K, T420R, T420V, W421L, W421Q, W421S, A422P, A422T, A422V, K423D, K423L, K423M, K423R, F424C, F424L, F424N, F424T, D425E, L4260, L426M, L426Q, T427D, T427F, T427G, T427K, T427M, T427P, T427Q, T427R, T427S, T427W, S428F, S428K, S428W, T429D, T429P, I430C, I430D, I430E, I430L, I430M, I430Q, I430S, I430T, I430W, N431D, N431E, N431G, N431L, N431M, N431R, N431V, N431Y, R432A, R432E, R432F, R432G, R432N, R432Q, R432V, R432Y, D433C, D433G, D433H, D433I, D433P, D433Q, D433W, R434L, R434M, R434N, R434P, R434S, R434T, R434V, N435E, N435F, N435H, N435K, N435L, N435M, N435R, N435V, N435W, A436C, A436D, A436E, A436G, A436I, A436L, A436M, A436Q, A436S, P437A, P437D, P437K, P437L, P437Q, P437R, P437S, P437V, P437W, S438G, V439C, V439E, V439G, V439I, V439K, V439Q, V439T, V439Y, I440C, I440D, I440F, I440K, I440P, I440R, I440S, I440T, I440V, I440W, M441A, M441E, M441G, M441Q, M441R, M441T, M441V, W442E, W442G, W442M, W442P, W442Q, W442R, S443C, S443D, S443G, S443M, S443Q, S443Y, L4440, L444D, L444E, L444F, L444G, L444H, L444K, L444Q, L444V, L444W, G445A, G445C, G445V, N446D, N446T, M448A, M448C, M448D, M448E, M448I, M448L, M448P, M448Q, M448S, M448V, M448W, M449D, M449E, M449F, M449T, M449V, M449W, M449Y, E450F, E450S, E450T, E450V, E450W, G451C, G451F, G451L, G451P, G451V, G451W, I452G, I452K, I452L, I452M, I452Q, I452S, I452V, S453C, S453F, S453G, S453H, S453L, S453M, S453N, S453P, S453Q, S453R, S453V, G454L, G454W, S455A, S455E, S455K, S455M, S455P, S455R, S455V, S455W, V456A, V456D, V456E, V456F, V456K, V456L, V456W, S457E, S457H, S457K, S457L, S457M, S457P, S457Q, S457T, S457V, G458A, G458C, G458D, G458F, G458L, G458P, G458Q, G458S, G458V, G458W, F459A, F459C, F459E, F459G, F459N, F459R, F459S, F459T, F459W, P460C, P460M, P460Q, P460W, P460Y, A461D, A461G, A461M, A461N, A461Q, A461S, A461V, A461Y, T462C, T462E, T462F, T462L, T462M, T462S, S463G, S463K, S463Q, S463R, S463T, S463V, A464E, A464H, A464L, A464M, A464P, A464V, A464W, K4650, K465F, K465G, K465L, K465Q, K465R, K465V, K465W, K465Y, L466A, L466C, L466D, L466E, L466F, L466G, L466M, L466P, L466Q, L466S, L466V, L466Y, V467A, V467C, V467D, V467E, V467G, V467T, V467W, A468D, A468E, A468F, A468K, A468L, A468P, A468S, A468V, A468W, W469A, W4690, W469D, W469G, W469L, W469M, W469R, W469V, W469Y, T470E, T470L, T470M, T470Q, K471F, K471G, K471Q, K471W, K471Y, A472G, A472Y, A473E, A473M, A473P, D474A, D474C, D474E, D474K, D474M, D474R, D474W, S475E, S475F, S475Q, S475T, S475V, T476C, T476L, T476S, R477A, R477C, R477G, R477L, P478A, P478D, P478G, P478L, P478V, M479G, M479I, M479R, M479W, T480C, T480G, T480Q, K485E, K485R, K487A, K4870, K487F, K487G, K487N, K487S, K487W, A488C, A488G, A488H, A488L, A488N, A488S, A488V, N491A, N491E, N491W, E492A, E492W, S493E, S493G, S493H, S493L, S493M, S493Q, S493V, N494A, N494I, N494M, N494R, N494V, T495K, T495R, T495V, T495W, M496A, M496F, M496T, G497D, D498A, D498C, D498M, D498N, D498S, N499K, N499R, N499T, N499Y, L500A, L500E, L500N, L500V, T501C, T501G, T501M, A502L, A502Q, N503A, N503E, N503M, N503S, G504H, G504K, G504P, G505A, G505D, G505E, G505H, G505L, G505N, G505R, G505S, G505V, V506C, V506D, V506E, V506G, V506I, V506L, V506P, V506R, V506S, V506T, V506W, V507A, V507F, V507G, V507L, V507N, V507P, V507R, V507S, V507T, G508C, G508E, T509A, T509D, T509E, T509I, T509K, T509M, T509Q, T509S, T509V, T509Y, N510A, N510F, N510I, N510Q, Y511A, Y511K, S512C, S512E, S512F, S512G, S512I, S512M, S512Q, S512T, S512V, S512Y, D513C, D513G, D513K, D513L, D513M, D513P, D513Q, D513R, D513W, G514F, G514L, G514N, G514P, G514R, A515A, A515D, A515E, A515F, A515G, A515K, A515P, A515R, A515S, N516C, N516E, N516G, N516I, N516M, N516Q, N516S, N516T, N516V, Y517G, Y517I, Y517N, D518Q, D518Y, K519C, K519E, K519F, K519G, K519I, K519L, K519M, K519N, K519Q, K519S, K519T, I520A, I520C, I520G, I520H, I520M, I520N, I520Q, I520S, I520T, I520W, I520Y, R521A, R521C, R521K, R521N, R521Q, R521V, T522G, T522I, T522N, T523A, T523M, H524R, H524V, P525D, P525G, P525R, P525T, P525V, S526G, S526I, S526W, W527A, W527E, W527G, W527H, W527N, W527R, W527S, W527A, A528C, A528E, A528G, A528I, A528L, I529F, I529G, I529L, I529Y, Y530A, Y530M, G531E, G531S, G531T, T534A, T534I, T534Q, A535E, A535G, A535I, A535M, A537D, A537M, A537P, A537S, I538H, I538M, N539G, N539W, S540E, S540G, S540M, G542E, G542Q, G542S, G542T, I543V, I543W, N545G, N545I, N545Q, N545S, R546A, R546C, R546L, R546P, R546S, T547A, T547D, T547H, T547K, T547N, T547S, T548D, T548E, T548F, T548K, T548L, T548P, T548W, G549D, G549F, G549P, G549W, G550Q, G550R, G550S, A551D, A551I, A551Q, S553C, S553F, S553N, S553P, S553R, S553T, S553V, S554F, S554N, S554R, S554T, S554V, S554W, D555E, D555P, D555S, K556A, K556C, K556R, K556W, Q557F, Q557R, Q557S, L558E, L558H, L558I, L558P, T559A, T559G, T559I, T559Q, T559V, T559Y, S560P, S560V, Y561R, N563R, N563S, S564A, S564C, S564F, S564W, A565C, A565D, A565E, A565F, A565G, A565I, A565L, A565M, A565R, A565S, A565T, A565V, A565W, G567N, G567Q, G567V, A570G, A570K, A570L, A570M, A570S, A570T, A570W, V571W, A572S, A572W, S573G, S573K, S573Y, S574K, S574Q, S574V, S574W, A575D, A575M, A575V, W576A, W576F, W576V, W576Y, Y577G, Y577I, Y577L, Y577R, D578E, D578M, D578N, D578T, V579E, V579G, V579L, V579T, V580A, V580D, V580E, V580K, V580L, V580S, Q581F, Q581G, Q581P, Q581R, Q581S, Q581T, Q581Y, R582A, R582D, R582G, R582I, R582L, R582Y, D583V, D583W, F584E, F584I, F584W, V585I, V585M, V585Q, A586C, A586D, A586H, A586K, G587A, G587C, T588C, T588D, T588G, T588I, T588L, T588M, T588P, Y589A, Y589I, Y589Q, Y589V, Y589W, V590A, V590H, V590I, W591F, T592C, T592L, T592Q, T592S, G593C, G593I, F594C, F594I, F594L, F594M, D595E, D595Q, D595S, L597C, L597D, L597E, L597T, G598N, P600A, P600E, P600G, P600S, N604E, N604S, G605R, T606G, G607A, G607Q, G607S, S608E, S608I, S608M, S608N, S608Q, S608T, S608V, G609A, G609H, G609L, G609N, G609R, G609S, A610D, A610F, A610M, A610T, V611K, G612N, G612T, G612V, S613A, W614A, W614F, W614P, P615L, P615S, P615V, S616A, S616W, N619A, N619I, N619L, N619S, S620G, Y621W, I624A, I624V, V625A, V625E, V625F, V625M, V625Y, T627F, T627C, T627K, T627Q, A628C, A628D, A628N, G629T, F630A, F630C, F630D, F630G, F630S, F630Y, P631A, P631D, P631G, P631H, P631S, P631V, P631Y, K632C, K632D, K632G, K632T, D633G, T634A, T634E, T634F, T634S, T634V, Y635R, Y636K, F637C, F637G, F637I, F637S, F637T, F637V, Y638A, Y638W, Q639D, Q639N, Q639R, S640C, S640D, Q641T, W642I, N643R, D644C, D644G, D644Y, D645S, D645V, V646C, V646L, V646N, V646R, V646S, H647G, H647V, T648C, L649V, H650E, H650F, H650S, H650R, I651F, I651T, I651V, L652C, L652D, L652V, L652W, P653Q, A654D, A654K, A654M, A654R, W655F, W655N, N656A, N656K, N656V, E657K, E657R, E657V, V659D, V659N, A661E, A661G, A661H, A661K, A661L, A661M, A661Q, A661W, K662H, K662S, K662V, K662W, K662Y, N667L, N667P, P669A, P669E, P669F, P669L, P669R, P669T, P669W, V670C, V672L, Y673E, Y673G, Y673I, Y673R, Y673S, Y673W, T674C, T674D, T674G, T674H, T674M, T674Q, D675A, D675E, D675P, D675Q, D675S, D675V, D675Y, A676C, A676E, A676G, A676K, A676L, A676P, A676S, A676W, A677E, A677G, A677L, A677R, A677T, A677V, A677Y, K678A, K678C, K678T, K678V, V679G, V679Q, V679S, V679T, V679Y, K680A, K680E, K680G, K680H, K680I, K680L, K680N, K680Q, K680S, K680V, K680W, L681E, L681F, L681G, L681M, L681S, L681T, Y682D, Y682E, Y682I, Y682M, Y682S, Y682V, Y682W, F683H, F683L, F683M, F683Q, F683R, F683W, T684A, T684D, T684G, T684L, T684R, T684S, T684V, P685A, P685E, P685I, P685L, P685W, K686A, K686E, K686I, K686M, K686T, K686V, G687A, G687K, G687N, G687P, G687Q, G687R, S688C, S688D, S688E, S688G, S688K, S688L, S688P, S688T, T689A, T689D, T689E, T689G, T689L, T689P, T689S, T689W, T689Y, E690D, E690M, E690P, E690T, E690V, K691E, K691H, K691N, K691P, K691R, K691S, R692G, R692H, R692I, R692L, R692P, R692S, R692T, R692V, R692W, L693A, L693M, L693P, I694L, I694W, G695C, G695K, G695L, G695R, G695W, E696A, E696L, E696R, K697A, K697E, K697G, K697R, K697V, K697W, S698C, S698D, S698E, S698I, S698L, S698M, S698P, S698Q, S698R, S698T, T700A, T700C, T700D, T700E, T700G, T700K, T700Y, K701A, K701D, K701E, K701G, K701H, K701L, K701M, K701P, K701S, K701W, T703E, T703I, T703K, T703W, T704M, T704R, T704Y, A705C, A705D, A705E, A705K, A705N, A705P, A705R, A705V, A705W, A706C, A706G, A706T, A706W, A706Y, Y708C, Y708F, Y708G, Y708K, Y708L, Y708P, Y708T, T709M, Y710C, Y710D, Y710E, Y710G, Y710M, Y710N, Y710T, Y710V, Y710W, Q711D, Q711E, Q711G, Q711L, Q711M, Q711T, Q711Y, V712G, V712M, V712P, V712Q, V712R, Y713A, Y713E, Y713G, Y713L, Y713Q, E714D, E714H, E714I, E714K, E714M, E714N, E714R, E714S, E714V, E714Y, G715K, A716C, A716G, A716L, A716M, A716P, A716R, A716T, A716V, D717C, D717G, D717L, D717S, K718A, K718L, K718Q, K718T, K718W, K718Y, D719E, D719L, D719P, D719S, D719T, D719V, S720A, S720M, S720R, S720Y, T721D, T721H, T721K, T721L, T721N, T721P, T721Q, T721S, T721V, T721W, T721Y, A722Q, A722T, A722V, H723G, H723P, K724A, K724G, K724R, N725A, N725D, N725I, M726A, M726D, M726E, M726K, M726Q, M726V, M726W, Y727L, Y727T, L728C, L728K, L728Q, L728S, L728T, L728W, T729A, T729E, T729M, W730A, N731A, N731E, N731Q, N731S, N731Y, V732G, V732P, V732R, V732W, P733A, P733R, P733W, W734D, W734G, W734R, W734V, A735Q, A735R, A735S, A735T, A735W, E736S, G737F, G737K, G737N, G737Y, T738G, T738L, T738S, I739E, I739K, I739M, I739W, I739Y, S740D, S740E, S740F, S740H, S740L, A741I, A741P, A741S, A741V, A741Y, E742D, E742M, E742Q, E742V, A743C, A743E, A743H, A743I, A743L, Y744A, Y744E, Y744I, Y744K, Y744L, Y744R, D745C, D745F, D745N, D745R, E746A, E746C, E746K, E746T, N747E, N747F, N747G, N747P, N747R, N748S, R749H, R749M, R749S, R749T, L750G, L750M, L750P, L750Q, L750S, I751C, I751H, I751Q, I751S, P752A, P752C, P752H, P752L, P752S, P752V, P752Y, E753Q, G754H, G754I, G754P, G754R, S755C, S755I, S755T, T756E, T756N, T756P, T756Q, T756S, T756W, E757A, G758A, G758V, N759D, N759R, N759S, N759V, A760G, A760N, A760P, A760Q, S761A, S761K, S761Q, V762D, V762G, V762K, V762W, T765A, T765P, T765R, T765W, G766M, G766S, A768H, A769F, A769G, A769I, A769N, A769V, A769Y, K770H, L771A, L771I, K772A, K772C, K772P, K772V, K772W, A773C, A773G, A773H, A773M, A773R, A773S, A773V, D774A, D774R, A775L, A775V, A775W, D776I, D776L, D776R, D776S, D776V, R777D, R777E, R777G, R777H, R777P, R777S, R777T, K778A, K778C, K778F, K778G, K778L, K778N, K778R, T779C, T779I, I780V, T781A, T781C, T781E, T781F, T781G, T781M, T781P, T781R, T781Y, A782C, A782E, A782K, A782N, A782P, A782Q, A782Y, D783A, D783C, D783E, D783R, G784A, G784F, G784L, G784S, G784T, K785C, K785I, K785S, K785V, K785W, K785Y, D786S, D786V, L787D, L787K, L787P, L787T, L787Y, S788A, S788G, S788I, Y789C, Y789D, Y789I, Y789V, I790A, I790C, I790F, I790R, I790V, E791A, E791D, E791F, E791M, E791S, E791T, E791V, E791W, V792C, V792G, V792L, V792S, V792Y, D793C, D793F, D793H, D793K, D793N, D793Y, V794C, V794D, V794L, V794Q, V794T, V794W, T795P, T795Y, D796M, D796Q, D796S, D796T, A797H, A797K, N798G, N798I, N798P, N798Q, G799D, G799K, G799L, G799M, G799Q, G799Y, H800A, H800F, H800G, H800L, H800S, H800V, I801C, I801E, I801W, V802E, V802I, V802P, V802S, V802Y, P803A, P803F, P803G, P803K, P803S, P803Y, D804E, D804G, D804K, D804N, D804S, A805C, A805F, A805G, A805I, A805N, A805P, A806F, A806I, A806Q, N807F, N807Q, N807V, N807W, R808C, R808F, R808G, R808I, R808N, R808P, R808Q, V809A, V809C, V809L, V809M, V809P, L810P, T810P, T810Q, T810R, T810Y, F811L, F811Y, D812E, D812F, D812I, D812Q, V813F, V813H, V813T, V813W, V813Y, K814G, K814H, K814I, K814L, K814P, G815A, G815F, G815M, G815P, G815V, A816C, A816D, A816F, A816I, A816N, A816V, A816W, G817C, G817H, G817I, G817N, G817S, K818D, K818F, K818L, K818Q, K818R, K818S, K818V, K818W, L819F, L819W, V820C, V820F, V820I, V820K, V820R, V820W, G821A, G821C, G821E, G821F, G821I, G821K, G821M, G821N, G821V, G821Y, V822A, V822D, V822E, V822T, V823E, N824A, N824C, N824G, N824Q, G825A, S826A, S826F, S826G, S826I, S826L, S826R, S826W, S827C, S827Q, P828C, P828G, P828I, P828L, P828Y, D829C, D829I, D829S, D829T, D829V, H830E, H830G, H830M, H830P, H830Q, H830R, H830V, D831A, D831F, D831G, D831I, D831M, D831P, D831R, D831V, S832E, S832F, S832G, S832L, S832M, S832P, S832R, S832V, S832W, Y833C, Y833D, Y833E, Y833I, Y833K, Y833N, Y833P, Y833V, Q834F, Q834G, Q834M, A835D, A835E, A835F, A835H, A835K, A835W, D836C, D836E, D836H, D836Q, D836R, D836S, D836T, D836V, D836W, D836Y, N837D, N837F, N837G, N837H, N837L, N837P, N837T, R838D, R838F, R838G, R838K, R838M, R838N, R838S, R838W, K839A, K839C, K839D, K839E, K839G, K839L, K839N, K839P, K839R, A840G, A840I, A840P, A840V, F841C, F841D, F841I, F841K, F841W, S842A, S842L, S842M, G843A, G843C, K844A, K844G, K844L, K844W, K844Y, V845N, V845W, L846G, L846I, L846M, L846S, A847L, A847T, I848M, V849A, V849L, V849S, V849T, Q850C, Q850G, Q850I, Q850L, Q850T, Q850V, Q850Y, S851C, S851D, S851E, S851L, S851T, T852D, T852G, T852L, K853N, K853P, K853Q, K853V, E854C, E854I, E854M, E854R, A855K, A855V, A855Y, E857P, E857V, I858D, I858E, I858F, I858G, I858K, I858M, I858P, I858Q, I858Y, T859V, V860T, V860Y, T861F, T861Q, T861V, T861W, A862C, A862P, A862V, K863F, K863I, K863L, K863N, K863W, A864E, A864H, A864K, A864L, D865A, D865G, G866H, G866R, L867W, S870E, S870M, S870R, S870T, T871P, V872C, V872G, K873G, K873Y, I874G, A875R, T877A, V879P, V879S, P880S, G881W, T882A, T882M, T882R, S883L, T884A, E885V, K886E, K886L, K886V, K886W, T887A, T887D, T887F, T887G, T887N, T887R, T887V, V888A, V888D, V888G, R889G, Y892D, Y892P, Y892R, Y893E, Y893G, S894D, S894G, R895M, N896M, Y897V, Y898T, V899G, K900E, K900G, T901G, T901Q, T901R, T901V, T901Y, G902A, G902D, G902F, G902L, G902P, G902Q, G902R, G902S, G902W, N903D, N903I, K904D, K904E, K904M, K904N, K904R, K904S, K904V, K904W, P905A, P905C, P905R, P905V, P905W, P905Y, I906A, I906D, I906N, I906S, I906T, I906V, I906W, I906Y, L907F, L907S, L907Y, P908C, P908D, P908G, P908I, P908L, P908M, P908T, S909E, S909F, S909G, S909W, S909Y, D910C, D910I, D910S, D910W, V911A, V911S, E912A, E912K, E912L, E912T, E912V, V913G, V913Q, V913R, V913W, R914A, R914E, R914F, R914I, R914K, R914V, R914W, R914Y, Y915A, Y915C, Y915G, Y915I, Y915M, Y915Q, Y915V, S916G, D917C, D917E, D917F, D917L, D917M, D917Q, D917S, G918E, G918H, G918T, G918V, G918W, T919D, T919K, T919Q, T919W, T919Y, S920C, S920E, S920M, S920P, S920R, S920V, S920W, D921C, D921P, D921Q, D921V, R922A, R922G, R922M, R922V, R922W, Q923A, Q923C, Q923E, Q923L, Q923M, Q923V, Q923W, N924A, N924L, N924P, N924Q, N924S, N924W, V925A, V925C, V925E, V925G, V925K, V925N, V925S, V925W, T926G, T926P, T926R, T926S, T926V, T926W, W927C, W927G, W927P, D928A, D928E, D928H, D928L, D928Q, A929C, A929P, A929V, V930A, V930E, V930I, V930K, V930M, V930T, S931G, S931P, S931R, D932F, D932R, D932S, D932T, D932V, D933I, D933R, D933S, Q934S, Q934V, I935A, I935C, I935D, I935E, I935L, I935P, I935V, I935W, A936I, A936L, A936Q, A936R, A936Y, K937G, K937I, K937M, K937P, K937Q, K937R, K937V, A938C, A938H, A938N, A938T, A938V, A938W, G939D, G939K, S940C, S940E, S940M, S940R, S940T, S940V, S940W, F941C, F941M, F941W, S942A, S942E, S942K, S942L, S942P, S942T, S942V, V943A, V943H, V943Q, V943R, A944D, A944G, A944H, A944P, A944R, A944V, G945E, G945P, G945T, T946A, T946E, T946G, T946L, T946P, T946V, T946W, V947G, V947H, V947L, V947M, V947P, V947R, V947T, A948C, A948I, A948R, A948W, G949A, G949F, G949V, Q950D, Q950G, Q950K, Q950M, Q950W, K951D, K951G, K951P, K951Q, K951S, K951W, K951Y, I952H, I952Q, S953F, S953M, S953N, S953R, S953W, V954D, V954L, V954Q, V954S, V954T, R955A, R955C, R955E, R955K, R955Q, R955W, V956A, V956D, V956G, V956H, V956I, V956M, V956Q, V956W, T957D, T957S, T957W, M958D, M958I, M958K, I959A, I959L, I959S, I959V, I959Y, D960G, D960H, D960L, D960P, D960S, D960W, E961D, E961F, E961K, E961P, E961S, E961T, I962A, I962C, I962D, I962G, I962K, I962N, I962Q, I962T, G963C, G963E, G963L, G963P, A964C, A964E, A964H, L965C, L965E, L965G, L965K, L965M, L965P, L965Q, L965S, L965V, L965Y, L966A, L966G, L966H, L966K, L966N, L966P, L966Q, L966S, L966T, L966W, N967C, N967D, N967I, N967L, N967M, N967P, N967S, N967T, N967V, Y968G, Y968L, Y968Q, Y968V, S969C, S969D, S969G, S969H, S969I, S969L, S969M, S969P, S969Q, S969Y, A970I, A970L, S971E, S971F, S971G, S971H, S971V, S971W, P973C, P973D, P973K, P973N, P973Q, P973R, P973V, P973W, P973Y, V974C, V974E, V974Q, V974N, V974T, V974Y, G975D, G975F, G975K, G975L, G975Q, G975V, T976D, T976F, T976G, T976K, T976L, T976P, T976S, T976Y, P977A, P977C, P977K, P977R, P977T, P977Y, A978F, A978G, A978M, A978N, A978P, A978R, A978S, A978Y, V979G, V979N, V979R, V979Y, L980A, L980F, L980H, L980I, L980K, L980N, L980Q, L980T, L980Y, P981L, P981M, G982A, G982H, G982M, G982P, G982Q, G982W, R984P, R984S, P985E, P985F, P985H, P985K, P985L, P985W, A986C, A986E, A986F, A986I, A986K, A986L, A986M, A986N, A986S, A986W, V987A, V987C, V987F, V987I, V987K, V987L, V987Q, V987T, L988A, L988C, L988E, L988G, L988H, L988M, L988Q, L988R, L988S, L988V, L988Y, P989A, P989C, P989D, P989G, P989H, P989I, P989M, P989N, P989Q, P989W, D990F, D990P, D990S, D990W, G991C, G991F, G991H, G991K, G991P, G991Y, T992E, T992H, T992M, T992N, T992Y, V993D, V993G, V993N, V993S, T994I, T994S, T994V, S995E, S995L, S995R, S995V, A996Q, A996R, A996V, N997A, N997C, N997E, N997K, N997L, N997S, N997V, N997W, N997Y, F998M, F998W, A999F, A999G, A999L, A999M, A999R, A999S, V1000C, V1000L, V1000M, V1000N, V1000P, V1000W, D1001G, D1001K, D1001L, D1001M, D1001Q, D1001S, D1001T, D1001V, D1001Y, W1002A, W1002D, W1002E, W1002H, W1002N, W1002P, W1002Q, W1002S, T1003F, T1003G, T1003L, T1003N, T1003P, T1003R, T1003S, T1003W, T1003Y, K1004D, K1004E, K1004F, K1004G, K1004H, K1004M, K1004P, K1004R, K1004S, K1004V, P1005I, P1005N, P1005Q, P1005V, P1005Y, A1006C, A1006I, A1006N, A1006P, A1006S, A1006V, A1006W, A1006Y, D1007C, D1007L, D1007P, D1007V, T1008G, V1009G, V1009S, Y1010A, Y1010P, Y1010R, Y1010T, N1011A, N1011S, N1011T, N1011W, T1012E, T1012H, T1012I, T1012Q, T1012Y, A1013D, A1013K, A1013Q, A1013T, A1013V, G1014E, G1014I, G1014L, G1014M, G1014V, G1014W, G1014Y, T1015A, T1015F, T1015G, T1015V, V1016C, V1016D, V1016P, K1017E, K1017G, V1018I, V1018K, V1018L, V1018M, V1018R, V1018S, V1018W, T1021C, T1021E, T1021F, T1021G, T1021K, T1021L, T1021S, T1021V, A1022H, A1022L, A1022S, A1022Y, T1023D, T1023M, T1023Q, T1023R, V1024E, V1024G, V1024H, V1024K, V1024N, V1024R, V1024S, V1024W, G1026E, G1026H, G1026L, G1026R, G1026S, G1026V, G1026Y, K1027C, K1027N, K1027Q, K1027R, K1027V, E1028G, E1028S, E1028T, F1029I, F1029K, F1029L, F1029P, F1029V, F1029W, F1029Y, K1030D, K1030F, K1030H, K1030L, K1030M, K1030W, V1031H, V1031K, V1031Y, A1033G, A1033S, A1033V, T1034G, T1034H, T1034N, T1034W, I1035D, I1035G, I1035Q, R1036G, R1036L, R1036T, R1036Y, V1037C, V1037F, V1037P, V1037Q, Q1038A, Q1038D, Q1038K, R1039S, R1039V, S1040A, S1040M, S1040N, S1040R, S1040W, Q1041P, V1042N, T1043F, T1043G, T1043N, T1043R, I1044A, I1044L, G1045S, S1046I, S1046M, S1047D, V1048C, V1048F, V1048G, V1048I, V1048M, V1048Q, G1050L, G1050S, G1050V, N1051A, N1051E, N1051K, A1052C, A1052K, A1052M, A1052P, A1052R, L1053A, L1053W, R1054C, R1054L, R1054N, L1055R, L1055T, Q1057A, Q1057E, Q1057P, Q1057R, N1058R, N1058S, N1058V, N1058W, I1059W, P1060G, P1060N, P1060Q, P1060S, P1060T, A1061E, A1061G, A1061K, A1061W, D1062A, D1062F, D1062G, D1062I, D1062L, D1062M, D1062S, K1063D, K1063M, Q1064C, Q1064M, Q1064R, Q1064T, Q1064V, S1065A, S1065C, S1065E, S1065G, S1065T, S1065W, D1066A, D1066G, D1066M, D1066V, D1066W, T1067G, T1067M, L1068C, L1068E, L1068P, L1068Q, L1068Y, D1069G, D1069K, D1069R, D1069W, A1070P, A1070T, I1071M, I1071R, I1071W, K1072E, K1072G, K1072P, K1072Q, K1072S, D1073F, D1073L, D1073M, D1073P, D1073W, G1074I, G1074L, G1074R, S1075C, S1075G, S1075I, S1075L, S1075V, T1076C, T1076E, T1076H, T1076Q, T1076S, T1077K, T1077L, T1077R, V1078D, V1078E, V1078L, V1078W, D1079G, D1079L, N1081D, N1081E, N1081G, T1082A, T1082C, T1082E, T1082F, T1082G, T1082K, T1082N, T1082S, G1083E, G1083F, G1083L, G1083P, G1083S, G1084C, G1084M, G1084V, G1084W, G1084Y, G1085A, G1085P, G1085R, G1085S, A1086H, A1086K, A1086Q, A1086R, A1086T, N1087A, N1087E, N1087I, N1087R, N1087V, N1087W, P1088D, P1088E, P1088G, P1088R, P1088W, S1089C, S1089E, S1089G, S1089K, S1089Q, S1089R, S1089V, A1090F, A1090G, A1090I, A1090K, W1091A, W1091E, W1091G, W1091H, W1091T, W1091V, W1091Y, T1092A, T1092E, T1092G, T1092K, T1092Q, T1092S, T1092V, N1093A, N1093G, N1093L, N1093P, N1093Q, N1093T, N1093V, W1094D, W1094E, W1094P, W1094R, W1094T, A1095P, A1095R, A1095T, A1095W, Y1096A, Y1096D, Y1096H, Y1096L, Y1096R, S1097D, S1097E, S1097K, S1097L, S1097T, S1097W, K1098D, K1098F, K1098G, K1098Q, K1098S, A1099C, A1099D, A1099F, A1099S, A1099V, A1099W, G1100D, G1100E, G1100H, G1100M, G1100N, G1100T, H1101K, H1101L, H1101Q, H1101R, H1101V, N1102E, N1102F, N1102H, N1102K, N1102L, N1102Q, N1102R, N1102T, T1103A, T1103E, T1103H, T1103S, T1103W, A1104I, A1104K, A1104R, E1105L, E1105S, I1106T, I1106V, T1107C, T1107M, T1107R, T1107S, F1108D, F1108K, F1108L, F1108T, F1108W, E1109A, E1109D, E1109L, E1109W, A1111G, A1111S, E1113D, E1113G, E1113P, E1113V, Q1114E, Q1114I, Q1114L, Q1114R, Q1114S, Q1114T, Q1114V, Q1115A, Q1115K, Q1115L, Q1115P, Q1115T, Q1115W, L1116D, L1116G, L1116H, L1116K, L1116V, L1116W, G1117E, G1117I, G1117M, G1117R, G1117S, G1117T, G1117V, G1117W, Q1118A, Q1118M, Q1118S, Q1118T, Q1118W, I1119D, I1119E, I1119G, I1119N, I1119S, V1120N, V1120S, V1120T, M1121G, M1121K, M1121N, M1121P, M1121S, M1121V, M1121Y, Y1122A, Y1122C, Y1122I, Y1122K, Y1122R, Y1122V, Y1122Y, F1123E, F1123H, F1123I, F1123T, F1124E, F1124R, F1124V, F1124W, R1125D, R1125E, R1125F, R1125K, R1125T, R1125V, R1125W, D1126H, D1126K, D1126L, D1126R, S1127F, S1127I, S1127K, S1127M, S1127Q, S1127T, S1127W, N1128A, N1128C, N1128R, N1128S, N1128T, N1128W, A1129E, A1129L, A1129N, A1129Q, A1129R, A1129V, V1130A, V1130G, V1130P, V1130R, V1130S, R1131A, R1131N, R1131Q, R1131S, R1131W, F1132E, F1132K, F1132M, F1132P, F1132Q, F1132T, P1133D, P1133G, P1133L, P1133Q, P1133R, P1133V, D1134E, D1134G, D1134L, A1135E, A1135K, A1135L, A1135M, A1135S, A1135W, A1135Y, G1136A, G1136E, G1136P, G1136Q, G1136T, K1137A, K1137C, K1137G, K1137L, K1137P, K1137Q, K1137R, K1137S, K1137T, K1137V, T1138R, T1138Y, K1139A, K1139L, K1139R, K1139T, I1140A, I1140C, I1140G, I1140L, I1140M, I1140P, I1140R, I1140T, Q1141A, Q1141C, Q1141G, Q1141K, Q1141N, Q1141P, Q1141T, Q1141W, I1142E, I1142R, I1142S, I1142W, I1142Y, S1143G, A1144C, A1144D, A1144E, A1144N, A1144P, A1144S, A1144T, A1144V, A1144W, D1145C, D1145R, D1145T, G1146A, G1146C, G1146D, G1146K, G1146L, G1146R, G1146V, K1147A, K1147G, K1147T, K1147V, N1148H, N1148I, N1148K, N1148P, N1148Q, N1148R, N1148S, N1148T, N1148W, W1149C, W1149G, W1149I, W1149K, W1149N, W1149Q, W1149S, W1149T, W1149V, W1149Y, T1150G, T1150K, T1150P, D1151C, D1151G, D1151R, D1151T, D1151W, L1152A, L1152C, L1152E, L1152Q, L1152W, A1153E, A1153G, A1153K, A1153L, A1154C, A1154D, A1154E, A1154G, A1154R, A1154S, T1155E, T1155L, T1155Q, T1155R, T1157V, T1157W, I1158R, I1158S, I1158W, A1159C, A1159E, A1159I, A1159P, A1159R, A1159V, A1160K, A1160L, A1160Q, A1160S, Q1161A, Q1161P, Q1161S, E1162A, E1162C, E1162D, E1162F, E1162I, E1162N, E1162Q, E1162T, E1162W, E1162Y, E1165D, E1165H, E1165L, E1165M, E1165R, E1165S, E1165W, R1166D, R1166K, R1166Q, V1167A, V1167C, V1167L, V1167P, V1167R, K1168L, K1168Q, K1168R, K1168W, P1169M, P1169R, P1169S, Y1170E, Y1170K, Y1170M, Y1170Q, Y1170R, Y1170V, T1171A, T1171G, T1171M, T1171Q, T1171R, T1171S, Y1172D, Y1172E, Y1172H, Y1172I, YI172K, Y1172L, Y1172S, Y1172V, D1173A, D1173E, D1173F, D1173G, D1173K, D1173L, D1173P, D1173R, D1173T, D1173W, F1174D, F1174P, F1174Q, F1174R, F1174S, F1174T, F1174V, F1174W, A1175G, A1175I, A1175N, A1175Q, A1175S, A1175V, A1175Y, V1177N, V1177P, V1177S, V1177T, G1178M, G1178Q, G1178S, G1178T, A1179L, A1179Q, A1179W, T1180A, T1180G, T1180I, T1180L, T1180M, T1180Q, T1180S, T1180Y, F1181E, F1181L, F1181V, V1182M, K1183A, K1183E, K1183T, K1183V, V1184C, V1184E, V1184K, V1184L, V1184P, V1184Q, V1184Y, T1185Q, T1185V, V1186S, N1188V, N1188W, A1189C, A1189K, A1189T, A1189V, D1190R, D1190S, D1190T, D1190Y, T1191E, T1191L, T1192H, T1192P, T1193G, P1194A, P1194E, P1194G, P1194W, S1195G, V1197A, V1198E, C1199D, C1199T, A1200G, A1200V, A1200W, L1202A, L1202C, T1203E, T1203K, E1204G, E1204S, I1205V, K1208R, K1208V, K1208W, T1209A, T1209C, T1209E, T1209K, T1209N, T1209Q, T1209R, T1209W, A1210D, A1210E, A1210G, A1210K, A1210L, A1210Q, A1210R, A1210T, A1210W, T1211C, T1211D, T1211E, T1211G, T1211H, T1211K, T1211P, T1211Q, T1211R, T1211S, T1211V, K1213A, K1213D, K1213S, K1213T, K1213W, F1214A, F1214E, F1214K, F1214L, F1214P, F1214R, F1214S, F1214V, V1215D, V1215E, V1215K, V1215L, V1215Q, V1215S, V1215W, T1216A, T1216L, T1216P, T1216Q, T1216R, N1217A, N1217D, N1217E, N1217F, N1217P, N1217R, N1217S, N1217T, T1218A, T1218C, T1218E, T1218G, T1218Q, T1218S, T1218V, T1218W, S1219A, S1219E, S1219F, S1219I, S1219K, S1219R, S1219V, A1220C, A1220G, A1220L, A1220P, A1220R, A1220V, A1221D, A1221G, A1221K, A1221L, A1221R, A1221V, A1221W, L1222A, L1222C, L1222E, L1222F, L1222Q, L1222R, L1222V, L1222W, S1223C, S1223F, S1223G, S1223K, S1223L, S1223V, S1224A, S1224D, S1224G, S1224L, S1224M, S1224P, S1224R, S1224W, L1225C, L1225D, L1225E, L1225F, L1225G, L1225K, L1225P, L1225T, L1225V, L1225W, T1226A, T1226G, T1226M, T1226P, T1226R, T1226S, T1226V, T1226Y, V1227A, V1227C, V1227D, V1227E, V1227G, V1227L, V1227P, V1227Q, V1227S, N1228A, N1228D, N1228F, N1228K, N1228L, N1228T, G1229A, G1229C, G1229E, G1229Q, G1229S, G1229V, T1230F, T1230H, T1230I, T1230K, T1230L, T1230P, T1230R, T1230S, T1230W, K1231F, K1231G, K1231L, K1231M, K1231P, K1231S, K1231W, V1232E, V1232K, V1232Q, V1232R, V1232S, V1232T, V1232W, S1233P, S1233W, D1234C, D1234K, D1234R, D1234V, S1235D, S1235E, S1235G, S1235L, S1235P, S1235R, S1235W, S1235Y, V1236A, V1236C, V1236G, V1236I, V1236P, V1236Q, V1236R, L1237D, L1237E, L1237R, L1237V, L1237W, A1238D, A1238E, A1238K, A1238L, A1238N, A1238P, A1238R, A1238S, A1238T, A1239D, A1239P, A1239R, G1240D, G1240L, G1240N, G1240Q, G1240S, G1240T, G1240W, S1241D, S1241G, S1241I, S1241L, S1241M, S1241P, Y1242C, Y1242E, Y1242K, Y1242R, Y1242S, Y1242W, N1243C, N1243L, N1243M, N1243P, N1243Q, N1243S, N1243T, N1243V, N1243W, T1244A, T1244D, T1244E, T1244G, T1244L, T1244Q, T1244S, T1244V, T1244W, A1246F, A1246M, A1246N, A1246P, A1246Q, A1246R, A1246S, A1246T, I1247A, I1247G, I1247M, I1247Q, I1247R, I1247S, I1247T, I1247V, I1247W, I1248A, I1248G, I1248K, I1248L, I1248R, I1248S, I1248Y, A1249E, A1249G, A1249H, A1249I, A1249R, A1249T, A1249V, D1250I, D1250K, D1250S, D1250T, D1250W, D1250Y, V1251I, V1251T, V1251W, K1252D, K1252G, K1252V, K1252W, A1253P, A1253V, E1254F, E1254G, E1254H, E1254L, E1254R, E1254V, G1255H, G1255M, G1255S, G1255V, E1256G, E1256M, E1256N, E1256R, E1256V, E1256W, G1257F, G1257K, G1257L, G1257Q, G1257R, G1257W, N1258O, N1258G, N1258H, N1258K, N1258S, A1259K, A1259L, A1259W, V1261I, V1261L, V1261P, V1261Q, V1261R, V1261T, T1262A, T1262F, T1262M, T1262Q, T1262R, V1263E, V1263G, V1263Q, V1263R, V1263T, V1263W, L1264A, L1264E, L1264H, L1264R, L1264S, L1264Y, P1265C, P1265K, P1265L, P1265R, P1265S, P1265V, P1265W, A1266F, A1266L, A1266P, A1266S, A1266V, H1267A, H1267E, H1267F, N1269A, N1269E, N1269K, N1269R, N1269S, N1269T, N1269W, V1270D, V1270E, V1270G, V1270I, V1270L, V1270T, V1270W, I1271A, I1271H, I1271Q, R1272E, R1272F, R1272M, R1272P, R1272V, V1273R, I1274F, I1274M, I1274R, T1275A, T1275L, T1275W, E1276R, E1276W, S1277L, S1277T, S1277W, E1278Q, E1278R, D1279G, D1279I, D1279R, D1279T, D1279V, D1279W, H1280C, H1280E, H1280G, H1280V, H1280W, V1281F, V1281I, V1281S, V1281W, T1282D, T1282L, T1282V, R1283A, R1283D, R1283E, R1283P, R1283W, K1284G, T1285A, T1285E, T1285F, T1285G, T1285M, T1285R, T1285Y, F1286A, F1286E, F1286P, F1286R, F1286S, F1286T, T1287C, T1287K, T1287L, T1287M, T1287Q, T1287R, T1287S, T1287W, I1288A, I1288D, I1288F, I1288G, I1288K, N1289A, N1289Q, N1289T, L1290A, L1290G, L1290R, L1290V, L1290W, G1291K, G1291P, G1291V, G1291W, G1291Y, T1292G, T1292L, T1292Y, E1293G, E1293K, E1293L, E1293S, E1293V, Q1294E, Q1294L, Q1294P, Q1294W, E1295K, F1296A, F1296G, F1296I, P1297F, A1298Y, D1301I, E1302G, E1302R, E1302S, R1303S, D1304A or D1304V.

186. The method of the preceding embodiment wherein the substitutions are the substitutions listed in any one of embodiments 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144 or 146.

187. The method of any of the four preceding embodiments, wherein the variant has 1-50 substitutions, preferably 1-30, 1-20, 1-10 or 1-5, such as 1, 2, 3, 4, 5, 6, 7, 8, 9, 10, 11, 12, 13, 14, 15, 16, 17, 18, 19 or 20 substitutions, compared to the parent lactase.

188. The method of any of the five preceding embodiments, wherein the parent lactase is obtained from *Bifidobacterium*, preferably *Bifidobacterium bifidum*.

189. The method of any of the six preceding embodiments, wherein the parent lactase has an amino acid sequence which is at least 85%, 90%, or 95%, preferably at least 97%, 98%, or 99%, more preferably at least 99.5%, 99.7%, 99.8% or 99.9%, most preferably 100%, identical to SEQ ID NO: 1.

190. The method of any of the seven preceding embodiments, wherein the parent lactase has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

191. The method of any of the eight preceding embodiments, wherein the parent lactase comprises the same number of amino acid residues as the lactase of SEQ ID NO: 1.

192. The method of any of the nine preceding embodiments, wherein the variant has a decreased or an increased galactose inhibition, preferably measured as a galactose inhibition improvement factor (GI-IF) of at least 1.1, such as at least 1.2, at least 1.3, at least 1.4 or at least 1.5, or at most 0.9, such as at most 0.8, at most 0.7, at most 0.6 or at most 0.5, compared to the parent lactase.

193. The method of any of the ten preceding embodiments, wherein the variant has a decreased galactose inhibition, preferably measured as a galactose inhibition improvement factor (GI-IF) of at least 1.1, such as at least 1.2, at least 1.3, at least 1.4 or at least 1.5, compared to the parent lactase.

194. The method of any of the eleven preceding embodiments, wherein the variant has a decreased or an increased galactose inhibition, preferably measured as a galactose inhibition improvement factor (GI-IF) of at least 1.1, such as at least 1.2, at least 1.3, at least 1.4, at least 1.5, at least 1.6, at least 1.7, at least 1.8 or at least 1.9, or at most 0.9, such as at most 0.8, at most 0.7, at most 0.6, at most 0.5, at most 0.4, at most 0.3, at most 0.2 or at most 0.1, compared to the lactase of SEQ ID NO: 1.

195. The method of any of the twelve preceding embodiments, wherein the variant has a decreased galactose inhibition, preferably measured as a galactose inhibition improvement factor (GI-IF) of at least 1.1, such as at least 1.2, at least 1.3, at least 1.4, at least 1.5, at least 1.6, at least 1.7, at least 1.8 or at least 1.9, compared to the lactase of SEQ ID NO: 1.

196. The lactase variant of embodiment 97 having an amino acid sequence which is at least 99.4% identical to SEQ ID NO: 1.

197. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

198. The lactase variant of embodiment 101 having an amino acid sequence which is at least 99.4% identical to SEQ ID NO: 1.

199. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

200. The lactase variant of embodiment 105 having an amino acid sequence which is at least 99.4% identical to SEQ ID NO: 1.

201. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

202. The lactase variant of embodiment 109 having an amino acid sequence which is at least 99.4% identical to SEQ ID NO: 1.

203. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

204. The lactase variant of embodiment 113 having an amino acid sequence which is at least 99.4% identical to SEQ ID NO: 1.

205. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

206. The lactase variant of embodiment 117 having an amino acid sequence which is at least 99.4% identical to SEQ ID NO: 1.

207. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

208. The lactase variant of embodiment 121 having an amino acid sequence which is at least 99.4% identical to SEQ ID NO: 1.

209. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

210. The lactase variant of embodiment 125 having an amino acid sequence which is at least 99.4% identical to SEQ ID NO: 1.

211. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

212. The lactase variant of embodiment 129 having an amino acid sequence which is at least 99.4% identical to SEQ ID NO: 1.

213. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

214. The lactase variant of embodiment 133 having an amino acid sequence which is at least 99.4% identical to SEQ ID NO: 1.

215. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

216. The lactase variant of embodiment 137 having an amino acid sequence which is at least 99.4% identical to SEQ ID NO: 1.

217. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

218. The lactase variant of embodiment 141 having an amino acid sequence which is at least 99.4% identical to SEQ ID NO: 1.

219. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

220. The lactase variant of embodiment 145 having an amino acid sequence which is at least 99.4% identical to SEQ ID NO: 1.

221. The lactase variant of the preceding embodiment which has a length of 800-2000 amino acids, such as 1200-2000 amino acids, preferably 1200-1500 amino acids, more preferably 1250-1400 amino acids or 1250-1350 amino acids, even more preferably 1280-1320 amino acids, such as 1300-1320 amino acids or 1300-1310 amino acids, most preferably 1300-1305, such as 1302-1304 amino acids.

EXAMPLES

Example 1: Site-Saturation Library Generation

A gene encoding the lactase of SEQ ID NO: 1* was cloned into a *Bacillus subtilis* expression cassette and transformed in a *Bacillus subtilis* expression host. Site-saturation libraries were generated by Mega PCR approach in each position in the gene of SEQ ID NO: 1 with NNS doping in the forward mutagenic primer.

Two PCR reactions were performed: 1) generation of C-terminal fragment with the flanking C-terminal reverse primer and the forward mutagenic primer 2) generation of Mega PCR product using the C-terminal fragment as the reverse mega-primer and the flanking N-terminal forward primer to give the full-length cassette. The Mega PCR product was then transformed into the *Bacillus* host, where site-specific homologous recombination in the *Bacillus* chromosome takes place. The polymerase used for the PCR reaction was Phusion Hot Start Flex DNA polymerase (New England Biolabs, Cat. No.: M0535L).

After overnight growth in TB (Terrific Broth) media with appropriate antibiotic in 96-well plates at 37° C. with 700 rpm, a second overnight culture was started in fresh TB media with appropriate antibiotic and incubated overnight at same conditions. This culture was diluted into single cells in 384-well plates in LB (Luria-Bertani) media and incubated overnight at 37° C.

Culture PCR was carried out on 384-well plates by initial heat lysis of cells, followed by PCR. The polymerase used for the culture PCR reaction was Phire Hot Start II DNA polymerase (ThermoScientific, Cat. No.: F126L).

The PCR products were sequence confirmed and the unique substitutions were collected and combined in 384-well plates and grown in LB media. The polymerase used for the PCR reaction was Phusion Hot Start Flex DNA polymerase (New England Biolabs, Cat. No.: M0535L).

The variants obtained in the resulting 384-well plates were confirmed by an additional sequencing, and confirmed variants were used in screening assays.

*Note regarding backbone: Some clones of our template backbone for the site saturation library (SEQ ID NO: 1) contain a G856E mutation, so all substitution variants we describe are in the backbone context of SEQ ID NO: 1 with either Gly or Glu at position 856. That mutation is far away from the active site of the enzyme, and our experimental data showed no significant difference for Gly or Glu at position 856 in any of the characteristics we tested in purified samples, such as specific activity (Km at pH 6.5: 17.8 mM (G856) vs. 17.4 mM (E856); IF=0.98), galactose inhibition (Ki at pH 6.5: 41.5 mM (G856) vs. 40.6 mM (E856); IF=0.98) or melting point (Tm at pH 6.5: 54.7° C. (G856) vs. 54.4° C. (E856); IF=0.99). All characteristics are the same for the two backbones within the range of uncertainty of the measurements.

Example 2: Galactose Inhibition Assay

The *Bifidobacterium* lactase SSL libraries, grown in *Bacillus subtilis*, were grown in microtiter plates (MTP) in TB+10% w/v Sucrose (80 μL/MTP well) for expression, for 3 days at 37° C. in 384-well lidded MTP's with agitation. The expression plates contained wild-type control expressed in *B. subtilis*, as well as non-inoculated control wells (used as the blanks in the calculation of relative activity below). The supernatants were diluted 8-fold in dilution buffer (MES (100 mM), pH 6.0), and the diluted enzyme solutions (10 μL) were transferred to two separate transparent 384-well plates containing 1) reference assay solution (40 μL, MES (100 mM), ONPG (10.66 mM), DMSO (140 mM), pH 6.0, in working concentrations) and 2) galactose assay solution (40 μL, D-(+)-Galactose (80 mM), MES (100 mM), ortho-Nitrophenyl-ß-galactoside (ONPG, 10.66 mM), Dimethyl sulfoxide (DMSO, 140 mM), pH 6.0, in working concentrations). The assay plates were briefly agitated, followed by incubation at 30 min at 23° C. Stop solution (Na2CO3, 10% w/v in H2O) was added to the assay plates to stop the reaction. The endpoint absorbance was recorded at 405 nm of the two assay plates.

The adjusted absorbances from the assay plates were used to calculate the ratio of activity (RA), defined as RA= (Abs405 Galactose sample−Abs405 Galactose Blank)/ (Abs405 Reference sample−Abs405 Reference Blank).

The samples that displayed an absorbance at 405 nm below 0.2 in either the galactose or reference condition were removed.

The galactose inhibition assay improvement factor (GI-IF) of a given variant is calculated relative to the RA of the wild type enzyme of SEQ ID NO: 1, which is normalized to have an IF=1.0, per expression plate or per entire experiment if the given plate did not contain any wild types with assay data that passed the QC filter.

QC (quality control) filter: As quality control, from all variants constructed, we retained only those variants with an unstressed reference absorbance (Abs405 Reference sample) bigger than 0.2 and a ratio of activity (RA) bigger than 0.0 and less than 1.0.

A GI-IF above 1 means that the variant has a decreased galactose inhibition compared to the wild type enzyme, whereas a GI-IF below 1 means that the variant has an increased galactose inhibition.

Variants showing decreased galactose inhibition (i.e. GI-IF at least 1.5, or at least 1.4, or at least 1.3, or at least 1.2, or at least 1.1, but more than 1.0) are beneficial in application, since they lead to higher lactase performance. A decreased galactose inhibition will allow the enzyme to retain more activity at higher levels of galactose and thus allow for degradation of lactose down to a lower final lactose level. Moreover, variants showing increased galactose inhibition (i.e. GI-IF at most 0.5, or at most 0.6, or at most 0.7, or at most 0.8, or at most 0.9, but less than 1.0) are also beneficial in application, since they allow to fine-tune the galactose inhibition propensity of the lactase. An increased galactose inhibition may reduce or stop the activity of the enzyme when a certain decreased level of lactose has been obtained which may be advantageous in some commercial applications.

The variants that displayed a GI-IF of at least 1.1 or at most 0.9 are shown below.

TABLE 1

Variants having a GI-IF of at least 1.1

| Position | Mutation | GI-IF |
|---|---|---|
| 1 | V1D | 1.23 |
| 1 | V1F | 1.25 |
| 1 | V1H | 1.31 |
| 1 | V1K | 1.11 |
| 1 | V1L | 1.35 |
| 1 | V1R | 1.12 |
| 2 | E2D | 1.36 |
| 2 | E2G | 1.17 |
| 2 | E2Q | 1.25 |
| 2 | E2V | 1.45 |
| 3 | D3A | 1.13 |
| 3 | D3I | 1.41 |
| 3 | D3N | 1.12 |
| 3 | D3V | 1.48 |
| 4 | A4H | 1.19 |
| 5 | T5A | 1.12 |
| 5 | T5S | 1.22 |
| 6 | R6G | 1.15 |
| 6 | R6H | 1.13 |
| 6 | R6L | 1.14 |
| 6 | R6W | 1.13 |
| 7 | S7L | 1.11 |
| 7 | S7N | 1.39 |
| 7 | S7P | 2.24 |
| 7 | S7T | 1.12 |
| 9 | S9G | 1.15 |
| 9 | S9H | 1.21 |
| 9 | S9W | 1.10 |
| 10 | T10K | 1.15 |
| 10 | T10L | 1.21 |
| 10 | T10S | 1.21 |
| 12 | Q12V | 1.17 |
| 13 | M13C | 1.34 |
| 13 | M13D | 1.29 |
| 13 | M13E | 1.10 |
| 13 | M13H | 1.14 |
| 13 | M13K | 1.20 |
| 13 | M13R | 1.48 |
| 13 | M13W | 1.11 |
| 14 | S14G | 1.19 |
| 14 | S14H | 1.16 |

TABLE 1-continued

Variants having a GI-IF of at least 1.1

| Position | Mutation | GI-IF |
|---|---|---|
| 14 | S14T | 1.16 |
| 14 | S14V | 1.36 |
| 14 | S14Y | 1.14 |
| 15 | S15C | 1.45 |
| 15 | S15F | 1.13 |
| 15 | S15I | 2.18 |
| 15 | S15K | 1.58 |
| 15 | S15L | 1.11 |
| 15 | S15P | 1.25 |
| 15 | S15R | 1.27 |
| 15 | S15T | 1.38 |
| 15 | S15V | 1.33 |
| 15 | S15W | 1.19 |
| 16 | T16C | 1.57 |
| 16 | T16I | 1.20 |
| 17 | P17A | 1.15 |
| 17 | P17I | 1.37 |
| 17 | P17S | 1.14 |
| 19 | V19A | 1.10 |
| 19 | V19F | 1.15 |
| 19 | V19I | 1.14 |
| 19 | V19K | 1.25 |
| 19 | V19L | 1.16 |
| 19 | V19N | 1.15 |
| 19 | V19S | 1.18 |
| 20 | V20C | 1.35 |
| 20 | V20F | 1.19 |
| 20 | V20G | 1.23 |
| 20 | V20I | 1.12 |
| 20 | V20L | 1.21 |
| 20 | V20M | 1.36 |
| 20 | V20P | 1.89 |
| 20 | V20Q | 1.28 |
| 20 | V20R | 1.26 |
| 20 | V20T | 1.10 |
| 21 | Y21A | 1.14 |
| 21 | Y21C | 1.40 |
| 21 | Y21D | 1.16 |
| 21 | Y21G | 1.12 |
| 21 | Y21H | 1.12 |
| 21 | Y21M | 1.19 |
| 21 | Y21P | 1.32 |
| 21 | Y21R | 1.43 |
| 21 | Y21T | 1.45 |
| 22 | S22A | 1.18 |
| 22 | S22N | 1.22 |
| 22 | S22R | 1.12 |
| 22 | S22T | 1.21 |
| 22 | S22W | 1.36 |
| 23 | S23A | 1.17 |
| 24 | A24F | 1.45 |
| 24 | A24L | 1.36 |
| 24 | A24R | 1.21 |
| 24 | A24T | 1.93 |
| 24 | A24W | 1.39 |
| 25 | V25D | 1.29 |
| 25 | V25E | 1.12 |
| 25 | V25F | 1.13 |
| 25 | V25G | 1.16 |
| 25 | V25M | 1.23 |
| 25 | V25Q | 1.33 |
| 25 | V25S | 1.21 |
| 25 | V25T | 1.18 |
| 25 | V25W | 1.12 |
| 26 | D26C | 1.47 |
| 26 | D26I | 1.25 |
| 26 | D26L | 1.24 |
| 26 | D26M | 1.13 |
| 26 | D26V | 1.12 |
| 27 | S27A | 1.76 |
| 27 | S27C | 1.36 |
| 27 | S27G | 1.25 |
| 27 | S27H | 1.34 |
| 27 | S27P | 1.11 |
| 27 | S27Y | 1.26 |
| 28 | K28C | 1.52 |
| 28 | K28G | 1.10 |
| 28 | K28I | 1.11 |
| 28 | K28L | 1.27 |
| 28 | K28R | 1.19 |
| 28 | K28S | 1.15 |
| 28 | K28V | 1.25 |
| 28 | K28W | 1.18 |
| 29 | Q29F | 1.11 |
| 29 | Q29G | 1.21 |
| 29 | Q29L | 1.52 |
| 29 | Q29M | 1.45 |
| 29 | Q29R | 1.41 |
| 29 | Q29S | 1.12 |
| 30 | N30M | 1.21 |
| 30 | N30V | 1.26 |
| 30 | N30W | 1.11 |
| 30 | N30Y | 1.16 |
| 31 | R31E | 1.70 |
| 31 | R31M | 1.25 |
| 31 | R31V | 1.41 |
| 32 | T32Q | 1.19 |
| 32 | T32S | 1.59 |
| 33 | S33K | 1.12 |
| 34 | D34F | 1.12 |
| 34 | D34G | 1.27 |
| 34 | D34H | 1.25 |
| 35 | F35A | 1.12 |
| 35 | F35C | 1.34 |
| 35 | F35G | 1.12 |
| 35 | F35V | 1.15 |
| 36 | D36Q | 1.28 |
| 37 | A37N | 1.12 |
| 38 | N38S | 1.26 |
| 39 | W39G | 1.37 |
| 39 | W39S | 1.23 |
| 40 | K40C | 1.40 |
| 40 | K40F | 1.42 |
| 40 | K40G | 1.23 |
| 40 | K40I | 1.46 |
| 40 | K40M | 1.18 |
| 40 | K40P | 1.11 |
| 40 | K40W | 1.27 |
| 41 | F41A | 1.35 |
| 41 | F41C | 1.28 |
| 42 | M42T | 1.40 |
| 43 | L43A | 1.21 |
| 43 | L43G | 1.13 |
| 43 | L43I | 1.21 |
| 43 | L43S | 1.33 |
| 44 | S44M | 1.17 |
| 45 | D45L | 1.16 |
| 45 | D45P | 1.68 |
| 45 | D45V | 1.11 |
| 47 | V47K | 1.43 |
| 47 | V47R | 1.68 |
| 49 | A49C | 1.13 |
| 49 | A49D | 1.57 |
| 49 | A49H | 1.73 |
| 49 | A49T | 1.46 |
| 51 | D51G | 1.23 |
| 51 | D51I | 1.61 |
| 51 | D51K | 1.42 |
| 51 | D51M | 1.19 |
| 53 | A53G | 1.20 |
| 55 | D55C | 1.33 |
| 55 | D55F | 1.28 |
| 55 | D55G | 1.27 |
| 55 | D55H | 1.53 |
| 55 | D55M | 1.42 |
| 55 | D55N | 1.14 |
| 55 | D55P | 1.36 |
| 55 | D55S | 1.25 |
| 55 | D55V | 1.13 |
| 57 | S57A | 1.28 |
| 57 | S57C | 1.69 |
| 57 | S57E | 2.31 |

TABLE 1-continued

Variants having a GI-IF of at least 1.1

| Position | Mutation | GI-IF |
|---|---|---|
| 57 | S57G | 1.79 |
| 58 | A58I | 1.17 |
| 58 | A58N | 1.15 |
| 58 | A58Q | 1.32 |
| 58 | A58R | 1.14 |
| 58 | A58T | 1.51 |
| 59 | W59D | 1.10 |
| 59 | W59I | 1.30 |
| 59 | W59K | 1.39 |
| 59 | W59L | 1.11 |
| 59 | W59N | 1.11 |
| 59 | W59P | 1.86 |
| 59 | W59V | 1.22 |
| 60 | Q60E | 1.11 |
| 60 | Q60F | 1.16 |
| 60 | Q60G | 1.17 |
| 60 | Q60L | 1.12 |
| 60 | Q60M | 1.24 |
| 60 | Q60R | 1.34 |
| 60 | Q60S | 1.34 |
| 60 | Q60V | 1.15 |
| 60 | Q60Y | 1.22 |
| 61 | Q61P | 1.22 |
| 62 | V62G | 1.18 |
| 62 | V62N | 1.47 |
| 62 | V62T | 1.39 |
| 62 | V62W | 1.34 |
| 63 | D63G | 1.29 |
| 63 | D63L | 1.18 |
| 63 | D63S | 1.11 |
| 64 | L64E | 1.48 |
| 64 | L64G | 1.28 |
| 66 | H66R | 1.32 |
| 66 | H66T | 1.20 |
| 70 | I70H | 1.18 |
| 70 | I70K | 1.30 |
| 70 | I70P | 1.11 |
| 70 | I70R | 1.14 |
| 71 | T71H | 1.12 |
| 71 | T71L | 1.12 |
| 71 | T71P | 1.11 |
| 71 | T71R | 1.18 |
| 71 | T71S | 1.18 |
| 73 | K73A | 1.15 |
| 73 | K73D | 1.49 |
| 73 | K73G | 1.11 |
| 73 | K73Q | 1.12 |
| 73 | K73V | 1.13 |
| 74 | Y74G | 1.20 |
| 74 | Y74K | 1.22 |
| 75 | S75G | 1.53 |
| 75 | S75L | 1.43 |
| 75 | S75Q | 1.29 |
| 75 | S75R | 1.42 |
| 75 | S75V | 1.40 |
| 76 | Q76G | 1.51 |
| 76 | Q76I | 1.40 |
| 76 | Q76P | 1.11 |
| 77 | S77C | 1.20 |
| 77 | S77D | 1.36 |
| 77 | S77E | 1.41 |
| 77 | S77G | 1.35 |
| 77 | S77H | 1.73 |
| 77 | S77I | 1.15 |
| 77 | S77K | 1.51 |
| 77 | S77L | 1.25 |
| 77 | S77M | 1.23 |
| 77 | S77R | 1.35 |
| 77 | S77T | 1.24 |
| 77 | S77V | 1.29 |
| 77 | S77W | 1.17 |
| 78 | N78C | 1.43 |
| 78 | N78F | 1.17 |
| 78 | N78S | 1.21 |
| 79 | E79H | 1.44 |
| 79 | E79S | 1.45 |
| 79 | E79T | 1.45 |
| 83 | A83E | 1.16 |
| 83 | A83T | 1.33 |
| 85 | L85A | 1.33 |
| 85 | L85C | 1.19 |
| 85 | L85D | 1.19 |
| 85 | L85F | 2.06 |
| 85 | L85N | 1.34 |
| 85 | L85S | 1.47 |
| 85 | L85V | 1.42 |
| 85 | L85W | 1.53 |
| 86 | P86E | 1.11 |
| 86 | P86G | 1.24 |
| 86 | P86Q | 1.99 |
| 86 | P86R | 1.24 |
| 86 | P86V | 1.29 |
| 86 | P86W | 1.21 |
| 86 | P86Y | 1.22 |
| 87 | G87D | 1.74 |
| 87 | G87N | 1.21 |
| 88 | G88A | 1.11 |
| 88 | G88F | 1.74 |
| 88 | G88M | 1.11 |
| 89 | T89C | 1.12 |
| 89 | T89L | 1.11 |
| 89 | T89M | 1.29 |
| 89 | T89N | 1.17 |
| 89 | T89W | 1.15 |
| 89 | T89Y | 1.28 |
| 90 | G90A | 1.24 |
| 90 | G90D | 1.11 |
| 90 | G90L | 1.22 |
| 90 | G90S | 1.21 |
| 90 | G90T | 1.61 |
| 91 | W91E | 1.29 |
| 91 | W91L | 1.27 |
| 91 | W91P | 1.35 |
| 91 | W91Q | 1.22 |
| 91 | W91Y | 1.43 |
| 92 | Y92F | 1.21 |
| 92 | Y92H | 1.46 |
| 92 | Y92I | 1.31 |
| 92 | Y92M | 1.67 |
| 92 | Y92N | 1.29 |
| 92 | Y92S | 1.70 |
| 92 | Y92T | 1.30 |
| 92 | Y92V | 1.70 |
| 92 | Y92W | 1.16 |
| 93 | R93A | 2.08 |
| 93 | R93D | 1.42 |
| 93 | R93F | 1.94 |
| 93 | R93H | 1.55 |
| 93 | R93I | 1.36 |
| 93 | R93L | 1.95 |
| 93 | R93N | 1.50 |
| 93 | R93T | 1.83 |
| 93 | R93V | 1.76 |
| 93 | R93Y | 1.93 |
| 94 | K94A | 1.33 |
| 94 | K94C | 1.20 |
| 94 | K94G | 1.21 |
| 94 | K94R | 1.14 |
| 94 | K94S | 1.60 |
| 94 | K94T | 1.31 |
| 94 | K94V | 1.26 |
| 95 | S95A | 1.28 |
| 95 | S95C | 1.49 |
| 95 | S95D | 1.35 |
| 95 | S95E | 1.15 |
| 95 | S95G | 1.50 |
| 95 | S95I | 1.59 |
| 95 | S95L | 1.14 |
| 95 | S95Q | 1.28 |
| 95 | S95R | 1.26 |
| 96 | F96A | 1.77 |
| 96 | F96C | 1.61 |

TABLE 1-continued

Variants having a GI-IF of at least 1.1

| Position | Mutation | GI-IF |
|---|---|---|
| 96 | F96I | 1.49 |
| 96 | F96K | 1.35 |
| 96 | F96L | 1.13 |
| 96 | F96M | 1.35 |
| 96 | F96P | 1.31 |
| 96 | F96V | 1.66 |
| 96 | F96W | 1.25 |
| 97 | T97F | 1.42 |
| 97 | T97S | 1.18 |
| 97 | T97V | 1.29 |
| 98 | I98C | 1.33 |
| 98 | I98H | 1.51 |
| 98 | I98S | 1.17 |
| 98 | I98W | 1.22 |
| 100 | R100T | 1.40 |
| 101 | D101A | 1.46 |
| 101 | D101P | 1.71 |
| 101 | D101V | 1.20 |
| 102 | L102A | 1.16 |
| 102 | L102G | 1.11 |
| 102 | L102M | 1.18 |
| 102 | L102P | 1.51 |
| 102 | L102S | 1.15 |
| 104 | G104C | 1.12 |
| 105 | K105D | 1.20 |
| 105 | K105Q | 1.12 |
| 105 | K105R | 1.14 |
| 105 | K105W | 1.14 |
| 105 | K105Y | 1.13 |
| 106 | R106K | 1.19 |
| 106 | R106V | 1.24 |
| 106 | R106W | 1.39 |
| 107 | I107A | 1.19 |
| 107 | I107F | 1.24 |
| 107 | I107S | 1.31 |
| 108 | A108E | 1.35 |
| 108 | A108V | 1.16 |
| 109 | I109M | 1.50 |
| 109 | I109T | 1.16 |
| 110 | N110A | 1.36 |
| 110 | N110F | 1.15 |
| 110 | N110S | 1.35 |
| 110 | N110T | 1.42 |
| 110 | N110V | 1.30 |
| 110 | N110W | 1.33 |
| 111 | F111A | 1.48 |
| 111 | F111C | 1.14 |
| 111 | F111L | 1.48 |
| 111 | F111Q | 1.28 |
| 111 | F111V | 1.16 |
| 112 | D112A | 1.13 |
| 114 | V114F | 1.23 |
| 114 | V114R | 1.50 |
| 115 | Y115E | 1.43 |
| 116 | M116A | 1.19 |
| 116 | M116C | 1.39 |
| 116 | M116D | 1.14 |
| 116 | M116W | 1.17 |
| 117 | N117K | 1.13 |
| 118 | A118P | 1.35 |
| 119 | T119G | 1.12 |
| 120 | V120A | 1.58 |
| 120 | V120K | 1.32 |
| 121 | W121C | 1.14 |
| 121 | W121D | 1.28 |
| 121 | W121R | 1.69 |
| 121 | W121T | 1.16 |
| 121 | W121V | 1.54 |
| 124 | G124M | 1.22 |
| 125 | V125D | 1.18 |
| 126 | K126E | 1.12 |
| 126 | K126V | 1.16 |
| 129 | T129V | 1.20 |
| 130 | H130A | 1.43 |
| 130 | H130C | 1.20 |
| 130 | H130S | 1.22 |
| 130 | H130T | 1.50 |
| 131 | P131K | 1.17 |
| 132 | Y132E | 1.42 |
| 137 | F137C | 1.22 |
| 137 | F137D | 1.15 |
| 137 | F137L | 1.50 |
| 137 | F137P | 1.16 |
| 138 | S138A | 1.26 |
| 138 | S138D | 1.11 |
| 138 | S138H | 1.14 |
| 138 | S138M | 1.14 |
| 140 | D140V | 1.20 |
| 141 | L141G | 1.27 |
| 142 | T142S | 1.31 |
| 148 | G148K | 1.13 |
| 149 | G149E | 1.25 |
| 149 | G149I | 1.14 |
| 149 | G149M | 1.56 |
| 149 | G149Y | 1.20 |
| 150 | E150A | 1.15 |
| 150 | E150C | 1.22 |
| 150 | E150G | 1.21 |
| 150 | E150L | 1.44 |
| 150 | E150N | 1.10 |
| 150 | E150R | 1.26 |
| 151 | N151L | 1.13 |
| 154 | V154E | 1.18 |
| 154 | V154I | 1.25 |
| 154 | V154K | 1.33 |
| 154 | V154L | 1.40 |
| 154 | V154M | 1.14 |
| 157 | V157A | 1.19 |
| 157 | V157G | 1.17 |
| 157 | V157P | 1.44 |
| 157 | V157Q | 1.19 |
| 157 | V157S | 1.39 |
| 158 | E158H | 1.58 |
| 158 | E158K | 1.19 |
| 158 | E158Q | 1.12 |
| 158 | E158V | 1.30 |
| 159 | N159D | 1.12 |
| 159 | N159H | 1.21 |
| 159 | N159T | 1.52 |
| 160 | R160G | 1.12 |
| 161 | L161E | 1.15 |
| 161 | L161K | 1.41 |
| 161 | L161M | 1.39 |
| 161 | L161S | 1.75 |
| 161 | L161W | 1.57 |
| 162 | P162F | 1.14 |
| 162 | P162G | 1.12 |
| 162 | P162N | 2.00 |
| 162 | P162T | 1.64 |
| 162 | P162W | 1.48 |
| 164 | S164A | 1.33 |
| 165 | R165H | 1.88 |
| 166 | W166S | 1.83 |
| 167 | Y167A | 1.97 |
| 167 | Y167C | 1.29 |
| 169 | G169A | 1.15 |
| 169 | G169S | 1.11 |
| 170 | S170Q | 1.72 |
| 171 | G171C | 1.22 |
| 171 | G171F | 1.16 |
| 172 | I172G | 1.12 |
| 172 | I172K | 1.32 |
| 172 | I172P | 1.55 |
| 172 | I172Q | 1.19 |
| 173 | Y173A | 1.19 |
| 173 | Y173H | 1.30 |
| 173 | Y173M | 1.25 |
| 173 | Y173P | 1.19 |
| 173 | Y173S | 1.17 |
| 174 | R174E | 2.27 |
| 174 | R174K | 1.22 |
| 175 | D175Y | 1.11 |

TABLE 1-continued

Variants having a GI-IF of at least 1.1

| Position | Mutation | GI-IF |
|---|---|---|
| 176 | V176E | 1.44 |
| 176 | V176K | 1.41 |
| 176 | V176T | 1.27 |
| 177 | T177C | 1.14 |
| 177 | T177E | 1.20 |
| 177 | T177K | 1.45 |
| 178 | L178I | 1.54 |
| 178 | L178Q | 1.51 |
| 178 | L178W | 1.25 |
| 179 | T179A | 1.26 |
| 179 | T179C | 1.44 |
| 179 | T179D | 1.26 |
| 179 | T179H | 1.19 |
| 179 | T179I | 1.39 |
| 179 | T179K | 1.26 |
| 179 | T179L | 1.15 |
| 179 | T179N | 1.38 |
| 179 | T179P | 1.29 |
| 179 | T179S | 1.28 |
| 180 | V180A | 1.28 |
| 180 | V180C | 1.19 |
| 180 | V180D | 1.33 |
| 180 | V180E | 1.15 |
| 180 | V180G | 1.48 |
| 180 | V180M | 1.19 |
| 181 | T181A | 1.37 |
| 181 | T181F | 1.22 |
| 183 | G183W | 1.25 |
| 184 | V184F | 1.29 |
| 184 | V184H | 1.16 |
| 184 | V184P | 1.22 |
| 184 | V184Q | 1.20 |
| 184 | V184R | 1.31 |
| 184 | V184S | 1.29 |
| 184 | V184W | 1.24 |
| 185 | H185G | 1.43 |
| 185 | H185L | 1.79 |
| 185 | H185R | 1.12 |
| 186 | V186A | 1.15 |
| 186 | V186E | 1.26 |
| 186 | V186G | 1.16 |
| 186 | V186N | 1.26 |
| 187 | G187A | 1.10 |
| 187 | G187D | 1.40 |
| 187 | G187H | 1.25 |
| 188 | N188R | 1.23 |
| 188 | N188S | 1.16 |
| 188 | N188V | 1.56 |
| 188 | N188W | 1.12 |
| 189 | N189A | 1.16 |
| 190 | G190F | 1.33 |
| 190 | G190V | 1.18 |
| 191 | V191T | 1.12 |
| 191 | V191Y | 1.12 |
| 193 | I193N | 1.27 |
| 193 | I193Q | 1.26 |
| 193 | I193T | 1.15 |
| 193 | I193V | 1.10 |
| 194 | K194I | 1.38 |
| 195 | T195M | 1.19 |
| 195 | T195W | 1.25 |
| 196 | P196A | 1.21 |
| 196 | P196I | 1.20 |
| 196 | P196M | 1.15 |
| 196 | P196S | 1.12 |
| 196 | P196W | 1.14 |
| 197 | S197C | 1.45 |
| 197 | S197E | 1.25 |
| 197 | S197L | 1.25 |
| 198 | L198I | 1.17 |
| 199 | A199E | 1.27 |
| 199 | A199P | 1.32 |
| 199 | A199T | 1.10 |
| 201 | Q201E | 1.33 |
| 201 | Q201K | 1.19 |
| 202 | N202A | 1.17 |
| 202 | N202M | 1.11 |
| 202 | N202Q | 1.30 |
| 202 | N202S | 1.40 |
| 202 | N202W | 1.30 |
| 203 | G203Q | 1.16 |
| 204 | G204R | 1.16 |
| 205 | N205W | 1.11 |
| 206 | V206C | 1.19 |
| 207 | T207L | 1.15 |
| 213 | K213A | 1.19 |
| 215 | A215D | 1.21 |
| 216 | N216D | 1.12 |
| 217 | D217F | 1.20 |
| 217 | D217G | 1.14 |
| 217 | D217L | 2.29 |
| 217 | D217M | 1.77 |
| 218 | T218D | 1.11 |
| 218 | T218G | 1.61 |
| 218 | T218H | 1.18 |
| 219 | K219A | 1.13 |
| 220 | A220G | 1.70 |
| 221 | A221C | 1.10 |
| 221 | A221D | 1.15 |
| 222 | A222R | 2.01 |
| 223 | N223S | 1.67 |
| 224 | I224G | 1.12 |
| 225 | T225L | 1.14 |
| 226 | L226Q | 1.28 |
| 228 | Q228N | 1.25 |
| 228 | Q228R | 1.40 |
| 231 | F231L | 1.20 |
| 232 | P232T | 1.19 |
| 234 | G234V | 1.22 |
| 235 | G235K | 1.21 |
| 236 | K236M | 1.66 |
| 236 | K236P | 1.28 |
| 237 | T237D | 2.25 |
| 238 | D238K | 1.13 |
| 240 | A240Q | 1.11 |
| 242 | G242K | 1.34 |
| 242 | G242L | 1.20 |
| 242 | G242M | 1.21 |
| 242 | G242P | 1.20 |
| 243 | T243I | 1.21 |
| 247 | A247K | 1.22 |
| 248 | S248F | 1.16 |
| 251 | I251F | 1.19 |
| 251 | I251W | 1.28 |
| 251 | I251Y | 1.52 |
| 252 | A252H | 1.15 |
| 252 | A252P | 1.19 |
| 252 | A252W | 1.43 |
| 252 | A252Y | 1.71 |
| 257 | A257D | 1.30 |
| 257 | A257G | 1.12 |
| 257 | A257N | 1.28 |
| 257 | A257V | 1.25 |
| 260 | T260V | 1.14 |
| 261 | S261A | 1.11 |
| 261 | S261H | 1.37 |
| 261 | S261Y | 1.14 |
| 262 | T262E | 1.13 |
| 262 | T262F | 1.16 |
| 262 | T262P | 1.15 |
| 263 | I263A | 1.16 |
| 264 | T264L | 1.10 |
| 266 | A266D | 1.38 |
| 267 | S267V | 1.35 |
| 268 | P268F | 1.23 |
| 268 | P268R | 2.22 |
| 270 | L270N | 1.20 |
| 271 | W271T | 1.16 |
| 272 | S272T | 1.36 |
| 272 | S272W | 1.56 |
| 273 | I273W | 1.11 |
| 274 | K274Q | 1.16 |

TABLE 1-continued

Variants having a GI-IF of at least 1.1

| Position | Mutation | GI-IF |
|---|---|---|
| 275 | N275M | 1.15 |
| 277 | N277F | 1.28 |
| 280 | T280D | 1.11 |
| 281 | V281Q | 1.37 |
| 282 | R282W | 1.20 |
| 283 | T283M | 1.10 |
| 285 | V285H | 1.20 |
| 286 | L286W | 1.25 |
| 291 | V291H | 1.18 |
| 291 | V291L | 1.20 |
| 291 | V291P | 1.51 |
| 291 | V291S | 1.16 |
| 292 | L292A | 1.12 |
| 292 | L292D | 1.28 |
| 292 | L292E | 1.20 |
| 292 | L292Q | 1.14 |
| 292 | L292S | 1.17 |
| 292 | L292V | 1.45 |
| 293 | D293C | 1.47 |
| 293 | D293I | 1.23 |
| 293 | D293W | 1.33 |
| 294 | T294C | 1.19 |
| 294 | T294M | 1.13 |
| 294 | T294Q | 1.22 |
| 294 | T294S | 1.22 |
| 295 | Y295F | 1.31 |
| 295 | Y295G | 1.13 |
| 295 | Y295L | 1.12 |
| 295 | Y295S | 1.16 |
| 296 | D296F | 1.48 |
| 296 | D296H | 1.21 |
| 296 | D296K | 1.34 |
| 297 | T297I | 1.23 |
| 297 | T297S | 1.19 |
| 298 | E298I | 1.60 |
| 298 | E298L | 1.22 |
| 298 | E298M | 1.16 |
| 298 | E298R | 1.40 |
| 298 | E298T | 1.12 |
| 299 | Y299F | 1.11 |
| 299 | Y299S | 1.10 |
| 301 | F301C | 1.75 |
| 302 | R302I | 1.23 |
| 302 | R302K | 1.11 |
| 302 | R302M | 1.16 |
| 302 | R302T | 1.11 |
| 303 | W303A | 1.63 |
| 303 | W303C | 1.33 |
| 303 | W303D | 1.33 |
| 303 | W303F | 1.22 |
| 303 | W303T | 1.19 |
| 304 | T304D | 1.32 |
| 304 | T304E | 1.23 |
| 304 | T304I | 1.24 |
| 304 | T304K | 1.31 |
| 304 | T304P | 3.20 |
| 304 | T304S | 1.19 |
| 304 | T304W | 1.15 |
| 305 | G305E | 1.12 |
| 305 | G305L | 1.21 |
| 305 | G305M | 1.13 |
| 305 | G305N | 1.47 |
| 305 | G305P | 1.44 |
| 305 | G305T | 1.21 |
| 307 | D307A | 1.24 |
| 307 | D307E | 1.22 |
| 307 | D307F | 1.18 |
| 307 | D307S | 1.21 |
| 307 | D307V | 1.12 |
| 307 | D307W | 1.24 |
| 308 | A308G | 1.10 |
| 308 | A308I | 1.12 |
| 309 | T309C | 1.37 |
| 309 | T309D | 1.49 |
| 309 | T309E | 1.38 |
| 309 | T309I | 1.28 |

TABLE 1-continued

Variants having a GI-IF of at least 1.1

| Position | Mutation | GI-IF |
|---|---|---|
| 309 | T309K | 1.19 |
| 309 | T309V | 1.25 |
| 310 | S310A | 1.21 |
| 310 | S310C | 1.17 |
| 310 | S310G | 1.20 |
| 310 | S310H | 1.33 |
| 310 | S310I | 1.19 |
| 310 | S310L | 1.30 |
| 310 | S310M | 1.22 |
| 310 | S310N | 1.34 |
| 310 | S310R | 1.13 |
| 310 | S310V | 1.30 |
| 311 | G311F | 1.11 |
| 311 | G311L | 1.17 |
| 312 | F312H | 1.48 |
| 312 | F312L | 1.16 |
| 312 | F312V | 1.17 |
| 314 | L314A | 1.31 |
| 314 | L314V | 1.39 |
| 314 | L314Y | 1.12 |
| 315 | N315S | 1.36 |
| 316 | G316N | 1.12 |
| 316 | G316R | 1.20 |
| 316 | G316W | 1.16 |
| 316 | G316Y | 1.16 |
| 317 | E317V | 1.11 |
| 317 | E317W | 1.20 |
| 317 | E317Y | 1.19 |
| 318 | K318C | 1.25 |
| 318 | K318E | 1.16 |
| 318 | K318F | 1.15 |
| 318 | K318H | 1.15 |
| 318 | K318M | 1.18 |
| 318 | K318N | 1.33 |
| 318 | K318P | 1.12 |
| 318 | K318Q | 1.13 |
| 320 | K320E | 1.26 |
| 320 | K320I | 1.21 |
| 320 | K320V | 1.42 |
| 320 | K320W | 1.49 |
| 321 | L321H | 1.19 |
| 321 | L321M | 1.39 |
| 321 | L321Y | 1.14 |
| 322 | K322C | 1.19 |
| 322 | K322I | 1.34 |
| 324 | V324E | 1.17 |
| 324 | V324G | 1.16 |
| 324 | V324T | 1.31 |
| 325 | S325G | 1.48 |
| 326 | M326T | 1.57 |
| 326 | M326V | 1.11 |
| 328 | H328C | 1.42 |
| 328 | H328D | 1.11 |
| 328 | H328F | 1.32 |
| 328 | H328G | 1.33 |
| 328 | H328I | 1.12 |
| 328 | H328L | 1.23 |
| 328 | H328M | 1.42 |
| 328 | H328R | 1.27 |
| 328 | H328T | 1.40 |
| 331 | G331V | 1.39 |
| 335 | A335C | 1.21 |
| 335 | A335G | 1.38 |
| 335 | A335L | 1.31 |
| 337 | A337D | 1.19 |
| 337 | A337E | 1.20 |
| 337 | A337G | 1.49 |
| 337 | A337L | 1.89 |
| 338 | N338P | 1.26 |
| 338 | N338R | 1.13 |
| 340 | R340A | 1.45 |
| 340 | R340L | 1.35 |
| 341 | A341M | 1.54 |
| 342 | I342A | 1.10 |
| 342 | I342G | 1.33 |
| 342 | I342P | 1.21 |

TABLE 1-continued

Variants having a GI-IF of at least 1.1

| Position | Mutation | GI-IF |
|---|---|---|
| 343 | E343A | 1.19 |
| 343 | E343N | 1.40 |
| 343 | E343R | 1.17 |
| 343 | E343T | 1.28 |
| 343 | E343Y | 1.37 |
| 344 | R344G | 1.37 |
| 344 | R344Y | 1.15 |
| 345 | Q345F | 1.25 |
| 345 | Q345N | 1.28 |
| 345 | Q345S | 1.54 |
| 346 | V346A | 1.39 |
| 346 | V346I | 1.22 |
| 346 | V346S | 1.23 |
| 347 | E347A | 1.33 |
| 347 | E347D | 1.17 |
| 347 | E347I | 1.24 |
| 348 | I348A | 1.12 |
| 348 | I348D | 1.52 |
| 348 | I348G | 1.13 |
| 348 | I348M | 1.37 |
| 348 | I348Q | 1.29 |
| 348 | I348R | 1.26 |
| 349 | L349A | 1.21 |
| 349 | L349E | 1.11 |
| 349 | L349S | 1.24 |
| 349 | L349V | 1.15 |
| 350 | Q350G | 1.43 |
| 350 | Q350N | 1.29 |
| 350 | Q350W | 1.16 |
| 351 | K351R | 1.15 |
| 351 | K351W | 1.17 |
| 352 | M352L | 1.14 |
| 352 | M352T | 1.37 |
| 353 | G353K | 1.40 |
| 354 | V354E | 1.22 |
| 354 | V354G | 1.18 |
| 354 | V354S | 1.28 |
| 354 | V354W | 1.29 |
| 355 | N355H | 1.10 |
| 357 | I357T | 1.39 |
| 359 | T359E | 1.53 |
| 359 | T359L | 1.35 |
| 360 | T360V | 1.47 |
| 362 | N362S | 1.42 |
| 362 | N362T | 2.65 |
| 363 | P363A | 1.38 |
| 363 | P363D | 1.30 |
| 363 | P363I | 1.51 |
| 363 | P363L | 1.49 |
| 363 | P363M | 1.43 |
| 363 | P363S | 1.20 |
| 363 | P363V | 1.21 |
| 364 | A364C | 1.28 |
| 364 | A364E | 1.22 |
| 364 | A364F | 1.24 |
| 364 | A364G | 1.22 |
| 364 | A364I | 2.12 |
| 364 | A364M | 1.58 |
| 364 | A364P | 1.49 |
| 364 | A364V | 1.27 |
| 364 | A364W | 1.13 |
| 365 | A365C | 1.41 |
| 365 | A365I | 1.39 |
| 365 | A365P | 1.36 |
| 365 | A365V | 1.33 |
| 365 | A365W | 1.21 |
| 366 | K366D | 1.29 |
| 366 | K366I | 1.17 |
| 366 | K366L | 1.33 |
| 366 | K366M | 1.35 |
| 366 | K366P | 1.21 |
| 366 | K366S | 1.39 |
| 366 | K366V | 1.22 |
| 367 | A367I | 1.18 |
| 367 | A367N | 1.17 |
| 367 | A367Q | 1.26 |
| 368 | L368A | 1.34 |
| 368 | L368Q | 1.40 |
| 368 | L368S | 1.83 |
| 368 | L368V | 1.15 |
| 368 | L368Y | 1.21 |
| 369 | I369A | 1.22 |
| 369 | I369D | 1.22 |
| 369 | I369E | 1.35 |
| 369 | I369G | 1.48 |
| 369 | I369K | 4.08 |
| 369 | I369M | 1.22 |
| 369 | I369V | 1.39 |
| 369 | I369W | 1.56 |
| 370 | D370L | 1.58 |
| 370 | D370Q | 1.24 |
| 370 | D370R | 1.19 |
| 370 | D370T | 1.19 |
| 371 | V371F | 1.32 |
| 371 | V371G | 1.11 |
| 371 | V371I | 1.16 |
| 371 | V371L | 1.21 |
| 371 | V371Q | 1.33 |
| 372 | C372P | 1.31 |
| 373 | N373G | 1.60 |
| 373 | N373L | 1.49 |
| 373 | N373R | 1.19 |
| 374 | E374L | 1.12 |
| 375 | K375D | 1.30 |
| 375 | K375I | 1.12 |
| 375 | K375N | 1.14 |
| 375 | K375Q | 1.11 |
| 375 | K375S | 1.23 |
| 376 | G376A | 1.47 |
| 376 | G376S | 1.87 |
| 377 | V377A | 1.22 |
| 377 | V377M | 1.44 |
| 377 | V377T | 1.30 |
| 378 | L378I | 1.13 |
| 378 | L378P | 1.19 |
| 378 | L378Y | 1.14 |
| 379 | V379A | 1.46 |
| 379 | V379C | 1.15 |
| 379 | V379M | 1.19 |
| 379 | V379N | 1.36 |
| 380 | V380P | 1.45 |
| 380 | V380S | 1.17 |
| 381 | E381A | 1.54 |
| 381 | E381C | 1.17 |
| 381 | E381G | 1.30 |
| 381 | E381Q | 1.31 |
| 381 | E381T | 1.71 |
| 383 | V383A | 1.33 |
| 386 | M386G | 1.61 |
| 386 | M386N | 1.57 |
| 386 | M386S | 2.15 |
| 386 | M386V | 1.25 |
| 387 | W387H | 1.36 |
| 388 | N388E | 1.22 |
| 388 | N388L | 1.48 |
| 389 | R389A | 1.45 |
| 389 | R389C | 1.29 |
| 389 | R389E | 1.61 |
| 389 | R389K | 1.16 |
| 389 | R389M | 1.16 |
| 389 | R389Q | 2.11 |
| 389 | R389S | 2.92 |
| 389 | R389T | 1.53 |
| 389 | R389V | 1.17 |
| 390 | S390C | 1.81 |
| 390 | S390D | 1.64 |
| 390 | S390H | 1.17 |
| 390 | S390P | 1.60 |
| 390 | S390T | 1.70 |
| 393 | G393E | 1.34 |
| 393 | G393R | 1.80 |
| 393 | G393V | 6.87 |

TABLE 1-continued

Variants having a GI-IF of at least 1.1

| Position | Mutation | GI-IF |
|---|---|---|
| 395 | T395A | 1.20 |
| 395 | T395C | 1.58 |
| 395 | T395F | 1.20 |
| 396 | E396K | 1.80 |
| 396 | E396L | 2.25 |
| 396 | E396V | 2.70 |
| 396 | E396W | 1.78 |
| 398 | Y398M | 1.35 |
| 399 | G399S | 1.58 |
| 400 | K400A | 1.52 |
| 400 | K400C | 1.50 |
| 400 | K400M | 1.17 |
| 400 | K400N | 1.64 |
| 400 | K400T | 1.23 |
| 400 | K400V | 1.51 |
| 401 | W401F | 1.53 |
| 401 | W401K | 2.38 |
| 402 | F402W | 1.71 |
| 402 | F402Y | 1.88 |
| 403 | G403A | 2.67 |
| 403 | G403D | 1.20 |
| 403 | G403H | 1.17 |
| 403 | G403K | 1.70 |
| 403 | G403Q | 1.32 |
| 403 | G403T | 1.19 |
| 403 | G403V | 1.62 |
| 403 | G403Y | 1.28 |
| 404 | Q404F | 1.67 |
| 404 | Q404L | 1.70 |
| 404 | Q404M | 2.15 |
| 404 | Q404P | 1.98 |
| 404 | Q404S | 1.23 |
| 404 | Q404V | 2.92 |
| 405 | A405C | 1.84 |
| 405 | A405E | 1.50 |
| 405 | A405K | 1.33 |
| 405 | A405R | 1.58 |
| 405 | A405T | 2.14 |
| 405 | A405V | 1.17 |
| 406 | I406C | 1.23 |
| 406 | I406D | 1.67 |
| 406 | I406N | 1.63 |
| 407 | A407C | 1.39 |
| 407 | A407G | 1.33 |
| 407 | A407Q | 1.30 |
| 410 | N410R | 1.25 |
| 410 | N410Y | 1.32 |
| 411 | A411E | 1.50 |
| 411 | A411R | 1.24 |
| 411 | A411S | 1.22 |
| 412 | V412S | 1.20 |
| 414 | G414M | 1.40 |
| 414 | G414N | 1.32 |
| 414 | G414T | 1.14 |
| 415 | G415A | 1.13 |
| 415 | G415Q | 1.24 |
| 416 | D416M | 1.19 |
| 417 | K417F | 1.53 |
| 417 | K417R | 1.31 |
| 422 | A422P | 1.36 |
| 423 | K423L | 1.18 |
| 423 | K423R | 1.10 |
| 426 | L426C | 1.25 |
| 427 | T427D | 1.45 |
| 427 | T427F | 1.33 |
| 427 | T427Q | 2.11 |
| 427 | T427S | 1.62 |
| 427 | T427W | 1.25 |
| 429 | T429D | 1.82 |
| 429 | T429P | 1.12 |
| 430 | I430L | 1.28 |
| 430 | I430M | 1.20 |
| 431 | N431L | 1.11 |
| 431 | N431M | 1.51 |
| 432 | R432F | 1.17 |
| 432 | R432G | 1.15 |
| 432 | R432Q | 1.24 |
| 432 | R432Y | 1.21 |
| 433 | D433C | 1.17 |
| 433 | D433G | 1.33 |
| 433 | D433I | 1.31 |
| 433 | D433P | 1.50 |
| 433 | D433Q | 1.33 |
| 433 | D433W | 1.69 |
| 434 | R434N | 1.86 |
| 434 | R434T | 1.12 |
| 434 | R434V | 1.74 |
| 435 | N435E | 1.38 |
| 435 | N435F | 1.20 |
| 435 | N435H | 1.17 |
| 435 | N435L | 1.50 |
| 435 | N435V | 1.23 |
| 436 | A436C | 1.19 |
| 436 | A436G | 1.22 |
| 436 | A436L | 1.52 |
| 436 | A436M | 1.12 |
| 437 | P437K | 1.16 |
| 437 | P437L | 1.17 |
| 437 | P437W | 1.11 |
| 438 | S438G | 1.15 |
| 439 | V439C | 1.52 |
| 439 | V439K | 1.52 |
| 440 | I440S | 1.13 |
| 440 | I440T | 1.14 |
| 440 | I440V | 1.10 |
| 441 | M441R | 1.12 |
| 441 | M441T | 1.17 |
| 442 | W442E | 1.41 |
| 442 | W442G | 1.51 |
| 443 | S443C | 1.50 |
| 443 | S443G | 1.31 |
| 443 | S443M | 1.23 |
| 443 | S443Q | 1.36 |
| 444 | L444E | 1.33 |
| 444 | L444F | 1.25 |
| 444 | L444V | 1.76 |
| 446 | N446D | 1.37 |
| 448 | M448C | 1.50 |
| 448 | M448E | 1.14 |
| 448 | M448L | 3.81 |
| 449 | M449D | 1.86 |
| 449 | M449E | 1.24 |
| 449 | M449F | 1.11 |
| 449 | M449T | 1.58 |
| 449 | M449V | 1.13 |
| 449 | M449W | 1.81 |
| 449 | M449Y | 2.48 |
| 450 | E450F | 2.52 |
| 450 | E450S | 2.73 |
| 450 | E450T | 2.36 |
| 450 | E450V | 3.02 |
| 450 | E450W | 1.98 |
| 451 | G451C | 2.60 |
| 451 | G451F | 2.67 |
| 451 | G451L | 3.39 |
| 451 | G451P | 2.77 |
| 451 | G451V | 1.57 |
| 451 | G451W | 1.85 |
| 452 | I452K | 1.77 |
| 452 | I452L | 1.28 |
| 452 | I452Q | 1.25 |
| 452 | I452S | 1.35 |
| 452 | I452V | 1.32 |
| 453 | S453C | 1.11 |
| 453 | S453G | 1.15 |
| 453 | S453H | 1.25 |
| 453 | S453L | 1.25 |
| 453 | S453M | 1.18 |
| 453 | S453N | 1.23 |
| 453 | S453P | 1.13 |
| 453 | S453Q | 1.25 |
| 453 | S453R | 1.13 |

TABLE 1-continued

| Variants having a GI-IF of at least 1.1 | | |
|---|---|---|
| Position | Mutation | GI-IF |
| 453 | S453V | 1.19 |
| 454 | G454L | 1.49 |
| 454 | G454W | 1.27 |
| 455 | S455E | 1.21 |
| 455 | S455M | 1.24 |
| 455 | S455P | 1.61 |
| 455 | S455R | 1.63 |
| 455 | S455V | 1.20 |
| 456 | V456D | 1.56 |
| 456 | V456E | 1.47 |
| 456 | V456F | 1.62 |
| 456 | V456K | 1.42 |
| 457 | S457H | 1.33 |
| 457 | S457Q | 1.24 |
| 457 | S457T | 1.49 |
| 457 | S457V | 1.54 |
| 458 | G458A | 1.52 |
| 458 | G458D | 1.15 |
| 458 | G458P | 1.47 |
| 458 | G458S | 1.38 |
| 459 | F459C | 1.27 |
| 459 | F459R | 2.04 |
| 460 | P460M | 1.15 |
| 460 | P460Y | 1.21 |
| 461 | A461G | 1.21 |
| 461 | A461M | 1.38 |
| 461 | A461S | 1.19 |
| 462 | T462E | 1.32 |
| 462 | T462L | 1.30 |
| 464 | A464W | 1.26 |
| 465 | K465C | 1.12 |
| 465 | K465G | 1.11 |
| 465 | K465L | 1.30 |
| 465 | K465Q | 1.13 |
| 465 | K465V | 1.34 |
| 465 | K465Y | 1.56 |
| 466 | L466G | 1.23 |
| 466 | L466P | 1.74 |
| 467 | V467T | 1.20 |
| 468 | A468D | 2.95 |
| 469 | W469L | 1.15 |
| 469 | W469R | 1.17 |
| 471 | K471F | 1.36 |
| 471 | K471Q | 1.22 |
| 471 | K471Y | 1.11 |
| 472 | A472G | 2.00 |
| 472 | A472Y | 2.65 |
| 473 | A473M | 1.10 |
| 473 | A473P | 1.16 |
| 474 | D474C | 1.16 |
| 474 | D474E | 1.10 |
| 474 | D474M | 1.17 |
| 474 | D474W | 1.28 |
| 475 | S475E | 1.44 |
| 475 | S475T | 1.16 |
| 476 | T476L | 1.13 |
| 476 | T476S | 1.14 |
| 477 | R477A | 1.12 |
| 477 | R477G | 1.18 |
| 477 | R477L | 1.49 |
| 478 | P478A | 1.13 |
| 478 | P478D | 1.18 |
| 478 | P478V | 1.22 |
| 479 | M479G | 2.01 |
| 480 | T480Q | 1.14 |
| 485 | K485E | 1.49 |
| 485 | K485R | 1.35 |
| 487 | K487A | 1.27 |
| 487 | K487C | 1.20 |
| 487 | K487F | 1.54 |
| 487 | K487S | 1.37 |
| 487 | K487W | 1.37 |
| 488 | A488C | 1.25 |
| 488 | A488L | 1.11 |
| 488 | A488V | 1.18 |
| 493 | S493E | 1.21 |

TABLE 1-continued

| Variants having a GI-IF of at least 1.1 | | |
|---|---|---|
| Position | Mutation | GI-IF |
| 493 | S493G | 1.37 |
| 493 | S493H | 1.23 |
| 493 | S493L | 1.32 |
| 493 | S493Q | 1.45 |
| 494 | N494A | 1.13 |
| 494 | N494I | 1.13 |
| 494 | N494M | 1.21 |
| 494 | N494R | 1.40 |
| 494 | N494V | 1.25 |
| 495 | T495K | 1.10 |
| 497 | G497D | 1.39 |
| 499 | N499T | 1.50 |
| 505 | G505D | 2.06 |
| 505 | G505H | 1.26 |
| 505 | G505L | 1.27 |
| 505 | G505R | 1.38 |
| 505 | G505S | 1.93 |
| 505 | G505V | 1.13 |
| 506 | V506C | 1.75 |
| 506 | V506E | 2.03 |
| 506 | V506R | 1.75 |
| 507 | V507F | 1.12 |
| 507 | V507P | 1.18 |
| 507 | V507R | 1.69 |
| 508 | G508C | 2.24 |
| 508 | G508E | 2.53 |
| 509 | T509A | 1.37 |
| 509 | T509D | 1.17 |
| 509 | T509E | 1.12 |
| 509 | T509I | 1.22 |
| 509 | T509K | 1.86 |
| 509 | T509M | 1.54 |
| 509 | T509Q | 1.14 |
| 509 | T509S | 1.14 |
| 509 | T509V | 1.29 |
| 509 | T509Y | 1.21 |
| 510 | N510A | 2.45 |
| 510 | N510F | 1.62 |
| 510 | N510I | 2.74 |
| 511 | Y511A | 2.86 |
| 512 | S512C | 1.26 |
| 512 | S512E | 1.19 |
| 512 | S512F | 1.52 |
| 512 | S512I | 1.25 |
| 512 | S512M | 1.29 |
| 512 | S512Q | 1.35 |
| 512 | S512T | 1.63 |
| 512 | S512V | 1.31 |
| 512 | S512Y | 1.46 |
| 513 | D513G | 1.18 |
| 513 | D513P | 1.91 |
| 513 | D513R | 1.66 |
| 515 | A515E | 2.73 |
| 515 | A515F | 1.13 |
| 515 | A515G | 1.22 |
| 515 | A515P | 1.31 |
| 515 | A515S | 1.17 |
| 516 | N516C | 1.55 |
| 516 | N516E | 1.39 |
| 516 | N516G | 1.22 |
| 516 | N516I | 1.22 |
| 516 | N516M | 1.17 |
| 516 | N516Q | 1.40 |
| 516 | N516S | 1.10 |
| 516 | N516T | 1.23 |
| 516 | N516V | 1.33 |
| 517 | Y517G | 1.98 |
| 517 | Y517I | 1.15 |
| 518 | D518Y | 1.54 |
| 519 | K519C | 1.42 |
| 519 | K519E | 1.25 |
| 519 | K519F | 1.10 |
| 519 | K519G | 1.23 |
| 519 | K519I | 1.45 |
| 519 | K519L | 1.18 |
| 519 | K519M | 1.11 |

TABLE 1-continued

| Variants having a GI-IF of at least 1.1 | | |
|---|---|---|
| Position | Mutation | GI-IF |
| 519 | K519N | 1.19 |
| 519 | K519Q | 1.26 |
| 519 | K519S | 1.16 |
| 519 | K519T | 1.16 |
| 520 | I520A | 1.25 |
| 520 | I520C | 1.30 |
| 520 | I520G | 1.45 |
| 520 | I520H | 1.49 |
| 520 | I520M | 1.34 |
| 520 | I520N | 1.20 |
| 520 | I520Q | 1.26 |
| 520 | I520S | 1.45 |
| 520 | I520T | 1.36 |
| 520 | I520W | 1.20 |
| 520 | I520Y | 1.18 |
| 521 | R521A | 1.20 |
| 521 | R521C | 1.16 |
| 521 | R521K | 1.14 |
| 521 | R521Q | 1.12 |
| 521 | R521V | 2.64 |
| 523 | T523A | 1.14 |
| 523 | T523M | 1.19 |
| 524 | H524R | 1.80 |
| 524 | H524V | 1.54 |
| 525 | P525R | 1.13 |
| 526 | S526G | 2.24 |
| 527 | W527A | 1.36 |
| 527 | W527E | 1.22 |
| 527 | W527G | 1.24 |
| 527 | W527H | 1.38 |
| 527 | W527N | 2.54 |
| 527 | W527R | 1.58 |
| 527 | W527S | 1.43 |
| 528 | A528E | 1.41 |
| 528 | A528G | 1.15 |
| 528 | A528L | 1.11 |
| 529 | I529G | 1.27 |
| 535 | A535E | 1.16 |
| 535 | A535G | 1.20 |
| 535 | A535I | 1.21 |
| 537 | A537M | 1.35 |
| 537 | A537P | 1.59 |
| 537 | A537S | 1.23 |
| 538 | I538H | 1.16 |
| 538 | I538M | 1.29 |
| 540 | S540E | 1.55 |
| 545 | N545G | 1.12 |
| 547 | T547K | 1.19 |
| 549 | G549D | 1.39 |
| 549 | G549P | 1.40 |
| 549 | G549W | 1.71 |
| 550 | G550Q | 1.19 |
| 550 | G550R | 1.17 |
| 553 | S553P | 1.20 |
| 553 | S553R | 1.17 |
| 555 | D555E | 1.18 |
| 555 | D555P | 1.19 |
| 556 | K556C | 1.12 |
| 556 | K556R | 1.23 |
| 558 | L558E | 1.31 |
| 558 | L558H | 1.23 |
| 558 | L558P | 1.77 |
| 559 | T559G | 1.11 |
| 559 | T559Q | 1.29 |
| 559 | T559V | 1.10 |
| 559 | T559Y | 1.41 |
| 560 | S560P | 1.15 |
| 560 | S560V | 1.18 |
| 564 | S564A | 1.25 |
| 564 | S564C | 1.56 |
| 564 | S564F | 1.85 |
| 564 | S564W | 1.36 |
| 565 | A565C | 1.29 |
| 565 | A565D | 1.32 |
| 565 | A565E | 1.46 |
| 565 | A565F | 1.24 |

TABLE 1-continued

| Variants having a GI-IF of at least 1.1 | | |
|---|---|---|
| Position | Mutation | GI-IF |
| 565 | A565G | 1.27 |
| 565 | A565I | 1.57 |
| 565 | A565L | 1.39 |
| 565 | A565M | 1.19 |
| 565 | A565R | 1.52 |
| 565 | A565S | 1.24 |
| 565 | A565T | 1.35 |
| 565 | A565V | 1.12 |
| 565 | A565W | 1.20 |
| 567 | G567N | 1.11 |
| 567 | G567Q | 2.29 |
| 567 | G567V | 1.78 |
| 570 | A570G | 1.40 |
| 570 | A570L | 1.12 |
| 572 | A572W | 1.27 |
| 574 | S574V | 1.18 |
| 575 | A575D | 1.37 |
| 577 | Y577R | 1.14 |
| 578 | D578T | 1.18 |
| 580 | V580D | 1.20 |
| 581 | Q581T | 1.13 |
| 581 | Q581Y | 1.27 |
| 582 | R582A | 1.23 |
| 582 | R582G | 1.26 |
| 582 | R582I | 1.18 |
| 582 | R582L | 1.88 |
| 583 | D583V | 1.13 |
| 583 | D583W | 1.67 |
| 584 | F584I | 1.16 |
| 584 | F584W | 1.21 |
| 586 | A586D | 1.24 |
| 588 | T588P | 1.11 |
| 589 | Y589I | 1.26 |
| 589 | Y589Q | 1.24 |
| 591 | W591F | 1.39 |
| 592 | T592L | 1.42 |
| 593 | G593C | 1.11 |
| 594 | F594C | 1.14 |
| 597 | L597D | 1.29 |
| 597 | L597T | 1.10 |
| 598 | G598N | 1.36 |
| 600 | P600A | 1.51 |
| 600 | P600E | 2.15 |
| 600 | P600G | 1.49 |
| 600 | P600S | 2.01 |
| 604 | N604E | 1.25 |
| 604 | N604S | 1.11 |
| 605 | G605R | 1.20 |
| 607 | G607Q | 1.44 |
| 607 | G607S | 1.26 |
| 608 | S608E | 1.14 |
| 608 | S608I | 1.12 |
| 608 | S608N | 1.19 |
| 608 | S608Q | 1.19 |
| 608 | S608T | 1.21 |
| 609 | G609A | 1.28 |
| 609 | G609S | 1.18 |
| 610 | A610T | 1.25 |
| 612 | G612V | 1.10 |
| 613 | S613A | 1.15 |
| 614 | W614A | 1.86 |
| 615 | P615V | 1.11 |
| 619 | N619I | 1.31 |
| 619 | N619L | 1.43 |
| 619 | N619S | 1.10 |
| 621 | Y621W | 1.12 |
| 625 | V625A | 1.12 |
| 625 | V625E | 1.28 |
| 625 | V625F | 1.16 |
| 625 | V625M | 2.18 |
| 625 | V625Y | 2.15 |
| 627 | T627K | 1.39 |
| 627 | T627Q | 1.38 |
| 628 | A628C | 1.11 |
| 628 | A628D | 1.32 |
| 628 | A628N | 1.27 |

TABLE 1-continued

Variants having a GI-IF of at least 1.1

| Position | Mutation | GI-IF |
|---|---|---|
| 629 | G629T | 1.21 |
| 630 | F630C | 1.39 |
| 630 | F630Y | 1.39 |
| 631 | P631D | 1.36 |
| 631 | P631Y | 1.22 |
| 632 | K632C | 1.17 |
| 632 | K632D | 1.23 |
| 632 | K632G | 1.27 |
| 633 | D633G | 1.15 |
| 634 | T634F | 1.14 |
| 634 | T634S | 1.15 |
| 634 | T634V | 1.45 |
| 636 | Y636K | 1.19 |
| 637 | F637C | 1.17 |
| 637 | F637G | 1.23 |
| 637 | F637I | 1.23 |
| 637 | F637S | 1.21 |
| 637 | F637T | 1.29 |
| 637 | F637V | 1.26 |
| 639 | Q639R | 1.73 |
| 643 | N643R | 1.13 |
| 644 | D644Y | 1.21 |
| 645 | D645S | 1.21 |
| 645 | D645V | 1.14 |
| 646 | V646C | 1.17 |
| 646 | V646L | 1.16 |
| 646 | V646N | 1.17 |
| 646 | V646R | 1.21 |
| 646 | V646S | 1.12 |
| 647 | H647G | 1.24 |
| 647 | H647V | 1.18 |
| 648 | T648C | 1.27 |
| 649 | L649V | 1.10 |
| 650 | H650F | 1.12 |
| 651 | I651T | 1.24 |
| 651 | I651V | 1.16 |
| 652 | L652C | 1.25 |
| 652 | L652D | 1.17 |
| 652 | L652V | 1.14 |
| 652 | L652W | 1.20 |
| 653 | P653Q | 1.23 |
| 654 | A654D | 1.13 |
| 654 | A654R | 1.23 |
| 655 | W655F | 1.15 |
| 655 | W655R | 1.62 |
| 656 | N656K | 1.16 |
| 657 | E657K | 1.12 |
| 657 | E657R | 1.30 |
| 657 | E657V | 1.16 |
| 661 | A661E | 1.75 |
| 661 | A661G | 1.18 |
| 661 | A661H | 1.23 |
| 661 | A661K | 1.38 |
| 661 | A661L | 1.19 |
| 661 | A661M | 1.26 |
| 661 | A661Q | 1.36 |
| 661 | A661W | 1.20 |
| 662 | K662H | 1.14 |
| 662 | K662S | 1.26 |
| 662 | K662V | 1.27 |
| 662 | K662W | 1.16 |
| 662 | K662Y | 1.26 |
| 667 | N667L | 1.39 |
| 667 | N667R | 1.30 |
| 669 | P669A | 1.18 |
| 669 | P669E | 1.13 |
| 669 | P669L | 1.27 |
| 669 | P669R | 1.16 |
| 669 | P669T | 1.62 |
| 669 | P669W | 1.23 |
| 672 | V672L | 1.12 |
| 673 | Y673S | 2.06 |
| 674 | T674D | 1.14 |
| 674 | T674M | 1.36 |
| 674 | T674Q | 1.17 |
| 675 | D675A | 1.21 |

TABLE 1-continued

Variants having a GI-IF of at least 1.1

| Position | Mutation | GI-IF |
|---|---|---|
| 675 | D675V | 1.17 |
| 675 | D675Y | 1.17 |
| 676 | A676L | 1.14 |
| 676 | A676P | 1.46 |
| 677 | A677T | 1.19 |
| 679 | V679Q | 1.25 |
| 679 | V679S | 1.32 |
| 680 | K680I | 1.42 |
| 680 | K680N | 1.23 |
| 682 | Y682V | 1.20 |
| 683 | F683W | 1.18 |
| 684 | T684R | 1.17 |
| 686 | K686E | 1.11 |
| 687 | G687P | 1.49 |
| 688 | S688K | 1.36 |
| 688 | S688L | 2.15 |
| 689 | T689G | 1.26 |
| 689 | T689W | 1.39 |
| 690 | E690D | 1.35 |
| 691 | K691E | 1.10 |
| 691 | K691H | 1.16 |
| 691 | K691P | 1.26 |
| 691 | K691R | 1.26 |
| 692 | R692G | 1.35 |
| 692 | R692H | 1.48 |
| 692 | R692I | 1.22 |
| 692 | R692L | 1.16 |
| 692 | R692P | 1.12 |
| 692 | R692S | 1.24 |
| 692 | R692T | 1.26 |
| 692 | R692V | 1.12 |
| 692 | R692W | 1.15 |
| 693 | L693M | 1.11 |
| 693 | L693P | 1.16 |
| 694 | I694L | 1.61 |
| 694 | I694W | 1.58 |
| 695 | G695C | 1.84 |
| 695 | G695K | 1.15 |
| 695 | G695L | 2.14 |
| 695 | G695R | 1.21 |
| 695 | G695W | 1.42 |
| 696 | E696R | 1.26 |
| 697 | K697A | 1.22 |
| 697 | K697G | 1.30 |
| 697 | K697R | 1.54 |
| 697 | K697V | 1.12 |
| 697 | K697W | 1.13 |
| 698 | S698D | 1.15 |
| 698 | S698E | 1.73 |
| 698 | S698M | 1.38 |
| 698 | S698Q | 1.10 |
| 698 | S698R | 1.14 |
| 700 | T700A | 1.19 |
| 700 | T700D | 1.17 |
| 700 | T700Y | 1.13 |
| 701 | K701A | 2.49 |
| 701 | K701D | 1.27 |
| 701 | K701G | 1.68 |
| 701 | K701H | 1.10 |
| 701 | K701L | 1.23 |
| 701 | K701M | 1.90 |
| 701 | K701P | 1.20 |
| 701 | K701S | 1.31 |
| 703 | T703K | 1.16 |
| 705 | A705D | 1.11 |
| 705 | A705K | 1.18 |
| 705 | A705P | 1.14 |
| 705 | A705R | 1.27 |
| 705 | A705W | 1.47 |
| 706 | A706C | 1.23 |
| 706 | A706T | 1.21 |
| 706 | A706W | 1.13 |
| 708 | Y708F | 1.35 |
| 708 | Y708L | 1.11 |
| 710 | Y710E | 1.12 |
| 710 | Y710T | 1.97 |

TABLE 1-continued

Variants having a GI-IF of at least 1.1

| Position | Mutation | GI-IF |
|---|---|---|
| 710 | Y710V | 1.21 |
| 711 | Q711A | 1.26 |
| 711 | Q711D | 1.17 |
| 711 | Q711T | 1.11 |
| 712 | V712M | 1.41 |
| 712 | V712P | 1.26 |
| 712 | V712Q | 1.30 |
| 713 | Y713E | 1.14 |
| 713 | Y713G | 1.29 |
| 714 | E714H | 1.20 |
| 714 | E714I | 1.14 |
| 714 | E714K | 1.93 |
| 714 | E714N | 1.18 |
| 715 | G715K | 1.27 |
| 716 | A716M | 1.12 |
| 716 | A716P | 1.15 |
| 716 | A716R | 1.47 |
| 716 | A716T | 1.22 |
| 717 | D717G | 1.59 |
| 717 | D717L | 1.16 |
| 717 | D717S | 1.45 |
| 718 | K718A | 1.56 |
| 718 | K718Q | 1.25 |
| 718 | K718T | 1.39 |
| 718 | K718W | 1.19 |
| 718 | K718Y | 1.24 |
| 719 | D719E | 1.33 |
| 719 | D719S | 1.12 |
| 719 | D719T | 1.52 |
| 719 | D719V | 1.57 |
| 720 | S720A | 1.24 |
| 720 | S720M | 1.18 |
| 720 | S720R | 1.17 |
| 720 | S720Y | 1.13 |
| 721 | T721D | 1.16 |
| 721 | T721H | 1.35 |
| 721 | T721K | 1.13 |
| 721 | T721L | 1.33 |
| 721 | T721N | 1.45 |
| 721 | T721P | 1.13 |
| 721 | T721Q | 1.15 |
| 721 | T721S | 2.10 |
| 721 | T721V | 1.38 |
| 721 | T721W | 1.47 |
| 721 | T721Y | 1.18 |
| 722 | A722Q | 1.16 |
| 722 | A722T | 1.21 |
| 722 | A722V | 1.29 |
| 723 | H723G | 1.42 |
| 723 | H723P | 1.28 |
| 724 | K724A | 1.16 |
| 724 | K724G | 1.17 |
| 725 | N725A | 1.10 |
| 725 | N725I | 1.19 |
| 726 | M726D | 1.40 |
| 726 | M726Q | 1.11 |
| 727 | Y727L | 1.39 |
| 728 | L728C | 1.18 |
| 728 | L728K | 1.16 |
| 728 | L728S | 1.50 |
| 728 | L728W | 1.19 |
| 729 | T729A | 1.19 |
| 729 | T729E | 1.11 |
| 729 | T729M | 1.28 |
| 731 | N731E | 1.30 |
| 731 | N731Q | 1.22 |
| 732 | V732R | 1.40 |
| 733 | P733W | 1.25 |
| 734 | W734G | 1.43 |
| 734 | W734R | 1.10 |
| 735 | A735Q | 1.43 |
| 735 | A735R | 1.21 |
| 735 | A735S | 1.54 |
| 735 | A735T | 1.11 |
| 737 | G737F | 1.25 |
| 737 | G737K | 1.18 |
| 737 | G737N | 1.15 |
| 737 | G737Y | 1.14 |
| 738 | T738L | 1.16 |
| 738 | T738S | 1.34 |
| 739 | I739E | 1.15 |
| 739 | I739K | 1.50 |
| 740 | S740D | 1.47 |
| 740 | S740F | 1.20 |
| 741 | A741I | 1.51 |
| 741 | A741P | 1.21 |
| 741 | A741S | 1.30 |
| 741 | A741V | 1.16 |
| 742 | E742V | 1.14 |
| 743 | A743E | 1.15 |
| 743 | A743I | 1.16 |
| 744 | Y744L | 1.15 |
| 744 | Y744R | 1.32 |
| 745 | D745C | 1.29 |
| 745 | D745N | 1.34 |
| 745 | D745R | 1.10 |
| 746 | E746C | 1.11 |
| 746 | E746K | 1.16 |
| 746 | E746T | 1.12 |
| 747 | N747E | 1.17 |
| 747 | N747F | 1.25 |
| 747 | N747P | 1.12 |
| 749 | R749M | 1.11 |
| 750 | L750M | 1.14 |
| 750 | L750P | 1.15 |
| 750 | L750Q | 1.14 |
| 750 | L750S | 2.42 |
| 751 | I751C | 1.25 |
| 751 | I751H | 1.13 |
| 752 | P752C | 1.68 |
| 752 | P752Y | 1.51 |
| 754 | G754H | 1.26 |
| 754 | G754I | 1.15 |
| 754 | G754R | 1.20 |
| 755 | S755T | 1.15 |
| 756 | T756N | 1.88 |
| 756 | T756Q | 1.14 |
| 757 | E757A | 1.99 |
| 758 | G758V | 1.14 |
| 759 | N759S | 1.28 |
| 759 | N759V | 1.24 |
| 760 | A760G | 1.19 |
| 761 | S761A | 1.17 |
| 762 | V762W | 1.13 |
| 765 | T765P | 1.13 |
| 766 | G766M | 1.21 |
| 769 | A769F | 1.84 |
| 769 | A769G | 1.27 |
| 769 | A769I | 1.62 |
| 769 | A769N | 1.86 |
| 769 | A769V | 2.29 |
| 769 | A769Y | 1.46 |
| 770 | K770H | 1.90 |
| 771 | L771A | 1.31 |
| 772 | K772A | 1.55 |
| 772 | K772C | 1.40 |
| 772 | K772P | 2.23 |
| 772 | K772W | 1.23 |
| 773 | A773C | 1.42 |
| 773 | A773M | 1.36 |
| 773 | A773R | 1.34 |
| 774 | D774A | 1.43 |
| 775 | A775V | 1.15 |
| 776 | D776R | 1.15 |
| 776 | D776V | 1.32 |
| 777 | R777H | 1.62 |
| 777 | R777S | 1.41 |
| 777 | R777T | 1.15 |
| 778 | K778F | 1.30 |
| 778 | K778G | 1.22 |
| 778 | K778N | 1.34 |
| 778 | K778R | 1.18 |

TABLE 1-continued

Variants having a GI-IF of at least 1.1

| Position | Mutation | GI-IF |
|---|---|---|
| 779 | T779I | 1.14 |
| 781 | T781A | 1.81 |
| 781 | T781E | 1.10 |
| 781 | T781F | 1.36 |
| 781 | T781G | 1.65 |
| 781 | T781P | 1.60 |
| 781 | T781Y | 1.59 |
| 782 | A782C | 1.17 |
| 782 | A782N | 1.19 |
| 782 | A782Q | 1.47 |
| 782 | A782Y | 1.28 |
| 783 | D783A | 1.32 |
| 785 | K785C | 1.30 |
| 785 | K785I | 1.15 |
| 785 | K785S | 1.68 |
| 785 | K785V | 1.14 |
| 785 | K785W | 2.09 |
| 785 | K785Y | 1.31 |
| 786 | D786V | 1.58 |
| 787 | L787D | 1.12 |
| 787 | L787K | 1.13 |
| 789 | Y789V | 1.41 |
| 790 | I790R | 1.34 |
| 790 | I790V | 1.15 |
| 791 | E791D | 1.11 |
| 791 | E791F | 1.11 |
| 791 | E791S | 1.26 |
| 791 | E791V | 1.11 |
| 791 | E791W | 1.17 |
| 792 | V792S | 1.21 |
| 792 | V792Y | 1.20 |
| 793 | D793C | 1.12 |
| 793 | D793Y | 1.10 |
| 794 | V794D | 1.11 |
| 796 | D796S | 1.12 |
| 796 | D796T | 1.13 |
| 797 | A797H | 1.10 |
| 798 | N798I | 1.44 |
| 798 | N798Q | 1.10 |
| 799 | G799D | 1.10 |
| 799 | G799K | 1.51 |
| 799 | G799L | 1.58 |
| 799 | G799Y | 1.19 |
| 800 | H800F | 1.14 |
| 800 | H800G | 1.16 |
| 800 | H800V | 1.24 |
| 801 | I801W | 1.11 |
| 802 | V802E | 1.20 |
| 802 | V802I | 1.27 |
| 802 | V802S | 1.22 |
| 802 | V802Y | 1.31 |
| 803 | P803G | 1.19 |
| 803 | P803S | 1.69 |
| 803 | P803Y | 1.22 |
| 804 | D804E | 1.10 |
| 805 | A805C | 1.13 |
| 805 | A805F | 1.25 |
| 805 | A805I | 1.11 |
| 805 | A805N | 1.11 |
| 805 | A805P | 1.19 |
| 806 | A806F | 1.20 |
| 806 | A806I | 1.32 |
| 806 | A806Q | 1.43 |
| 807 | N807F | 1.10 |
| 808 | R808F | 1.39 |
| 808 | R808G | 1.26 |
| 808 | R808I | 1.20 |
| 808 | R808P | 1.11 |
| 809 | V809L | 1.20 |
| 809 | V809M | 1.28 |
| 809 | V809P | 1.18 |
| 810 | T810L | 1.18 |
| 810 | T810P | 1.98 |
| 810 | T810Q | 1.35 |
| 810 | T810R | 1.10 |
| 810 | T810Y | 1.24 |
| 811 | F811L | 1.21 |
| 813 | V813H | 1.11 |
| 813 | V813W | 1.39 |
| 813 | V813Y | 1.11 |
| 814 | K814G | 1.22 |
| 814 | K814P | 1.27 |
| 815 | G815F | 1.11 |
| 815 | G815M | 1.29 |
| 815 | G815P | 1.20 |
| 816 | A816D | 1.22 |
| 816 | A816N | 1.13 |
| 816 | A816W | 1.21 |
| 817 | G817H | 1.18 |
| 818 | K818D | 1.21 |
| 818 | K818F | 1.53 |
| 818 | K818L | 1.46 |
| 818 | K818Q | 1.22 |
| 818 | K818R | 1.18 |
| 818 | K818S | 1.13 |
| 818 | K818W | 1.53 |
| 818 | K818Y | 1.35 |
| 819 | L819F | 1.40 |
| 820 | V820C | 1.24 |
| 820 | V820R | 1.22 |
| 820 | V820W | 1.15 |
| 821 | G821I | 1.52 |
| 822 | V822A | 1.25 |
| 822 | V822D | 1.78 |
| 822 | V822E | 1.42 |
| 822 | V822T | 1.13 |
| 823 | D823E | 1.12 |
| 824 | N824A | 1.14 |
| 825 | G825A | 1.21 |
| 826 | S826A | 1.19 |
| 826 | S826G | 1.30 |
| 826 | S826I | 1.12 |
| 826 | S826W | 1.17 |
| 828 | P828G | 1.15 |
| 829 | D829C | 1.12 |
| 829 | D829I | 1.15 |
| 829 | D829S | 1.32 |
| 830 | H830Q | 1.14 |
| 831 | D831A | 1.14 |
| 831 | D831M | 1.12 |
| 831 | D831P | 1.44 |
| 832 | S832P | 1.19 |
| 832 | S832R | 1.47 |
| 832 | S832W | 1.15 |
| 833 | Y833C | 1.14 |
| 833 | Y833D | 1.17 |
| 833 | Y833E | 1.27 |
| 833 | Y833N | 1.16 |
| 834 | Q834M | 1.21 |
| 835 | A835G | 1.90 |
| 835 | A835H | 1.80 |
| 835 | A835K | 1.33 |
| 836 | D836C | 1.37 |
| 836 | D836E | 1.52 |
| 836 | D836Q | 1.21 |
| 836 | D836R | 1.13 |
| 836 | D836S | 1.74 |
| 836 | D836T | 1.26 |
| 836 | D836V | 1.34 |
| 836 | D836Y | 1.79 |
| 838 | R838N | 1.33 |
| 838 | R838S | 1.17 |
| 839 | K839A | 1.32 |
| 839 | K839D | 1.63 |
| 839 | K839L | 1.14 |
| 839 | K839N | 1.18 |
| 840 | A840G | 1.43 |
| 840 | A840I | 1.26 |
| 840 | A840P | 1.37 |
| 840 | A840V | 1.32 |
| 841 | F841I | 1.19 |
| 841 | F841K | 1.17 |

TABLE 1-continued

Variants having a GI-IF of at least 1.1

| Position | Mutation | GI-IF |
|---|---|---|
| 842 | S842A | 1.17 |
| 844 | K844A | 1.27 |
| 844 | K844Y | 1.14 |
| 847 | A847T | 1.15 |
| 848 | I848M | 1.16 |
| 850 | Q850L | 1.17 |
| 851 | S851C | 1.18 |
| 851 | S851D | 1.17 |
| 851 | S851E | 1.13 |
| 851 | S851T | 1.12 |
| 852 | T852L | 1.14 |
| 853 | K853P | 1.26 |
| 854 | E854C | 1.58 |
| 854 | E854I | 1.26 |
| 855 | A855K | 1.10 |
| 855 | A855V | 1.15 |
| 855 | A855Y | 1.12 |
| 858 | I858D | 1.46 |
| 858 | I858G | 1.14 |
| 858 | I858K | 1.28 |
| 858 | I858P | 1.21 |
| 860 | V860Y | 1.11 |
| 861 | T861F | 1.23 |
| 861 | T861I | 1.29 |
| 861 | T861Q | 1.14 |
| 861 | T861V | 1.14 |
| 861 | T861W | 1.35 |
| 862 | A862C | 1.11 |
| 864 | A864K | 1.16 |
| 865 | D865A | 1.49 |
| 865 | D865G | 1.71 |
| 866 | G866H | 1.30 |
| 866 | G866R | 1.25 |
| 867 | L867W | 1.73 |
| 870 | S870E | 1.30 |
| 870 | S870M | 1.27 |
| 870 | S870T | 1.23 |
| 872 | V872C | 1.72 |
| 872 | V872G | 1.25 |
| 873 | K873G | 1.39 |
| 873 | K873Y | 1.38 |
| 874 | I874G | 1.43 |
| 875 | A875R | 1.13 |
| 879 | V879S | 1.20 |
| 882 | T882A | 1.26 |
| 882 | T882M | 1.15 |
| 882 | T882R | 1.23 |
| 883 | S883L | 1.50 |
| 885 | E885V | 1.27 |
| 886 | K886L | 1.30 |
| 886 | K886V | 1.34 |
| 886 | K886W | 1.33 |
| 887 | T887A | 1.27 |
| 887 | T887D | 1.28 |
| 887 | T887G | 1.40 |
| 887 | T887N | 1.25 |
| 888 | V888A | 1.42 |
| 889 | R889G | 1.23 |
| 892 | Y892P | 1.43 |
| 893 | Y893E | 1.55 |
| 893 | Y893G | 1.18 |
| 894 | S894D | 1.30 |
| 894 | S894G | 1.18 |
| 897 | Y897V | 1.32 |
| 898 | Y898T | 1.11 |
| 900 | K900E | 1.36 |
| 900 | K900G | 1.12 |
| 901 | T901Q | 1.32 |
| 901 | T901R | 1.35 |
| 901 | T901Y | 1.56 |
| 902 | G902A | 1.22 |
| 902 | G902D | 1.10 |
| 902 | G902F | 1.38 |
| 902 | G902P | 1.22 |
| 902 | G902Q | 1.21 |
| 902 | G902R | 1.47 |
| 902 | G902S | 1.77 |
| 902 | G902W | 1.41 |
| 903 | N903D | 1.42 |
| 903 | N903I | 1.25 |
| 904 | K904D | 1.24 |
| 904 | K904E | 1.21 |
| 904 | K904M | 1.44 |
| 904 | K904N | 1.32 |
| 904 | K904R | 1.24 |
| 904 | K904S | 1.32 |
| 904 | K904V | 1.52 |
| 904 | K904W | 1.20 |
| 905 | P905C | 1.16 |
| 905 | P905C | 1.37 |
| 905 | P905R | 1.48 |
| 905 | P905V | 1.10 |
| 905 | P905W | 1.29 |
| 905 | P905Y | 1.45 |
| 906 | I906A | 1.12 |
| 906 | I906N | 1.25 |
| 906 | I906T | 1.12 |
| 906 | I906W | 1.44 |
| 907 | L907F | 1.34 |
| 907 | L907S | 1.23 |
| 908 | P908C | 1.20 |
| 908 | P908D | 1.22 |
| 908 | P908G | 1.26 |
| 908 | P908I | 1.40 |
| 908 | P908L | 1.37 |
| 908 | P908T | 1.16 |
| 909 | S909E | 1.18 |
| 909 | S909F | 1.14 |
| 909 | S909S | 1.11 |
| 909 | S909W | 1.13 |
| 909 | S909Y | 1.19 |
| 910 | D910I | 1.11 |
| 910 | D910W | 1.47 |
| 911 | V911A | 1.19 |
| 912 | E912A | 1.15 |
| 912 | E912K | 1.16 |
| 912 | E912L | 1.20 |
| 912 | E912T | 2.02 |
| 912 | E912V | 1.12 |
| 913 | V913G | 1.11 |
| 913 | V913R | 1.11 |
| 914 | R914A | 1.81 |
| 914 | R914E | 1.11 |
| 914 | R914F | 1.84 |
| 914 | R914I | 1.34 |
| 914 | R914K | 1.76 |
| 914 | R914V | 1.36 |
| 914 | R914W | 1.21 |
| 914 | R914Y | 1.53 |
| 915 | Y915A | 1.46 |
| 915 | Y915C | 1.52 |
| 915 | Y915G | 1.33 |
| 915 | Y915I | 1.21 |
| 915 | Y915M | 1.70 |
| 915 | Y915Q | 1.36 |
| 915 | Y915V | 1.58 |
| 916 | S916G | 1.73 |
| 917 | D917C | 1.47 |
| 917 | D917E | 1.25 |
| 917 | D917F | 1.72 |
| 917 | D917L | 1.29 |
| 917 | D917M | 1.21 |
| 917 | D917Q | 1.26 |
| 917 | D917S | 1.80 |
| 918 | G918E | 1.40 |
| 918 | G918H | 1.53 |
| 918 | G918T | 1.33 |
| 918 | G918V | 1.11 |
| 919 | T919D | 1.31 |
| 919 | T919K | 1.16 |
| 919 | T919Q | 1.93 |
| 919 | T919W | 1.23 |

TABLE 1-continued

Variants having a GI-IF of at least 1.1

| Position | Mutation | GI-IF |
|---|---|---|
| 920 | S920P | 1.17 |
| 920 | S920V | 1.16 |
| 921 | D921C | 1.16 |
| 921 | D921V | 1.54 |
| 922 | R922A | 1.95 |
| 922 | R922M | 1.30 |
| 922 | R922V | 1.19 |
| 922 | R922W | 1.26 |
| 923 | Q923A | 1.21 |
| 923 | Q923E | 1.10 |
| 923 | Q923L | 1.15 |
| 923 | Q923M | 1.10 |
| 923 | Q923V | 2.01 |
| 924 | N924Q | 1.11 |
| 924 | N924S | 1.11 |
| 925 | V925C | 1.29 |
| 925 | V925E | 1.15 |
| 925 | V925G | 1.17 |
| 925 | V925K | 1.28 |
| 925 | V925N | 1.11 |
| 925 | V925W | 1.10 |
| 926 | T926P | 1.15 |
| 926 | T926R | 1.32 |
| 927 | W927P | 1.40 |
| 928 | D928A | 1.27 |
| 928 | D928H | 1.13 |
| 928 | D928Q | 1.21 |
| 929 | A929P | 1.31 |
| 930 | V930E | 1.15 |
| 930 | V930I | 1.22 |
| 930 | V930T | 1.11 |
| 931 | S931P | 1.11 |
| 931 | S931R | 1.30 |
| 933 | D933R | 1.33 |
| 934 | Q934S | 1.56 |
| 934 | Q934V | 1.30 |
| 935 | I935A | 1.30 |
| 935 | I935C | 1.32 |
| 935 | I935D | 1.15 |
| 935 | I935E | 1.40 |
| 935 | I935L | 1.19 |
| 935 | I935P | 1.54 |
| 935 | I935V | 1.20 |
| 935 | I935W | 1.32 |
| 936 | A936I | 1.39 |
| 936 | A936L | 1.11 |
| 936 | A936Q | 1.54 |
| 936 | A936R | 1.13 |
| 936 | A936Y | 1.26 |
| 937 | K937G | 1.34 |
| 937 | K937I | 1.64 |
| 937 | K937M | 1.28 |
| 937 | K937P | 1.55 |
| 937 | K937Q | 1.32 |
| 938 | A938C | 1.46 |
| 938 | A938H | 1.18 |
| 938 | A938N | 1.15 |
| 938 | A938T | 1.21 |
| 938 | A938V | 1.14 |
| 938 | A938W | 1.15 |
| 939 | G939D | 1.30 |
| 939 | G939K | 1.17 |
| 940 | S940C | 1.34 |
| 940 | S940E | 1.26 |
| 940 | S940R | 1.21 |
| 940 | S940V | 1.25 |
| 941 | F941C | 1.32 |
| 941 | F941M | 1.17 |
| 942 | S942A | 1.19 |
| 942 | S942E | 1.20 |
| 942 | S942K | 1.46 |
| 942 | S942P | 1.17 |
| 942 | S942V | 1.41 |
| 943 | V943A | 1.60 |
| 943 | V943G | 1.20 |
| 943 | V943Q | 1.19 |
| 946 | T946A | 1.23 |
| 946 | T946L | 1.13 |
| 946 | T946P | 1.44 |
| 946 | T946W | 1.25 |
| 947 | V947G | 1.46 |
| 947 | V947L | 1.26 |
| 947 | V947P | 1.28 |
| 947 | V947R | 1.37 |
| 947 | V947T | 1.36 |
| 948 | A948I | 1.21 |
| 948 | A948W | 1.36 |
| 949 | G949A | 1.24 |
| 949 | G949V | 1.11 |
| 950 | Q950K | 1.15 |
| 950 | Q950W | 1.16 |
| 951 | K951D | 1.30 |
| 951 | K951G | 1.19 |
| 951 | K951P | 1.18 |
| 951 | K951S | 1.36 |
| 951 | K951W | 1.23 |
| 951 | K951Y | 1.21 |
| 952 | I952Q | 1.15 |
| 953 | S953F | 1.22 |
| 953 | S953M | 1.37 |
| 953 | S953N | 1.15 |
| 953 | S953R | 1.29 |
| 954 | V954D | 1.23 |
| 954 | V954Q | 1.29 |
| 955 | R955A | 1.12 |
| 955 | R955C | 1.36 |
| 955 | R955K | 1.18 |
| 955 | R955Q | 1.19 |
| 955 | R955W | 1.35 |
| 956 | V956A | 1.13 |
| 956 | V956D | 1.31 |
| 956 | V956G | 1.12 |
| 956 | V956H | 1.13 |
| 956 | V956I | 1.17 |
| 956 | V956M | 1.18 |
| 956 | V956Q | 1.57 |
| 956 | V956W | 1.19 |
| 957 | T957D | 1.12 |
| 957 | T957S | 1.21 |
| 957 | T957W | 1.17 |
| 959 | I959A | 1.20 |
| 959 | I959L | 1.14 |
| 959 | I959S | 1.20 |
| 959 | I959V | 1.20 |
| 959 | I959Y | 1.30 |
| 960 | D960P | 1.13 |
| 960 | D960S | 1.25 |
| 961 | E961D | 1.52 |
| 961 | E961F | 1.91 |
| 961 | E961K | 1.18 |
| 961 | E961S | 1.53 |
| 961 | E961T | 1.21 |
| 962 | I962A | 1.25 |
| 962 | I962C | 1.44 |
| 962 | I962D | 1.11 |
| 962 | I962G | 1.13 |
| 962 | I962K | 1.32 |
| 962 | I962N | 1.43 |
| 963 | G963C | 1.18 |
| 963 | G963E | 1.12 |
| 963 | G963P | 1.12 |
| 965 | L965C | 1.55 |
| 965 | L965E | 1.16 |
| 965 | L965G | 1.50 |
| 965 | L965K | 1.32 |
| 965 | L965M | 1.56 |
| 965 | L965P | 1.50 |
| 965 | L965Q | 1.19 |
| 965 | L965S | 1.13 |
| 965 | L965V | 1.27 |
| 965 | L965Y | 1.53 |
| 966 | L966A | 1.46 |

TABLE 1-continued

Variants having a GI-IF of at least 1.1

| Position | Mutation | GI-IF |
|---|---|---|
| 966 | L966K | 1.13 |
| 966 | L966N | 1.28 |
| 966 | L966Q | 1.16 |
| 966 | L966S | 1.13 |
| 966 | L966V | 1.10 |
| 967 | N967D | 1.28 |
| 967 | N967I | 1.17 |
| 967 | N967L | 1.13 |
| 967 | N967M | 1.33 |
| 967 | N967P | 1.27 |
| 967 | N967T | 1.23 |
| 967 | N967V | 1.15 |
| 968 | Y968G | 1.52 |
| 968 | Y968L | 1.30 |
| 968 | Y968Q | 1.33 |
| 968 | Y968V | 1.48 |
| 969 | S969C | 1.42 |
| 969 | S969D | 1.23 |
| 969 | S969G | 1.19 |
| 969 | S969H | 1.30 |
| 969 | S969I | 1.67 |
| 969 | S969L | 1.39 |
| 969 | S969M | 1.72 |
| 969 | S969P | 1.18 |
| 969 | S969Q | 1.36 |
| 969 | S969Y | 1.27 |
| 970 | A970I | 1.32 |
| 970 | A970L | 1.17 |
| 971 | S971G | 1.15 |
| 971 | S971V | 1.30 |
| 971 | S971W | 1.30 |
| 973 | P973C | 1.74 |
| 973 | P973D | 1.22 |
| 973 | P973K | 1.19 |
| 973 | P973N | 1.23 |
| 973 | P973Q | 1.13 |
| 973 | P973R | 1.26 |
| 973 | P973V | 1.10 |
| 973 | P973W | 1.38 |
| 973 | P973Y | 1.10 |
| 974 | V974C | 1.14 |
| 974 | V974E | 1.23 |
| 974 | V974G | 1.16 |
| 974 | V974N | 1.11 |
| 974 | V974T | 1.35 |
| 974 | V974Y | 1.23 |
| 975 | G975F | 1.11 |
| 975 | G975K | 1.19 |
| 976 | T976D | 1.11 |
| 976 | T976F | 1.21 |
| 976 | T976G | 1.25 |
| 976 | T976K | 1.45 |
| 976 | T976L | 1.11 |
| 976 | T976P | 1.41 |
| 976 | T976S | 1.11 |
| 977 | P977C | 1.35 |
| 977 | P977K | 1.16 |
| 977 | P977R | 1.16 |
| 977 | P977T | 1.49 |
| 977 | P977Y | 1.23 |
| 978 | A978F | 1.31 |
| 978 | A978G | 1.11 |
| 978 | A978M | 1.42 |
| 978 | A978N | 1.27 |
| 978 | A978R | 1.27 |
| 978 | A978S | 1.16 |
| 978 | A978Y | 1.17 |
| 979 | V979G | 1.11 |
| 979 | V979N | 1.14 |
| 979 | V979Y | 1.16 |
| 980 | L980A | 1.28 |
| 980 | L980F | 1.15 |
| 980 | L980H | 1.44 |
| 980 | L980I | 1.29 |
| 980 | L980K | 1.13 |
| 980 | L980N | 1.46 |
| 980 | L980Q | 1.30 |
| 980 | L980T | 1.28 |
| 980 | L980Y | 1.15 |
| 981 | P981L | 1.13 |
| 981 | P981M | 1.55 |
| 984 | R984P | 1.13 |
| 985 | P985F | 1.12 |
| 985 | P985H | 1.13 |
| 985 | P985K | 1.14 |
| 985 | P985L | 2.25 |
| 985 | P985W | 1.49 |
| 986 | A986C | 1.15 |
| 986 | A986I | 1.88 |
| 986 | A986L | 1.38 |
| 986 | A986M | 1.17 |
| 986 | A986W | 1.30 |
| 987 | V987A | 1.31 |
| 987 | V987C | 1.18 |
| 987 | V987F | 1.31 |
| 987 | V987K | 1.43 |
| 988 | L988V | 1.13 |
| 989 | P989M | 1.23 |
| 989 | P989W | 1.12 |
| 990 | D990F | 1.11 |
| 990 | D990P | 1.18 |
| 990 | D990W | 1.50 |
| 991 | G991C | 1.18 |
| 991 | G991F | 1.23 |
| 991 | G991H | 1.25 |
| 991 | G991K | 1.15 |
| 991 | G991P | 1.17 |
| 991 | G991Y | 1.38 |
| 992 | T992M | 1.29 |
| 992 | T992N | 1.11 |
| 993 | V993G | 1.14 |
| 995 | S995E | 1.15 |
| 995 | S995L | 1.41 |
| 995 | S995R | 1.18 |
| 996 | A996R | 1.16 |
| 997 | N997K | 1.44 |
| 997 | N997V | 1.15 |
| 998 | F998M | 1.25 |
| 998 | F998W | 1.21 |
| 1000 | V1000W | 1.20 |
| 1001 | D1001L | 1.45 |
| 1001 | D1001S | 1.20 |
| 1002 | W1002A | 1.61 |
| 1002 | W1002D | 1.72 |
| 1002 | W1002E | 1.30 |
| 1002 | W1002H | 1.42 |
| 1002 | W1002N | 1.77 |
| 1002 | W1002P | 1.66 |
| 1002 | W1002Q | 1.32 |
| 1002 | W1002S | 1.20 |
| 1003 | T1003F | 1.17 |
| 1003 | T1003G | 1.20 |
| 1003 | T1003N | 1.15 |
| 1003 | T1003R | 1.19 |
| 1003 | T1003S | 1.17 |
| 1003 | T1003W | 1.13 |
| 1003 | T1003Y | 1.40 |
| 1004 | K1004D | 1.15 |
| 1004 | K1004E | 1.13 |
| 1004 | K1004S | 1.16 |
| 1005 | P1005I | 1.20 |
| 1005 | P1005N | 1.11 |
| 1005 | P1005V | 1.19 |
| 1005 | P1005Y | 1.31 |
| 1006 | A1006C | 1.31 |
| 1006 | A1006N | 1.11 |
| 1006 | A1006P | 1.13 |
| 1006 | A1006S | 2.01 |
| 1006 | A1006V | 1.10 |
| 1006 | A1006W | 1.17 |
| 1006 | A1006Y | 1.16 |
| 1007 | D1007C | 1.16 |

TABLE 1-continued

Variants having a GI-IF of at least 1.1

| Position | Mutation | GI-IF |
|---|---|---|
| 1007 | D1007L | 1.24 |
| 1007 | D1007P | 1.61 |
| 1007 | D1007V | 1.21 |
| 1008 | T1008G | 1.19 |
| 1010 | Y1010A | 1.15 |
| 1010 | Y1010P | 1.10 |
| 1010 | Y1010R | 1.10 |
| 1010 | Y1010T | 1.21 |
| 1011 | N1011A | 1.20 |
| 1011 | N1011S | 1.10 |
| 1011 | N1011T | 1.35 |
| 1011 | N1011W | 1.11 |
| 1012 | T1012H | 1.11 |
| 1012 | T1012I | 1.17 |
| 1012 | T1012Q | 1.31 |
| 1013 | A1013D | 1.18 |
| 1013 | A1013Q | 1.28 |
| 1013 | A1013V | 1.24 |
| 1014 | G1014I | 1.35 |
| 1014 | G1014M | 1.13 |
| 1014 | G1014V | 1.18 |
| 1014 | G1014W | 1.17 |
| 1015 | T1015A | 1.11 |
| 1016 | V1016D | 1.21 |
| 1016 | V1016P | 1.10 |
| 1017 | K1017E | 1.11 |
| 1017 | K1017G | 1.12 |
| 1018 | V1018K | 1.48 |
| 1018 | V1018L | 1.18 |
| 1018 | V1018R | 1.11 |
| 1018 | V1018S | 1.12 |
| 1021 | T1021C | 1.10 |
| 1021 | T1021E | 1.11 |
| 1021 | T1021G | 1.24 |
| 1022 | A1022H | 1.41 |
| 1024 | V1024G | 1.40 |
| 1024 | V1024H | 1.35 |
| 1024 | V1024K | 1.27 |
| 1024 | V1024R | 1.24 |
| 1024 | V1024S | 1.20 |
| 1024 | V1024W | 1.25 |
| 1026 | G1026E | 1.14 |
| 1026 | G1026S | 1.30 |
| 1026 | G1026V | 1.32 |
| 1026 | G1026Y | 1.18 |
| 1027 | K1027Q | 1.13 |
| 1027 | K1027R | 1.13 |
| 1028 | E1028G | 1.10 |
| 1028 | E1028T | 1.11 |
| 1029 | F1029I | 1.10 |
| 1029 | F1029K | 1.20 |
| 1029 | F1029P | 1.21 |
| 1029 | F1029V | 1.22 |
| 1030 | K1030D | 1.36 |
| 1030 | K1030H | 1.14 |
| 1030 | K1030M | 1.20 |
| 1030 | K1030W | 1.59 |
| 1031 | V1031H | 1.29 |
| 1031 | V1031K | 1.27 |
| 1033 | A1033V | 1.15 |
| 1034 | T1034G | 1.14 |
| 1034 | T1034H | 1.23 |
| 1034 | T1034N | 1.14 |
| 1035 | I1035D | 1.51 |
| 1035 | I1035G | 1.10 |
| 1035 | I1035Q | 1.13 |
| 1036 | R1036G | 1.21 |
| 1036 | R1036L | 1.23 |
| 1036 | R1036T | 1.29 |
| 1036 | R1036Y | 1.11 |
| 1037 | V1037C | 1.11 |
| 1038 | Q1038D | 1.16 |
| 1039 | R1039V | 1.11 |
| 1040 | S1040M | 1.14 |
| 1041 | Q1041P | 1.33 |
| 1042 | V1042N | 1.32 |
| 1043 | T1043F | 1.22 |
| 1043 | T1043G | 1.16 |
| 1043 | T1043R | 1.17 |
| 1044 | I1044A | 1.30 |
| 1044 | I1044L | 1.18 |
| 1046 | S1046M | 1.27 |
| 1048 | V1048C | 1.31 |
| 1048 | V1048F | 1.21 |
| 1048 | V1048G | 1.38 |
| 1048 | V1048I | 1.19 |
| 1048 | V1048M | 1.46 |
| 1048 | V1048Q | 1.60 |
| 1051 | N1051A | 1.10 |
| 1051 | N1051E | 2.06 |
| 1051 | N1051K | 1.33 |
| 1052 | A1052C | 1.10 |
| 1052 | A1052K | 1.42 |
| 1052 | A1052R | 1.18 |
| 1053 | L1053A | 1.57 |
| 1053 | L1053W | 1.26 |
| 1054 | R1054C | 1.17 |
| 1054 | R1054L | 1.14 |
| 1055 | L1055R | 1.21 |
| 1055 | L1055T | 1.19 |
| 1057 | Q1057A | 1.16 |
| 1057 | Q1057E | 1.48 |
| 1057 | Q1057P | 1.14 |
| 1058 | N1058R | 1.26 |
| 1058 | N1058S | 1.24 |
| 1060 | P1060G | 1.29 |
| 1060 | P1060N | 1.23 |
| 1060 | P1060Q | 1.14 |
| 1061 | A1061G | 1.33 |
| 1061 | A1061K | 1.17 |
| 1061 | A1061W | 1.15 |
| 1062 | D1062A | 1.21 |
| 1062 | D1062G | 1.16 |
| 1062 | D1062I | 1.17 |
| 1062 | D1062M | 1.32 |
| 1063 | K1063M | 1.14 |
| 1064 | Q1064M | 1.34 |
| 1064 | Q1064R | 1.22 |
| 1064 | Q1064T | 1.10 |
| 1064 | Q1064V | 1.19 |
| 1065 | S1065A | 1.38 |
| 1065 | S1065C | 1.23 |
| 1066 | D1066A | 1.30 |
| 1066 | D1066G | 1.28 |
| 1066 | D1066V | 1.34 |
| 1067 | T1067G | 1.19 |
| 1067 | T1067M | 1.35 |
| 1068 | L1068P | 1.38 |
| 1068 | L1068Q | 1.29 |
| 1068 | L1068Y | 1.15 |
| 1069 | D1069R | 1.10 |
| 1070 | A1070T | 1.15 |
| 1071 | I1071M | 1.13 |
| 1072 | K1072P | 1.15 |
| 1072 | K1072S | 1.34 |
| 1073 | D1073F | 1.17 |
| 1073 | D1073W | 1.18 |
| 1074 | G1074L | 1.36 |
| 1074 | G1074R | 1.23 |
| 1075 | S1075G | 1.15 |
| 1075 | S1075L | 1.25 |
| 1076 | T1076E | 1.11 |
| 1076 | T1076S | 1.29 |
| 1077 | T1077R | 1.17 |
| 1078 | V1078D | 1.10 |
| 1078 | V1078W | 1.10 |
| 1079 | D1079G | 1.13 |
| 1079 | D1079L | 1.14 |
| 1081 | N1081E | 1.12 |
| 1082 | T1082E | 1.21 |
| 1082 | T1082F | 1.42 |
| 1082 | T1082G | 1.11 |

TABLE 1-continued

Variants having a GI-IF of at least 1.1

| Position | Mutation | GI-IF |
|---|---|---|
| 1082 | T1082K | 1.12 |
| 1083 | G1083E | 1.41 |
| 1083 | G1083F | 1.31 |
| 1083 | G1083L | 1.35 |
| 1084 | G1084M | 1.11 |
| 1084 | G1084V | 1.73 |
| 1084 | G1084W | 1.18 |
| 1084 | G1084Y | 1.25 |
| 1085 | G1085P | 1.13 |
| 1085 | G1085R | 1.12 |
| 1085 | G1085S | 1.77 |
| 1086 | A1086H | 1.25 |
| 1086 | A1086K | 1.17 |
| 1086 | A1086R | 1.13 |
| 1087 | N1087A | 1.12 |
| 1087 | N1087E | 1.14 |
| 1087 | N1087I | 1.17 |
| 1087 | N1087R | 1.25 |
| 1088 | P1088D | 1.18 |
| 1088 | P1088E | 1.47 |
| 1088 | P1088G | 1.12 |
| 1088 | P1088R | 1.40 |
| 1088 | P1088W | 1.10 |
| 1089 | S1089G | 1.30 |
| 1089 | S1089K | 1.23 |
| 1089 | S1089Q | 1.58 |
| 1089 | S1089V | 1.15 |
| 1090 | A1090F | 1.12 |
| 1091 | W1091Y | 1.33 |
| 1093 | N1093A | 1.35 |
| 1093 | N1093G | 1.10 |
| 1093 | N1093L | 1.17 |
| 1093 | N1093P | 2.25 |
| 1093 | N1093Q | 1.40 |
| 1094 | W1094D | 1.62 |
| 1094 | W1094E | 1.51 |
| 1094 | W1094P | 1.27 |
| 1094 | W1094R | 1.13 |
| 1094 | W1094T | 1.11 |
| 1095 | A1095P | 1.12 |
| 1095 | A1095T | 1.17 |
| 1095 | A1095W | 1.22 |
| 1096 | Y1096D | 1.26 |
| 1096 | Y1096L | 1.12 |
| 1097 | S1097E | 1.15 |
| 1097 | S1097K | 1.13 |
| 1097 | S1097T | 1.28 |
| 1098 | K1098D | 1.31 |
| 1098 | K1098F | 1.24 |
| 1098 | K1098G | 1.14 |
| 1098 | K1098Q | 1.19 |
| 1098 | K1098S | 1.11 |
| 1099 | A1099D | 1.26 |
| 1099 | A1099S | 1.21 |
| 1099 | A1099V | 1.40 |
| 1099 | A1099W | 1.12 |
| 1100 | G1100E | 1.15 |
| 1100 | G1100H | 1.30 |
| 1100 | G1100N | 1.18 |
| 1101 | H1101K | 1.11 |
| 1101 | H1101Q | 1.17 |
| 1101 | H1101R | 1.12 |
| 1101 | H1101V | 1.38 |
| 1102 | N1102H | 1.66 |
| 1102 | N1102Q | 1.15 |
| 1102 | N1102T | 1.19 |
| 1103 | T1103A | 1.15 |
| 1103 | T1103E | 1.30 |
| 1103 | T1103S | 1.15 |
| 1103 | T1103W | 1.11 |
| 1105 | E1105L | 1.27 |
| 1105 | E1105S | 1.15 |
| 1109 | E1109A | 1.32 |
| 1109 | E1109D | 1.74 |
| 1109 | E1109L | 1.71 |
| 1109 | E1109W | 1.47 |

TABLE 1-continued

Variants having a GI-IF of at least 1.1

| Position | Mutation | GI-IF |
|---|---|---|
| 1111 | A1111G | 1.42 |
| 1111 | A1111S | 1.16 |
| 1113 | E1113G | 1.14 |
| 1113 | E1113P | 1.61 |
| 1113 | E1113V | 1.34 |
| 1114 | Q1114E | 1.34 |
| 1114 | Q1114L | 1.16 |
| 1114 | Q11MR | 1.38 |
| 1114 | Q1114S | 1.69 |
| 1114 | Q1114T | 1.30 |
| 1114 | Q1114V | 1.79 |
| 1115 | Q1115A | 1.56 |
| 1115 | Q1115K | 1.48 |
| 1115 | Q1115L | 1.27 |
| 1115 | Q1115P | 1.22 |
| 1116 | L1116D | 1.14 |
| 1116 | L1116G | 1.26 |
| 1116 | L1116H | 1.16 |
| 1116 | L1116K | 2.13 |
| 1116 | L1116W | 1.55 |
| 1117 | G1117E | 1.29 |
| 1117 | G1117I | 1.47 |
| 1117 | G1117M | 1.27 |
| 1117 | G1117R | 1.37 |
| 1117 | G1117S | 1.58 |
| 1117 | G1117T | 1.51 |
| 1117 | G1117V | 1.83 |
| 1117 | G1117W | 2.52 |
| 1118 | Q1118M | 1.17 |
| 1118 | Q1118W | 1.20 |
| 1119 | I1119D | 1.10 |
| 1119 | I1119E | 1.22 |
| 1119 | I1119N | 1.50 |
| 1119 | I1119S | 1.21 |
| 1120 | V1120N | 1.14 |
| 1120 | V1120S | 1.12 |
| 1121 | M1121G | 1.37 |
| 1121 | M1121K | 1.24 |
| 1121 | M1121N | 1.19 |
| 1121 | M1121P | 1.19 |
| 1121 | M1121S | 1.17 |
| 1123 | F1123E | 1.14 |
| 1123 | F1123R | 1.28 |
| 1124 | F1124V | 1.21 |
| 1124 | F1124W | 1.23 |
| 1125 | R1125D | 1.25 |
| 1125 | R1125F | 1.12 |
| 1125 | R1125K | 1.21 |
| 1125 | R1125V | 1.87 |
| 1125 | R1125W | 1.68 |
| 1127 | S1127I | 1.30 |
| 1127 | S1127Q | 1.63 |
| 1128 | N1128A | 1.51 |
| 1129 | A1129E | 1.61 |
| 1129 | A1129R | 1.11 |
| 1130 | V1130A | 1.42 |
| 1130 | V1130R | 1.60 |
| 1131 | R1131W | 1.18 |
| 1132 | F1132M | 1.18 |
| 1132 | F1132P | 1.13 |
| 1132 | F1132Q | 1.18 |
| 1133 | P1133D | 1.45 |
| 1133 | P1133G | 1.21 |
| 1133 | P1133L | 1.14 |
| 1133 | P1133R | 1.72 |
| 1135 | A1135E | 1.15 |
| 1135 | A1135K | 1.14 |
| 1135 | A1135L | 1.35 |
| 1135 | A1135W | 1.35 |
| 1136 | G1136P | 1.31 |
| 1137 | K1137G | 1.12 |
| 1137 | K1137P | 1.21 |
| 1137 | K1137R | 1.45 |
| 1137 | K1137S | 1.70 |
| 1137 | K1137T | 1.14 |
| 1137 | K1137V | 1.16 |

TABLE 1-continued

Variants having a GI-IF of at least 1.1

| Position | Mutation | GI-IF |
|---|---|---|
| 1138 | T1138R | 1.25 |
| 1138 | T1138Y | 1.18 |
| 1140 | I1140C | 1.23 |
| 1140 | I1140P | 1.33 |
| 1140 | I1140R | 1.15 |
| 1141 | Q1141A | 1.15 |
| 1141 | Q1141G | 1.11 |
| 1141 | Q1141K | 1.33 |
| 1141 | Q1141N | 1.14 |
| 1141 | Q1141T | 1.10 |
| 1142 | I1142E | 1.19 |
| 1142 | I1142R | 1.19 |
| 1142 | I1142Y | 1.39 |
| 1143 | S1143G | 1.23 |
| 1144 | A1144D | 1.17 |
| 1144 | A1144N | 1.38 |
| 1144 | A1144P | 1.42 |
| 1144 | A1144S | 1.53 |
| 1144 | A1144T | 1.24 |
| 1144 | A1144V | 1.34 |
| 1144 | A1144W | 1.33 |
| 1145 | D1145E | 1.64 |
| 1145 | D1145R | 1.58 |
| 1145 | D1145T | 1.68 |
| 1146 | G1146A | 1.16 |
| 1146 | G1146K | 1.15 |
| 1146 | G1146R | 1.13 |
| 1146 | G1146V | 1.21 |
| 1148 | N1148H | 1.16 |
| 1148 | N1148I | 1.13 |
| 1148 | N1148P | 1.33 |
| 1148 | N1148Q | 1.16 |
| 1148 | N1148R | 1.16 |
| 1148 | N1148S | 1.18 |
| 1148 | N1148T | 1.11 |
| 1149 | W1149C | 1.35 |
| 1149 | W1149G | 1.28 |
| 1149 | W1149K | 1.17 |
| 1149 | W1149S | 1.27 |
| 1149 | W1149V | 1.39 |
| 1150 | T1150K | 1.58 |
| 1150 | T1150P | 1.11 |
| 1151 | D1151C | 1.17 |
| 1151 | D1151W | 1.53 |
| 1152 | L1152A | 1.20 |
| 1152 | L1152C | 1.10 |
| 1152 | L1152E | 1.21 |
| 1152 | L1152Q | 1.28 |
| 1152 | L1152W | 1.34 |
| 1153 | A1153E | 1.12 |
| 1153 | A1153G | 1.34 |
| 1153 | A1153L | 1.12 |
| 1154 | A1154D | 1.15 |
| 1154 | A1154E | 1.19 |
| 1154 | A1154R | 1.23 |
| 1158 | I1158S | 1.13 |
| 1158 | I1158W | 1.26 |
| 1159 | A1159E | 1.10 |
| 1159 | A1159I | 1.27 |
| 1161 | Q1161P | 1.24 |
| 1161 | Q1161S | 1.20 |
| 1162 | E1162A | 1.31 |
| 1162 | E1162C | 1.29 |
| 1162 | E1162Q | 1.23 |
| 1162 | E1162W | 1.12 |
| 1165 | E1165M | 1.19 |
| 1165 | E1165S | 1.21 |
| 1166 | R1166Q | 1.15 |
| 1167 | V1167A | 1.11 |
| 1167 | V1167R | 1.67 |
| 1168 | K1168L | 1.13 |
| 1168 | K1168R | 1.13 |
| 1169 | P1169M | 1.16 |
| 1169 | P1169S | 1.26 |
| 1170 | Y1170K | 1.22 |
| 1170 | Y1170M | 1.12 |
| 1170 | Y1170V | 1.16 |
| 1172 | Y1172H | 1.15 |
| 1172 | Y1172S | 1.11 |
| 1173 | D1173G | 1.16 |
| 1173 | D1173T | 1.18 |
| 1174 | F1174D | 1.13 |
| 1175 | A1175S | 1.26 |
| 1178 | G1178M | 1.85 |
| 1178 | G1178Q | 1.27 |
| 1178 | G1178S | 1.18 |
| 1178 | G1178T | 1.33 |
| 1179 | A1179L | 1.37 |
| 1179 | A1179Q | 1.17 |
| 1179 | A1179W | 2.03 |
| 1180 | T1180A | 1.45 |
| 1180 | T1180G | 1.53 |
| 1180 | T1180I | 1.56 |
| 1180 | T1180L | 1.15 |
| 1180 | T1180M | 1.56 |
| 1180 | T1180Q | 1.66 |
| 1180 | T1180S | 1.18 |
| 1180 | T1180Y | 1.41 |
| 1181 | F1181E | 1.19 |
| 1181 | F1181V | 1.12 |
| 1182 | V1182M | 1.26 |
| 1183 | K1183A | 1.14 |
| 1183 | K1183E | 1.22 |
| 1183 | K1183T | 1.16 |
| 1183 | K1183V | 1.12 |
| 1184 | V1184C | 1.28 |
| 1184 | V1184E | 1.87 |
| 1184 | V1184K | 1.28 |
| 1184 | V1184L | 1.73 |
| 1184 | V1184P | 1.65 |
| 1184 | V1184Q | 1.34 |
| 1184 | V1184Y | 1.32 |
| 1185 | T1185Q | 1.19 |
| 1185 | T1185V | 1.10 |
| 1186 | V1186S | 1.41 |
| 1188 | N1188V | 1.13 |
| 1188 | N1188W | 1.45 |
| 1189 | A1189C | 1.30 |
| 1189 | A1189K | 1.27 |
| 1189 | A1189T | 1.28 |
| 1189 | A1189V | 1.20 |
| 1190 | D1190R | 1.22 |
| 1190 | D1190T | 1.39 |
| 1190 | D1190Y | 1.11 |
| 1191 | T1191L | 1.32 |
| 1193 | T1193G | 1.10 |
| 1194 | P1194E | 1.11 |
| 1194 | P1194W | 1.14 |
| 1197 | V1197A | 1.35 |
| 1199 | C1199D | 1.17 |
| 1200 | A1200G | 1.20 |
| 1203 | T1203K | 1.25 |
| 1204 | E1204G | 1.39 |
| 1204 | E1204S | 1.11 |
| 1205 | I1205V | 1.21 |
| 1208 | K1208R | 1.23 |
| 1208 | K1208V | 1.29 |
| 1208 | K1208W | 1.57 |
| 1209 | T1209A | 1.25 |
| 1209 | T1209C | 1.27 |
| 1209 | T1209E | 1.48 |
| 1209 | T1209K | 1.45 |
| 1209 | T1209N | 1.21 |
| 1209 | T1209Q | 1.20 |
| 1209 | T1209R | 1.18 |
| 1209 | T1209W | 1.16 |
| 1210 | A1210D | 1.59 |
| 1210 | A1210G | 1.73 |
| 1210 | A1210K | 1.39 |
| 1210 | A1210L | 1.34 |
| 1210 | A1210Q | 1.14 |
| 1210 | A1210R | 1.53 |

TABLE 1-continued

Variants having a GI-IF of at least 1.1

| Position | Mutation | GI-IF |
|---|---|---|
| 1210 | A1210T | 1.94 |
| 1210 | A1210W | 1.40 |
| 1211 | T1211C | 1.12 |
| 1211 | T1211D | 1.24 |
| 1211 | T1211E | 1.18 |
| 1211 | T1211G | 1.84 |
| 1211 | T1211H | 1.11 |
| 1211 | T1211K | 1.35 |
| 1211 | T1211P | 1.92 |
| 1211 | T1211Q | 1.16 |
| 1211 | T1211R | 1.44 |
| 1211 | T1211S | 1.30 |
| 1211 | T1211V | 1.18 |
| 1213 | K1213A | 1.13 |
| 1213 | K1213D | 1.12 |
| 1213 | K1213S | 1.14 |
| 1213 | K1213T | 1.22 |
| 1214 | F1214A | 1.54 |
| 1214 | F1214E | 1.25 |
| 1214 | F1214K | 1.73 |
| 1214 | F1214L | 1.25 |
| 1214 | F1214P | 1.27 |
| 1214 | F1214S | 1.31 |
| 1214 | F1214V | 1.65 |
| 1215 | V1215D | 1.44 |
| 1215 | V1215E | 1.12 |
| 1215 | V1215L | 1.36 |
| 1215 | V1215Q | 1.23 |
| 1215 | V1215W | 1.13 |
| 1216 | T1216A | 1.24 |
| 1216 | T1216L | 1.55 |
| 1216 | T1216P | 1.28 |
| 1216 | T1216Q | 1.75 |
| 1216 | T1216R | 1.13 |
| 1217 | N1217A | 1.42 |
| 1217 | N1217E | 1.14 |
| 1217 | N1217P | 1.28 |
| 1217 | N1217R | 1.22 |
| 1217 | N1217S | 1.31 |
| 1217 | N1217T | 1.32 |
| 1218 | T1218A | 1.27 |
| 1218 | T1218C | 1.34 |
| 1218 | T1218E | 1.40 |
| 1218 | T1218G | 1.20 |
| 1218 | T1218Q | 1.10 |
| 1218 | T1218S | 1.31 |
| 1218 | T1218V | 1.16 |
| 1218 | T1218W | 1.45 |
| 1219 | S1219I | 1.21 |
| 1219 | S1219K | 1.20 |
| 1219 | S1219R | 1.26 |
| 1219 | S1219V | 1.10 |
| 1220 | A1220C | 1.19 |
| 1220 | A1220G | 1.20 |
| 1220 | A1220P | 1.26 |
| 1221 | A1221K | 1.19 |
| 1221 | A1221R | 1.21 |
| 1221 | A1221V | 1.20 |
| 1221 | A1221W | 1.24 |
| 1222 | L1222A | 1.34 |
| 1222 | L1222E | 1.38 |
| 1222 | L1222F | 1.43 |
| 1222 | L1222Q | 1.17 |
| 1222 | L1222R | 1.17 |
| 1222 | L1222V | 1.71 |
| 1222 | L1222W | 1.27 |
| 1224 | S1224P | 1.51 |
| 1224 | S1224W | 1.47 |
| 1225 | L1225E | 1.66 |
| 1225 | L1225K | 1.84 |
| 1225 | L1225V | 1.18 |
| 1226 | T1226P | 1.76 |
| 1227 | V1227C | 1.10 |
| 1227 | V1227D | 1.28 |
| 1227 | V1227P | 1.29 |
| 1227 | V1227Q | 1.14 |
| 1229 | G1229C | 1.15 |
| 1229 | G1229E | 1.13 |
| 1229 | G1229V | 1.57 |
| 1230 | T1230H | 1.22 |
| 1230 | T1230K | 1.47 |
| 1230 | T1230W | 1.73 |
| 1231 | K1231G | 1.18 |
| 1232 | V1232E | 1.11 |
| 1232 | V1232Q | 1.15 |
| 1232 | V1232R | 1.39 |
| 1234 | D1234V | 1.19 |
| 1235 | S1235D | 1.20 |
| 1235 | S1235E | 1.23 |
| 1235 | S1235G | 1.27 |
| 1235 | S1235P | 1.12 |
| 1235 | S1235R | 1.20 |
| 1235 | S1235W | 1.31 |
| 1235 | S1235Y | 1.12 |
| 1236 | V1236A | 1.32 |
| 1236 | V1236C | 1.11 |
| 1236 | V1236G | 1.35 |
| 1236 | V1236P | 1.34 |
| 1236 | V1236Q | 1.21 |
| 1237 | L1237V | 1.14 |
| 1238 | A1238D | 1.10 |
| 1238 | A1238E | 1.95 |
| 1238 | A1238L | 1.22 |
| 1238 | A1238R | 1.41 |
| 1239 | A1239W | 1.22 |
| 1240 | G1240D | 1.20 |
| 1240 | G1240Q | 1.13 |
| 1243 | N1243C | 1.20 |
| 1247 | I1247R | 1.28 |
| 1255 | G1255H | 1.30 |
| 1259 | A1259K | 1.58 |
| 1261 | V1261R | 1.15 |
| 1262 | T1262F | 1.19 |
| 1262 | T1262M | 1.11 |
| 1262 | T1262R | 1.33 |
| 1263 | V1263T | 1.40 |
| 1264 | L1264H | 1.22 |
| 1264 | L1264R | 1.12 |
| 1265 | P1265W | 1.93 |
| 1273 | V1273R | 1.26 |
| 1274 | I1274F | 1.91 |
| 1274 | I1274R | 1.63 |
| 1275 | T1275A | 1.11 |
| 1275 | T1275W | 1.98 |
| 1276 | E1276R | 1.12 |
| 1277 | S1277L | 1.36 |
| 1277 | S1277T | 1.32 |
| 1277 | S1277W | 1.97 |
| 1278 | E1278Q | 1.78 |
| 1278 | E1278R | 1.20 |
| 1279 | D1279I | 1.25 |
| 1279 | D1279R | 1.63 |
| 1279 | D1279W | 1.78 |
| 1280 | H1280C | 1.19 |
| 1280 | H1280E | 1.48 |
| 1280 | H1280G | 1.25 |
| 1281 | V1281I | 1.74 |
| 1281 | V1281W | 1.52 |
| 1284 | K1284G | 2.25 |
| 1285 | T1285A | 1.16 |
| 1285 | T1285M | 1.11 |
| 1286 | F1286A | 1.27 |
| 1286 | F1286E | 1.60 |
| 1286 | F1286P | 1.32 |
| 1286 | F1286R | 1.11 |
| 1287 | T1287C | 3.44 |
| 1287 | T1287L | 1.15 |
| 1287 | T1287S | 1.31 |
| 1287 | T1287W | 1.76 |
| 1288 | U288A | 1.85 |
| 1288 | I1288D | 2.34 |
| 1288 | I1288G | 1.52 |

TABLE 1-continued

| Variants having a GI-IF of at least 1.1 | | |
|---|---|---|
| Position | Mutation | GI-IF |
| 1288 | I1288K | 1.60 |
| 1293 | E1293K | 1.27 |
| 1293 | E1293L | 1.22 |
| 1294 | Q1294E | 1.25 |
| 1295 | E1295K | 1.36 |
| 1296 | F1296A | 1.37 |
| 1302 | E1302G | 1.15 |
| 1302 | E1302R | 2.50 |
| 1302 | E1302S | 2.76 |
| 1303 | R1303S | 1.27 |
| 1304 | D1304V | 1.51 |

TABLE 2

| Variants having a GI-IF of at most 0.9 | | |
|---|---|---|
| Position | Mutation | GI-IF |
| 3 | D3H | 0.90 |
| 3 | D3S | 0.55 |
| 3 | D3W | 0.62 |
| 4 | A4C | 0.85 |
| 4 | A4G | 0.85 |
| 4 | A4I | 0.80 |
| 4 | A4L | 0.80 |
| 4 | A4M | 0.90 |
| 4 | A4P | 0.85 |
| 5 | T5D | 0.78 |
| 5 | T5F | 0.89 |
| 5 | T5K | 0.86 |
| 5 | T5R | 0.89 |
| 5 | T5V | 0.81 |
| 6 | R6A | 0.76 |
| 6 | R6D | 0.82 |
| 6 | R6F | 0.73 |
| 6 | R6M | 0.68 |
| 6 | R6P | 0.65 |
| 6 | R6S | 0.89 |
| 7 | S7A | 0.82 |
| 7 | S7D | 0.69 |
| 7 | S7I | 0.79 |
| 7 | S7W | 0.86 |
| 9 | S9P | 0.76 |
| 9 | S9R | 0.89 |
| 10 | T10G | 0.84 |
| 10 | T10P | 0.71 |
| 10 | T10R | 0.89 |
| 10 | T10W | 0.86 |
| 11 | T11L | 0.78 |
| 11 | T11P | 0.76 |
| 12 | Q12L | 0.88 |
| 12 | Q12R | 0.76 |
| 12 | Q12Y | 0.88 |
| 13 | M13F | 0.65 |
| 14 | S14A | 0.83 |
| 14 | S14L | 0.84 |
| 15 | S15Y | 0.42 |
| 16 | T16A | 0.86 |
| 16 | T16N | 0.83 |
| 16 | T16S | 0.80 |
| 17 | P17C | 0.84 |
| 17 | P17D | 0.64 |
| 17 | P17E | 0.86 |
| 17 | P17L | 0.65 |
| 17 | P17N | 0.81 |
| 17 | P17R | 0.90 |
| 17 | P17T | 0.74 |
| 19 | V19G | 0.64 |
| 19 | V19W | 0.82 |
| 20 | V20K | 0.74 |
| 20 | V20N | 0.89 |
| 20 | V20W | 0.79 |
| 21 | Y21F | 0.88 |

TABLE 2-continued

| Variants having a GI-IF of at most 0.9 | | |
|---|---|---|
| Position | Mutation | GI-IF |
| 22 | S22E | 0.77 |
| 22 | S22F | 0.89 |
| 22 | S22G | 0.74 |
| 22 | S22L | 0.82 |
| 22 | S22M | 0.84 |
| 23 | S23C | 0.80 |
| 23 | S23D | 0.86 |
| 23 | S23L | 0.56 |
| 23 | S23M | 0.58 |
| 23 | S23R | 0.74 |
| 24 | A24G | 0.89 |
| 25 | V25H | 0.86 |
| 25 | V25K | 0.68 |
| 25 | V25L | 0.88 |
| 25 | V25R | 0.88 |
| 26 | D26T | 0.90 |
| 27 | S27F | 0.80 |
| 29 | Q29D | 0.84 |
| 29 | Q29V | 0.62 |
| 29 | Q29W | 0.78 |
| 30 | N30A | 0.72 |
| 30 | N30G | 0.89 |
| 30 | N30H | 0.89 |
| 30 | N30P | 0.85 |
| 31 | R31G | 0.74 |
| 31 | R31I | 0.72 |
| 32 | T32M | 0.88 |
| 32 | T32R | 0.81 |
| 33 | S33C | 0.64 |
| 33 | S33E | 0.85 |
| 33 | S33H | 0.90 |
| 33 | S33N | 0.77 |
| 33 | S33Q | 0.66 |
| 33 | S33R | 0.66 |
| 33 | S33V | 0.88 |
| 34 | D34C | 0.73 |
| 34 | D34E | 0.79 |
| 34 | D34L | 0.76 |
| 34 | D34S | 0.55 |
| 34 | D34W | 0.78 |
| 34 | D34Y | 0.67 |
| 35 | F35E | 0.59 |
| 35 | F35K | 0.75 |
| 35 | F35N | 0.69 |
| 35 | F35T | 0.85 |
| 36 | D36H | 0.89 |
| 37 | A37Q | 0.81 |
| 38 | N38C | 0.84 |
| 38 | N38G | 0.83 |
| 40 | K40D | 0.74 |
| 40 | K40N | 0.78 |
| 41 | F41G | 0.64 |
| 41 | F41I | 0.78 |
| 41 | F41Q | 0.73 |
| 41 | F41S | 0.88 |
| 41 | F41Y | 0.81 |
| 42 | M42E | 0.60 |
| 42 | M42N | 0.79 |
| 43 | L43C | 0.64 |
| 43 | L43T | 0.58 |
| 43 | L43V | 0.69 |
| 44 | S44C | 0.76 |
| 44 | S44N | 0.83 |
| 44 | S44Y | 0.82 |
| 45 | D45A | 0.70 |
| 48 | Q48S | 0.90 |
| 49 | A49R | 0.31 |
| 49 | A49S | 0.74 |
| 49 | A49V | 0.78 |
| 51 | D51P | 0.57 |
| 51 | D51V | 0.69 |
| 53 | A53C | 0.79 |
| 53 | A53L | 0.84 |
| 53 | A53R | 0.77 |
| 53 | A53S | 0.60 |
| 53 | A53T | 0.83 |

TABLE 2-continued

Variants having a GI-IF of at most 0.9

| Position | Mutation | GI-IF |
|---|---|---|
| 53 | A53V | 0.71 |
| 53 | A53W | 0.74 |
| 54 | F54M | 0.81 |
| 54 | F54S | 0.80 |
| 58 | A58D | 0.73 |
| 58 | A58G | 0.65 |
| 58 | A58M | 0.84 |
| 60 | Q60A | 0.89 |
| 60 | Q60C | 0.82 |
| 60 | Q60K | 0.61 |
| 61 | Q61K | 0.87 |
| 61 | Q61S | 0.85 |
| 62 | V62S | 0.68 |
| 63 | D63P | 0.84 |
| 63 | D63V | 0.81 |
| 66 | H66C | 0.90 |
| 66 | H66L | 0.74 |
| 66 | H66W | 0.85 |
| 66 | H66Y | 0.44 |
| 67 | D67E | 0.81 |
| 68 | Y68P | 0.68 |
| 68 | Y68V | 0.84 |
| 70 | I70A | 0.74 |
| 71 | T71C | 0.71 |
| 71 | T71E | 0.82 |
| 71 | T71G | 0.80 |
| 71 | T71K | 0.77 |
| 71 | T71N | 0.88 |
| 71 | T71Q | 0.79 |
| 73 | K73F | 0.82 |
| 74 | Y74T | 0.85 |
| 74 | Y74W | 0.80 |
| 76 | Q76K | 0.74 |
| 76 | Q76M | 0.87 |
| 76 | Q76S | 0.83 |
| 76 | Q76V | 0.79 |
| 76 | Q76Y | 0.90 |
| 77 | S77F | 0.50 |
| 77 | S77Y | 0.85 |
| 78 | N78E | 0.67 |
| 78 | N78K | 0.71 |
| 78 | N78Q | 0.78 |
| 78 | N78R | 0.74 |
| 78 | N78T | 0.86 |
| 79 | E79Q | 0.70 |
| 79 | E79W | 0.84 |
| 80 | A80K | 0.78 |
| 81 | E81A | 0.56 |
| 81 | E81Q | 0.44 |
| 85 | L85M | 0.84 |
| 86 | P86H | 0.86 |
| 86 | P86N | 0.74 |
| 87 | G87A | 0.84 |
| 87 | G87E | 0.81 |
| 87 | G87Q | 0.73 |
| 88 | G88I | 0.90 |
| 88 | G88Q | 0.60 |
| 88 | G88S | 0.76 |
| 89 | T89G | 0.84 |
| 89 | T89H | 0.79 |
| 89 | T89K | 0.80 |
| 89 | T89P | 0.89 |
| 90 | G90C | 0.88 |
| 90 | G90V | 0.71 |
| 91 | W91R | 0.78 |
| 91 | W91S | 0.81 |
| 96 | F96S | 0.28 |
| 106 | R106P | 0.83 |
| 107 | I107G | 0.70 |
| 107 | I107Q | 0.88 |
| 108 | A108S | 0.76 |
| 112 | D112F | 0.71 |
| 112 | D112G | 0.84 |
| 112 | D112T | 0.24 |
| 113 | G113A | 0.88 |
| 113 | G113S | 0.80 |
| 114 | V114G | 0.83 |
| 114 | V114M | 0.80 |
| 116 | M116Y | 0.86 |
| 117 | N117R | 0.89 |
| 117 | N117T | 0.89 |
| 117 | N117W | 0.76 |
| 118 | A118K | 0.66 |
| 118 | A118Y | 0.66 |
| 119 | T119A | 0.71 |
| 119 | T119L | 0.82 |
| 121 | W121Y | 0.70 |
| 122 | F122A | 0.77 |
| 122 | F122M | 0.86 |
| 122 | F122S | 0.69 |
| 122 | F122Y | 0.69 |
| 123 | N123P | 0.68 |
| 124 | G124E | 0.45 |
| 124 | G124Q | 0.73 |
| 124 | G124R | 0.79 |
| 125 | V125E | 0.79 |
| 125 | V125I | 0.77 |
| 128 | G128A | 0.89 |
| 128 | G128D | 0.79 |
| 129 | T129E | 0.73 |
| 130 | H130Q | 0.88 |
| 131 | P131L | 0.89 |
| 131 | P131S | 0.85 |
| 132 | Y132C | 0.66 |
| 132 | Y132S | 0.87 |
| 133 | G133E | 0.88 |
| 135 | S135E | 0.86 |
| 135 | S135P | 0.81 |
| 135 | S135V | 0.85 |
| 136 | P136R | 0.51 |
| 136 | P136Y | 0.78 |
| 137 | F137A | 0.90 |
| 137 | F137G | 0.81 |
| 138 | S138G | 0.86 |
| 138 | S138L | 0.73 |
| 138 | S138R | 0.73 |
| 138 | S138V | 0.89 |
| 139 | F139A | 0.84 |
| 139 | F139E | 0.90 |
| 139 | F139Q | 0.78 |
| 139 | F139W | 0.81 |
| 140 | D140G | 0.83 |
| 140 | D140L | 0.81 |
| 141 | L141T | 0.87 |
| 142 | T142E | 0.85 |
| 142 | T142V | 0.79 |
| 146 | K146A | 0.56 |
| 148 | G148H | 0.90 |
| 148 | G148T | 0.74 |
| 149 | G149H | 0.89 |
| 149 | G149Q | 0.80 |
| 153 | H53A | 0.49 |
| 153 | I153Y | 0.81 |
| 154 | V154S | 0.89 |
| 155 | V155F | 0.74 |
| 157 | V157L | 0.69 |
| 158 | E158G | 0.56 |
| 159 | N159S | 0.77 |
| 168 | S168C | 0.84 |
| 169 | G169C | 0.84 |
| 169 | G169D | 0.67 |
| 170 | S170L | 0.73 |
| 171 | G171T | 0.77 |
| 173 | Y173W | 0.72 |
| 175 | D175E | 0.83 |
| 177 | T177A | 0.84 |
| 177 | T177L | 0.81 |
| 181 | T181D | 0.83 |
| 181 | T181K | 0.88 |
| 181 | T181R | 0.87 |
| 182 | D182F | 0.73 |
| 182 | D182L | 0.88 |

TABLE 2-continued

Variants having a GI-IF of at most 0.9

| Position | Mutation | GI-IF |
|---|---|---|
| 182 | D182S | 0.80 |
| 188 | N188E | 0.70 |
| 189 | N189E | 0.46 |
| 190 | G190C | 0.52 |
| 190 | G190H | 0.88 |
| 190 | G190Q | 0.88 |
| 191 | V191C | 0.84 |
| 191 | V191W | 0.85 |
| 194 | K194A | 0.82 |
| 194 | K194L | 0.82 |
| 194 | K194R | 0.83 |
| 195 | T195A | 0.88 |
| 195 | T195E | 0.84 |
| 195 | T195S | 0.69 |
| 196 | P196H | 0.83 |
| 197 | S197A | 0.88 |
| 197 | S197K | 0.85 |
| 197 | S197P | 0.83 |
| 198 | L198E | 0.82 |
| 198 | L198F | 0.83 |
| 198 | L198H | 0.80 |
| 198 | L198K | 0.80 |
| 198 | L198R | 0.67 |
| 198 | L198V | 0.72 |
| 198 | L198W | 0.85 |
| 199 | A199F | 0.87 |
| 199 | A199K | 0.72 |
| 199 | A199R | 0.87 |
| 201 | Q201C | 0.86 |
| 201 | Q201I | 0.81 |
| 201 | Q201M | 0.87 |
| 201 | Q201V | 0.87 |
| 202 | N202D | 0.71 |
| 202 | N202F | 0.89 |
| 202 | N202G | 0.89 |
| 202 | N202K | 0.88 |
| 202 | N202L | 0.78 |
| 202 | N202R | 0.64 |
| 202 | N202T | 0.79 |
| 203 | G203C | 0.79 |
| 203 | G203K | 0.70 |
| 203 | G203M | 0.87 |
| 203 | G203R | 0.90 |
| 203 | G203S | 0.77 |
| 203 | G203V | 0.65 |
| 203 | G203W | 0.75 |
| 203 | G203Y | 0.79 |
| 204 | G204A | 0.75 |
| 204 | G204C | 0.84 |
| 204 | G204D | 0.80 |
| 204 | G204K | 0.71 |
| 204 | G204S | 0.88 |
| 204 | G204Y | 0.66 |
| 205 | N205E | 0.68 |
| 205 | N205G | 0.65 |
| 205 | N205H | 0.68 |
| 205 | N205L | 0.80 |
| 205 | N205P | 0.83 |
| 205 | N205Y | 0.86 |
| 206 | V206A | 0.88 |
| 206 | V206D | 0.88 |
| 206 | V206F | 0.86 |
| 206 | V206G | 0.82 |
| 206 | V206I | 0.75 |
| 206 | V206K | 0.67 |
| 206 | V206Q | 0.86 |
| 206 | V206R | 0.81 |
| 206 | V206S | 0.79 |
| 206 | V206T | 0.81 |
| 207 | T207A | 0.78 |
| 207 | T207C | 0.77 |
| 207 | T207G | 0.71 |
| 207 | T207I | 0.75 |
| 207 | T207K | 0.73 |
| 207 | T207M | 0.88 |
| 207 | T207N | 0.82 |
| 207 | T207Q | 0.63 |
| 207 | T207R | 0.80 |
| 207 | T207W | 0.84 |
| 208 | M208A | 0.88 |
| 208 | M208S | 0.74 |
| 208 | M208T | 0.83 |
| 209 | N209C | 0.83 |
| 209 | N209D | 0.70 |
| 209 | N209G | 0.88 |
| 209 | N209K | 0.70 |
| 209 | N209L | 0.83 |
| 209 | N209Q | 0.87 |
| 209 | N209R | 0.90 |
| 209 | N209V | 0.71 |
| 210 | L210A | 0.89 |
| 210 | L210C | 0.81 |
| 210 | L210F | 0.86 |
| 210 | L210G | 0.77 |
| 210 | L210H | 0.87 |
| 210 | L210I | 0.78 |
| 210 | L210Q | 0.76 |
| 210 | L210R | 0.81 |
| 210 | L210S | 0.85 |
| 210 | L210T | 0.83 |
| 210 | L210V | 0.75 |
| 211 | T211A | 0.77 |
| 211 | T211D | 0.86 |
| 211 | T211E | 0.83 |
| 211 | T211F | 0.79 |
| 211 | T211K | 0.88 |
| 211 | T211N | 0.89 |
| 211 | T211Q | 0.77 |
| 211 | T211R | 0.63 |
| 211 | T211S | 0.80 |
| 212 | T212A | 0.86 |
| 212 | T212C | 0.88 |
| 212 | T212E | 0.64 |
| 212 | T212F | 0.87 |
| 212 | T212G | 0.76 |
| 212 | T212H | 0.72 |
| 212 | T212K | 0.87 |
| 212 | T212L | 0.77 |
| 212 | T212M | 0.88 |
| 212 | T212S | 0.74 |
| 212 | T212W | 0.80 |
| 213 | K213C | 0.66 |
| 213 | K213D | 0.66 |
| 213 | K213F | 0.74 |
| 213 | K213I | 0.80 |
| 213 | K213L | 0.79 |
| 213 | K213M | 0.80 |
| 213 | K213N | 0.84 |
| 213 | K213Q | 0.85 |
| 213 | K213R | 0.84 |
| 213 | K213S | 0.81 |
| 213 | K213T | 0.70 |
| 213 | K213V | 0.82 |
| 213 | K213Y | 0.76 |
| 214 | V214A | 0.66 |
| 214 | V214C | 0.77 |
| 214 | V214T | 0.84 |
| 214 | V214W | 0.74 |
| 215 | A215E | 0.75 |
| 215 | A215F | 0.90 |
| 215 | A215I | 0.77 |
| 215 | A215K | 0.76 |
| 215 | A215L | 0.79 |
| 215 | A215Q | 0.64 |
| 215 | A215R | 0.74 |
| 215 | A215S | 0.88 |
| 215 | A215V | 0.79 |
| 216 | N216T | 0.87 |
| 216 | N216V | 0.81 |
| 217 | D217T | 0.75 |
| 217 | D217V | 0.83 |
| 219 | K219C | 0.87 |

TABLE 2-continued

Variants having a GI-IF of at most 0.9

| Position | Mutation | GI-IF |
|---|---|---|
| 219 | K219F | 0.80 |
| 219 | K219H | 0.76 |
| 219 | K219M | 0.74 |
| 220 | A220C | 0.74 |
| 220 | A220I | 0.81 |
| 220 | A220L | 0.79 |
| 220 | A220M | 0.81 |
| 220 | A220T | 0.82 |
| 220 | A220V | 0.53 |
| 220 | A220W | 0.86 |
| 221 | A221E | 0.68 |
| 221 | A221L | 0.76 |
| 221 | A221N | 0.82 |
| 221 | A221R | 0.78 |
| 221 | A221V | 0.90 |
| 221 | A221Y | 0.80 |
| 222 | A222D | 0.74 |
| 222 | A222I | 0.80 |
| 222 | A222L | 0.80 |
| 222 | A222P | 0.72 |
| 222 | A222W | 0.75 |
| 222 | A222Y | 0.80 |
| 223 | N223A | 0.82 |
| 223 | N223E | 0.76 |
| 223 | N223F | 0.79 |
| 223 | N223G | 0.84 |
| 223 | N223K | 0.70 |
| 223 | N223L | 0.76 |
| 223 | N223M | 0.86 |
| 223 | N223R | 0.84 |
| 223 | N223T | 0.77 |
| 223 | N223V | 0.85 |
| 223 | N223W | 0.84 |
| 224 | I224Q | 0.84 |
| 225 | T225A | 0.90 |
| 225 | T225G | 0.86 |
| 226 | L226C | 0.88 |
| 226 | L226M | 0.80 |
| 227 | K227T | 0.84 |
| 229 | T229A | 0.70 |
| 229 | T229C | 0.77 |
| 229 | T229D | 0.73 |
| 229 | T229G | 0.70 |
| 229 | T229H | 0.90 |
| 229 | T229M | 0.75 |
| 229 | T229N | 0.75 |
| 229 | T229Q | 0.75 |
| 229 | T229R | 0.74 |
| 229 | T229V | 0.68 |
| 230 | V230F | 0.82 |
| 230 | V230L | 0.74 |
| 230 | V230M | 0.61 |
| 230 | V230Q | 0.81 |
| 230 | V230R | 0.77 |
| 230 | V230S | 0.71 |
| 231 | F231A | 0.90 |
| 231 | F231E | 0.71 |
| 231 | F231G | 0.66 |
| 231 | F231I | 0.78 |
| 231 | F231K | 0.82 |
| 231 | F231Q | 0.85 |
| 231 | F231S | 0.81 |
| 231 | F231V | 0.70 |
| 231 | F231W | 0.79 |
| 231 | F231Y | 0.69 |
| 232 | P232G | 0.80 |
| 232 | P232H | 0.87 |
| 232 | P232L | 0.80 |
| 232 | P232M | 0.71 |
| 232 | P232R | 0.80 |
| 232 | P232S | 0.65 |
| 232 | P232V | 0.85 |
| 232 | P232W | 0.86 |
| 232 | P232Y | 0.82 |
| 233 | K233A | 0.84 |
| 233 | K233C | 0.66 |
| 233 | K233E | 0.72 |
| 233 | K233F | 0.75 |
| 233 | K233G | 0.87 |
| 233 | K233L | 0.69 |
| 233 | K233P | 0.59 |
| 233 | K233R | 0.80 |
| 233 | K233S | 0.89 |
| 233 | K233V | 0.80 |
| 233 | K233W | 0.88 |
| 233 | K233Y | 0.82 |
| 234 | G234A | 0.79 |
| 234 | G234C | 0.70 |
| 234 | G234D | 0.71 |
| 234 | G234E | 0.76 |
| 234 | G234K | 0.89 |
| 234 | G234L | 0.65 |
| 234 | G234Q | 0.78 |
| 234 | G234R | 0.78 |
| 234 | G234W | 0.85 |
| 234 | G234Y | 0.68 |
| 235 | G235C | 0.84 |
| 235 | G235F | 0.81 |
| 235 | G235H | 0.70 |
| 235 | G235I | 0.76 |
| 235 | G235M | 0.64 |
| 235 | G235Q | 0.76 |
| 235 | G235R | 0.90 |
| 235 | G235T | 0.75 |
| 235 | G235W | 0.78 |
| 235 | G235Y | 0.67 |
| 236 | K236A | 0.78 |
| 236 | K236D | 0.63 |
| 236 | K236E | 0.88 |
| 236 | K236G | 0.84 |
| 236 | K236L | 0.65 |
| 236 | K236R | 0.73 |
| 236 | K236S | 0.75 |
| 236 | K236T | 0.84 |
| 236 | K236W | 0.66 |
| 236 | K236Y | 0.62 |
| 237 | T237F | 0.81 |
| 237 | T237I | 0.84 |
| 237 | T237K | 0.77 |
| 237 | T237M | 0.82 |
| 237 | T237Q | 0.88 |
| 237 | T237R | 0.78 |
| 237 | T237S | 0.88 |
| 237 | T237V | 0.89 |
| 237 | T237Y | 0.88 |
| 238 | D238A | 0.79 |
| 238 | D238E | 0.63 |
| 238 | D238F | 0.60 |
| 238 | D238G | 0.73 |
| 238 | D238H | 0.84 |
| 238 | D238I | 0.82 |
| 238 | D238L | 0.83 |
| 238 | D238M | 0.76 |
| 238 | D238N | 0.90 |
| 238 | D238P | 0.70 |
| 238 | D238Q | 0.81 |
| 238 | D238R | 0.73 |
| 239 | A239C | 0.84 |
| 239 | A239E | 0.72 |
| 239 | A239G | 0.29 |
| 239 | A239I | 0.80 |
| 239 | A239K | 0.85 |
| 239 | A239T | 0.48 |
| 240 | A240C | 0.63 |
| 240 | A240E | 0.85 |
| 240 | A240L | 0.72 |
| 240 | A240P | 0.71 |
| 240 | A240T | 0.79 |
| 240 | A240V | 0.81 |
| 240 | A240W | 0.90 |
| 240 | A240Y | 0.78 |
| 241 | I241T | 0.71 |

TABLE 2-continued

Variants having a GI-IF of at most 0.9

| Position | Mutation | GI-IF |
|---|---|---|
| 242 | G242T | 0.83 |
| 242 | G242Y | 0.52 |
| 243 | T243M | 0.64 |
| 243 | T243R | 0.78 |
| 243 | T243V | 0.83 |
| 244 | V244A | 0.85 |
| 244 | V244E | 0.73 |
| 244 | V244G | 0.84 |
| 244 | V244L | 0.83 |
| 244 | V244R | 0.76 |
| 245 | T245E | 0.79 |
| 245 | T245G | 0.67 |
| 245 | T245L | 0.83 |
| 245 | T245M | 0.84 |
| 245 | T245N | 0.85 |
| 245 | T245Q | 0.64 |
| 245 | T245R | 0.77 |
| 245 | T245S | 0.81 |
| 246 | T246D | 0.89 |
| 246 | T246E | 0.86 |
| 246 | T246G | 0.77 |
| 246 | T246K | 0.79 |
| 246 | T246V | 0.90 |
| 247 | A247D | 0.87 |
| 247 | A247E | 0.74 |
| 247 | A247N | 0.83 |
| 247 | A247P | 0.59 |
| 247 | A247Q | 0.84 |
| 247 | A247R | 0.49 |
| 247 | A247S | 0.74 |
| 247 | A247V | 0.70 |
| 247 | A247W | 0.65 |
| 248 | S248A | 0.77 |
| 248 | S248E | 0.58 |
| 248 | S248H | 0.88 |
| 248 | S248I | 0.89 |
| 248 | S248L | 0.79 |
| 248 | S248Q | 0.78 |
| 248 | S248T | 0.68 |
| 248 | S248Y | 0.88 |
| 249 | K249A | 0.77 |
| 249 | K249D | 0.71 |
| 249 | K249G | 0.53 |
| 249 | K249H | 0.76 |
| 249 | K249I | 0.86 |
| 249 | K249L | 0.76 |
| 249 | K249M | 0.84 |
| 249 | K249N | 0.66 |
| 249 | K249P | 0.78 |
| 249 | K249Q | 0.73 |
| 249 | K249S | 0.85 |
| 249 | K249T | 0.90 |
| 249 | K249V | 0.74 |
| 249 | K249Y | 0.58 |
| 250 | S250H | 0.73 |
| 250 | S250M | 0.88 |
| 250 | S250W | 0.89 |
| 251 | I251L | 0.77 |
| 251 | I251V | 0.81 |
| 252 | A252C | 0.81 |
| 252 | A252E | 0.83 |
| 252 | A252F | 0.58 |
| 252 | A252I | 0.80 |
| 252 | A252R | 0.88 |
| 252 | A252S | 0.83 |
| 254 | G254D | 0.75 |
| 254 | G254F | 0.75 |
| 254 | G254I | 0.47 |
| 254 | G254L | 0.74 |
| 254 | G254M | 0.69 |
| 254 | G254Q | 0.77 |
| 254 | G254R | 0.57 |
| 254 | G254W | 0.64 |
| 255 | A255C | 0.87 |
| 255 | A255F | 0.83 |
| 255 | A255K | 0.59 |
| 255 | A255L | 0.83 |
| 255 | A255M | 0.81 |
| 255 | A255S | 0.69 |
| 255 | A255T | 0.90 |
| 255 | A255W | 0.90 |
| 255 | A255Y | 0.63 |
| 256 | S256A | 0.63 |
| 256 | S256C | 0.78 |
| 256 | S256F | 0.83 |
| 256 | S256G | 0.85 |
| 256 | S256K | 0.69 |
| 256 | S256L | 0.81 |
| 256 | S256M | 0.78 |
| 256 | S256N | 0.67 |
| 256 | S256Q | 0.81 |
| 256 | S256R | 0.77 |
| 256 | S256V | 0.84 |
| 256 | S256W | 0.76 |
| 256 | S256Y | 0.54 |
| 257 | A257I | 0.76 |
| 257 | A257T | 0.82 |
| 258 | D258A | 0.74 |
| 258 | D258L | 0.65 |
| 258 | D258M | 0.88 |
| 258 | D258W | 0.68 |
| 259 | V259E | 0.76 |
| 259 | V259L | 0.84 |
| 259 | V259S | 0.86 |
| 259 | V259T | 0.75 |
| 260 | T260A | 0.87 |
| 260 | T260D | 0.74 |
| 260 | T260G | 0.79 |
| 260 | T260I | 0.90 |
| 260 | T260K | 0.88 |
| 261 | S261D | 0.80 |
| 261 | S261R | 0.52 |
| 261 | S261W | 0.66 |
| 262 | T262D | 0.56 |
| 262 | T262G | 0.81 |
| 262 | T262H | 0.87 |
| 262 | T262L | 0.87 |
| 262 | T262W | 0.77 |
| 263 | I263C | 0.83 |
| 263 | I263G | 0.87 |
| 263 | I263L | 0.86 |
| 263 | I263S | 0.82 |
| 263 | I263V | 0.86 |
| 264 | T264F | 0.78 |
| 264 | T264G | 0.88 |
| 264 | T264K | 0.83 |
| 264 | T264M | 0.45 |
| 264 | T264P | 0.84 |
| 264 | T264Q | 0.74 |
| 264 | T264R | 0.85 |
| 264 | T264S | 0.83 |
| 264 | T264Y | 0.74 |
| 265 | A265G | 0.83 |
| 265 | A265I | 0.77 |
| 265 | A265K | 0.85 |
| 265 | A265R | 0.85 |
| 265 | A265S | 0.75 |
| 265 | A265V | 0.90 |
| 266 | A266E | 0.88 |
| 266 | A266G | 0.76 |
| 266 | A266K | 0.66 |
| 266 | A266L | 0.86 |
| 266 | A266M | 0.85 |
| 266 | A266P | 0.88 |
| 266 | A266Q | 0.68 |
| 266 | A266S | 0.86 |
| 266 | A266T | 0.74 |
| 267 | S267A | 0.75 |
| 267 | S267D | 0.80 |
| 267 | S267K | 0.85 |
| 267 | S267M | 0.80 |
| 267 | S267N | 0.79 |

TABLE 2-continued

Variants having a GI-IF of at most 0.9

| Position | Mutation | GI-IF |
|---|---|---|
| 267 | S267P | 0.77 |
| 267 | S267Q | 0.86 |
| 267 | S267R | 0.75 |
| 268 | P268G | 0.76 |
| 268 | P268M | 0.84 |
| 268 | P268V | 0.90 |
| 268 | P268W | 0.70 |
| 268 | P268Y | 0.73 |
| 269 | K269G | 0.87 |
| 269 | K269R | 0.81 |
| 269 | K269V | 0.73 |
| 269 | K269Y | 0.71 |
| 270 | L270D | 0.74 |
| 270 | L270M | 0.84 |
| 270 | L270R | 0.84 |
| 270 | L270V | 0.85 |
| 272 | S272E | 0.88 |
| 272 | S272G | 0.70 |
| 272 | S272K | 0.88 |
| 272 | S272L | 0.83 |
| 272 | S272N | 0.83 |
| 273 | I273K | 0.89 |
| 273 | I273L | 0.80 |
| 273 | I273P | 0.89 |
| 273 | I273R | 0.78 |
| 273 | I273S | 0.80 |
| 274 | K274D | 0.88 |
| 274 | K274P | 0.87 |
| 274 | K274R | 0.84 |
| 275 | N275K | 0.88 |
| 275 | N275V | 0.87 |
| 275 | N275W | 0.75 |
| 277 | N277K | 0.81 |
| 277 | N277R | 0.77 |
| 278 | L278A | 0.84 |
| 278 | L278G | 0.81 |
| 278 | L278H | 0.66 |
| 278 | L278I | 0.73 |
| 278 | L278K | 0.72 |
| 278 | L278M | 0.69 |
| 278 | L278P | 0.83 |
| 278 | L278Q | 0.65 |
| 278 | L278R | 0.65 |
| 278 | L278S | 0.89 |
| 278 | L278V | 0.60 |
| 279 | Y279M | 0.85 |
| 279 | Y279T | 0.89 |
| 279 | Y279W | 0.49 |
| 280 | T280A | 0.80 |
| 280 | T280E | 0.61 |
| 280 | T280F | 0.71 |
| 280 | T280H | 0.86 |
| 280 | T280M | 0.89 |
| 280 | T280Q | 0.73 |
| 281 | V281A | 0.87 |
| 281 | V281I | 0.75 |
| 281 | V281L | 0.86 |
| 282 | R282E | 0.74 |
| 282 | R282F | 0.75 |
| 282 | R282H | 0.70 |
| 282 | R282I | 0.63 |
| 282 | R282K | 0.74 |
| 282 | R282N | 0.71 |
| 282 | R282S | 0.78 |
| 282 | R282T | 0.81 |
| 282 | R282V | 0.71 |
| 283 | T283R | 0.72 |
| 283 | T283V | 0.71 |
| 284 | E284A | 0.72 |
| 284 | E284D | 0.72 |
| 284 | E284F | 0.88 |
| 284 | E284H | 0.76 |
| 284 | E284L | 0.70 |
| 284 | E284M | 0.89 |
| 284 | E284N | 0.85 |
| 284 | E284Q | 0.86 |
| 284 | E284R | 0.79 |
| 284 | E284Y | 0.71 |
| 285 | V285I | 0.85 |
| 285 | V285T | 0.60 |
| 286 | L286A | 0.89 |
| 286 | L286C | 0.84 |
| 286 | L286D | 0.88 |
| 286 | L286F | 0.57 |
| 286 | L286N | 0.74 |
| 286 | L286R | 0.81 |
| 286 | L286T | 0.79 |
| 286 | L286Y | 0.81 |
| 287 | N287I | 0.83 |
| 287 | N287L | 0.83 |
| 288 | G288F | 0.84 |
| 288 | G288L | 0.83 |
| 288 | G288S | 0.79 |
| 291 | V291C | 0.84 |
| 291 | V291D | 0.59 |
| 291 | V291F | 0.78 |
| 291 | V291G | 0.84 |
| 291 | V291T | 0.75 |
| 291 | V291Y | 0.74 |
| 292 | L292H | 0.67 |
| 293 | D293E | 0.89 |
| 293 | D293F | 0.88 |
| 293 | D293S | 0.66 |
| 293 | D293V | 0.89 |
| 294 | T294G | 0.83 |
| 295 | Y295I | 0.87 |
| 295 | Y295R | 0.87 |
| 295 | Y295W | 0.63 |
| 296 | D296L | 0.86 |
| 296 | D296N | 0.88 |
| 296 | D296R | 0.66 |
| 296 | D296V | 0.75 |
| 297 | T297G | 0.80 |
| 297 | T297Q | 0.86 |
| 297 | T297R | 0.88 |
| 298 | E298G | 0.86 |
| 301 | F301L | 0.88 |
| 302 | R302E | 0.84 |
| 302 | R302N | 0.79 |
| 303 | W303S | 0.75 |
| 305 | G305F | 0.83 |
| 305 | G305W | 0.44 |
| 306 | F306D | 0.90 |
| 306 | F306K | 0.73 |
| 306 | F306L | 0.72 |
| 306 | F306S | 0.84 |
| 307 | D307G | 0.78 |
| 307 | D307L | 0.85 |
| 307 | D307M | 0.87 |
| 307 | D307N | 0.85 |
| 307 | D307Q | 0.83 |
| 308 | A308C | 0.88 |
| 308 | A308E | 0.78 |
| 308 | A308M | 0.64 |
| 308 | A308Y | 0.64 |
| 309 | T309M | 0.87 |
| 309 | T309S | 0.78 |
| 311 | G311E | 0.87 |
| 311 | G311Q | 0.80 |
| 311 | G311R | 0.81 |
| 311 | G311V | 0.69 |
| 312 | F312R | 0.72 |
| 314 | L314C | 0.69 |
| 314 | L314T | 0.71 |
| 316 | G316A | 0.82 |
| 316 | G316C | 0.82 |
| 316 | G316S | 0.73 |
| 317 | E317D | 0.82 |
| 317 | E317H | 0.90 |
| 317 | E317I | 0.87 |
| 317 | E317K | 0.72 |
| 318 | K318G | 0.83 |

TABLE 2-continued

Variants having a GI-IF of at most 0.9

| Position | Mutation | GI-IF |
|---|---|---|
| 318 | K318L | 0.82 |
| 318 | K318V | 0.90 |
| 320 | K320C | 0.61 |
| 320 | K320F | 0.75 |
| 320 | K320L | 0.76 |
| 320 | K320R | 0.74 |
| 320 | K320T | 0.79 |
| 321 | L321C | 0.81 |
| 321 | L321G | 0.88 |
| 321 | L321V | 0.89 |
| 322 | K322F | 0.61 |
| 322 | K322N | 0.85 |
| 322 | K322P | 0.71 |
| 322 | K322Q | 0.83 |
| 322 | K322R | 0.89 |
| 322 | K322S | 0.78 |
| 325 | S325D | 0.67 |
| 325 | S325T | 0.65 |
| 326 | M326E | 0.54 |
| 326 | M326G | 0.51 |
| 326 | M326S | 0.84 |
| 326 | M326Y | 0.57 |
| 329 | D329S | 0.74 |
| 329 | D329T | 0.87 |
| 337 | A337Q | 0.89 |
| 338 | N338V | 0.87 |
| 340 | R340C | 0.72 |
| 341 | A341S | 0.75 |
| 342 | I342K | 0.54 |
| 343 | E343H | 0.88 |
| 343 | E343S | 0.85 |
| 344 | R344L | 0.83 |
| 345 | Q345G | 0.53 |
| 345 | Q345K | 0.56 |
| 346 | V346C | 0.79 |
| 346 | V346F | 0.88 |
| 346 | V346L | 0.88 |
| 347 | E347C | 0.72 |
| 347 | E347F | 0.72 |
| 347 | E347R | 0.71 |
| 347 | E347S | 0.82 |
| 349 | L349Q | 0.78 |
| 351 | K351N | 0.89 |
| 351 | K351V | 0.73 |
| 352 | M352G | 0.71 |
| 352 | M352W | 0.70 |
| 355 | N355M | 0.77 |
| 355 | N355R | 0.83 |
| 355 | N355W | 0.78 |
| 362 | N362G | 0.89 |
| 365 | A365E | 0.74 |
| 366 | K366A | 0.79 |
| 366 | K366E | 0.85 |
| 367 | A367C | 0.90 |
| 368 | L368E | 0.53 |
| 369 | I369R | 0.78 |
| 370 | D370C | 0.84 |
| 370 | D370S | 0.76 |
| 371 | V371D | 0.69 |
| 371 | V371S | 0.79 |
| 374 | E374K | 0.81 |
| 374 | E374R | 0.71 |
| 378 | L378W | 0.81 |
| 380 | V380M | 0.87 |
| 381 | E381L | 0.90 |
| 383 | V383K | 0.77 |
| 383 | V383L | 0.75 |
| 386 | M386Q | 0.86 |
| 387 | W387L | 0.42 |
| 388 | N388A | 0.73 |
| 388 | N388R | 0.58 |
| 389 | R389N | 0.75 |
| 390 | S390G | 0.55 |
| 390 | S390N | 0.83 |
| 390 | S390Q | 0.18 |
| 390 | S390V | 0.70 |
| 391 | K391E | 0.36 |
| 392 | N392D | 0.02 |
| 393 | G393A | 0.67 |
| 393 | G393N | 0.77 |
| 393 | G393S | 0.63 |
| 394 | N394L | 0.11 |
| 395 | T395H | 0.31 |
| 395 | T395I | 0.80 |
| 395 | T395M | 0.74 |
| 395 | T395N | 0.15 |
| 395 | T395Q | 0.86 |
| 395 | T395S | 0.41 |
| 395 | T395W | 0.07 |
| 396 | E396M | 0.64 |
| 398 | Y398N | 0.33 |
| 400 | K400D | 0.86 |
| 400 | K400E | 0.89 |
| 400 | K400P | 0.43 |
| 400 | K400Q | 0.70 |
| 400 | K400S | 0.32 |
| 401 | W401H | 0.77 |
| 401 | W401L | 0.64 |
| 401 | W401M | 0.81 |
| 401 | W401R | 0.85 |
| 402 | F402T | 0.85 |
| 403 | G403P | 0.71 |
| 403 | G403S | 0.76 |
| 404 | Q404H | 0.42 |
| 404 | Q404R | 0.77 |
| 405 | A405H | 0.55 |
| 405 | A405P | 0.72 |
| 407 | A407M | 0.86 |
| 407 | A407S | 0.82 |
| 407 | A407T | 0.69 |
| 407 | A407W | 0.89 |
| 408 | G408D | 0.84 |
| 408 | G408I | 0.71 |
| 408 | G408M | 0.72 |
| 408 | G408N | 0.71 |
| 408 | G408W | 0.51 |
| 409 | D409N | 0.59 |
| 409 | D409W | 0.84 |
| 410 | N410C | 0.89 |
| 411 | A411N | 0.86 |
| 411 | A411V | 0.70 |
| 412 | V412M | 0.86 |
| 413 | L413D | 0.87 |
| 413 | L413E | 0.85 |
| 413 | L413F | 0.83 |
| 413 | L413I | 0.77 |
| 413 | L413P | 0.41 |
| 413 | L413T | 0.77 |
| 414 | G414A | 0.41 |
| 414 | G414C | 0.80 |
| 414 | G414R | 0.51 |
| 414 | G414W | 0.86 |
| 415 | G415R | 0.68 |
| 416 | D416I | 0.41 |
| 416 | D416R | 0.64 |
| 416 | D416T | 0.81 |
| 416 | D416Y | 0.58 |
| 417 | K417C | 0.77 |
| 417 | K417G | 0.77 |
| 417 | K417T | 0.79 |
| 418 | D418L | 0.89 |
| 418 | D418P | 0.59 |
| 418 | D418R | 0.26 |
| 418 | D418Y | 0.80 |
| 419 | E419M | 0.54 |
| 419 | E419R | 0.58 |
| 419 | E419W | 0.68 |
| 420 | T420E | 0.72 |
| 420 | T420F | 0.73 |
| 420 | T420G | 0.76 |
| 420 | T420K | 0.50 |
| 420 | T420R | 0.37 |

TABLE 2-continued

Variants having a GI-IF of at most 0.9

| Position | Mutation | GI-IF |
|---|---|---|
| 420 | T420V | 0.71 |
| 421 | W421L | 0.73 |
| 421 | W421Q | 0.63 |
| 421 | W421S | 0.82 |
| 422 | A422T | 0.62 |
| 422 | A422V | 0.83 |
| 423 | K423D | 0.43 |
| 423 | K423M | 0.86 |
| 424 | F424C | 0.58 |
| 424 | F424L | 0.44 |
| 424 | F424N | 0.69 |
| 424 | F424T | 0.87 |
| 425 | D425E | 0.87 |
| 426 | L426M | 0.52 |
| 426 | L426Q | 0.73 |
| 427 | T427G | 0.77 |
| 427 | T427K | 0.69 |
| 427 | T427M | 0.67 |
| 427 | T427P | 0.73 |
| 427 | T427R | 0.86 |
| 428 | S428F | 0.72 |
| 428 | S428K | 0.74 |
| 428 | S428W | 0.87 |
| 430 | I430C | 0.76 |
| 430 | I430D | 0.89 |
| 430 | I430E | 0.82 |
| 430 | I430Q | 0.78 |
| 430 | I430S | 0.70 |
| 430 | I430T | 0.78 |
| 430 | I430W | 0.88 |
| 431 | N431D | 0.79 |
| 431 | N431E | 0.78 |
| 431 | N431G | 0.86 |
| 431 | N431R | 0.83 |
| 431 | N431V | 0.89 |
| 431 | N431Y | 0.80 |
| 432 | R432A | 0.78 |
| 432 | R432E | 0.78 |
| 432 | R432N | 0.78 |
| 432 | R432V | 0.85 |
| 433 | D433H | 0.84 |
| 434 | R434L | 0.89 |
| 434 | R434M | 0.89 |
| 434 | R434P | 0.81 |
| 434 | R434S | 0.78 |
| 435 | N435K | 0.79 |
| 435 | N435M | 0.82 |
| 435 | N435R | 0.68 |
| 435 | N435W | 0.79 |
| 436 | A436D | 0.84 |
| 436 | A436E | 0.86 |
| 436 | A436I | 0.81 |
| 436 | A436Q | 0.85 |
| 436 | A436S | 0.85 |
| 437 | P437A | 0.76 |
| 437 | P437D | 0.85 |
| 437 | P437Q | 0.65 |
| 437 | P437R | 0.62 |
| 437 | P437S | 0.83 |
| 437 | P437V | 0.74 |
| 439 | V439E | 0.69 |
| 439 | V439G | 0.50 |
| 439 | V439I | 0.75 |
| 439 | V439Q | 0.82 |
| 439 | V439T | 0.56 |
| 439 | V439Y | 0.73 |
| 440 | I440C | 0.80 |
| 440 | I440D | 0.81 |
| 440 | I440F | 0.72 |
| 440 | I440K | 0.70 |
| 440 | I440P | 0.86 |
| 440 | I440R | 0.63 |
| 440 | I440W | 0.78 |
| 441 | M441A | 0.70 |
| 441 | M441E | 0.76 |
| 441 | M441G | 0.83 |
| 441 | M441Q | 0.78 |
| 441 | M441V | 0.80 |
| 442 | W442M | 0.88 |
| 442 | W442P | 0.79 |
| 442 | W442Q | 0.89 |
| 442 | W442R | 0.55 |
| 443 | S443D | 0.86 |
| 443 | S443Y | 0.56 |
| 444 | L444C | 0.90 |
| 444 | L444D | 0.77 |
| 444 | L444G | 0.70 |
| 444 | L444H | 0.88 |
| 444 | L444K | 0.70 |
| 444 | L444Q | 0.76 |
| 444 | L444W | 0.73 |
| 445 | G445A | 0.58 |
| 445 | G445C | 0.41 |
| 445 | G445V | 0.39 |
| 446 | N446T | 0.67 |
| 448 | M448A | 0.74 |
| 448 | M448D | 0.72 |
| 448 | M448I | 0.71 |
| 448 | M448P | 0.78 |
| 448 | M448Q | 0.68 |
| 448 | M448S | 0.51 |
| 448 | M448V | 0.68 |
| 448 | M448W | 0.84 |
| 452 | I452G | 0.67 |
| 452 | I452M | 0.63 |
| 453 | S453F | 0.70 |
| 455 | S455A | 0.80 |
| 455 | S455K | 0.80 |
| 455 | S455W | 0.63 |
| 456 | V456A | 0.80 |
| 456 | V456L | 0.80 |
| 456 | V456W | 0.83 |
| 457 | S457E | 0.89 |
| 457 | S457K | 0.79 |
| 457 | S457L | 0.89 |
| 457 | S457M | 0.87 |
| 457 | S457P | 0.71 |
| 458 | G458C | 0.89 |
| 458 | G458F | 0.90 |
| 458 | G458L | 0.81 |
| 458 | G458Q | 0.82 |
| 458 | G458V | 0.70 |
| 458 | G458W | 0.65 |
| 459 | F459A | 0.88 |
| 459 | F459E | 0.81 |
| 459 | F459F | 0.88 |
| 459 | F459N | 0.66 |
| 459 | F459S | 0.58 |
| 459 | F459T | 0.88 |
| 459 | F459W | 0.81 |
| 460 | P460C | 0.86 |
| 460 | P460Q | 0.82 |
| 460 | P460W | 0.81 |
| 461 | A461D | 0.79 |
| 461 | A461N | 0.74 |
| 461 | A461Q | 0.85 |
| 461 | A461V | 0.85 |
| 461 | A461Y | 0.73 |
| 462 | T462C | 0.77 |
| 462 | T462F | 0.76 |
| 462 | T462M | 0.83 |
| 462 | T462S | 0.80 |
| 463 | S463G | 0.85 |
| 463 | S463K | 0.73 |
| 463 | S463Q | 0.73 |
| 463 | S463R | 0.87 |
| 463 | S463T | 0.77 |
| 463 | S463V | 0.69 |
| 464 | A464E | 0.85 |
| 464 | A464H | 0.84 |
| 464 | A464L | 0.83 |
| 464 | A464M | 0.76 |

TABLE 2-continued

Variants having a GI-IF of at most 0.9

| Position | Mutation | GI-IF |
|---|---|---|
| 464 | A464P | 0.67 |
| 464 | A464V | 0.67 |
| 465 | K465F | 0.67 |
| 465 | K465R | 0.82 |
| 465 | K465W | 0.86 |
| 466 | L466A | 0.63 |
| 466 | L466C | 0.83 |
| 466 | L466D | 0.85 |
| 466 | L466E | 0.62 |
| 466 | L466F | 0.72 |
| 466 | L466M | 0.71 |
| 466 | L466Q | 0.77 |
| 466 | L466S | 0.68 |
| 466 | L466V | 0.59 |
| 466 | L466Y | 0.80 |
| 467 | V467A | 0.89 |
| 467 | V467C | 0.89 |
| 467 | V467D | 0.77 |
| 467 | V467E | 0.80 |
| 467 | V467G | 0.73 |
| 467 | V467W | 0.75 |
| 468 | A468E | 0.77 |
| 468 | A468F | 0.80 |
| 468 | A468K | 0.78 |
| 468 | A468L | 0.80 |
| 468 | A468P | 0.85 |
| 468 | A468S | 0.85 |
| 468 | A468V | 0.71 |
| 468 | A468W | 0.68 |
| 469 | W469A | 0.80 |
| 469 | W469C | 0.84 |
| 469 | W469D | 0.88 |
| 469 | W469G | 0.73 |
| 469 | W469M | 0.78 |
| 469 | W469V | 0.87 |
| 469 | W469Y | 0.85 |
| 470 | T470E | 0.88 |
| 470 | T470L | 0.83 |
| 470 | T470M | 0.68 |
| 470 | T470Q | 0.88 |
| 471 | K471G | 0.87 |
| 471 | K471W | 0.75 |
| 473 | A473E | 0.86 |
| 474 | D474A | 0.88 |
| 474 | D474K | 0.83 |
| 474 | D474R | 0.64 |
| 475 | S475F | 0.76 |
| 475 | S475Q | 0.83 |
| 475 | S475V | 0.83 |
| 476 | T476C | 0.83 |
| 477 | R477C | 0.89 |
| 478 | P478G | 0.76 |
| 478 | P478L | 0.74 |
| 479 | M479I | 0.65 |
| 479 | M479R | 0.49 |
| 479 | M479W | 0.77 |
| 480 | T480C | 0.61 |
| 480 | T480G | 0.69 |
| 487 | K487G | 0.80 |
| 487 | K487N | 0.59 |
| 488 | A488G | 0.77 |
| 488 | A488H | 0.62 |
| 488 | A488N | 0.34 |
| 488 | A488S | 0.68 |
| 491 | N491A | 0.73 |
| 491 | N491E | 0.82 |
| 491 | N491W | 0.09 |
| 492 | E492A | 0.64 |
| 492 | E492W | 0.76 |
| 493 | S493M | 0.47 |
| 493 | S493V | 0.90 |
| 495 | T495R | 0.68 |
| 495 | T495V | 0.78 |
| 495 | T495W | 0.52 |
| 496 | M496A | 0.80 |
| 496 | M496F | 0.72 |
| 496 | M496T | 0.85 |
| 498 | D498A | 0.76 |
| 498 | D498C | 0.50 |
| 498 | D498M | 0.71 |
| 498 | D498S | 0.70 |
| 499 | N499K | 0.89 |
| 499 | N499R | 0.54 |
| 499 | N499Y | 0.20 |
| 500 | L500A | 0.49 |
| 500 | L500E | 0.90 |
| 500 | L500N | 0.74 |
| 500 | L500V | 0.87 |
| 501 | T501C | 0.87 |
| 501 | T501G | 0.72 |
| 501 | T501M | 0.70 |
| 502 | A502L | 0.74 |
| 502 | A502Q | 0.81 |
| 503 | N503A | 0.80 |
| 503 | N503E | 0.74 |
| 503 | N503M | 0.73 |
| 503 | N503S | 0.90 |
| 504 | G504H | 0.29 |
| 504 | G504K | 0.74 |
| 504 | G504P | 0.69 |
| 505 | G505A | 0.74 |
| 505 | G505E | 0.73 |
| 505 | G505N | 0.67 |
| 506 | V506D | 0.65 |
| 506 | V506G | 0.66 |
| 506 | V506I | 0.85 |
| 506 | V506L | 0.76 |
| 506 | V506P | 0.79 |
| 506 | V506S | 0.77 |
| 506 | V506T | 0.81 |
| 506 | V506W | 0.86 |
| 507 | V507A | 0.75 |
| 507 | V507G | 0.74 |
| 507 | V507L | 0.38 |
| 507 | V507N | 0.72 |
| 507 | V507S | 0.75 |
| 507 | V507T | 0.82 |
| 510 | N510Q | 0.80 |
| 511 | Y511K | 0.82 |
| 512 | S512G | 0.75 |
| 513 | D513C | 0.86 |
| 513 | D513K | 0.60 |
| 513 | D513L | 0.45 |
| 513 | D513M | 0.90 |
| 513 | D513Q | 0.82 |
| 513 | D513W | 0.89 |
| 514 | G514F | 0.58 |
| 514 | G514L | 0.77 |
| 514 | G514N | 0.84 |
| 514 | G514P | 0.81 |
| 514 | G514R | 0.84 |
| 515 | A515C | 0.66 |
| 515 | A515D | 0.78 |
| 515 | A515K | 0.62 |
| 515 | A515R | 0.66 |
| 517 | Y517N | 0.74 |
| 518 | D518Q | 0.75 |
| 521 | R521N | 0.35 |
| 522 | T522G | 0.61 |
| 522 | T522I | 0.84 |
| 522 | T522N | 0.29 |
| 525 | P525D | 0.87 |
| 525 | P525G | 0.80 |
| 525 | P525T | 0.53 |
| 525 | P525V | 0.89 |
| 526 | S526I | 0.90 |
| 526 | S526W | 0.88 |
| 527 | W527V | 0.84 |
| 528 | A528C | 0.72 |
| 528 | A528I | 0.79 |
| 529 | I529F | 0.87 |
| 529 | I529L | 0.85 |

TABLE 2-continued

Variants having a GI-IF of at most 0.9

| Position | Mutation | GI-IF |
|---|---|---|
| 529 | I529Y | 0.81 |
| 530 | Y530A | 0.74 |
| 530 | Y530M | 0.62 |
| 531 | G531E | 0.63 |
| 531 | G531S | 0.67 |
| 531 | G531T | 0.59 |
| 534 | T534A | 0.69 |
| 534 | T534I | 0.70 |
| 534 | T534Q | 0.90 |
| 535 | A535M | 0.65 |
| 537 | A537D | 0.68 |
| 539 | N539G | 0.90 |
| 539 | N539W | 0.77 |
| 540 | S540G | 0.64 |
| 540 | S540M | 0.80 |
| 542 | G542E | 0.85 |
| 542 | G542Q | 0.65 |
| 542 | G542S | 0.89 |
| 542 | G542T | 0.82 |
| 543 | I543V | 0.68 |
| 543 | I543W | 0.82 |
| 545 | N545I | 0.88 |
| 545 | N545Q | 0.74 |
| 545 | N545S | 0.69 |
| 546 | R546A | 0.81 |
| 546 | R546C | 0.72 |
| 546 | R546L | 0.46 |
| 546 | R546P | 0.53 |
| 546 | R546S | 0.14 |
| 547 | T547A | 0.53 |
| 547 | T547D | 0.68 |
| 547 | T547H | 0.85 |
| 547 | T547N | 0.70 |
| 547 | T547S | 0.56 |
| 548 | T548D | 0.89 |
| 548 | T548E | 0.70 |
| 548 | T548F | 0.51 |
| 548 | T548K | 0.50 |
| 548 | T548L | 0.73 |
| 548 | T548P | 0.41 |
| 548 | T548W | 0.80 |
| 549 | G549F | 0.78 |
| 550 | G550S | 0.28 |
| 551 | A551D | 0.89 |
| 551 | A551I | 0.64 |
| 551 | A551Q | 0.47 |
| 553 | S553C | 0.85 |
| 553 | S553F | 0.75 |
| 553 | S553N | 0.53 |
| 553 | S553T | 0.85 |
| 553 | S553V | 0.86 |
| 554 | S554F | 0.89 |
| 554 | S554N | 0.33 |
| 554 | S554R | 0.83 |
| 554 | S554T | 0.82 |
| 554 | S554V | 0.70 |
| 554 | S554W | 0.80 |
| 555 | D555S | 0.23 |
| 556 | K556A | 0.80 |
| 556 | K556W | 0.37 |
| 557 | Q557F | 0.90 |
| 557 | Q557R | 0.73 |
| 557 | Q557S | 0.83 |
| 558 | L558I | 0.89 |
| 559 | T559A | 0.81 |
| 559 | T559I | 0.88 |
| 561 | Y561R | 0.66 |
| 563 | N563R | 0.85 |
| 563 | N563S | 0.67 |
| 570 | A570K | 0.34 |
| 570 | A570M | 0.59 |
| 570 | A570S | 0.86 |
| 570 | A570T | 0.88 |
| 570 | A570W | 0.62 |
| 571 | V571W | 0.89 |
| 572 | A572S | 0.56 |
| 573 | S573G | 0.78 |
| 573 | S573K | 0.63 |
| 573 | S573Y | 0.81 |
| 574 | S574K | 0.61 |
| 574 | S574Q | 0.66 |
| 574 | S574W | 0.45 |
| 575 | A575M | 0.83 |
| 575 | A575V | 0.63 |
| 576 | W576A | 0.82 |
| 576 | W576F | 0.77 |
| 576 | W576V | 0.78 |
| 576 | W576Y | 0.54 |
| 577 | Y577G | 0.68 |
| 577 | Y577I | 0.86 |
| 577 | Y577L | 0.52 |
| 578 | D578E | 0.89 |
| 578 | D578M | 0.79 |
| 578 | D578N | 0.64 |
| 579 | V579E | 0.71 |
| 579 | V579G | 0.52 |
| 579 | V579L | 0.78 |
| 579 | V579T | 0.62 |
| 580 | V580A | 0.77 |
| 580 | V580E | 0.89 |
| 580 | V580K | 0.67 |
| 580 | V580L | 0.77 |
| 580 | V580S | 0.70 |
| 581 | Q581F | 0.75 |
| 581 | Q581G | 0.70 |
| 581 | Q581P | 0.77 |
| 581 | Q581R | 0.80 |
| 581 | Q581S | 0.73 |
| 582 | R582D | 0.89 |
| 582 | R582Y | 0.71 |
| 584 | F584E | 0.67 |
| 585 | V585I | 0.57 |
| 585 | V585M | 0.78 |
| 585 | V585Q | 0.81 |
| 586 | A586C | 0.82 |
| 586 | A586H | 0.79 |
| 586 | A586K | 0.48 |
| 587 | G587A | 0.71 |
| 587 | G587C | 0.62 |
| 588 | T588C | 0.71 |
| 588 | T588D | 0.52 |
| 588 | T588G | 0.87 |
| 588 | T588I | 0.61 |
| 588 | T588L | 0.76 |
| 588 | T588M | 0.77 |
| 589 | Y589A | 0.82 |
| 589 | Y589V | 0.69 |
| 589 | Y589W | 0.60 |
| 590 | V590A | 0.75 |
| 590 | V590H | 0.66 |
| 590 | V590I | 0.87 |
| 592 | T592C | 0.50 |
| 592 | T592Q | 0.81 |
| 592 | T592S | 0.32 |
| 593 | G593I | 0.79 |
| 594 | F594I | 0.81 |
| 594 | F594L | 0.34 |
| 594 | F594M | 0.81 |
| 595 | D595E | 0.68 |
| 595 | D595Q | 0.49 |
| 595 | D595S | 0.68 |
| 597 | L597C | 0.89 |
| 597 | L597E | 0.78 |
| 606 | T606S | 0.68 |
| 607 | G607A | 0.88 |
| 608 | S608M | 0.84 |
| 608 | S608V | 0.11 |
| 609 | G609H | 0.84 |
| 609 | G609L | 0.78 |
| 609 | G609N | 0.44 |
| 609 | G609R | 0.25 |
| 610 | A610D | 0.83 |

TABLE 2-continued

Variants having a GI-IF of at most 0.9

| Position | Mutation | GI-IF |
|---|---|---|
| 610 | A610F | 0.75 |
| 610 | A610M | 0.57 |
| 611 | V611K | 0.54 |
| 612 | G612N | 0.72 |
| 612 | G612T | 0.76 |
| 614 | W614F | 0.90 |
| 614 | W614P | 0.69 |
| 615 | P615L | 0.75 |
| 615 | P615S | 0.87 |
| 616 | S616A | 0.84 |
| 616 | S616W | 0.75 |
| 619 | N619A | 0.79 |
| 620 | S620G | 0.59 |
| 624 | I624A | 0.76 |
| 624 | I624V | 0.87 |
| 627 | T627F | 0.81 |
| 627 | T627G | 0.84 |
| 630 | F630A | 0.86 |
| 630 | F630D | 0.64 |
| 630 | F630G | 0.32 |
| 630 | F630S | 0.81 |
| 631 | P631A | 0.68 |
| 631 | P631G | 0.82 |
| 631 | P631H | 0.86 |
| 631 | P631S | 0.88 |
| 631 | P631V | 0.79 |
| 632 | K632T | 0.75 |
| 634 | T634A | 0.80 |
| 634 | T634E | 0.71 |
| 635 | Y635R | 0.57 |
| 638 | Y638A | 0.78 |
| 638 | Y638W | 0.71 |
| 639 | Q639D | 0.86 |
| 639 | Q639N | 0.90 |
| 640 | S640C | 0.89 |
| 640 | S640D | 0.90 |
| 641 | Q641T | 0.85 |
| 642 | W642I | 0.85 |
| 644 | D644C | 0.33 |
| 644 | D644G | 0.86 |
| 650 | H650E | 0.62 |
| 650 | H650R | 0.19 |
| 651 | I651F | 0.82 |
| 654 | A654K | 0.73 |
| 654 | A654M | 0.78 |
| 656 | N656A | 0.90 |
| 656 | N656V | 0.46 |
| 659 | V659D | 0.83 |
| 659 | V659N | 0.71 |
| 669 | P669F | 0.88 |
| 670 | V670C | 0.10 |
| 673 | Y673E | 0.75 |
| 673 | Y673G | 0.79 |
| 673 | Y673I | 0.80 |
| 673 | Y673R | 0.67 |
| 673 | Y673W | 0.89 |
| 674 | T674C | 0.80 |
| 674 | T674G | 0.85 |
| 674 | T674H | 0.83 |
| 675 | D675E | 0.83 |
| 675 | D675P | 0.66 |
| 675 | D675Q | 0.73 |
| 675 | D675S | 0.80 |
| 676 | A676C | 0.71 |
| 676 | A676E | 0.71 |
| 676 | A676G | 0.86 |
| 676 | A676K | 0.89 |
| 676 | A676S | 0.83 |
| 676 | A676W | 0.83 |
| 677 | A677E | 0.74 |
| 677 | A677G | 0.67 |
| 677 | A677L | 0.86 |
| 677 | A677R | 0.87 |
| 677 | A677V | 0.81 |
| 677 | A677Y | 0.85 |
| 678 | K678A | 0.71 |
| 678 | K678C | 0.87 |
| 678 | K678T | 0.67 |
| 678 | K678V | 0.89 |
| 679 | V679G | 0.64 |
| 679 | V679T | 0.87 |
| 679 | V679Y | 0.72 |
| 680 | K680A | 0.89 |
| 680 | K680E | 0.80 |
| 680 | K680G | 0.89 |
| 680 | K680H | 0.78 |
| 680 | K680L | 0.84 |
| 680 | K680Q | 0.88 |
| 680 | K680S | 0.86 |
| 680 | K680V | 0.74 |
| 680 | K680W | 0.84 |
| 681 | L681E | 0.72 |
| 681 | L681F | 0.64 |
| 681 | L681G | 0.83 |
| 681 | L681M | 0.90 |
| 681 | L681S | 0.75 |
| 681 | L681T | 0.80 |
| 682 | Y682D | 0.87 |
| 682 | Y682E | 0.74 |
| 682 | Y682I | 0.89 |
| 682 | Y682M | 0.88 |
| 682 | Y682S | 0.84 |
| 682 | Y682W | 0.84 |
| 683 | F683H | 0.83 |
| 683 | F683L | 0.90 |
| 683 | F683M | 0.73 |
| 683 | F683Q | 0.70 |
| 683 | F683R | 0.85 |
| 684 | T684A | 0.87 |
| 684 | T684D | 0.89 |
| 684 | T684G | 0.69 |
| 684 | T684L | 0.87 |
| 684 | T684S | 0.83 |
| 684 | T684V | 0.54 |
| 685 | P685A | 0.80 |
| 685 | P685E | 0.82 |
| 685 | P685I | 0.80 |
| 685 | P685L | 0.85 |
| 685 | P685W | 0.84 |
| 686 | K686A | 0.89 |
| 686 | K686I | 0.80 |
| 686 | K686M | 0.79 |
| 686 | K686T | 0.85 |
| 686 | K686V | 0.84 |
| 687 | G687A | 0.78 |
| 687 | G687K | 0.82 |
| 687 | G687N | 0.88 |
| 687 | G687Q | 0.79 |
| 687 | G687R | 0.74 |
| 688 | S688C | 0.90 |
| 688 | S688D | 0.85 |
| 688 | S688E | 0.74 |
| 688 | S688G | 0.81 |
| 688 | S688P | 0.88 |
| 688 | S688T | 0.79 |
| 689 | T689A | 0.86 |
| 689 | T689D | 0.78 |
| 689 | T689E | 0.85 |
| 689 | T689L | 0.84 |
| 689 | T689P | 0.74 |
| 689 | T689S | 0.87 |
| 689 | T689Y | 0.88 |
| 690 | E690M | 0.87 |
| 690 | E690P | 0.89 |
| 690 | E690T | 0.88 |
| 690 | E690V | 0.73 |
| 691 | K691N | 0.83 |
| 691 | K691S | 0.84 |
| 693 | L693A | 0.88 |
| 696 | E696A | 0.77 |
| 696 | E696L | 0.86 |
| 697 | K697E | 0.80 |

TABLE 2-continued

Variants having a GI-IF of at most 0.9

| Position | Mutation | GI-IF |
|---|---|---|
| 698 | S698C | 0.89 |
| 698 | S698I | 0.77 |
| 698 | S698L | 0.70 |
| 698 | S698P | 0.87 |
| 698 | S698T | 0.73 |
| 700 | T700C | 0.33 |
| 700 | T700E | 0.81 |
| 700 | T700G | 0.84 |
| 700 | T700K | 0.85 |
| 701 | K701E | 0.89 |
| 701 | K701W | 0.89 |
| 703 | T703E | 0.89 |
| 703 | T703I | 0.80 |
| 703 | T703W | 0.82 |
| 704 | T704M | 0.70 |
| 704 | T704R | 0.90 |
| 704 | T704Y | 0.66 |
| 705 | A705C | 0.77 |
| 705 | A705E | 0.61 |
| 705 | A705N | 0.75 |
| 705 | A705V | 0.89 |
| 706 | A706G | 0.89 |
| 706 | A706Y | 0.72 |
| 708 | Y708C | 0.78 |
| 708 | Y708G | 0.82 |
| 708 | Y708K | 0.86 |
| 708 | Y708P | 0.88 |
| 708 | Y708T | 0.80 |
| 709 | T709M | 0.50 |
| 710 | Y710C | 0.84 |
| 710 | Y710D | 0.66 |
| 710 | Y710G | 0.80 |
| 710 | Y710M | 0.82 |
| 710 | Y710N | 0.71 |
| 710 | Y710W | 0.68 |
| 711 | Q711G | 0.87 |
| 711 | Q711L | 0.73 |
| 711 | Q711M | 0.78 |
| 711 | Q711Y | 0.68 |
| 712 | V712G | 0.86 |
| 712 | V712R | 0.87 |
| 713 | Y713A | 0.81 |
| 713 | Y713L | 0.83 |
| 713 | Y713Q | 0.88 |
| 714 | E714D | 0.83 |
| 714 | E714M | 0.90 |
| 714 | E714R | 0.81 |
| 714 | E714S | 0.80 |
| 714 | E714V | 0.79 |
| 714 | E714Y | 0.85 |
| 716 | A716C | 0.80 |
| 716 | A716G | 0.89 |
| 716 | A716L | 0.79 |
| 716 | A716V | 0.80 |
| 717 | D717C | 0.76 |
| 718 | K718L | 0.79 |
| 719 | D719L | 0.87 |
| 719 | D719P | 0.89 |
| 724 | K724R | 0.86 |
| 725 | N725D | 0.88 |
| 726 | M726A | 0.82 |
| 726 | M726E | 0.84 |
| 726 | M726K | 0.83 |
| 726 | M726V | 0.75 |
| 726 | M726W | 0.81 |
| 727 | Y727T | 0.85 |
| 728 | L728Q | 0.89 |
| 728 | L728T | 0.86 |
| 730 | W730A | 0.89 |
| 731 | N731A | 0.88 |
| 731 | N731S | 0.30 |
| 731 | N731Y | 0.86 |
| 732 | V732G | 0.82 |
| 732 | V732P | 0.83 |
| 732 | V732W | 0.78 |
| 733 | P733A | 0.83 |
| 733 | P733R | 0.73 |
| 734 | W734D | 0.84 |
| 734 | W734V | 0.28 |
| 735 | A735W | 0.80 |
| 736 | E736S | 0.88 |
| 738 | T738G | 0.89 |
| 739 | I739M | 0.89 |
| 739 | I739W | 0.87 |
| 739 | I739Y | 0.87 |
| 740 | S740E | 0.88 |
| 740 | S740H | 0.90 |
| 740 | S740L | 0.89 |
| 742 | E742D | 0.84 |
| 742 | E742M | 0.89 |
| 742 | E742Q | 0.80 |
| 743 | A743C | 0.86 |
| 743 | A743H | 0.85 |
| 743 | A743L | 0.86 |
| 744 | Y744A | 0.87 |
| 744 | Y744E | 0.84 |
| 744 | Y744I | 0.88 |
| 744 | Y744K | 0.90 |
| 745 | D745F | 0.16 |
| 746 | E746A | 0.82 |
| 747 | N747G | 0.86 |
| 747 | N747R | 0.65 |
| 748 | N748S | 0.88 |
| 749 | R749H | 0.90 |
| 749 | R749S | 0.84 |
| 749 | R749T | 0.88 |
| 750 | L750G | 0.85 |
| 751 | I751Q | 0.90 |
| 751 | I751S | 0.88 |
| 752 | P752A | 0.51 |
| 752 | P752H | 0.89 |
| 752 | P752L | 0.89 |
| 752 | P752S | 0.81 |
| 752 | P752V | 0.82 |
| 753 | E753Q | 0.89 |
| 754 | G754P | 0.45 |
| 755 | S755C | 0.84 |
| 755 | S755I | 0.83 |
| 756 | T756E | 0.83 |
| 756 | T756P | 0.86 |
| 756 | T756S | 0.55 |
| 756 | T756W | 0.86 |
| 758 | G758A | 0.84 |
| 759 | N759D | 0.87 |
| 759 | N759R | 0.88 |
| 760 | A760N | 0.53 |
| 760 | A760P | 0.87 |
| 760 | A760Q | 0.84 |
| 761 | S761K | 0.84 |
| 761 | S761Q | 0.90 |
| 762 | V762D | 0.84 |
| 762 | V762G | 0.84 |
| 762 | V762K | 0.90 |
| 765 | T765A | 0.82 |
| 765 | T765R | 0.89 |
| 765 | T765W | 0.86 |
| 766 | G766S | 0.89 |
| 768 | A768H | 0.87 |
| 771 | L771I | 0.71 |
| 772 | K772V | 0.62 |
| 773 | A773G | 0.82 |
| 773 | A773H | 0.51 |
| 773 | A773S | 0.77 |
| 773 | A773V | 0.51 |
| 774 | D774R | 0.66 |
| 775 | A775L | 0.36 |
| 775 | A775W | 0.26 |
| 776 | D776I | 0.18 |
| 776 | D776L | 0.26 |
| 776 | D776S | 0.46 |
| 777 | R777D | 0.31 |
| 777 | R777E | 0.52 |

TABLE 2-continued

Variants having a GI-IF of at most 0.9

| Position | Mutation | GI-IF |
|---|---|---|
| 777 | R777G | 0.36 |
| 777 | R777P | 0.31 |
| 778 | K778A | 0.73 |
| 778 | K778C | 0.83 |
| 778 | K778L | 0.68 |
| 779 | T779C | 0.86 |
| 780 | I780V | 0.70 |
| 781 | T781C | 0.79 |
| 781 | T781M | 0.68 |
| 781 | T781R | 0.73 |
| 782 | A782E | 0.74 |
| 782 | A782K | 0.72 |
| 782 | A782P | 0.64 |
| 783 | D783C | 0.26 |
| 783 | D783E | 0.13 |
| 783 | D783R | 0.21 |
| 784 | G784A | 0.77 |
| 784 | G784F | 0.84 |
| 784 | G784L | 0.02 |
| 784 | G784S | 0.55 |
| 784 | G784T | 0.61 |
| 786 | D786S | 0.88 |
| 787 | L787P | 0.38 |
| 787 | L787T | 0.57 |
| 787 | L787Y | 0.85 |
| 788 | S788A | 0.72 |
| 788 | S788G | 0.62 |
| 788 | S788I | 0.62 |
| 789 | Y789C | 0.85 |
| 789 | Y789D | 0.86 |
| 789 | Y789I | 0.82 |
| 790 | I790A | 0.71 |
| 790 | I790C | 0.68 |
| 790 | I790F | 0.78 |
| 791 | E791A | 0.90 |
| 791 | E791M | 0.89 |
| 791 | E791T | 0.75 |
| 792 | V792C | 0.88 |
| 792 | V792G | 0.36 |
| 792 | V792L | 0.84 |
| 793 | D793F | 0.89 |
| 793 | D793H | 0.48 |
| 793 | D793K | 0.79 |
| 793 | D793N | 0.83 |
| 794 | V794C | 0.63 |
| 794 | V794L | 0.89 |
| 794 | V794Q | 0.80 |
| 794 | V794T | 0.33 |
| 794 | V794W | 0.65 |
| 795 | T795P | 0.44 |
| 795 | T795Y | 0.85 |
| 796 | D796M | 0.83 |
| 796 | D796Q | 0.70 |
| 797 | A797K | 0.87 |
| 798 | N798G | 0.83 |
| 798 | N798P | 0.87 |
| 799 | G799M | 0.42 |
| 799 | G799Q | 0.59 |
| 800 | H800A | 0.53 |
| 800 | H800L | 0.55 |
| 800 | H800S | 0.89 |
| 801 | I801C | 0.76 |
| 801 | I801E | 0.86 |
| 802 | V802P | 0.81 |
| 803 | P803A | 0.86 |
| 803 | P803F | 0.74 |
| 803 | P803K | 0.79 |
| 804 | D804G | 0.66 |
| 804 | D804K | 0.72 |
| 804 | D804N | 0.83 |
| 804 | D804S | 0.74 |
| 805 | A805G | 0.89 |
| 807 | N807Q | 0.71 |
| 807 | N807V | 0.85 |
| 807 | N807W | 0.67 |
| 808 | R808C | 0.54 |
| 808 | R808N | 0.69 |
| 808 | R808Q | 0.75 |
| 809 | V809A | 0.83 |
| 809 | V809C | 0.74 |
| 811 | F811Y | 0.79 |
| 812 | D812E | 0.84 |
| 812 | D812F | 0.88 |
| 812 | D812I | 0.88 |
| 812 | D812Q | 0.69 |
| 813 | V813F | 0.88 |
| 813 | V813T | 0.57 |
| 814 | K814H | 0.11 |
| 814 | K814I | 0.82 |
| 814 | K814L | 0.69 |
| 815 | G815A | 0.48 |
| 815 | G815V | 0.66 |
| 816 | A816C | 0.41 |
| 816 | A816F | 0.47 |
| 816 | A816I | 0.89 |
| 816 | A816V | 0.79 |
| 817 | G817C | 0.89 |
| 817 | G817I | 0.80 |
| 817 | G817N | 0.80 |
| 817 | G817S | 0.84 |
| 818 | K818V | 0.87 |
| 819 | L819W | 0.82 |
| 820 | V820F | 0.87 |
| 820 | V820I | 0.87 |
| 820 | V820K | 0.69 |
| 821 | G821A | 0.80 |
| 821 | G821C | 0.88 |
| 821 | G821E | 0.52 |
| 821 | G821F | 0.68 |
| 821 | G821K | 0.87 |
| 821 | G821M | 0.87 |
| 821 | G821N | 0.67 |
| 821 | G821V | 0.78 |
| 821 | G821Y | 0.87 |
| 824 | N824C | 0.88 |
| 824 | N824G | 0.83 |
| 824 | N824Q | 0.85 |
| 826 | S826F | 0.74 |
| 826 | S826L | 0.36 |
| 826 | S826R | 0.77 |
| 827 | S827C | 0.81 |
| 827 | S827Q | 0.78 |
| 828 | P828C | 0.69 |
| 828 | P828I | 0.85 |
| 828 | P828L | 0.87 |
| 828 | P828Y | 0.77 |
| 829 | D829T | 0.90 |
| 829 | D829V | 0.90 |
| 830 | H830E | 0.63 |
| 830 | H830G | 0.71 |
| 830 | H830M | 0.76 |
| 830 | H830P | 0.78 |
| 830 | H830R | 0.35 |
| 830 | H830V | 0.69 |
| 831 | D831F | 0.64 |
| 831 | D831G | 0.82 |
| 831 | D831I | 0.59 |
| 831 | D831R | 0.70 |
| 831 | D831V | 0.60 |
| 832 | S832E | 0.87 |
| 832 | S832F | 0.84 |
| 832 | S832G | 0.76 |
| 832 | S832L | 0.73 |
| 832 | S832M | 0.79 |
| 832 | S832V | 0.89 |
| 833 | Y833I | 0.74 |
| 833 | Y833K | 0.69 |
| 833 | Y833P | 0.76 |
| 833 | Y833V | 0.69 |
| 834 | Q834F | 0.77 |
| 834 | Q834G | 0.82 |
| 835 | A835E | 0.63 |

TABLE 2-continued

Variants having a GI-IF of at most 0.9

| Position | Mutation | GI-IF |
|---|---|---|
| 835 | A835F | 0.90 |
| 835 | A835W | 0.57 |
| 836 | D836H | 0.44 |
| 836 | D836W | 0.74 |
| 837 | N837D | 0.61 |
| 837 | N837F | 0.90 |
| 837 | N837G | 0.71 |
| 837 | N837H | 0.78 |
| 837 | N837L | 0.74 |
| 837 | N837P | 0.87 |
| 837 | N837T | 0.84 |
| 838 | R838D | 0.88 |
| 838 | R838F | 0.86 |
| 838 | R838G | 0.57 |
| 838 | R838K | 0.87 |
| 838 | R838M | 0.61 |
| 838 | R838W | 0.77 |
| 839 | K839C | 0.90 |
| 839 | K839E | 0.71 |
| 839 | K839G | 0.88 |
| 839 | K839P | 0.88 |
| 839 | K839R | 0.83 |
| 841 | F841C | 0.69 |
| 841 | F841D | 0.88 |
| 841 | F841W | 0.66 |
| 842 | S842L | 0.86 |
| 842 | S842M | 0.75 |
| 843 | G843A | 0.85 |
| 843 | G843C | 0.77 |
| 844 | K844G | 0.18 |
| 844 | K844L | 0.89 |
| 844 | K844W | 0.82 |
| 845 | V845N | 0.79 |
| 845 | V845W | 0.68 |
| 846 | L846G | 0.83 |
| 846 | L846I | 0.79 |
| 846 | L846M | 0.72 |
| 846 | L846S | 0.89 |
| 847 | A847L | 0.87 |
| 849 | V849A | 0.78 |
| 849 | V849L | 0.65 |
| 849 | V849S | 0.65 |
| 849 | V849T | 0.84 |
| 850 | Q850C | 0.57 |
| 850 | Q850G | 0.47 |
| 850 | Q850I | 0.90 |
| 850 | Q850T | 0.87 |
| 850 | Q850V | 0.89 |
| 850 | Q850Y | 0.62 |
| 851 | S851L | 0.86 |
| 852 | T852D | 0.88 |
| 852 | T852G | 0.88 |
| 853 | K853N | 0.75 |
| 853 | K853Q | 0.75 |
| 853 | K853V | 0.81 |
| 854 | E854M | 0.83 |
| 854 | E854R | 0.81 |
| 857 | E857P | 0.68 |
| 857 | E857V | 0.84 |
| 858 | I858E | 0.75 |
| 858 | I858F | 0.85 |
| 858 | I858M | 0.77 |
| 858 | I858Q | 0.54 |
| 858 | I858Y | 0.53 |
| 859 | T859V | 0.70 |
| 860 | V860T | 0.68 |
| 862 | A862P | 0.84 |
| 862 | A862V | 0.69 |
| 863 | K863F | 0.60 |
| 863 | K863I | 0.72 |
| 863 | K863L | 0.86 |
| 863 | K863N | 0.54 |
| 863 | K863W | 0.65 |
| 864 | A864E | 0.86 |
| 864 | A864H | 0.89 |
| 864 | A864L | 0.74 |
| 870 | S870R | 0.50 |
| 871 | T871P | 0.72 |
| 877 | T877A | 0.67 |
| 879 | V879P | 0.83 |
| 880 | P880S | 0.73 |
| 881 | G881W | 0.64 |
| 884 | T884A | 0.67 |
| 886 | K886E | 0.69 |
| 887 | T887F | 0.54 |
| 887 | T887R | 0.89 |
| 887 | T887V | 0.78 |
| 888 | V888D | 0.76 |
| 888 | V888G | 0.88 |
| 892 | Y892D | 0.80 |
| 892 | Y892R | 0.57 |
| 895 | R895M | 0.87 |
| 896 | N896M | 0.64 |
| 899 | V899G | 0.74 |
| 901 | T901G | 0.64 |
| 901 | T901V | 0.42 |
| 902 | G902L | 0.67 |
| 906 | I906D | 0.83 |
| 906 | I906S | 0.73 |
| 906 | I906Y | 0.76 |
| 907 | L907Y | 0.80 |
| 908 | P908M | 0.89 |
| 910 | D910C | 0.87 |
| 910 | D910S | 0.89 |
| 911 | V911S | 0.84 |
| 913 | V913Q | 0.71 |
| 913 | V913W | 0.85 |
| 918 | G918W | 0.85 |
| 919 | T919Y | 0.78 |
| 920 | S920C | 0.83 |
| 920 | S920E | 0.68 |
| 920 | S920M | 0.81 |
| 920 | S920R | 0.85 |
| 920 | S920W | 0.80 |
| 921 | D921P | 0.84 |
| 921 | D921Q | 0.74 |
| 922 | R922G | 0.78 |
| 923 | Q923C | 0.81 |
| 923 | Q923W | 0.89 |
| 924 | N924A | 0.86 |
| 924 | N924L | 0.74 |
| 924 | N924P | 0.84 |
| 924 | N924W | 0.86 |
| 925 | V925A | 0.75 |
| 925 | V925S | 0.79 |
| 926 | T926G | 0.66 |
| 926 | T926S | 0.80 |
| 926 | T926V | 0.84 |
| 926 | T926W | 0.80 |
| 927 | W927C | 0.77 |
| 927 | W927G | 0.56 |
| 928 | D928E | 0.86 |
| 928 | D928L | 0.84 |
| 929 | A929C | 0.78 |
| 929 | A929V | 0.81 |
| 930 | V930A | 0.78 |
| 930 | V930K | 0.81 |
| 930 | V930M | 0.87 |
| 931 | S931G | 0.74 |
| 932 | D932F | 0.80 |
| 932 | D932R | 0.83 |
| 932 | D932S | 0.74 |
| 932 | D932T | 0.80 |
| 932 | D932V | 0.70 |
| 933 | D933I | 0.76 |
| 933 | D933S | 0.87 |
| 937 | K937R | 0.79 |
| 937 | K937V | 0.85 |
| 940 | S940M | 0.82 |
| 940 | S940T | 0.58 |
| 940 | S940W | 0.76 |
| 941 | F941W | 0.71 |

TABLE 2-continued

Variants having a GI-IF of at most 0.9

| Position | Mutation | GI-IF |
|---|---|---|
| 942 | S942L | 0.77 |
| 942 | S942T | 0.88 |
| 943 | V943H | 0.38 |
| 943 | V943R | 0.25 |
| 944 | A944D | 0.70 |
| 944 | A944G | 0.85 |
| 944 | A944H | 0.62 |
| 944 | A944P | 0.24 |
| 944 | A944R | 0.63 |
| 944 | A944V | 0.83 |
| 945 | G945E | 0.85 |
| 945 | G945P | 0.83 |
| 945 | G945T | 0.78 |
| 946 | T946E | 0.85 |
| 946 | T946G | 0.75 |
| 946 | T946V | 0.34 |
| 947 | V947H | 0.86 |
| 947 | V947M | 0.68 |
| 948 | A948C | 0.58 |
| 948 | A948R | 0.62 |
| 949 | G949F | 0.82 |
| 950 | Q950D | 0.59 |
| 950 | Q950G | 0.76 |
| 950 | Q950M | 0.82 |
| 951 | K951Q | 0.79 |
| 952 | I952H | 0.70 |
| 953 | S953W | 0.69 |
| 954 | V954L | 0.87 |
| 954 | V954S | 0.88 |
| 954 | V954T | 0.72 |
| 955 | R955E | 0.88 |
| 958 | M958D | 0.66 |
| 958 | M958I | 0.72 |
| 958 | M958K | 0.85 |
| 960 | D960G | 0.83 |
| 960 | D960H | 0.73 |
| 960 | D960L | 0.74 |
| 960 | D960W | 0.86 |
| 961 | E961P | 0.85 |
| 962 | I962Q | 0.89 |
| 962 | I962T | 0.89 |
| 963 | G963L | 0.86 |
| 964 | A964C | 0.81 |
| 964 | A964E | 0.89 |
| 964 | A964H | 0.89 |
| 966 | L966G | 0.75 |
| 966 | L966H | 0.69 |
| 966 | L966P | 0.78 |
| 966 | L966T | 0.77 |
| 967 | N967C | 0.83 |
| 967 | N967S | 0.72 |
| 971 | S971E | 0.89 |
| 971 | S971F | 0.87 |
| 971 | S971H | 0.73 |
| 975 | G975D | 0.89 |
| 975 | G975L | 0.83 |
| 975 | G975Q | 0.78 |
| 975 | G975V | 0.90 |
| 976 | T976Y | 0.86 |
| 977 | P977A | 0.86 |
| 978 | A978P | 0.86 |
| 979 | V979R | 0.53 |
| 982 | G982A | 0.80 |
| 982 | G982H | 0.88 |
| 982 | G982M | 0.86 |
| 982 | G982P | 0.78 |
| 982 | G982Q | 0.74 |
| 982 | G982W | 0.88 |
| 984 | R984S | 0.88 |
| 985 | P985E | 0.74 |
| 986 | A986E | 0.85 |
| 986 | A986F | 0.85 |
| 986 | A986K | 0.88 |
| 986 | A986N | 0.76 |
| 986 | A986S | 0.89 |
| 987 | V987I | 0.86 |
| 987 | V987L | 0.90 |
| 987 | V987Q | 0.85 |
| 987 | V987T | 0.83 |
| 988 | L988A | 0.85 |
| 988 | L988C | 0.88 |
| 988 | L988E | 0.77 |
| 988 | L988G | 0.79 |
| 988 | L988H | 0.82 |
| 988 | L988M | 0.87 |
| 988 | L988Q | 0.87 |
| 988 | L988R | 0.86 |
| 988 | L988S | 0.75 |
| 988 | L988Y | 0.86 |
| 989 | P989A | 0.75 |
| 989 | P989C | 0.87 |
| 989 | P989D | 0.89 |
| 989 | P989G | 0.90 |
| 989 | P989H | 0.89 |
| 989 | P989I | 0.82 |
| 989 | P989N | 0.86 |
| 989 | P989Q | 0.84 |
| 990 | D990S | 0.86 |
| 992 | T992E | 0.89 |
| 992 | T992H | 0.87 |
| 992 | T992Y | 0.88 |
| 993 | V993D | 0.89 |
| 993 | V993N | 0.86 |
| 993 | V993S | 0.84 |
| 994 | T994I | 0.85 |
| 994 | T994S | 0.79 |
| 994 | T994V | 0.87 |
| 995 | S995V | 0.79 |
| 996 | A996Q | 0.77 |
| 996 | A996V | 0.76 |
| 997 | N997A | 0.75 |
| 997 | N997C | 0.83 |
| 997 | N997E | 0.78 |
| 997 | N997L | 0.72 |
| 997 | N997S | 0.82 |
| 997 | N997W | 0.87 |
| 997 | N997Y | 0.71 |
| 999 | A999F | 0.90 |
| 999 | A999G | 0.63 |
| 999 | A999L | 0.85 |
| 999 | A999M | 0.79 |
| 999 | A999R | 0.78 |
| 999 | A999S | 0.76 |
| 1000 | V1000C | 0.79 |
| 1000 | V1000L | 0.78 |
| 1000 | V1000M | 0.71 |
| 1000 | V1000N | 0.67 |
| 1000 | V1000P | 0.88 |
| 1001 | D1001G | 0.79 |
| 1001 | D1001K | 0.79 |
| 1001 | D1001M | 0.82 |
| 1001 | D1001Q | 0.85 |
| 1001 | D1001T | 0.77 |
| 1001 | D1001V | 0.77 |
| 1001 | D1001Y | 0.88 |
| 1003 | T1003L | 0.62 |
| 1003 | T1003P | 0.79 |
| 1004 | K1004F | 0.77 |
| 1004 | K1004G | 0.89 |
| 1004 | K1004H | 0.54 |
| 1004 | K1004M | 0.83 |
| 1004 | K1004P | 0.78 |
| 1004 | K1004R | 0.75 |
| 1004 | K1004V | 0.80 |
| 1005 | P1005Q | 0.87 |
| 1006 | A1006I | 0.76 |
| 1009 | V1009G | 0.79 |
| 1009 | V1009S | 0.86 |
| 1012 | T1012E | 0.86 |
| 1012 | T1012Y | 0.85 |
| 1013 | A1013K | 0.87 |
| 1013 | A1013T | 0.88 |

TABLE 2-continued

Variants having a GI-IF of at most 0.9

| Position | Mutation | GI-IF |
|---|---|---|
| 1014 | G1014E | 0.87 |
| 1014 | G1014L | 0.80 |
| 1014 | G1014Y | 0.90 |
| 1015 | T1015F | 0.83 |
| 1015 | T1015G | 0.79 |
| 1015 | T1015V | 0.88 |
| 1016 | V1016C | 0.79 |
| 1018 | V1018I | 0.83 |
| 1018 | V1018M | 0.85 |
| 1018 | V1018W | 0.88 |
| 1021 | T1021F | 0.67 |
| 1021 | T1021K | 0.86 |
| 1021 | T1021L | 0.89 |
| 1021 | T1021S | 0.89 |
| 1021 | T1021V | 0.75 |
| 1022 | A1022L | 0.76 |
| 1022 | A1022S | 0.84 |
| 1022 | A1022Y | 0.88 |
| 1023 | T1023D | 0.78 |
| 1023 | T1023M | 0.89 |
| 1023 | T1023Q | 0.88 |
| 1023 | T1023R | 0.85 |
| 1024 | V1024E | 0.81 |
| 1024 | V1024N | 0.76 |
| 1026 | G1026H | 0.86 |
| 1026 | G1026L | 0.72 |
| 1026 | G1026R | 0.58 |
| 1027 | K1027C | 0.80 |
| 1027 | K1027N | 0.76 |
| 1027 | K1027V | 0.85 |
| 1028 | E1028S | 0.88 |
| 1029 | F1029L | 0.84 |
| 1029 | F1029W | 0.85 |
| 1029 | F1029Y | 0.88 |
| 1030 | K1030F | 0.86 |
| 1030 | K1030L | 0.89 |
| 1031 | V1031Y | 0.84 |
| 1033 | A1033G | 0.84 |
| 1033 | A1033S | 0.88 |
| 1034 | T1034W | 0.82 |
| 1037 | V1037F | 0.73 |
| 1037 | V1037P | 0.90 |
| 1037 | V1037Q | 0.83 |
| 1038 | Q1038A | 0.87 |
| 1038 | Q1038K | 0.87 |
| 1039 | R1039S | 0.88 |
| 1040 | S1040A | 0.87 |
| 1040 | S1040N | 0.84 |
| 1040 | S1040R | 0.90 |
| 1040 | S1040W | 0.86 |
| 1043 | T1043N | 0.89 |
| 1045 | G1045S | 0.84 |
| 1046 | S1046I | 0.82 |
| 1047 | S1047D | 0.88 |
| 1050 | G1050L | 0.84 |
| 1050 | G1050S | 0.45 |
| 1050 | G1050V | 0.90 |
| 1052 | A1052M | 0.87 |
| 1052 | A1052P | 0.87 |
| 1054 | R1054N | 0.89 |
| 1057 | Q1057R | 0.50 |
| 1058 | N1058V | 0.62 |
| 1058 | N1058W | 0.84 |
| 1059 | I1059W | 0.69 |
| 1060 | P1060S | 0.82 |
| 1060 | P1060T | 0.72 |
| 1061 | A1061E | 0.82 |
| 1062 | D1062F | 0.83 |
| 1062 | D1062L | 0.66 |
| 1062 | D1062P | 0.87 |
| 1062 | D1062S | 0.87 |
| 1063 | K1063D | 0.71 |
| 1064 | Q1064C | 0.84 |
| 1065 | S1065E | 0.73 |
| 1065 | S1065G | 0.83 |
| 1065 | S1065T | 0.86 |
| 1065 | S1065W | 0.87 |
| 1066 | D1066M | 0.64 |
| 1066 | D1066W | 0.31 |
| 1068 | L1068C | 0.31 |
| 1068 | L1068E | 0.82 |
| 1069 | D1069G | 0.87 |
| 1069 | D1069K | 0.81 |
| 1069 | D1069W | 0.82 |
| 1070 | A1070P | 0.69 |
| 1071 | I1071R | 0.77 |
| 1071 | I1071W | 0.54 |
| 1072 | K1072E | 0.75 |
| 1072 | K1072G | 0.56 |
| 1072 | K1072Q | 0.57 |
| 1073 | D1073L | 0.78 |
| 1073 | D1073M | 0.81 |
| 1073 | D1073P | 0.65 |
| 1074 | G1074I | 0.65 |
| 1075 | S1075C | 0.69 |
| 1075 | S1075I | 0.88 |
| 1075 | S1075V | 0.82 |
| 1076 | T1076C | 0.81 |
| 1076 | T1076H | 0.72 |
| 1076 | T1076Q | 0.79 |
| 1077 | T1077K | 0.90 |
| 1077 | T1077L | 0.88 |
| 1078 | V1078E | 0.88 |
| 1078 | V1078L | 0.77 |
| 1081 | N1081D | 0.84 |
| 1081 | N1081G | 0.89 |
| 1082 | T1082A | 0.82 |
| 1082 | T1082C | 0.81 |
| 1082 | T1082N | 0.88 |
| 1082 | T1082S | 0.83 |
| 1083 | G1083P | 0.84 |
| 1083 | G1083S | 0.65 |
| 1084 | G1084C | 0.82 |
| 1085 | G1085A | 0.85 |
| 1086 | A1086Q | 0.79 |
| 1086 | A1086T | 0.81 |
| 1087 | N1087V | 0.82 |
| 1087 | N1087W | 0.75 |
| 1089 | S1089C | 0.67 |
| 1089 | S1089E | 0.89 |
| 1089 | S1089R | 0.72 |
| 1090 | A1090G | 0.78 |
| 1090 | A1090I | 0.85 |
| 1090 | A1090K | 0.84 |
| 1091 | W1091A | 0.53 |
| 1091 | W1091E | 0.61 |
| 1091 | W1091G | 0.69 |
| 1091 | W1091H | 0.73 |
| 1091 | W1091T | 0.68 |
| 1091 | W1091V | 0.54 |
| 1092 | T1092A | 0.86 |
| 1092 | T1092E | 0.85 |
| 1092 | T1092G | 0.69 |
| 1092 | T1092K | 0.90 |
| 1092 | T1092Q | 0.59 |
| 1092 | T1092S | 0.75 |
| 1092 | T1092V | 0.77 |
| 1093 | N1093T | 0.70 |
| 1093 | N1093V | 0.76 |
| 1095 | A1095R | 0.89 |
| 1096 | Y1096A | 0.73 |
| 1096 | Y1096H | 0.87 |
| 1096 | Y1096R | 0.88 |
| 1097 | S1097D | 0.87 |
| 1097 | S1097L | 0.74 |
| 1097 | S1097W | 0.36 |
| 1099 | A1099C | 0.74 |
| 1099 | A1099F | 0.81 |
| 1100 | G1100D | 0.87 |
| 1100 | G1100M | 0.69 |
| 1100 | G1100T | 0.76 |
| 1101 | H1101L | 0.85 |

TABLE 2-continued

Variants having a GI-IF of at most 0.9

| Position | Mutation | GI-IF |
|---|---|---|
| 1102 | N1102E | 0.59 |
| 1102 | N1102F | 0.81 |
| 1102 | N1102K | 0.72 |
| 1102 | N1102L | 0.85 |
| 1102 | N1102R | 0.86 |
| 1103 | T1103H | 0.88 |
| 1104 | A1104I | 0.89 |
| 1104 | A1104K | 0.88 |
| 1104 | A1104R | 0.58 |
| 1106 | I1106T | 0.67 |
| 1106 | I1106V | 0.83 |
| 1107 | T1107C | 0.83 |
| 1107 | T1107M | 0.87 |
| 1107 | T1107R | 0.75 |
| 1107 | T1107S | 0.54 |
| 1108 | F1108D | 0.69 |
| 1108 | F1108K | 0.87 |
| 1108 | F1108L | 0.68 |
| 1108 | F1108T | 0.73 |
| 1108 | F1108W | 0.81 |
| 1113 | E1113D | 0.79 |
| 1114 | Q1114I | 0.87 |
| 1115 | Q1115T | 0.81 |
| 1115 | Q1115W | 0.86 |
| 1116 | L1116V | 0.81 |
| 1118 | Q1118A | 0.85 |
| 1118 | Q1118S | 0.82 |
| 1118 | Q1118T | 0.88 |
| 1119 | I1119G | 0.71 |
| 1120 | V1120T | 0.76 |
| 1121 | M1121V | 0.61 |
| 1121 | M1121Y | 0.87 |
| 1122 | Y1122A | 0.86 |
| 1122 | Y1122C | 0.90 |
| 1122 | Y1122I | 0.85 |
| 1122 | Y1122K | 0.71 |
| 1122 | Y1122R | 0.80 |
| 1122 | Y1122V | 0.72 |
| 1122 | Y1122W | 0.85 |
| 1123 | F1123H | 0.89 |
| 1123 | F1123T | 0.78 |
| 1124 | F1124E | 0.88 |
| 1124 | F1124R | 0.85 |
| 1125 | R1125E | 0.79 |
| 1125 | R1125T | 0.85 |
| 1126 | D1126H | 0.68 |
| 1126 | D1126K | 0.83 |
| 1126 | D1126L | 0.77 |
| 1126 | D1126R | 0.85 |
| 1127 | S1127F | 0.75 |
| 1127 | S1127K | 0.77 |
| 1127 | S1127M | 0.87 |
| 1127 | S1127T | 0.88 |
| 1127 | S1127W | 0.76 |
| 1128 | N1128C | 0.86 |
| 1128 | N1128R | 0.70 |
| 1128 | N1128S | 0.74 |
| 1128 | N1128T | 0.83 |
| 1128 | N1128W | 0.73 |
| 1129 | A1129L | 0.77 |
| 1129 | A1129N | 0.87 |
| 1129 | A1129Q | 0.65 |
| 1129 | A1129V | 0.65 |
| 1130 | V1130G | 0.58 |
| 1130 | V1130P | 0.87 |
| 1130 | V1130S | 0.77 |
| 1131 | R1131A | 0.71 |
| 1131 | R1131N | 0.90 |
| 1131 | R1131Q | 0.88 |
| 1131 | R1131S | 0.75 |
| 1132 | F1132E | 0.73 |
| 1132 | F1132K | 0.84 |
| 1132 | F1132T | 0.89 |
| 1133 | P1133Q | 0.87 |
| 1133 | P1133V | 0.84 |
| 1134 | D1134E | 0.89 |
| 1134 | D1134G | 0.74 |
| 1134 | D1134L | 0.64 |
| 1135 | A1135M | 0.88 |
| 1135 | A1135S | 0.61 |
| 1135 | A1135Y | 0.76 |
| 1136 | G1136A | 0.69 |
| 1136 | G1136E | 0.51 |
| 1136 | G1136Q | 0.82 |
| 1136 | G1136T | 0.88 |
| 1137 | K1137A | 0.84 |
| 1137 | K1137C | 0.61 |
| 1137 | K1137L | 0.70 |
| 1137 | K1137Q | 0.69 |
| 1139 | K1139A | 0.88 |
| 1139 | K1139L | 0.80 |
| 1139 | K1139R | 0.90 |
| 1139 | K1139T | 0.86 |
| 1140 | I1140A | 0.86 |
| 1140 | I1140G | 0.64 |
| 1140 | I1140L | 0.61 |
| 1140 | I1140M | 0.85 |
| 1140 | I1140T | 0.81 |
| 1141 | Q1141C | 0.86 |
| 1141 | Q1141P | 0.60 |
| 1141 | Q1141W | 0.78 |
| 1142 | I1142S | 0.89 |
| 1142 | I1142W | 0.87 |
| 1144 | A1144C | 0.68 |
| 1144 | A1144E | 0.87 |
| 1146 | G1146C | 0.88 |
| 1146 | G1146D | 0.78 |
| 1146 | G1146L | 0.80 |
| 1147 | K1147A | 0.84 |
| 1147 | K1147G | 0.89 |
| 1147 | K1147T | 0.76 |
| 1147 | K1147V | 0.70 |
| 1148 | N1148K | 0.88 |
| 1148 | N1148W | 0.86 |
| 1149 | W1149I | 0.66 |
| 1149 | W1149N | 0.80 |
| 1149 | W1149Q | 0.79 |
| 1149 | W1149T | 0.90 |
| 1149 | W1149Y | 0.89 |
| 1150 | T1150G | 0.81 |
| 1151 | D1151G | 0.84 |
| 1151 | D1151R | 0.38 |
| 1151 | D1151T | 0.81 |
| 1153 | A1153K | 0.83 |
| 1154 | A1154C | 0.69 |
| 1154 | A1154G | 0.82 |
| 1154 | A1154S | 0.85 |
| 1155 | T1155E | 0.85 |
| 1155 | T1155L | 0.78 |
| 1155 | T1155Q | 0.86 |
| 1155 | T1155R | 0.87 |
| 1157 | T1157V | 0.85 |
| 1157 | T1157W | 0.90 |
| 1158 | I1158R | 0.76 |
| 1159 | A1159C | 0.85 |
| 1159 | A1159P | 0.90 |
| 1159 | A1159R | 0.76 |
| 1159 | A1159V | 0.75 |
| 1160 | A1160K | 0.82 |
| 1160 | A1160L | 0.87 |
| 1160 | A1160Q | 0.80 |
| 1160 | A1160S | 0.82 |
| 1161 | Q1161A | 0.80 |
| 1162 | E1162D | 0.86 |
| 1162 | E1162F | 0.82 |
| 1162 | E1162I | 0.75 |
| 1162 | E1162N | 0.82 |
| 1162 | E1162T | 0.87 |
| 1162 | E1162Y | 0.73 |
| 1165 | E1165D | 0.78 |
| 1165 | E1165H | 0.82 |
| 1165 | E1165L | 0.65 |

TABLE 2-continued

Variants having a GI-IF of at most 0.9

| Position | Mutation | GI-IF |
|---|---|---|
| 1165 | E1165R | 0.81 |
| 1165 | E1165W | 0.87 |
| 1166 | R1166D | 0.85 |
| 1166 | R1166K | 0.82 |
| 1167 | V1167C | 0.85 |
| 1167 | V1167L | 0.89 |
| 1167 | V1167P | 0.82 |
| 1168 | K1168Q | 0.80 |
| 1168 | K1168W | 0.61 |
| 1169 | P1169R | 0.86 |
| 1170 | Y1170E | 0.65 |
| 1170 | Y1170Q | 0.88 |
| 1170 | Y1170R | 0.83 |
| 1171 | T1171A | 0.68 |
| 1171 | T1171G | 0.69 |
| 1171 | T1171M | 0.87 |
| 1171 | T1171Q | 0.87 |
| 1171 | T1171R | 0.89 |
| 1171 | T1171S | 0.83 |
| 1172 | Y1172D | 0.87 |
| 1172 | Y1172E | 0.80 |
| 1172 | Y1172I | 0.81 |
| 1172 | Y1172K | 0.77 |
| 1172 | Y1172L | 0.88 |
| 1172 | Y1172V | 0.84 |
| 1173 | D1173A | 0.78 |
| 1173 | D1173E | 0.88 |
| 1173 | D1173F | 0.80 |
| 1173 | D1173K | 0.80 |
| 1173 | D1173L | 0.75 |
| 1173 | D1173P | 0.86 |
| 1173 | D1173R | 0.83 |
| 1173 | D1173W | 0.84 |
| 1174 | F1174P | 0.80 |
| 1174 | F1174Q | 0.89 |
| 1174 | F1174R | 0.89 |
| 1174 | F1174S | 0.84 |
| 1174 | F1174T | 0.80 |
| 1174 | F1174V | 0.70 |
| 1174 | F1174W | 0.79 |
| 1175 | A1175G | 0.90 |
| 1175 | A1175I | 0.81 |
| 1175 | A1175N | 0.58 |
| 1175 | A1175Q | 0.68 |
| 1175 | A1175V | 0.72 |
| 1175 | A1175Y | 0.76 |
| 1177 | V1177N | 0.68 |
| 1177 | V1177P | 0.84 |
| 1177 | V1177S | 0.87 |
| 1177 | V1177T | 0.65 |
| 1179 | A1179P | 0.88 |
| 1181 | F1181L | 0.85 |
| 1190 | D1190S | 0.89 |
| 1191 | T1191E | 0.77 |
| 1192 | T1192H | 0.62 |
| 1192 | T1192P | 0.88 |
| 1194 | P1194A | 0.85 |
| 1194 | P1194G | 0.89 |
| 1195 | S1195G | 0.88 |
| 1198 | V1198E | 0.72 |
| 1199 | C1199T | 0.51 |
| 1200 | A1200V | 0.70 |
| 1200 | A1200W | 0.67 |
| 1202 | L1202A | 0.65 |
| 1202 | L1202C | 0.82 |
| 1203 | T1203E | 0.89 |
| 1210 | A1210E | 0.70 |
| 1213 | K1213W | 0.82 |
| 1214 | F1214R | 0.88 |
| 1215 | V1215K | 0.89 |
| 1215 | V1215S | 0.86 |
| 1217 | N1217D | 0.88 |
| 1217 | N1217F | 0.79 |
| 1219 | S1219A | 0.50 |
| 1219 | S1219E | 0.84 |
| 1219 | S1219F | 0.60 |
| 1220 | A1220L | 0.69 |
| 1220 | A1220R | 0.76 |
| 1220 | A1220V | 0.85 |
| 1221 | A1221D | 0.75 |
| 1221 | A1221G | 0.84 |
| 1221 | A1221L | 0.86 |
| 1222 | L1222C | 0.83 |
| 1223 | S1223C | 0.83 |
| 1223 | S1223F | 0.75 |
| 1223 | S1223G | 0.85 |
| 1223 | S1223K | 0.79 |
| 1223 | S1223L | 0.77 |
| 1223 | S1223V | 0.38 |
| 1224 | S1224A | 0.65 |
| 1224 | S1224D | 0.72 |
| 1224 | S1224G | 0.66 |
| 1224 | S1224L | 0.80 |
| 1224 | S1224M | 0.83 |
| 1224 | S1224R | 0.87 |
| 1225 | L1225C | 0.75 |
| 1225 | L1225D | 0.90 |
| 1225 | L1225F | 0.79 |
| 1225 | L1225G | 0.83 |
| 1225 | L1225P | 0.87 |
| 1225 | L1225T | 0.82 |
| 1225 | L1225W | 0.65 |
| 1226 | T1226A | 0.75 |
| 1226 | T1226G | 0.75 |
| 1226 | T1226M | 0.86 |
| 1226 | T1226R | 0.83 |
| 1226 | T1226S | 0.66 |
| 1226 | T1226V | 0.63 |
| 1226 | T1226Y | 0.89 |
| 1227 | V1227A | 0.71 |
| 1227 | V1227E | 0.83 |
| 1227 | V1227G | 0.89 |
| 1227 | V1227L | 0.76 |
| 1227 | V1227S | 0.76 |
| 1228 | N1228A | 0.87 |
| 1228 | N1228D | 0.63 |
| 1228 | N1228F | 0.58 |
| 1228 | N1228K | 0.89 |
| 1228 | N1228L | 0.85 |
| 1228 | N1228T | 0.73 |
| 1229 | G1229A | 0.86 |
| 1229 | G1229Q | 0.83 |
| 1229 | G1229S | 0.89 |
| 1230 | T1230F | 0.85 |
| 1230 | T1230I | 0.62 |
| 1230 | T1230L | 0.87 |
| 1230 | T1230P | 0.86 |
| 1230 | T1230R | 0.82 |
| 1230 | T1230S | 0.77 |
| 1231 | K1231F | 0.58 |
| 1231 | K1231L | 0.73 |
| 1231 | K1231M | 0.78 |
| 1231 | K1231P | 0.63 |
| 1231 | K1231S | 0.88 |
| 1231 | K1231W | 0.90 |
| 1232 | V1232K | 0.68 |
| 1232 | V1232S | 0.86 |
| 1232 | V1232T | 0.86 |
| 1232 | V1232W | 0.88 |
| 1233 | S1233P | 0.56 |
| 1233 | S1233W | 0.63 |
| 1234 | D1234G | 0.88 |
| 1234 | D1234K | 0.71 |
| 1234 | D1234R | 0.78 |
| 1235 | S1235L | 0.83 |
| 1236 | V1236I | 0.79 |
| 1236 | V1236R | 0.80 |
| 1237 | L1237D | 0.61 |
| 1237 | L1237E | 0.73 |
| 1237 | L1237R | 0.87 |
| 1237 | L1237W | 0.82 |
| 1238 | A1238K | 0.88 |

TABLE 2-continued

Variants having a GI-IF of at most 0.9

| Position | Mutation | GI-IF |
|---|---|---|
| 1238 | A1238N | 0.73 |
| 1238 | A1238P | 0.73 |
| 1238 | A1238S | 0.81 |
| 1238 | A1238T | 0.86 |
| 1239 | A1239D | 0.74 |
| 1239 | A1239P | 0.73 |
| 1240 | G1240L | 0.88 |
| 1240 | G1240N | 0.78 |
| 1240 | G1240S | 0.86 |
| 1240 | G1240T | 0.81 |
| 1240 | G1240W | 0.62 |
| 1241 | S1241D | 0.76 |
| 1241 | S1241G | 0.87 |
| 1241 | S1241I | 0.84 |
| 1241 | S1241L | 0.86 |
| 1241 | S1241M | 0.88 |
| 1241 | S1241P | 0.89 |
| 1242 | Y1242C | 0.90 |
| 1242 | Y1242E | 0.67 |
| 1242 | Y1242K | 0.88 |
| 1242 | Y1242R | 0.67 |
| 1242 | Y1242S | 0.87 |
| 1242 | Y1242W | 0.90 |
| 1243 | N1243L | 0.89 |
| 1243 | N1243M | 0.66 |
| 1243 | N1243P | 0.80 |
| 1243 | N1243Q | 0.86 |
| 1243 | N1243S | 0.90 |
| 1243 | N1243T | 0.56 |
| 1243 | N1243V | 0.76 |
| 1243 | N1243W | 0.78 |
| 1244 | T1244A | 0.73 |
| 1244 | T1244D | 0.84 |
| 1244 | T1244E | 0.71 |
| 1244 | T1244G | 0.83 |
| 1244 | T1244L | 0.89 |
| 1244 | T1244Q | 0.56 |
| 1244 | T1244S | 0.83 |
| 1244 | T1244V | 0.86 |
| 1244 | T1244W | 0.76 |
| 1246 | A1246F | 0.81 |
| 1246 | A1246M | 0.51 |
| 1246 | A1246N | 0.79 |
| 1246 | A1246P | 0.79 |
| 1246 | A1246Q | 0.77 |
| 1246 | A1246R | 0.80 |
| 1246 | A1246S | 0.81 |
| 1246 | A1246T | 0.82 |
| 1247 | I1247A | 0.83 |
| 1247 | I1247G | 0.71 |
| 1247 | I1247M | 0.88 |
| 1247 | I1247Q | 0.72 |
| 1247 | I1247S | 0.77 |
| 1247 | I1247T | 0.86 |
| 1247 | I1247V | 0.89 |
| 1247 | I1247W | 0.74 |
| 1248 | I1248A | 0.84 |
| 1248 | I1248G | 0.64 |
| 1248 | I1248K | 0.83 |
| 1248 | I1248L | 0.74 |
| 1248 | I1248R | 0.73 |
| 1248 | I1248S | 0.72 |
| 1248 | I1248Y | 0.90 |
| 1249 | A1249E | 0.83 |
| 1249 | A1249G | 0.77 |
| 1249 | A1249H | 0.69 |
| 1249 | A1249I | 0.69 |
| 1249 | A1249R | 0.74 |
| 1249 | A1249T | 0.72 |
| 1249 | A1249V | 0.67 |
| 1250 | D1250I | 0.60 |
| 1250 | D1250K | 0.70 |
| 1250 | D1250S | 0.54 |
| 1250 | D1250T | 0.70 |
| 1250 | D1250W | 0.54 |
| 1250 | D1250Y | 0.64 |
| 1251 | V1251I | 0.81 |
| 1251 | V1251T | 0.78 |
| 1251 | V1251W | 0.79 |
| 1252 | K1252D | 0.66 |
| 1252 | K1252G | 0.85 |
| 1252 | K1252V | 0.79 |
| 1252 | K1252W | 0.74 |
| 1253 | A1253P | 0.87 |
| 1253 | A1253V | 0.81 |
| 1254 | E1254F | 0.83 |
| 1254 | E1254G | 0.87 |
| 1254 | E1254H | 0.87 |
| 1254 | E1254L | 0.87 |
| 1254 | E1254R | 0.83 |
| 1254 | E1254V | 0.71 |
| 1255 | G1255M | 0.71 |
| 1255 | G1255S | 0.83 |
| 1255 | G1255V | 0.89 |
| 1256 | E1256G | 0.85 |
| 1256 | E1256M | 0.78 |
| 1256 | E1256N | 0.73 |
| 1256 | E1256R | 0.83 |
| 1256 | E1256V | 0.74 |
| 1256 | E1256W | 0.77 |
| 1257 | G1257F | 0.80 |
| 1257 | G1257K | 0.83 |
| 1257 | G1257L | 0.75 |
| 1257 | G1257Q | 0.76 |
| 1257 | G1257R | 0.85 |
| 1257 | G1257W | 0.88 |
| 1258 | N1258C | 0.85 |
| 1258 | N1258G | 0.86 |
| 1258 | N1258H | 0.61 |
| 1258 | N1258K | 0.83 |
| 1258 | N1258S | 0.77 |
| 1259 | A1259L | 0.89 |
| 1259 | A1259W | 0.89 |
| 1261 | V1261I | 0.80 |
| 1261 | V1261L | 0.79 |
| 1261 | V1261P | 0.89 |
| 1261 | V1261Q | 0.85 |
| 1261 | V1261T | 0.85 |
| 1262 | T1262A | 0.74 |
| 1262 | T1262Q | 0.77 |
| 1263 | V1263E | 0.79 |
| 1263 | V1263G | 0.81 |
| 1263 | V1263Q | 0.83 |
| 1263 | V1263R | 0.72 |
| 1263 | V1263W | 0.67 |
| 1264 | L1264A | 0.83 |
| 1264 | L1264E | 0.83 |
| 1264 | L1264S | 0.87 |
| 1264 | L1264Y | 0.90 |
| 1265 | P1265C | 0.90 |
| 1265 | P1265K | 0.87 |
| 1265 | P1265L | 0.71 |
| 1265 | P1265R | 0.64 |
| 1265 | P1265S | 0.83 |
| 1265 | P1265V | 0.87 |
| 1266 | A1266F | 0.81 |
| 1266 | A1266L | 0.82 |
| 1266 | A1266P | 0.74 |
| 1266 | A1266S | 0.87 |
| 1266 | A1266V | 0.78 |
| 1267 | H1267A | 0.82 |
| 1267 | H1267E | 0.75 |
| 1267 | H1267F | 0.87 |
| 1269 | N1269A | 0.44 |
| 1269 | N1269E | 0.82 |
| 1269 | N1269K | 0.58 |
| 1269 | N1269R | 0.76 |
| 1269 | N1269S | 0.78 |
| 1269 | N1269T | 0.82 |
| 1269 | N1269W | 0.89 |
| 1270 | V1270D | 0.77 |
| 1270 | V1270E | 0.80 |

TABLE 2-continued

Variants having a GI-IF of at most 0.9

| Position | Mutation | GI-IF |
|---|---|---|
| 1270 | V1270G | 0.81 |
| 1270 | V1270I | 0.83 |
| 1270 | V1270L | 0.89 |
| 1270 | V1270T | 0.81 |
| 1270 | V1270W | 0.83 |
| 1271 | I1271A | 0.84 |
| 1271 | I1271H | 0.71 |
| 1271 | I1271Q | 0.89 |
| 1272 | R1272E | 0.82 |
| 1272 | R1272F | 0.81 |
| 1272 | R1272M | 0.79 |
| 1272 | R1272P | 0.80 |
| 1272 | R1272V | 0.72 |
| 1274 | I1274M | 0.89 |
| 1275 | T1275L | 0.80 |
| 1276 | E1276W | 0.86 |
| 1279 | D1279G | 0.71 |
| 1279 | D1279T | 0.77 |
| 1279 | D1279V | 0.84 |
| 1280 | H1280V | 0.87 |
| 1280 | H1280W | 0.84 |
| 1281 | V1281F | 0.90 |
| 1281 | V1281S | 0.87 |
| 1282 | T1282D | 0.80 |
| 1282 | T1282L | 0.88 |
| 1282 | T1282V | 0.88 |
| 1283 | R1283A | 0.78 |
| 1283 | R1283D | 0.76 |
| 1283 | R1283E | 0.77 |
| 1283 | R1283P | 0.84 |
| 1283 | R1283W | 0.73 |
| 1285 | T1285E | 0.84 |
| 1285 | T1285F | 0.72 |
| 1285 | T1285G | 0.84 |
| 1285 | T1285R | 0.85 |
| 1285 | T1285Y | 0.85 |
| 1286 | F1286S | 0.78 |
| 1286 | F1286T | 0.89 |
| 1287 | T1287K | 0.81 |
| 1287 | T1287M | 0.82 |
| 1287 | T1287Q | 0.85 |
| 1287 | T1287R | 0.76 |
| 1288 | I1288F | 0.90 |
| 1289 | N1289A | 0.74 |
| 1289 | N1289Q | 0.81 |
| 1289 | N1289T | 0.79 |
| 1290 | L1290A | 0.75 |
| 1290 | L1290G | 0.88 |
| 1290 | L1290R | 0.75 |
| 1290 | L1290V | 0.87 |
| 1290 | L1290W | 0.83 |
| 1290 | G1291K | 0.89 |
| 1291 | G1291P | 0.68 |
| 1291 | G1291V | 0.70 |
| 1291 | G1291W | 0.82 |
| 1291 | G1291Y | 0.68 |
| 1292 | T1292G | 0.87 |
| 1292 | T1292L | 0.87 |
| 1292 | T1292Y | 0.69 |
| 1293 | E1293G | 0.86 |
| 1293 | E1293S | 0.79 |
| 1293 | E1293V | 0.78 |
| 1294 | Q1294L | 0.83 |
| 1294 | Q1294P | 0.78 |
| 1294 | Q1294W | 0.77 |
| 1296 | F1296G | 0.89 |
| 1296 | F1296I | 0.88 |
| 1297 | P1297F | 0.79 |
| 1298 | A1298Y | 0.87 |
| 1301 | D1301I | 0.88 |
| 1304 | D1304A | 0.78 |

The invention claimed is:

1. A lactase variant which has lactase activity, wherein the amino acid sequence of the lactase variant is at least 80% identical to SEQ ID NO: 1, and wherein the lactase variant comprises an alteration, preferably a substitution, at one or more positions corresponding to positions 372, 389, 1076, 1125, or 1199 of the polypeptide of SEQ ID NO: 1.

2. The lactase variant of claim 1, wherein the lactase variant comprises one or more of the following substitutions, wherein position numbering corresponds to the numbering of positions of SEQ ID NO: 1: C372P, R389C, R389E, R389K, R389M, R389N, R389Q, R389S, R389T, R389V, T1076C, T1076E, T1076H, T1076Q, R1125D, R1125E, R1125F, R1125K, R1125T, R1125V, R1125W, C1199D, or C1199T.

3. The lactase variant of claim 1 wherein the variant has a decreased or an increased galactose inhibition, preferably measured as a galactose inhibition improvement factor (GI-IF) of at least 1.1 or at most 0.9, compared to the lactase of SEQ ID NO: 1.

4. The lactase variant of claim 1 wherein the variant has an amino acid sequence which has at least 85% but less than 100% sequence identity to SEQ ID NO 1.

5. The lactase variant of claim 1 wherein the variant has an amino acid sequence which has at least 90% but less than 100% sequence identity to SEQ ID NO 1.

6. The lactase variant of claim 1 wherein the variant is a variant of a lactase obtained from *Bifidobacterium*.

7. An isolated polynucleotide encoding the variant of claim 1.

8. A nucleic acid construct or expression vector comprising the polynucleotide of claim 7.

9. An isolated recombinant host cell transformed with the polynucleotide of claim 7.

10. A method of producing a lactase variant, comprising:
  a) cultivating the host cell of claim 9 under conditions suitable for expression of the variant; and
  b) recovering the variant.

11. A method for producing a dairy product comprising:
  a) providing a milk-based substrate comprising lactose; and
  b) treating said substrate with the variant of claim 1.

12. The lactase variant of claim 1 wherein the variant has an amino acid sequence which has at least 95% but less than 100% sequence identity to SEQ ID NO 1.

13. The lactase variant of claim 1 wherein the variant has an amino acid sequence which has at least 97% but less than 100% sequence identity to SEQ ID NO 1.

14. The lactase variant of claim 1 wherein the variant has an amino acid sequence which has at least 99% but less than 100% sequence identity to SEQ ID NO 1.

15. The lactase variant of claim 1 wherein the variant has an amino acid sequence which has at least 99.5% but less than 100% sequence identity to SEQ ID NO 1.

* * * * *

SEQUENCE LISTING

<160> NUMBER OF SEQ ID NOS: 15

<210> SEQ ID NO 1
<211> LENGTH: 1304
<212> TYPE: PRT
<213> ORGANISM: Artificial sequence
<220> FEATURE:
<223> OTHER INFORMATION: Synthetic construct

<400> SEQUENCE: 1

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
```

```
              115                 120                 125
Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asn Val Thr Met
            195                 200                 205

Asn Leu Thr Thr Lys Val Ala Asn Asp Thr Lys Ala Ala Ala Asn Ile
            210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
            450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540
```

```
Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ala Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Glu Asn Asn Arg Leu Ile Pro
                740                 745                 750

Glu Gly Ser Thr Glu Gly Asn Ala Ser Val Thr Thr Thr Gly Lys Ala
            755                 760                 765

Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960
```

-continued

Glu Ile Gly Ala Leu Leu Asn Tyr Ser Ala Ser Thr Pro Val Gly Thr
             965                 970                 975

Pro Ala Val Leu Pro Gly Ser Arg Pro Ala Val Leu Pro Asp Gly Thr
         980                 985                 990

Val Thr Ser Ala Asn Phe Ala Val Asp Trp Thr Lys Pro Ala Asp Thr
         995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Glu Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr Ser Lys Phe Val Thr Asn Thr
    1205                1210                1215

Ser Ala Ala Leu Ser Ser Leu Thr Val Asn Gly Thr Lys Val Ser
    1220                1225                1230

Asp Ser Val Leu Ala Ala Gly Ser Tyr Asn Thr Pro Ala Ile Ile
    1235                1240                1245

Ala Asp Val Lys Ala Glu Gly Glu Gly Asn Ala Ser Val Thr Val
    1250                1255                1260

Leu Pro Ala His Asp Asn Val Ile Arg Val Ile Thr Glu Ser Glu
    1265                1270                1275

Asp His Val Thr Arg Lys Thr Phe Thr Ile Asn Leu Gly Thr Glu
    1280                1285                1290

Gln Glu Phe Pro Ala Asp Ser Asp Glu Arg Asp
    1295                1300

<210> SEQ ID NO 2
<211> LENGTH: 1931
<212> TYPE: PRT
<213> ORGANISM: Artificial sequence
<220> FEATURE:
<223> OTHER INFORMATION: Synthetic construct

<400> SEQUENCE: 2

```
Met Lys Lys Pro Leu Gly Lys Ile Val Ala Ser Thr Ala Leu Leu Ile
 1               5                  10                 15
Ser Val Ala Phe Ser Ser Ile Ala Ser Ala Val Glu Asp Ala
             20                  25                 30
Thr Arg Ser Asp Ser Thr Gln Met Ser Ser Thr Pro Glu Val Ala
         35                  40                 45
Tyr Ser Ser Ala Val Asp Ser Lys Gln Asn Arg Thr Ser Asp Phe Asp
 50                  55                  60
Ala Asn Trp Lys Phe Met Leu Ser Asp Ser Val Gln Ala Gln Asp Pro
 65                  70                  75                 80
Ala Phe Asp Asp Ser Ala Trp Gln Gln Val Asp Leu Pro His Asp Tyr
             85                  90                 95
Ser Ile Thr Gln Lys Tyr Ser Gln Ser Asn Glu Ala Glu Ser Ala Tyr
            100                 105                110
Leu Pro Gly Gly Thr Gly Trp Tyr Arg Lys Ser Phe Thr Ile Asp Arg
         115                 120                125
Asp Leu Ala Gly Lys Arg Ile Ala Ile Asn Phe Asp Gly Val Tyr Met
         130                 135                 140
Asn Ala Thr Val Trp Phe Asn Gly Val Lys Leu Gly Thr His Pro Tyr
145                 150                 155                160
Gly Tyr Ser Pro Phe Ser Phe Asp Leu Thr Gly Asn Ala Lys Phe Gly
                 165                 170                175
Gly Glu Asn Thr Ile Val Val Lys Val Glu Asn Arg Leu Pro Ser Ser
             180                 185                190
Arg Trp Tyr Ser Gly Ser Gly Ile Tyr Arg Asp Val Thr Leu Thr Val
         195                 200                 205
Thr Asp Gly Val His Val Gly Asn Asn Gly Val Ala Ile Lys Thr Pro
 210                 215                 220
Ser Leu Ala Thr Gln Asn Gly Gly Asp Val Thr Met Asn Leu Thr Thr
225                 230                 235                240
Lys Val Ala Asn Asp Thr Glu Ala Ala Asn Ile Thr Leu Lys Gln
             245                 250                 255
Thr Val Phe Pro Lys Gly Gly Lys Thr Asp Ala Ala Ile Gly Thr Val
             260                 265                 270
Thr Thr Ala Ser Lys Ser Ile Ala Ala Gly Ala Ser Ala Asp Val Thr
         275                 280                 285
Ser Thr Ile Thr Ala Ala Ser Pro Lys Leu Trp Ser Ile Lys Asn Pro
         290                 295                 300
Asn Leu Tyr Thr Val Arg Thr Glu Val Leu Asn Gly Gly Lys Val Leu
305                 310                 315                320
Asp Thr Tyr Asp Thr Glu Tyr Gly Phe Arg Trp Thr Gly Phe Asp Ala
                 325                 330                335
Thr Ser Gly Phe Ser Leu Asn Gly Glu Lys Val Lys Leu Lys Gly Val
             340                 345                350
Ser Met His His Asp Gln Gly Ser Leu Gly Ala Val Ala Asn Arg Arg
         355                 360                 365
Ala Ile Glu Arg Gln Val Glu Ile Leu Gln Lys Met Gly Val Asn Ser
 370                 375                 380
Ile Arg Thr Thr His Asn Pro Ala Ala Lys Ala Leu Ile Asp Val Cys
385                 390                 395                400
Asn Glu Lys Gly Val Leu Val Val Glu Val Phe Asp Met Trp Asn
             405                 410                 415
Arg Ser Lys Asn Gly Asn Thr Glu Asp Tyr Gly Lys Trp Phe Gly Gln
```

```
              420                 425                 430
Ala Ile Ala Gly Asp Asn Ala Val Leu Gly Gly Asp Lys Asp Glu Thr
            435                 440                 445

Trp Ala Lys Phe Asp Leu Thr Ser Thr Ile Asn Arg Asp Arg Asn Ala
450                 455                 460

Pro Ser Val Ile Met Trp Ser Leu Gly Asn Glu Met Met Glu Gly Ile
465                 470                 475                 480

Ser Gly Ser Val Ser Gly Phe Pro Ala Thr Ser Ala Lys Leu Val Ala
                485                 490                 495

Trp Thr Lys Ala Ala Asp Ser Thr Arg Pro Met Thr Tyr Gly Asp Asn
            500                 505                 510

Lys Ile Lys Ala Asn Trp Asn Glu Ser Asn Thr Met Gly Asp Asn Leu
            515                 520                 525

Thr Ala Asn Gly Gly Val Val Gly Thr Asn Tyr Ser Asp Gly Ala Asn
            530                 535                 540

Tyr Asp Lys Ile Arg Thr Thr His Pro Ser Trp Ala Ile Tyr Gly Ser
545                 550                 555                 560

Glu Thr Ala Ser Ala Ile Asn Ser Arg Gly Ile Tyr Asn Arg Thr Thr
                565                 570                 575

Gly Gly Ala Gln Ser Ser Asp Lys Gln Leu Thr Ser Tyr Asp Asn Ser
            580                 585                 590

Ala Val Gly Trp Gly Ala Val Ala Ser Ser Ala Trp Tyr Asp Val Val
            595                 600                 605

Gln Arg Asp Phe Val Ala Gly Thr Tyr Val Trp Thr Gly Phe Asp Tyr
            610                 615                 620

Leu Gly Glu Pro Thr Pro Trp Asn Gly Thr Gly Ser Gly Ala Val Gly
625                 630                 635                 640

Ser Trp Pro Ser Pro Lys Asn Ser Tyr Phe Gly Ile Val Asp Thr Ala
                645                 650                 655

Gly Phe Pro Lys Asp Thr Tyr Tyr Phe Tyr Gln Ser Gln Trp Asn Asp
            660                 665                 670

Asp Val His Thr Leu His Ile Leu Pro Ala Trp Asn Glu Asn Val Val
            675                 680                 685

Ala Lys Gly Ser Gly Asn Asn Val Pro Val Val Val Tyr Thr Asp Ala
            690                 695                 700

Ala Lys Val Lys Leu Tyr Phe Thr Pro Lys Gly Ser Thr Glu Lys Arg
705                 710                 715                 720

Leu Ile Gly Glu Lys Ser Phe Thr Lys Lys Thr Thr Ala Ala Gly Tyr
                725                 730                 735

Thr Tyr Gln Val Tyr Glu Gly Ser Asp Lys Asp Ser Thr Ala His Lys
            740                 745                 750

Asn Met Tyr Leu Thr Trp Asn Val Pro Trp Ala Glu Gly Thr Ile Ser
            755                 760                 765

Ala Glu Ala Tyr Asp Glu Asn Asn Arg Leu Ile Pro Glu Gly Ser Thr
            770                 775                 780

Glu Gly Asn Ala Ser Val Thr Thr Gly Lys Ala Ala Lys Leu Lys
785                 790                 795                 800

Ala Asp Ala Asp Arg Lys Thr Ile Thr Ala Asp Gly Lys Asp Leu Ser
            805                 810                 815

Tyr Ile Glu Val Asp Val Thr Asp Ala Asn Gly His Ile Val Pro Asp
            820                 825                 830

Ala Ala Asn Arg Val Thr Phe Asp Val Lys Gly Ala Gly Lys Leu Val
            835                 840                 845
```

```
Gly Val Asp Asn Gly Ser Ser Pro Asp His Asp Ser Tyr Gln Ala Asp
    850                 855                 860

Asn Arg Lys Ala Phe Ser Gly Lys Val Leu Ala Ile Val Gln Ser Thr
865                 870                 875                 880

Lys Glu Ala Gly Glu Ile Thr Val Thr Ala Lys Ala Asp Gly Leu Gln
                885                 890                 895

Ser Ser Thr Val Lys Ile Ala Thr Thr Ala Val Pro Gly Thr Ser Thr
                900                 905                 910

Glu Lys Thr Val Arg Ser Phe Tyr Tyr Ser Arg Asn Tyr Tyr Val Lys
                915                 920                 925

Thr Gly Asn Lys Pro Ile Leu Pro Ser Asp Val Glu Val Arg Tyr Ser
    930                 935                 940

Asp Gly Thr Ser Asp Arg Gln Asn Val Thr Trp Asp Ala Val Ser Asp
945                 950                 955                 960

Asp Gln Ile Ala Lys Ala Gly Ser Phe Ser Val Ala Gly Thr Val Ala
                965                 970                 975

Gly Gln Lys Ile Ser Val Arg Val Thr Met Ile Asp Glu Ile Gly Ala
                980                 985                 990

Leu Leu Asn Tyr Ser Ala Ser Thr Pro Val Gly Thr Pro Ala Val Leu
        995                 1000                1005

Pro Gly Ser Arg Pro Ala Val Leu Pro Asp Gly Thr Val Thr Ser
    1010                1015                1020

Ala Asn Phe Ala Val His Trp Thr Lys Pro Ala Asp Thr Val Tyr
    1025                1030                1035

Asn Thr Ala Gly Thr Val Lys Val Pro Gly Thr Ala Thr Val Phe
    1040                1045                1050

Gly Lys Glu Phe Lys Val Thr Ala Thr Ile Arg Val Gln Arg Ser
    1055                1060                1065

Gln Val Thr Ile Gly Ser Ser Val Ser Gly Asn Ala Leu Arg Leu
    1070                1075                1080

Thr Gln Asn Ile Pro Ala Asp Lys Gln Ser Asp Thr Leu Asp Ala
    1085                1090                1095

Ile Lys Asp Gly Ser Thr Thr Val Asp Ala Asn Thr Gly Gly Gly
    1100                1105                1110

Ala Asn Pro Ser Ala Trp Thr Asn Trp Ala Tyr Ser Lys Ala Gly
    1115                1120                1125

His Asn Thr Ala Glu Ile Thr Phe Glu Tyr Ala Thr Glu Gln Gln
    1130                1135                1140

Leu Gly Gln Ile Val Met Tyr Phe Phe Arg Asp Ser Asn Ala Val
    1145                1150                1155

Arg Phe Pro Asp Ala Gly Lys Thr Lys Ile Gln Ile Ser Ala Asp
    1160                1165                1170

Gly Lys Asn Trp Thr Asp Leu Ala Ala Thr Glu Thr Ile Ala Ala
    1175                1180                1185

Gln Glu Ser Ser Asp Arg Val Lys Pro Tyr Thr Tyr Asp Phe Ala
    1190                1195                1200

Pro Val Gly Ala Thr Phe Val Lys Val Thr Val Thr Asn Ala Asp
    1205                1210                1215

Thr Thr Thr Pro Ser Gly Val Val Cys Ala Gly Leu Thr Glu Ile
    1220                1225                1230

Glu Leu Lys Thr Ala Thr Ser Lys Phe Val Thr Asn Thr Ser Ala
    1235                1240                1245
```

-continued

```
Ala Leu Ser Ser Leu Thr Val Asn Gly Thr Lys Val Ser Asp Ser
    1250                1255                1260

Val Leu Ala Ala Gly Ser Tyr Asn Thr Pro Ala Ile Ile Ala Asp
    1265                1270                1275

Val Lys Ala Glu Gly Glu Gly Asn Ala Ser Val Thr Val Leu Pro
    1280                1285                1290

Ala His Asp Asn Val Ile Arg Val Ile Thr Glu Ser Glu Asp His
    1295                1300                1305

Val Thr Arg Lys Thr Phe Thr Ile Asn Leu Gly Thr Glu Gln Glu
    1310                1315                1320

Phe Pro Ala Asp Ser Asp Glu Arg Asp Tyr Pro Ala Ala Asp Met
    1325                1330                1335

Thr Val Thr Val Gly Ser Glu Gln Thr Ser Gly Thr Ala Thr Glu
    1340                1345                1350

Gly Pro Lys Lys Phe Ala Val Asp Gly Asn Thr Ser Thr Tyr Trp
    1355                1360                1365

His Ser Asn Trp Thr Pro Thr Thr Val Asn Asp Leu Trp Ile Ala
    1370                1375                1380

Phe Glu Leu Gln Lys Pro Thr Lys Leu Asp Ala Leu Arg Tyr Leu
    1385                1390                1395

Pro Arg Pro Ala Gly Ser Lys Asn Gly Ser Val Thr Glu Tyr Lys
    1400                1405                1410

Val Gln Val Ser Asp Asp Gly Thr Asn Trp Thr Asp Ala Gly Ser
    1415                1420                1425

Gly Thr Trp Thr Thr Asp Tyr Gly Trp Lys Leu Ala Glu Phe Asn
    1430                1435                1440

Gln Pro Val Thr Thr Lys His Val Arg Leu Lys Ala Val His Thr
    1445                1450                1455

Tyr Ala Asp Ser Gly Asn Asp Lys Phe Met Ser Ala Ser Glu Ile
    1460                1465                1470

Arg Leu Arg Lys Ala Val Asp Thr Thr Asp Ile Ser Gly Ala Thr
    1475                1480                1485

Val Thr Val Pro Ala Lys Leu Thr Val Asp Arg Val Asp Ala Asp
    1490                1495                1500

His Pro Ala Thr Phe Ala Thr Lys Asp Val Thr Val Thr Leu Gly
    1505                1510                1515

Asp Ala Thr Leu Arg Tyr Gly Val Asp Tyr Leu Leu Asp Tyr Ala
    1520                1525                1530

Gly Asn Thr Ala Val Gly Lys Ala Thr Val Thr Val Arg Gly Ile
    1535                1540                1545

Asp Lys Tyr Ser Gly Thr Val Ala Lys Thr Phe Thr Ile Glu Leu
    1550                1555                1560

Lys Asn Ala Pro Ala Pro Glu Pro Thr Leu Thr Ser Val Ser Val
    1565                1570                1575

Lys Thr Lys Pro Ser Lys Leu Thr Tyr Val Val Gly Asp Ala Phe
    1580                1585                1590

Asp Pro Ala Gly Leu Val Leu Gln Leu Asn Tyr Asp Asp Asp Ser
    1595                1600                1605

Thr Gly Thr Val Thr Trp Asn Thr Gln Thr Ala Gly Asp Phe Thr
    1610                1615                1620

Phe Lys Pro Ala Leu Asp Ala Lys Leu Lys Val Thr Asp Lys Thr
    1625                1630                1635

Val Thr Val Thr Tyr Gln Gly Lys Ser Ala Val Ile Asp Ile Thr
```

1640                1645                1650

Val Ser Gln Pro Ala Pro Thr Val Ser Lys Thr Asp Leu Asp Lys
    1655                1660                1665

Ala Ile Lys Ala Ile Glu Ala Lys Asn Pro Asp Ser Ser Lys Tyr
    1670                1675                1680

Thr Ala Asp Ser Trp Lys Thr Phe Ala Asp Ala Met Ala His Ala
    1685                1690                1695

Lys Ala Val Ile Ala Asp Asp Ser Ala Thr Gln Gln Asp Val Asp
    1700                1705                1710

Asn Ala Leu Lys Ala Leu Thr Asp Ala Tyr Ala Gly Leu Thr Glu
    1715                1720                1725

Lys Thr Pro Glu Pro Ala Pro Val Ser Lys Ser Glu Leu Asp Lys
    1730                1735                1740

Lys Ile Lys Ala Ile Glu Ala Glu Lys Leu Asp Gly Ser Lys Tyr
    1745                1750                1755

Thr Ala Glu Ser Trp Lys Ala Phe Glu Thr Ala Leu Ala His Ala
    1760                1765                1770

Lys Ala Val Ile Ala Ser Asp Ser Ala Thr Gln Gln Asn Val Asp
    1775                1780                1785

Ala Ala Leu Gly Ala Leu Thr Ser Ala Arg Asp Gly Leu Thr Glu
    1790                1795                1800

Lys Gly Glu Val Lys Pro Asp Pro Lys Pro Glu Pro Gly Thr Val
    1805                1810                1815

Asp Lys Ala Ala Leu Asp Lys Ala Val Lys Lys Val Glu Ala Glu
    1820                1825                1830

Lys Leu Asp Gly Ser Lys Tyr Thr Ala Asp Ser Trp Lys Ala Phe
    1835                1840                1845

Glu Thr Ala Leu Ala His Ala Lys Ala Val Ile Gly Asn Ala Asn
    1850                1855                1860

Ser Thr Gln Phe Asp Ile Asp Asn Ala Leu Ser Met Leu Asn Asp
    1865                1870                1875

Ala Arg Ala Ala Leu Lys Glu Lys Pro Gly Arg Ile Ile Ala Ile
    1880                1885                1890

Ile Asp Gly Ser Ala Leu Ser Lys Thr Gly Ala Ser Val Ala Ile
    1895                1900                1905

Ile Ala Ser Val Ala Ala Ala Met Leu Ala Val Gly Ala Gly Val
    1910                1915                1920

Met Ala Leu Arg Arg Lys Arg Ser
    1925                1930

<210> SEQ ID NO 3
<211> LENGTH: 1341
<212> TYPE: PRT
<213> ORGANISM: Artificial sequence
<220> FEATURE:
<223> OTHER INFORMATION: Synthetic construct

<400> SEQUENCE: 3

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ile Glu Asp Ala Thr
                20                  25                  30

Arg Ser Asp Ser Thr Thr Gln Met Ser Ser Thr Pro Glu Val Ala Tyr
        35                  40                  45

Ser Ser Ala Val Asp Ser Lys Gln Asn Arg Thr Ser Asp Phe Asp Ala

-continued

```
                50                  55                  60
Asn Trp Lys Phe Met Leu Ser Asp Ser Val Gln Ala Gln Asp Pro Ala
 65                  70                  75                  80

Phe Asp Ser Ala Trp Gln Gln Val Asp Leu Pro His Asp Tyr Ser
                 85                  90                  95

Ile Thr Gln Lys Tyr Ser Gln Ser Asn Glu Ala Glu Ser Ala Tyr Leu
                100                 105                 110

Pro Gly Gly Thr Gly Trp Tyr Arg Lys Ser Phe Thr Ile Asp Arg Asp
                115                 120                 125

Leu Ala Gly Lys Arg Ile Ala Ile Asn Phe Asp Gly Val Tyr Met Asn
130                 135                 140

Ala Thr Val Trp Phe Asn Gly Val Lys Leu Gly Thr His Pro Tyr Gly
145                 150                 155                 160

Tyr Ser Pro Phe Ser Phe Asp Leu Thr Gly Asn Ala Lys Phe Gly Gly
                165                 170                 175

Glu Asn Thr Ile Val Val Lys Val Glu Asn Arg Leu Pro Ser Ser Arg
                180                 185                 190

Trp Tyr Ser Gly Ser Gly Ile Tyr Arg Asp Val Thr Leu Thr Val Thr
                195                 200                 205

Asp Gly Val His Val Gly Asn Asn Gly Val Ala Ile Lys Thr Pro Ser
210                 215                 220

Leu Ala Thr Gln Asn Gly Gly Asp Val Thr Met Asn Leu Thr Thr Lys
225                 230                 235                 240

Val Ala Asn Asp Thr Glu Ala Ala Asn Ile Thr Leu Lys Gln Thr
                245                 250                 255

Val Phe Pro Lys Gly Gly Lys Thr Asp Ala Ala Ile Gly Thr Val Thr
                260                 265                 270

Thr Ala Ser Lys Ser Ile Ala Ala Gly Ala Ser Ala Asp Val Thr Ser
                275                 280                 285

Thr Ile Thr Ala Ala Ser Pro Lys Leu Trp Ser Ile Lys Asn Pro Asn
290                 295                 300

Leu Tyr Thr Val Arg Thr Glu Val Leu Asn Gly Gly Lys Val Leu Asp
305                 310                 315                 320

Thr Tyr Asp Thr Glu Tyr Gly Phe Arg Trp Thr Gly Phe Asp Ala Thr
                325                 330                 335

Ser Gly Phe Ser Leu Asn Gly Glu Lys Val Lys Leu Lys Gly Val Ser
                340                 345                 350

Met His His Asp Gln Gly Ser Leu Gly Ala Val Ala Asn Arg Arg Ala
                355                 360                 365

Ile Glu Arg Gln Val Glu Ile Leu Gln Lys Met Gly Val Asn Ser Ile
                370                 375                 380

Arg Thr Thr His Asn Pro Ala Ala Lys Ala Leu Ile Asp Val Cys Asn
385                 390                 395                 400

Glu Lys Gly Val Leu Val Val Glu Glu Val Phe Asp Met Trp Asn Arg
                405                 410                 415

Ser Lys Asn Gly Asn Thr Glu Asp Tyr Gly Lys Trp Phe Gly Gln Ala
                420                 425                 430

Ile Ala Gly Asp Asn Ala Val Leu Gly Gly Asp Lys Asp Glu Thr Trp
                435                 440                 445

Ala Lys Phe Asp Leu Thr Ser Thr Ile Asn Arg Asp Arg Asn Ala Pro
                450                 455                 460

Ser Val Ile Met Trp Ser Leu Gly Asn Glu Met Met Glu Gly Ile Ser
465                 470                 475                 480
```

```
Gly Ser Val Ser Gly Phe Ser Ala Thr Ser Lys Leu Val Ala Trp
                485                 490                 495

Thr Lys Ala Ala Asp Ser Thr Arg Pro Met Thr Tyr Gly Asp Asn Lys
            500                 505                 510

Ile Lys Ala Asn Trp Asn Glu Ser Asn Thr Met Gly Asp Asn Leu Thr
            515                 520                 525

Ala Asn Gly Gly Val Val Gly Thr Asn Tyr Ser Asp Gly Ala Asn Tyr
    530                 535                 540

Asp Lys Ile Arg Thr Thr His Pro Ser Trp Ala Ile Tyr Gly Ser Glu
545                 550                 555                 560

Thr Ala Ser Ala Ile Asn Ser Arg Gly Ile Tyr Asn Arg Thr Thr Gly
                565                 570                 575

Gly Ala Gln Ser Ser Asp Lys Gln Leu Thr Ser Tyr Asp Asn Ser Ala
            580                 585                 590

Val Gly Trp Gly Ala Val Ala Ser Ser Ala Trp Tyr Asp Val Val Gln
    595                 600                 605

Arg Asp Phe Val Ala Gly Thr Tyr Val Trp Thr Gly Phe Asp Tyr Leu
610                 615                 620

Gly Glu Pro Thr Pro Trp Asn Gly Thr Gly Ser Gly Ala Val Gly Ser
625                 630                 635                 640

Trp Pro Ser Pro Lys Asn Ser Tyr Phe Gly Ile Val Asp Thr Ala Gly
                645                 650                 655

Phe Pro Lys Asp Thr Tyr Tyr Phe Tyr Gln Ser Gln Trp Asn Asp Asp
            660                 665                 670

Val His Thr Leu His Ile Leu Pro Ala Trp Asn Glu Asn Val Val Ala
            675                 680                 685

Lys Gly Ser Gly Asn Asn Val Pro Val Val Tyr Thr Asp Ala Ala
            690                 695                 700

Lys Val Lys Leu Tyr Phe Thr Pro Lys Gly Ser Thr Glu Gln Arg Leu
705                 710                 715                 720

Ile Gly Glu Lys Ser Phe Thr Lys Lys Thr Thr Ala Ala Gly Tyr Thr
                725                 730                 735

Tyr Gln Val Tyr Glu Gly Ser Asp Lys Asp Ser Thr Ala His Lys Asn
            740                 745                 750

Met Tyr Leu Thr Trp Asn Val Pro Trp Ala Glu Gly Thr Ile Ser Ala
            755                 760                 765

Glu Ala Tyr Asp Glu Asn Asn Arg Leu Ile Pro Glu Gly Ser Thr Glu
    770                 775                 780

Gly Asn Ala Ser Val Thr Thr Gly Lys Ala Ala Lys Leu Lys Ala
785                 790                 795                 800

Asp Ala Asp Arg Lys Thr Ile Thr Ala Asp Gly Lys Asp Leu Ser Tyr
                805                 810                 815

Ile Glu Val Asp Val Thr Asp Ala Asn Gly His Ile Val Pro Asp Ala
            820                 825                 830

Ala Asn Arg Val Thr Phe Asp Val Lys Gly Ala Gly Lys Leu Val Gly
            835                 840                 845

Val Asp Asn Gly Ser Ser Pro Asp His Asp Ser Tyr Gln Ala Asp Asn
850                 855                 860

Arg Lys Ala Phe Ser Gly Lys Val Leu Ala Ile Val Gln Ser Thr Lys
865                 870                 875                 880

Glu Ala Gly Glu Ile Thr Val Thr Ala Lys Ala Asp Gly Leu Gln Ser
                885                 890                 895
```

```
Ser Thr Val Lys Ile Ala Thr Thr Ala Val Pro Gly Thr Ser Thr Glu
            900                 905                 910

Lys Thr Val Arg Ser Phe Tyr Tyr Ser Arg Asn Tyr Tyr Val Lys Thr
        915                 920                 925

Gly Asn Lys Pro Ile Leu Pro Ser Asp Val Glu Val Arg Tyr Ser Asp
    930                 935                 940

Gly Thr Ser Asp Arg Gln Asn Val Thr Trp Asp Ala Val Ser Asp Asp
945                 950                 955                 960

Gln Ile Ala Lys Ala Gly Ser Phe Ser Val Ala Gly Thr Val Ala Gly
                965                 970                 975

Gln Lys Ile Ser Val Arg Val Thr Met Ile Asp Glu Ile Gly Ala Leu
        980                 985                 990

Leu Asn Tyr Ser Ala Ser Thr Pro  Val Gly Thr Pro Ala  Val Leu Pro
            995                 1000                1005

Gly Ser  Arg Pro Ala Val Leu  Pro Asp Gly Thr Val  Thr Ser Ala
    1010                1015                1020

Asn Phe Ala Val His Trp Thr  Lys Pro Ala Asp Thr  Val Tyr Asn
    1025                1030                1035

Thr Ala  Gly Thr Val Lys Val  Pro Gly Thr Ala Thr  Val Phe Gly
    1040                1045                1050

Lys Glu  Phe Lys Val Thr Ala  Thr Ile Arg Val Gln  Arg Ser Gln
    1055                1060                1065

Val Thr  Ile Gly Ser Ser Val  Ser Gly Asn Ala Leu  Arg Leu Thr
    1070                1075                1080

Gln Asn  Ile Pro Ala Asp Lys  Gln Ser Asp Thr Leu  Asp Ala Ile
    1085                1090                1095

Lys Asp  Gly Ser Thr Thr Val  Asp Ala Asn Thr Gly  Gly Gly Ala
    1100                1105                1110

Asn Pro  Ser Ala Trp Thr Asn  Trp Ala Tyr Ser Lys  Ala Gly His
    1115                1120                1125

Asn Thr  Ala Glu Ile Thr Phe  Glu Tyr Ala Thr Glu  Gln Gln Leu
    1130                1135                1140

Gly Gln  Ile Val Met Tyr Phe  Phe Arg Asp Ser Asn  Ala Val Arg
    1145                1150                1155

Phe Pro  Asp Ala Gly Lys Thr  Lys Ile Gln Ile Ser  Ala Asp Gly
    1160                1165                1170

Lys Asn  Trp Thr Asp Leu Ala  Ala Thr Glu Thr Ile  Ala Ala Gln
    1175                1180                1185

Glu Ser  Ser Asp Arg Val Lys  Pro Tyr Thr Tyr Asp  Phe Ala Pro
    1190                1195                1200

Val Gly  Ala Thr Phe Val Arg  Val Thr Val Thr Asn  Ala Asp Thr
    1205                1210                1215

Thr Thr  Pro Ser Gly Val Val  Cys Ala Gly Leu Thr  Glu Ile Glu
    1220                1225                1230

Leu Lys  Thr Ala Thr Ser Lys  Phe Val Ala Asn Thr  Ser Ala Ala
    1235                1240                1245

Leu Ser  Ser Leu Thr Val Asn  Gly Thr Lys Val Ser  Asp Ser Val
    1250                1255                1260

Leu Ala  Ala Gly Ser Tyr Asn  Thr Pro Ala Ile Ile  Ala Asp Val
    1265                1270                1275

Lys Ala  Glu Gly Glu Gly Asn  Ala Ser Val Thr Val  Leu Pro Ala
    1280                1285                1290

His Asp  Asn Val Ile Arg Val  Ile Thr Glu Ser Glu  Asp His Val
```

-continued

```
            1295                1300                1305

Thr Arg Lys Thr Phe Thr Ile Asn Leu Gly Thr Glu  Gln Glu Phe
    1310                1315                1320

Pro Ala Asp Ser Asp Glu Arg  Asp Gln His Gln His  Gln His Gln
    1325                1330                1335

His Gln Gln
    1340

<210> SEQ ID NO 4
<211> LENGTH: 1752
<212> TYPE: PRT
<213> ORGANISM: Artificial sequence
<220> FEATURE:
<223> OTHER INFORMATION: Synthetic construct

<400> SEQUENCE: 4

Met Ala Val Arg Arg Leu Gly Gly Arg Ile Val Ala Phe Ala Ala Thr
1               5                   10                  15

Val Ala Leu Ser Ile Pro Leu Gly Leu Leu Thr Asn Ser Ala Trp Ala
            20                  25                  30

Val Glu Asp Ala Thr Arg Ser Asp Ser Thr Thr Gln Met Ser Ser Thr
        35                  40                  45

Pro Glu Val Val Tyr Ser Ser Ala Val Asp Ser Lys Gln Asn Arg Thr
    50                  55                  60

Ser Asp Phe Asp Ala Asn Trp Lys Phe Met Leu Ser Asp Ser Val Gln
65                  70                  75                  80

Ala Gln Asp Pro Ala Phe Asp Asp Ser Ala Trp Gln Gln Val Asp Leu
                85                  90                  95

Pro His Asp Tyr Ser Ile Thr Gln Lys Tyr Ser Gln Ser Asn Glu Ala
            100                 105                 110

Glu Ser Ala Tyr Leu Pro Gly Gly Thr Gly Trp Tyr Arg Lys Ser Phe
        115                 120                 125

Thr Ile Asp Arg Asp Leu Ala Gly Lys Arg Ile Ala Ile Asn Phe Asp
    130                 135                 140

Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                165                 170                 175

Ala Lys Phe Gly Gly Glu Asn Thr Ile Val Val Lys Val Glu Asn Arg
            180                 185                 190

Leu Pro Ser Ser Arg Trp Tyr Ser Gly Ser Gly Ile Tyr Arg Asp Val
        195                 200                 205

Thr Leu Thr Val Thr Asp Gly Val His Val Gly Asn Asn Gly Val Ala
    210                 215                 220

Ile Lys Thr Pro Ser Leu Ala Thr Gln Asn Gly Gly Asp Val Thr Met
225                 230                 235                 240

Asn Leu Thr Thr Lys Val Ala Asn Asp Thr Glu Ala Ala Ala Asn Ile
                245                 250                 255

Thr Leu Lys Gln Thr Val Phe Pro Lys Gly Gly Lys Thr Asp Ala Ala
            260                 265                 270

Ile Gly Thr Val Thr Thr Ala Ser Lys Ser Ile Ala Ala Gly Ala Ser
        275                 280                 285

Ala Asp Val Thr Ser Thr Ile Thr Ala Ala Ser Pro Lys Leu Trp Ser
    290                 295                 300

Ile Lys Asn Pro Asn Leu Tyr Thr Val Arg Thr Glu Val Leu Asn Gly
```

```
                305                 310                 315                 320
Gly Lys Val Leu Asp Thr Tyr Asp Thr Glu Tyr Gly Phe Arg Trp Thr
            325                 330                 335
Gly Phe Asp Ala Thr Ser Gly Phe Ser Leu Asn Gly Glu Lys Val Lys
            340                 345                 350
Leu Lys Gly Val Ser Met His His Asp Gln Gly Ser Leu Gly Ala Val
            355                 360                 365
Ala Asn Arg Arg Ala Ile Glu Arg Gln Val Glu Ile Leu Gln Lys Met
            370                 375                 380
Gly Val Asn Ser Ile Arg Thr Thr His Asn Pro Ala Ala Lys Ala Leu
385                 390                 395                 400
Ile Asp Val Cys Asn Glu Lys Gly Val Leu Val Glu Glu Val Phe
                405                 410                 415
Asp Met Trp Asn Arg Ser Lys Asn Gly Asn Thr Glu Tyr Gly Lys
            420                 425                 430
Trp Phe Gly Gln Ala Ile Ala Gly Asp Asn Ala Val Leu Gly Gly Asp
            435                 440                 445
Lys Asp Glu Thr Trp Ala Lys Phe Asp Leu Thr Ser Thr Ile Asn Arg
450                 455                 460
Asp Arg Asn Ala Pro Ser Val Ile Met Trp Ser Leu Gly Asn Glu Met
465                 470                 475                 480
Met Glu Gly Ile Ser Gly Ser Val Ser Gly Phe Pro Ala Thr Ser Ala
            485                 490                 495
Lys Leu Val Ala Trp Thr Lys Ala Ala Asp Ser Thr Arg Pro Met Thr
            500                 505                 510
Tyr Gly Asp Asn Lys Ile Lys Ala Asn Trp Asn Glu Ser Asn Thr Met
            515                 520                 525
Gly Asp Asn Leu Thr Ala Asn Gly Gly Val Val Gly Thr Asn Tyr Ser
            530                 535                 540
Asp Gly Ala Asn Tyr Asp Lys Ile Arg Thr Thr His Pro Ser Trp Ala
545                 550                 555                 560
Ile Tyr Gly Ser Glu Thr Ala Ser Ala Ile Asn Ser Arg Gly Ile Tyr
                565                 570                 575
Asn Arg Thr Thr Gly Gly Ala Gln Ser Ser Asp Lys Gln Leu Thr Ser
            580                 585                 590
Tyr Asp Asn Ser Ala Val Gly Trp Gly Ala Val Ala Ser Ser Ala Trp
            595                 600                 605
Tyr Asp Val Val Gln Arg Asp Phe Val Ala Gly Thr Tyr Val Trp Thr
            610                 615                 620
Gly Phe Asp Tyr Leu Gly Glu Pro Thr Pro Trp Asn Gly Thr Gly Ser
625                 630                 635                 640
Gly Ala Val Gly Ser Trp Pro Ser Pro Lys Asn Ser Tyr Phe Gly Ile
            645                 650                 655
Val Asp Thr Ala Gly Phe Pro Lys Asp Thr Tyr Tyr Phe Tyr Gln Ser
            660                 665                 670
Gln Trp Asn Asp Asp Val His Thr Leu His Ile Leu Pro Ala Trp Asn
            675                 680                 685
Glu Asn Val Val Ala Lys Gly Ser Gly Asn Asn Val Pro Val Val Val
            690                 695                 700
Tyr Thr Asp Ala Ala Lys Val Lys Leu Tyr Phe Thr Pro Lys Gly Ser
705                 710                 715                 720
Thr Glu Lys Arg Leu Ile Gly Glu Lys Ser Phe Thr Lys Lys Thr Thr
            725                 730                 735
```

```
Ala Ala Gly Tyr Thr Tyr Gln Val Tyr Glu Gly Ser Asp Lys Asp Ser
            740                 745                 750

Thr Ala His Lys Asn Met Tyr Leu Thr Trp Asn Val Pro Trp Ala Glu
            755                 760                 765

Gly Thr Ile Ser Ala Glu Ala Tyr Asp Glu Asn Arg Leu Ile Pro
            770                 775             780

Glu Gly Ser Thr Glu Gly Asn Ala Ser Val Thr Thr Thr Gly Lys Ala
785             790                 795                 800

Ala Lys Leu Lys Ala Asp Ala Asp Arg Lys Thr Ile Thr Ala Asp Gly
                805                 810                 815

Lys Asp Leu Ser Tyr Ile Glu Val Asp Val Thr Asp Ala Asn Gly His
            820                 825                 830

Ile Val Pro Asp Ala Ala Asn Arg Val Thr Phe Asp Val Lys Gly Ala
            835                 840                 845

Gly Lys Leu Val Gly Val Asp Asn Gly Ser Ser Pro Asp His Asp Ser
850             855                 860

Tyr Gln Ala Asp Asn Arg Lys Ala Phe Ser Gly Lys Val Leu Ala Ile
865             870                 875                 880

Val Gln Ser Thr Lys Glu Ala Gly Glu Ile Thr Val Thr Ala Lys Ala
                885                 890                 895

Asp Gly Leu Gln Ser Ser Thr Val Lys Ile Ala Thr Thr Ala Val Pro
            900                 905                 910

Gly Thr Ser Thr Glu Lys Thr Val Arg Ser Phe Tyr Tyr Ser Arg Asn
            915                 920                 925

Tyr Tyr Val Lys Thr Gly Asn Lys Pro Ile Leu Pro Ser Asp Val Glu
            930                 935                 940

Val Arg Tyr Ser Asp Gly Thr Ser Asp Arg Gln Asn Val Thr Trp Asp
945             950                 955                 960

Ala Val Ser Asp Asp Gln Ile Ala Lys Ala Gly Ser Phe Ser Val Ala
                965                 970                 975

Gly Thr Val Ala Gly Gln Lys Ile Ser Val Arg Val Thr Met Ile Asp
            980                 985                 990

Glu Ile Gly Ala Leu Leu Asn Tyr Ser Ala Ser Thr Pro Val Gly Thr
            995                 1000                1005

Pro Ala Val Leu Pro Gly Ser Arg Pro Ala Val Leu Pro Asp Gly
            1010                1015                1020

Thr Val Thr Ser Ala Asn Phe Ala Val His Trp Thr Lys Pro Ala
            1025                1030                1035

Asp Thr Val Tyr Asn Thr Ala Gly Thr Val Lys Val Pro Gly Thr
            1040                1045                1050

Ala Thr Val Phe Gly Lys Glu Phe Lys Val Thr Ala Thr Ile Arg
            1055                1060                1065

Val Gln Arg Ser Gln Val Thr Ile Gly Ser Ser Val Ser Gly Asn
            1070                1075                1080

Ala Leu Arg Leu Thr Gln Asn Ile Pro Ala Asp Lys Gln Ser Asp
            1085                1090                1095

Thr Leu Asp Ala Ile Lys Asp Gly Ser Thr Thr Val Asp Ala Asn
            1100                1105                1110

Thr Gly Gly Gly Ala Asn Pro Ser Ala Trp Thr Asn Trp Ala Tyr
            1115                1120                1125

Ser Lys Ala Gly His Asn Thr Ala Glu Ile Thr Phe Glu Tyr Ala
            1130                1135                1140
```

-continued

```
Thr Glu Gln Gln Leu Gly Gln Ile Val Met Tyr Phe Phe Arg Asp
    1145                1150                1155
Ser Asn Ala Val Arg Phe Pro Asp Ala Gly Lys Thr Lys Ile Gln
    1160                1165                1170
Ile Ser Ala Asp Gly Lys Asn Trp Thr Asp Leu Ala Ala Thr Glu
    1175                1180                1185
Thr Ile Ala Ala Gln Glu Ser Ser Asp Arg Val Lys Pro Tyr Thr
    1190                1195                1200
Tyr Asp Phe Ala Pro Val Gly Ala Thr Phe Val Lys Val Thr Val
    1205                1210                1215
Thr Asn Ala Asp Thr Thr Thr Pro Ser Gly Val Val Cys Ala Gly
    1220                1225                1230
Leu Thr Glu Ile Glu Leu Lys Thr Ala Thr Ser Lys Phe Val Thr
    1235                1240                1245
Asn Thr Ser Ala Ala Leu Ser Ser Leu Thr Val Asn Gly Thr Lys
    1250                1255                1260
Val Ser Asp Ser Val Leu Ala Ala Gly Ser Tyr Asn Thr Pro Ala
    1265                1270                1275
Ile Ile Ala Asp Val Lys Ala Glu Gly Glu Gly Asn Ala Ser Val
    1280                1285                1290
Thr Val Leu Pro Ala His Asp Asn Val Ile Arg Val Ile Thr Glu
    1295                1300                1305
Ser Glu Asp His Val Thr Arg Lys Thr Phe Thr Ile Asn Leu Gly
    1310                1315                1320
Thr Glu Gln Glu Phe Pro Ala Asp Ser Asp Glu Arg Asp Tyr Pro
    1325                1330                1335
Ala Ala Asp Met Thr Val Thr Val Gly Ser Glu Gln Thr Ser Gly
    1340                1345                1350
Thr Ala Thr Glu Gly Pro Lys Lys Phe Ala Val Asp Gly Asn Thr
    1355                1360                1365
Ser Thr Tyr Trp His Ser Asn Trp Thr Pro Thr Thr Val Asn Asp
    1370                1375                1380
Leu Trp Ile Ala Phe Glu Leu Gln Lys Pro Thr Lys Leu Asp Ala
    1385                1390                1395
Leu Arg Tyr Leu Pro Arg Pro Ala Gly Ser Lys Asn Gly Ser Val
    1400                1405                1410
Thr Glu Tyr Lys Val Gln Val Ser Asp Asp Gly Thr Asn Trp Thr
    1415                1420                1425
Asp Ala Gly Ser Gly Thr Trp Thr Thr Asp Tyr Gly Trp Lys Leu
    1430                1435                1440
Ala Glu Phe Asn Gln Pro Val Thr Thr Lys His Val Arg Leu Lys
    1445                1450                1455
Ala Val His Thr Tyr Ala Asp Ser Gly Asn Asp Lys Phe Met Ser
    1460                1465                1470
Ala Ser Glu Ile Arg Leu Arg Lys Ala Val Asp Thr Thr Asp Ile
    1475                1480                1485
Ser Gly Ala Thr Val Thr Val Pro Ala Lys Leu Thr Val Asp Arg
    1490                1495                1500
Val Asp Ala Asp His Pro Ala Thr Phe Ala Thr Lys Asp Val Thr
    1505                1510                1515
Val Thr Leu Gly Asp Ala Thr Leu Arg Tyr Gly Val Asp Tyr Leu
    1520                1525                1530
Leu Asp Tyr Ala Gly Asn Thr Ala Val Gly Lys Ala Thr Val Thr
```

```
              1535                1540                1545

Val Arg Gly Ile Asp Lys Tyr Ser Gly Thr Val Ala Lys Thr Phe
              1550                1555                1560

Thr Ile Glu Leu Lys Asn Ala Pro Ala Pro Glu Pro Thr Leu Thr
              1565                1570                1575

Ser Val Ser Val Lys Thr Lys Pro Ser Lys Leu Thr Tyr Val Val
              1580                1585                1590

Gly Asp Ala Phe Asp Pro Ala Gly Leu Val Leu Gln His Asp Arg
              1595                1600                1605

Gln Ala Asp Arg Pro Pro Gln Pro Leu Val Gly Glu Gln Ala Asp
              1610                1615                1620

Glu Arg Gly Leu Thr Cys Gly Thr Arg Cys Asp Arg Val Glu Gln
              1625                1630                1635

Leu Arg Lys His Glu Asn Arg Glu Ala His Arg Thr Gly Leu Asp
              1640                1645                1650

His Leu Glu Phe Val Gly Ala Ala Asp Gly Ala Val Gly Glu Gln
              1655                1660                1665

Ala Thr Phe Lys Val His Val His Ala Asp Gln Gly Asp Gly Arg
              1670                1675                1680

His Asp Asp Ala Asp Glu Arg Asp Ile Asp Pro His Val Pro Val
              1685                1690                1695

Asp His Ala Val Gly Glu Leu Ala Arg Ala Ala Cys His His Val
              1700                1705                1710

Ile Gly Leu Arg Val Asp Thr His Arg Leu Lys Ala Ser Gly Phe
              1715                1720                1725

Gln Ile Pro Ala Asp Asp Met Ala Glu Ile Asp Arg Ile Thr Gly
              1730                1735                1740

Phe His Arg Phe Glu Arg His Val Gly
              1745                1750

<210> SEQ ID NO 5
<211> LENGTH: 1935
<212> TYPE: PRT
<213> ORGANISM: Artificial sequence
<220> FEATURE:
<223> OTHER INFORMATION: Synthetic construct

<400> SEQUENCE: 5

Met Ala Val Arg Arg Leu Gly Gly Arg Ile Val Ala Phe Ala Ala Thr
  1               5                  10                  15

Val Ala Leu Ser Ile Pro Leu Gly Leu Leu Thr Asn Ser Ala Trp Ala
                 20                  25                  30

Val Glu Asp Ala Thr Arg Ser Asp Ser Thr Thr Gln Met Ser Ser Thr
             35                  40                  45

Pro Glu Val Val Tyr Ser Ser Ala Val Asp Ser Lys Gln Asn Arg Thr
         50                  55                  60

Ser Asp Phe Asp Ala Asn Trp Lys Phe Met Leu Ser Asp Ser Val Gln
 65                  70                  75                  80

Ala Gln Asp Pro Ala Phe Asp Asp Ser Ala Trp Gln Gln Val Asp Leu
                 85                  90                  95

Pro His Asp Tyr Ser Ile Thr Gln Lys Tyr Ser Gln Ser Asn Glu Ala
            100                 105                 110

Glu Ser Ala Tyr Leu Pro Gly Gly Thr Gly Trp Tyr Arg Lys Ser Phe
        115                 120                 125

Thr Ile Asp Arg Asp Leu Ala Gly Lys Arg Ile Ala Ile Asn Phe Asp
```

-continued

```
            130                 135                 140
Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                    165                 170                 175

Ala Lys Phe Gly Gly Glu Asn Thr Ile Val Val Lys Val Glu Asn Arg
                180                 185                 190

Leu Pro Ser Ser Arg Trp Tyr Ser Gly Ser Gly Ile Tyr Arg Asp Val
                195                 200                 205

Thr Leu Thr Val Thr Asp Gly Val His Val Gly Asn Asn Gly Val Ala
                210                 215                 220

Ile Lys Thr Pro Ser Leu Ala Thr Gln Asn Gly Gly Asn Val Thr Met
225                 230                 235                 240

Asn Leu Thr Thr Lys Val Ala Asn Asp Thr Lys Ala Ala Ala Asn Ile
                    245                 250                 255

Thr Leu Lys Gln Thr Val Phe Pro Lys Gly Lys Thr Asp Ala Ala
                260                 265                 270

Ile Gly Thr Val Thr Thr Ala Ser Lys Ser Ile Ala Ala Gly Ala Ser
                275                 280                 285

Ala Asp Val Thr Ser Thr Ile Thr Ala Ala Ser Pro Lys Leu Trp Ser
                290                 295                 300

Ile Lys Asn Pro Asn Leu Tyr Thr Val Arg Thr Glu Val Leu Asn Gly
305                 310                 315                 320

Gly Lys Val Leu Asp Thr Tyr Asp Thr Glu Tyr Gly Phe Arg Trp Thr
                    325                 330                 335

Gly Phe Asp Ala Thr Ser Gly Phe Ser Leu Asn Gly Glu Lys Val Lys
                340                 345                 350

Leu Lys Gly Val Ser Met His His Asp Gln Gly Ser Leu Gly Ala Val
                355                 360                 365

Ala Asn Arg Arg Ala Ile Glu Arg Gln Val Glu Ile Leu Gln Lys Met
                370                 375                 380

Gly Val Asn Ser Ile Arg Thr Thr His Asn Pro Ala Ala Lys Ala Leu
385                 390                 395                 400

Ile Asp Val Cys Asn Glu Lys Gly Val Leu Val Glu Glu Val Phe
                    405                 410                 415

Asp Met Trp Asn Arg Ser Lys Asn Gly Asn Thr Glu Tyr Gly Lys
                420                 425                 430

Trp Phe Gly Gln Ala Ile Ala Gly Asp Asn Ala Val Leu Gly Gly Asp
                435                 440                 445

Lys Asp Glu Thr Trp Ala Lys Phe Asp Leu Thr Ser Thr Ile Asn Arg
450                 455                 460

Asp Arg Asn Ala Pro Ser Val Ile Met Trp Ser Leu Gly Asn Glu Met
465                 470                 475                 480

Met Glu Gly Ile Ser Gly Ser Val Ser Gly Phe Pro Ala Thr Ser Ala
                    485                 490                 495

Lys Leu Val Ala Trp Thr Lys Ala Ala Asp Ser Thr Arg Pro Met Thr
                500                 505                 510

Tyr Gly Asp Asn Lys Ile Lys Ala Asn Trp Asn Glu Ser Asn Thr Met
                515                 520                 525

Gly Asp Asn Leu Thr Ala Asn Gly Gly Val Val Gly Thr Asn Tyr Ser
                530                 535                 540

Asp Gly Ala Asn Tyr Asp Lys Ile Arg Thr Thr His Pro Ser Trp Ala
545                 550                 555                 560
```

```
Ile Tyr Gly Ser Glu Thr Ala Ser Ala Ile Asn Ser Arg Gly Ile Tyr
            565                 570                 575

Asn Arg Thr Thr Gly Gly Ala Gln Ser Ser Asp Lys Gln Leu Thr Ser
            580                 585                 590

Tyr Asp Asn Ser Ala Val Gly Trp Gly Ala Val Ala Ser Ser Ala Trp
            595                 600                 605

Tyr Asp Val Val Gln Arg Asp Phe Val Ala Gly Thr Tyr Val Trp Thr
            610                 615                 620

Gly Phe Asp Tyr Leu Gly Glu Pro Thr Pro Trp Asn Gly Thr Gly Ser
625                 630                 635                 640

Gly Ala Val Gly Ser Trp Pro Ser Pro Lys Asn Ser Tyr Phe Gly Ile
            645                 650                 655

Val Asp Thr Ala Gly Phe Pro Lys Asp Thr Tyr Tyr Phe Tyr Gln Ser
            660                 665                 670

Gln Trp Asn Asp Asp Val His Thr Leu His Ile Leu Pro Ala Trp Asn
            675                 680                 685

Glu Asn Val Val Ala Lys Gly Ser Gly Asn Asn Val Pro Val Val Val
            690                 695                 700

Tyr Thr Asp Ala Ala Lys Val Lys Leu Tyr Phe Thr Pro Lys Gly Ser
705                 710                 715                 720

Thr Glu Lys Arg Leu Ile Gly Glu Lys Ser Phe Thr Lys Lys Thr Thr
            725                 730                 735

Ala Ala Gly Tyr Thr Tyr Gln Val Tyr Glu Gly Ala Asp Lys Asp Ser
            740                 745                 750

Thr Ala His Lys Asn Met Tyr Leu Thr Trp Asn Val Pro Trp Ala Glu
            755                 760                 765

Gly Thr Ile Ser Ala Glu Ala Tyr Asp Glu Asn Asn Arg Leu Ile Pro
            770                 775                 780

Glu Gly Ser Thr Glu Gly Asn Ala Ser Val Thr Thr Gly Lys Ala
785                 790                 795                 800

Ala Lys Leu Lys Ala Asp Ala Asp Arg Lys Thr Ile Thr Ala Asp Gly
            805                 810                 815

Lys Asp Leu Ser Tyr Ile Glu Val Asp Val Thr Asp Ala Asn Gly His
            820                 825                 830

Ile Val Pro Asp Ala Ala Asn Arg Val Thr Phe Asp Val Lys Gly Ala
            835                 840                 845

Gly Lys Leu Val Gly Val Asp Asn Gly Ser Ser Pro Asp His Asp Ser
850                 855                 860

Tyr Gln Ala Asp Asn Arg Lys Ala Phe Ser Gly Lys Val Leu Ala Ile
865                 870                 875                 880

Val Gln Ser Thr Lys Glu Ala Gly Glu Ile Thr Val Thr Ala Lys Ala
            885                 890                 895

Asp Gly Leu Gln Ser Ser Thr Val Lys Ile Ala Thr Ala Val Pro
            900                 905                 910

Gly Thr Ser Thr Glu Lys Thr Val Arg Ser Phe Tyr Tyr Ser Arg Asn
            915                 920                 925

Tyr Tyr Val Lys Thr Gly Asn Lys Pro Ile Leu Pro Ser Asp Val Glu
            930                 935                 940

Val Arg Tyr Ser Asp Gly Thr Ser Asp Arg Gln Asn Val Thr Trp Asp
945                 950                 955                 960

Ala Val Ser Asp Asp Gln Ile Ala Lys Ala Gly Ser Phe Ser Val Ala
            965                 970                 975
```

```
Gly Thr Val Ala Gly Gln Lys Ile Ser Val Arg Val Thr Met Ile Asp
            980                 985                 990

Glu Ile Gly Ala Leu Leu Asn Tyr  Ser Ala Ser Thr Pro  Val Gly Thr
            995                1000                1005

Pro Ala  Val Leu Pro Gly Ser  Arg Pro Ala Val Leu  Pro Asp Gly
    1010                1015                1020

Thr Val  Thr Ser Ala Asn Phe  Ala Val Asp Trp Thr  Lys Pro Ala
    1025                1030                1035

Asp Thr  Val Tyr Asn Thr Ala  Gly Thr Val Lys Val  Pro Gly Thr
    1040                1045                1050

Ala Thr  Val Phe Gly Lys Glu  Phe Lys Val Thr Ala  Thr Ile Arg
    1055                1060                1065

Val Gln  Arg Ser Gln Val Thr  Ile Gly Ser Ser Val  Ser Gly Asn
    1070                1075                1080

Ala Leu  Arg Leu Thr Gln Asn  Ile Pro Ala Asp Lys  Gln Ser Asp
    1085                1090                1095

Thr Leu  Asp Ala Ile Lys Asp  Gly Ser Thr Thr Val  Asp Ala Asn
    1100                1105                1110

Thr Gly  Gly Gly Ala Asn Pro  Ser Ala Trp Thr Asn  Trp Ala Tyr
    1115                1120                1125

Ser Lys  Ala Gly His Asn Thr  Ala Glu Ile Thr Phe  Glu Tyr Ala
    1130                1135                1140

Thr Glu  Gln Gln Leu Gly Gln  Ile Val Met Tyr Phe  Phe Arg Asp
    1145                1150                1155

Ser Asn  Ala Val Arg Phe Pro  Asp Ala Gly Lys Thr  Lys Ile Gln
    1160                1165                1170

Ile Ser  Ala Asp Gly Lys Asn  Trp Thr Asp Leu Ala  Ala Thr Glu
    1175                1180                1185

Thr Ile  Ala Ala Gln Glu Ser  Ser Asp Arg Val Lys  Pro Tyr Thr
    1190                1195                1200

Tyr Asp  Phe Ala Pro Val Gly  Ala Thr Phe Val Lys  Val Thr Val
    1205                1210                1215

Thr Asn  Ala Asp Thr Thr Thr  Pro Ser Gly Val Val  Cys Ala Gly
    1220                1225                1230

Leu Thr  Glu Ile Glu Leu Lys  Thr Ala Thr Ser Lys  Phe Val Thr
    1235                1240                1245

Asn Thr  Ser Ala Ala Leu Ser  Ser Leu Thr Val Asn  Gly Thr Lys
    1250                1255                1260

Val Ser  Asp Ser Val Leu Ala  Ala Gly Ser Tyr Asn  Thr Pro Ala
    1265                1270                1275

Ile Ile  Ala Asp Val Lys Ala  Glu Gly Glu Gly Asn  Ala Ser Val
    1280                1285                1290

Thr Val  Leu Pro Ala His Asp  Asn Val Ile Arg Val  Ile Thr Glu
    1295                1300                1305

Ser Glu  Asp His Val Thr Arg  Lys Thr Phe Thr Ile  Asn Leu Gly
    1310                1315                1320

Thr Glu  Gln Glu Phe Pro Ala  Asp Ser Asp Glu Arg  Asp Tyr Pro
    1325                1330                1335

Ala Ala  Asp Met Thr Val Thr  Ala Gly Ser Glu Gln  Thr Ser Gly
    1340                1345                1350

Thr Ala  Thr Glu Gly Pro Lys  Lys Phe Ala Val Asp  Gly Asn Thr
    1355                1360                1365

Ser Thr  Tyr Trp His Ser Asn  Trp Thr Pro Thr Thr  Val Asn Asp
```

-continued

```
            1370                1375                1380
Leu Trp Ile Ala Phe Glu Leu Gln Lys Pro Thr Lys Leu Asp Ala
    1385                1390                1395
Leu Arg Tyr Leu Pro Arg Pro Ala Gly Ser Lys Asn Gly Ser Val
    1400                1405                1410
Thr Glu Tyr Lys Val Gln Val Ser Asp Asp Gly Thr Asn Trp Thr
    1415                1420                1425
Asp Ala Gly Ser Gly Thr Trp Thr Thr Asp Tyr Gly Trp Lys Leu
    1430                1435                1440
Ala Glu Phe Asn Gln Pro Val Thr Thr Lys His Val Arg Leu Lys
    1445                1450                1455
Ala Val His Thr Tyr Ala Asp Ser Gly Asn Asp Lys Phe Met Ser
    1460                1465                1470
Ala Ser Glu Ile Arg Leu Arg Lys Ala Val Asp Thr Thr Asp Ile
    1475                1480                1485
Ser Gly Ala Thr Val Thr Val Pro Ala Lys Leu Thr Val Asp Arg
    1490                1495                1500
Val Asp Ala Asp His Pro Ala Thr Phe Ala Thr Lys Asp Val Thr
    1505                1510                1515
Val Thr Leu Gly Asp Ala Thr Leu Arg Tyr Gly Val Asp Tyr Leu
    1520                1525                1530
Leu Asp Tyr Ala Gly Asn Thr Ala Val Gly Lys Ala Thr Val Thr
    1535                1540                1545
Val Arg Gly Ile Asp Lys Tyr Ser Gly Thr Val Ala Lys Thr Phe
    1550                1555                1560
Thr Ile Glu Leu Lys Asn Ala Pro Ala Pro Glu Pro Thr Leu Thr
    1565                1570                1575
Ser Val Ser Val Lys Thr Lys Pro Ser Lys Leu Thr Tyr Val Val
    1580                1585                1590
Gly Asp Ala Phe Asp Pro Ala Gly Leu Val Leu Gln Leu Asn Tyr
    1595                1600                1605
Asp Asp Asp Ser Thr Gly Thr Val Thr Trp Asn Thr Gln Thr Ala
    1610                1615                1620
Gly Asp Phe Thr Phe Lys Pro Ala Leu Asp Ala Lys Leu Lys Val
    1625                1630                1635
Thr Asp Lys Thr Val Thr Val Thr Tyr Gln Gly Lys Ser Ala Val
    1640                1645                1650
Ile Asp Ile Thr Val Ser Gln Pro Ala Pro Thr Val Ser Lys Thr
    1655                1660                1665
Asp Leu Asp Lys Ala Ile Lys Ala Ile Glu Ala Lys Asn Pro Asp
    1670                1675                1680
Ser Ser Lys Tyr Thr Ala Asp Ser Trp Lys Thr Phe Ala Asp Ala
    1685                1690                1695
Met Ala His Ala Lys Ala Val Ile Ala Asp Asp Ser Ala Thr Gln
    1700                1705                1710
Gln Asp Val Asp Lys Ala Leu Lys Ala Leu Thr Asp Ala Tyr Ala
    1715                1720                1725
Gly Leu Thr Glu Lys Thr Pro Glu Pro Ala Pro Val Ser Lys Ser
    1730                1735                1740
Glu Leu Asp Lys Lys Ile Lys Ala Ile Glu Ala Glu Lys Leu Asp
    1745                1750                1755
Gly Ser Lys Tyr Thr Ala Glu Ser Trp Lys Ala Phe Glu Thr Ala
    1760                1765                1770
```

```
Leu Ala His Ala Lys Ala Val Ile Ala Ser Asp Ser Ala Thr Gln
    1775                1780                1785

Gln Asp Val Asp Ala Ala Leu Gly Ala Leu Thr Ser Ala Arg Asp
    1790                1795                1800

Gly Leu Thr Glu Lys Gly Glu Val Lys Pro Asp Pro Lys Pro Glu
    1805                1810                1815

Pro Gly Thr Val Asp Lys Ala Ala Leu Asp Lys Ala Val Lys Lys
    1820                1825                1830

Val Glu Ala Glu Lys Leu Asp Gly Ser Lys Tyr Thr Ala Asp Ser
    1835                1840                1845

Trp Lys Ala Phe Glu Thr Ala Leu Ala His Ala Lys Ala Val Ile
    1850                1855                1860

Gly Asn Ala Asn Ser Thr Gln Phe Asp Ile Asp Asn Ala Leu Ser
    1865                1870                1875

Met Leu Asn Asp Ala Arg Ala Ala Leu Lys Glu Lys Pro Gly Arg
    1880                1885                1890

Ile Ile Ala Ile Ile Asp Gly Ala Leu Ser Lys Thr Gly Ala
    1895                1900                1905

Ser Val Ala Ile Ile Ala Ser Val Ala Ala Ala Met Lys Ala Val
    1910                1915                1920

Gly Ala Gly Val Met Ala Leu Arg Pro Pro Lys Trp
    1925                1930                1935

<210> SEQ ID NO 6
<211> LENGTH: 887
<212> TYPE: PRT
<213> ORGANISM: Bifidobacterium bifidum

<400> SEQUENCE: 6

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
```

```
              195                 200                 205
Asn Leu Thr Thr Lys Val Ala Asn Asp Thr Glu Ala Ala Asn Ile
    210                 215                 220
Thr Leu Lys Gln Thr Val Phe Pro Lys Gly Gly Lys Thr Asp Ala Ala
225                 230                 235                 240
Ile Gly Thr Val Thr Thr Ala Ser Lys Ser Ile Ala Ala Gly Ala Ser
                245                 250                 255
Ala Asp Val Thr Ser Thr Ile Thr Ala Ala Ser Pro Lys Leu Trp Ser
                260                 265                 270
Ile Lys Asn Pro Asn Leu Tyr Thr Val Arg Thr Glu Val Leu Asn Gly
            275                 280                 285
Gly Lys Val Leu Asp Thr Tyr Asp Thr Glu Tyr Gly Phe Arg Trp Thr
290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
            355                 360                 365
Ile Asp Val Cys Asn Glu Lys Gly Val Leu Val Glu Glu Val Phe
370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
            420                 425                 430
Asp Arg Asn Ala Pro Ser Val Ile Met Trp Ser Leu Gly Asn Glu Met
        435                 440                 445
Met Glu Gly Ile Ser Gly Ser Val Ser Gly Phe Pro Ala Thr Ser Ala
    450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
                500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
        530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
            610                 615                 620
```

```
Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
            645                 650                 655

Glu Asn Val Val Ala Lys Gly Ser Gly Asn Asn Val Pro Val Val Val
        660                 665                 670

Tyr Thr Asp Ala Ala Lys Val Lys Leu Tyr Phe Thr Pro Lys Gly Ser
    675                 680                 685

Thr Glu Lys Arg Leu Ile Gly Glu Lys Ser Phe Thr Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735

Gly Thr Ile Ser Ala Glu Ala Tyr Asp Glu Asn Asn Arg Leu Ile Pro
        740                 745                 750

Glu Gly Ser Thr Glu Gly Asn Ala Ser Val Thr Thr Gly Lys Ala
    755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
        820                 825                 830

Tyr Gln Ala Asp Asn Arg Lys Ala Phe Ser Gly Lys Val Leu Ala Ile
    835                 840                 845

Val Gln Ser Thr Lys Glu Ala Gly Glu Ile Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr
                885

<210> SEQ ID NO 7
<211> LENGTH: 965
<212> TYPE: PRT
<213> ORGANISM: Bifidobacterium bifidum

<400> SEQUENCE: 7

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
            85                  90                  95

Thr Ile Asp Arg Asp Leu Ala Gly Lys Arg Ile Ala Ile Asn Phe Asp
```

-continued

```
                100                 105                 110
Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Ile Tyr Arg Asp Val
            165                 170                 175

Thr Leu Thr Val Thr Asp Gly Val His Val Gly Asn Asn Gly Val Ala
        180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
        210                 215                 220

Thr Leu Lys Gln Thr Val Phe Pro Lys Gly Gly Lys Thr Asp Ala Ala
225                 230                 235                 240

Ile Gly Thr Val Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
        290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Ser Leu Gly Ala Val
            325                 330                 335

Ala Asn Arg Arg Ala Ile Glu Arg Gln Val Glu Ile Leu Gln Lys Met
        340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
            405                 410                 415

Lys Asp Glu Thr Trp Ala Lys Phe Asp Leu Thr Ser Thr Ile Asn Arg
        420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
        450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
            485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525
```

-continued

```
Ile Tyr Gly Ser Glu Thr Ala Ser Ala Ile Asn Ser Arg Gly Ile Tyr
        530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940
```

-continued

Gly Thr Val Ala Gly Gln Lys Ile Ser Val Arg Val Thr Met Ile Asp
945                 950                 955                 960

Glu Ile Gly Ala Leu
            965

<210> SEQ ID NO 8
<211> LENGTH: 1038
<212> TYPE: PRT
<213> ORGANISM: Bifidobacterium bifidum

<400> SEQUENCE: 8

Val Glu Asp Ala Thr Arg Ser Asp Ser Thr Gln Met Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

```
Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
            450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
                515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Thr Gly Lys Ala
            755                 760                 765
```

```
Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
            850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val  His Trp Thr Lys Pro Ala Asp Thr
            995                 1000                1005

Val Tyr  Asn Thr Ala Gly Thr  Val Lys Val Pro Gly  Thr Ala Thr
            1010                1015                1020

Val Phe  Gly Lys Glu Phe Lys  Val Thr Ala Thr Ile  Arg Val Gln
            1025                1030                1035

<210> SEQ ID NO 9
<211> LENGTH: 1142
<212> TYPE: PRT
<213> ORGANISM: Bifidobacterium bifidum

<400> SEQUENCE: 9

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
            85                  90                  95

Thr Ile Asp Arg Asp Leu Ala Gly Lys Arg Ile Ala Ile Asn Phe Asp
            100                 105                 110
```

```
Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
        210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
        290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
            325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Val Val Gly Thr Asn Tyr Ser
            500                 505                 510

Asp Gly Ala Asn Tyr Asp Lys Ile Arg Thr Thr His Pro Ser Trp Ala
            515                 520                 525
```

```
Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
    595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val
                660                 665                 670

Tyr Thr Asp Ala Ala Lys Val Lys Leu Tyr Phe Thr Pro Lys Gly Ser
    675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
        740                 745                 750

Glu Gly Ser Thr Glu Gly Asn Ala Ser Val Thr Thr Gly Lys Ala
                755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
    835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
```

```
                945                 950                 955                 960
Glu Ile Gly Ala Leu Leu Asn Tyr Ser Ala Ser Thr Pro Val Gly Thr
                    965                 970                 975

Pro Ala Val Leu Pro Gly Ser Arg Pro Ala Val Leu Pro Asp Gly Thr
                    980                 985                 990

Val Thr Ser Ala Asn Phe Ala Val His Trp Thr Lys Pro Ala Asp Thr
                    995                 1000                1005

Val Tyr Asn Thr Ala Gly Thr Val Lys Val Pro Gly Thr Ala Thr
            1010                1015                1020

Val Phe Gly Lys Glu Phe Lys Val Thr Ala Thr Ile Arg Val Gln
            1025                1030                1035

Arg Ser Gln Val Thr Ile Gly Ser Ser Val Ser Gly Asn Ala Leu
            1040                1045                1050

Arg Leu Thr Gln Asn Ile Pro Ala Asp Lys Gln Ser Asp Thr Leu
            1055                1060                1065

Asp Ala Ile Lys Asp Gly Ser Thr Thr Val Asp Ala Asn Thr Gly
            1070                1075                1080

Gly Gly Ala Asn Pro Ser Ala Trp Thr Asn Trp Ala Tyr Ser Lys
            1085                1090                1095

Ala Gly His Asn Thr Ala Glu Ile Thr Phe Glu Tyr Ala Thr Glu
            1100                1105                1110

Gln Gln Leu Gly Gln Ile Val Met Tyr Phe Phe Arg Asp Ser Asn
            1115                1120                1125

Ala Val Arg Phe Pro Asp Ala Gly Lys Thr Lys Ile Gln Ile
            1130                1135                1140

<210> SEQ ID NO 10
<211> LENGTH: 1211
<212> TYPE: PRT
<213> ORGANISM: Bifidobacterium bifidum

<400> SEQUENCE: 10

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175
```

-continued

```
Thr Leu Thr Val Thr Asp Gly Val His Val Gly Asn Asn Gly Val Ala
            180                 185                 190
Ile Lys Thr Pro Ser Leu Ala Thr Gln Asn Gly Gly Asp Val Thr Met
        195                 200                 205
Asn Leu Thr Thr Lys Val Ala Asn Asp Thr Glu Ala Ala Ala Asn Ile
    210                 215                 220
Thr Leu Lys Gln Thr Val Phe Pro Lys Gly Gly Lys Thr Asp Ala Ala
225                 230                 235                 240
Ile Gly Thr Val Thr Thr Ala Ser Lys Ser Ile Ala Ala Gly Ala Ser
                245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
        275                 280                 285
Gly Lys Val Leu Asp Thr Tyr Asp Thr Glu Tyr Gly Phe Arg Trp Thr
    290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
        355                 360                 365
Ile Asp Val Cys Asn Glu Lys Gly Val Leu Val Val Glu Glu Val Phe
    370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
            420                 425                 430
Asp Arg Asn Ala Pro Ser Val Ile Met Trp Ser Leu Gly Asn Glu Met
        435                 440                 445
Met Glu Gly Ile Ser Gly Ser Val Ser Gly Phe Pro Ala Thr Ser Ala
    450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
            500                 505                 510
Asp Gly Ala Asn Tyr Asp Lys Ile Arg Thr Thr His Pro Ser Trp Ala
        515                 520                 525
Ile Tyr Gly Ser Glu Thr Ala Ser Ala Ile Asn Ser Arg Gly Ile Tyr
    530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Val Ala Ser Ser Ala Trp Trp
                565                 570                 575
Tyr Asp Val Val Gln Arg Asp Phe Val Ala Gly Thr Tyr Val Trp Thr
            580                 585                 590
Gly Phe Asp Tyr Leu Gly Glu Pro Thr Pro Trp Asn Gly Thr Gly Ser
```

-continued

```
                 595                 600                 605
Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
                755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
                835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
    915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val  His Trp Thr Lys Pro  Ala Asp Thr
    995                 1000                1005

Val Tyr  Asn Thr Ala Gly Thr  Val Lys Val Pro Gly  Thr Ala Thr
    1010                1015                1020
```

```
Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr
    1205                1210

<210> SEQ ID NO 11
<211> LENGTH: 1296
<212> TYPE: PRT
<213> ORGANISM: Bifidobacterium bifidum

<400> SEQUENCE: 11

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
```

-continued

```
                165                 170                 175
Thr Leu Thr Val Thr Asp Gly Val His Val Gly Asn Asn Gly Val Ala
                    180                 185                 190
Ile Lys Thr Pro Ser Leu Ala Thr Gln Asn Gly Gly Asp Val Thr Met
                    195                 200                 205
Asn Leu Thr Thr Lys Val Ala Asn Asp Thr Glu Ala Ala Ala Asn Ile
                    210                 215                 220
Thr Leu Lys Gln Thr Val Phe Pro Lys Gly Gly Lys Thr Asp Ala Ala
225                 230                 235                 240
Ile Gly Thr Val Thr Thr Ala Ser Lys Ser Ile Ala Ala Gly Ala Ser
                    245                 250                 255
Ala Asp Val Thr Ser Thr Ile Thr Ala Ala Ser Pro Lys Leu Trp Ser
                    260                 265                 270
Ile Lys Asn Pro Asn Leu Tyr Thr Val Arg Thr Glu Val Leu Asn Gly
                    275                 280                 285
Gly Lys Val Leu Asp Thr Tyr Asp Thr Glu Tyr Gly Phe Arg Trp Thr
                    290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                    325                 330                 335
Ala Asn Arg Arg Ala Ile Glu Arg Gln Val Glu Ile Leu Gln Lys Met
                    340                 345                 350
Gly Val Asn Ser Ile Arg Thr Thr His Asn Pro Ala Ala Lys Ala Leu
                    355                 360                 365
Ile Asp Val Cys Asn Glu Lys Gly Val Leu Val Val Glu Glu Val Phe
                    370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                    405                 410                 415
Lys Asp Glu Thr Trp Ala Lys Phe Asp Leu Thr Ser Thr Ile Asn Arg
                    420                 425                 430
Asp Arg Asn Ala Pro Ser Val Ile Met Trp Ser Leu Gly Asn Glu Met
                    435                 440                 445
Met Glu Gly Ile Ser Gly Ser Val Ser Gly Phe Pro Ala Thr Ser Ala
                    450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                    485                 490                 495
Gly Asp Asn Leu Thr Ala Asn Gly Gly Val Val Gly Thr Asn Tyr Ser
                    500                 505                 510
Asp Gly Ala Asn Tyr Asp Lys Ile Arg Thr Thr His Pro Ser Trp Ala
                    515                 520                 525
Ile Tyr Gly Ser Glu Thr Ala Ser Ala Ile Asn Ser Arg Gly Ile Tyr
                    530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                    565                 570                 575
Tyr Asp Val Val Gln Arg Asp Phe Val Ala Gly Thr Tyr Val Trp Thr
                    580                 585                 590
```

Gly Phe Asp Tyr Leu Gly Glu Pro Thr Pro Trp Asn Gly Thr Gly Ser
            595             600                 605

Gly Ala Val Gly Ser Trp Pro Ser Pro Lys Asn Ser Tyr Phe Gly Ile
    610             615                 620

Val Asp Thr Ala Gly Phe Pro Lys Asp Thr Tyr Tyr Phe Tyr Gln Ser
625             630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660             665                 670

Tyr Thr Asp Ala Ala Lys Val Lys Leu Tyr Phe Thr Pro Lys Gly Ser
        675             680                 685

Thr Glu Lys Arg Leu Ile Gly Glu Lys Ser Phe Thr Lys Lys Thr Thr
        690             695                 700

Ala Ala Gly Tyr Thr Tyr Gln Val Tyr Glu Gly Ser Asp Lys Asp Ser
705             710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
        820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

```
Val Tyr Asn Thr Ala Gly Thr Val Lys Val Pro Gly Thr Ala Thr
1010                1015                1020

Val Phe Gly Lys Glu Phe Lys Val Thr Ala Thr Ile Arg Val Gln
1025                1030                1035

Arg Ser Gln Val Thr Ile Gly Ser Ser Val Ser Gly Asn Ala Leu
1040                1045                1050

Arg Leu Thr Gln Asn Ile Pro Ala Asp Lys Gln Ser Asp Thr Leu
1055                1060                1065

Asp Ala Ile Lys Asp Gly Ser Thr Thr Val Asp Ala Asn Thr Gly
1070                1075                1080

Gly Gly Ala Asn Pro Ser Ala Trp Thr Asn Trp Ala Tyr Ser Lys
1085                1090                1095

Ala Gly His Asn Thr Ala Glu Ile Thr Phe Glu Tyr Ala Thr Glu
1100                1105                1110

Gln Gln Leu Gly Gln Ile Val Met Tyr Phe Phe Arg Asp Ser Asn
1115                1120                1125

Ala Val Arg Phe Pro Asp Ala Gly Lys Thr Lys Ile Gln Ile Ser
1130                1135                1140

Ala Asp Gly Lys Asn Trp Thr Asp Leu Ala Ala Thr Glu Thr Ile
1145                1150                1155

Ala Ala Gln Glu Ser Ser Asp Arg Val Lys Pro Tyr Thr Tyr Asp
1160                1165                1170

Phe Ala Pro Val Gly Ala Thr Phe Val Lys Val Thr Val Thr Asn
1175                1180                1185

Ala Asp Thr Thr Thr Pro Ser Gly Val Val Cys Ala Gly Leu Thr
1190                1195                1200

Glu Ile Glu Leu Lys Thr Ala Thr Ser Lys Phe Val Thr Asn Thr
1205                1210                1215

Ser Ala Ala Leu Ser Ser Leu Thr Val Asn Gly Thr Lys Val Ser
1220                1225                1230

Asp Ser Val Leu Ala Ala Gly Ser Tyr Asn Thr Pro Ala Ile Ile
1235                1240                1245

Ala Asp Val Lys Ala Glu Gly Glu Gly Asn Ala Ser Val Thr Val
1250                1255                1260

Leu Pro Ala His Asp Asn Val Ile Arg Val Ile Thr Glu Ser Glu
1265                1270                1275

Asp His Val Thr Arg Lys Thr Phe Thr Ile Asn Leu Gly Thr Glu
1280                1285                1290

Gln Glu Phe
1295

<210> SEQ ID NO 12
<211> LENGTH: 1720
<212> TYPE: PRT
<213> ORGANISM: Bifidobacterium bifidum

<400> SEQUENCE: 12

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60
```

-continued

```
Pro His Asp Tyr Ser Ile Thr Gln Lys Tyr Ser Gln Ser Asn Glu Ala
 65                  70                  75                  80

Glu Ser Ala Tyr Leu Pro Gly Gly Thr Gly Trp Tyr Arg Lys Ser Phe
                 85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480
```

```
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
            500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
            530                 535                 540
Asn Arg Thr Thr Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
            580                 585                 590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
            610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val
            660                 665                 670
Tyr Thr Asp Ala Ala Lys Val Lys Leu Tyr Phe Thr Pro Lys Gly Ser
            675                 680                 685
Thr Glu Lys Arg Leu Ile Gly Glu Lys Ser Phe Thr Lys Lys Thr Thr
            690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
                725                 730                 735
Gly Thr Ile Ser Ala Glu Ala Tyr Asp Glu Asn Asn Arg Leu Ile Pro
            740                 745                 750
Glu Gly Ser Thr Glu Gly Asn Ala Ser Val Thr Thr Gly Lys Ala
            755                 760                 765
Ala Lys Leu Lys Ala Asp Ala Asp Arg Lys Thr Ile Thr Ala Asp Gly
            770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
            820                 825                 830
Tyr Gln Ala Asp Asn Arg Lys Ala Phe Ser Gly Lys Val Leu Ala Ile
            835                 840                 845
Val Gln Ser Thr Lys Glu Ala Gly Glu Ile Thr Val Thr Ala Lys Ala
            850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
                885                 890                 895
Tyr Tyr Val Lys Thr Gly Asn Lys Pro Ile Leu Pro Ser Asp Val Glu
```

```
              900            905            910
Val Arg Tyr Ser Asp Gly Thr Ser Asp Arg Gln Asn Val Thr Trp Asp
        915            920            925
Ala Val Ser Asp Asp Gln Ile Ala Lys Ala Gly Ser Phe Ser Val Ala
        930            935            940
Gly Thr Val Ala Gly Gln Lys Ile Ser Val Arg Val Thr Met Ile Asp
945            950            955            960
Glu Ile Gly Ala Leu Leu Asn Tyr Ser Ala Ser Thr Pro Val Gly Thr
                965            970            975
Pro Ala Val Leu Pro Gly Ser Arg Pro Ala Val Leu Pro Asp Gly Thr
                980            985            990
Val Thr Ser Ala Asn Phe Ala Val His Trp Thr Lys Pro Ala Asp Thr
        995            1000           1005
Val Tyr Asn Thr Ala Gly Thr Val Lys Val Pro Gly Thr Ala Thr
        1010           1015           1020
Val Phe Gly Lys Glu Phe Lys Val Thr Ala Thr Ile Arg Val Gln
        1025           1030           1035
Arg Ser Gln Val Thr Ile Gly Ser Ser Val Ser Gly Asn Ala Leu
        1040           1045           1050
Arg Leu Thr Gln Asn Ile Pro Ala Asp Lys Gln Ser Asp Thr Leu
        1055           1060           1065
Asp Ala Ile Lys Asp Gly Ser Thr Thr Val Asp Ala Asn Thr Gly
        1070           1075           1080
Gly Gly Ala Asn Pro Ser Ala Trp Thr Asn Trp Ala Tyr Ser Lys
        1085           1090           1095
Ala Gly His Asn Thr Ala Glu Ile Thr Phe Glu Tyr Ala Thr Glu
        1100           1105           1110
Gln Gln Leu Gly Gln Ile Val Met Tyr Phe Phe Arg Asp Ser Asn
        1115           1120           1125
Ala Val Arg Phe Pro Asp Ala Gly Lys Thr Lys Ile Gln Ile Ser
        1130           1135           1140
Ala Asp Gly Lys Asn Trp Thr Asp Leu Ala Ala Thr Glu Thr Ile
        1145           1150           1155
Ala Ala Gln Glu Ser Ser Asp Arg Val Lys Pro Tyr Thr Tyr Asp
        1160           1165           1170
Phe Ala Pro Val Gly Ala Thr Phe Val Lys Val Thr Val Thr Asn
        1175           1180           1185
Ala Asp Thr Thr Thr Pro Ser Gly Val Val Cys Ala Gly Leu Thr
        1190           1195           1200
Glu Ile Glu Leu Lys Thr Ala Thr Ser Lys Phe Val Thr Asn Thr
        1205           1210           1215
Ser Ala Ala Leu Ser Ser Leu Thr Val Asn Gly Thr Lys Val Ser
        1220           1225           1230
Asp Ser Val Leu Ala Ala Gly Ser Tyr Asn Thr Pro Ala Ile Ile
        1235           1240           1245
Ala Asp Val Lys Ala Glu Gly Glu Gly Asn Ala Ser Val Thr Val
        1250           1255           1260
Leu Pro Ala His Asp Asn Val Ile Arg Val Ile Thr Glu Ser Glu
        1265           1270           1275
Asp His Val Thr Arg Lys Thr Phe Thr Ile Asn Leu Gly Thr Glu
        1280           1285           1290
Gln Glu Phe Pro Ala Asp Ser Asp Glu Arg Asp Tyr Pro Ala Ala
        1295           1300           1305
```

```
Asp Met Thr Val Thr Val Gly Ser Glu Gln Thr Ser Gly Thr Ala
    1310            1315                1320
Thr Glu Gly Pro Lys Lys Phe Ala Val Asp Gly Asn Thr Ser Thr
    1325            1330                1335
Tyr Trp His Ser Asn Trp Thr Pro Thr Thr Val Asn Asp Leu Trp
    1340            1345                1350
Ile Ala Phe Glu Leu Gln Lys Pro Thr Lys Leu Asp Ala Leu Arg
    1355            1360                1365
Tyr Leu Pro Arg Pro Ala Gly Ser Lys Asn Gly Ser Val Thr Glu
    1370            1375                1380
Tyr Lys Val Gln Val Ser Asp Asp Gly Thr Asn Trp Thr Asp Ala
    1385            1390                1395
Gly Ser Gly Thr Trp Thr Thr Asp Tyr Gly Trp Lys Leu Ala Glu
    1400            1405                1410
Phe Asn Gln Pro Val Thr Thr Lys His Val Arg Leu Lys Ala Val
    1415            1420                1425
His Thr Tyr Ala Asp Ser Gly Asn Asp Lys Phe Met Ser Ala Ser
    1430            1435                1440
Glu Ile Arg Leu Arg Lys Ala Val Asp Thr Thr Asp Ile Ser Gly
    1445            1450                1455
Ala Thr Val Thr Val Pro Ala Lys Leu Thr Val Asp Arg Val Asp
    1460            1465                1470
Ala Asp His Pro Ala Thr Phe Ala Thr Lys Asp Val Thr Val Thr
    1475            1480                1485
Leu Gly Asp Ala Thr Leu Arg Tyr Gly Val Asp Tyr Leu Leu Asp
    1490            1495                1500
Tyr Ala Gly Asn Thr Ala Val Gly Lys Ala Thr Val Thr Val Arg
    1505            1510                1515
Gly Ile Asp Lys Tyr Ser Gly Thr Val Ala Lys Thr Phe Thr Ile
    1520            1525                1530
Glu Leu Lys Asn Ala Pro Ala Pro Glu Pro Thr Leu Thr Ser Val
    1535            1540                1545
Ser Val Lys Thr Lys Pro Ser Lys Leu Thr Tyr Val Val Gly Asp
    1550            1555                1560
Ala Phe Asp Pro Ala Gly Leu Val Leu Gln His Asp Arg Gln Ala
    1565            1570                1575
Asp Arg Pro Pro Gln Pro Leu Val Gly Glu Gln Ala Asp Glu Arg
    1580            1585                1590
Gly Leu Thr Cys Gly Thr Arg Cys Asp Arg Val Glu Gln Leu Arg
    1595            1600                1605
Lys His Glu Asn Arg Glu Ala His Arg Thr Gly Leu Asp His Leu
    1610            1615                1620
Glu Phe Val Gly Ala Ala Asp Gly Ala Val Gly Glu Gln Ala Thr
    1625            1630                1635
Phe Lys Val His Val His Ala Asp Gln Gly Asp Gly Arg His Asp
    1640            1645                1650
Asp Ala Asp Glu Arg Asp Ile Asp Pro His Val Pro Val Asp His
    1655            1660                1665
Ala Val Gly Glu Leu Ala Arg Ala Ala Cys His His Val Ile Gly
    1670            1675                1680
Leu Arg Val Asp Thr His Arg Leu Lys Ala Ser Gly Phe Gln Ile
    1685            1690                1695
```

```
Pro Ala  Asp  Asp  Met  Ala  Glu  Ile  Asp  Arg  Ile  Thr  Gly  Phe  His
    1700           1705               1710

Arg Phe  Glu  Arg  His  Val  Gly
    1715           1720

<210> SEQ ID NO 13
<211> LENGTH: 1396
<212> TYPE: PRT
<213> ORGANISM: Bacillus circulans

<400> SEQUENCE: 13

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Ser Gln Glu Lys
210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350
```

-continued

```
Leu Leu Ile Glu Glu Ala Phe Asp Cys Trp Ser Gln Ser Lys Lys Thr
            355                 360                 365
Tyr Asp Tyr Gly Arg Phe Phe Thr Arg Trp Ala Glu His Asp Val Lys
    370                 375                 380
Glu Met Val Asp Arg Gly Lys Asn Glu Pro Ser Ile Ile Met Trp Ser
385                 390                 395                 400
Ile Gly Asn Glu Ile Tyr Asp Thr Thr Ser Pro Ser Gly Val Glu Thr
                405                 410                 415
Ala Arg Asn Leu Val Arg Trp Ile Lys Glu Ile Asp Thr Thr Arg Pro
            420                 425                 430
Thr Thr Ile Gly Glu Asp Lys Thr Arg Gly Asp Lys Val Asn Val Thr
        435                 440                 445
Pro Ile Asp Pro Asn Ile Leu Glu Ile Phe His Thr Val Asp Val Val
    450                 455                 460
Gly Leu Asn Tyr Ser Glu Asn Asn Tyr Val Gly Tyr His Glu Gln His
465                 470                 475                 480
Pro Asn Trp Lys Leu Tyr Gly Ser Glu Thr Ser Ser Ala Thr Arg Ser
                485                 490                 495
Arg Gly Val Tyr Thr His Pro Tyr Glu Tyr Asn Leu Gly Thr Lys Tyr
            500                 505                 510
Asp Asp Leu Gln Gln Ser Ser Tyr Asp Asn Asp Tyr Val Pro Trp Gly
        515                 520                 525
Arg Thr Ala Glu Asp Ala Trp Lys Ser Asp Arg Asp Leu Lys His Phe
    530                 535                 540
Ala Gly Gln Phe Ile Trp Thr Gly Phe Asp Tyr Ile Gly Glu Pro Thr
545                 550                 555                 560
Pro Tyr Tyr Asp Ser Tyr Pro Ala Lys Ser Ser Tyr Phe Gly Ala Val
                565                 570                 575
Asp Thr Ala Gly Phe Pro Lys Asp Ile Phe Tyr Tyr Gln Ser Gln
            580                 585                 590
Trp Lys Lys Glu Pro Met Val His Leu Leu Pro His Trp Asn Trp Thr
    595                 600                 605
Glu Gly Glu Pro Val Arg Val Leu Ala Tyr Thr Asn Ala His Gln Val
        610                 615                 620
Glu Leu Phe Leu Asn Gly Lys Ser Leu Gly Val Arg Gly Tyr Glu Asn
625                 630                 635                 640
Lys Lys Thr Ser Trp Gly Ala Pro Tyr Lys Glu Thr Lys Asp Gly Lys
                645                 650                 655
Thr Tyr Leu Glu Trp Ala Val Pro Phe Lys Ala Gly Thr Leu Glu Ala
            660                 665                 670
Val Ala Met Asp Glu Asn Gly Lys Glu Ile Ala Arg Asp Gln Val Thr
        675                 680                 685
Thr Ala Gly Ala Pro Ala Ala Val Lys Leu Thr Ala Asp Arg Lys Val
    690                 695                 700
Ile Lys Ala Asp Gly Thr Asp Leu Ser Phe Ile Thr Ala Glu Ile Val
705                 710                 715                 720
Asp Ser Lys Gly Asn Val Val Pro Asn Ala Asp His Leu Ile Gln Phe
                725                 730                 735
His Leu Ser Gly His Gly Glu Leu Ala Gly Val Asp Asn Gly Asp Ala
            740                 745                 750
Ala Ser Val Glu Arg Tyr Lys Asp Asn Lys Arg Lys Ala Phe Ser Gly
        755                 760                 765
```

```
Lys Ala Leu Ala Ile Val Gln Ser Asn Lys Leu Asp Gly Asn Ile Thr
770                 775                 780

Leu His Ala Ser Ala Glu Gly Leu Ser Ser Gly Asn Val Thr Ile Phe
785                 790                 795                 800

Thr Thr Ala Ser Ala Asp Gln Asn Ser Ile Thr Ile Ala Gly Ile Asp
                805                 810                 815

Glu Val Asn Val Leu Val Asp Phe Asn Val Val Pro Glu Leu Pro Ser
                820                 825                 830

Gln Ile Lys Val Tyr Tyr Ser Asp Ser Thr Val Glu Met Lys Pro Val
                835                 840                 845

Thr Trp Asp Ala Val Asp Pro Asn Leu Leu Asn Thr Ala Gly Lys Ile
850                 855                 860

Ile Val Glu Gly Thr Val Glu Gly Thr Asp Lys Lys Ala Lys Ala Leu
865                 870                 875                 880

Leu Ile Val Lys Gly Asn Gly Gln Glu Asn Ser Glu Tyr Arg Ile Asp
                885                 890                 895

Leu Phe Ser Pro Asp Pro Lys Leu Ile Ser Thr Glu Leu Thr Val Glu
                900                 905                 910

Lys Thr Asn Ile Met Glu Asp Asp Phe Ile Asp Ile Lys Val Ile Gly
                915                 920                 925

Gln Leu Glu Asn Lys Glu Val Val Asp Leu Ser Asn Phe Met Pro Ile
930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
                965                 970                 975

Gly Arg Thr Val Thr Ser Pro Glu Met Met Leu Lys Ile Thr Lys Asn
                980                 985                 990

Pro Val Pro Lys Thr Ile Thr His Ile Asp Ser Ile Thr Val Val Ala
                995                 1000                1005

Gly Lys Gly Glu Ala Pro Val Leu Pro Ala Thr Ala Val Ala His
        1010                1015                1020

Phe Asp Arg Gly Met Pro Arg Asp Val Lys Val Lys Trp Glu Ile
        1025                1030                1035

Val Asn Pro Ala Leu Tyr Gln Asn Leu Gly Glu Phe Thr Val Ser
        1040                1045                1050

Gly Asp Val Glu Gly Thr Glu Ile Lys Ala Gln Ala Lys Val Met
        1055                1060                1065

Val Arg Ser Ala Leu Ala Ile Glu Thr Ile Ser Met Ala Val Leu
        1070                1075                1080

Pro Asn Gln Lys Pro Glu Leu Pro Gln Lys Val Thr Val Tyr Tyr
        1085                1090                1095

Ser Asp Gly Thr Glu Glu Gln Ala Asp Val Asp Trp Asp Ala Met
        1100                1105                1110

Pro Ser Ala Glu Leu Lys Ser Glu Gly Val Val Lys Val Lys Gly
        1115                1120                1125

Ser Val Lys Gly Val Asp Leu Lys Ala Thr Ala Gln Ile Arg Val
        1130                1135                1140

Thr Ser Glu Val Gly Gly Val Gln Asn Ile Ser Arg Ala Lys Asn
        1145                1150                1155

Gly Tyr Glu Tyr Pro Lys Ala Glu Ala Ser Phe Thr Asn Thr Gly
        1160                1165                1170

Pro Gly Ser Asn Asp Arg Ile Glu Ala Ile Asn Asp Asp Val Ile
```

```
              1175                1180                1185

Ser Tyr Asp Ala Glu Pro His Asn Arg Trp Thr Asn Trp Gln Pro
    1190                1195                1200

Thr Pro Arg Pro Gly Asp Trp Val Ser Ile Thr Phe Gly Asp Ser
    1205                1210                1215

Lys Pro Arg Lys Tyr Asp Ile Asp Ser Met Glu Ile His Trp Tyr
    1220                1225                1230

Glu Asp Leu Gly Thr Ser Ser Pro Ala Tyr Phe Arg Ile Gln Tyr
    1235                1240                1245

Lys Ser Gly Asp Glu Trp Lys Asp Val Ser Gly Leu Lys Thr Asn
    1250                1255                1260

Pro Ser Asn Thr Val Leu Arg Gln Ala Asn Val Tyr Thr Phe Asp
    1265                1270                1275

Lys Val Arg Thr Ser Ala Ile Arg Val Asp Met Thr Ala Lys Thr
    1280                1285                1290

Gly Lys Ser Leu Ala Ile Thr Glu Ile Lys Val Phe Ser Lys Trp
    1295                1300                1305

Ala Lys Ala His Thr His Pro Met Val Thr Asp Ile Lys Leu Gly
    1310                1315                1320

Asp Leu Ser Ile Leu Asp Asp Phe Ser Lys Lys Gly Asp Asn Asn
    1325                1330                1335

Glu Leu Thr Phe Gln Val Lys Asp Pro Arg Asp Ile Pro Glu Ile
    1340                1345                1350

Lys Val Lys Ala Glu Asp Asn Thr Ser Ile Thr Ile Ile Pro Thr
    1355                1360                1365

Phe Thr Ala Pro Ser Thr Ala Lys Ile Ile Ala Lys Ser Glu Asp
    1370                1375                1380

Gly Met Lys Val Glu Ile Tyr Asn Ile Arg Phe Thr Glu
    1385                1390                1395

<210> SEQ ID NO 14
<211> LENGTH: 1737
<212> TYPE: PRT
<213> ORGANISM: Bacillus species

<400> SEQUENCE: 14

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
        50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
                100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
        130                 135                 140
```

```
Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
    290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
    450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
```

```
                565                 570                 575
Ala Trp Lys Tyr Asp Arg Asp Leu Lys His Ile Ala Gly Gln Phe Ile
                580                 585                 590

Trp Thr Gly Phe Asp Tyr Ile Gly Glu Pro Thr Pro Tyr Tyr Asn Ser
            595                 600                 605

Tyr Pro Ala Lys Ser Ser Tyr Phe Gly Ala Val Asp Thr Ala Gly Phe
        610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Lys Val
                645                 650                 655

Arg Val Leu Ala Tyr Thr Asn Ala Ser Lys Val Glu Leu Val Leu Asn
                660                 665                 670

Gly Glu Ser Leu Gly Glu Lys Asn Tyr Asp Asn Lys Gln Thr Ser Trp
            675                 680                 685

Gly Ala Pro Tyr Lys Glu Thr Lys Asp Gly Lys Thr Tyr Leu Glu Trp
        690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Lys Ala Asp Gly
                740                 745                 750

Thr Asp Leu Ser Phe Ile Thr Ala Asp Ile Val Asp Ser Lys Gly Ile
            755                 760                 765

Val Val Pro Asp Ala Asp His Leu Ile Thr Phe Asn Val Thr Gly Gln
        770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
                820                 825                 830

Ala Gly Leu Ser Ser Asp Ser Thr Ser Val Phe Thr Val Thr Pro Ala
            835                 840                 845

Asp His Asp Lys Lys Ile Val Ala Gly Ile Asp Asp Val Asn Leu Thr
        850                 855                 860

Val Asp Val Asn Glu Ala Pro Lys Leu Pro Ser Glu Ile Lys Val Tyr
865                 870                 875                 880

Tyr Ser Asp Glu Ser Ala Ala Ala Lys Asn Val Thr Trp Asp Glu Val
                885                 890                 895

Asp Pro Lys Gln Tyr Ser Thr Val Gly Glu Phe Thr Val Glu Gly Ser
                900                 905                 910

Val Glu Gly Thr Ser Leu Lys Ala Lys Ala Phe Val Ile Val Lys Gly
            915                 920                 925

Ile Val Ala Val Lys Pro Tyr Ser Thr Ala Thr Lys Val Gly Val Gln
        930                 935                 940

Pro Val Leu Pro Glu Lys Ala Thr Leu Leu Tyr Ser Asp Gly Thr Thr
945                 950                 955                 960

Lys Gly Ala Thr Val Thr Trp Asp Glu Ile Pro Glu Asp Lys Leu Ala
                965                 970                 975

Lys Glu Gly Arg Phe Thr Val Glu Gly Ser Val Glu Gly Thr Asp Leu
                980                 985                 990
```

Lys Ala Asn Val Tyr Val Arg Val Thr Asn Glu Val Lys Ser Val Asn
        995                 1000                1005

Ile Met Leu Gln Glu Gln Gly Ser Ala Tyr Pro Lys Leu Glu Ala
   1010               1015                1020

Thr Phe Thr Asn Pro Ala Asp Asn Leu Gln His Leu Asn Asp Gly
   1025               1030                1035

Ile Lys Ser Tyr Thr Asn Asn Pro Val Asn Arg Trp Thr Asn Trp
   1040               1045                1050

Thr Arg Thr Pro Arg Asp Ala Gly Asp Ser Ile Thr Val Asn Phe
   1055               1060                1065

Gly Lys Lys His Val Ile Asn Asn Leu Asp Leu Phe Val Phe Thr
   1070               1075                1080

Asp Ser Gly Thr Val Val Pro Glu Lys Ala Glu Val Gln Tyr Trp
   1085               1090                1095

Asp Gly Thr Ala Trp Lys Asp Val Glu Asn Leu Thr Gln Pro Ser
   1100               1105                1110

Pro Tyr Val Val Glu Lys Asn Glu Leu Thr Phe Asp Ala Val Ala
   1115               1120                1125

Thr Glu Lys Leu Lys Phe His Leu Thr Pro Ser Val Lys Gly Lys
   1130               1135                1140

Phe Leu Ala Leu Thr Glu Ala Glu Val Tyr Ala Asp Gln Ile Val
   1145               1150                1155

Met Gly Glu Thr Ala Lys Leu Gln Ser Ile Thr Val Asn Gly Lys
   1160               1165                1170

Ala Leu Glu Gly Phe Asp His Ala Lys Lys Asn Tyr Glu Leu Val
   1175               1180                1185

Leu Pro Tyr Gly Ser Glu Leu Pro Lys Ile Glu Ala Ala Ala Ala
   1190               1195                1200

Asp Asn Ala Thr Val Thr Ile Leu Pro Ala Phe Ser Tyr Pro Gly
   1205               1210                1215

Thr Ala Lys Leu Phe Val Thr Ser Glu Asp Gly Lys Val Thr Thr
   1220               1225                1230

Glu Tyr Ser Ile Gly Val Ser Thr Glu Pro Lys Leu Val Ser
   1235               1240                1245

Ala Glu Leu Ser Ala Asp Lys Thr Asn Val Met Glu Asp Asp Ile
   1250               1255                1260

Ile Asp Leu Lys Val Ile Gly Leu Phe Glu Ser Lys Glu Lys Ile
   1265               1270                1275

Asp Val Thr Asp Ser Gln Pro Thr Tyr Glu Phe Asp Gln Gln Ile
   1280               1285                1290

Ile Lys Ile Glu Gly Asn Lys Leu Tyr Ala Leu Glu Thr Gly Asn
   1295               1300                1305

Val Lys Val Lys Val Thr Val Thr Tyr Lys Gly Val Ser Val Thr
   1310               1315                1320

Thr Pro Ala Leu Glu Phe Thr Ile Ala Lys Asn Pro Ala Pro Lys
   1325               1330                1335

Tyr Ile Thr Ser Leu Glu Pro Val Thr Val Val Lys Lys Gly
   1340               1345                1350

Glu Ala Pro Glu Leu Pro Ala Thr Val Val Ala His Tyr Asn Arg
   1355               1360                1365

Gly Ile Pro Arg Asp Val Lys Val Lys Trp Glu Arg Ile Asn Pro
   1370               1375                1380

-continued

Ser Lys Tyr Gln Gln Leu Gly Glu Phe Thr Val Ser Gly Met Val
    1385                1390                1395

Glu Gly Thr Asp Ile Lys Ala Gln Ala Lys Val Ile Val Lys Gly
1400                1405                1410

Ala Val Ala Val Glu Asp Ile Arg Met Ala Val Leu Leu Lys Gln
1415                1420                1425

Met Pro Gln Leu Pro Gly Lys Val Thr Val Tyr Tyr Ser Asp Gly
1430                1435                1440

Ala Glu Gln Arg Ala Val Lys Trp Glu Glu Ile Pro Gln Glu
1445                1450                1455

Glu Leu Glu Asn Val Gly Glu Phe Lys Val Lys Gly Asp Val Asn
1460                1465                1470

Gly Val Lys Leu Lys Ala Thr Ala Thr Ile Arg Val Thr Asp Glu
1475                1480                1485

Val Gly Gly Glu Gln Asn Ile Ser Arg Ala Lys Asn Gly Tyr Glu
1490                1495                1500

Tyr Pro Lys Ala Glu Ala Ser Phe Thr Asn Asn Gly Pro Gly Ser
1505                1510                1515

Ser Asp Arg Ile Glu Ala Ile Asn Asp Asp Val Ile Ser Tyr Glu
1520                1525                1530

Ala Asn Pro His Asn Arg Trp Thr Asn Trp Gln Pro Val Pro Arg
1535                1540                1545

Ala Gly Asp Trp Val Ser Ile Thr Phe Gly Asp Tyr Glu Pro Thr
1550                1555                1560

Glu Tyr Asp Val Asp Ser Met Glu Ile His Trp Phe Ala Asp His
1565                1570                1575

Gly Thr Ser Tyr Pro Glu Arg Phe Gln Ile Glu Tyr Lys Ser Gly
1580                1585                1590

Asp Ser Trp Lys Glu Val Thr Ser Leu Lys Ser Asp Pro Ala Ser
1595                1600                1605

Pro Ala Leu Gly Lys Ala Asn Val Tyr Ser Phe Asp Arg Val Lys
1610                1615                1620

Thr Ser Ala Ile Arg Val Lys Met Thr Ala Gln Ala Gly Lys Ser
1625                1630                1635

Leu Ala Ile Thr Glu Leu Lys Val Phe Ser Lys Trp Pro Lys Ala
1640                1645                1650

Gly Thr Glu Pro Glu Val Thr Asp Ile Lys Val Gly Gly Lys Ser
1655                1660                1665

Ile Leu Glu Asp Phe Glu Gln Lys Gly Asp His Tyr Glu Val Thr
1670                1675                1680

Ile Asp Ala Gly Asp Ala Asn Val Met Pro Lys Ile Asn Val Lys
1685                1690                1695

Ala Lys Asp Gln Thr Ser Ile Thr Ile Val Pro Ala Val Thr Ser
1700                1705                1710

Pro Ser Thr Ala Lys Val Ile Ala Lys Ser Glu Asp Gly Lys Lys
1715                1720                1725

Val Lys Val Tyr Ser Ile His Tyr Lys
1730                1735

<210> SEQ ID NO 15
<211> LENGTH: 1025
<212> TYPE: PRT
<213> ORGANISM: Kluyveromyces lactis

<400> SEQUENCE: 15

```
Met Ser Cys Leu Ile Pro Glu Asn Leu Arg Asn Pro Lys Lys Val His
1               5                   10                  15

Glu Asn Arg Leu Pro Thr Arg Ala Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
        50                  55                  60

Ser Thr Ile Ser Val Pro Ser His Trp Glu Leu Gln Glu Asp Trp Lys
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
            115                 120                 125

Phe Glu Gly Val Asp Asn Cys Tyr Glu Leu Tyr Val Asn Gly Gln Tyr
        130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
            195                 200                 205

Ile Glu Asp Val Arg Val Thr Thr Thr Phe Val Asp Ser Gln Tyr Gln
210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
            245                 250                 255

Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
            275                 280                 285

Phe Lys Ile Asn Val Lys Ala Pro Glu His Trp Thr Ala Glu Asn Pro
            290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
            325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
            355                 360                 365

Phe Val Val Arg Asp Leu Ile Leu Met Lys Lys Phe Asn Ile Asn Ala
            370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
            405                 410                 415
```

-continued

Gly Val Gln Glu Pro Phe Asn Arg His Thr Asn Leu Glu Ala Glu Tyr
            420                 425                 430

Pro Asp Thr Lys Asn Lys Leu Tyr Asp Val Asn Ala His Tyr Leu Ser
        435                 440                 445

Asp Asn Pro Glu Tyr Glu Val Ala Tyr Leu Asp Arg Ala Ser Gln Leu
    450                 455                 460

Val Leu Arg Asp Val Asn His Pro Ser Ile Ile Ile Trp Ser Leu Gly
465                 470                 475                 480

Asn Glu Ala Cys Tyr Gly Arg Asn His Lys Ala Met Tyr Lys Leu Ile
                485                 490                 495

Lys Gln Leu Asp Pro Thr Arg Leu Val His Tyr Glu Gly Asp Leu Asn
            500                 505                 510

Ala Leu Ser Ala Asp Ile Phe Ser Phe Met Tyr Pro Thr Phe Glu Ile
        515                 520                 525

Met Glu Arg Trp Arg Lys Asn His Thr Asp Glu Asn Gly Lys Phe Glu
    530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Glu Lys Phe Tyr
                565                 570                 575

Gln Gly Gly Phe Ile Trp Glu Trp Ala Asn His Gly Ile Glu Phe Glu
            580                 585                 590

Asp Val Ser Thr Ala Asp Gly Lys Leu His Lys Ala Tyr Ala Tyr Gly
        595                 600                 605

Gly Asp Phe Lys Glu Glu Val His Asp Gly Val Phe Ile Met Asp Gly
    610                 615                 620

Leu Cys Asn Ser Glu His Asn Pro Thr Pro Gly Leu Val Glu Tyr Lys
625                 630                 635                 640

Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
            660                 665                 670

Asp Lys Asp Thr Gly Lys Thr Ile Asp Val Pro Ser Leu Lys Pro Glu
        675                 680                 685

Glu Ser Val Thr Ile Pro Ser Asp Thr Thr Tyr Val Val Ala Val Leu
    690                 695                 700

Lys Asp Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
                725                 730                 735

Glu Lys Ala Ala Lys Ile Asn Asp Gly Lys Arg Tyr Val Ser Val Glu
            740                 745                 750

Ser Ser Gly Leu His Phe Ile Leu Asp Lys Leu Leu Gly Lys Ile Glu
        755                 760                 765

Ser Leu Lys Val Lys Gly Lys Glu Ile Ser Ser Lys Phe Glu Gly Ser
    770                 775                 780

Ser Ile Thr Phe Trp Arg Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
            820                 825                 830

Thr Val Asn Ser Arg Ile Ser Pro Val Val Phe Tyr Tyr Gly Phe Glu

-continued

```
                    835                   840                        845
Thr Val Gln Lys Tyr Thr Ile Phe Ala Asn Lys Ile Asn Leu Asn Thr
        850                 855                 860

Ser Met Lys Leu Thr Gly Glu Tyr Gln Pro Pro Asp Phe Pro Arg Val
865                 870                 875                     880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
            900                 905                 910

Phe Gly Leu Tyr Asp Ser Lys Asp Val Glu Glu Phe Val Tyr Asp Tyr
            915                 920                 925

Pro Gln Glu Asn Gly Asn His Thr Asp Thr His Phe Leu Asn Ile Lys
    930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
            980                 985                 990

Ile His Gly Val Gly Ser Glu Ala  Cys Gly Pro Ala Val  Leu Asp Gln
        995                 1000                1005

Tyr Arg Leu Lys Ala Gln Asp  Phe Asn Phe Glu Phe  Asp Leu Ala
    1010                1015                1020

Phe Glu
    1025
```